(12) United States Patent
Wohlfahrt et al.

(10) Patent No.: US 9,890,139 B2
(45) Date of Patent: Feb. 13, 2018

(54) CYP17 INHIBITORS/ANTIANDROGENS

(71) Applicant: Orion Corporation, Espoo (FI)

(72) Inventors: Gerd Wohlfahrt, Helsinki (FI); Petteri Rummakko, Siuntio (FI); Arja Karjalainen, Espoo (FI); Mikko Passiniemi, Helsinki (FI); Pekka Pietikäinen, Espoo (FI); Anssi Haikarainen, Järvenpää (FI); Emilia Väisänen, Helsinki (FI); Eija Tiainen, Espoo (FI)

(73) Assignee: ORION CORPORATION (FI)

( * ) Notice: Subject to any disclaimer, the term of this patent is extended or adjusted under 35 U.S.C. 154(b) by 0 days.

(21) Appl. No.: 14/897,326

(22) PCT Filed: Jun. 10, 2014

(86) PCT No.: PCT/FI2014/000009
§ 371 (c)(1),
(2) Date: Dec. 10, 2015

(87) PCT Pub. No.: WO2014/202827
PCT Pub. Date: Dec. 24, 2014

(65) Prior Publication Data
US 2016/0130254 A1    May 12, 2016

Related U.S. Application Data

(60) Provisional application No. 61/833,846, filed on Jun. 11, 2013.

(51) Int. Cl.

| | |
|---|---|
| C07D 271/10 | (2006.01) |
| C07D 403/04 | (2006.01) |
| C07D 231/12 | (2006.01) |
| C07D 233/58 | (2006.01) |
| C07D 233/64 | (2006.01) |
| C07D 401/04 | (2006.01) |
| C07D 235/08 | (2006.01) |
| C07D 405/04 | (2006.01) |
| C07D 413/04 | (2006.01) |
| C07D 417/04 | (2006.01) |
| C07D 249/04 | (2006.01) |
| C07D 249/08 | (2006.01) |
| C07D 257/04 | (2006.01) |
| C07D 213/38 | (2006.01) |

(52) U.S. Cl.
CPC ......... *C07D 403/04* (2013.01); *C07D 213/38* (2013.01); *C07D 231/12* (2013.01); *C07D 233/58* (2013.01); *C07D 233/64* (2013.01); *C07D 235/08* (2013.01); *C07D 249/04* (2013.01); *C07D 249/08* (2013.01); *C07D 257/04* (2013.01); *C07D 271/10* (2013.01); *C07D 401/04* (2013.01); *C07D 405/04* (2013.01); *C07D 413/04* (2013.01); *C07D 417/04* (2013.01)

(58) Field of Classification Search
None
See application file for complete search history.

(56) References Cited

U.S. PATENT DOCUMENTS 9,346,810 B2 *   5/2016   Su ..................... C07D 471/04

FOREIGN PATENT DOCUMENTS

| WO | WO 2005/000795 A2 | 1/2005 | |
|---|---|---|---|
| WO | WO 2005/108351 A1 | 11/2005 | |
| WO | WO 2006/044707 A1 | 4/2006 | |
| WO | WO 2006/122011 A2 | 11/2006 | |
| WO | WO 2006/133216 A2 | 12/2006 | |
| WO | WO 2007/065093 A2 | 6/2007 | |
| WO | WO 2007065093 A2 * | 6/2007 | ........... C07D 207/12 |
| WO | WO 2007/092727 A1 | 8/2007 | |
| WO | WO 2008/021796 A2 | 2/2008 | |
| WO | WO 2008/077089 A1 | 6/2008 | |
| WO | WO 2010/149755 A1 | 12/2010 | |

(Continued)

OTHER PUBLICATIONS

International Search Report for PCT/FI2014/000009, dated Oct. 15, 2014.

Seung-Hwa, Baek et al.; "Inhibitory Effect of 4-Aryl 2-Substituted Aniline-thiazole Analogs on Growth of Human Prostate Cancer LNCap Cells"; Bulletin of the Korean Chemical Society; vol. 33, No. 1; pp. 111-114; Jan. 20, 2012.

Slayden, O. D. et al.; "Progesterone Antagonists Increase Androgen Receptor Expression in the Rhesus Macaque and Human Endometrium"; Journal of Clinical Endocrinology and Metabolism, The Endocrine Society; vol. 86, No. 6; pp. 2668-2679; Jun. 1, 2001.

(Continued)

*Primary Examiner* — Heidi Reese
(74) *Attorney, Agent, or Firm* — Finnegan, Henderson, Farabow, Garrett & Dunner, L.L.P.

(57) ABSTRACT

Compounds of formula (I)

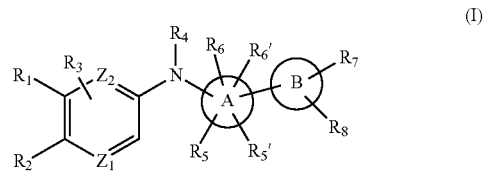

wherein $R_1$ to $R_8$, A, B, $Z_1$, and $Z_2$ are as defined in the claims and pharmaceutically acceptable salts and esters thereof are disclosed. The compounds of formula (I) possess utility as androgen receptor antagonists (inhibitors) and/or cytochrome P450 monooxygenase 17α-hydroxylase/17,20-lyase (CYP17) inhibitors. The compounds are useful as medicaments in the treatment of cancer, particularly prostate cancer, and other androgen dependent conditions and diseases where androgen antagonism is desired.

22 Claims, No Drawings

(56) References Cited

FOREIGN PATENT DOCUMENTS

WO     WO 2012/022265 A1     2/2012

OTHER PUBLICATIONS

Wakabayashi, K. I. et al.; "4-(Anilino)pyrrole-2-carboxamides: Novel Non-steroidal/Non-anilide Type Androgen Antagonists Effective upon Human Prostate Tumor LNCaP Cells with Mutated Nuclear Androgen Receptor"; Bioorganic & Medicinal Chemistry, Pergamon; vol. 16, No. 14; pp. 6799-6812; Jul. 15, 2008.

Zhang et al.; "Serendipitous Discovery of Novel Imidazolopyrazole Scaffold as Selective Androgen Receptor Modulators"; Bioorganic & Medicinal Chemistry Letters, Pergamon; vol. 17, No. 2; pp. 439-443; Jan. 11, 2007.

STN Registry, CAS Registry No. 1355594-56-7, Entered STN Feb. 7, 2012.

Trump, R. P. et al.; "Design and Synthesis of an Array of Selective Androgen Receptor Modulators"; J. Comb. Chem.; vol. 9, pp. 107-114; 2007.

\* cited by examiner

CYP17 INHIBITORS/ANTIANDROGENS

This is a national stage application under § 371 of International Patent Application No. PCT/FI2014/000009, filed Jun. 10, 2014, which claims the benefit of priority of U.S. Provisional Application No. 61/833,846, filed Jun. 11, 2013, and all of which is incorporated herein by reference.

TECHNICAL FIELD

The present invention relates to therapeutically active nonsteroidal compounds and pharmaceutically acceptable salts thereof useful in the treatment of nuclear receptor, especially steroid receptor, and in particular androgen receptor (AR) dependent conditions and diseases, and to pharmaceutical compositions containing such compounds.

BACKGROUND OF THE INVENTION

In recent years, there has been growing interest in the development of nonsteroidal modulators for steroid receptors for therapeutical use. It has been shown that nonsteroidal ligands can achieve better receptor selectivity and better physicochemical, pharmacokinetic and pharmacological properties. For androgen receptor (AR), nonsteroidal AR antagonists (antiandrogens), such as bicalutamide, are now used clinically to counteract the undesirable actions of excessive androgens, particularly in the treatment of prostate cancer.

Androgens such as testosterone and its conversion product dihydrotestosterone (DHT), functioning through the AR, are essential for the initiation and progression of prostate cancer. Thus, treatment of advanced prostate cancer involves androgen-ablation therapies, such as surgical castration or hormonal manipulation using gonadotropin-releasing hormone (GnRH) agonists, anti-androgens or both. Although such therapies initially lead to disease regression, eventually all patients progress to a castration resistant late stage that is refractory to current therapies. Castration-resistant prostate cancer (CRPC) is often associated with increased levels of AR. First generation anti-androgens such as bicalutamide display agonistic properties in cells engineered to express higher AR levels. In vitro and in vivo, increased AR expression has been shown to confer resistance of prostate cancer cell lines to anti-androgen therapy. To overcome resistance problems, second generation anti-androgens that retain antagonism in cells expressing excess AR may have utility in the treatment of CRPC.

Prostate cancer can be also treated by inhibiting the biosynthesis of androgens. In the testes and adrenal glands, the last step in the biosynthesis of testosterone involves two key reactions, which are both catalyzed by a single enzyme, the cytochrome P450 monooxygenase 17α-hydroxylase/17,20-lyase (CYP17). Ketoconazole, an antifungal agent, which is also a modest CYP17 inhibitor has been used clinically for the treatment of prostate cancer. It has been reported that careful scheduling of treatment can produce prolonged responses in otherwise hormone-refractory prostate cancer patients. Although ketoconazole has been withdrawn from the use because of liver toxicity and other side effects, this suggests that more potent and selective inhibitors of CYP17 could provide useful agents for treating prostate cancer, even in advanced stages and in some patients who may appear to be hormone refractory.

Recently, a potent CYP17 inhibitor abiraterone was approved in combination with prednisone for the treatment of CRPC. Abiraterone has been reported to increase survival and to delay clinical decline and initiation of chemotherapy in CRPC patients who have had no prior chemotherapy.

SUMMARY OF THE INVENTION

It has been found that compounds of formula (I) are potent androgen receptor antagonists (inhibitors) and/or potent CYP17 inhibitors. The compounds of the invention are therefore useful as medicaments in the treatment of cancer, particularly prostate cancer, and other androgen dependent conditions and diseases where androgen antagonism is desired. The compounds of formula (I) which possess both AR antagonism and CYP17 inhibition are useful as dual inhibitors combining the benefits of both inhibitory mechanisms.

The present invention provides compounds of formula (I)

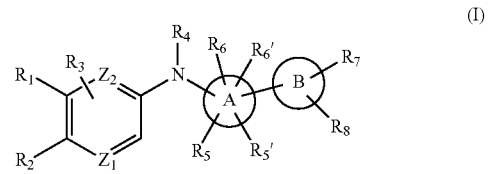

wherein ring atoms $Z_1$ and $Z_2$ are, independently, C or N provided that at least one of ring atoms $Z_1$ and $Z_2$ is C;

A is a non-aromatic 3-7 membered carbocyclic or a non-aromatic 5-6 membered heterocyclic ring;

B is a 5-6 membered heterocyclic ring, or, in case that A is a non-aromatic 3-7 membered carbocyclic ring, B can also be a 7-12 membered heterocyclic ring;

$R_1$ is halogen, $CHF_2$, $CF_3$, $C_{1-7}$ alkyl or $C_{1-7}$ alkoxy;

$R_2$ is cyano or nitro;

$R_3$ is H, halogen or $C_{1-7}$ alkyl;

$R_4$ is $C_{1-7}$ alkyl, $C_{2-7}$ alkenyl, $C_{3-7}$ cycloalkyl, $C_{3-7}$ cycloalkyl $C_{1-7}$ alkyl, hydroxy $C_{1-7}$ alkyl, halo $C_{1-7}$ alkyl, $C_{1-7}$ alkoxy $C_{1-7}$ alkyl, $C_{1-7}$ alkylcarbonyl or phenyl $C_{1-7}$ alkyl, or, in case A is a non-aromatic 3-7 membered carbocyclic ring and B is an aromatic 5-6 membered heterocyclic ring, $R_4$ can also be hydrogen;

$R_5$ is H, OH, $C_{1-7}$ alkyl, $C_{1-7}$ alkoxy or hydroxy $C_{1-7}$ alkyl;

$R_5'$, $R_6'$ and $R_6$ are, independently, H, OH, $C_{1-7}$ alkyl or halogen;

or, in case $R_6'$ and $R_6$ are attached to the same carbon atom of the ring, $R_6'$ and $R_6$ may, together with the carbon atom which they are attached to, form a $C_{3-7}$ cycloalkyl ring;

$R_7$ is H, OH, cyano, halogen, $C_{1-7}$ alkyl, $C_{3-7}$ cycloalkyl, $C_{1-7}$ alkoxy, hydroxy $C_{1-7}$ alkyl, halo $C_{1-7}$ alkyl, cyano $C_{1-7}$ alkyl, halo $C_{1-7}$ alkoxy, $C_{1-7}$ alkoxy $C_{1-7}$ alkyl, hydroxy $C_{1-7}$ alkoxy $C_{1-7}$ alkyl, $C_{1-7}$ alkyl carbonyl $C_{1-7}$ alkyl or —$C_{1-7}$ alkyl-X—$(CH_2)_n$—$R_9$ or $R_9$;

$R_8$ is H or $C_{1-7}$ alkyl;

$R_9$ is an optionally substituted 3-7 membered carbocyclic ring, an optionally substituted 4-6 membered heterocyclic ring, or —$NR_{10}R_{11}$;

X is a bond, oxygen or —NH—;

n=0-3;

$R_{10}$ and $R_{11}$ are, independently, H, $C_{1-7}$ alkyl or $C_{1-7}$ alkyl carbonyl;

or a pharmaceutically acceptable salt thereof.

In one embodiment of compounds of formula (I) are compounds, wherein ring atom $Z_2$ is C. In another embodiment of compounds of formula (I) are compounds, wherein ring atom $Z_1$ is C. In still another embodiment both ring atoms $Z_1$ and $Z_2$ are C.

In another embodiment of compounds of formula (I) are compounds, wherein A is a non-aromatic 3-7 membered carbocyclic ring. In another embodiment, A is a non-aromatic 5-6 membered heterocyclic ring.

In another embodiment of compounds of formula (I) are compounds, wherein A is a cyclobutyl, cyclopentyl, cyclohexyl, cyclopentenyl, cyclohexenyl, piperidinyl, pyrrolidinyl, dihydropyranyl, tetrahydropyranyl, tetrahydropyridazinyl, dihydrothiopyranyl or azabicyclo[2.2.1]heptanyl ring.

In another embodiment of compounds of formula (I) are compounds, wherein A is a cyclopentyl, cyclohexyl, cyclopentenyl or cyclohexenyl ring.

In another embodiment of compounds of formula (I) are compounds, wherein A is any one of the following groups wherein the asterisk denotes the point of attachment to the non-cyclic nitrogen atom of formula (I)

(1)

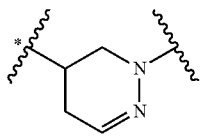

(2)

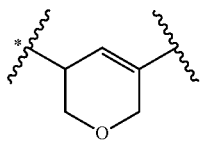

(3)

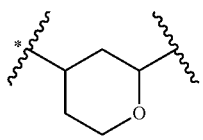

(4)

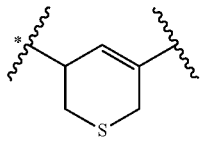

(5)

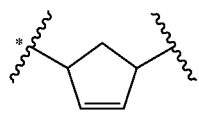

(6)

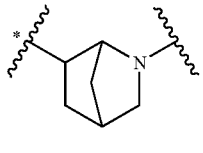

(7)

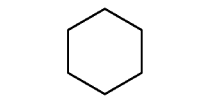

(8)

(9)

(10)

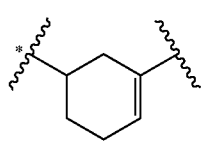

(11)

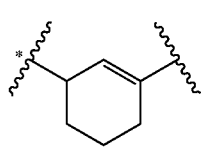

(12)

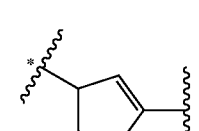

(13)

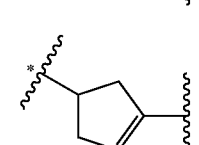

(14)

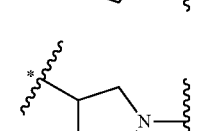

(15)

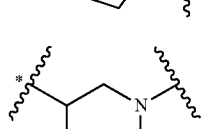

and wherein $R_5$, $R_5'$, $R_6$ and $R_6'$, as defined above, are attached to the above A-rings.

In another embodiment of compounds of formula (I) are compounds, wherein B is a imidazolyl, 1,2,4-triazolyl, 1,2,3-triazolyl, pyridinyl, tetrazolyl, pyrimidinyl, 1,3,4-oxadiazolyl, pyrazolyl, benzo[d]imidazolyl, pyrazinyl, 1,3,4-thiadiazolyl, oxazolyl, thiazolyl or isoxazolyl ring.

In another embodiment of compounds of formula (I) are compounds wherein B is a imidazolyl, pyridinyl, 1,2,4-triazolyl, 1,2,3-triazolyl, thiazolyl or oxazolyl ring.

In another embodiment of compounds of formula (I) are compounds, wherein B is any one of the following groups or tautomers thereof wherein the asterisk denotes the point of attachment to the A-ring of formula (I)

(1')

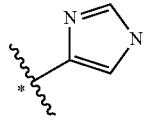

(2')

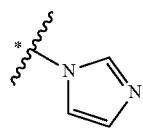

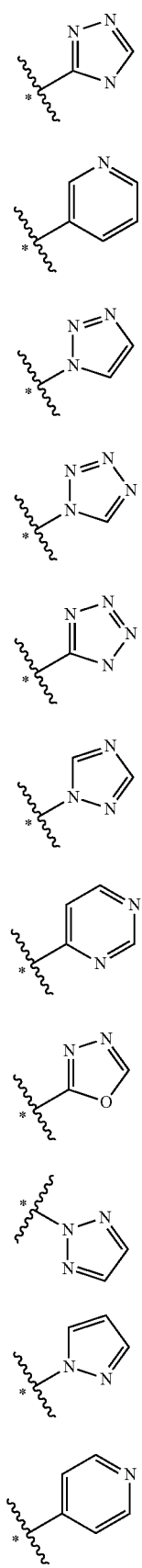
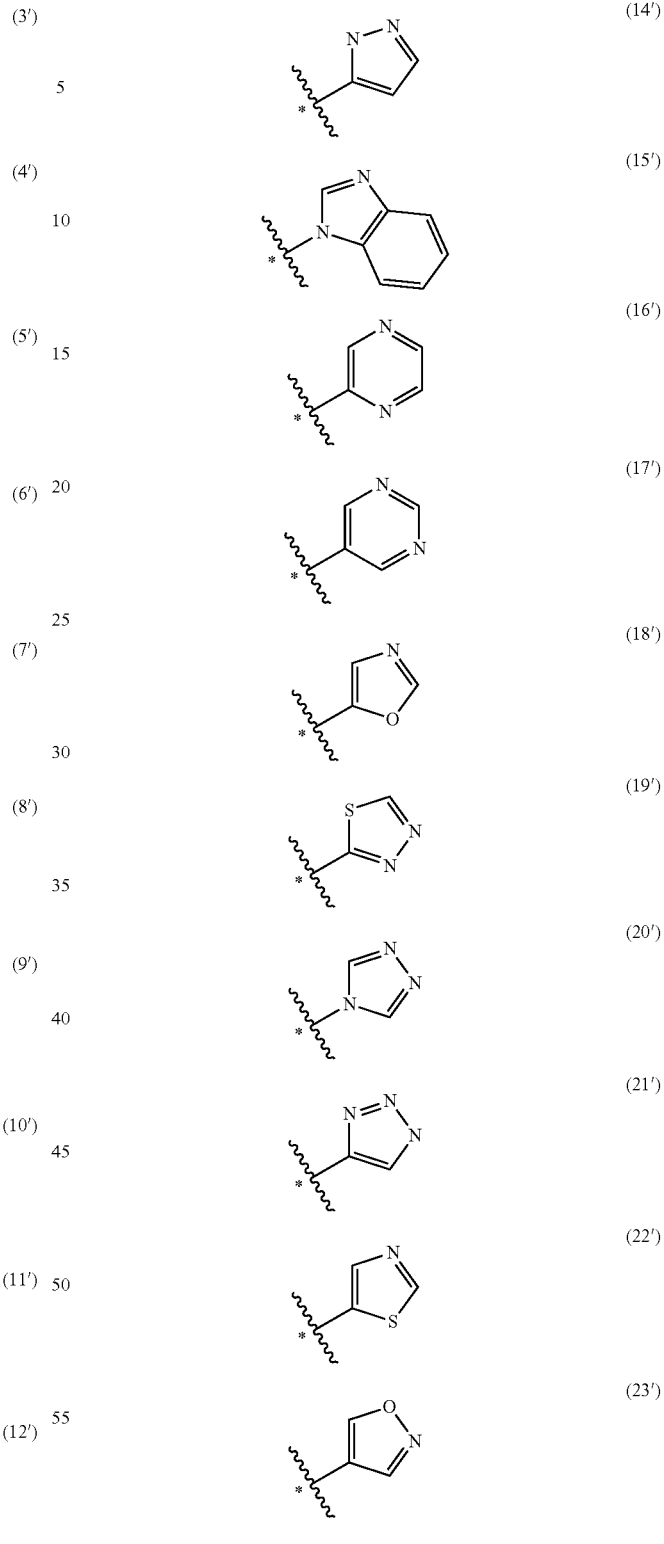
wherein each of the above rings are substituted by $R_7$ and $R_8$, as defined above.
In another embodiment of compounds of formula (I) are compounds, wherein $R_9$ is a imidazolyl, pyrazolyl, oxetanyl, thiazolyl, pyridinyl, phenyl or morpholinyl ring which may be substituted with one $C_{1-7}$ alkyl or one $C_{1-7}$ alkoxy group.

In a subclass of the above embodiments of compounds of formula (I), $R_1$ is $CF_3$ or chloro, $R_2$ is cyano and $R_3$ is H, methyl or fluoro.

In a subclass of the above embodiments of compounds of formula (I), $R_4$ is $C_{1-7}$ alkyl, $C_{2-7}$ alkenyl, $C_{3-7}$ cycloalkyl or $C_{3-7}$ cycloalkyl $C_{1-7}$ alkyl, in particular $C_{1-7}$ alkyl, and especially methyl or ethyl.

In a subclass of the above embodiments of compounds of formula (I), $R_5$ and $R_5'$ are, independently, H or $C_{1-7}$ alkyl, and $R_6$ and $R_6'$ are, independently, H or OH. In another subclass of the above embodiments of compounds of formula (I), $R_5$ and $R_5'$ are, independently, H or methyl, and $R_6$ and $R_6'$ are, independently, H or OH. In still another subclass of the above embodiments of compounds of formula (I), $R_5$ and $R_5'$ are methyl, and $R_6$ and $R_6'$ are, independently, H or OH. In one particular subclass of the above class, $R_5$ and $R_5'$ are attached to a same carbon atom of the ring A.

In a subclass of the above embodiments of compounds of formula (I), $R_7$ is H, halogen, $C_{1-7}$ alkyl, $C_{1-7}$ alkoxy, hydroxy $C_{1-7}$ alkyl or $C_{1-7}$ alkoxy $C_{1-7}$ alkyl.

According to one particular embodiment, $Z_1$ and $Z_2$ are C, $R_1$ is $CF_3$ or chloro, $R_2$ is cyano, $R_3$ is H, methyl or fluoro, $R_4$ is methyl or ethyl, A is a ring of formula (1), (2), (4), (5), (6), (7), (8), (9) or (14), $R_5$ and $R_5'$ are, independently, H or methyl, and $R_6$ and $R_6'$ are H, B is a ring of formula (1'), (2'), (3'), (4'), (5'), (8'), (11'), (13'), (18') or (22') or a tautomer thereof.

The present invention provides further a method for the treatment or prevention of androgen receptor (AR) dependent conditions, comprising administering to a subject in need thereof a therapeutically effective amount of a compound of formula (I). For example, the AR dependent condition to be treated or prevented is cancer such as prostate cancer, benign prostatic hyperplasia, androgenic alopecia or acne. According to one embodiment, the AR dependent condition to be treated or prevented is castration-resistant prostate cancer (CRPC).

The present invention also provides a pharmaceutical composition comprising a compound of formula (I) together with a pharmaceutically acceptable carrier.

DETAILED DESCRIPTION OF THE INVENTION

The compounds of the invention can be prepared by a variety of synthetic routes analogously to the methods known in the literature using suitable starting materials. The compounds according to formula (I) can be prepared e.g. analogously or according to the following reaction Schemes.

Optically active enantiomers or diastereomers of compounds of formula (I) can be prepared e.g. by resolution of the racemic end product by known methods or by using suitable optically active starting materials. Similarly, racemic compounds of formula (I) can be prepared by using racemic starting materials. Resolution of racemic compounds of formula (I) or a racemic starting material thereof can be carried out, for example, by converting the racemic compound into its diastereomeric salt mixture by reaction with an optically active acid and subsequent separation of the diastereomers by crystallization. Representative examples of said optically active acids include, but are not limited to, D-tartaric acid and dibenzoyl-D-tartaric acid. Alternatively, preparative chiral chromatography may be used for resolution of the racemic mixture.

Some compounds included in the formula (I) can be obtained by converting the functional groups of the other compounds of formula (I) obtained in accordance with the following Schemes, by well known reaction steps such as oxidation, reduction, hydrolysis, acylation, alkylation, amidation, amination, sulfonation and others. It should be noted that any appropriate leaving groups, e.g. N-protecting groups, such as a t-butoxycarbonyl (t-BOC) group or a phenylsulfonyl group, can be used in well known manner during the syntheses in order to improve the selectivity of the reaction steps. Any protected functionality can be subsequently deprotected in a manner known in the art.

For example, compounds of formula (I) can be prepared according to the reaction Scheme 1, wherein $R_1$ to $R_8$, A, B, $Z_1$ and $Z_2$ are as defined above, $X_1$ is a halogen, suitably fluoro or iodo, and $X_2$ is a halogen, suitably iodo. In the method of Scheme 1, the amine compound [1] is coupled with the halide [2] in the presence of DIPEA or $Cs_2CO_3$ in a suitable solvent such as DMSO or DMF at elevated temperature to obtain amine [3]. This compound can be reacted with halide [4] in the presence of a strong base, such as sodium hydride, sodium hexamethyldisilazide or t-BuONa, in a suitable solvent such as DMF to obtain the compound of formula (I).

SCHEME 1

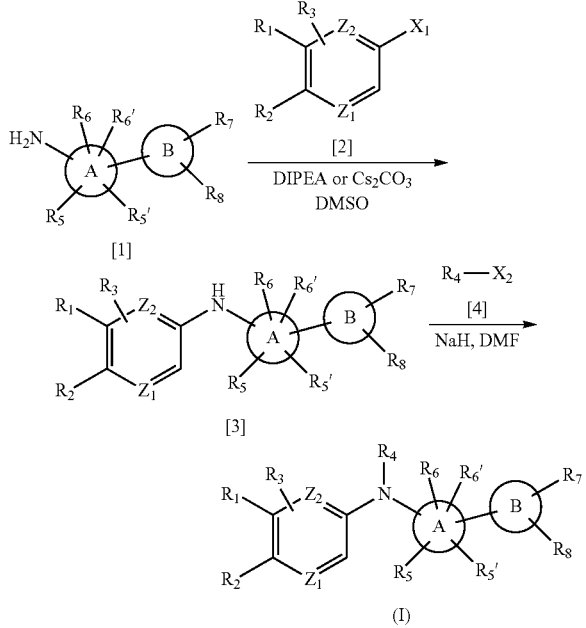

Alternatively, in the first step of the above Scheme 1 compound [1'] can be used instead of compound [1] such as to obtain directly a compound of formula (I).

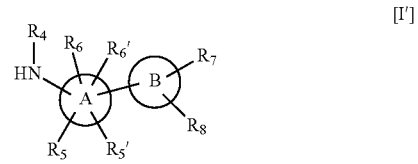

[1']

Compound [3] of Scheme 1 can also be prepared according to the Scheme 2, wherein $R_1$ to $R_8$, A, B, $Z_1$ and $Z_2$ are as defined above.

SCHEME 2

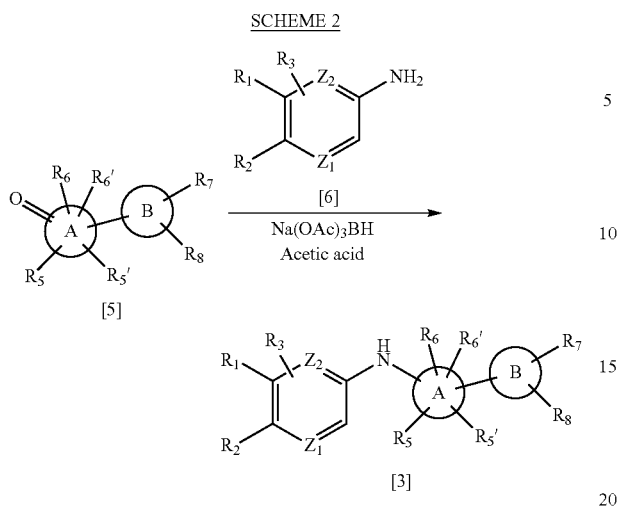

Compound [1] of Scheme 1 can be prepared according to the Scheme 3, wherein $R_5$ to $R_8$, A and B are as defined above, by reacting compound [5] with hydroxylamine hydrochloride in suitable solvent such as pyridine, followed by reduction of the oxime group to amine group by hydrogenation or by using a reducing agent such as zinc or $LiAlH_4$.

SCHEME 3

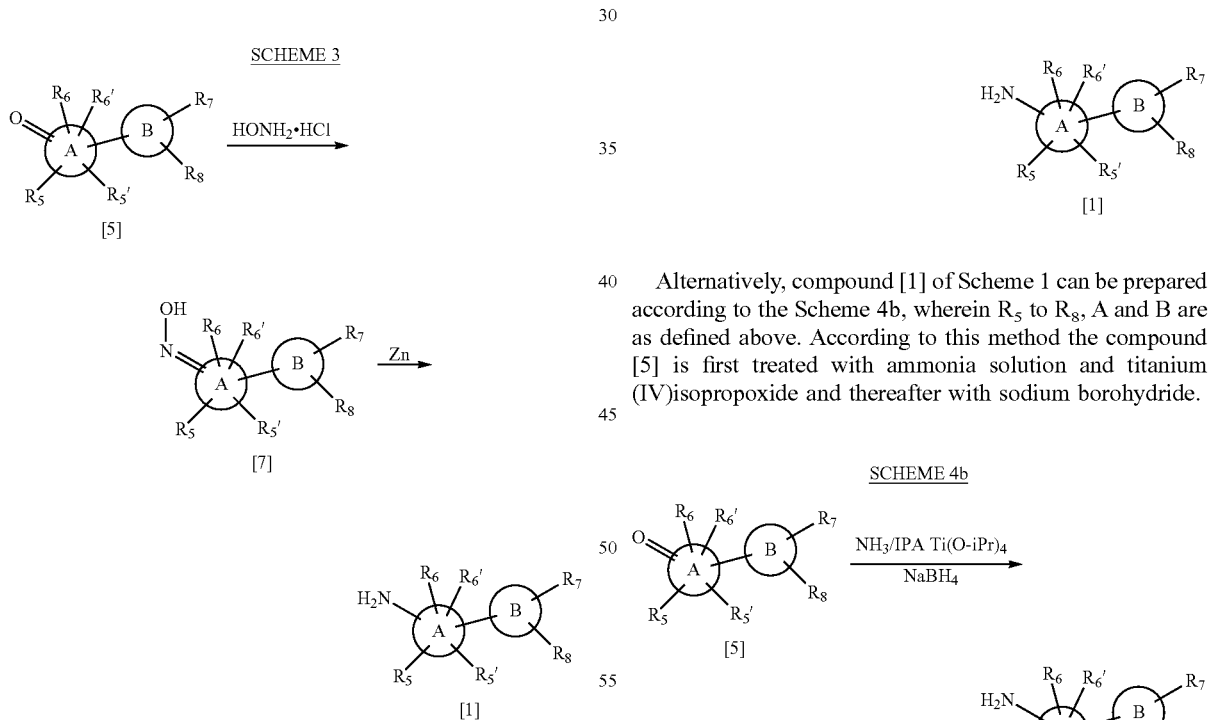

Alternatively, compound [1] of Scheme 1 can be prepared according to the Scheme 4, wherein $R_5$ to $R_8$, A and B are as defined above. Cerium (III) chloride in conjunction with sodium borohydride in suitable solvent such as methanol can be used to reduce compound [5] to corresponding alcohol [8] which is then reacted with diphenylphosphoryl azide in the presence of DBU to yield azide derivative [9]. The azide group can be reduced to amine group using triphenylphosphine in a suitable solvent such as methanol.

SCHEME 4

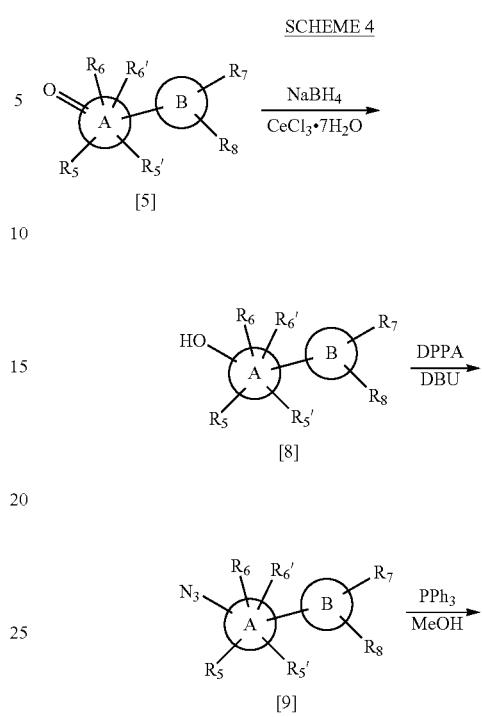

Alternatively, compound [1] of Scheme 1 can be prepared according to the Scheme 4b, wherein $R_5$ to $R_8$, A and B are as defined above. According to this method the compound [5] is first treated with ammonia solution and titanium (IV)isopropoxide and thereafter with sodium borohydride.

SCHEME 4b

Compounds of formula (I) wherein A is a non-aromatic 5-6 membered heterocyclic ring attached to the carbon atom of the B-ring via the ring atom N can be suitably prepared according to Scheme 5, wherein $R_1$ to $R_8$, A, B, $Z_1$ and $Z_2$ are as defined above, and $X_3$ is a halogen, suitably bromo.

SCHEME 5

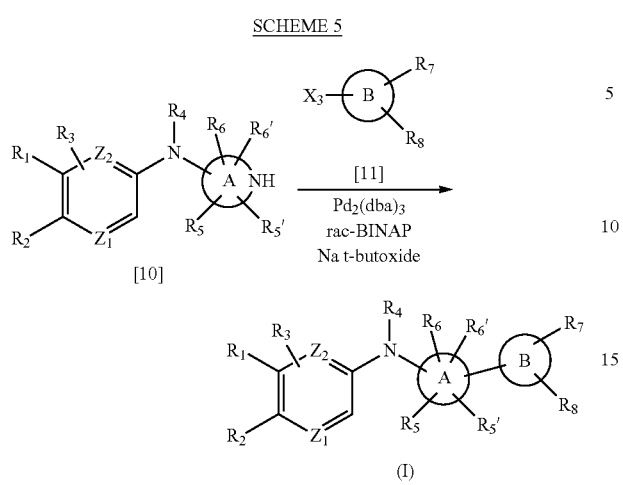

Compounds of formula (I) can also be prepared according to Scheme 6, wherein $R_1$ to $R_8$, A, B, $Z_1$ and $Z_2$ are as defined above, using Suzuki reaction in the presence of palladium catalyst.

SCHEME 6

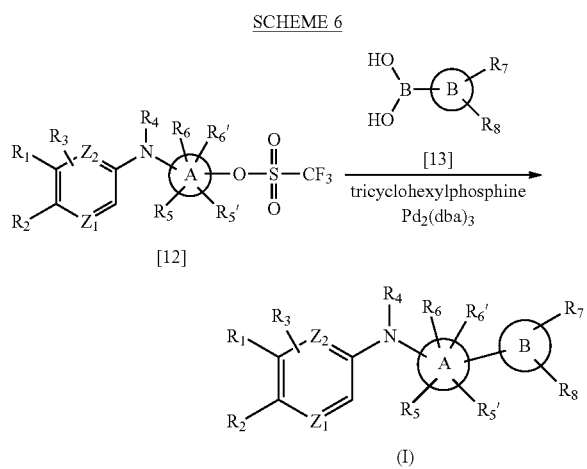

Compounds of formula (I) wherein A is a 3-7 membered unsaturated carbocyclic ring can also be suitably prepared using the method of Scheme 7, wherein $R_1$ to $R_8$, B, $Z_1$ and $Z_2$ are as defined above, and $X_4$ is a halogen, suitably bromo or iodo.

SCHEME 7

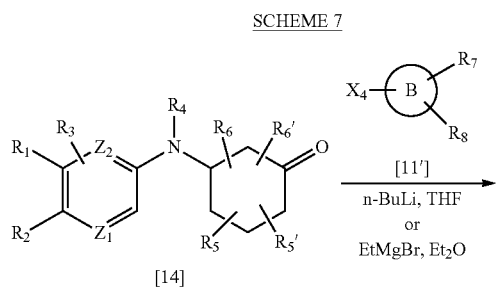

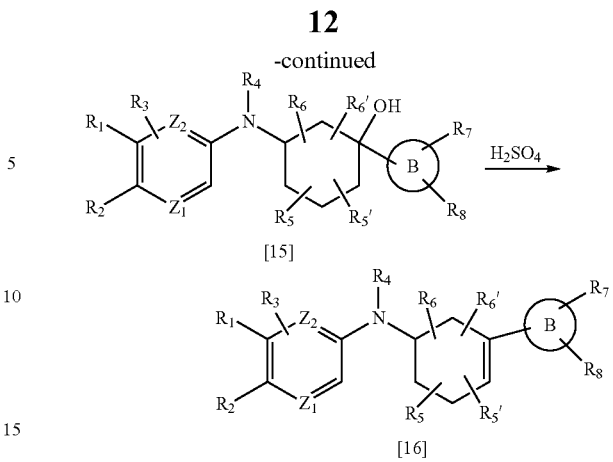

Starting materials of the above Schemes are commercially available or can be prepared according to known methods.

Pharmaceutically acceptable salts are well known in the field of pharmaceuticals. Non-limiting examples of suitable salts include metal salts, ammonium salts, salts with an organic base, salts with an inorganic acid, salts with organic acid, and salts with basic or acidic amino acid. Non-limiting examples of metal salts include alkali metal salts such as sodium salt and potassium salt; alkaline earth metal salts such as calcium salt, and magnesium salt. Non-limiting examples of salts with inorganic or organic acids include chlorides, bromides, sulfates, nitrates, phosphates, sulfonates, methane sulfonates, formates, tartrates, maleates, citrates, benzoates, salicylates, ascorbates, acetates, oxalates, fumarates, hemifumarates, and succinates. Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, propyl, isopropyl, butyl, isobutyl, sec-butyl, tert-butyl esters. Phosphate esters and carbonate esters, are also within the scope of the invention.

The terms employed herein have the following meanings:

The term "halo" or "halogen", as employed herein as such or as part of another group, refers to chlorine, bromine, fluorine or iodine.

The term "$C_{1-7}$ alkyl", as employed herein as such or as part of another group, refers to a straight or branched chain saturated hydrocarbon group having 1, 2, 3, 4, 5, 6 or 7 carbon atom(s). Representative examples of $C_{1-7}$ alkyl include, but are not limited to, methyl, ethyl, n-propyl, iso-propyl, n-butyl, iso-butyl, sec-butyl, tert-butyl, n-pentyl, iso-pentyl and n-hexyl. One preferred embodiment of "$C_{1-7}$ alkyl" is $C_{1-3}$ alkyl. The term "$C_{1-3}$ alkyl" refers to a preferred embodiment of "$C_{1-7}$ alkyl" having 1, 2 or 3 carbon atoms.

The term "$C_{2-7}$ alkenyl", as employed herein as such or as part of another group, refers to an aliphatic hydrocarbon group having 2, 3, 4, 5, 6 or 7 carbon atoms and containing one or several double bonds. Representative examples include, but are not limited to, ethenyl, propenyl and cyclohexenyl.

The term "$C_{3-7}$ cycloalkyl", as employed herein as such or as part of another group, refers to a saturated cyclic hydrocarbon group containing 3, 4, 5, 6 or 7 carbon atoms. Representative examples of cycloalkyl include, but are not limited to, cyclopropyl, cyclobutyl, cyclopentyl and cyclohexyl.

The term "$C_{3-7}$ cycloalkyl $C_{1-7}$ alkyl", as employed herein refers to a $C_{3-7}$ cycloalkyl group, as defined herein, appended to the parent molecular moiety through a $C_{1-7}$ alkyl group, as defined herein.

The term "hydroxy", as employed herein as such or as part of another group, refers to an —OH group.

The term "cyano", as employed herein as such or as part of another group, refers to a —CN group.

The term "carboxy", as employed herein as such or as part of another group, refers to —COOH group.

The term "carbonyl", as employed herein as such or as part of another group, refers to a carbon atom double-bonded to an oxygen atom (C=O).

The term "oxo", as employed herein as such or as part of another group, refers to oxygen atom linked to another atom by a double bond (=O).

The term "$C_{1-7}$ alkoxy", as employed herein as such or as part of another group, refers to $C_{1-7}$ alkyl, as defined herein, appended to the parent molecular moiety through an oxygen atom. Representative examples of $C_{1-7}$ alkoxy include, but are not limited to methoxy, ethoxy, propoxy, butoxy, isobutoxy, sec-butoxy and tert-butoxy.

The term "hydroxy $C_{1-7}$ alkyl", as employed herein, refers to at least one hydroxy group, as defined herein, appended to the parent molecular moiety through a $C_{1-7}$ alkyl group, as defined herein. Representative examples of hydroxy $C_{1-7}$ alkyl include, but are not limited to, hydroxymethyl, 2,2-dihydroxyethyl, 1-hydroxyethyl, 3-hydroxypropyl, 1-hydroxypropyl, 1-methyl-1-hydroxyethyl and 1-methyl-1-hydroxypropyl.

The term "halo $C_{1-7}$ alkyl", as employed herein, refers to at least one halogen, as defined herein, appended to the parent molecular moiety through a $C_{1-7}$ alkyl group, as defined herein. Representative examples of halo $C_{1-7}$ alkyl include, but are not limited to, fluoromethyl, difluoromethyl, trifluoromethyl, 2-chloroethyl and 3-bromopropyl.

The term "cyano $C_{1-7}$ alkyl", as employed herein, refers to a cyano group, as defined herein, appended to the parent molecular moiety through a $C_{1-7}$ alkyl group, as defined herein. Representative examples of cyano $C_{1-7}$ alkyl include, but are not limited to, cyanomethyl, 1-cyanoethyl, 1-cyanopropyl and 2-cyanopropyl.

The term "halo $C_{1-7}$ alkoxy", as employed herein, refers to at least one halogen, as defined herein, appended to the parent molecular moiety through a $C_{1-7}$ alkoxy group, as defined herein.

The term "phenyl $C_{1-7}$ alkyl", as employed herein, refers to at least one phenyl group appended to the parent molecular moiety through a $C_{1-7}$ alkyl group, as defined herein.

The term "$C_{1-7}$ alkyl carbonyl", as employed herein as such or as part of another group, refers to a $C_{1-7}$ alkyl group, as defined herein, appended to the parent molecular moiety through a carbonyl group, as defined herein.

The term "$C_{1-7}$ alkoxy $C_{1-7}$ alkyl", as employed herein as such or as part of another group, refers to at least one $C_{1-7}$ alkoxy group, as defined herein, appended to the parent molecular moiety through an $C_{1-7}$ alkyl group, as defined herein.

The term "hydroxy $C_{1-7}$ alkoxy", as employed herein such or as part of another group, refers to at least one hydroxy group, as defined herein, appended to the parent molecular moiety through an $C_{1-7}$ alkoxy group, as defined herein.

The term "hydroxy $C_{1-7}$ alkoxy $C_{1-7}$ alkyl", as employed herein, refers to a hydroxy $C_{1-7}$ alkoxy group, as defined herein, appended to the parent molecular moiety through an $C_{1-7}$ alkyl group, as defined herein.

The term "4-6 membered heterocyclic ring" as employed herein, refers to a saturated, partially saturated or aromatic ring with 4, 5 or 6 ring atoms, of which 1-4 atoms are heteroatoms selected from a group consisting of N, O and S. Representative examples of a 4-6 membered heterocyclic ring include, but are not limited to, oxetanyl, pyrazolyl, 1,2,4-triazol-1-yl, 1,2,3-triazol-1-yl, pyrimidinyl, pyridinyl, tetrazolyl, piperazinyl, furanyl, morpholinyl, piperidinyl, pyrrolidinyl, thiazolyl, isoxazolyl, pyrazinyl tetrahydropyranyl, 1,2,4-oxadiazolyl, oxazolyl, imidazolyl, indolyl and 4,5-dihydroimidazolyl rings.

The term "5-6 membered heterocyclic ring" as employed herein, refers to a saturated, partially saturated or aromatic ring with 5 or 6 ring atoms, of which 1-4 atoms are heteroatoms selected from a group consisting of N, O and S. Representative examples of a 5-6 membered heterocyclic ring include, but are not limited to, pyrazolyl, 1,2,4-triazol-1-yl, 1,2,3-triazol-1-yl, pyrimidinyl, pyridinyl, tetrazolyl, piperazinyl, furanyl, morpholinyl, piperidinyl, pyrrolidinyl, thiazolyl, isoxazolyl, pyrazinyl tetrahydropyranyl, 1,2,4-oxadiazolyl, oxazolyl, imidazolyl, indolyl and 4,5-dihydroimidazolyl rings.

The term "7-12 membered heterocyclic ring" as employed herein, refers to a monocyclic or bicyclic saturated, partially saturated or aromatic ring with 7 to 12 ring atoms, of which 1-5 atoms are heteroatoms selected from a group consisting of N, O and S. Representative examples of a 7-12 membered heterocyclic ring include, but are not limited to, indazolyl, pyrazolo[1,5-a]pyrimidinyl, benzo[d]imidazolyl, imidazo[4,5-b]pyridinyl, 4,5,6,7-tetrahydrobenzo[d]imidazolyl and benzofuranyl rings.

The term "3-7 membered carbocyclic ring" as employed herein, refers to a saturated, partially saturated or aromatic ring with 3 to 7 ring atoms consisting of carbon atoms only. Representative examples of a 3-7 membered carbocyclic ring include, but are not limited to, phenyl, cyclohexyl, cyclohexenyl, cyclopentyl, cyclopentenyl and cyclobutyl rings.

The term "non-aromatic 3-7 membered carbocyclic ring" as employed herein, refers to a saturated or partially saturated ring with 3 to 7 ring atoms consisting of carbon atoms only. Representative examples of a non-aromatic 3-7 membered carbocyclic ring include, but are not limited to, cyclohexyl, cyclohexenyl, cyclopentyl, cyclopentenyl and cyclobutyl rings.

The term "non-aromatic 5-6 membered heterocyclic ring" as employed herein, refers to a saturated or partially saturated ring with 5 or 6 ring atoms, of which 1-3 atoms are heteroatoms each independently selected from N, O and S, and wherein the Hückel rule is not satisfied by the ring system. Representative examples of a non-aromatic 5-6 membered heterocyclic ring include, but are not limited to, pyrrolidinyl, piperidinyl, dihydropyranyl, dihydrothiopyranyl and tetrahydropyridazinyl rings.

The term "aromatic 5-6 membered heterocyclic ring" as employed herein, refers to a aromatic ring with 5 or 6 ring atoms, of which 1-4 atoms are heteroatoms each independently selected from N, O and S, and wherein the Hückel rule is satisfied by the ring system. Examples of aromatic 5-6 membered heterocyclic rings include imidazolyl, 1,2,4-triazolyl, 1,2,3-triazolyl, pyridinyl, tetrazolyl, pyrimidinyl, 1,3,4-oxadiazolyl, pyrazolyl, benzo[d]imidazolyl, pyrazinyl, 1,3,4-thiadiazolyl, oxazolyl, thiazolyl or isoxazolyl rings. Preferred aromatic 5-6 membered heterocyclic rings are imidazolyl, pyridinyl, 1,2,4-triazolyl, 1,2,3-triazolyl, thiazolyl and oxazolyl rings.

The term "substituted" as used herein in connection with various residues refers to halogen substituents, such as fluorine, chlorine, bromine, iodine, or $C_{1-7}$ alkyl, $C_{3-7}$ cycloalkyl, hydroxy, amino, nitro, cyano, thiol, methylsulfonyl, $C_{1-7}$ alkoxy, halo $C_{1-7}$ alkyl, hydroxy $C_{1-7}$ alkyl or amino $C_{1-7}$ alkyl substituents. Preferred are halogen, $C_{1-7}$ alkyl, hydroxy, amino, halo $C_{1-7}$ alkyl, $C_{1-7}$ alkoxy and methylsulfonyl substituents. In one group of preferred substituents are one or two $C_{1-7}$ alkyl substituents, particularly one or two $C_{1-3}$ alkyl substituents, particularly methyl and ethyl substituents.

The "substituted" groups may contain 1 to 3, preferably 1 or 2, of the above mentioned substituents.

The definition of formula (I) above is inclusive of all the possible isotopes and isomers, such as stereoisomers, of the compounds, including geometric isomers, for example Z and E isomers (cis and trans isomers), and optical isomers, e.g. diastereomers and enantiomers, and prodrug esters, e.g. phosphate esters and carbonate esters.

It will be appreciated by those skilled in the art that the present compounds may contain at least one chiral center. Accordingly, the compounds may exist in optically active or racemic forms. It is to be understood that the formula (I) includes any racemic or optically active form, or mixtures thereof. In one embodiment, the compounds are the pure (R)-isomers. In another embodiment, the compounds are the pure (S)-isomers. In another embodiment, the compounds are a mixture of the (R) and the (S) isomers. In another embodiment, the compounds are a racemic mixture comprising an equal amount of the (R) and the (S) isomers. The compounds may contain two chiral centers. In such case, according to one embodiment, the compounds are a mixture of diasteromers. According to another embodiment, the compounds of the invention are a mixture of enantiomers. According to still another embodiment, the compounds are pure enantiomers. The individual isomers may be obtained using the corresponding isomeric forms of the starting material or they may be separated after the preparation of the end compound according to conventional separation methods. For the separation of optical isomers, e.g. enantiomers or diastereomers, from the mixture thereof the conventional resolution methods, e.g. fractional crystallisation, may be used.

The present compounds may also exist as tautomers or equilibrium mixtures thereof wherein a proton of a compound shifts from one atom to another. Examples of tautomerism include, but are not limited to, amido-imido, keto-enol, phenol-keto, oxime-nitroso, nitro-aci, imine-enamine, annular tautomerism of heterocyclic rings, and the like. Tautomeric forms are intended to be encompassed by compounds of formula (I), even though only one tautomeric form may be depicted.

Examples of preferred compounds of formula (I) include
4-(Ethyl(3-(2-methyl-2H-tetrazol-5-yl)cyclohexyl)amino)-2-trifluoromethyl)benzonitrile;
4-(Ethyl(3-(2-methyl-2H-tetrazol-5-yl)cyclohexyl)amino)-2-(trifluoromethyl)benzonitrile cis-diastereomer;
4-((3-(1H-imidazol-1-yl)-6,6-dimethylcyclohex-2-en-1-yl)(ethyl)amino)-2-(trifluoromethyl)benzonitrile;
4-((3-(1H-imidazol-1-yl)-6,6-dimethylcyclohex-2-en-1-yl)(ethyl)amino)-2-(trifluoromethyl)benzonitrile enantiomer 1;
4-((3-(1H-imidazol-1-yl)-6,6-dimethylcyclohex-2-en-1-yl)(ethyl)amino)-2-(trifluoromethyl)benzonitrile enantiomer 2;
4-((3-(1H-imidazol-1-yl)cyclohexyl)(ethyl)amino)-2-chloro-3-methylbenzonitrile;
4-((3-(1H-imidazol-1-yl)cyclohexyl)(ethyl)amino)-2-chloro-3-methylbenzonitrile cis-diastereomer;
4-((3-(1H-imidazol-1-yl)cyclohexyl)(ethyl)amino)-2-chloro-3-methylbenzonitrile cis-enantiomer 1;
4-((3-(1,3,4-Oxadiazol-2-yl)cyclohexyl)(ethyl)amino)-2-(trifluoromethyl)benzonitrile;
4-((3-(1,3,4-Oxadiazol-2-yl)cyclohexyl)(ethyl)amino)-2-(trifluoromethyl)benzonitrile cis-diastereomer;
4-((3-(1H-imidazol-1-yl)-6,6-dimethylcyclohex-2-enyl)(ethyl)amino)-2-chlorobenzonitrile;
4-((3-(1H-imidazol-1-yl)-6,6-dimethylcyclohex-2-enyl)(ethyl)amino)-2-(difluoromethyl)benzonitrile;
4-((3-(1H-imidazol-1-yl)-6,6-dimethylcyclohex-2-enyl)(ethyl)amino)-2-(difluoromethyl)benzonitrile enantiomer 1;
4-((5-(1H-Imidazol-1-yl)-2,2-dimethylcyclohexyl)(ethyl)amino)-2-(trifluoromethyl)benzonitrile;
4-((5-(1H-Imidazol-1-yl)-2,2-dimethylcyclohexyl)(ethyl)amino)-2-(trifluoromethyl)benzonitrile cis-diastereomer;
4-((5-(1H-Imidazol-1-yl)-2,2-dimethylcyclohexyl)(ethyl)amino)-2-(trifluoromethyl)benzonitrile cis-enantiomer 1;
4-((-3-(1H-Pyrazol-1-yl)cyclohexyl)(ethyl)amino)-2-(trifluoromethyl)benzonitrile;
4-((-3-(1H-Pyrazol-1-yl)cyclohexyl)(ethyl)amino)-2-(trifluoromethyl)benzonitrile cis-diastereomer;
4-(Ethyl(3-(1-isopropyl-1H-imidazol-5-yl)cyclopent-3-enyl)amino)-2-(trifluoromethyl)benzonitrile;
4-(Ethyl(3-(1-isopropyl-1H-imidazol-5-yl)cyclopent-3-enyl)amino)-2-(trifluoromethyl)benzonitrile enantiomer 2;
4-((3-(1-Cyclopropyl-1H-imidazol-5-yl)cyclopent-3-enyl)(ethyl)amino)-2-(trifluoromethyl)benzonitrile;
4-(Ethyl(3-(pyridin-4-yl)cyclohexyl)amino)-2-(trifluoromethyl)benzonitrile;
4-(Ethyl(3-(pyridin-4-yl)cyclohexyl)amino)-2-(trifluoromethyl)benzonitrile cis-diastereomer;
4-((3-(1H-imidazol-1-yl)cyclohex-2-en-1-yl)(ethyl)amino)-2-(trifluoromethyl)benzonitrile;
4-((3-(1H-imidazol-1-yl)cyclohexyl)(ethyl)amino)-2-(trifluoromethyl)benzonitrile;
4-((3-(1H-imidazol-1-yl)cyclohexyl)(ethyl)amino)-2-(trifluoromethyl)benzonitrile cis-diastereomer;
4-((3-(1H-imidazol-1-yl)cyclohexyl)(ethyl)amino)-2-(trifluoromethyl)benzonitrile cis-enantiomer 2;
2-Chloro-4-(ethyl(3-(pyridin-3-yl)cyclohexyl)amino)benzonitrile;
2-Chloro-4-(ethyl(3-(pyridin-3-yl)cyclohexyl)amino)benzonitrile cis-diastereomer;
4-(Ethyl(3-(pyridin-4-yl)cyclohex-3-en-1-yl)amino)-2-(trifluoromethyl)benzonitrile;
2-Chloro-4-(ethyl(3-(5-methoxypyridin-3-yl)cyclohexyl)amino)benzonitrile;
2-Chloro-4-(ethyl(3-(5-methoxypyridin-3-yl)cyclohexyl)amino)benzonitrile cis-diastereomer;
4-(Ethyl(3-(3-methoxypyridin-4-yl)cyclohex-3-en-1-yl)amino)-2-(trifluoromethyl)benzonitrile;
4-((-3-(1H-imidazol-1-yl)cyclopentyl)(ethyl)amino)-2-(trifluoromethyl)benzonitrile;
4-((-3-(1H-imidazol-1-yl)cyclopentyl)(ethyl)amino)-2-(trifluoromethyl)benzonitrile trans-diastereomer;
4-((-3-(1H-imidazol-1-yl)cyclopentyl)(ethyl)amino)-2-(trifluoromethyl)benzonitrile trans-enantiomer 1;
4-((3-(1H-imidazol-1-yl)cyclohexyl)(ethyl)amino)-2-chlorobenzonitrile;
4-((3-(1H-imidazol-1-yl)cyclohexyl)(ethyl)amino)-2-chlorobenzonitrile cis-diastereomer;

4-(Ethyl(3-(1-propyl-1H-imidazol-5-yl)cyclopent-3-en-1-yl)amino)-2-(trifluoromethyl)benzonitrile;
4-((4-(1H-imidazol-1-yl)spiro[2.5]oct-4-en-6-yl)(ethyl)amino)-2-(trifluoromethyl)benzonitrile;
4-{[3-(1H-Imidazol-1-yl)-6,6-dimethylcyclohex-2-enyl](methyl)amino}-2-(trifluoromethyl)benzonitrile;
4-{[3-(1H-Imidazol-1-yl)-6,6-dimethylcyclohex-2-enyl](methyl)amino}-2-(trifluoromethyl)benzonitrile enantiomer 1;
4-{[3-(1H-Imidazol-1-yl)-6,6-dimethylcyclohex-2-enyl](methyl)amino}-2-(trifluoromethyl)benzonitrile enantiomer 2;
2-Chloro-4-(ethyl(3-(pyridin-3-yl)cyclohex-3-en-1-yl)amino)-6-fluorobenzonitrile;
(R)-4-(Ethyl(1-(3-fluoropyridin-4-yl)piperidin-3-yl)amino)-2-(trifluoromethyl)benzonitrile;
4-(ethyl(3-(1-ethyl-1H-imidazol-5-yl)cyclohex-3-en-1-yl)amino)-2-(trifluoromethyl)benzonitrile;
4-((3-(1H-1,2,4-triazol-1-yl)cyclohexyl)(ethyl)amino)-2-(trifluoromethyl)-benzonitrile;
4-((3-(1H-1,2,4-triazol-1-yl)cyclohexyl)(ethyl)amino)-2-(trifluoromethyl)-benzonitrile cis-diastereomer;
4-((3-(1H-1,2,4-triazol-1-yl)cyclohex-2-en-1-yl)(ethyl)amino)-2-(trifluoromethyl)benzonitrile;
4-(Ethyl(3-hydroxy-3-(pyridin-3-yl)cyclohexyl)amino)-2-(trifluoromethyl)-benzonitrile;
4-(Ethyl(3-hydroxy-3-(pyridin-3-yl)cyclohexyl)amino)-2-(trifluoromethyl)-benzonitrile diastereomer 2;
4-((3-(1H-1,2,3-triazol-1-yl)cyclohexyl)(ethyl)amino)-2-(trifluoromethyl)-benzonitrile;
4-((3-(1H-1,2,3-triazol-1-yl)cyclohexyl)(ethyl)amino)-2-(trifluoromethyl)-benzonitrile cis-diastereomer;
4-((Cyclopropylmethyl)(3-(1-ethyl-1H-imidazol-5-yl)cyclopent-3-en-1-yl)-amino)-2-(trifluoromethyl)benzonitrile;
2-Chloro-4-(ethyl(3-(1-ethyl-1H-imidazol-5-yl)cyclopent-3-en-1-yl)amino)-benzonitrile;
4-((3-(1H-imidazol-4-yl)-6,6-dimethylcyclohex-3-enyl)(methyl)amino)-2-chlorobenzonitrile;
4-((3-(1H-imidazol-4-yl)-6,6-dimethylcyclohex-3-enyl)(methyl)amino)-2-chlorobenzonitrile enantiomer 1;
4-((3-(1H-imidazol-1-yl)cyclohex-2-enyl)(methyl)amino)-2-(trifluoromethyl)-benzonitrile;
4-((3-(1H-imidazol-1-yl)cyclohex-2-enyl)(methyl)amino)-2-(trifluoromethyl)-benzonitrile enantiomer 1;
4-(-3-(1H-imidazol-1-yl)cyclohexyl)(ethyl)amino)-2,6-difluorobenzonitrile;
4-(-3-(1H-imidazol-1-yl)cyclohexyl)(ethyl)amino)-2,6-difluorobenzonitrile cis-diastereomer;
4-((5-(1H-Imidazol-1-yl)-2,2-dimethylcyclohexyl)(methyl)amino)-2-(trifluoromethyl)benzonitrile;
4-((5-(1H-Imidazol-1-yl)-2,2-dimethylcyclohexyl)(methyl)amino)-2-(trifluoromethyl)benzonitrile cis-diastereomer;
4-((5-(1H-Imidazol-1-yl)-2,2-dimethylcyclohexyl)(methyl)amino)-2-(trifluoromethyl)benzonitrile cis-enantiomer 1;
4-((2,2-dimethyl-3-(pyridin-3-yl)cyclohex-3-en-1-yl)(ethyl)amino)-2-(trifluoromethyl)benzonitrile;
4-((3-(1H-imidazol-4-yl)-2,2-dimethylcyclohex-3-en-1-yl)(ethyl)amino)-2-(trifluoromethyl)benzonitrile;
4-((3-(1H-Imidazol-4-yl)cyclopent-3-en-1-yl)(ethyl)amino)-2-chlorobenzonitrile;
4-((3-(1H-imidazol-4-yl)cyclopent-3-en-1-yl)(ethyl)amino)-2-(trifluoromethyl)benzonitrile;
4-((3-(1H-imidazol-5-yl)cyclopentyl)(ethyl)amino)-2-(trifluoromethyl)benzonitrile;
4-((3-(1-(2-(benzyloxy)ethyl)-1H-imidazol-5-yl)-6,6-dimethylcyclohex-2-en-1-yl)(methyl)amino)-2-(trifluoromethyl)benzonitrile;
4-((3-(1H-imidazol-5-yl)cyclohexyl)(ethyl)amino)-2-(trifluoromethyl)benzonitrile;
4-((3-(1H-imidazol-5-yl)cyclohexyl)(ethyl)amino)-2-(trifluoromethyl)benzonitrile cis-diastereomer;
4-((6,6-Dimethyl-3-(oxazol-5-yl)cyclohex-2-en-1-yl)(methyl)amino)-2-(trifluoromethyl)benzonitrile;
2-Chloro-4-((6,6-dimethyl-3-(oxazol-5-yl)cyclohex-2-en-1-yl)amino)-benzonitrile;
4-(Ethyl(3-(oxazol-5-yl)cyclopent-3-enyl)amino)-2-(trifluoromethyl)benzonitrile enantiomer 1;
4-(Ethyl(3-(oxazol-5-yl)cyclopent-3-enyl)amino)-2-(trifluoromethyl)benzonitrile enantiomer 2;
4-((5-(1H-imidazol-1-yl)-2,2-dimethylcyclohexyl)(methyl)amino)-2-chlorobenzonitrile cis-enantiomer 2;
2-Chloro-4-{[4-hydroxy-3-(1H-imidazol-1-yl)-6,6-dimethylcyclohex-2-enyl]-(methyl)amino}benzonitrile;
2-Chloro-4-{[4-hydroxy-3-(1H-imidazol-1-yl)-6,6-dimethylcyclohex-2-enyl]-(methyl)amino}benzonitrile enantiomer 1 of diastereomer 1;
2-Chloro-4-{[4-hydroxy-3-(1H-imidazol-1-yl)-6,6-dimethylcyclohex-2-enyl]-(methyl)amino}benzonitrile enantiomer 1 of diastereomer 2;
4-((3-(1H-imidazol-1-yl)-6,6-dimethylcyclohex-2-en-1-yl)(methyl)amino)-2-bromobenzonitrile;
4-((3-(1H-imidazol-1-yl)-6,6-dimethylcyclohex-2-en-1-yl)(methyl)amino)-2-bromobenzonitrile enantiomer 1;
4-((3-(1-ethyl-1H-imidazol-5-yl)cyclopent-3-en-1-yl)(2-methoxyethyl)-amino)-2-(trifluoromethyl)benzonitrile;
4-((3-(1H-imidazol-1-yl)-6,6-dimethylcyclohex-2-en-1-yl)(methyl)amino)-2-(difluoromethyl)benzonitrile enantiomer 1;
2-Chloro-4-((6,6-dimethyl-3-(1H-1,2,4-triazol-1-yl)cyclohex-2-en-1-yl)-(ethyl)amino)benzonitrile enantiomer 2;
N-[3-(1H-Imidazol-1-yl)-6,6-dimethylcyclohex-2-enyl]-N,6-dimethyl-5-nitropyridin-2-amine enantiomer 1;
4-(Methyl(3-(thiazol-5-yl)cyclohex-2-en-1-yl)amino)-2-(trifluoromethyl)-benzonitrile enantiomer 1;
Cis-4-((4-hydroxy-3-(1H-imidazol-1-yl)-6,6-dimethylcyclohex-2-enyl)-(methyl)amino)-2-(trifluoromethyl)benzonitrile;
6-{[3-(1H-Imidazol-1-yl)-6,6-dimethylcyclohex-2-enyl](methyl)amino}-2-(trifluoromethyl)nicotinonitrile;
4-{[3-(1H-Imidazol-1-yl)-6,6-dimethylcyclohex-2-enyl](methyl)amino}-2-methoxybenzonitrile;
4-(((1R,4S)-4-hydroxy-3-(1H-imidazol-1-yl)-6,6-dimethylcyclohex-2-en-1-yl)(methyl)-amino)-2-(trifluoromethyl)benzonitrile;
4-((3-(1H-imidazol-1-yl)-2,2-dimethylcyclopent-3-en-1-yl)(ethyl)amino)-2-(trifluoromethyl)benzonitrile;
4-(Ethyl(4-(hydroxymethyl)-3-(1H-imidazol-1-yl)-2,2-dimethylcyclopent-3-en-1-yl)amino)-2-(trifluoromethyl)benzonitrile enantiomer 1;
4-{[3-(1H-Imidazol-4-yl)-6,6-dimethylcyclohex-3-enyl](methyl)amino}-2-(trifluoromethyl)benzonitrile diastereomer 1;
4-{[2-Hydroxy-3-(1H-imidazol-4-yl)-6,6-dimethylcyclohex-3-enyl](methyl)-amino}-2-(trifluoromethyl)benzonitrile;
and tautomers and pharmaceutically acceptable salts thereof.

Compounds of the invention may be administered to a patient in therapeutically effective amounts which range usually from about 0.1 to about 1000 mg per day depending on the age, weight, ethnic group, condition of the patient, condition to be treated, administration route and the active ingredient used. The compounds of the invention can be formulated into dosage forms using the principles known in the art. The compound can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. Suitable carriers, solvents, gel forming ingredients, dispersion forming ingredients, antioxidants, colours, sweeteners, wetting compounds and other ingredients normally used in this field of technology may also be used. The compositions containing the active compound can be given enterally or parenterally, the oral route being the preferred way. The contents of the active compound in the composition is from about 0.5 to 100%, preferably from about 0.5 to about 20%, per weight of the total composition.

The compounds of the invention can be given to the subject as the sole active ingredient or in combination with one of more other active ingredients for treatment of a particular disease, for example cancer.

The present invention will be explained in more detail by the following experiments and examples. The experiments and examples are meant only for illustrating purposes and do not limit the scope of the invention defined in claims.

EXPERIMENTS

AR Antagonism

Antagonism of test compounds for AR was measured by reporter gene assay in human embryonic kidney (HEK293) cells stably transfected with an expression vector encoding full-length human AR and androgen responsive luciferase reporter gene construct (hAR/HEK293 cells). To determine antagonism for hAR, the cells were treated simultaneously with increasing concentrations of the test compound and submaximal concentration of testosterone (usually 0.45 nM). The final DMSO concentration was 1%. All test compounds were studied in triplicates. The cells were incubated for 24 before measurement of luciferase activity using Luciferase Assay System (Promega Corporation).

The results of the AR antagonism assay are shown in Table 1.

TABLE 1

| AR antagonism | |
|---|---|
| Compound of Example No. | AR antagonism $IC_{50}$ (nM) |
| Ex. 11 cis of 2,5-isomer | 26 |
| Ex. 13 | 60 |
| Ex. 19 cis-diastereomer | 65 |
| Ex. 21 | 19 |
| Ex. 31 enantiomer 1 | 73 |
| Ex. 46 cis-enantiomer 2 | 40 |
| Ex. 48 cis-diastereomer | 24 |
| Ex. 51 enantiomer 2 | 17 |
| Ex. 53 | 57 |
| Ex. 61 | 35 |
| Ex. 63 | 34 |
| Ex. 72 cis-enantiomer 2 | 27 |
| Ex. 76 cis-diastereomer | 1 |
| Ex. 77 | 40 |
| Ex. 83 cis-diastereomer | 16 |
| Ex. 84 3,4-isomer | 50 |
| Ex. 86 trans-enantiomer 1 | 73 |
| Ex. 91 cis-diastereomer | 64 |
| Ex. 103 | 58 |
| Ex. 107 | 51 |
| Ex. 130 racemate | 65 |

TABLE 1-continued

| AR antagonism | |
|---|---|
| Compound of Example No. | AR antagonism $IC_{50}$ (nM) |
| Ex. 132 | 7 |
| Ex. 160 | 27 |
| Ex. 203 enantiomer 1 | 17. |
| Ex. 208 1,5-isomer | 34 |
| Ex. 209 cis-diastereomer | 56 |
| Ex. 210 | 23 |
| Ex. 216 diastereomer 2 | 28 |
| Ex. 223 | 79 |
| Ex. 226 racemate | 29 |
| Ex. 227 racemate | 57 |
| Ex. 232 enantiomer 1 | 33 |
| Ex. 233 enantiomer 1 | 59 |
| Ex. 233 enantiomer 2 | 29 |
| Ex. 236 | 124 |
| Ex. 240(b) | 52 |
| Ex. 250 | 205 |
| Ex. 252 | 141 |
| Ex. 253(b) | 140 |
| Ex. 262 | 89 |
| Ex. 270 enantiomer 1 | 56 |
| Ex. 275 | 63 |

17,20 Lyase (CYP17) Inhibition

The ability of the test compounds to inhibit 17,20 lyase catalysed conversion of 17α-hydroxypregnenolone to dehydroepiandrosterone and acetic acid was measured by acetic acid release assay (AARA) on human H295R adrenocortical carcinoma cell line (Grigoryev, D. N. et al., Analytical Biochemistry 1999; 267:319-330). The cell line has been shown to express all the key steroidogenic enzymes. To determine the half maximal inhibitory concentration ($IC_{50}$) of the test compounds on 17,20 lyase inhibition, the cells were treated overnight (16-19 h) with increasing concentrations of the test compounds in the presence of 17α-[21-$^3$H] hydroxypregnenolone (American Radiolabelled Chemicals). The final DMSO concentration was 1%. Cell culture medium was extracted with dextran-coated charcoal suspension (Isomaa, V. et al., Endocrinology 1982; 111(3):833-843). $^3$H-acetic acid was determined by mixing 100 μl of supernatant fraction in 200 μl of scintillation fluid (OptiPhase SuperMix, Perkin Elmer). Radioactivity was measured using a Microbeta scintillation counter (1450 MicroBeta Trilux, Wallac). All the test compounds were studied in quadruplicates.

TABLE 2

| 17,20 Lyase (CYP17) inhibition | |
|---|---|
| Compound of Example No. | CYP17 inhibition $IC_{50}$ (nM) |
| Ex. 2 enantiomer 1 | 27 |
| Ex. 6 enantiomer 1 | 74 |
| Ex. 12 cis-diastereomer | 18 |
| Ex. 13 | 92 |
| Ex. 21 | 76 |
| Ex. 31 enantiomer 1 | 23 |
| Ex. 46 cis-enantiomer 2 | 49 |
| Ex. 47 cis-enantiomer 3 | 18 |
| Ex. 51 enantiomer 2 | 166 |
| Ex. 53 | 19 |
| Ex. 61 | 108 |
| Ex. 63 | 70 |
| Ex. 84 3,4-isomer | 96 |
| Ex. 86 trans-enantiomer 1 | 27 |
| Ex. 91 cis-diastereomer | 36 |
| Ex. 97 | 66 |
| Ex. 100 | 36 |
| Ex. 103 | 29 |

TABLE 2-continued 17,20 Lyase (CYP17) inhibition

| Compound of Example No. | CYP17 inhibition IC$_{50}$ (nM) |
|---|---|
| Ex. 107 | 33 |
| Ex. 130 racemate | 14 |
| Ex. 133 | 7 |
| Ex. 150 | 17 |
| Ex. 160 | 111 |
| Ex. 203 enantiomer 1 | 16 |
| Ex. 208 1,5-isomer | 137 |
| Ex. 209 cis-diastereomer | 154 |
| Ex. 219 | 105 |
| Ex. 220 | 10 |
| Ex. 224 cis-diasteromer | 59 |
| Ex. 226 racemate | 43 |
| Ex. 227 racemate | 19 |
| Ex. 233 enantiomer 1 | 66 |
| Ex. 236 | 247 |
| Ex. 240(b) | 33 |
| Ex. 244 diastereomer 1 | 116 |
| Ex. 245 | 97 |
| Ex. 250 | 27 |
| Ex. 252 | 33 |
| Ex. 253(b) | 124 |
| Ex. 270 enantiomer 1 | 321 |
| Ex. 275 | 82 |

EXAMPLES

Intermediate Example 1

(1-Ethyl-1H-imidazol-5-yl)boronic acid a) (2-Chloro-1-ethyl-1H-imidazol-5-yl)boronic acid To a stirred solution of 2-chloro-1-ethyl-1H-imidazole (1.19 g, 9.11 mmol) in dry THF (60 ml) under $N_2$ (cooled to −78° C.) were added TMEDA (2.04 ml, 13.66 mmol) and 2.5 M n-BuLi (5.46 ml, 13.66 mmol) over a period of 45 min. The mixture was stirred at this temperature for 45 min. Then, triisopropyl borate (3.15 ml, 13.66 mmol) was added. The mixture stirred for 1.5 h and then warmed to RT over a period of 30 min. Aqueous HCl was added until pH reached 5. The organic phase was separated, dried and evaporated. Triturating with diethyl ether gave 1.29 g of the title compound. [M+1]=175. $^1$H NMR (400 MHz, MeOH-d$_4$): 1.30 (t, 3 H) 4.28 (q, 2 H) 7.38 (s, 1 H).

b) (1-Ethyl-1H-imidazol-5-yl)boronic acid

The compound of Intermediate Example 1(a) (500 mg, 2.87 mmol) was dissolved in methanol (55 ml). The mixture was hydrogenated in H-Cube using 10% Pd/C as a catalyst (20 bar, 20° C., 1 ml/min). Methanol was evaporated giving 0.41 g of the title compound. [M+1]=140. $^1$H NMR (400 MHz, MeOH-d$_4$): 1.50 (t, 3 H) 4.48 (q, 2 H) 7.81 (s, 1 H) 9.02 (s, 1 H).

Example 1

4-((3-(1H-imidazol-4-yl)-6,6-dimethylcyclohex-3-enyl)(ethyl)amino)-2-(trifluoromethyl)benzonitrile a) 4-(2,2-Dimethyl-5-oxocyclohexylamino)-2-(trifluoromethyl)benzonitrile A mixture of 4-amino-2-(trifluoromethyl)benzonitrile (2.12 g, 11.4 mmol), 3,4-dihydroxycyclobut-3-ene-1,2-dione (59 mg, 0.51 mmol), and 4,4-dimethylcyclohex-2-enone (1.5 ml, 1.42 g, 11.4 mmol) was stirred at 60° C. for 12 h. The mixture was triturated in 1:1 diethyl ether-heptane yielding 2.74 g of the title compound. $^1$H NMR (400 MHz, DMSO-d$_6$): 1.01 (3H, s), 1.07 (3H, s), 1.61-1.80 (2H, m), 2.17-2.26 (1H, m), 2.33-2.48 (3H, m), 3.80-3.92 (1H, m), 6.95-7.02 (2H, m), 7.21 (1H, broad s), 7.70 (1H, d).) m/z=311.3 (M+1)$^+$.

b) 4-(5-hydroxy-2,2-dimethylcyclohexylamino)-2-(trifluoromethyl)benzonitrile

The mixture of the compound of Example 1(a) (5.48 g, 17.7 mmol) in dry methanol (100 ml) and NaBH$_4$ (0.67 g, 17.7 mmol) was stirred at 0° C. for 1.5 h. Yield 5.50 g of the title compound. m/z=313.3 (M+1)$^+$.

c) 4-(5-(tert-Butyldimethylsilyloxy)-2,2-dimethylcyclohexylamino)-2-(trifluoromethyl)benzonitrile The compound was prepared from the compound of Example 1(b) (5.50 g, 17.6 mmol), 1H-imidazole (3.60 g, 52.8 mmol) and TBSCl (3.98 g, 26.4 mmol) in dry DCM (105 ml). The crude product was purified by flash chromatography. Yield 6.90 g. m/z=427.4 (M+1)$^+$.

d) 4-((5-(tert-Butyldimethylsilyloxy)-2,2-dimethylcyclohexyl)(ethyl)amino)-2-(trifluoromethyl)benzonitrile The mixture of the compound of Example 1(c) (4.05 g, 9.5 mmol), 60% dispersion of NaH in mineral oil (1.14 g, 28.5 mmol) and iodoethane (2.29 ml, 4.44 g, 28.5 mmol) in dry DMF (45 ml) was heated at 80° C. until the reaction was completed. Crude product was crystallized from heptane yielding 3.13 g of the title compound. m/z=455.5 (M+1)$^+$.

e) 4-(Ethyl(5-hydroxy-2,2-dimethylcyclohexyl)amino)-2-(trifluoromethyl)-benzonitrile The compound was prepared from the compound of Example 1(d) (3.11 g, 6.8 mmol) and SOCl$_2$ (2.0 ml, 3.26 g, 27.4 mmol) in dry MeOH (50 ml). Yield 2.32 g. m/z=341.4 (M+1)$^+$.

f) 4-((2,2-Dimethyl-5-oxocyclohexyl)(ethyl)amino)-2-(trifluoromethyl)benzonitrile The compound was prepared from the compound of Example 1(e) (2.38 g, 7.0 mmol) and Dess-Martin periodinane (4.45 g, 10.5 mmol) in dry DCM (75 ml). Yield 2.14 g. m/z=339.4 (M+1)$^+$.

g) 4-(3-((4-Cyano-3-(trifluoromethyl)phenyl)(ethyl)amino)-1-hydroxy-4,4-dimethylcyclohexyl)-N,N-dimethyl-1H-imidazole-1-sulfonamide The compound was prepared from 4-iodo-N,N-dimethyl-1H-imidazole-1-sulfonamide (0.58 g, 1.92 mmol), 3 M EtMgBr solution in Et$_2$O (0.74 ml, 2.22 mmol) and the compound of Example 1(f) (0.50 g, 1.48 mmol) in dry DCM (18 ml). The crude product was purified with flash chromatography. Yield 0.32 g. m/z=514.5 (M+1)$^+$.

h) 4-((3-(1H-imidazol-4-yl)-6,6-dimethylcyclohex-3-enyl)(ethyl)amino)-2-(trifluoromethyl)benzonitrile The compound of Example 1(g) (1.09 g, 2.12 mmol) was cooled in an ice-bath. Ice-cold concentrated H$_2$SO$_4$ (5.66 ml, 106 mmol) was added and the mixture was stirred for 15 min in an icebath and allowed to warm to RT. After stirring for 1 h 50 g of crushed ice was added. pH was adjusted to 9 with 25% NaOH solution. The mixture was extracted with ethyl acetate. Combined extracts were washed with water and brine, dried, and evaporated. The residue was dissolved in 1,4-dioxane (6 ml), and concentrated HCl (6.11 ml, 74.5 mmol) was added. The resulting solution was stirred for 1.5 h at 90° C., cooled and diluted with water. pH was adjusted to 9 with 2 M NaOH. The mixture was extracted with ethyl acetate. Combined organic phases were washed and evaporated as above. The residue was purified with flash chromatography (heptanes-ethyl acetate gradient) yielding 219 mg of the racemate. The enantiomers were separated using preparative HPLC (Daicel Chiralpack IA, 2 cm×25 cm, 97% TBME+0.2% DEA−3% EtOH+0.2% DEA, 20 ml/min, run time 35 min), yielding 57 mg of enantiomer 1 (rt 15 min), and 41 mg of enantiomer 2 (rt 25 min). $^1$H NMR (400 MHz, CDCl$_3$): 1.01 (3H, s), 1.07 (3H, s), 1.21 (3H, t), 2.13-2.34 (2H, m), 2.60-2.78 (2H, m), 3.48-3.63 (2H, m), 4.16-4.21 (1H, m), 6.27-6.34 (1H, m), 6.93 (1H, dd), 6.96 (1H, s), 7.08 (1H, s), 7.56 (1H, d), 7.65 (1H, s).

Example 2

4-((3-(1H-imidazol-4-yl)-6,6-dimethylcyclohex-3-enyl)(methyl)amino)-2-chlorobenzonitrile a) 2-Chloro-4-(2,2-dimethyl-5-oxocyclohexylamino)benzonitrile The compound was prepared from 4-amino-2-chlorobenzonitrile (1.74 g, 11.4 mmol), 3,4-dihydroxycyclobut-3-ene-1,2-dione (59 mg, 0.51 mmol) and 4,4-dimethylcyclohex-2-enone (1.5 ml, 1.42 g, 11.4 mmol). Yield 2.71 g. $^1$H NMR (400 MHz, DMSO-d$_6$): 1.00 (3H, s), 1.06 (3H, s), 1.59-1.78 (2H, m), 2.15-2.26 (1H, m), 2.31-2.47 (3H, m), 3.74-3.83 (1H, m), 6.75 (1H, dd), 6.94 (1H, d), 7.50 (1H, d).) m/z=277.3 (M+1)$^+$.

b) 2-Chloro-4-(5-hydroxy-2,2-dimethylcyclohexylamino)benzonitrile

The compound was prepared from the compound of Example 2(a) (2.20 g, 8.0 mmol) and NaBH$_4$ (0.30 g, 8.0 mmol) in MeOH (50 ml). Yield 2.20 g. m/z=279.3 (M+1)$^+$.

c) 4-(5-(tert-butyldimethylsilyloxy)-2,2-dimethylcyclohexylamino)-2-chlorobenzonitrile The compound was prepared from the compound of Example 2(b) (2.20 g, 7.9 mmol), 1H-imidazole (1.61 g, 23.7 mmol) and TBSCl (1.78 g, 11.8 mmol). Yield 2.65 g. m/z=393.4, 395.4 (M+1)$^+$.

d) 4-((5-(tert-Butyldimethylsilyloxy)-2,2-dimethylcyclohexyl)(methyl)amino)-2-chlorobenzonitrile The compound was prepared from the compound of Example 2(c) (2.38 g, 6.1 mmol), 60% NaH dispersion in mineral oil (0.48 g, 12.1 mmol) and iodomethane (0.75 ml, 1.72 g, 12.1 mmol) in DMF (20 ml). Crude product (2.61 g) was used in the next step without further purification. m/z=407.5, 409.4 (M+1)$^+$.

e) 2-Chloro-4-((5-hydroxy-2,2-dimethylcyclohexyl)(methyl)amino)benzonitrile

The compound was prepared from the compound of Example 2(d) (2.38 g, 6.1 mmol) and SOCl$_2$ (1.76 ml, 2.88 g, 24.2 mmol) in methanol (50 ml). Yield 1.63 g. m/z=293.4, (M+1)$^+$.

f) 2-Chloro-4-((2,2-dimethyl-5-oxocyclohexyl)(methyl)amino)benzonitrile

The compound was prepared from the compound of Example 2(e) (1.62 g, 5.5 mmol) and Dess-Martin periodinane (3.52 g, 8.3 mmol) in DCM (50 ml). Yield 1.43 g. $^1$H NMR (400 MHz, CDCl$_3$): 1.05 (3H, s), 1.23 (3H, s), 1.61-1.80 (2H, m), 2.36-2.52 (3H, m), 2.79-2.87 (1H, m), 2.89 (3H, s), 3.97 (1H, dd), 6.69 (1H, dd), 6.81 (1H, d), 7.43 (1H, d).) m/z=291.3, (M+1)$^+$.

g) 4-((3-(1H-imidazol-4-yl)-6,6-dimethylcyclohex-3-enyl)(methyl)amino)-2-chlorobenzonitrile The compound was prepared from 4-iodo-1-trityl-1H-imidazole (2.56 g, 5.9 mmol), 3 M EtMgBr in Et$_2$O (2.12 ml, 6.4 ml) and the compound of Example 2(f) (1.42 g, 4.9 mmol) in dry DCM (55 ml). The crude product was purified using flash chromatography, and the residue (1.15 g) was treated with H$_2$SO$_4$ (8 ml, 151 mmol), yielding 290 mg of the racemate. The enantiomers were separated on preparative HPLC (Daicel Chiralpack IA, 2 cm×25 cm, 95% TBME+0.2% DEA−5% EtOH+0.2% DEA, 20 ml/min, run time 30 min), yielding 99 mg of enantiomer 1 (rt 15 min) and 97 mg of enantiomer 2 (rt 20 min). $^1$H NMR (400 MHz, CDCl$_3$): 0.99 (3H, s), 1.04 (3H, s), 2.06-2.15 (1H, m), 2.20-2.30 (1H, m), 2.62-2.69 (2H, m), 2.95 (3H, s), 4.09 (1H, t), 6.24-6.33 (1H, m), 6.71 (1H, dd), 6.91 (1H, d), 6.97 (1H, d), 7.39 (1H, d), 7.61 (1H, d).

Example 3

4-((-3-(1H-imidazol-1-yl)-2,2,4,4-tetramethylcyclobutyl)(ethyl)amino)-2-(trifluoromethyl)benzonitrile a) 2,2,4,4-Tetramethylcyclobutane-1,3-dione dioxime A mixture of hydroxylamine HCl (5.95 g, 86 mmol) and 2,2,4,4-tetramethyl-1,3-cyclobutanedione (3.00 g, 21.4 mmol) in pyridine (15 ml) was stirred for 3 days at RT. Water was added, the precipitate was filtered off and washed with water yielding 3.57 g of the title compound. $^1$H NMR (400 MHz, DMSO-d$_6$): 1.27 (3H, s), 1.37 (6H, s), 1.49 (3H, s), 10.26 (1H, s), 10.31 (1H, s).

b) 2,2,4,4-Tetramethylcyclobutane-1,3-diamine dihydrochloride

A mixture of the compound of Example 3(a) (1.00 g, 5.9 mmol) and Ni/Al alloy (4.02 g, 46.9 mmol) in THF (20 ml) was stirred for 30 min at 60° C. NaOH (2.18 g, 9.3 mmol) in water (20 ml) was added slowly and refluxing was continued for 2 h. The cooled mixture was filtered through a pad of Celite, and the filter cake was washed with THF. The filtrate was evaporated almost to dryness, brine was added, and the solution was extracted with EtOAc. The combined organic phases were washed with brine, dried, and evaporated. The residue was dissolved in EtOAc (20 ml) and filtered. 1 M HCl in Et$_2$O (12 ml) was added to the filtrate with stirring. The precipitate was filtered off and washed with EtOAc and Et$_2$O yielding 0.84 g of the title compound. $^1$H NMR (400 MHz, DMSO-d$_6$): 1.16 (3H, s), 1.24 (9H, s), 3.00 (2H, m), 8.54 (6H, broad s).

c) 4-(3-Amino-2,2,4,4-tetramethylcyclobutylamino)-2-(trifluoromethyl)benzonitrile A mixture of 4-fluoro-(2-trifluoromethyl)benzonitrile (0.29 g, 1.53 mmol), the compound of Example 3(b) (0.83 g, 3.83 mmol), DIPEA (1.60 ml. 1.19 g, 9.20 mmol), and DMSO (7 ml) was microwave heated for 2 h at 120° C. Water was added, and the mixture extracted with EtOAc. The combined organic phases were washed with water and brine, dried, and evaporated. The residue was dissolved in EtOAc (5 ml) and 1 M HCl in Et$_2$O (2 ml) was added. The solvents were decanted off and the residue was triturated in 1:5 EtOAc-Et$_2$O yielding 0.21 g of the title compound. $^1$H NMR (400 MHz, DMSO-d$_6$): 1.07 (3H, s), 1.10 (3H, s), 1.27 (3H, s), 1.28 (3H, s), 2.94-3.16 (1H, m), 3.58-3.68 (1H, m), 6.88 (1H, d), 7.34 (1H, m), 7.75 (1H, d), 8.37 (3H, broad s).

d) 4-(3-(1H-imidazol-1-yl)-2,2,4,4-tetramethylcyclobutylamino)-2-(trifluoromethyl)benzonitrile The compound of Example 3(c) (0.20 g, 0.58 mmol) was dissolved in water and pH adjusted to 10 with 2 M NaOH. The free base was extracted into EtOAc, dried, and evaporated. The residue was dissolved in MeOH (2 ml), and 30 w-% aqueous solution of glyoxal (0.22 g, 1.15 mmol), NH$_4$OAc (89 mg, 1.15 mmol), and 37% aqueous formaldehyde (0.051 ml, 1.15 mmol) were added. The residue was purified with flash chromatography yielding 0.14 g of the title compound. m/z=363.4, (M+1)$^+$.

e) 4-((-3-(1H-imidazol-1-yl)-2,2,4,4-tetramethylcyclobutyl)(ethyl)amino)-2-(trifluoromethyl)benzonitrile The compound was prepared from the compound of Example 3(d) (0.14 g, 0.39 mmol), 60% NaH (50 mg, 1.27 mmol) and iodoethane (0.092 ml, 0.18 g, 1.15 mmol) in dry DMF (3 ml). The crude residue was filtered through a plug of silica. The trans- and cis-isomers were separated on reverse phase preparative HPLC yielding 22 mg of trans-isomer, $^1$H NMR (400 MHz, CDCl$_3$): 1.06 (3H, t), 1.20 (6H, s), 1.30 (6H, s), 3.42 (2H, q), 4.04 (1H, s), 4.05 (1H, s), 7.04 (1H, m), 7.10 (1H, s), 7.17 (1H, dd), 7.29 (1H, d), 7.50 (1H, s), 7.68 (1H, d), and 23 mg of cis-isomer, $^1$H NMR (400 MHz, CDCl$_3$): 1.00 (3H, t), 1.20 (6H, s), 1.36 (6H, s), 3.37 (2H, q), 3.63 (1H, s), 3.92 (1H, s), 7.01 (1H, m), 7.07 (1H, s), 7.24 (1H, dd), 7.36 (1H, d), 7.53 (1H, s), 7.70 (1H, d).

Example 4

4-(Ethyl-3-(4-(2-methoxyethyl)-4H-1,2,4-triazol-3-yl)cyclohexyl)amino)-2-(trifluoromethyl)benzonitrile a) 4-(3-(4-(2-methoxyethyl)-4H-1,2,4-triazol-3-yl)cyclohexylamino)-2-(trifluoromethyl)benzonitrile The compound was prepared from 3-(4-(2-methoxyethyl)-4H-1,2,4-triazol-3-yl)cyclohexanamine (139 mg, 0.62 mmol) (cis-enantiomer 1), 4-fluoro-2-(trifluoromethyl)benzonitrile (117 mg, 0.62 mmol) and DIPEA (0.27 ml, 200 mg, 1.55 mmol) in DMSO (4 ml), 100° C., 3 h. Yield 110 mg. $^1$H NMR (400 MHz, CDCl$_3$): 1.39-1.62 (2H, m), 1.67-1.80 (1H, m), 1.93-2.03 (1H, m), 2.15 (1H, d), 2.25 (1H, d), 2.88-3.00 (1H, m), 3.33 (3H, s), 3.44-3.58 (1H, m), 3.63 (2H, t), 4.10 (2H, t), 6.17 (1H, d), 6.77 (1H, d), 6.98 (1H, d), 7.48 (1H, d), 8.18 (1H, s).

b) 4-(Ethyl(3-(4-(2-methoxyethyl)-4H-1,2,4-triazol-3-yl)cyclohexyl)amino)-2-(trifluoromethyl)benzonitrile The compound was prepared from the compound of Example 4(a) (110 mg, 0.28 mmol), 60% NaH dispersion (22 mg, 0.56 mmol), and iodoethane (0.045 ml, 87 mg, 0.56 mmol). Yield 100 mg (cis-enantiomer 1). $^1$H NMR (400 MHz, CDCl$_3$): 1.21 (3H, t), 1.53-2.19 (8H, m), 2.90-3.00 (1H, m), 3.31 (3H, s), 3.44 (2H, q), 3.58-3.68 (2H, m), 3.77-3.87 (1H, m), 4.11 (2H, t), 6.82 (1H, dd), 6.95 (1H, d), 7.54 (1H, d), 8.16 (1H, d).

Example 5

4-(Ethyl(3-(4-(2-methoxyethyl)-4H-1,2,4-triazol-3-yl)cyclohexyl)amino)-2-(trifluoromethyl)benzonitrile a) 4-(3-(4-(2-Methoxyethyl)-4H-1,2,4-triazol-3-yl)cyclohexylamino)-2-(trifluoromethyl)benzonitrile The compound was prepared from 3-(4-(2-methoxyethyl)-4H-1,2,4-triazol-3-yl)cyclohexanamine (109 mg, 0.49 mmol) (cis-enantiomer 2), 4-fluoro-2-(trifluoromethyl)benzonitrile (92 mg, 0.49 mmol) and DIPEA (0.21 ml, 157 mg, 1.22 mmol) in DMSO (3 ml), 120° C., 3 h. Yield 70 mg. $^1$H NMR (400 MHz, CDCl$_3$): 1.39-1.62 (2H, m), 1.67-1.80 (1H, m), 1.93-2.03 (1H, m), 2.15 (1H, d), 2.25 (1H, d), 2.88-3.00 (1H, m), 3.33 (3H, s), 3.44-3.58 (1H, m), 3.63 (2H, t), 4.10 (2H, t), 5.85 (1H, d), 6.77 (1H, d), 6.98 (1H, d), 7.48 (1H, d), 8.18 (1H, s).

b) 4-(Ethyl(3-(4-(2-methoxyethyl)-4H-1,2,4-triazol-3-yl)cyclohexyl)amino)-2-(trifluoromethyl)benzonitrile The compound was prepared from the compound of Example 5(a) (70 mg, 0.18 mmol), 60% NaH dispersion (14 mg, 0.36 mmol), and iodoethane (0.029 ml, 56 mg, 0.36 mmol). Yield 55 mg (cis-enantiomer 2). $^1$H NMR (400 MHz, CDCl$_3$): 1.21 (3H, t), 1.53-2.19 (8H, m), 2.90-3.00 (1H, m), 3.31 (3H, s), 3.44 (2H, q), 3.58-3.68 (2H, m), 3.77-3.87 (1H, m), 4.11 (2H, t), 6.82 (1H, dd), 6.95 (1H, d), 7.54 (1H, d), 8.16 (1H, d).

Example 6

4-((3-(1H-imidazol-1-yl)cyclohex-2-enyl)(methyl)amino)-2-(trifluoromethyl)benzonitrile a) 3-Chlorocyclohex-2-enone To a solution of cyclohexane-1,3-dione (5.0 g, 0.045 mol) in DCM (50 ml) were added oxalyl chloride (5.8 ml, 0.067 mol) and DMF (1 drop) at 0° C. and stirred at RT for 3 h. The mixture was poured into ice-water and extracted with DCM. The organic layer was washed with water, dried (anhydrous Na$_2$SO$_4$), filtered and concentrated under reduced pressure. The crude product was purified by column chromatography over silica gel using 10% EtOAc in hexane as the eluent to give 2.52 of the title compound. $^1$H-NMR (400 MHz; CDCl$_3$): 6.22 (s, 1H), 2.68 (t, 2H), 2.40 (t, 2H), 2.05-2.16 (m, 2H); MS: m/z 131.12 [M+H]$^+$.

b) 3-(1H-Imidazol-1-yl)cyclohex-2-enone

To a solution of the compound of Example 6(a) (2.5 g, 0.019 mol) in DMF (15 ml) were added K$_2$CO$_3$ (7.96 g, 0.058 mol) and imidazole (1.96 g, 0.029 mol). The mixture was stirred for 5 h at RT, poured into ice-water and extracted with DCM. The organic layer was washed with water, dried, filtered and concentrated. The crude product was purified by column chromatography over basic alumina using 5% MeOH in DCM as the eluent. Yield 800 mg. $^1$H-NMR (400 MHz; CDCl$_3$): 8.33 (s, 1H), 7.82 (s, 1H), 7.12 (s, 1H), 6.37 (s, 1H), 2.93 (t, 2H), 2.36 (t, 2H), 2.01-2.09 (m, 2H); LC-MS: m/z 163.0 [M+H]$^+$.

c) 3-(1H-Imidazol-1-yl)cyclohex-2-enol

To a solution of the compound of Example 6(b) (8.5 g, 0.052 mol) in MeOH (100 ml) were added CeCl$_3$ (25.8 g, 0.105 mol) and NaBH$_4$ (1.9 g, 0.052 mol). The mixture was stirred at RT for 1 h, quenched with 10% aqueous HCl solution and extracted with EtOAc. The organic layer was washed with water, dried, filtered and concentrated. The crude product was purified by recrystallization from DCM/hexane. Yield 6.9 g. $^1$H-NMR (400 MHz; DMSO-d$_6$): 7.94 (s, 1H), 7.49 (s, 1H), 6.97 (s, 1H), 5.91 (bs, 1H), 4.87 (d, 1H), 4.22 (bs, 1H), 2.43-2.50 (m, 1H), 2.36-2.42 (m, 1H), 1.84-1.92 (m, 1H), 1.72-1.80 (m, 1H), 1.59-1.69 (m, 1H), 1.45-1.54 (m, 1H); LC-MS: m/z 165.09 [M+H]$^+$.

d) 1-(3-Azidocyclohex-1-enyl)-1H-imidazole

To a mixture of the compound of Example 6(c) (1.6 g, 9.75 mmol) and DPPA (4.02 g, 14.62 mmol) in toluene (40 ml) was added DBU (2.52 g, 16.57 mmol) at 0° C. followed by stirring at RT overnight. The mixture was quenched with water and extracted with EtOAc. The organic layer was washed with water, dried, filtered and concentrated. The crude product was purified by column chromatography over silica gel using 3% MeOH in DCM as the eluent. Yield 1.31 g. $^1$H-NMR (400 MHz; CDCl$_3$): 7.74 (s, 1H), 7.15 (s, 1H), 7.11 (s, 1H), 5.86 (bs, 1H), 4.16 (bs, 1H), 2.40-2.58 (m, 2H), 1.90-2.04 (m, 2H), 1.78-1.88 (m, 2H); LC-MS: m/z 190.31 [M+H]$^+$.

e) 3-(1H-Imidazol-1-yl)cyclohex-2-enamine

To a solution of the compound of Example 6(d) (0.35 g, 1.852 mmol) in THF (15 ml) and H$_2$O (5 ml) were added PPh$_3$ (0.53 g, 2.036 mmol) and KOH (0.1 g, 1.852 mmol) at RT followed by stirring for 12 h. The mixture was quenched with water and extracted with EtOAc. The organic layer was washed with water, dried, filtered and concentrated. The crude product was purified by column chromatography over silica gel using 0.1% NH$_3$ and 4.9% MeOH in DCM as the eluent. Yield 180 mg. $^1$H-NMR (400 MHz; DMSO-d$_6$): 7.89 (s, 1H), 7.45 (s, 1H), 6.96 (s, 1H), 5.84 (bs, 1H), 3.40 (bs, 1H), 2.32-2.46 (m, 2H), 1.74-1.92 (m, 2H), 1.56-1.67 (m, 1H), 1.23-1.33 (m, 1H); LC-MS: m/z 164.12 [M+H]$^+$.

f) 4-(3-(1H-imidazol-1-yl)cyclohex-2-enylamino)-2-(trifluoromethyl)benzonitrile

The compound was prepared from the compound of Example 6(e) (0.55 g, 3.4 mmol), 4-fluoro-2-(trifluoromethyl)benzonitrile (0.64 g, 3.4 mmol) and DIPEA (1.47 ml, 1.09 g, 8.4 mmol) in DMSO (8 ml), 90° C., 3 h. Yield 0.70 g. $^1$H NMR (400 MHz, CDCl$_3$): 1.71-1.82 (1H, m), 1.86-2.07 (3H, m), 2.48-2.63 (2H, m), 4.27-4.37 (1H, m), 4.67 (1H, d), 5.80-5.86 (1H, m), 6.74 (1H, dd), 6.90 (1H, d), 7.11 (1H, t), 7.14 (1H, t), 7.58 (1H, d), 7.71 (1H, s).

g) 4-((3-(1H-imidazol-1-yl)cyclohex-2-enyl)(methyl)amino)-2-(trifluoromethyl)benzonitrile The compound was prepared from the compound of Example 6(f) (0.70 g, 2.1 mmol), 60% NaH dispersion (0.17 g, 4.2 mmol) and iodomethane (0.20 ml, 0.45 g, 3.2 mmol) in DMF (7 ml), 1 h, yielding 0.32 g of the title compound as a racemic mixture. Enantiomers were separated on preparative HPLC (Daicel Chiralpack IA, 2 cm×25 cm, 96% TBME+0.2% DEA–4% EtOH+0.2% DEA, 25 ml/min, run time 52 min) from 0.27 g of racemic mixture yielding 79 mg of enantiomer 1 (rt 22 min) and 65 mg of enantiomer 2 (rt 43 min). $^1$H NMR (400 MHz, CDCl$_3$): 1.66-1.77 (1H, m), 1.87-2.17 (3H, m), 2.49-2.70 (2H, m), 2.96 (3H, s), 4.70-4.79 (1H, m), 5.71-5.76 (1H, m), 6.89 (1H, dd), 7.03 (1H, d), 7.12 (1H, m), 7.17 (1H, t), 7.59 (1H, dd), 7.74 (1H, t).

Example 7

4-(Ethyl(2-(pyridin-3-yl)-2,3,4,5-tetrahydropyridazin-4-yl)amino)-2-(trifluoromethyl)benzonitrile and 4-(Ethyl(1-(pyridin-3-yl)-1,4,5,6-tetrahydropyridazin-4-yl)amino)-2-(trifluoromethyl)benzonitrile a) di-tert-Butyl 4-(tert-butyldimethylsilyloxy)piperazine-1,2-dicarboxylate 60% NaH dispersion (1.12 g, 28.0 mmol) was washed with dry heptane. Dry DMF (11 ml) was added. Di-tert-butyl hydrazodiformate (2.95 g, 12.7 mmol) in dry DMF (22 ml) was added dropwise. After stirring for 30 min at RT, tert-butyl(1,4-dibromobutan-2-yloxy)dimethylsilane (4.40 g, 12.7 mmol), prepared as in Kumar, A. et al., Bioorg. Med. Chem. Lett., 2012, 4740, in dry DMF (5 ml) was added dropwise. The mixture was stirred at RT overnight and water was added. The resulting mixture was extracted with EtOAc, washed with water and brine, dried and evaporated yielding 4.97 g of the title compound. m/z=417.4, (M+1)$^+$.

b) di-tert-butyl 4-hydroxypiperazine-1,2-dicarboxylate

The compound of Example 7(a) (4.40 g, 10.6 mmol) was dissolved in dry THF (50 ml). 1 M TBAF in THF (13.2 ml, 13.2 mmol) was added, and the resulting solution was stirred overnight at RT, evaporated, and the residue was purified using flash chromatography. Yield 3.12 g. m/z=325.2, (M+Na)$^+$.

c) di-tert-Butyl 4-(methylsulfonyloxy)piperazine-1,2-dicarboxylate

The compound of Example 7(b) (0.75 g, 2.5 mmol) was dissolved in dry DCM (15 ml) and cooled to 0° C. TEA (0.69 ml, 0.50 g, 5.0 mmol) was added, followed by methanesulfonyl chloride (0.29 ml, 0.43 g, 3.7 mmol). After stirring for 1 h, the mixture was diluted with DCM, washed with saturated NH₄Cl solution, water and brine, dried, and evaporated. Yield 0.83 g. m/z=381.2, (M+1)⁺.

d) di-tert-Butyl 4-azidopiperazine-1,2-dicarboxylate

The compound of Example 7(c) (0.81 g, 2.1 mmol) was dissolved in DMF (8 ml) and NaN₃ (0.28 g, 4.3 mmol) was added. The mixture was stirred for 3 h at 70° C., then overnight at RT, 1 h at 80° C., 8 h at 90° C. and overnight at RT. Water was added and the mixture was extracted with EtOAc. The organic phase was washed with water and brine, dried and evaporated. Yield 0.67 g. m/z=328.3, (M+1)⁺.

e) di-tert-Butyl 4-aminopiperazine-1,2-dicarboxylate

The compound of Example 7(d) (0.66 g, 2.0 mmol) was dissolved in MeOH (15 ml) and 10% Pd/C (0.22 g) was added. The mixture was hydrogenated under atmospheric pressure for 2.5 h, filtered through a pad of Celite and evaporated yielding 0.55 g of the title compound. m/z=302.3, (M+1)⁺.

f) di-tert-Butyl 4-(4-cyano-3-(trifluoromethyl)phenylamino)piperazine-1,2-dicarboxylate The title compound was prepared from the compound of Example 7(e) (0.54 g, 1.8 mmol), 4-fluoro-2-(trifluoromethyl)benzonitrile (0.34 g, 1.8 mmol) and DIPEA (0.78 ml, 0.58 g, 4.5 mmol) in DMSO (8 ml), 90° C., 3 h. Yield 0.33 g. m/z=471.4, (M+1)⁺.

g) di-tert-Butyl 4-((4-cyano-3-(trifluoromethyl)phenyl)(ethyl)amino)piperazine-1,2-dicarboxylate The compound was prepared from the compound of Example 7(f) (0.32 g, 0.68 mmol), 60% NaH dispersion (0.054 g, 1.4 mmol) and iodoethane (0.11 ml, 0.21 g, 1.4 mmol) in DMF (5 ml). Yield 0.33 g. ¹H NMR (400 MHz, CDCl₃): 1.21 (3H, t), 1.50 (18H, broad s), 1.91 (2H, m), 2.73-3.27 (2H, m), 3.38 (2H, q), 3.79-3.92 (1H, m), 4.16-4.47 (2H, m), 6.91 (1H, m), 7.05 (1H, m), 7.62 (1H, d).

h) 4-(Ethyl(piperazin-4-yl)amino)-2-(trifluoromethyl)benzonitrile dihydrochloride The compound of Example 7(g) (0.33 g, 0.68 mmol) was dissolved in EtOAc (2 ml) and 1 M HCl in Et₂O (2.73 ml, 2.7 mmol) was added. After stirring for 1.5 h at RT, another 2.73 ml of 1 M HCl in Et₂O was added. After stirring overnight, MeOH (8 ml) was added and stirring was continued for 13 days. The mixture was evaporated and the residue was triturated with a mixture of EtOAc (5 ml) and Et₂O (2 ml) yielding 0.19 g of the title compound. m/z=299.3, (M+1)⁺.

i) 4-(Ethyl(2-(pyridin-3-yl)-2,3,4,5-tetrahydropyridazin-4-yl)amino)-2-(trifluoromethyl)benzonitrile and 4-(Ethyl(1-(pyridin-3-yl)-1,4,5,6-tetrahydropyridazin-4-yl)amino)-2-(trifluoromethyl)benzonitrile The compound of Example 7(h) (177 mg, 0.48 mmol), dry toluene (4 ml) and DIPEA (0.17 ml, 128 mg, 0.99 mmol) were stirred for 15 min while bubbling with N₂. 3-Bromopyridine (0.051 ml, 83 mg, 0.52 mmol), Pd₂(dba)₃ (22 mg, 0.024 mmol), rac-BINAP (30 mg, 0.048 mmol) and sodium tert-butoxide (64 mg, 0.67 mmol) were added. The mixture was stirred for 8 h at 80° C., diluted with TBME, filtered and evaporated. The crude product was purified with flash chromatography, and the regioisomers were separated using reversed phase HPLC yielding 20 mg of 4-(ethyl(2-(pyridin-3-yl)-2,3,4,5-tetrahydropyridazin-4-yl)amino)-2-(trifluoromethyl)benzonitrile, ¹H NMR (400 MHz, CDCl₃): δ 1.27 (3H, t), 2.50-2.67 (2H, m), 3.35-3.50 (3H, m), 3.87-3.94 (1H, m), 4.39-4.47 (1H, m), 6.89 (1H, dd), 6.95 (1H, dd), 7.03 (1H, d), 7.21 (1H, q), 7.52 (1H, dq), 7.63 (1H, d), 8.20 (1H, dd), 8.49 (1H, d), and 41 mg of 4-(ethyl(1-(pyridin-3-yl)-1,4,5,6-tetrahydropyridazin-4-yl)amino)-2-(trifluoromethyl)benzonitrile, ¹H NMR (400 MHz, CDCl₃): δ 1.30 (3H, t), 2.26-2.35 (2H, m), 3.43-3.59 (2H, m), 3.65-3.76 (1H, m), 3.88-3.99 (1H, m), 4.47-4.56 (1H, m), 6.72 (1H, d), 6.87 (1H, dd), 7.02 (1H, d), 7.23 (1H, dd), 7.57 (1H, dq), 7.62 (1H, d), 8.21 (1H, dd), 8.53 (1 H, d).

Example 8

4-((3-(1H-imidazol-1-yl)-2-methylcyclopent-2-enyl)(ethyl)amino)-2-(trifluoromethyl)benzonitrile a) 3-(1H-imidazol-1-yl)-2-methylcyclopent-2-enone The compound was prepared from 3-chloro-2-methylcyclopent-2-enone (2.00 g, 15.3 mmol) prepared as in E. Mewshaw, Tetrahedron Lett., 1989, 30, 3753, 1H-imidazole (2.09 g, 30.6 mmol), TEA (10.7 ml, 7.75 g, 77 mmol) and KHCO₃ (0.31 g, 3.1 mmol) in toluene (10 ml), 160° C., 1.5 h. Yield 1.89 g. ¹H NMR (400 MHz, CDCl₃): 2.03 (3H, t), 2.62-2.67 (2H, m), 2.99-3.04 (2H, m), 7.25 (1H, s), 7.41 (1H, s), 8.02 (1H, s).

b) 3-(1H-imidazol-1-yl)-2-methylcyclopent-2-enone oxime

To the compound of Example 8(a) (2.00 g, 12.3 mmol) in pyridine (3 ml) hydroxylamine HCl (1.71 g, 24.7 mmol) was added. The mixture was stirred overnight and diluted with water. The precipitate was filtered off and washed with water. Yield 1.79 g. ¹H NMR (400 MHz, CDCl₃): 2.00 (3H, t), 2.84-2.94 (4H, m), 7.19 (1H, s), 7.22 (1H, m), 7.29 (1H, broad s), 7.80 (1H, s).

c) 3-(1H-imidazol-1-yl)-2-methylcyclopent-2-enamine

The compound of Example 8(b) (0.75 g, 4.2 mmol) was dissolved in a mixture of EtOH (25 ml) and AcOH (25 ml) and cooled to 0° C. Zn dust (1.66 g, 25.4 mmol) was added in portions and the mixture was warmed to RT and stirred overnight. The mixture was filtered and evaporated. Water was added, pH was adjusted to 10 with NH₄OH and the mixture was saturated with NaCl, extracted with THF, dried and evaporated yielding 0.10 g of the title compound which was used in the next step without further purification. m/z=163.9, (M+1)⁺.

d) 4-(3-(1H-imidazol-1-yl)-2-methylcyclopent-2-enylamino)-2-(trifluoromethyl)benzonitrile The compound was prepared from the compound of Example 8(c) (0.10 g, 0.61 mmol), 4-fluoro-2-(trifluoromethyl)benzonitrile (0.12 g, 0.61 mmol) and DIPEA (0.32 ml, 0.24 g, 1.8 mmol) in DMSO (4 ml), 120° C., 2 h. Yield 0.17 g. m/z=333.4, (M+1)⁺.

e) 4-((3-(1H-imidazol-1-yl)-2-methylcyclopent-2-enyl)(ethyl)amino)-2-(trifluoromethyl)benzonitrile The compound was prepared from the compound of Example 8(d) (0.17 g, 0.51 mmol), 60% NaH dispersion (41 mg, 1.0 mmol) and iodoethane (0.061 ml, 0.12 g, 0.77 mmol) in DMF (4 ml). Yield 20 mg after reversed phase preparative HPLC. $^1$H NMR (400 MHz, CDCl$_3$): 1.24 (3H, t), 1.75 (3H, s), 1.92-2.03 (1H, m), 2.46-2.58 (1H, m), 2.78-2.99 (2H, m), 3.34-3.50 (2H, m), 4.92-5.02 (1H, m), 6.91 (1H, dd), 7.09 (1H, d), 7.13 (1H, s), 7.17 (1H, s), 7.60 (1H, d), 7.70 (1H, s).

Example 9

4-(Ethyl(3-(5-methyl-1H-1,2,3-triazol-1-yl)cyclohexyl)amino)-2-(trifluoromethyl)benzonitrile a) 3-((4-cyano-3-(trifluoromethyl)phenyl)(ethyl)amino)cyclohexyl methanesulfonate 4-(Ethyl(3-hydroxycyclohexyl)amino)-2-(trifluoromethyl) (1.75 g, 5.6 mmol) and TEA (1.17 ml, 0.85 g, 8.4 mmol) were dissolved in dry DCM (60 ml) and cooled to 0° C. Methanesulfonyl chloride (0.65 ml, 0.96 g, 8.4 mmol) was added dropwise. Stirring was continued for 1 h, and the mixture was warmed to RT and stirred for 4 h. The mixture was washed with saturated NH$_4$Cl solution, water and brine, dried and evaporated. Yield 2.11 g. m/z=391.3, (M+1)$^+$.

b) 4-((3-Azidocyclohexyl)(ethyl)amino)-2-(trifluoromethyl)benzonitrile

The compound of Example 9(a) (2.10 g, 5.4 mmol) and 15-Crown-5 (0.11 ml, 0.12 g, 0.54 mmol) were dissolved in DMF (30 ml). NaN$_3$ (0.70 g, 10.8 mmol) was added and the mixture was stirred overnight at RT, followed by 12 h at 70° C. and overnight at RT. Water was added and the mixture was extracted with EtOAc. The combined organic phases were washed water and brine, dried and evaporated. Yield 1.67 g. m/z=338.5, (M+1)$^+$.

c) 4-(Ethyl(3-(5-methyl-1H-1,2,3-triazol-1-yl)cyclohexyl)amino)-2-(trifluoromethyl)benzonitrile The compound of Example 9(b) (1.65 g, 4.9 mmol) was dissolved in dry toluene (20 ml). 1-(Triphenylphosphoranylidene)propan-2-one (1.56 g, 4.9 mmol) was added and the mixture was refluxed for 17 h. After evaporation, the residue was purified by flash chromatography followed by separation of diastereomers by reverse phase preparative HPLC yielding 190 mg of cis-diastereomer, $^1$H NMR (400 MHz, CDCl$_3$): 1.22 (3H, t), 1.56-1.72 (2H, m), 1.94-2.23 (5H, m), 2.34 (3H, s), 2.39-2.50 (1H, m), 3.45 (2H, q), 3.81-3.93 (1H, m), 4.20-4.33 (1H, m), 6.82 (1H, dd), 6.96 (1H, d), 7.45 (1H, s), 7.58 (1H, d) and 50 mg of trans-diastereomer, $^1$H NMR (400 MHz, CDCl$_3$): 1.24 (3H, t), 1.67-2.01 (6H, m), 2.03-2.12 (1H, m), 2.25-2.30 (1H, m), 2.32 (3H, s), 3.29-3.52 (2H, m), 4.72-4.79 (1H, m), 5.01-5.13 (1H, m), 7.02 (1H, dd), 7.13 (1H, d), 7.51 (1H, s), 7.56 (1H, d).

Example 10

4-((3-(1H-tetrazol-1-yl)cyclohexyl)(ethyl)amino)-2-(trifluoromethyl)benzonitrile 4-((3-Aminocyclohexyl)(ethyl)amino)-2-(trifluoromethyl)benzonitrile HCl (1.00 g, 2.9 mmol), NaN$_3$ (0.22 g, 3.5 mmol) and triethyl orthoformate (0.62 ml, 0.55 g, 3.7 mmol) were mixed in AcOH (5 ml) and stirred for 7 h at 100° C. Water was added and the mixture was extracted with EtOAc. Combined organic phases were washed with water and brine, dried and evaporated. The residue was purified by flash chromatography and diastereomers were separated using reversed phase preparative HPLC yielding 4 mg of trans-diastereomer, $^1$H NMR (400 MHz, CDCl$_3$): 1.25 (3H, t), 1.60-1.82 (2H, m), 1.87-2.10 (4H, m), 2.16-2.26 (1H, m), 2.52-2.62 (1H, m), 3.34-3.52 (2H, m), 4.98-5.06 (1H, m), 6.93 (1H, dd), 7.10 (1H, d), 7.60 (1H, d), 8.67 (1H, s), and 36 mg of cis-diastereomer, $^1$H NMR (400 MHz, CDCl$_3$): 1.23 (3H, t), 1.60-1.75 (2H, m), 1.86-2.05 (2H, m), 2.11-2.22 (2H, m), 2.29-2.37 (1H, m), 2.39-2.47 (1H, m), 3.45 (2H, q), 3.89-4.00 (1H, m), 4.69-4.79 (1H, m), 6.85 (1H, dd), 6.97 (1H, d), 7.58 (1H, d), 8.69 (1H, s).

Example 11

4-(Ethyl(3-(1-methyl-1H-tetrazol-5-yl)cyclohexyl)amino)-2-(trifluoromethyl)benzonitrile and 4-(Ethyl(3-(2-methyl-2H-tetrazol-5-yl)cyclohexyl)amino)-2-(trifluoromethyl)benzonitrile a) 4-((3-Cyanocyclohexyl)(ethyl)amino)-2-(trifluoromethyl)benzonitrile

The compound of Example 9(a) (2.39 g, 6.1 mmol) was dissolved in DMF (40 ml). NaN$_3$ (0.90 g, 18.4 mmol) and 15-Crown-5 (0.12 ml, 0.14 g, 0.61 mmol) were added, and the mixture heated for 20 h at 100° C. Water was added and the mixture was extracted with EtOAc. The combined organic phases were washed with water and brine, dried and evaporated. Yield 1.96 g. m/z=322.3, (M+1)$^+$.

b) 4-((3-(1H-tetrazol-5-yl)cyclohexyl)(ethyl)amino)-2-(trifluoromethyl)benzonitrile The compound of Example 11(a) (1.96 g, 6.1 mmol) dissolved in toluene (50 ml). NaN$_3$ (1.19 g, 18.3 mmol) and triethylamine HCl (2.52 g, 18.3 mmol) were added. The mixture was heated for 29 h at 100° C. The mixture was extracted with water and the pH of the combined aqueous phases was adjusted to 1.5 with 2 M HCl. The acidic aqueous mixture was extracted with DCM. Combined organic phases were washed with saturated NH$_4$Cl solution and brine, dried and evaporated. The residue was dissolved in dilute NaHCO$_3$ solution and washed with EtOAc. After acidification the aqueous phase was extracted with DCM, the combined organic phases were washed with saturated NH$_4$Cl solution, dried and evaporated yielding 0.47 g of the title compound which was used in the next step without further purification. m/z=365.3, (M+1)$^+$.

c) 4-(Ethyl(3-(1-methyl-1H-tetrazol-5-yl)cyclohexyl)amino)-2-(trifluoromethyl)benzonitrile and 4-(Ethyl(3-(2-methyl-2H-tetrazol-5-yl)cyclohexyl)amino)-2-(trifluoromethyl)benzonitrile The compound of Example 11 (b) (0.45 g, 1.2 mmol) was dissolved in ACN (10 ml). K$_2$CO$_3$ (0.34 g, 2.5 mmol) was added and the mixture stirred for 10 min. Iodomethane (0.12 ml, 0.26 g, 1.9 mmol) was added and the mixture was stirred overnight. Water was added and the mixture was extracted with DCM. Combined organic phases were washed with water and brine, dried and evaporated. The residue was purified using reversed phase preparative HPLC yielding 9 mg of cis-diastereomer, $^1$H NMR (400 MHz, CDCl$_3$): 1.22 (3H, t), 1.56-1.76 (3H, m), 1.95-2.05 (2H, m), 2.07-2.17 (3H, m), 2.98-3.09 (1H, m), 3.44 (2H, q), 3.81-3.91 (1H, m), 4.05 (3H, s), 6.81 (1H, dd), 6.95 (1H, d), 7.57 (1H, d), and 38 mg of trans-diastereomer of the first title compound, $^1$H NMR (400 MHz, CDCl$_3$): 1.23 (3H, t), 1.50-1.91 (6H, m), 1.97-2.04 (1H, m), 2.10-2.18 (1H, m), 3.30-3.52 (2H, m), 3.53-3.59 (1H, m), 4.02 (3H, s), 4.91-5.02 (1H, s), 7.15 (1H, dd), 7.32 (1H, d), 7.57 (1H, d), and 10 mg of cis-diastereomer, $^1$H NMR (400 MHz, CDCl$_3$): 1.22 (3H, t), 1.51-1.68 (3H, m), 1.81-1.98 (2H, m), 2.03-2.12 (1H, m), 2.14-2.27 (2H, m), 3.11-3.21 (1H, m), 3.42 (2H, q), 3.80-3.90 (1H, m), 4.31 (3H, s), 6.81 (1H, dd), 6.96 (1H, d), 7.57 (1H, d), and 41 mg of trans-diastereomer of the second title compound, $^1$H NMR (400 MHz, CDCl$_3$): 1.24 (3H, t), 1.37-1.51 (1H, m), 1.62-1.95 (5H, m), 2.23-2.40 (2H, m), 3.31-3.54 (2H, m), 3.59-3.67 (1H, m), 4.25-4.35 (1H, m), 4.38 (3H, s), 6.92 (1H, dd), 7.28 (1H, d), 7.56 (1H, d).

Example 12

4-(-3-(1H-imidazol-1-yl)cyclohexyl)(ethyl)amino)-2,6-difluorobenzonitrile a) 4-(3-(1H-imidazol-1-yl)cyclohexylamino)-2,6-difluorobenzonitrile The compound was from 3-(1H-imidazol-1-yl)cyclohexanamine (0.53 g, 3.2 mmol), 2,4,6-trifluorobenzonitrile (0.50 g, 3.2 mmol) and DIPEA (1.66 ml, 1.23 g, 9.5 mmol) in DMSO (13 ml), 100° C., 2 h. Yield 88 mg. m/z=303.5, (M+1)$^+$.

b) 4-(-3-(1H-imidazol-1-yl)cyclohexyl)(ethyl) amino)-2,6-difluorobenzonitrile

The compound was prepared from the compound of Example 12(a) (0.16 g, 0.53 mmol), 60% NaH dispersion (57 mg, 1.4 mmol) and iodoethane (0.078 ml, 0.15 g, 0.98 mmol) in DMF (4 ml), yielding, after separation of diastereomers using reversed phase preparative HPLC, 11 mg of trans-diastereomer, $^1$H NMR (400 MHz, CDCl$_3$): 1.00 (3H, t), 1.62-1.75 (2H, m), 1.78-1.94 (3H, m), 1.99-2.10 (2H, m), 2.13-2.22 (1H, m), 3.35 (2H, q), 3.73-3.80 (1H, m), 4.41-4.50 (1H, m), 6.59-6.69 (2H, m), 6.97 (1H, s), 7.06 (1H, s), 7.56 (1H, s), and 28 mg of cis-diastereomer, $^1$H NMR (400 MHz, CDCl$_3$): 1.12 (3H, t), 1.47-1.68 (3H, m), 1.82-1.91 (1H, m), 1.97-2.06 (2H, m), 2.11-2.20 (1H, m), 2.33-2.41 (1H, m), 3.23-3.37 (2H, m), 3.86-3.96 (1H, m), 4.06-4.16 (1H, m), 6.36-6.46 (2H, m), 6.98 (1H, s), 7.05 (1H, s), 7.57 (1H, s).

Example 13

4-((3-(1H-imidazol-1-yl)cyclohexyl)(ethyl)amino)-2-chloro-3-methylbenzonitrile a) 3-(1H-imidazol-1-yl)cyclohexanamine dihydrochloride Acetyl chloride (0.67 ml, 0.74 g, 9.4 mmol) was added to MeOH (5 ml) and stirred for 1 h. tert-Butyl-3-(1H-imidazol-1-yl)cyclohexylcarbamate (cis-enantiomer 1) (0.25 g, 0.94 mmol) dissolved in MeOH (5 ml) was added, and the resulting solution was stirred overnight and evaporated. Yield 0.22 g (cis-enantiomer 1). m/z=166.2, (M+1)$^+$.

b) 4-(3-(1H-imidazol-1-yl)cyclohexylamino)-2-chloro-3-methylbenzonitrile

A mixture of the compound of Example 13(a), cis-enantiomer 1, (0.22 g, 0.92 mmol), 2-chloro-4-fluoro-3-methylbenzonitrile (0.16 g, 0.92 mmol) and Cs$_2$CO$_3$ (0.90 g, 2.8 mmol) in DMSO (4 ml) was heated for 3 h at 140° C. Water was added and the mixture was extracted with EtOAc. The combined organic phases were washed with water and brine, dried and evaporated. The residue was purified by flash chromatography. Yield 60 mg (cis-enantiomer 1). m/z=315.6, (M+1)$^+$.

c) 4-((3-(1H-imidazol-1-yl)cyclohexyl)(ethyl) amino)-2-chloro-3-methylbenzonitrile The title compound was prepared from the compound of Example 13(b), cis-enantiomer 1, (60 mg, 0.19 mmol), 60% NaH dispersion (23 mg, 0.58 mmol) and iodoethane (0.033 ml, 64 mg, 0.41 mmol) in DMF (3 ml), yielding 15 mg of the title compound (cis-enantiomer 1). $^1$H NMR (400 MHz, CDCl$_3$): 0.92 (3H, t), 1.24-1.64 (3H, m), 1.74-1.84 (1H, m), 1.88-2.14 (3H, m), 2.17-2.24 (1H, m), 2.37 (3H, s), 2.84-2.96 (1H, m), 3.08-3.22 (2H, m), 3.86-3.98 (1H, m), 6.94 (1H, broad s), 7.00-7.09 (2H, m), 7.46 (1H, d), 7.52 (1H, broad s).

Example 14

4-((3-(1H-imidazol-1-yl)cyclohexyl)(ethyl)amino)-2-chloro-3-methylbenzonitrile a) 3-(1H-imidazol-1-yl)cyclohexanamine dihydrochloride The title compound was prepared as in Example 13(a) using tert-butyl 3-(1H-imidazol-1-yl)cyclohexylcarbamate (cis-enantiomer 2) (0.16 g, 0.60 mmol) yielding 0.14 g of the title compound (cis-enantiomer 2). m/z=166.1, (M+1)$^+$.

b) 4-(3-(1H-imidazol-1-yl)cyclohexylamino)-2-chloro-3-methylbenzonitrile

A mixture of 2-chloro-4-iodo-3-methyl benzonitrile (0.16 g, 0.59 mmol), the compound of Example 14(a), cis-enantiomer 2, (0.14 g, 0.59 mmol) and Cs$_2$CO$_3$ (0.77 g, 2.4 mmol) in DMF (8 ml) was bubbled with N$_2$. X-Phos (71 mg, 0.15 mmol) and Pd$_2$(dba)$_3$ (53 mg, 0.06 mmol) were added. The mixture was heated for 21 h at 90° C. NH$_4$Cl solution and water were added, and the mixture was extracted with EtOAc. The combined organic phases were washed with water and brine, dried and evaporated. The residue was purified using flash chromatography yielding 20 mg of the title compound (cis-enantiomer 2). m/z=315.3, (M+1)$^+$.

c) 4-((3-(1H-imidazol-1-yl)cyclohexyl)(ethyl) amino)-2-chloro-3-methylbenzonitrile The compound was prepared from the compound of Example 14(b), cis-enantiomer 2, (20 mg, 0.06 mmol), 60% NaH dispersion (10 mg, 0.25 mmol) and iodoethane (0.020 ml, 40 mg, 0.25 mmol) in DMF (2 ml), yielding 5 mg of the title compound (cis-enantiomer 2). $^1$H NMR (400 MHz, CDCl$_3$): 0.92 (3H, t), 1.24-1.64 (3H, m), 1.74-1.84 (1H, m), 1.88-2.14 (3H, m), 2.17-2.24 (1H, m), 2.37 (3H, s), 2.84-

2.96 (1H, m), 3.08-3.22 (2H, m), 3.86-3.98 (1H, m), 6.94 (1H, broad s), 7.00-7.09 (2H, m), 7.46 (1H, d), 7.52 (1H, broad s).

Example 15

4-((6,6-Dimethyl-3-(1H-1,2,4-triazol-1-yl)cyclohex-2-enyl)(ethyl)amino)-2-(trifluoromethyl)benzonitrile a) 6,6-Dimethyl-3-(1H-1,2,4-triazol-1-yl)cyclohex-2-enone 1,2,4-Triazole sodium salt (0.80 g, 8.8 mmol) was dissolved in DMF (10 ml). 3-Chloro-6,6-dimethylcyclohex-2-enone (1.00 g, 6.3 mmol) was added. The mixture was stirred for 2.5 h at 90° C. Water was added and the mixture was extracted with EtOAc. The combined organic phases were washed with water and brine, dried and evaporated. Yield 1.20 g. m/z=192.5, (M+1)$^+$.

b) 6,6-Dimethyl-3-(1H-1,2,4-triazol-1-yl)cyclohex-2-enol

The compound was prepared from the compound of Example 15(a) (1.08 g, 5.7 mmol), CeCl$_3$.7H$_2$O (2.32 g, 6.2 mmol) and NaBH$_4$ (0.26 g, 6.8 mmol) in MeOH (15 ml). Yield 0.96 g. m/z=194.5, (M+1)$^+$.

c) 1-(3-Azido-4,4-dimethylcyclohex-1-enyl)-1H-1,2,4-triazole

The compound was prepared from the compound of Example 15(b) (0.95 g, 4.9 mmol), DPPA (1.59 ml, 2.03 g, 7.4 mmol) and DBU (1.18 ml, 1.20 g, 7.9 mmol) in a mixture of toluene (20 ml) and THF (20 ml). Yield 0.90 g. m/z=219.6, (M+1)$^+$.

d) 6,6-Dimethyl-3-(1H-1,2,4-triazol-1-yl)cyclohex-2-enamine

The compound was prepared from the compound of Example 15(c) (0.89 g, 4.1 mmol) and PPh$_3$ (2.14 g, 8.2 mmol) in MeOH (25 ml). Yield 0.55 g. m/z=193.2, (M+1)$^+$.

e) 4-(6,6-Dimethyl-3-(1H-1,2,4-triazol-1-yl)cyclohex-2-enylamino)-2-(trifluoromethyl)benzonitrile The compound was prepared from the compound of Example 15(d) (0.54 g, 2.8 mmol), 4-fluoro-2-(trifluoromethyl)benzonitrile (0.53 g, 2.8 mmol) and DIPEA (1.22 ml, 0.91 g, 7.0 mmol) in DMSO (9 ml), 4.5 h, 120° C. Yield 0.63 g. m/z=362.7, (M+1)$^+$.

f) 4-((6,6-Dimethyl-3-(1H-1,2,4-triazol-1-yl)cyclohex-2-enyl)(ethyl)amino)-2-(trifluoromethyl)benzonitrile The compound was prepared from the compound of Example 15(e) (0.62 g, 1.7 mmol), 60% NaH dispersion (0.14 g, 3.4 mmol) and iodoethane (0.27 ml, 0.54 g, 3.4 mmol) in DMF (10 ml), yielding 0.51 g of the title compound as a racemic mixture. Enantiomers were separated using preparative HPLC (Daicel Chiralpack AD, 4.8 cm×27 cm, 80% heptane—20% EtOH, 220 ml/min, run time 15 min) from 300 mg of racemic mixture, yielding 133 mg of enantiomer 1 (rt 5.6 min) and 122 mg of enantiomer 2 (rt 8.8 min). $^1$H NMR (400 MHz, CDCl$_3$): 0.99 (3H, s), 1.11 (3H, s), 1.16-1.23 (2H, m), 2.59-2.69 (1H, m), 2.73-2.83 (1H, m), 3.44-3.54 (2H, m), 4.49-4.57 (1H, m), 6.22-6.26 (1H, m), 6.93 (1H, dd), 7.09 (1H, d), 7.60 (1H, d), 8.01 (1H, s), 8.31 (1H, s).

Example 16

4-((6,6-Dimethyl-3-(1H-1,2,4-triazol-1-yl)cyclohex-2-enyl)(methyl)amino)-2-(trifluoromethyl)benzonitrile The compound was prepared from the compound of Example 15(e) (0.52 g, 1.4 mmol), 60% NaH dispersion (0.12 g, 2.9 mmol) and iodomethane (0.18 ml, 0.41 g, 2.9 mmol) in DMF (8 ml), yielding 0.35 g of the title compound as a racemic mixture. Enantiomers were separated using preparative HPLC (Daicel Chiralpack IA, 2 cm×25 cm, 95% TBME+0.2% DEA–5% EtOH+0.2% DEA, 20 ml/min, run time 30 min) yielding 115 mg of enantiomer 1 (rt 15 min) and 78 mg of enantiomer 2 (rt 20 min). $^1$H NMR (400 MHz, CDCl$_3$): 0.99 (3H, s), 1.12 (3H, s), 1.75-1.88 (2H, m), 2.58-2.69 (1H, m), 2.75-2.85 (1H, m), 2.99 (3H, s), 4.55-4.61 (1H, m), 6.12-6.17 (1H, m), 6.95 (1H, dd), 7.09 (1H, d), 7.61 (1H, d), 8.00 (1H, s), 8.33 (1H, s).

Example 17

(S)-4-(ethyl(1-(pyrimidin-4-yl)pyrrolidin-3-yl)amino)-2-(trifluoromethyl)benzonitrile a) (S)-4-((1-(2-chloropyrimidin-4-yl)pyrrolidin-3-yl)(ethyl)amino)-2-(trifluoromethyl)benzonitrile (S)-4-(ethyl(pyrrolidin-3-yl)amino)-2-(trifluoromethyl)benzonitrile hydrochloride (0.40 g, 1.3 mmol) and 2,4-dichloropyrimidine (0.24 g, 1.6 mmol) were dissolved in MeOH (6 ml). DIPEA (0.76 ml, 0.57 g, 4.4 mmol) was added, and the mixture was stirred for 3 h at RT. Silica was added and the solution was evaporated. Purification by flash chromatography yielded 0.22 g of the title compound. m/z=396.7, (M+1)$^+$.

b) (S)-4-(ethyl(1-(pyrimidin-4-yl)pyrrolidin-3-yl)amino)-2-(trifluoromethyl)-benzonitrile The compound of Example 17(a) (0.22 g, 0.56 mmol) and anhydrous NaOAc (91 mg, 1.1 mmol) were dissolved in EtOH (15 ml). 10% Pd/C (0.12 g) was added, and the mixture was hydrogenated at atmospheric pressure for 6 h. The catalyst was filtered off and the solvent was evaporated. The residue was dissolved in EtOAc and washed with water and brine, dried and evaporated. Yield 0.15 g. $^1$H NMR (400 MHz, CDCl$_3$): 1.26 (3H, t), 2.22-2.32 (1H, m), 2.37-2.46 (1H, m), 3.38-3.61 (4H, m), 3.76 (1H, broad s), 3.91 (1H, broad s), 4.52-4.64 (1H, m), 6.34 (1H, d), 6.90 (1H, dd), 7.05 (1H, d), 7.63 (1H, d), 8.24 (1H, d), 8.64 (1H, s).

Example 18

4-((2,2-Dimethyl-5-(1H-1,2,4-triazol-1-yl)cyclohexyl)(ethyl)amino)-2-(trifluoromethyl)benzonitrile The compound of Example 15(f), racemic, (0.15 g, 0.39 mmol) was dissolved in MeOH (10 ml) and hydrogenated (10% Pd/C, RT, 10 bar) in H-Cube yielding 26 mg of the title compound (cis-diastereomer). $^1$H NMR (400 MHz, CDCl$_3$): 0.97 (3H, s), 1.14 (3H, t), 1.18 (3H, s), 1.54-1.75 (2H, m), 1.99-2.19 (3H, m), 2.45-2.54 (1H, m), 3.46 (2H, q), 3.87-3.93 (1H, m), 4.36-4.46 (1H, m), 6.93 (1H, dd), 7.09 (1H, d), 7.58 (1H, d), 7.98 (1H, s), 8.16 (1H, s).

Example 19

4-((3-(1,3,4-Oxadiazol-2-yl)cyclohexyl)(ethyl)amino)-2-(trifluoromethyl)benzonitrile a) Methyl 3-(4-cyano-3-(trifluoromethyl)phenylamino)cyclohexanecarboxylate The compound was prepared from cis-diastereomer of methyl 3-aminocyclohexanecarboxylate (1.00 g, 6.4 mmol) (WO 2011/110612), 4-fluoro-2-(trifluoromethyl)benzonitrile (1.20 g, 6.4 mmol) and DIPEA (2.77 ml, 2.06 g, 15.9 mmol) in DMSO (15 ml), 3 h, 100° C., yielding 1.01 g of the title compound (cis-diastereomer). m/z=327.4, (M+1)$^+$.

b) 3-(4-Cyano-3-(trifluoromethyl)phenylamino)cyclohexanecarbohydrazide

The compound of Example 19(a), cis-diastereomer, (1.00 g, 3.1 mmol) was dissolved in 1-BuOH (10 ml) and hydrazine monohydrate (0.75 ml, 0.77 g, 15.3 mmol) was added. The mixture was heated for 12 h at 130° C. Water was added and the mixture was extracted with EtOAc, washed with water and brine, dried and evaporated yielding 0.88 g of the title compound (cis-diastereomer). m/z=327.4, (M+1)$^+$.

c) 4-(3-(1,3,4-Oxadiazol-2-yl)cyclohexylamino)-2-(trifluoromethyl)benzonitrile

A mixture of the compound of Example 19(b), cis-diastereomer, (0.88 g, 2.7 mmol) and triethyl orthoformate (3.59 ml, 3.20 g, 21.6 mmol) was heated for 3 h at 160° C. After evaporation, the residue was triturated with 1:1 heptane/Et$_2$O and Et$_2$O yielding 0.50 g of the title compound (cis-diastereomer). m/z=337.3, (M+1)$^+$.

d) 4-((3-(1,3,4-Oxadiazol-2-yl)cyclohexyl)(ethyl)amino)-2-(trifluoromethyl)-benzonitrile The compound was prepared from the compound of Example 19(c), cis-diastereomer, (0.50 g, 1.5 mmol), 60% NaH dispersion (0.12 g, 3.0 mmol) and iodoethane (0.24 ml, 0.46 g, 3.0 mmol) in DMF (10 ml), 4 h, yielding 0.22 g of the title compound (cis-diastereomer). Enantiomers were separated using preparative HPLC (Daicel Chiralpack IA, 2 cm×25 cm, 97% TBME+0.2% DEA−3% THF+0.2% DEA, 20 ml/min, run time 35 min) yielding 87 mg of cis-enantiomer 1 (rt 14 min) and 86 mg of cis-enantiomer 2 (rt 19 min). $^1$H NMR (400 MHz, CDCl$_3$): 1.23 (3H, t), 1.53-1.68 (5H, m), 1.84-2.16 (3H, m), 2.19-2.34 (2H, m), 3.09-3.20 (1H, m), 3.42 (2H, q), 3.78-3.89 (1H, m), 6.81 (1H, dd), 6.96 (1H, d), 7.59 (1H, d), 8.35 (1H, s).

Example 20

4-(Ethyl(3-(4-isopropyl-4H-1,2,4-triazol-3-yl)cyclohexyl)amino)-2-(trifluoromethyl)benzonitrile The compound of Example 19, cis-diastereomer, (0.15 g, 0.41 mmol), isopropylamine (0.11 ml, 73 mg, 1.2 mmol) and pyridinium acetate (0.46 g, 3.3 mmol) were microwave heated for 12 h at 110° C. The mixture was diluted with DCM and washed with water and brine, dried and evaporated. The residue was purified using flash chromatography yielding 17 mg of the title compound (cis-diastereomer). $^1$H NMR (400 MHz, CDCl$_3$): 1.21 (3H, t), 1.48-1.57 (6H, m), 1.56-2.12 (8H, m), 2.81-2.92 (1H, m), 3.44 (2H, q), 3.77-3.87 (1H, m), 4.29-4.40 (1H, m), 6.81 (1H, dd), 6.95 (1H, d), 7.57 (1H, d), 8.17 (1H, s).

Example 21

4-((3-(1H-imidazol-1-yl)-6,6-dimethylcyclohex-2-enyl)(ethyl)amino)-2-chlorobenzonitrile (enantiomer 1)

a) 3-(1H-imidazol-1-yl)-6,6-dimethylcyclohex-2-enamine (enantiomer 1)

Compound of Example 96(e) (150.71 g, 788 mmol) dissolved in 950 ml of methanol was heated to 60° C. D-(−)-tartaric acid (118 g, 788 mmol) in 320 ml of methanol was added at 60-65° C. Thereafter the solution was slowly cooled to 45° C. and stirring was continued at 45° C. for 30 min. Then the mixture was slowly cooled to RT. Stirring was continued at RT for 2.5 h. The precipitate was filtered off at RT, washed with ice-cold methanol (2×100 ml) and dried overnight at 40° C. under vacuum. Yield 127.66 g, HPLC optical purity 80.4%. The precipitate was dissolved in the mixture of methanol (2067 ml) and water (10 ml) at 65° C. Hot solution was allowed to cool slowly to RT overnight. Then the precipitate was filtered off at RT, washed with ice-cold methanol and dried at 40° C. under vacuum overnight to give the title compound (enantiomer 1) as a salt of D-(−)-tartaric acid. Yield 73.90 g, HPLC optical purity 94.8%. The salt was dissolved in water. The solution was made basic (pH >9) with aqueous NaOH and extracted with DCM (4×). The combined organic phases were washed with water and brine, dried, filtered and evaporated to obtain the enantiomer 1 as a free base. $^1$H NMR (400 MHz, CDCl$_3$): d 0.91 (3H, s), 1.03 (3H, s), 1.52-1.62 (1H, m), 1.67-1.75 (1H, m), 2.45 (1H, m), 3.19 (1H, m), 5.70 (1H, m), 7.07 (1H, s), 7.13 (1H, s), 7.70 (1H, s).

b) 4-(3-(1H-imidazol-1-yl)-6,6-dimethylcyclohex-2-enylamino)-2-chlorobenzonitrile (enantiomer 1)

The compound was prepared from the compound of Example 21(a), enantiomer 1, (0.30 g, 1.6 mmol), 2-chloro-4-fluorobenzonitrile (0.25 g, 1.6 mmol) and DIPEA (0.69 ml, 0.51 g, 4.0 mmol) in DMSO (4 ml), 5 h, 100° C. Yield 0.19 g. m/z=327.3, (M+1)$^+$.

c) 4-((3-(1H-imidazol-1-yl)-6,6-dimethylcyclohex-2-enyl)(ethyl)amino)-2-chlorobenzonitrile (enantiomer 1)

The compound was prepared from the compound of Example 21(b), enantiomer 1, (0.13 g, 0.40 mmol), 60% NaH dispersion (47 mg, 1.2 mmol) and iodoethane (0.084 ml, 0.16 g, 1.1 mmol) in DMF (4 ml), yielding 81 mg of the title compound (enantiomer 1). $^1$H NMR (400 MHz, CDCl$_3$): 0.97 (3H, s), 1.10 (3H, s), 1.18 (3H, t), 1.66-1.83 (2H, m), 2.49-2.69 (2H, m), 3.43 (2H, q), 4.39-4.46 (1H, m), 5.70 (1H, d), 6.70 (1H, dd), 6.83 (1H, d), 7.13 (1H, s), 7.16 (1H, s), 7.44 (1H, d), 7.76 (1H, s).

Example 22

4-((3-(1H-imidazol-1-yl)-6,6-dimethylcyclohex-2-enyl)(methyl)amino)-2-chlorobenzonitrile (enantiomer 1)

The compound was prepared from the compound of Example 21(b), enantiomer 1, (60 mg, 0.18 mmol), 60% NaH dispersion (30 mg, 0.75 mmol) and iodomethane (0.024 ml, 55 mg, 0.39 mmol) in DMF (2 ml). Yield 47 mg. $^1$H NMR (400 MHz, CDCl$_3$): 0.96 (3H, s), 1.10 (3H, s), 1.69-1.84 (2H, m), 2.50-2.70 (2H, m), 2.93 (3H, s), 4.45-4.51 (1H, m), 5.62 (1H, d), 6.73 (1H, dd), 6.83 (1H, d), 7.13 (1H, s), 7.17 (1H, s), 7.44 (1H, d), 7.76 (1H, s).

Example 23

4-((6,6-dimethyl-3-(1H-1,2,3-triazol-1-yl)cyclohex-2-en-1-yl)(ethyl)amino)-2-(trifluoromethyl)benzonitrile a) 6,6-dimethyl-3-(1H-1,2,3-triazol-1-yl)cyclohex-2-enone and 6,6-dimethyl-3-(2H-1,2,3-triazol-2-yl)cyclohex-2-enone A mixture of 3-chloro-6,6-dimethylcyclohex-2-enone (5.00 g, 31.5 mmol), 1H-1,2,3-triazole (4.35 g, 63.0 mmol) and TEA (16 g, 22 ml, 158 mmol) in toluene (30 ml) was stirred for 5 h at 80° C. The mixture was diluted with DCM and washed with water and brine, dried, and evaporated. The regioisomers were separated using flash chromatography yielding 0.75 g of 6,6-dimethyl-3-(1H-1,2,3-triazol-1-yl)cyclohex-2-enone, m/z=192.2, (M+1)+, and 1.04 g of 6,6-dimethyl-3-(2H-1,2,3-triazol-2-yl)cyclohex-2-enone. m/z=192.2, (M+1)$^+$.

b) 6,6-Dimethyl-3-(1H-1,2,3-triazol-1-yl)cyclohex-2-enol

The compound was prepared from 6,6-dimethyl-3-(1H-1,2,3-triazol-1-yl)cyclohex-2-enone (0.74 g, 3.9 mmol), CeCl$_3$.7H$_2$O (1.59 g, 4.3 mmol) and NaBH$_4$ (0.18 g, 4.6 mmol) in MeOH (30 ml). Yield 0.73 g. m/z=194.2, (M+1)$^+$.

c) 1-(3-Azido-4,4-dimethylcyclohex-1-en-1-yl)-1H-1,2,3-triazole

The compound was prepared from the compound of Example 23(b) (0.72 g, 3.7 mmol), DPPA (1.33 g, 1.04 ml, 4.8 mmol) and DBU (0.85 g, 0.84 ml, 5.6 mmol) in toluene (15 ml) and THF (5 ml) yielding 1.13 g of impure title compound which was used in the next step without purification. m/z=219.6, (M+1)$^+$.

d) 6,6-Dimethyl-3-(1H-1,2,3-triazol-1-yl)cyclohex-2-enamine

The compound was prepared from the compound of Example 23(c) (1.10 g) and PPh$_3$ (1.95 g, 7.4 mmol) in MeOH (20 ml). Yield 0.46 g. m/z=193.2, (M+1)$^+$.

e) 4-((6,6-Dimethyl-3-(1H-1,2,3-triazol-1-yl)cyclohex-2-en-1-yl)amino)-2-(trifluoromethyl)benzonitrile The compound was prepared from the compound of Example 23(d) (0.46 g, 2.4 mmol), 4-fluoro-2-(trifluoromethyl)benzonitrile (0.45 g, 2.4 mmol) and DIPEA (0.77 g, 1.04 ml, 6.0 mmol) in DMSO (4 ml). Yield 0.47 g. m/z=362.7, (M+1)$^+$.

f) 4-((6,6-Dimethyl-3-(1H-1,2,3-triazol-1-yl)cyclohex-2-en-1-yl)(ethyl)-amino)-2-(trifluoromethyl)benzonitrile The compound was prepared from the compound of Example 23(e) (0.24 g, 0.65 mmol), 60% NaH dispersion (0.052 g, 1.3 mmol) and iodoethane (0.20 g, 0.11 ml, 1.3 mmol) in DMF (4 ml) yielding 0.18 g of the title compound as a racemic mixture. Enantiomers were separated using preparative HPLC (Daicel Chiralpack IA, 2 cm×25 cm, 95% TBME+0.2% DEA–5% THF+0.2% DEA, 20 ml/min, run time 30 min) yielding enantiomer 1 (rt 9 min) and enantiomer 2 (rt 15 min). $^1$H NMR (400 MHz, CDCl$_3$): δ 1.01 (3H, s), 1.13 (3H, s), 1.21 (3H, t), 1.73-1.87 (2H, m), 2.68-2.80 (1H, m), 2.87-2.98 (1H, m), 3.45-3.56 (2H, m), 4.52-4.59 (1H, m), 6.19-6.25 (1H, m), 6.95 (1H, dd), 7.10 (1H, d), 7.59 (1H, d), 7.77 (1H, d), 7.82 (1H, d).

Example 24

4-((6,6-Dimethyl-3-(1H-1,2,3-triazol-1-yl)cyclohex-2-en-1-yl)(methyl)-amino)-2-(trifluoromethyl)benzonitrile The compound was prepared from the compound of Example 23(e) (0.24 g, 0.65 mmol), 60% NaH dispersion (0.052 g, 1.3 mmol) and iodomethane (0.19 g, 0.081 ml, 1.3 mmol) in DMF (4 ml) yielding 0.22 g of the title compound as a racemic mixture. Enantiomers were separated using preparative HPLC (Daicel Chiralpack IA, 2 cm×25 cm, 97% TBME+0.2% DEA–3% EtOH+0.2% DEA, 20 ml/min, run time 15 min) yielding 78 mg of enantiomer 1 (rt 10 min) and 77 mg of enantiomer 2 (rt 13 min). $^1$H NMR (400 MHz, CDCl$_3$): 1.01 (3H, s), 1.13 (3H, s), 1.76-1.90 (2H, m), 2.70-2.80 (1H, m), 2.89-2.99 (1H, m), 3.00 (3H, s), 4.58-4.64 (1H, m), 6.10-6.15 (1H, m), 6.96 (1H, dd), 7.10 (1H, d), 7.61 (1H, d), 7.77 (1H, d), 7.81 (1H, d).

Example 25

4-((6,6-Dimethyl-3-(2H-1,2,3-triazol-2-yl)cyclohex-2-en-1-yl)(ethyl)amino)-2-(trifluoromethyl)benzonitrile a) 6,6-Dimethyl-3-(2H-1,2,3-triazol-2-yl)cyclohex-2-enol The compound was prepared 6,6-dimethyl-3-(2H-1,2,3-triazol-1-yl)cyclohex-2-enone of Example 23(a) (1.85 g, 9.7 mmol), CeCl$_3$.7H$_2$O (3.96 g, 10.6 mmol) and NaBH$_4$ (0.44 g, 11.6 mmol) in MeOH (80 ml). Yield 1.87 g. m/z=194.2, (M+1)$^+$.

b) 1-(3-Azido-4,4-dimethylcyclohex-1-en-1-yl)-2H-1,2,3-triazole

The compound was prepared from the compound of Example 25(a) (1.87 g, 9.7 mmol), DPPA (3.46 g, 2.71 ml, 12.6 mmol) and DBU (2.21 g, 2.17 ml, 14.5 mmol) in toluene (30 ml) yielding 2.91 g of crude title compound which was used in the next step without purification. m/z=219.2, (M+1)$^+$.

c) 6,6-Dimethyl-3-(2H-1,2,3-triazol-1-yl)cyclohex-2-enamine

The compound was prepared from the compound of Example 25(b) (2.90 g) and PPh₃ (5.05 g, 19.2 mmol) in MeOH (50 ml). Yield 1.18 g. m/z=193.2, (M+1)⁺.

d) 4-((6,6-Dimethyl-3-(2H-1,2,3-triazol-1-yl)cyclohex-2-en-1-yl)amino)-2-(trifluoromethyl)benzonitrile The compound was prepared from the compound of Example 25(c) (1.17 g, 6.1 mmol), 4-fluoro-2-(trifluoromethyl)benzonitrile (1.15 g, 6.1 mmol) and DIPEA (1.97 g, 2.65 ml, 15.2 mmol) in DMSO (10 ml). Yield 0.90 g. m/z=362.3, (M+1)⁺.

e) 4-((6,6-Dimethyl-3-(2H-1,2,3-triazol-1-yl)cyclohex-2-en-1-yl)(ethyl)-amino)-2-(trifluoromethyl)benzonitrile The compound was prepared from the compound of Example 25(d) (0.45 g, 1.2 mmol), 60% NaH dispersion (0.10 g, 2.5 mmol) and iodoethane (0.39 g, 0.20 ml, 2.5 mmol) in DMF (8 ml) yielding 0.37 g of the title compound as a racemic mixture. Enantiomers were separated using preparative HPLC (Daicel Chiralpack IA, 2 cm×25 cm, 90% hexane+0.2% DEA–10% EtOH+0.2% DEA, 20 ml/min, run time 30 min) yielding enantiomer 1 (0.15 g, rt 8 min) and enantiomer 2 (0.16 g, rt 13 min). ¹H NMR (400 MHz, CDCl₃): 0.99 (3H, s), 1.11 (3H, s), 1.20 (3H, t), 1.68-1.86 (2H, m), 2.75-2.87 (1H, m), 2.93-3.03 (1H, m), 3.42-3.60 (2H, m), 4.50-4.60 (1H, m), 6.45-6.50 (1H, m), 6.93 (1H, dd), 7.10 (1H, d), 7.59 (1H, d), 7.72 (2H, s).

Example 26

4-((6,6-Dimethyl-3-(2H-1,2,3-triazol-1-yl)cyclohex-2-en-1-yl)(methyl)-amino)-2-(trifluoromethyl)benzonitrile The compound was prepared from the compound of Example 25(d) (0.45 g, 1.2 mmol), 60% NaH dispersion (0.10 g, 2.5 mmol) and iodomethane (0.35 g, 0.16 ml, 2.5 mmol) in DMF (8 ml) yielding 0.34 g of the title compound as a racemic mixture. Enantiomers were separated using preparative HPLC (Daicel Chiralpack IA, 2 cm×25 cm, 80% hexane+0.2% DEA–20% EtOH+0.2% DEA, 20 ml/min, run time 25 min) yielding 0.14 g of enantiomer 1 (rt 13 min) and 0.14 g of enantiomer 2 (rt 16 min). ¹H NMR (400 MHz, CDCl₃): 0.99 (3H, s), 1.12 (3H, s), 1.72-1.88 (2H, m), 2.79-2.89 (1H, m), 2.93-3.03 (1H, m), 3.00 (3H, s), 4.58-4.64 (1H, m), 6.36-6.41 (1H, m), 6.96 (1H, dd), 7.10 (1H, d), 7.60 (1H, d), 7.73 (2H, s).

Example 27

N-(3-(1H-imidazol-1-yl)-6,6-dimethylcyclohex-2-en-1-yl)-N,3-dimethyl-4-nitroaniline a) N-(3-(1H-imidazol-1-yl)-6,6-dimethylcyclohex-2-en-1-yl)-3-methyl-4-nitroaniline The compound was prepared from 3-(1H-imidazol-1-yl)-6,6-dimethylcyclohex-2-enamine (0.30 g, 1.6 mmol), 4-fluoro-2-methyl-1-nitrobenzene (0.24 g, 1.6 mmol) and DIPEA (0.51 g, 0.68 ml, 3.9 mmol) in DMSO (5 ml). Yield 0.065 g. m/z=327.3, (M+1)⁺.

b) N-(3-(1H-imidazol-1-yl)-6,6-dimethylcyclohex-2-en-1-yl)-N,3-dimethyl-4-nitroaniline The compound was prepared from the compound of Example 27(a) (0.065 g, 0.20 mmol), 60% NaH dispersion (16 mg, 0.4 mmol) and iodomethane (0.057 g, 0.025 ml, 0.4 mmol) in DMF (2 ml). Yield 24 mg. ¹H NMR (400 MHz, CDCl₃): 0.97 (3H, s), 1.11 (3H, s), 1.69-1.85 (2H, m), 2.50-2.72 (2H, m), 2.67 (3H, s), 2.97 (3H, s), 4.55-4.61 (1H, m), 5.63-5.67 (1H, m), 6.58 (1H, d), 6.69 (1H, dd), 7.16 (1H, broad s), 7.22 (1H, broad s), 7.79 (1H, broad s), 8.12 (1H, dd).

Example 28

4-((3-(1H-imidazol-1-yl)-6,6-dimethylcyclohex-2-en-1-yl)(methyl)amino)-2-fluorobenzonitrile a) 4-((3-(1H-imidazol-1-yl)-6,6-dimethylcyclohex-2-en-1-yl)amino)-2-fluorobenzonitrile The compound was prepared from 3-(1H-imidazol-1-yl)-6,6-dimethylcyclohex-2-enamine (0.30 g, 1.6 mmol), 4-bromo-2-fluorobenzonitrile (0.31 g, 1.6 mmol), sodium tert-butoxide (0.21 g, 2.2 mmol), Pd₂(dba)₃ (0.072 g, 0.08 mmol) and rac-BINAP (0.098 g, 0.16 mmol) in toluene (10 ml). Yield 0.15 g. m/z=311.3, (M+1)⁺.

b) 4-((3-(1H-imidazol-1-yl)-6,6-dimethylcyclohex-2-en-1-yl)(methyl)amino)-2-fluorobenzonitrile The compound was prepared from the compound of Example 28(a) (0.15 g, 0.48 mmol), iodomethane (0.14 g, 0.06 ml, 0.97 mmol) in DMF (3 ml) and 60% NaH dispersion (39 mg, 0.97 mmol). Yield 14 mg. ¹H NMR (400 MHz, CDCl₃): 0.97 (3H, s), 1.10 (3H, s), 1.68-1.85 (2H, m), 2.49-2.71 (2H, m), 2.92 (3H, s), 4.43-4.48 (1H, m), 5.62-5.66 (1H, m), 6.52 (1H, dd), 6.61 (1H, dd), 7.14 (1H, broad s), 7.17 (1H, broad s), 7.37-7.43 (1H, m), 7.81 (1H, broad s).

Example 29

N-(3-(1H-imidazol-1-yl)-6,6-dimethylcyclohex-2-en-1-yl)-N-(4-cyano-3-(trifluoromethyl)phenyl)acetamide The compound was prepared from the compound of Example 96(f), enantiomer 1, (0.16 g, 0.44 mmol), 60% NaH dispersion (36 mg, 0.89 mmol) and acetyl chloride (0.070 g, 0.063 ml, 0.89 mmol) in DMF (2 ml), yielding, after purification using reversed phase preparative HPLC, 5 mg of the title compound, enantiomer 1. ¹H NMR (400 MHz, CDCl₃): 1.09 (3H, s), 1.14 (3H, s), 1.23-1.44 (2H, m), 1.88 (3H, s), 2.15-2.26 (1H, m), 2.34-2.46 (1H, m), 5.31-5.65 (1H, m), 5.76-5.83 (1H, m), 7.08 (1H, broad s), 7.14 (1H, broad s), 7.57 (1H, d), 7.66 (1H, s), 7.69 (1H, broad s), 7.88 (1H, d).

Example 30

4-((3-(1H-imidazol-1-yl)-6,6-dimethylcyclohex-2-en-1-yl)(methyl)amino)-2-(difluoromethyl)benzonitrile a) 4-((3-(1H-imidazol-1-yl)-6,6-dimethylcyclohex-2-en-1-yl)amino)-2-(difluoromethyl)benzonitrile The compound was prepared from 3-(1H-imidazol-1-yl)-6,6-dimethylcyclohex-2-enamine (0.44 g, 2.3 mmol), 2-(difluoromethyl)-4-fluorobenzonitrile (0.36 g, 2.3 mmol) and DIPEA (0.82 g, 1.10 ml, 6.3 mmol) in DMSO (8 ml). Yield 0.24 g. m/z=343.3, (M+1)$^+$.

b) 4-((3-(1H-imidazol-1-yl)-6,6-dimethylcyclohex-2-en-1-yl)(methyl)amino)-2-(difluoromethyl)benzonitrile The compound was prepared from the compound of Example 30(a) (0.24 g, 0.70 mmol), 60% NaH dispersion (42 mg, 1.1 mmol) and iodomethane (0.12 g, 0.052 ml, 0.84 mmol) in DMF (4 ml) yielding, after purification using reversed phase preparative HPLC, 12 mg of the title compound. $^1$H NMR (400 MHz, CDCl$_3$): 0.97 (3H, s), 1.11 (3H, s), 1.70-1.85 (2H, m), 2.50-2.73 (2H, m), 2.97 (3H, s), 4.54-4.59 (1H, m), 5.62-5.66 (1H, m), 6.87 (1H, t), 6.90 (1H, dd), 7.08 (1H, d), 7.13 (1H, s), 7.17 (1H, s), 7.55 (1H, d), 7.76 (1H, s).

Example 31

4-((3-(1H-imidazol-1-yl)-6,6-dimethylcyclohex-2-enyl)(ethyl)amino)-2-(difluoromethyl)benzonitrile The compound was prepared from the compound of Example 30(a) (0.36 g, 1.0 mmol), 60% NaH dispersion (62 mg, 1.6 mmol) and iodoethane (0.19 g, 0.10 ml, 1.2 mmol) in DMF (5 ml) yielding 60 mg of the title compound after purification using reversed phase HPLC as a racemic mixture. Enantiomers were separated using preparative HPLC (Daicel Chiralpack IA, 2 cm×25 cm, 95% TMBE+0.2% DEA−5% THF+0.2% DEA, 20 ml/min, run time 50 min) yielding 26 mg of enantiomer 1 (rt 22 min) and 25 mg of enantiomer 2 (rt 39 min). $^1$H NMR (400 MHz, CDCl$_3$): 0.98 (3H, s), 1.11 (3H, s), 1.19 (3H, t), 1.67-1.76 (1H, m), 1.77-1.86 (1H, m), 2.51-2.71 (2H, m), 3.42-3.55 (2H, m), 4.47-4.55 (1H, m), 5.69-5.74 (1H, m), 6.85 (1H, t), 6.89 (1H, dd), 7.08 (1H, d), 7.13 (1H, s), 7.18 (1H, s), 7.53 (1H, d), 7.76 (1H, s).

Example 32

4-(Ethyl(3-(4-(2-hydroxy-2-methylpropyl)-4H-1,2,4-triazol-3-yl)cyclohexyl)-amino)-2-(trifluoromethyl)benzonitrile The compound of Example 19(d) (0.22 g, 0.60 mmol), 1-amino-2-methylpropan-2-ol (0.16 g, 1.8 mmol) and pyridinium acetate (0.67 g, 4.8 mmol) were microwave heated for 12 h at 110° C. The mixture was diluted with DCM and washed with water and brine, dried and evaporated. The residue was purified using reversed phase preparative HPLC yielding 18 mg of the title compound (cis-diastereomer). $^1$H NMR (400 MHz, CDCl$_3$): 1.20 (3H, t), 1.29 (3H, s), 1.30 (3H, s), 1.50-2.14 (9H, m), 2.95-3.15 (1H, m), 3.35-3.47 (2H, m), 3.70-3.84 (2H, m), 3.86-3.91 (1H, m), 6.79 (1H, dd), 6.93 (1H, d), 7.55 (1H, d), 8.14 (1H, s).

Example 33

4-((3-(1,3,4-Oxadiazol-2-yl)cyclohexyl)(methyl)amino)-2-(trifluoromethyl)-benzonitrile The compound was prepared from the compound of Example 19(c) (0.75 g, 2.2 mmol), 60% NaH dispersion (0.18 g, 4.5 mmol) and iodomethane (0.48 g, 0.21 ml, 3.4 mmol) in DMF (15 ml) yielding 0.21 g of the title compound (cis-diastereomer). $^1$H NMR (400 MHz, CDCl$_3$): 1.51-1.70 (3H, m), 1.86-1.99 (2H, m), 2.07-2.14 (1H, m), 2.20-2.29 (2H, m), 2.93 (3H, s), 3.11-3.21 (1H, m), 3.79-3.90 (1H, m), 6.85 (1H, dd), 6.99 (1H, d), 7.60 (1H, d), 8.35 (1H, s).

Example 34

4-(5-(1H-imidazol-1-yl)-2,2-dimethyl-3,6-dihydro-2H-pyran-3-ylamino)-2-(trifluoromethyl)benzonitrile a) 5-Chloro-2,2-dimethyl-2H-pyran-3(6H)-one The compound was prepared from 2,2-dimethyl-2H-pyran-3,5(4H,6H)-dione (2.00 g, 14.1 mmol) and oxalyl chloride (2.32 g, 1.55 ml, 18.3 mmol) in DCM (30 ml). Yield 1.82 g. $^1$H NMR (400 MHz, CDCl$_3$): 1.37 (6H, s), 4.43 (2H, s), 6.23 (1H, s).

b) 5-(1H-imidazol-1-yl)-2,2-dimethyl-2H-pyran-3(6H)-one

The compound was prepared from the compound of Example 34(a) (1.80 g, 11.2 mmol), 1H-imidazole (1.53 g, 22.4 mmol), TEA (3.40 g, 4.69 ml, 33.6 mmol) and KHCO$_3$ (0.22 g, 2.2 mmol) in toluene (12 ml). Yield 1.35 g. m/z=193.1, (M+1)$^+$.

c) 5-(1H-imidazol-1-yl)-2,2-dimethyl-3,6-dihydro-2H-pyran-3-ol

The compound was prepared from the compound of Example 34(b) (1.34 g, 7.0 mmol), CeCl$_3$.7H$_2$O (2.86 g, 7.7 mmol) and NaBH$_4$ (0.32 g, 8.4 mmol) in MeOH (35 ml). Yield 1.06 g. $^1$H NMR (400 MHz, CDCl$_3$): 1.32 (3H, s), 1.33 (3H, s), 3.92-3.99 (1H, m), 4.36-4.47 (2H, m), 5.96-6.00 (1H, m), 7.06-7.08 (1H, m), 7.12-7.14 (1H, m), 7.63-7.66 (1H, m).

d) 1-(5-Azido-6,6-dimethyl-5,6-dihydro-2H-pyran-3-yl)-1H-imidazole

The compound was prepared from the compound of Example 34(c) (1.04 g, 5.4 mmol), DPPA (1.92 g, 1.50 ml, 7.0 mml) and DBU (1.22 g, 1.20 ml, 8.0 mmol) in toluene (15 ml)/THF (13 ml). Yield 0.82 g. m/z=220.2, (M+1)$^+$.

e) 5-(1H-imidazol-1-yl)-2,2-dimethyl-3,6-dihydro-2H-pyran-3-amine

The compound of Example 34(d) (0.81 g, 3.7 mmol) was dissolved in MeOH (10 ml) and 10% Pd/C (0.10 g) was added. The mixture was hydrogenated at RT and atmospheric pressure for 2 h. The catalyst was filtered off and the solvent evaporated. Yield 0.66 g. m/z=194.2, (M+1)$^+$.

f) 4-(5-(1H-imidazol-1-yl)-2,2-dimethyl-3,6-dihydro-2H-pyran-3-ylamino)-2-(trifluoromethyl)benzonitrile The compound was prepared from the compound of Example 34(e) (0.64 g, 3.3 mmol), 4-fluoro-2-(trifluoromethyl)benzonitrile (0.63 g, 3.3 mmol) and DIPEA (1.07 g, 1.44 ml, 8.3 mmol) in DMSO (10 ml) for 6 h at 100° C. yielding, after trituration with heptane/Et$_2$O 0.24 g of the title compound. m/z=363.7, (M+1)$^+$.

g) 4-((5-(1H-imidazol-1-yl)-2,2-dimethyl-3,6-di-hydro-2H-pyran-3-yl)-(methyl)amino)-2-(trifluoromethyl)benzonitrile The compound was prepared from the compound of Example 34(f) (0.28 g, 0.77 mmol), 60% NaH dispersion (62 mg, 1.5 mmol) and iodomethane (0.17 g, 0.072 ml, 1.2 mmol) in DMF (4 ml) yielding 0.20 g of the title compound as a racemic mixture. Enantiomers were separated using preparative HPLC (Daicel Chiralpack IA, 2 cm×25 cm, 80% hexane+0.2% DEA–20% EtOH+0.2% DEA, 20 ml/min, run time 35 min) yielding 66 mg of enantiomer 1 (rt 13 min) and 64 mg of enantiomer 2 (rt 17 min). $^1$H NMR (400 MHz, CDCl$_3$): 1.20 (3H, s), 1.45 (3H, s), 3.03 (3H, s), 4.29-4.36 (1H, m), 4.46-4.66 (2H, m), 5.77-5.83 (1H, m), 6.91 (1H, dd), 7.04 (1H, d), 7.12-7.14 (1H, m), 7.15-7.18 (1H, m), 7.61 (1H, d), 7.70 (1H, s).

Example 35

4-((3-(1H-1,2,4-triazol-1-yl)cyclopentyl)(methyl)amino)-2-(trifluoromethyl)-benzonitrile The title compound was prepared from 4-(3-(1H-1,2,4-triazol-1-yl)cyclopentylamino)-2-(trifluoromethyl)benzonitrile (1.06 g, 3.3 mmol), 60% NaH dispersion (0.26 g, 6.6 mmol) and iodomethane (0.70 g, 0.31 ml, 5.0 mmol) in DMF (10 ml) yielding 0.75 g of the title compound as a racemate. Enantiomers were separated using preparative HPLC (Daicel Chiralpack IA, 2 cm×25 cm, 97% TBME+0.2% DEA–3% EtOH+0.2% DEA, 10 ml/min, run time 50 min) yielding 58 mg of trans-enantiomer 1 (rt 26 min), 92 mg of cis-enantiomer 1 (rt 27.3 min), 100 mg of cis-enantiomer 2 (rt 34.4 min) and 71 mg of trans-enantiomer 2 (rt 37.7 min). $^1$H NMR (400 MHz, CDCl$_3$): cis; 1.83-1.93 (1H, m), 2.10-2.50 (5H, m), 2.96 (3H, s), 4.81-4.97 (2H, m), 6.92 (1H, dd), 7.08 (1H, d), 7.60 (1H, d), 7.99 (1H, s), 8.12 (1H, s), trans; 2.00-2.33 (5H, m), 2-55-2.62 (1H, m), 3.04 (3H, s), 4.40-4.51 (1H, m), 4.79-4.89 (1H, m), 6.89 (1H, dd), 7.04 (1H, d), 7.59 (1H, d), 7.98 (1H, s), 8.13 (1H, s).

Example 36

4-((2,2-Dimethyl-3-(pyridin-3-yl)cyclopent-3-enyl)(ethyl)amino)-2-(trifluoromethyl)benzonitrile a) tert-Butyl (2,2-dimethyl-3-oxocyclopentyl)carbamate

To a solution of 3-amino-2,2-dimethylcyclopentanone (1.3 g, 0.010 mol) in MeCN (50 ml) were added diisopropylamine (3.1 g, 0.031 mol) and Boc$_2$O (4.5 g, 0.021 mol) and the mixture was heated at 60° C. for 3 h. The solvent was removed from the mixture and the crude residue was purified by column chromatography over silica gel using 15% EtOAc in hexane as the eluent. Yield 1.3 g. m/z 228.1 [M+H]$^+$.

b) 4-((tert-Butoxycarbonyl)amino)-5,5-dimethylcyclopent-1-en-1-yl trifluoromethanesulfonate To a mixture of the compound of Example 36(a) (0.5 g, 0.002 mol) and 1,1,1-trifluoro-N-phenyl-N-((trifluoromethyl)sulfonyl)methanesulfonamide (1.57 g, 0.004 mol) in THF (30 ml) was added potassium bis(trimethylsilyl)amide (0.5 M solution in THF, 13.2 ml, 0.007 mol) at −78° C. followed by stirring for 2 h. The mixture was quenched by 1M NaOH solution and extracted with EtOAc. The organic layer was washed with water, dried, filtered and concentrated. The crude product was purified by column chromatography over silica gel using 10% EtOAc in hexane as the eluent. Yield: 1.0 g (crude). $^1$H-NMR (400 MHz; DMSO-d$_6$: 0.90 (s, 3H), 1.09 (s, 3H), 1.40 (s, 9H), 2.21-2.31 (m, 1H), 2.52-2.61 (m, 1H), 3.93-4.04 (m, 1H), 5.61 (br, s, 1H), 11.80 (br, s, 1H).

c) tert-Butyl (2,2-dimethyl-3-(pyridin-3-yl)cyclopent-3-en-1-yl)carbamate

To a mixture of the compound of Example 36(b) (1.0 g, 2.78 mmol) and pyridin-3-ylboronic acid (0.450 g, 3.62 mmol) in toluene (40 ml) and EtOH (20 ml) were added Pd(PPh$_3$)$_4$ (0.3 g, 0.278 mmol), Na$_2$CO$_3$ (1.5 g, 13.9 mmol) and water (1 ml) under argon atmosphere. The reaction was heated at 100° C. for 2 h. The mixture was filtered through a celite bed, washed with EtOH and the filtrate was concentrated under reduced pressure. The residue was purified by column chromatography over silica gel using 30% EtOAc in hexane as the eluent to give 0.380 g of the title compound. LCMS: m/z=289.16 [M+H]$^+$.

d) 2,2-Dimethyl-3-(pyridin-3-yl)cyclopent-3-enamine hydrochloride

To a solution of the compound of Example 36(c) (0.6 g, 2.08 mmol) in 1,4-dioxane (2 ml) was added 4N HCl in 1,4-dioxane (10 ml) and the mixture was stirred at RT for 2 h. The mixture was concentrated under reduced pressure and the solid formed was triturated with Et$_2$O, filtered and dried under vacuum to give 0.402 g of the title compound. LCMS: m/z=189.13 [M+H]$^+$.

e) 4-(2,2-Dimethyl-3-(pyridin-3-yl)cyclopent-3-enylamino)-2-(trifluoromethyl)benzonitrile The compound was prepared starting from the compound of Example 36(d) (0.200 g), 4-fluoro-2-(trifluoromethyl)benzonitrile (0.168 g) and DIPEA (0.465 ml). Crude product was purified by chromatography (CombiFlash C18-RP, eluent A: 0.5% HCOOH/H2O, B: MeOH, B: 40-90%) to obtain 0.135 g of the title compound as a mixture of enantiomers. $^1$H NMR (400 MHz, CDCl$_3$): 1.19 (s, 3 H), 1.25 (s, 3 H), 2.24-2.31 (m, 1 H), 2.88-2.95 (m, 1 H), 4.00-4.06 (m, 1 H), 4.61 (d, 1 H), 5.85 (t, 1 H), 6.79 (dd, 1 H), 6.95 (d, 1 H), 7.25-7.29 (m, 1 H), 7.57 (d, 1 H), 7.61 (m, 1 H), 8.54 (dd, 1 H), 8.58 (d, 1 H).

f) 4-((2,2-Dimethyl-3-(pyridin-3-yl)cyclopent-3-enyl)(ethyl)amino)-2-(trifluoromethyl)benzonitrile The compound was prepared from the compound of Example 36(e) (0.135 g), iodoethane (0.038 ml) and sodium hydride (60% dispersion in mineral oil, 0.044 g). Crude product was purified by chromatography (CombiFlash C18-RP, eluent A: 0.5% HCOOH/H2O, B: MeOH, B: 35-90%) to obtain 0.066 g of the title compound as a mixture of enantiomers. $^1$H NMR (400 MHz, CDCl$_3$): 1.01 (s, 3 H), 1.25 (t, 3 H), 1.32 (s, 3 H), 2.64-2.77 (m, 1 H), 2.92-2.99 (m, 1 H), 3.37-3.63 (m, 2 H), 4.51 (dd, 1 H), 5.89 (t, 1 H), 6.90 (dd, 1 H), 7.09 (d, 1 H), 7.26-7.31 (m, 1 H), 7.55-7.64 (m, 2 H), 8.51-8.59 (m, 2 H).

Example 37

4-(Ethyl(3-(1-ethyl-1H-imidazol-5-yl)-3-hydroxycyclohexyl)amino)-2-(trifluoromethyl)benzonitrile a) 4-(Ethyl(3-(1-ethyl-4-iodo-1H-imidazol-5-yl)-3-hydroxycyclohexyl)-amino)-2-(trifluoromethyl)benzonitrile The compound was prepared from 1-ethyl-4,5-diiodo-1H-imidazole (0.80 g), and 4-(ethyl(3-oxocyclohexyl)amino)-2-(trifluoromethyl)benzonitrile (0.71 g), and ethylmagnesium bromide (3 M in diethyl ether, 0.84 ml). Yield 1.29 g. LCMS: M+1 533. The product was used in the next step without purification.

b) 4-(Ethyl(3-(1-ethyl-1H-imidazol-5-yl)-3-hydroxycyclohexyl)amino)-2-(trifluoromethyl)benzonitrile The compound was prepared from the compound of Example 37(a) (crude product, 0.75 g) and EtMgBr (3M in diethyl ether, 1.88 ml), 2 h, −30° C. Crude product was purified by chromatography (CombiFlash C18-RP, eluent A: 0.5% HCOOH/H2O, B: MeOH, B: 50-90%) to obtain 42 mg of the title compound as a mixture of isomers. $^1$H NMR (400 MHz, CDCl$_3$): 1.18-1.22 (m, 3 H), 1.40-1.46 (m, 3 H), 1.58-1.65 (m, 1 H), 1.68-2.14 (m, 7 H), 2.19-2.22 (m, 1 H), 3.28-3.48 (m, 2 H), 4.18-4.38 (m, 3 H), 6.68-6.79 (m, 1 H), 6.84-6.93 (m, 1 H), 6.99-7.06 (m, 1 H), 7.34-7.44 (m, 1 H), 7.49-7.59 (m, 1 H).

Example 38

4-(Ethyl(3-hydroxy-3-(1-(2-methoxyethyl)-1H-imidazol-5-yl)cyclohexyl)-amino)-2-(trifluoromethyl)benzonitrile a) 4,5-Diiodo-1-(2-methoxyethyl)-1H-imidazole

The compound was prepared from 2-bromoethyl methyl ether (1.32 ml), 4,5-diiodo-1H-imidazole (3.00 g), sodium hydroxide 50% (20 ml) and tetrabutylammonium iodide (3.46 g) in toluene (120 ml), 9 h, 40° C. Yield 3.03 g. $^1$H NMR (400 MHz, CDCl$_3$): 3.32 (s, 3 H), 3.59 (t, 2 H), 4.14 (t, 2 H), 7.68 (s, 1H).

b) 4-(Ethyl(3-hydroxy-3-(4-iodo-1-(2-methoxyethyl)-1H-imidazol-5-yl)cyclohexyl)amino)-2-(trifluoromethyl)benzonitrile The compound was prepared from the compound of Example 38(a) (3.0 g), 4-(ethyl(3-oxocyclohexyl)amino)-2-(trifluoromethyl)benzonitrile (2.46 g) and EtMgBr (3M in diethyl ether, 2.91 ml). Reaction time was overnight at RT. Yield 4.47 g. LCMS: M+1 564. The product was used to next step without purification.

c) 4-(Ethyl(3-hydroxy-3-(1-(2-methoxyethyl)-1H-imidazol-5-yl)cyclohexyl)-amino)-2-(trifluoromethyl)benzonitrile The compound was prepared from the compound of Example 38(b) (2.0 g), potassium carbonate (1.23 g) and Pd 10% on activated C (0.035 g) in MeOH (120 ml). The mixture was hydrogenated under pressure (2.3 bar) for 2 h. The mixture was filtered through Celite and filtrate evaporated to dryness. 0.50 g of the crude title product was purified by chromatography (CombiFlash C18-RP, eluent A: 0.5% HCOOH/H2O, B: MeOH, B: 50-90%). Yield 0.120 g. $^1$H NMR (400 MHz, CDCl$_3$): 1.20 (t, 3 H), 1.56-2.18 (m, 9 H), 3.30 (s, 3H), 3.33-3.46 (m, 2 H), 3.62-3.70 (m, 2H), 4.39-4.46 (m, 3 H), 6.85-6.88 (m, 2 H), 7.07 (d, 1H), 7.48 (s, 1H), 7.57 (d, 1 H).

Example 39

4-(Ethyl(3-(1-(2-methoxyethyl)-1H-imidazol-5-yl)cyclohex-3-enyl)amino)-2-(trifluoromethyl)benzonitrile

The compound was prepared from the title compound of Example 38 (0.75 g) and sulphuric acid (4.58 ml), 30 min, 0° C. Crude product was purified by chromatography (CombiFlash silica column, eluent: heptane-EtOAc) to obtain 0.046 g of the title compound as a mixture of enantiomers. $^1$H NMR (400 MHz, CDCl$_3$): 1.26 (t, 3 H), 1.80-2.06 (m, 2 H), 2.28-2.48 (m, 4 H), 3.33 (s, 3H), 3.39-3.49 (m, 2 H), 3.62-3.65 (m, 2 H), 4.02-4.15 (m, 3 H), 5.83 (m, 1 H), 6.85 (dd, 1 H), 6.92 (s, 1 H), 6.99 (d, 1 H), 7.58 (s, 1H), 7.59 (d, 1 H).

Example 40

4-(Ethyl(3-hydroxy-3-(1-isobutyl-1H-imidazol-5-yl)cyclohexyl)amino)-2-(trifluoromethyl)benzonitrile a) 4,5-Diiodo-1-isobutyl-1H-imidazole

The compound was prepared from 1-iodo-2-methylpropane (2.59 g), 4,5-diiodo-1H-imidazole (3.0 g), NaOH 50% (20 ml) and tetrabutylammonium iodide (3.46 g) in toluene (120 ml), 4 h, 40° C. Yield 2.51 g. $^1$H NMR (400 MHz, CDCl$_3$): 0.94 (d, 6 H), 2.05-2.15 (m, 1 H), 3.77 (d, 2 H), 7.56 (s, 1 H).

b) 4-(Ethyl(3-hydroxy-3-(4-iodo-1-isobutyl-1H-imidazol-5-yl)cyclohexyl)-amino)-2-(trifluoromethyl)benzonitrile The compound was prepared from the compound of Example 40(a) (2.5 g), 4-(ethyl(3-oxocyclohexyl)amino)-2-(trifluoromethyl)benzonitrile (2.063 g) and EtMgBr (3M in diethyl ether, 2.44 ml). Reaction time was overnight at RT. Yield 3.73 g. LCM: M+1 562. Compound was used as such in the next step.

c) 4-(Ethyl(3-hydroxy-3-(1-isobutyl-1H-imidazol-5-yl)cyclohexyl)amino)-2-(trifluoromethyl)benzonitrile The compound was prepared from the compound of Example 40(b) (3.80 g), potassium carbonate (2.34 g) and Pd 10% on activated C (0.035 g). The mixture was hydrogenated under pressure (2.3 bar) for 1 h. Crude product was purified by chromatography (CombiFlash C18-RP, eluent A: 0.5% HCOOH/H2O, B: MeOH, B: 50-90%). Yield 0.473 g as a mixture of isomers. $^1$H NMR (400 MHz, DMSO-d$_6$): 0.81 (d, 3 H), 0.85 (d, 3 H), 1.10 (t, 3 H), 1.63-1.92 (m, 7 H), 1.93-2.08 (m, 2 H), 2.15 (m, 1 H), 3.35-3.57 (m, 2 H), 3.85-4.02 (m, 2 H), 4.18-4.28 (m, 1 H), 6.72 (s, 1 H), 7.03 (dd, 1 H), 7.09 (s, 1 H), 7.52 (s, 1 H), 7.79 (d, 1 H).

Example 41

4-(Ethyl(3-(1-isobutyl-1H-imidazol-5-yl)cyclohex-3-enyl)amino)-2-(trifluoromethyl)benzonitrile The compound was prepared from the title compound of Example 40 (0.10 g), and sulphuric acid (0.613 ml), 30 min, 0° C. Crude product was purified by chromatography (CombiFlash C18-RP, eluent A: 0.5% HCOOH/H2O, B: MeOH, B: 50-90%) to obtain 0.008 g of the title compound as a mixture of enantiomers. $^1$H NMR (400 MHz, CDCl$_3$): 0.89 (d, 3 H), 0.91 (d, 3H), 1.26 (t, 3 H), 1.80-1.94 (m, 1 H), 1.94-2.10 (m, 2 H), 2.42-2.50 (m, 4 H), 3.36-3.51 (m, 2 H), 3.73 (d, 2 H), 4.03-4.13 (m, 1 H), 5.81-5.87 (m, 1 H), 6.84 (dd, 1 H), 6.91 (s, 1 H), 6.99 (d, 1 H), 7.39 (s, 1 H), 7.59 (d, 1 H).

Example 42

4-((3-(1H-Imidazol-1-yl)cyclohex-3-enyl)(ethyl)amino)-2-(trifluoromethyl)-benzonitrile a) 3-(1H-imidazol-1-yl)cyclohex-3-enamine

To a solution of imidazole (57.8 g) in DCM (400 ml) SOCl$_2$ (18.8 ml) was added dropwise at 0° C. followed by stirring for 30 min. To this suspension was added slowly a solution of benzyl (3-oxocyclohexyl)carbamate (35 g) in DCM (200 ml) at 0° C. and the mixture was stirred at RT for 24 h. The mixture was adjusted to pH 11 by the addition of saturated aqueous NaHCO$_3$ solution. The resulting bi-phasic mixture was extracted with DCM, washed with H$_2$O, dried and concentrated. The resulting viscous oil was purified by reverse phase HPLC to give mixture (13 g) of benzyl (3-(1H-imidazol-1-yl)cyclohex-3-en-1-yl)carbamate and (3-(1H-imidazol-1-yl)cyclohex-2-en-1-yl)carbamate (regioisomers). The pure isomeric mixture was further separated by normal phase chiral HPLC (OJ-H (20×250) mm; 5μ) using hexane/ethanol (75% with 0.1% DEA) as the eluents. Yields: 4 g, benzyl (3-(1H-imidazol-1-yl)cyclohex-3-en-1-yl)carbamate (isomer 1); 3 g, benzyl (3-(1H-imidazol-1-yl)cyclohex-2-en-1-yl)carbamate (isomer 2). MS: m/z=298 [M+1]$^+$. Benzyloxycarbonyl group of the isomer 1 (0.20 g) was removed by adding KOH (5 eq) in 1,4-dioxane and heating the mixture at 80° C. for 24 h. Yield of the title compound: 0.050 g (purity about 85%). MS: m/z 164 [M+1]$^+$.

b) 4-(3-(1H-Imidazol-1-yl)cyclohex-3-enylamino)-2-(trifluoromethyl)benzonitrile The compound was prepared from 0.50 g of the compound of Example 42(a), 4-fluoro-2-(trifluoromethyl)benzonitrile (0.579 g, and DIPEA (1.60 ml). Yield 0.88 g. $^1$H NMR (400 MHz, CDCl$_3$): 1.71-1.84 (m, 1 H), 2.00-2.10 (m, 1 H), 2.35-2.50 (m, 3 H), 2.88-2.96 (m, 1 H), 3.89-4.02 (m, 1 H), 4.97 (d, 1 H), 5.88-5.95 (m, 1 H), 6.75 (dd, 1 H), 6.92 (d, 1 H), 7.05-7.12 (m, 2 H), 7.57 (d, 1 H), 7.64 (t, 1 H).

c) 4-((3-(1H-Imidazol-1-yl)cyclohex-3-enyl)(ethyl)amino)-2-(trifluoromethyl)benzonitrile The compound was prepared from the compound of Example 42(b) (0.88 g), iodoethane (0.42 ml) and sodium hydride (60% dispersion in mineral oil, 0.265 g). Crude title product was purified and isomers separated by chromatography (1$^{st}$ silica column, eluent 0-1% MeOH/DCM, 2$^{nd}$ Chiralpak IA 20×250 mm, 5 μm, A: n-hexane+0.2% DEA, B: EtOH+0.2% DEA, B: 10%, 20 ml/min) to obtain enantiomer 1 (yield 0.17 g, rt 32 min) and enantiomer 2 (yield 0.16 g, rt 38 min). $^1$H NMR (400 MHz, CDCl$_3$): 1.28 (t, 3 H), 1.84-1.99 (m, 1 H), 1.99-2.08 (m, 1 H), 2.40-2.50 (m, 2 H), 2.60-2.68 (m, 2 H), 3.37-3.55 (m, 2 H), 4.13-4.24 (m, 1 H), 5.88-5.94 (m, 1 H), 6.87 (dd, 1 H), 7.01 (d, 1H), 7.09 (m, 2 H), 7.60 (dd, 1H), 7.63-7.70 (m, 1 H).

Example 43

4-((3-(1H-Imidazol-1-yl)cyclohex-3-enyl)(methyl)amino)-2-(trifluoromethyl)-benzonitrile The compound was prepared from 4-(3-(1H-imidazol-1-yl)cyclohex-3-enylamino)-2-(trifluoromethyl)benzonitrile (0.83 g), iodomethane (0.709 g) and sodium hydride (60% dispersion in mineral oil, 0.25 g). Crude product was purified and isomers separated by chromatography (1$^{st}$ silica column, eluent 0-0.5% MeOH/–DCM, 2$^{nd}$ Chiralpak IA 20×250 mm, 5 μm, eluent A: MTBE+0.2% DEA, B: EtOH+0.2% DEA, B: 10%, 20 ml/min) to obtain enantiomer 1 (yield 0.077 g, rt 12.5 min) and enantiomer 2 (yield 0.088 g, rt 16 min). $^1$H NMR (400 MHz, CDCl$_3$): 1.89-2.00 (m, 2 H), 2.41-2.49 (m, 2 H), 2.62-2.69 (m, 2 H), 2.98 (s, 3 H), 4.12-4.26 (m, 1 H), 5.92 (d, 1 H), 6.90 (dd, 1 H), 7.04 (d, 1 H), 7.09-7.10 (m, 2 H), 7.62 (d, 1 H), 7.65-7.70 (m, 1 H).

Example 44

4-((2,2-Dimethyl-5-(1H-1,2,4-triazol-1-yl)cyclohexyl)(ethyl)amino)-2-(trifluoromethyl)benzonitrile a) 3-(4-Cyano-3-(trifluoromethyl)phenylamino)-4,4-dimethylcyclohexyl methanesulfonate To a suspension of 4-(5-hydroxy-2,2-dimethylcyclohexylamino)-2-(trifluoromethyl)benzonitrile (3.60 g), TEA (3.21 ml) and DCM (40 ml) at 0° C. was added slowly a solution of methanesulfonyl chloride (1.16 ml) in DCM (15 ml). The mixture was stirred at RT for 1.5 h. Water was added and the organic phase was washed with water and 0.5 M HCl, dried and evaporated to obtain the title product in 4.11 g yield as a mixture of diastereomers (1H NMR trans:cis 85:15). LCMS: M+1 391.

b) 3-((4-Cyano-3-(trifluoromethyl)phenyl)(ethyl)amino)-4,4-dimethylcyclohexyl methanesulfonate The compound was prepared from sodium hydride (60% dispersion in mineral oil, 0.615 g) in DMF (10 ml), the compound of Example 44(a) (2.0 g) and iodoethane (0.824 ml) to yield 1.786 g of the title product as a mixture of diastereomers (1H NMR trans:cis 85:15). LCMS: M+1 419.

c) 4-((2,2-Dimethyl-5-(1H-1,2,4-triazol-1-yl)cyclohexyl)(ethyl)amino)-2-(trifluoromethyl)benzonitrile The compound of Example 44(b) (0.50 g), 1,2,4-triazole sodium derivate (0.218 g) and DMF (5 ml) under N$_2$ was heated at 100° C. for 0.5 h. Ethyl acetate and water were added. The organic phase was washed with water, dried and evaporated to dryness. Crude product of the title compound was purified and isomers were separated by chromatography (1$^{st}$ silica column, eluent DCM+0.5% MeOH, 2$^{nd}$ Chiralpak IA 20×250 mm, 5 μm, eluent MTBE+0.2% DEA, 20 ml/min) to obtain pure diastereomers of the title compound. Retention times and yields: (1) 8 min, 0.075 g, (2) 9 min, 0.095 g, (3) 16 min, 0.006 g and (4) 20 min, 0.005 g. Trans-isomers (1) and (2): $^1$H NMR (400 MHz, CDCl$_3$): 0.88 (s, 3 H), 1.13-1.18 (m, 6H), 1.37-1.43 (m, 1 H), 1.79-1.87 (m, 1 H), 1.91-2.19 (m, 2 H), 2.19-2.35 (m, 1 H), 2.40-2.46 (m, 1 H), 3.33-3.58 (m, 2 H), 4.70 (dd, 1 H), 4.78-4.83 (m, 1 H), 6.90 (dd, 1H), 7.20 (d, 1 H), 7.54 (dd, 1 H), 7.99 (s, 1 H), 8.17 (s, 1 H). Cis-isomers (3) and (4): $^1$H NMR (400 MHz, CDCl$_3$): 0.97 (s, 3 H), 1.14 (t, 3 H), 1.18 (s, 3 H), 1.52-1.65 (m, 1 H), 1.66-1.75 (m, 1 H), 1.94-2.22 (m, 3 H), 2.49 (q, 1 H), 3.46 (q, 2 H), 3.88 (dd, 1 H), 4.35-4.43 (m, 1 H), 6.92 (dd, 1 H), 7.09 (d, 1 H), 7.58 (d, 1 H), 7.97 (s, 1 H), 8.12 (s, 1 H).

Example 45

4-((2,2-Dimethyl-5-(1H-1,2,4-triazol-1-yl)cyclohexyl)(methyl)amino)-2-(trifluoromethyl)benzonitrile a) 3-((4-Cyano-3-(trifluoromethyl)phenyl)(methyl)amino)-4,4-dimethylcyclohexyl methanesulfonate The compound was prepared from the compound of Example 44(a) (2.0 g), iodomethane (0.638 ml) and sodium hydride (60% dispersion in mineral oil, 0.615 g). Yield 1.844 g. Product is a mixture of diastereomers (1H NMR trans:cis 87:13). LCMS: M+1 405.

b) 4-((2,2-Dimethyl-5-(1H-1,2,4-triazol-1-yl)cyclohexyl)(methyl)amino)-2-(trifluoromethyl)benzonitrile The compound was prepared from the compound of Example 45(a) (0.75 g), and 1,2,4-triazole sodium derivate (0.338 g). Crude product of the title compound was purified and isomers were separated by chromatography (1$^{st}$ silica column, eluent DCM+0.5% MeOH gave mixture of isomers, 2$^{nd}$ and 3$^{rd}$ Chiralpak IA 20×250 mm, 5 µm, 1$^{st}$ eluent: A: MTBE+0.2% DEA, B: EtOH+0.2% DEA, B: 15%, 20 ml/min, gave mixture of trans-isomers (1) and (2), rt 6.5 min, and pure cis-isomers (3), rt 14 min, and (4), rt 16 min, 2$^{nd}$ eluent A: MTBE+0.2% DEA, B: EtOH+0.2% DEA, B: 3%, 20 ml/min, separated trans-isomers (1), rt 43 min, and (2), rt 59 min). Yields: (1) 0.086 g, (2) 0.105 g, (3) 0.010 g, (4) 0.010 g. Trans-isomers (1) and (2): $^1$H NMR (400 MHz, CDCl$_3$): 0.90 (s, 3H), 1.17 (s, 3 H), 1.37-1.46 (m, 1 H), 1.76-1.88 (m, 1 H), 1.98-2.23 (m, 3 H), 2.37-2.49 (m, 1 H), 2.92 (s, 3 H), 4.64 (dd, 1 H), 4.74-4.85 (m, 1 H), 6.88 (dd, 1 H), 7.19 (d, 1 H), 7.56 (d, 1 H), 8.00 (s, 1 H), 8.15 (s, 1 H). Cis-isomers (3) and (4): $^1$H NMR (400 MHz, CDCl$_3$): 1.00 (s, 3H), 1.20 (s, 3 H), 1.54-1.66 (m, 1 H), 1.68-1.79 (m, 1 H), 1.98-2.20 (m, 3H), 2.51 (q, 1 H), 2.94 (s, 3 H), 3.85 (dd, 1 H), 4.34-4.46 (m, 1 H), 6.93 (dd, 1 H), 7.09 (d, 1 H), 7.60 (dd, 1 H), 7.96 (s, 1 H), 8.11 (s, 1 H).

Example 46

4-((5-(1H-Imidazol-1-yl)-2,2-dimethylcyclohexyl)amino)-2-(trifluoromethyl)benzonitrile The compound was prepared from the compound of Example 44(b) (1.20 g) and sodium imidazol-1-ide (0.65 g). The mixture was heated at 100° C. for 45 min. Crude product was purified and isomers separated by chromatography (1$^{st}$ silica column, eluent DCM+0-1.5% MeOH, 2$^{nd}$ Chiralpak IA 20×250 mm, 5 µm, eluent A: MTBE+0.2% DEA, B: IPA+0.2% DEA, B: 8%, 20 ml/min) to obtain pure diastereomers. Retention times and yields: (1) 10 min, 0.183 g, (2) 14 min, 0.008 g, (3) 19 min, 0.010 g and (4) 22 min, 0.187 g. Trans-isomers (1) and (4): $^1$H NMR (400 MHz, CDCl$_3$): 0.86 (s, 3 H), 1.14 (s, 3 H), 1.20 (t, 3 H), 1.42-1.54 (m, 1 H), 1.60-1.72 (m, 1 H), 1.99-2.15 (m, 1 H), 2.17-2.31 (m, 2 H), 2.41-2.52 (m, 1 H), 3.41-3.51 (m, 2 H), 3.86-3.93 (dd, 1 H), 4.52-4.58 (m, 1 H), 6.75 (dd, 1 H), 6.93 (d, 1 H), 7.03 (t, 1 H), 7.16 (t, 1 H), 7.52 (dd, 1 H), 7.65 (t, 1 H). Cis-isomers (2) and (3): $^1$H NMR (400 MHz, CDCl$_3$): 0.96 (s, 3 H), 1.12-1.16 (m, 6 H), 1.53-1.62 (m, 1 H), 1.65-1.72 (m, 1 H), 1.90-1.99 (m, 1 H), 2.00-2.16 (m, 2 H), 2.26 (q, 1H), 3.41-3.48 (m, 2 H), 3.87 (dd, 1 H), 4.12-4.19 (m, 1 H), 6.92 (dd, 1 H), 6.98-7.02 (m, 1 H), 7.06-7.12 (m, 2 H), 7.55-7.62 (m, 2 H).

Example 47

4-((5-(1H-Imidazol-1-yl)-2,2-dimethylcyclohexyl)(methyl)amino)-2-(trifluoromethyl)benzonitrile The compound was prepared from the compound of Example 45(a) (0.90 g) and sodium imidazol-1-ide (0.50 g). Crude product of the title compound was purified and isomers were separated by chromatography (1$^{st}$ silica column, eluent DCM+0-2% MeOH, 2$^{nd}$ Chiralpak IA 20×250 mm, 5 µm, eluent A: MTBE+0.2% DEA, B: IPA+0.2% DEA, B: 2%, 20 ml/min) to obtain pure diastereomers. Retention times and yields: (1) 25 min, 0.027 g, (2) 31 min, 0.027 g, (3) 49 min, 0.005 g and (4) 62 min, 0.005 g. Trans-isomers (1) and (2): $^1$H NMR (400 MHz, CDCl$_3$): 0.88 (s, 3 H), 1.17 (s, 3 H), 1.45-1.56 (m, 1 H), 1.62-1.75 (m, 1 H), 2.01-2.21 (m, 2 H), 2.21-2.32 (m, 1 H), 2.44-2.54 (m, 1 H), 2.96 (s, 3H), 3.86 (dd, 1 H), 4.53-4.58 (m, 1 H), 6.75 (dd, 1 H), 6.92 (d, 1 H), 7.02 (t, 1 H), 7.16 (t, 1 H), 7.49-7.55 (m, 1 H), 7.65 (s, 1 H). Cis-isomers (3) and (4): $^1$H NMR (400 MHz, CDCl$_3$): 0.99 (s, 3H), 1.18 (s, 3 H), 1.55-1.64 (m, 1 H), 1.68-1.75 (m, 1 H), 1.87-1.99 (m, 1 H), 1.99-2.12 (m, 2 H), 2.29 (q, 1 H), 2.93 (s, 3 H), 3.84 (dd, 1 H), 4.12-4.22 (m, 1 H), 6.93 (dd, 1 H), 6.98-7.02 (m, 1 H), 7.07-7.12 (m, 2 H), 7.56-7.63 (m, 2 H).

Example 48

4-((-3-(1H-Pyrazol-1-yl)cyclohexyl)(ethyl)amino)-2-(trifluoromethyl)benzonitrile The compound was prepared from sodium hydride (60% dispersion in mineral oil, 0.143 g) in DMF (10 ml), pyrazole (0.122 g) and the compound of Example 9(a) (0.70 g) in DMF (5 ml). Crude product of the title compound was purified by chromatography (silica column, eluent 0-2% MeOH/DCM) to obtain 0.055 g of a mixture of trans-isomers and 0.013 g of a mixture of cis-isomers of the title compound. Trans-isomers: $^1$H NMR (400 MHz, CDCl$_3$): 1.23 (t, 3H), 1.62-1.89 (m, 5 H), 1.89-2.02 (m, 1 H), 2.18-2.29 (m, 1 H), 2.53-2.64 (m, 1 H), 3.27-3.53 (m, 2 H), 4.43-4.57 (m, 1 H), 4.59-4.69 (m, 1 H), 6.32-6.37 (m, 1 H), 6.88 (dd, 1 H), 7.36 (d, 1 H), 7.48 (d, 1 H), 7.54 (dd, 1 H), 7.60 (d, 1H). Cis-isomers: $^1$H NMR (400 MHz, CDCl$_3$): 1.21 (t, 3 H), 1.53-1.67 (m, 2 H), 1.78-1.97 (m, 2 H), 2.03-2.15 (m, 2 H), 2.15-2.24 (m, 1 H), 2.24-2.35 (m, 1 H), 3.43 (q, 2 H), 3.80-3.90(m, 1 H), 4.22-4.34 (m, 1 H), 6.23-6.28 (m, 1 H), 6.81 (dd, 1 H), 6.96 (d, 1 H), 7.44 (dd, 1 H), 7.53 (d, 1 H), 7.58 (d, 1 H).

Example 49

4-(Ethyl(1-(1-ethyl-1H-1,2,4-triazol-5-yl)piperidin-3-yl)amino)-2-(trifluoromethyl)benzonitrile a) tert-Butyl 3-(dibenzylamino)piperidine-1-carboxylate To a solution of tert-butyl 3-aminopiperidine-1-carboxylate (25 g, 125 mmol) in acetone (200 ml) was added $K_2CO_3$ (51.81 g, 375 mmol) at RT and the mixture was stirred for 10 min. A solution of benzyl bromide (40.94 g, 239 mmol) was added dropwise and stirring continued at RT for 16 h. The mixture was concentrated under reduced pressure, water (250 ml) was added and the mixture was extracted with EtOAc (2×500 ml). The organic layer was dried, filtered and concentrated to obtain the crude compound. The compound was purified by flash column using 100-200 mesh silica gel and eluted EtOAc in petroleum ether. Yield 20 g. m/z=381.2 $(M+1)^+$.

b) N,N-dibenzylpiperidin-3-amine

A solution of Example 49 (a) (20.00 g), in trifluoroacetic acid (100 ml) was stirred at RT for 16 h. The mixture was concentrated under reduced pressure, poured into water (250 ml) and extracted with EtOAc (2×500 ml). The organic layer was washed with 2N NaOH solution, dried, filtered and concentrated to obtain the crude compound. The compound was directly used for next step without further purification. m/z=281.2 $(M+1)^+$.

c) 5-Bromo-1-ethyl-1H-1,2,4-triazole

To a solution of 3-bromo-4H-1,2,4-triazole (5.0 g, 34.2 mmol) in DMF (100 ml) was added $K_2CO_3$ (9.45 g, 68.5 mmol) at RT and stirred for 10 min. A solution of ethyl iodide (11.70 g, 75 mmol) was added dropwise followed by stirring for 16 h. The mixture was poured into ice cold water (250 ml) and extracted with EtOAc (2×200 ml). The organic layer was dried, filtered and concentrated to give crude compound. This was purified by flash column using 230-400 mesh silica gel and eluted with EtOAc in petroleum ether. Yield 3.5 g. m/z=176.0, 178.0 $(M+1)^+$.

d) N,N-dibenzyl-1-(1-ethyl-1H-1,2,4-triazol-5-yl)piperidin-3-amine

To a stirred solution of the compound of Example 49 (b) (1.5 g, 5.33 mmol) and the compound of Example 49 (c) (1.39 g, 7.99 mmol) in DMSO (25 ml) were added $K_2CO_3$ (2.2 g, 16.0 mmol), L-proline (0.06 g, 0.53 mmol) and CuI (0.101 g, 0.53 mmol) sequentially. The mixture was stirred for 16 h at 100° C., poured into ice cold water (250 ml) and extracted with EtOAc (2×200 ml). The organic layer was dried, filtered and concentrated to give crude compound. This was purified by flash column using 230-400 mesh silica gel and eluted with 70% EtOAc in petroleum ether. Yield 0.66 g. m/z=376.2 $(M+1)^+$.

e) 1-(1-Ethyl-1H-1,2,4-triazol-5-yl)piperidin-3-amine

To a solution of the compound of Example 49 (d) (0.15 g, 0.401 mmol) in methanol (10 ml) was added $Pd(OH)_2$ (0.01 g) and the mixture was hydrogenated at 80 psi for 16 h. The mixture was filtered through celite pad and the filtrate was evaporated to dryness to give the title compound. The crude compound was directly used for next step without further purification. Yield: 0.050 g.

f) tert-Butyl (1-(1-ethyl-1H-1,2,4-triazol-5-yl)piperidin-3-yl)carbamate

To the compound of Example 49 (e) (0.2 g, 1.02 mmol) in $CH_2Cl_2$ (10 ml) was added $Et_3N$ (0.155 g, 1.54 mmol) and $(Boc)_2O$ (0.34 g, 1.54 mmol) followed by stirring for 16 h at RT. The mixture was poured into ice cold water (50 ml) and extracted with EtOAc (2×100 ml). The organic layer was dried, filtered and concentrated to give crude product. This was purified by flash column using 230-400 mesh silica gel and eluted with 50% EtOAc in petroleum ether. Yield 0.20 g. 1H NMR (400 MHz, $CDCl_3$): 1.40-1.11 (m, 12H), 1.55-1.65 (m, 1H), 1.65-1.75 (m, 1H), 1.80-1.95 (m, 2H), 2.85-2.93 (m, 1H), 3.00-3.08 (m, 1H), 3.10-3.18 (m, 1H), 3.30-3.40 (m, 1H), 3.78-3.85 (m, 1H), 4.00 (q, 2H), 4.87-4.92 (m, 1H), 7.62 (s, 1H).

g) 1-(1-Ethyl-1H-1,2,4-triazol-5-yl)piperidin-3-amine hydrochloride

A solution of the compound of Example 49 (f) (0.2 g) in HCl in dioxane (2 ml) was stirred for 3 h at RT. The mixture was concentrated under reduced pressure. Yield 0.13 g. m/z=196.1 $(M+1)^+$.

h) 4-(1-(1-Ethyl-1H-1,2,4-triazol-5-yl)piperidin-3-ylamino)-2-(trifluoromethyl)benzonitrile The compound was prepared from the compound of Example 49(g) (0.310 g), 4-fluoro-2-(trifluoromethyl)benzonitrile (0.253 g) and DIPEA (1.16 ml). Crude product was purified by chromatography (silica column, eluent 0-1% MeOH/DCM) to obtain 0.070 g of the title compound as a mixture of enantiomers. $^1$H NMR (400 MHz, $CDCl_3$): 1.46 (t, 3 H), 1.63-1.73 (m, 1 H), 1.75-1.99 (m, 3 H), 3.10-3.27 (m, 3 H), 3.50 (dd, 1 H), 3.77-3.86 (m, 1 H), 3.99 (q, 2 H), 5.93 (d, 1 H), 6.75 (dd, 1 H), 6.94 (d, 1H), 7.54 (d, 1 H), 7.66 (s, 1 H).

i) 4-(Ethyl(1-(1-ethyl-1H-1,2,4-triazol-5-yl)piperidin-3-yl)amino)-2-(trifluoromethyl)benzonitrile The compound was prepared from the compound of Example 49(h) (0.035 g), iodoethane (0.012 ml) and sodium hydride (60% dispersion in mineral oil, 0.008 g). Compound was purified by chromatography (silica column, eluent 0-2% MeOH/DCM) to obtain 0.010 g of the title compound as a mixture of enantiomers. $^1$H NMR (400 MHz, $CDCl_3$): 1.23 (t, 3 H), 1.47 (t, 3 H), 1.74-1.97 (m, 3 H), 2.05-2.13 (m, 1 H), 2.90-3.01 (m, 2 H), 3.27-3.34 (m, 1 H), 3.35-3.55 (m, 3 H), 4.01 (q, 2 H), 4.20-4.29 (m, 1 H), 6.95 (dd, 1 H), 7.29 (d, 1 H), 7.59 (dd, 1 H), 7.66 (s, 1 H).

Example 50

4-((1-(1-Ethyl-1H-1,2,4-triazol-5-yl)piperidin-3-yl)(methyl)amino)-2-(trifluoromethyl)benzonitrile The compound was prepared from the compound of Example 49(a) (0.035 g), iodomethane (0.009 ml) and sodium hydride (60% dispersion in mineral oil, 0.008 g).

Yield 0.036 g. $^1$H NMR (400 MHz, CDCl$_3$): 1.47 (t, 3 H), 1.75-1.96 (m, 3 H), 1.97-2.05 (m, 1 H), 2.87-2.96 (m, 1 H), 2.97 (s, 3 H), 3.03 (dd, 1 H), 3.27-3.37 (m, 1 H), 3.35-3.41 (m, 1 H), 4.01 (q, 2 H), 4.18-4.27 (m, 1 H), 6.96 (dd, 1 H), 7.26 (d, 1 H), 7.61 (dd, 1 H), 7.66 (s, 1 H).

Example 51

4-(Ethyl(3-(1-isopropyl-1H-imidazol-5-yl)cyclopent-3-enyl)amino)-2-(trifluoromethyl)benzonitrile a) tert-Butyl 3-(1-isopropyl-1H-imidazol-5-yl)cyclopent-3-enylcarbamate The compound was prepared from tert-butyl 3-formylcyclopent-3-enylcarbamate (0.47 g), isopropylamine (0.263 g), tosylmethyl isocyanide (0.521 g) and DBU (0.677 g). Crude product was purified by chromatography (silica column, eluent 0-1% MeOH/DCM). Yield 0.346 g as a mixture of enantiomers. $^1$H NMR (400 MHz, CDCl$_3$): 1.46 (s, 9 H), 1.48-1.53 (m, 6 H), 2.36-2.45 (m, 1 H), 2.52-2.68 (m, 1 H), 2.89-2.98 (m, 1 H), 3.03-3.13 (m, 1 H), 4.28-4.45 (m, 1 H), 4.48-4.58 (m, 1 H), 4.77 (br. s., 1 H), 5.74 (m, 1 H), 6.97 (s, 1 H), 7.60 (s, 1 H).

b) 3-(1-Isopropyl-1H-imidazol-5-yl)cyclopent-3-enamine dihydrochloride

The compound was prepared from the compound of Example 51(a) (0.42 g) and HCl, 4 M in dioxane (0.90 ml). The mixture was stirred overnight at RT. Yield 0.43 g. LCMS: M+1 192. The crude product was used as such in the next step.

c) 4-(3-(1-Isopropyl-1H-imidazol-5-yl)cyclopent-3-enylamino)-2-(trifluoromethyl)benzonitrile The compound was prepared from the compound of Example 51(b) (0.30 g), 4-fluoro-2-(trifluoromethyl)benzonitrile (0.215 g) and DIPEA (0.99 ml). The obtained product was purified by triturating with ether. Yield 0.15 g. $^1$H NMR (400 MHz, CDCl$_3$): 1.53 (m, 6 H), 2.52 (d, 1 H), 2.59-2.70 (m, 1 H), 3.02-3.16 (m, 1 H), 3.20-3.60 (m, 1 H), 4.23-4.35 (m, 1 H), 4.52-4.62 (m, 1 H), 4.83 (d, 1 H), 5.81 (m, 1 H), 6.71 (dd, 1 H), 6.88 (d, 1 H), 6.99 (s, 1 H), 7.58 (d, 1 H), 7.64 (s, 1 H).

d) 4-(Ethyl(3-(1-isopropyl-1H-imidazol-5-yl)cyclopent-3-enyl)amino)-2-(trifluoromethyl)benzonitrile The compound was prepared from the compound of Example 51(c) (0.60 g), iodoethane (0.133 ml) and sodium hydride (55% dispersion in mineral oil, 0.200 g). Crude product was purified by chromatography (silica column, eluent 0-1% MeOH/DCM) to obtain the title compound as a mixture of enantiomers. Yield 0.480 g. The enantiomers were separated by chiral chromatography (column Chiralpak IA 20×250 mm, 5 m, eluent A: n-hexan+0.2% DEA, B: EtOH+0.2% DEA, B: 10%, 20 ml/min). Retention times and yields: (1) 29 min, 0.167 g and (2) 37 min, 0.155 g. $^1$H NMR (400 MHz, CDCl$_3$): 1.24 (t, 3 H), 1.52-1.58 (m, 6 H), 2.65-2.75 (m, 1 H), 2.80-2.93 (m, 1 H), 2.95-3.04 (m, 1 H), 3.07-3.18 (m, 1 H), 3.42-3.58 (m, 2 H), 4.53-4.75 (m, 2 H), 5.85-5.93 (m, 1 H), 6.82 (dd, 1 H), 6.98 (d, 1 H), 7.00 (s, 1 H), 7.58 (d, 1 H), 7.66 (s, 1 H).

Example 52

4-((3-(1-Isopropyl-1H-imidazol-5-yl)cyclopent-3-enyl)(methyl)amino)-2-(trifluoromethyl)benzonitrile The compound was prepared from the compound of Example 51(c) (0.090 g), iodomethane (0.071 g) and sodium hydride (55% dispersion in mineral oil, 0.020 g). Crude product was purified by chromatography (silica column, eluent 0-1% MeOH/DCM). Yield 0.045 g as a mixture of enantiomers. $^1$H NMR (400 MHz, CDCl$_3$): 1.52-1.57 (m, 6 H), 2.60-2.70 (m, 1 H), 2.75-2.85 (m, 1 H), 2.94 (s, 3 H), 2.98-3.08 (m, 1 H), 3.09-3.19 (m, 1 H), 4.53-4.63 (m, 1 H), 4.76-4.85 (m, 1 H), 5.87 (m., 1 H), 6.87 (dd, 1 H), 7.01 (s, 1 H), 7.03 (d, 1 H), 7.60 (d, 1 H), 7.65 (s, 1 H).

Example 53

4-((3-(1-Cyclopropyl-1H-imidazol-5-yl)cyclopent-3-enyl)(ethyl)amino)-2-(trifluoromethyl)benzonitrile a) tert-Butyl 3-(1-cyclopropyl-1H-imidazol-5-yl)cyclopent-3-enylcarbamate The compound was prepared from tert-butyl 3-formylcyclopent-3-enylcarbamate (0.42 g), cyclopropylamine (0.227 g), tosylmethyl isocyanide (0.466 g) and DBU (0.600 ml). Crude product was purified by chromatography (silica column, eluent 0-2% MeOH/DCM) to obtain the title compound as a mixture of enantiomers. Yield 0.14 g. $^1$H NMR (400 MHz, CDCl$_3$): 1.01-1.04 (m, 2 H), 1.07-1.11 (m, 2 H), 1.46 (s, 9H), 2.35-2.47 (m, 1 H), 2.51-2.61 (m, 1 H), 2.96 (m, 1 H), 3.08 (m, 1 H), 3.20-3.30 (m, 1 H), 4.37 (br. s., 1 H), 4.77 (br. s., 1 H), 6.10-6.18 (m, 1 H), 6.92 (s, 1 H), 7.47 (s, 1 H).

b) 3-(1-Cyclopropyl-1H-imidazol-5-yl)cyclopent-3-enamine dihydrochloride

The compound was prepared from the compound of Example 53(a) (0.14 g) and HCl, 4 M in dioxane (0.30 ml). Yield 0.127 g. The obtained crude product of the title compound was used as such in the next step.

c) 4-(3-(1-Cyclopropyl-1H-imidazol-5-yl)cyclopent-3-enylamino)-2-(trifluoromethyl)benzonitrile The compound was prepared from the compound of Example 53(b) (0.127 g), 4-fluoro-2-(trifluoromethyl)benzonitrile (0.092 g) and DIPEA (0.313 g). The product was purified by chromatography (silica column, eluent 0-1% MeOH/DCM). Yield 0.040 g as a mixture of enantiomers. $^1$H NMR (400 MHz, MeOH-d$_4$): 1.00-1.09 (m, 2 H), 1.12-1.18 (m, 2 H), 2.52-2.59 (m, 1 H), 2.65-2.71 (m, 1 H), 3.07-3.15 (m, 1 H), 3.18-3.25 (m, 1 H), 3.38-3.42 (m, 1 H), 4.28-4.35 (m, 1 H), 6.33-6.30 (m, 1 H), 6.86 (d, 1 H), 6.91 (s, 1 H), 7.00 (s, 1 H), 7.61 (d, 1 H), 7.66 (s, 1 H).

d) 4-((3-(1-Cyclopropyl-1H-imidazol-5-yl)cyclopent-3-enyl)(ethyl)amino)-2-(trifluoromethyl)benzonitrile The compound was prepared from the compound of Example 53(c) (0.040 g), iodoethane (0.026 g) and sodium hydride (60% dispersion in mineral oil, 0.009 mg). Crude product was purified by chromatography (silica column, eluent 1% MeOH/DCM) to obtain the title compound as a mixture of enantiomers. Yield 0.010 g. ¹H NMR (400 MHz, CDCl₃): 1.03-1.10 (m, 2 H), 1.11-1.17 (m, 2 H), 1.24 (t, 3 H), 2.65-2.77 (m, 1 H), 2.80-2.89 (m, 1 H), 2.95-3.08 (m, 1 H), 3.08-3.15 (m, 1 H), 3.26-3.35 (m, 1 H), 3.45-3.52 (m, 2 H), 4.61-4.73 (m, 1 H), 6.27-6.31 (m, 1 H), 6.81 (dd, 1 H), 6.94 (s, 1 H), 6.99 (d, 1 H), 7.52 (s, 1 H), 7.58 (d, 1 H).

Example 54

4-((3-(1-tert-Butyl-1H-imidazol-5-yl)cyclopent-3-enyl)(ethyl)amino)-2-(trifluoromethyl)benzonitrile a) tert-Butyl 3-(1-tert-butyl-1H-imidazol-5-yl)cyclopent-3-enylcarbamate The compound was prepared from tert-butyl 3-formylcyclopent-3-enylcarbamate (0.42 g), tert-butylamine (0.418 ml), tosylmethyl isocyanide (0.466 g) and DBU (0.600 ml). The crude product was purified by chromatography (silica column, eluent 0-2.5% MeOH/DCM) to obtain the title product as a mixture of enantiomers. Yield 0.23 g. ¹H NMR (400 MHz, CDCl₃): 1.45 (s, 9 H), 1.59 (s, 9 H), 2.24-2.37 (m, 1 H), 2.43-2.56 (m, 1 H), 2.89 (m, 1 H), 3.01 (m, 1 H), 4.38 (br. s., 1 H), 4.76 (br. s., 1 H), 5.78-5.82 (m, 1 H), 6.84 (d, 1 H), 7.59 (d, 1 H).

b) 3-(1-tert-Butyl-1H-imidazol-5-yl)cyclopent-3-enamine dihydrochloride

The compound was prepared from the compound of Example 54(a) (0.23 g), and HCl, 4 M in dioxane (0.47 ml). Yield 0.21 g. The obtained crude product of the title compound was used as such in the next step.

c) 4-(3-(1-tert-Butyl-1H-imidazol-5-yl)cyclopent-3-enylamino)-2-(trifluoromethyl)benzonitrile The compound was prepared from the compound of Example 54(b) (0.210 g), 4-fluoro-2-(trifluoromethyl)benzonitrile (0.142 g) and DIPEA (0.657 ml). Yield 0.21 g as a mixture of enantiomers. ¹H NMR (400 MHz, CDCl₃): 1.61 (s, 9 H), 2.42-2.51 (m, 1 H), 2.55-2.65 (m, 1 H), 3.01-3.11 (m, 1 H), 3.11-3.23 (m, 1 H), 4.30 (m, 1 H), 4.89 (d, 1 H), 5.89 (m, 1 H), 6.71 (dd, 1 H), 6.88 (d, 2 H), 7.57 (d, 1 H), 7.61 (d, 1 H).

d) 4-((3-(1-tert-Butyl-1H-imidazol-5-yl)cyclopent-3-enyl)(ethyl)amino)-2-(trifluoromethyl)benzonitrile The compound was prepared from the compound of Example 54(c) (0.210 g), iodoethane (0.064 ml) and sodium hydride (60% dispersion in mineral oil, 0.043 g). Crude product was purified by chromatography (column: Waters XBridge C18 30-100 mm, eluent A: 0.1% NH₄OH, B: 0.1% NH₄OH/ACN, B: 30-90% 1-20 min, 30 ml/min). Yield 0.003 g as a mixture of enantiomers. ¹H NMR (400 MHz, CDCl₃): 1.26 (t, 3 H), 1.63 (s, 9 H), 2.62-2.73 (m, 1 H), 2.79 (m, 1 H), 2.87-2.98 (m, 1 H), 3.00-3.09 (m, 1 H), 3.50 (q, 2 H), 4.57-4.82 (m, 1 H), 5.97 (m, 1 H), 6.82 (dd, 1 H), 6.93 (s, 1 H), 6.98 (d, 1 H), 7.59 (d, 1H), 7.70 (s, 1 H).

Example 55

4-((3-(1-(3-(1H-Imidazol-1-yl)propyl)-1H-imidazol-5-yl)cyclopent-3-enyl)-(ethyl)amino)-2-(trifluoromethyl)benzonitrile a) tert-Butyl 3-(1-(3-(1H-imidazol-1-yl)propyl)-1H-imidazol-5-yl)cyclopent-3-enylcarbamate The compound was prepared from tert-butyl 3-formylcyclopent-3-enylcarbamate (0.60 g), 3-(1H-imidazol-1-yl)propan-1-amine (0.711 g), tosylmethyl isocyanide (0.665 g) and DBU (0.856 ml). Crude product was purified by chromatography (silica column, eluent 0-8% MeOH/DCM). Yield 0.29 g as a mixture of enantiomers. ¹H NMR (400 MHz, CDCl₃): 1.46 (s, 9 H), 2.23-2.30 (m, 2 H), 2.32-2.42 (m, 1 H), 2.47-2.58 (m, 1 H), 2.91 (dd, 1 H), 3.05 (dd, 1 H), 3.86-4.05 (m, 4 H), 4.35 (br. s., 1 H), 4.92 (br. s., 1 H), 5.46-5.56 (m, 1 H), 6.91 (t, 1 H), 7.00 (s, 1 H), 7.12 (t, 1 H), 7.40 (d, 1 H), 7.43-7.45 (m, 1 H).

b) 3-(1-(3-(1H-Imidazol-1-yl)propyl)-1H-imidazol-5-yl)cyclopent-3-enamine dihydrochloride The compound was prepared from the compound of Example 55(a) (0.23 g), and HCl, 4 M in dioxane (0.563 ml). Yield 0.21 g. Product was used as such in the next step.

c) 4-(3-(1-(3-(1H-Imidazol-1-yl)propyl)-1H-imidazol-5-yl)cyclopent-3-enylamino)-2-(trifluoromethyl)benzonitrile The compound was prepared from the compound of Example 55(b) (0.21 g), 4-fluoro-2-(trifluoromethyl)benzonitrile (0.212 g) and DIPEA (0.976 ml). Yield 0.24 g ¹H NMR (400 MHz, CDCl₃): 2.24-2.36 (m, 2 H), 2.39-2.45 (m, 1 H), 2.51-2.59 (m, 1 H), 2.94-3.05 (m, 1 H), 3.15-3.24 (m, 1 H), 3.80-4.05 (m, 4 H), 4.25 (m, 1 H), 5.45-5.51 (m, 1 H), 5.79 (d, 1 H), 6.77 (dd, 1 H), 6.91 (t, 1 H), 6.97 (d, 1 H), 7.00 (s, 1 H), 7.10 (t, 1 H), 7.30 (s, 1 H), 7.50 (d, 1 H), 7.56 (d, 1 H).

d) 4-((3-(1-(3-(1H-Imidazol-1-yl)propyl)-1H-imidazol-5-yl)cyclopent-3-enyl)-(ethyl)amino)-2-(trifluoromethyl)benzonitrile The compound was prepared from the compound of Example 55(c) (0.21 g), iodoethane (0.040 ml) and sodium hydride (60% dispersion in mineral oil, 0.039 g). Crude product was purified by chromatography (1ˢᵗ silica column, eluent 0-4% MeOH/DCM, 2ⁿᵈ C18-RP, eluent 0.1% HCOOH in H₂O-ACN gradient). Yield 0.031 g as a mixture of enantiomers. ¹H NMR (400 MHz, MeOH-d₄): 1.23 (t, 3 H), 2.33-2.45 (m, 2 H), 2.65-2.78 (m, 1 H), 2.80-2.87 (m, 1 H), 3.02 (dd, 1 H), 3.13 (dd, 1 H), 3.54 (q, 2 H), 4.19-4.36 (m, 4 H), 4.75-4.88 (m, 1 H), 5.87-5.96 (m, 1 H), 7.03 (dd, 1H), 7.07 (s, 1H), 7.11 (s, 1H), 7.24-7.32 (m, 1 H), 7.37-7.46 (m, 1 H), 7.67 (d, 1 H), 7.85-7.97 (m, 1 H), 8.17-8.31 (m, 3 H).

Example 56

4-((3-(1-(2-(1H-Pyrazol-1-yl)ethyl)-1H-imidazol-5-yl)cyclopent-3-enyl)-(ethyl)amino)-2-(trifluoromethyl)benzonitrile a) tert-Butyl 3-(1-(2-(1H-pyrazol-1-yl)ethyl)-1H-imidazol-5-yl)cyclopent-3-enylcarbamate The compound was prepared from tert-butyl 3-formylcyclopent-3-enylcarbamate (0.60 g), 2-(1H-pyrazol-1-yl)ethylamine (0.631 g), tosylmethyl isocyanide (0.665 g) and DBU (0.856 ml). Crude product was purified by chromatography (silica column, eluent 0-2% MeOH/DCM). Yield 0.15 g as a mixture of enantiomers. ¹H NMR (400 MHz, CDCl₃): 1.46 (s, 9 H), 2.36-2.49 (m, 1 H), 2.49-2.61 (m, 1 H), 2.96 (dd, 1 H), 3.07 (dd, 1 H), 4.33-4.45 (m, 3 H), 4.45-4.56 (m, 2 H), 4.85 (br, 1 H), 5.69-5.79 (m, 1 H), 6.18 (t, 1 H), 6.97 (s, 2 H), 6.99 (dd, 1 H), 7.57 (dd, 1 H).

b) 3-(1-(2-(1H-pyrazol-1-yl)ethyl)-1H-imidazol-5-yl)cyclopent-3-enamine dihydrochloride The compound was prepared from the compound of Example 56(a) (0.19 g), and HCl, 4 M in dioxane (0.484 ml). Yield 0.19 g. Product was used as such in the next step.

c) 4-(3-(1-(2-(1H-pyrazol-1-yl)ethyl)-1H-imidazol-5-yl)cyclopent-3-enylamino)-2-(trifluoromethyl)benzonitrile The compound was prepared from the compound of Example 56(b) (0.19 g), 4-fluoro-2-(trifluoromethyl)benzonitrile (0.114 g) and DIPEA (0.523 ml). Crude title product was triturated with ether. Yield 0.080 g. $^1$H NMR (400 MHz, CDCl$_3$): 2.48-2.56 (m, 1 H), 2.59-2.69 (m, 1 H), 3.03-3.14 (m, 1 H), 3.15-3.25 (m, 1 H), 4.23-4.33 (m, 1 H), 4.39-4.45 (m, 2 H), 4.49-4.58 (m, 2 H), 5.01 (d, 1 H), 5.76-5.85 (m, 1 H), 6.21 (t, 1 H), 6.72 (dd, 1 H), 6.89 (d, 1 H), 6.98 (s, 1H), 7.05 (dd, 1 H), 7.09 (d, 1 H), 7.54-7.62 (m, 2 H).

d) 4-((3-(1-(2-(1H-pyrazol-1-yl)ethyl)-1H-imidazol-5-yl)cyclopent-3-enyl)-(ethyl)amino)-2-(trifluoromethyl)benzonitrile The compound was prepared from the compound of Example 56(c) (0.080 g), iodoethane (0.019 ml) and sodium hydride (60% dispersion in mineral oil, 0.016 g). Crude title compound was purified by chromatography (silica column, eluent 0-2% MeOH/DCM). Yield 0.038 g. $^1$H NMR (400 MHz, CDCl$_3$): 1.25 (t, 3 H), 2.66-2.77 (m, 1 H), 2.80-2.90 (m, 1 H), 2.95-3.15 (m, 2 H), 3.47 (q, 2 H), 4.41-4.48 (m, 2 H), 4.54-4.60 (m, 2 H), 4.68 (m, 1 H), 5.88 (m, 1 H), 6.20 (t, 1 H), 6.82 (dd, 1 H), 6.96-7.01 (m, 2 H), 7.01-7.07 (m, 2 H), 7.55-7.62 (m, 2 H).

Example 57

4-(Ethyl(3-(1-((3-methyloxetan-3-yl)methyl)-1H-imidazol-5-yl)cyclopent-3-enyl)amino)-2-(trifluoromethyl)benzonitrile a) 4-(3-(1-((3-Methyloxetan-3-yl)methyl)-1H-imidazol-5-yl)cyclopent-3-enylamino)-2-(trifluoromethyl)benzonitrile The compound was prepared from 4-(3-formylcyclopent-3-enylamino)-2-(trifluoromethyl)benzonitrile (0.35 g), 3-oxetanemethanamine, 3-methyl- (0.133 g), tosylmethyl isocyanide (0.293 g) and DBU (0.380 ml). Crude product was purified by chromatography (silica column, eluent 0-3% MeOH/DCM). Yield 0.25 g as a mixture of enantiomers. $^1$H NMR (400 MHz, CDCl$_3$): 1.35 (s, 3 H), 2.48-2.56 (m, 1 H), 2.62-2.69 (m, 1 H), 3.03-3.16 (m, 1 H), 3.19-3.27 (m, 1 H), 4.25-4.32 (m, 1 H), 4.27 (s, 2 H), 4.37 (d, 2 H), 4.49 (dd, 2 H), 4.74 (d, 1 H), 5.77-5.82 (m, 1 H), 6.71 (dd, 1 H), 6.87 (d, 1 H), 7.04 (s, 1 H), 7.45 (d, 1 H), 7.58 (d, 1 H).

b) 4-(Ethyl(3-(1-((3-methyloxetan-3-yl)methyl)-1H-imidazol-5-yl)cyclopent-3-enyl)amino)-2-(trifluoromethyl)benzonitrile The compound was prepared from the compound of Example 57(a) (0.100 g), iodoethane (0.030 ml) and sodium hydride (60% dispersion in mineral oil, 0.020 g). Crude product was purified by chromatography (silica column, eluent 0-2% MeOH/DCM) to obtain the title compound as a mixture of enantiomers. Yield 0.045 g. $^1$H NMR (400 MHz, CDCl$_3$): 1.24 (t, 3 H), 1.38 (s, 3 H), 2.63-2.78 (m, 1 H), 2.82-2.90 (m, 1 H), 2.92-3.05 (m, 1 H), 3.06-3.15 (m, 1 H), 3.46 (q, 2 H), 4.28 (d, 2 H), 4.38 (d, 2 H), 4.55 (dd, 2 H), 4.63-4.72 (m, 1 H), 5.83-5.87 (m, 1 H), 6.81 (dd, 1 H), 6.98 (d, 1 H), 7.05 (br. s., 1 H), 7.48 (br. s., 1 H), 7.57 (dd, 1 H).

Example 58

4-(Ethyl(3-(1-(2-(2-methylthiazol-4-yl)ethyl)-1H-imidazol-5-yl)cyclopent-3-enyl)amino)-2-(trifluoromethyl)benzonitrile a) 4-(3-(1-(2-(2-Methylthiazol-4-yl)ethyl)-1H-imidazol-5-yl)cyclopent-3-enylamino)-2-(trifluoromethyl)benzonitrile The compound was prepared from 4-(3-formylcyclopent-3-enylamino)-2-(trifluoromethyl)benzonitrile (0.355 g), 2-(2-methylthiazol-4-yl)ethanamine (0.189 g), tosylmethyl isocyanide (0.300 g) and DBU (0.380 ml). Crude product was purified by chromatography (silica column, eluent 0-2% MeOH/DCM) to obtain the title compound as a mixture of enantiomers. Yield 0.21 g. $^1$H NMR (400 MHz, CDCl$_3$): 2.49-2.58 (m, 1 H), 2.62-2.72 (m, 4 H), 3.05-3.27 (m, 4 H), 4.23-4.35 (m, 1 H), 4.41 (t, 2 H), 4.89 (d, 1 H), 5.86-5.95 (m, 1 H), 6.66 (s, 1 H), 6.71 (dd, 1H), 6.87 (d, 1 H), 6.98 (s, 1 H), 7.29 (d, 1 H), 7.58 (d, 1 H).

b) 4-(Ethyl(3-(1-(2-(2-methylthiazol-4-yl)ethyl)-1H-imidazol-5-yl)cyclopent-3-enyl)amino)-2-(trifluoromethyl)benzonitrile The compound was prepared from the compound of Example 58(a) (0.210 g), iodoethane (0.057 ml) and sodium hydride (60% dispersion in mineral oil, 0.038 g). Crude product was purified by chromatography (silica column, eluent 0-1% MeOH/DCM) to obtain the title compound as a mixture of enantiomers. Yield 0.078 g. $^1$H NMR (400 MHz, MeOH-d$_4$): 1.23 (t, 3 H), 2.68 (s, 3 H), 2.69-2.79 (m, 1 H), 2.79-2.90 (m, 1 H), 2.98-3.23 (m, 4 H), 3.55 (q, 2 H), 4.50 (t, 2 H), 4.78-4.87 (m, 1 H), 6.09-6.14 (m, 1 H), 6.88-6.94 (m, 1 H), 6.96 (s, 1 H), 7.03 (dd, 1 H), 7.08 (d, 1 H), 7.45 (s, 1 H), 7.66 (d, 1 H).

Example 59

4-(Ethyl(3-(1-ethyl-1H-imidazol-5-yl)cyclohex-2-en-1-yl)amino)-2-(trifluoromethyl)benzonitrile a) 3-((4-Cyano-3-(trifluoromethyl)phenyl)(ethyl)amino)cyclohex-1-en-1-yl trifluoromethanesulfonate 4-(Ethyl(3-oxocyclohexyl)amino)-2-(trifluoromethyl)benzonitrile (2 g, 6.45 mmol) was dissolved in dry THF (50 ml) under N$_2$-atmosphere. The solution was cooled to −78° C. and lithium bis(trimethylsilyl)amide (9.67 ml, 9.67 mmol) was added. The solution was stirred at −78° C. for 30 min and then N-phenyltrifluoromethanesulfonimide (2.76 g, 7.73 mmol) was added. The mixture was stirred at −78° C. for 2 h and was left to reach RT overnight. Reaction mixture was quenched by adding saturated NH$_4$Cl, water and ethyl acetate. Water phase was extracted with ethyl acetate and the combined organic phases were dried and evaporated. The product was purified with flash-chromatography using ethyl acetate/heptane (3:7) as an eluent giving 1.205 g of the title compound. $^1$H NMR (400 MHz, DMSO-d$_6$): 1.12 (t, 3 H), 1.21-1.31 (m, 1 H), 1.46-1.66 (m, 1 H), 1.74-1.98 (m, 3 H), 2.25-2.39 (m, 1 H), 3.34-3.43 (m, 2 H), 4.88-5.02 (m, 1 H), 5.92 (s, 1 H), 7.09-7.16 (m, 2 H), 7.79 (d, 1 H).

b) 4-(Ethyl(3-(1-ethyl-1H-imidazol-5-yl)cyclohex-2-en-1-yl)amino)-2-(trifluoromethyl)benzonitrile The compound of Example 59(a) (0.253 g, 0.57 mmol), the compound of Intermediate Example 1 (0.08 g, 0.57 mmol), tricyclohexylphosphine (3.85 mg, 0.014 mmol), Pd$_2$(dba)$_3$ (5.23 mg, 5.72 µmol) and potassium phosphate (0.206 mg, 0.97 mmol) were dissolved in mixture of 1,4-dioxane (3.5 ml) and water (1.25 ml) under N$_2$-atmosphere. The mixture was heated in microwave (100° C., 2 h). A small amount of Pd$_2$(dba)$_3$ and tricyclohexylphosphine were added and the mixture was heated for another 2 h (100° C.). The mixture was then diluted with ethyl acetate (5 ml) and filtrated. The crude product was purified with preparative HPLC giving 10 mg of the title product as mixture of enantiomers. The enantiomers were separated with a chiral preparative HPLC using Daicel Chiralpak IA-colon (particle size 5 µm), eluent: line A: n-hexane+0.2% diethyl ether and line B: ethanol+0.2% diethyl ether. B=10%, 20 ml/min, 35 min, 300 nm. 22.24 mg of enantiomer 1 (rt 20.61 min) and 19.21 mg of enantiomer 2 (rt 24.48 min) were obtained. $^1$H NMR (400 MHz, MeOH-d$_4$) 1.24 (t, 3 H), 1.38 (t, 3 H), 1.73-1.97 (m, 2 H), 1.97-2.09 (m, 2 H), 2.31-2.54 (m, 2 H), 3.42-3.64 (m, 2 H), 4.09 (q, 2 H), 4.75 (dd, 1 H), 5.79 (br. s., 1 H), 6.91 (s, 1 H), 7.08 (dd, 1 H), 7.14 (d, 1 H), 7.59-7.72 (m, 2 H).

Example 60

4-(Ethyl(3-(pyridin-4-yl)cyclohex-2-en-1-yl)amino)-2-(trifluoromethyl)benzonitrile Compound of Example 59(a) (0.05 g, 0.1 mmol.), pyridin-4-yl boronic acid (0.021 g, 0.17 mmol), tricyclohexylphosphine (0.761 mg, 2.71 µmol), Pd$_2$(dba)$_3$ (1.04 mg, 1.13 µmol) and potassium phosphate (0.041 mg, 0,192 mmol) were dissolved in 1,4-dioxane (0.6 ml) and water (0.3 ml) under N$_2$-atmosphere. The mixture was heated in microwave (100° C., 1 h). Ethyl acetate (30 ml) was added and the mixture was filtrated through a short plug of silica. The product was purified with column chromatography (100% EtOAc) giving 0.027 g of the title compound. $^1$H NMR (400 MHz, CDCl$_3$): 1.20-1.30 (m, 3 H), 1.68-1.94 (m, 2 H), 1.99-2.20 (m, 2 H), 2.42-2.65 (m, 2 H), 3.31-3.55 (m, 2 H), 4.61 (m, 1 H), 6.16 (dd, 1 H), 6.85 (dd, 1 H), 7.03 (d, 1 H), 7.19-7.31 (m, 2 H), 7.58 (d, 1 H), 8.52-8.61 (m, 2 H).

Example 61 cis-4-(Ethyl(3-(pyridin-4-yl)cyclohexyl)amino)-2-(trifluoromethyl)benzonitrile

The compound of Example 60 (0.14 g, 0.377 mmol) was dissolved in methanol and hydrogenated in H-Cube (Pd/C, 20 bar, 20° C., 1 ml/min). The crude product was purified with flash chromatography (eluent 100% EtOAc). Yield 10 mg. $^1$H NMR (400 MHz, CDCl$_3$): 1.15-1.30 (m, 3 H), 1.36-1.52 (m, 1 H), 1.53-1.73 (m, 3 H), 1.89-2.16 (m, 4 H), 2.74 (tt, 1 H), 3.42 (q, 2H), 3.77-3.93 (m, 1 H), 6.81 (dd, 1 H), 6.96 (d, 1 H), 7.15 (d, 2 H), 7.58 (d, 1 H), 8.48-8.58 (m, 2 H).

Example 62

4-(Ethyl(3-(1-methyl-1H-pyrazol-5-yl)cyclohex-2-en-1-yl)amino)-2-(trifluoromethyl)benzonitrile Compound of Example 59(a) (0.1 g, 0.23 mmol), 1-methyl-5-(4,4,5,5-tetramethyl-1,3,2-dioxaborolan-2-yl)-1H-pyrazole (0.047 g, 0.23 mmol), tricyclohexylphosphine (1.52 mg, 5.43 µmol), Pd$_2$(dba)$_3$ (4.14 mg, 4.52 µmol) and potassium phosphate (0.144 g, 0.6 mmol) were dissolved in 1,4-dioxane (1 ml) under N$_2$-atmosphere. The mixture was heated in microwave (100° C., 1 h). Ethyl acetate was added and the mixture was filtrated. The crude product was purified with column chromatography (100% EtOAc). Yield 0.020 g. $^1$H NMR (400 MHz, CDCl$_3$): 1.19-1.29 (m, 3 H), 1.68-1.92 (m, 2 H), 1.99-2.10 (m, 2 H), 3.34-3.56 (m, 2 H), 3.89 (s, 3 H), 4.55-4.66 (m, 1 H), 5.77 (s, 1 H), 6.17 (d, 1 H), 6.85 (dd, 1 H), 7.03 (d, 1 H), 7.43 (d, 1 H), 7.58 (d, 1 H).

Example 63

4-((3-(1H-imidazol-1-yl)cyclohex-2-en-1-yl)(ethyl)amino)-2-(trifluoromethyl)benzonitrile a) 4-((3-(1H-imidazol-1-yl)cyclohex-2-en-1-yl)amino)-2-(trifluoromethyl)-benzonitrile A mixture of 4-fluoro-2-(trifluoromethyl)benzonitrile (0.189 g, 1.0 mmol), HCl-salt of 3-(1H-imidazol-1-yl)cyclohex-2-enamine (0.20 g, 1.00 mmol), N-ethyl-N-isopropylpropan-2-amine (0.52 ml, 3.0 mmol) and DMSO (4 ml) were loaded in a microwave vial and heated in microwave at 90° C. for 2 h. The mixture was poured into a large amount of water and extracted in ethyl acetate. The organic phase was washed with water and brine, dried and evaporated. The crude product was purified with flash-chromatography using DCM-MeOH as an eluent. Yield 81 mg. $^1$H NMR (400 MHz, MeOH-d$_4$): 1.65-1.80 (m, 1 H), 1.83-2.08 (m, 3 H), 2.50-2.67 (m, 2 H), 4.37 (br. s., 1 H), 5.92-6.01 (m, 1 H), 6.90 (dd, 1 H), 6.99-7.08 (m, 2 H), 7.41 (s, 1 H), 7.62 (d, 1 H), 7.94 (s, 1 H).

b) 4-((3-(1H-imidazol-1-yl)cyclohex-2-en-1-yl)(ethyl)amino)-2-(trifluoromethyl)benzonitrile The compound was prepared from the compound of Example 63(a) (160 mg, 0.481 mmol) in DMF (2.5 ml), 60% sodium hydride in oil (30.8 mg, 0.77 mmol) and iodoethane (77 µl, 0.96 mmol). The crude product was purified with flash chromatography using 2.5% MeOH-DCM as a solvent. Yield 169 mg. $^1$H NMR (400 MHz, MeOH-d$_4$): 1.25 (t, 3 H), 1.72-1.88 (m, 1 H), 1.88-2.16 (m, 3 H), 2.52-2.77 (m, 2 H), 3.41-3.62 (m, 2 H), 4.79-4.84 (m, 1 H), 5.93 (s, 1 H), 7.05 (s, 1 H), 7.09 (dd, 1 H), 7.15 (d, 1 H), 7.36-7.49 (m, 1 H), 7.66 (d, 1 H), 7.96 (s, 1 H).

Example 64

4-(Ethyl(3-(1-(2-oxobutyl)-1H-imidazol-5-yl)cyclopent-3-en-1-yl)amino)-2-(trifluoromethyl)benzonitrile (4-(4-((4-Cyano-3-(trifluoromethyl)phenyl)(ethyl)amino) cyclopent-1-en-1-yl)-1H-imidazol-1-yl)methyl pivalate (0.05 g, 0.109 mmol) was mixed with 0.55 ml (5.43 mmol) of 1-bromobutan-2-one. The mixture was stirred at 50° C. overnight. Ammonia (7 M) in methanol (1 ml) was added and the mixture was stirred at RT for 1 h. Solvents were evaporated and heptane was added. The product was collected by filtering through short plug of silica first with heptanes, then with EtOAc and methanol. The product was purified with preparative HPLC. Yield 2.1 mg. $^1$H NMR (400 MHz, CDCl$_3$): 1.11 (t, 3 H), 1.16-1.28 (m, 3 H), 2.43 (q, 2 H), 2.57-2.70 (m, 1 H), 2.82 (dd, 1 H), 2.94 (dd, 1 H), 3.08 (dd, 1 H), 3.43 (q, 2 H), 4.55-4.73 (m, 1 H), 4.84 (s, 2 H), 5.58 (s, 1 H), 6.78 (dd, 1 H), 6.96 (d, 1 H), 7.08 (br. s., 1 H), 7.50 (br. s., 1 H), 7.58 (d, 1 H).

Example 65

4-((3-(1H-1,2,4-triazol-1-yl)cyclohexyl)(methyl)amino)-2-(trifluoromethyl)-benzonitrile Sodium hydride (55 mg, 1.387 mmol) was dissolved in dry DMF (4 ml) at 0° C. 4-((3-(1H-1,2,4-triazol-1-yl)cyclohexyl)amino)-2-(trifluoromethyl)benzonitrile (186 mg, 0.555 mmol) in dry DMF (1 ml) was added dropwise. The mixture was stirred at 0° C. for 1 h. Iodomethane (0.069 ml, 1.1 mmol) was added at 0° C. The mixture was stirred at 0° C. for 1 h and RT for 2 h. Ice-water (20 ml) was added and the product was extracted in EtOAc. The organic phase was washed with water and brine, dried and evaporated. The crude product was purified with flash chromatography using DCM-acetone as a solvent. Trans-diastereomer (42 mg): $^1$H NMR (400 MHz, CDCl$_3$): 1.63-1.82 (m, 2 H), 1.82-2.02 (m, 4 H), 2.12-2.28 (m, 1 H), 2.46 (d, 1 H), 2.87-2.98 (m, 3 H), 4.51 (ddd, 1 H), 4.79 (br. s., 1 H), 6.87 (dd, 1 H), 7.24-7.35 (m, 1 H), 7.56 (d, 1 H), 8.03 (s, 1 H), 8.18 (s, 1 H). Cis-diastereomer (51 mg): $^1$H NMR (400 MHz, CDCl$_3$): 1.53-1.73 (m, 2 H), 1.77-1.96 (m, 2 H), 2.07-2.36 (m, 4H), 2.95 (s, 3 H), 3.83-3.97 (m, 1 H), 4.36-4.48 (m, 1 H), 6.86 (dd, 1H), 7.00 (d, 1 H), 7.58 (d, 1 H), 7.95 (s, 1 H), 8.13 (s, 1 H). The trans-enantiomers were separated from using chiral HPLC (Column: Chiralpak AD, 4.6×250 mm, 20 μm. Eluent: n-heptane/ethanol=70:30 (v:v), Q=2 ml/min) to yield 16.7 mg of enantiomer 1 (rt 4.9 min) and 16.21 mg of enantiomer 2 (rt 8.49 min). The cis-enantiomers were separated using chiral HPLC (Column: Chiralpak AD, 4.6×250 mm, 20 μm. Eluent: n-heptane/isopropanol=90:10 (v:v), Q=2 ml/min) to yield 13 mg of enantiomer 1 (rt 12.88 min) and 16.5 mg of enantiomer 2 (rt 18.99 min).

Example 66

4-(Ethyl(3-methyl-3-(pyridin-3-yl)cyclohexyl)amino)-2-(trifluoromethyl)-benzonitrile a) 3-Methyl-3-(pyridin-3-yl)cyclohexanone Copper iodide (3.3 g, 17.33 mmol) was dissolved in dry diethyl ether (40 ml) under N$_2$-atmosphere at 0° C. Methyl lithium (3 molar, 9.81 ml, 29.4 mmol) was added and the mixture was stirred at 0° C. for 30 min and after that cooled to −78° C. A mixture of 3-(pyridin-3-yl)cyclohex-2-enone (0.51 g, 2.94 mmol) in 20 ml of dry ether was added dropwise. After stirring for 30 min at −78° C. the mixture was left to reach RT overnight. The reaction was quenched by adding NH$_4$Cl and extracted in ethyl acetate. The organic phase was extracted with 1M HCl and the aqueous phase was basified with 5 M NaOH (aqueous). Extraction with ethyl acetate, drying and evaporation gave 0.47 g of the title product. [M+1]$^+$=189.

b) 3-Methyl-3-(pyridin-3-yl)cyclohexanone oxime

A mixture of the compound of Example 66(a) (0.5 g, 2.64 mmol), hydroxylamine hydrochloride (0.193 g, 2.77 mmol) and pyridine (5 ml) was stirred at RT for 2 days. Pyridine was evaporated and the crude material (0.6 g) was used in the next step without further purification. [M+1]=204.

c) 3-Methyl-3-(pyridin-3-yl)cyclohexanamine

The compound of Example 66(b) (0.5 g, 2.448 mmol) was dissolved in methanol (50 ml) and hydrogenated in H-Cube (RaNi, 60 bar, 80° C., 1 ml/min). Solvents were evaporated giving 0.475 mg of the title product which was used in the next step without further purification. [M+1]=190.

d) 4-((3-Methyl-3-(pyridin-3-yl)cyclohexyl)amino)-2-(trifluoromethyl)benzonitrile 4-Fluoro-2-(trifluoromethyl)benzonitrile (348 mg, 1.839 mmol), the compound of Example 66(c) (350 mg, 1.839 mmol), DIPEA (0.96 ml, 5.52 mmol) and DMSO (7 ml) were mixed and heated to 100° C. When the reaction was complete the mixture was poured in water and extracted in EtOAc. The organic phase was washed with water and brine, dried and evaporated. The product was purified with flash chromatography. Yield 0.22 g. [M+1]=360.

e) 4-(Ethyl(3-methyl-3-(pyridin-3-yl)cyclohexyl)amino)-2-(trifluoromethyl)-benzonitrile 60% sodium hydride (0.061 g, 1.53 mmol) was washed with pentane. Dry DMF (20 ml) was added and the mixture was cooled to 0° C. The compound of Example 66(d) (220 mg, 0.612 mmol) in dry DMF (7 ml) was added and the mixture was stirred at 0° C. for 1 h. Iodoethane (0.098 ml, 1.224 mmol) was added and the mixture was stirred at 0° C. for 1 h and thereafter left to reach RT overnight. Iodoethane (1 eq.) and NaH (1 eq.) were added and the mixture was stirred for 2 h. Water was added and the product was extracted in EtOAc, dried and evaporated. The crude product was purified with preparative HPLC. Yield 52 mg. $^1$H NMR (400 MHz, CDCl$_3$): 1.20-1.24 (m, 6 H), 1.43-1.46 (m, 2 H), 1.63-1.69 (m, 1 H), 1.75-1.87 (m, 2 H), 1.87-2.04 (m, 1 H), 2.30-2.45 (dd, 2 H), 3.39-3.43 (m, 3 H), 6.57-6.63 (dd, 1 H), 6.80 (dd, 1 H), 7.29 (dd, 2 H), 7.52 (d, 1 H), 8.63 (d, 2 H).

Example 67

4-((6,6-Dimethyl-3-(pyridin-3-yl)cyclohex-2-en-1-yl)(ethyl)amino)-2-(trifluoromethyl)benzonitrile and 4-((6,6-Dimethyl-3-(pyridin-3-yl)cyclohex-3-en-1-yl)(ethyl)amino)-2-(trifluoromethyl)benzonitrile a) 3-((4-Cyano-3-(trifluoromethyl)phenyl)(ethyl)amino)-4,4-dimethylcyclohex-1-en-1-yl trifluoromethanesulfonate The compound was prepared as in Example 59(a) using 4-((2,2-dimethyl-5-oxocyclohexyl)(ethyl)amino)-2-(trifluoromethyl)benzonitrile (317 mg, 0.94 mmol) as a starting material. Yield 212 mg. [M+1]=471. 5-((4-cyano-3-(trifluoromethyl)-phenyl)(ethyl)amino)-4,4-dimethylcyclohex-1-en-1-yl trifluoromethanesulfonate was obtained as a side product in less than 20 mg.

b) 4-((6,6-Dimethyl-3-(pyridin-3-yl)cyclohex-2-en-1-yl)(ethyl)amino)-2-(trifluoromethyl)benzonitrile and 4-((6,6-Dimethyl-3-(pyridin-3-yl)cyclohex-3-en-1-yl)(ethyl)amino)-2-(trifluoromethyl)benzonitrile The compound of Example 67(a) (0.091 g, 0.193 mmol), 3-pyridineboronic acid (0.036 g, 0.29 mmol), tricyclohexylphosphine (2.7 mg, 0.00967 mmol), Pd$_2$(dba)$_3$ (8.86 mg, 9.67 µmol) and potassium phosphate (0.070 mg, 0.329 mmol) were dissolved in 1,4-dioxane (1.2 ml) and water (0.6 l) under N$_2$-atmosphere. The mixture was heated in microwave (100° C., 1 h). Ethyl acetate was added and the mixture was filtrated. The crude product was purified with preparative HPLC giving 15.9 mg of 4-((6,6-dimethyl-3-(pyridin-3-yl)cyclohex-2-en-1-yl)(ethyl)amino)-2-(trifluoromethyl)benzonitrile $^1$H NMR (400 MHz, CDCl$_3$): 0.97 (s, 3 H), 1.08 (s, 3 H), 1.20 (t, 3 H), 1.31 (t, 1 H), 1.63-1.81 (m, 2 H), 2.37-2.66 (m, 2 H), 3.33-3.63 (m, 2 H), 4.47 (br. s., 1 H), 5.93-6.07 (m, 1 H), 6.93 (dd, 1 H), 7.11 (d, 1 H), 7.29 (dd, 1 H), 7.59 (d, 1 H), 7.71 (dt, 1 H), 8.54 (d, 1 H), 8.70 (br. s., 1 H) and 5 mg of 4-((6,6-dimethyl-3-(pyridin-3-yl)cyclohex-3-en-1-yl)(ethyl)amino)-2-(trifluoromethyl)benzonitrile $^1$H NMR (400 MHz, CDCl$_3$): 1.02 (s, 3 H), 1.11 (s, 3 H), 1.16-1.35 (m, 3 H), 2.04-2.27 (m, 1 H), 2.28-2.43 (m, 1 H), 2.58-2.72 (m, 1 H), 2.74-2.92 (m, 1 H), 3.46-3.71 (m, 2 H), 4.22 (dd, 1 H), 6.17 (d, 1 H), 6.89-7.02 (m, 1 H), 7.10 (d, 1 H), 7.52-7.60 (m, 1 H), 7.67 (dt, 1 H), 8.51 (d, 1 H), 8.67 (s, 1 H).

Example 68

4-(Ethyl(3-(4-methylpyridin-3-yl)cyclopent-2-enyl)amino)-2-(trifluoromethyl)benzonitrile a) 3-((4-Cyano-3-(trifluoromethyl)phenyl)(ethyl)amino)cyclopent-1-en-1-yl trifluoromethanesulfonate The compound was prepared as in Example 59(a) using 4-(ethyl(3-oxocyclopentyl)amino)-2-(trifluoromethyl)benzonitrile (1 g, 3.38 mmol) as a starting material. Yield 0.90 g. [M+1]=429.

b) 4-(Ethyl(3-(4-methylpyridin-3-yl)cyclopent-2-enyl)amino)-2-(trifluoromethyl)benzonitrile The compound was prepared using Suzuki-reaction conditions described in Example 67(b) starting from the compound of Example 68(a) (0.15 g, 0.35 mmol) and (4-methyl-3-pyridinyl)boronic acid (0.048 g, 0.35 mmol). Yield 50 mg after flash chromatography. The enantiomers were separated using chiral HPLC (Column: Chiralpak AD, 20×250 mm. Eluent: MTBE+0.2% DEA/isopropanol+0.2% DEA=95:5 (v:v), Q=2 ml/min) to yield 12 mg of enantiomer 1 (rt 6.93 min) and 12.6 mg of enantiomer 2 (8.61 min). $^1$H NMR (400 MHz, CDCl$_3$): 1.15-1.34 (m, 3 H), 1.75-1.93 (m, 1 H), 2.40 (s, 3 H), 2.62 (dtd, 1 H), 2.76-2.96 (m, 2 H), 3.35-3.60 (m, 2 H), 5.17 (ddd, 1 H), 5.85-5.93 (m, 1 H), 6.88 (dd, 1 H), 7.06 (d, 1 H), 7.15 (d, 1 H), 7.60 (d, 1 H), 8.41 (d, 1 H), 8.45 (s, 1 H).

Example 69

4-((3-(2-Chloro-1-methyl-1H-imidazol-5-yl)cyclohex-2-en-1-yl)(ethyl)-amino)-2-(trifluoromethyl)benzonitrile a) (2-Chloro-1-methyl-1H-imidazol-5-yl)boronic acid The compound was prepared following method described in Intermediate Example 1 using 2-chloro-1-methyl-1H-imidazole (1 g, 8.58 mmol) as a starting material. Yield 0.394 g. [M+1]=161.

b) 4-((3-(2-Chloro-1-methyl-1H-imidazol-5-yl)cyclohex-2-en-1-yl)(ethyl)-amino)-2-(trifluoromethyl)benzonitrile The compound was prepared using Suzuki-reaction conditions of Example 67(b) starting from the compounds of Example 59(a) (0.30 g, 0.68 mmol) and Example 69(a) (0.163 g, 1.02 mmol). Yield 50 mg after flash chromatography. $^1$H NMR (400 MHz, CDCl$_3$): 1.19-1.34 (m, 3 H), 1.68-1.93 (m, 2 H), 1.95-2.11 (m, 2 H), 2.29-2.52 (m, 2 H), 3.34-3.54 (m, 2 H), 3.55-3.62 (m, 3 H), 4.59 (br. s., 1 H), 5.72 (s, 1 H), 6.83-6.94 (m, 2 H), 7.03 (d, 1 H), 7.54-7.59 (m, 1 H).

Example 70

4-((3-(2-Chloro-1-methyl-1H-imidazol-5-yl)cyclohex-2-enyl)(methyl)amino)-2-(trifluoromethyl)benzonitrile a) 3-((4-Cyano-3-(trifluoromethyl)phenyl)(methyl)amino)cyclohex-1-enyl trifluoromethanesulfonate The compound was prepared as in Example 59(a) using 4-(methyl(3-oxocyclohexyl)amino)-2-(trifluoromethyl)benzonitrile (3 g, 10.13 mmol) as a starting material. Yield 1.74 g. [M+1]=429.

b) 4-((3-(2-Chloro-1-methyl-1H-imidazol-5-yl)cyclohex-2-enyl)(methyl)-amino)-2-(trifluoromethyl)benzonitrile The compound was prepared using Suzuki-reaction conditions of Example 67(b) starting from the compounds of Example 70(a) (0.28 g, 0.66 mmol) and Example 69(a) (0.158 g, 0.985 mmol). Yield 58 mg after flash chromatography. $^1$H NMR (400 MHz, CDCl$_3$): 1.62-1.76 (m, 1 H), 1.76-1.94 (m, 1 H), 1.96-2.10 (m, 2 H), 2.28-2.47 (m, 2 H), 2.97 (s, 3 H), 3.61 (s, 3 H), 4.69 (dd, 1 H), 5.72 (s, 1 H), 6.83-6.93 (m, 2 H), 7.02 (d, 1 H), 7.54-7.61 (m, 1 H).

Example 71

4-(Methyl(3-(1-methyl-1H-imidazol-5-yl)cyclohex-2-en-1-yl)amino)-2-(trifluoromethyl)benzonitrile The compound of Example 70 (0.58 g, 0.15 mmol) was dissolved in 2.5 ml of dry methanol. The mixture was hydrogenated in H-Cube using 10% Pd/C as a catalyst. Flow rate 0.5 ml/min. Yield 42 mg. The enantiomers were separated using chiral HPLC (Column: Phenomex C6-Phenyl 30*100 mm P36. Eluent: 0.2% NH$_4$OH/MeOH+0.2% NH$_4$OH (50-95% of B) Q=30 ml/min) to yield 5.7 mg of enantiomer 1 (rt 6.58 min) and 4.8 mg of enantiomer 2 (rt 10.68 min). $^1$H NMR (400 MHz, CDCl$_3$): 1.61-1.76 (m, 1H), 1.78-1.93 (m, 1H), 1.96-2.07 (m, 2 H), 2.37-2.50 (m, 2 H), 2.96 (s, 3 H), 3.68 (s, 3 H), 4.61-4.75 (m, 1 H), 5.70 (s, 1 H), 6.87 (dd, 1 H), 7.00-7.07 (m, 2 H), 7.41 (s, 1 H), 7.56-7.66 (m, 1 H).

Example 72

4-((3-(1H-imidazol-1-yl)cyclohexyl)(ethyl)amino)-2-(trifluoromethyl)benzonitrile a) 3-(1H-imidazol-1-yl)cyclohexanone oxime 3-(1H-imidazol-1-yl)cyclohexanone (0.695 g, 4.23 mmol) was dissolved in pyridine (4 ml). Hydroxylamine HCl (0.294 g, 4.23 mmol) was added and the mixture was stirred overnight. Next morning product was filtered off and dried in vacuum. Title compound was used as such in the following step. [M+H]$^+$=180.

b) 3-(1H-imidazol-1-yl)cyclohexanamine

The compound of Example 72(a) was dissolved in MeOH (20 ml) and hydrogenated in H-Cube reactor (Raney Ni, controlled mode, 60 bar, 80° C., 1 ml/min) until most of the oxime had reduced to the corresponding amine. Solvent was evaporated in vacuo and the crude amine (a mixture of diastereomers) was used as such in the following step. [M+H]$^+$=166.

c) 4-((3-(1H-imidazol-1-yl)cyclohexyl)amino)-2-(trifluoromethyl)benzonitrile

A mixture of the compound of Example 72(b) (0.301 g, 1.82 mmol), DMSO (7 ml), 4-fluoro-2-(trifluoromethyl) benzonitrile (0.265, 1.4 mmol) and DIPEA (0.61 ml, 0.45 g, 3.5 mmol) were heated to 120° C. for 6 h. The mixture was partitioned between water and EtOAc. Aqueous layer was extracted with EtOAc. Combined organic layers were washed with water, dried and concentrated. The crude product was purified by column chromatography. Yield 0.117 g. [M+H]$^+$=335.

d) 4-((3-(1H-imidazol-1-yl)cyclohexyl)(ethyl) amino)-2-(trifluoromethyl)-benzonitrile The compound of Example 72(c) (0.105 g, 0.31 mmol) was dissolved in DMF. NaH (0.019 mg, 0.47 mmol) was added at 0° C. followed by iodoethane (0.038 µl, 0.073 g, 0.47 mmol). The mixture was allowed to react at RT overnight. Next morning more of NaH (0.015 mg, 0.37 mmol) and iodoethane (0.038 µl, 0.073 g, 0.47 mmol) were added. The reaction was quenched with water and diluted with EtOAc. Aqueous layer was extracted with EtOAc. Combined organic layers were washed with water, dried and concentrated. Diastereomers were separated by preparative HPLC. Cis-diastereomer yield 0.032 g, $^1$H NMR (400 MHz, CDCl$_3$): 1.22 (3 H, t), 1.52-1.75 (3 H, m),1.83-1.99 (2 H, m), 2.06-2.14 (1 H, m), 2.19-2.32 (2 H, m), 3.42 (2 H, q), 3.86 (1 H, tt), 4.15 (1 H, tt), 6.82 (1 H, dd), 6.96 (1 H, d), 6.99 (1 H, s), 7.07 (1 H, s), 7.55-7.61 (2 H, m). [M+H]$^+$=363. Enantiomers of a 60 mg sample of racemic cis-diastereomer were separated by chiral HPLC (Column: Daicel Chiralpak 20 mm×250 mm 5 µm, solvent A: n-hexane+0.1% DEA, solvent B: EtOH+0.1% DEA, isocratic B 15%, 20 ml/min) to obtain first eluting enantiomer (enantiomer 1), yield 0.025 g, rt 14 min and second eluting enantiomer (enantiomer 2), yield 0.024 g, rt 17 min. Trans-diastereomer yield 0.012 g, $^1$H NMR (400 MHz, CDCl$_3$): 1.23 (3 H, t), 1.66-1.89 (3 H, m), 1.89-1.99 (2 H, m), 2.05 (1 H, m), 2.28-2.36 (1 H, m), 2.38-2.46 (1 H, m), 3.35-3.49 (2 H, m), 3.73-3.82 (1 H, m), 4.57 (1 H, m), 6.63 (1 H, dd), 6.85 (1 H, d), 7.08 (1 H, m), 7.19 (1 H, m), 7.52 (1 H, d), 7.68 (1 H, s). [M+H]$^+$=363. Enantiomers of a 0.103 g sample of racemic trans-diastereomer were separated by chiral HPLC (Column: Daicel Chiralpak 20 mm×250 mm 5 µm, solvent A: n-hexane+0.1% DEA, solvent B: EtOH+0.1% DEA, isocratic B 20%, 20 ml/min) to obtain first eluting enantiomer (enantiomer 1), rt 13 min and second eluting enantiomer (enantiomer 2), rt 14 min.

Example 73

4-(ethyl(-3-(5-ethyl-1H-imidazol-1-yl)cyclohexyl) amino)-2-(trifluoromethyl)-benzonitrile a) 4-((3-Aminocyclohexyl)amino)-2-(trifluoromethyl)benzonitrile 1,3-Cyclohexanediamine (a 4:1 mixture of cis:trans-isomers) (0.36 ml, 0.34 g, 3.0 mmol), DMSO (20 ml), 4-fluoro-2-(trifluoromethyl)benzonitrile (0.189 g, 1.0 mmol) and DIPEA (0.52 ml, 0.39 g, 3.0 mmol) were mixed. The mixture was heated to 100° C. for 4 h after which the reaction was quenched with the addition of water. The aqueous phase was extracted with EtOAc. Combined organic layers were washed with water, brine, dried and concentrated. Crude product was used as such in the following step. [M+H]$^+$=284.

b) 4-(3-(5-Ethyl-1H-imidazol-1-yl)cyclohexyl) amino)-2-(trifluoromethyl)-benzonitrile The compound of Example 73(a) was dissolved in DMF (2 ml) and propionaldehyde (0.082 g, 1.41 mmol) was added. The solution was stirred at RT for 1.5 h before tosylmethyl isocyanide (0.184 g, 0.94 mmol) and K$_2$CO$_3$ (0.13 g, 0.94 mmol) were added. The mixture was stirred at RT overnight. The reaction was quenched with water and diluted with EtOAc. The aqueous layer was extracted with EtOAc. Combined organic layers were washed with water, dried and concentrated. Crude product was purified by column chromatography (134 mg, impure). [M+H]$^+$=363.

c) 4-(Ethyl(-3-(5-ethyl-1H-imidazol-1-yl)cyclohexyl)amino)-2-(trifluoromethyl)benzonitrile The compound was prepared from the compound of Example 73(b) (134 mg), DMF (2 ml), NaH (17.6 mg, 0.44 mmol) and iodoethane (0.041 ml, 0.081 g, 0.52 mmol). The title compound was purified by preparative HPLC. Yield: 0.0081 mg (cis-isomer). $^1$H NMR (400 MHz, CDCl$_3$): 1.22 (3 H, t), 1.30 (3 H, t), 1.54-1.64 (2 H, m), 1.65-1.73 (1 H, m), 1.83 (1 H, m), 1.94-2.02 (1 H, m), 2.07-2.26 (3 H, m), 2.53-2.61 (2 H, m), 3.42 (2 H, q), 3.77-3.87 (1 H, m), 3.95 (1 H, tt), 6.76-6.84 (2 H, m), 6.95 (1 H, d), 7.54 (1 H, s), 7.60 (1 H, d). [M+H]$^+$=391.

Example 74

4-((3-(1H-imidazol-1-yl)-5,5-dimethylcyclohex-2-en-1-yl)(ethyl)amino)-2-(trifluoromethyl)benzonitrile a) 3-Chloro-5,5-dimethylcyclohex-2-enone A flask flushed with N$_2$ was charged with 5,5-dimethylcyclohexane-1,3-dione (2.8 g, 20 mmol), DMF (2 ml) and DCM (40 mol) and cooled to 0° C. Oxalyl chloride (2 ml, 2.96 g, 23.3 mmol) in DCM (10 ml) was added. Ice bath was removed and the solution was allowed to react at RT overnight. The reaction was quenched with saturated NaHCO$_3$. The aqueous layer was extracted with DCM. Combined organic layers were washed with brine, dried and concentrated. Title compound was used as such in the following step. Yield: 2.69 g. [M]$^+$=158.

b) 3-(1H-imidazol-1-yl)-5,5-dimethylcyclohex-2-enone

A mixture of the compound of Example 74(a) (2.69 g, 17 mmol), toluene (10 ml), imidazole (2.31 g, 34 mmol), KHCO$_3$ (0.34 g, 3.4 mmol) and triethylamine (12 ml, 8.7 g, 86 mmol) was heated to 160° C. in a microwave reactor. Within an hour the reaction was complete. The mixture was diluted with water and DCM. Aqueous layer was extracted with DCM. Combined organic layers were washed with water, brine, dried and concentrated. Title compound was used as such in the following step. Yield: 2.77 g. [M+H]$^+$=191.

c) 3-(1H-imidazol-1-yl)-5,5-dimethylcyclohex-2-enol

Flask was charged with the compound of Example 74(b) (0.76 g, 4 mmol) and MeOH (15 ml) and cooled to 0° C. CeCl$_3$.7H$_2$O (1.64 g, 4.4 mmol) was added and the mixture was stirred for 5 min. NaBH$_4$ (0.182 g, 4.8 mmol) was then added. The mixture was stirred for 30 min and then quenched with water and saturated NH$_4$Cl. The aqueous layer was extracted with EtOAc. Combined organic layers were washed with brine, dried and concentrated. Title compound was used as such in the following step. Yield 0.68 g. [M+H]$^+$=193.

d) 1-(3-Azido-5,5-dimethylcyclohex-1-en-1-yl)-1H-imidazole

Flask flushed with N$_2$ was charged with the compound of Example 74(c) (0.62 g, 3.2 mmol), toluene (15 ml), THF (15 ml) and DPPA (1.04 ml, 1.33 g, 4.85 mmol). It was cooled to 0° C. and DBU (0.83 ml, 0.84 g, 5.5 mmol) was added. The mixture was warmed to RT slowly and left overnight. The reaction was quenched with water. The aqueous layer was extracted with EtOAc. Combined organic extracts were treated with 1M HCl and phases were separated. The acidic aqueous layer was basified with 2 M NaOH solution and extracted with EtOAc. Combined EtOAc layers were washed with brine, dried and concentrated. Crude product was purified by column chromatography. Yield 0.313 g. $^1$H NMR (400 MHz, CDCl$_3$): 1.05 (3 H, s), 1.16 (3 H, s), 1.53 (1 H, dd), 1.89 (1 H, dd), 2.16-2.25 (1 H, m), 2.36-2.45 (1 H, m), 4.16 (1 H, m), 5.77-5.81 (1 H, m), 7.10-7.12 (1 H, m), 7.13-7.15 (1 H, m), 7.72 (1 H, s). [M+H]$^+$=218.

e) 3-(1H-imidazol-1-yl)-5,5-dimethylcyclohex-2-enamine

A flask was charged with polymer-supported PPh$_3$ (3 mmol/g, 0.951 g, 2.85 mmol), MeOH (15 ml) and the compound of Example 74(d) (0.31 g, 1.42 mmol). The mixture heated to reflux for 4 h. The resin was filtered off and the residue was evaporated to dryness. Crude title compound (0.194 g) was used as such in the following step. [M+H]$^+$=192.

f) 4-((3-(1H-imidazol-1-yl)-5,5-dimethylcyclohex-2-en-1-yl)amino)-2-(trifluoromethyl)benzonitrile A mixture of the compound of Example 74(e), DMSO (2 ml), 4-fluoro-2-(trifluoromethyl)benzonitrile (0.189 g, 1 mmol) and DIPEA (0.45 ml, 0.33 g, 2.6 mmol) was heated to 100° C. for 4 h. The mixture was allowed to cool to RT and water was added. The aqueous layer was extracted with EtOAc. Combined organic phases were washed with water, dried and concentrated. Crude product was purified by column chromatography. Yield 0.229 g. [M+H]$^+$=361.

g) 4-((3-(1H-imidazol-1-yl)-5,5-dimethylcyclohex-2-en-1-yl)(ethyl)amino)-2-(trifluoromethyl)benzonitrile A flask flushed with N$_2$ was charged with the compound of Example 74(f) (229 g, 0.63 mmol) and DMF (4 ml) and cooled to 0° C. NaH (0.041 g, 1.02 mmol) was added and the mixture was allowed to react for 10 min before iodoethane (0.066 ml, 0.129 g, 0.82 mmol) was added. Ice bath was removed and the mixture was allowed to warm to RT. The reaction was complete within an hour. Water was added and the aqueous layer was extracted with EtOAc. Combined organic layers were washed with water, dried and concentrated. Crude product was purified by preparative HPLC to yield 0.146 g of the title compound. Enantiomers were separated by chiral HPLC (Column: Daicel Chiralpak IA 20 mm×250 mm 5 μm, solvent A: n-hexane+0.1% DEA, solvent B: EtOH+0.1% DEA, isocratic B 3%, 20 ml/min) to obtain enantiomer 1 (yield 0.057 g, rt 48 min) and enantiomer 2 (yield 0.0527 g, rt 54 min). $^1$H NMR (400 MHz, CDCl$_3$): 1.15 (3 H, s), 1.18 (3 H, s), 1.25 (3 H, t), 1.52-1.61 (1 H, m), 1.71-1.80 (1 H, m), 2.24 (1 H, m), 2.51 (1 H, m), 3.40 (2 H, m), 4.62-4.71 (1 H, m), 5.71-5.76 (1 H, m), 6.85 (1 H, dd), 7.02 (1 H, d), 7.09-7.14 (2 H, m), 7.59 (1 H, d), 7.72 (1 H, s). [M+H]$^+$=389.

Example 75

2-Chloro-4-(ethyl(3-(pyridin-3-yl)cyclohex-3-en-1-yl)amino)benzonitrile a) 2-Chloro-4-(ethyl(3-hydroxy-3-(pyridin-3-yl)cyclohexyl)amino)benzonitrile 3-Bromopyridine (237 mg, 1.5 mmol) was dissolved in dry THF (6 ml). The solution was cooled to −78° C. and n-butyllithium (1.6 M in hexanes, 1.0 ml, 1.6 mmol) was added. The mixture was allowed to react for 30 min before 2-chloro-4-(ethyl(3-oxocyclohexyl)amino)benzonitrile (277 mg, 1.0 mml) dissolved in THF (4 ml) was added. The mixture was warmed to RT and left overnight. Next day the reaction was quenched with saturated NH$_4$Cl solution and diluted with water and EtOAc. The aqueous layer was extracted with EtOAc. Combined organic layers were washed with brine, dried and finally concentrated. Crude product was purified by column chromatography to yield 164 mg of the title compound as mixture of diastereomers. [M+H]$^+$=356.

b) 2-Chloro-4-(ethyl(3-(pyridin-3-yl)cyclohex-3-en-1-yl)amino)benzonitrile

The compound of Example 75(a) (164 mg, 0.46 mmol) was dissolved in concentrated H$_2$SO$_4$ (2.5 ml) at 0° C. The mixture was allowed to react at 0° C. for 30 min and the solution allowed to warm to RT. Reaction was complete in 1.5 h. The mixture was poured in ice cold water. Aqueous phase was made basic (pH >10) and extracted with EtOAc. Combined organic layers were dried and concentrated. Crude product was purified by column chromatography. Yield 99 mg. $^1$H NMR (400 MHz, CDCl$_3$): 1.27 (3 H, t), 1.82-1.94 (1 H, m), 1.95-2.03 (1H, m), 2.43-2.62 (4 H, m), 3.42 (2 H, m), 4.03-4.13 (1 H, m), 6.16-6.21 (1 H, m), 6.64 (1 H, dd), 6.77 (1 H, d), 7.22-7.26 (1 H, m), 7.42 (1 H, d), 7.60-7.65 (1 H, m), 8.49 (1 H, dd), 8.64 (1 H, d). [M+H]$^+$=338.

Example 76

2-Chloro-4-(ethyl(3-(pyridin-3-yl)cyclohexyl)amino) benzonitrile

The compound of Example 75 (100 mg, 0.296 mmol) was dissolved in 1 M HCl/EtOH (1:3, 4 ml) and hydrogenated in H-Cube reactor (10% Pd/C, full H$_2$, 50° C., 1 ml/min). EtOH was evaporated and the residue was partitioned between saturated NaHCO$_3$ solution and EtOAc. Aqueous layer was extracted with EtOAc. Combined organic layers were washed with brine, dried and concentrated. Crude product was purified by preparative HPLC to yield cis-diastereomer of the title compound (7.3 mg), $^1$H NMR (400 MHz, CDCl$_3$): 1.20 (3 H, t), 1.42-1.72 (4 H, m), 1.90-2.11 (4 H, m), 2.76 (1 H, tt), 3.37 (2 H, q), 3.80 (1 H, tt), 6.59 (1 H, dd), 6.71 (1 H, d), 7.22-7.28 (1 H, m), 7.41 (1 H, d), 7.54 (1 H, dt), 8.48 (1 H, dd), 8.52 (1 H, d). [M+H]$^+$=340, and trans-diastereomer of the title compound (9.3 mg), $^1$H NMR (400 MHz, CDCl$_3$): 1.20 (3H, t), 1.62-1.83 (3 H, m), 1.83-1.91 (2 H, m), 2.02 (1 H, ddd), 2.18-2.26 (1 H, m), 2.28-2.36 (1 H, m), 3.32-3.44 (3 H, m), 3.54-3.64 (1 H, m), 6.36 (1 H, dd), 6.46 (1 H, d), 7.33 (1 H, d), 7.38 (1 H, dd), 7.70-7.77 (1 H, m), 8.54 (1 H, d), 8.68 (1 H, d). [M+H]$^+$=340.

Example 77

4-(Ethyl(3-(pyridin-4-yl)cyclohex-3-en-1-yl)amino)-2-(trifluoromethyl)benzonitrile a) 3-((tert-Butyldimethylsilyl)oxy)cyclohexanamine To a stirred solution of 3-aminocyclohexanol (40.0 g, 0.348 mol) in DCM (350 ml) were added imidazole (71.0 g, 1.042 mol) and TBDMS-Cl (78.0 g, 0.520 mol) at 0° C. The mixture was allowed to stir at RT for 24 h. The reaction was quenched by H$_2$O, extracted with DCM, washed with brine solution, dried, filtered and concentrated to give title compound. Yield 78.1 g (crude); [M+H]$^+$=230.

b) tert-Butyl (3-((tert-butyldimethylsilyl)oxy)cyclohexyl)carbamate

To a stirred solution of the compound of Example 77(a) (78.1 g, 0.341 mol) in DCM (350 ml) were added Et$_3$N (94.0 ml, 0.681 mol) and Boc$_2$O (74.1 ml, 0.341 mol) at 0° C. The mixture was stirred at RT for 6 h. It was poured into ice water, extracted with EtOAc, washed with brine solution, dried, filtered and concentrated. The residue was purified by column chromatography. Yield 26.0 g. [M+H]$^+$=330.

c) tert-Butyl (3-((tert-butyldimethylsilyl)oxy)cyclohexyl)(ethyl)carbamate

To a stirred solution of NaH (18.9 g, 0.474 mol) in DMF (350 ml) was added the compound of Example 77(b) (26.0 g, 0.079 mol) in DMF (20 ml). The mixture was stirred at 0° C. for 30 min and EtBr (14.7 ml, 21.5 g, 0.198 mol) was added. The mixture was warmed to 70° C. for 16 h and quenched with ice water, extracted with EtOAc, washed with brine solution, dried, filtered and concentrated. The crude residue was purified by column chromatography. Yield 19.5 g. [M+H]$^+$=358.

d) tert-Butyl ethyl(3-hydroxycyclohexyl)carbamate

The compound of Example 77(c) (7.15 g, 20 mmol) was dissolved in THF (20 ml). TBAF (1 M in THF, 24 ml, 24 mmol) was added and the solution was allowed to react for 120 h at RT. Solvents were evaporated and the residue purified by filtration through a pad of silica. Yield 4.66 g. [M+H]$^+$=244.

e) tert-Butyl ethyl(3-oxocyclohexyl)carbamate

The compound of Example 77(d) (4.5 g, 18.5 mmol) was dissolved in dry DMSO (35 ml). The solution was cooled on an ice bath and triethylamine (15.46 ml, 11.23 g, 111 mmol) followed by sulphur dioxide-pyridine complex (7.36 g, 46.2 mmol) were added. The mixture was stirred on ice bath for a further 10 min before it was allowed to warm to RT. Reaction was complete within 1 h. Water and EtOAc were added. Phases were separated and the aqueous layer was extracted with EtOAc. Combined organic layers were washed with water, dried and concentrated. Crude ketone (4.31 g) was used as such in the following step. [M+H]$^+$=242.

f) tert-Butyl ethyl(3-hydroxy-3-(pyridin-4-yl)cyclohexyl)carbamate

Title compound was prepared from 4-Bromopyridine hydrochloride (1.011 g, 5.2 mmol), n-butyllithium (1.6 M in hexanes, 7.0 ml, 11.2 mmol) and the compound of Example 77(e) (0.965 g, 4 mmol) as described in Example 75(a). Yield: 0.269 g. [M+H]$^+$=321.

g) N-ethyl-3-(pyridin-4-yl)cyclohex-3-enamine

Title compound was prepared from the compound of Example 77(f) (0.250 g, 0.78 mmol) and concentrated sulphuric acid (4 ml) as described in Example 75(b). Yield: 0.101 g. $^1$H NMR (400 MHz, CDCl$_3$): 1.17 (3 H, t), 1.49 (1 H, m), 1.93-2.02 (1 H, m), 2.18-2.34 (2 H, m), 2.34-2.44 (1 H, m), 2.67 (1 H, m), 2.78 (2 H, m), 2.90-2.99 (1 H, m), 6.34 (1 H, m), 7.23-7.27 (2 H, m), 8.48-8.53 (2 H, m).

h) 4-(Ethyl(3-(pyridin-4-yl)cyclohex-3-en-1-yl) amino)-2-(trifluoromethyl)-benzonitrile The compound of Example 77(g) (100 mg, 0.50 mmol) was dissolved in DMSO (2 ml). 4-Fluoro-2-(trifluoromethyl)benzonitrile (85 mg, 0.45 mmol) followed by cesium carbonate (220 mg, 0.68 mmol) were added. The solution was kept at 100° C. for 9 h. The solution was partitioned between water and DCM and the aqueous layer was extracted with DCM. Combined organic layers were washed with water, dried and concentrated. Crude product was purified by preparative chromatography. Yield 2.5 mg. $^1$H NMR (400 MHz, CDCl$_3$): 1.30 (3 H, t), 1.85-1.97 (1 H, m), 1.99-2.07 (1 H, m), 2.40-2.69 (4 H, m), 3.38-3.55 (2 H, m), 4.14 (1 H, m), 6.43-6.48 (1 H, m), 6.86 (1 H, dd), 7.01 (1 H, d), 7.31-7.35 (2 H, m), 7.59 (1 H, d), 8.54-8.59 (2H, m). [M+H]$^+$=372.

Example 78

2-Chloro-4-(ethyl(3-(4-methoxypyridin-3-yl)cyclohex-2-en-1-yl)amino)-benzonitrile and 2-Chloro-4-(ethyl(3-(4-methoxypyridin-3-yl)cyclohex-3-en-1-yl)amino)benzonitrile a) 5-((tert-Butoxycarbonyl)(ethyl)amino)cyclohex-1-en-1-yl trifluoromethanesulfonate and 3-((tert-Butoxycarbonyl)(ethyl)amino)cyclohex-1-en-1-yl trifluoromethanesulfonate tert-Butyl ethyl(3-oxocyclohexyl)carbamate (241 mg, 1 mmol) was dissolved in dry THF (6 ml). The solution was cooled to −78° C. and lithium bis(trimethylsilyl)amide (1 M in THF, 1.5 ml, 1.5 mmol) was added. The solution was allowed to react for 30 min before N-phenyltrifluoromethanesulfonimide (429 mg, 1.2 mmol) dissolved in THF (3 ml) was added. The solution was kept at −78° C. for another 2 h before it was allowed to warm to RT. The completed reaction was quenched with saturated NH$_4$Cl solution and diluted with water and EtOAc. Aqueous layer was extracted with EtOAc. Combined organic layers were dried and concentrated. Crude product was purified by column chromatography to yield the title compounds as a mixture of double bond regioisomers (368 mg). [M+H]$^+$=374.

b) tert-Butyl ethyl(3-(4-methoxypyridin-3-yl)cyclohex-3-en-1-yl)carbamate and tert-Butyl ethyl(3-(4-methoxypyridin-3-yl)cyclohex-2-en-1-yl)carbamate The product of Example 78(a) (360 mg, 0.964 mmol) was dissolved in 1,4-dioxane (5 ml). To this solution were added 2-methoxy-5-pyridineboronic acid (192 mg, 1.253 mmol), Pd(PPh$_3$)$_4$ (28 mg, 0.02 mmol) and potassium phosphate (307 mg, 1.45 mmol) dissolved in water (2 ml). Solution was heated to 80° C. for 3 h before it was allowed to cool to RT. Aqueous layer was basified with 2 M NaOH solution, diluted with water and extracted with EtOAc. Combined organic layers were washed with brine, dried and concentrated. Crude product was purified by column chromatography to yield the title compounds as a 3:2 mixture of double bond regioisomers (166 mg). [M+H]$^+$=333.

c) N-ethyl-3-(4-methoxypyridin-3-yl)cyclohex-3-enamine and N-ethyl-3-(4-methoxypyridin-3-yl)cyclohex-2-enamine The product of Example 78(b) (165 mg, 0.50 mmol) was dissolved in DCM (2 ml) and cooled to 0° C. on an ice bath. Trifluoroacetic acid (0.6 ml, 921 mg, 8.1 mmol) was added and the solution was allowed to react at 0° C. for another 10 min before it was allowed to warm to RT. The reaction was quenched with saturated NaHCO$_3$ solution. Phases were separated and the aqueous layer was extracted with DCM. Combined organic layers were dried and concentrated to yield title compounds as a 3:2 mixture of double bond regioisomers (119 mg). [M+H]$^+$=233.

d) 2-Chloro-4-(ethyl(3-(4-methoxypyridin-3-yl)cyclohex-3-en-1-yl)amino)-benzonitrile The product of Example 78(c) (136 mg, 0.59 mmol) was dissolved in DMSO (2 ml). To this solution were added 2-chloro-4-fluorobenzonitrile (91 mg, 0.59 mmol) and DIPEA (0.3 ml, 223 mg, 1.72 mmol). The solution was heated to 120° C. and allowed to react overnight. The mixture was quenched with water and the aqueous layer was extracted with EtOAc. Combined organic layers were washed with water, dried and concentrated. Crude product was purified by preparative HPLC to obtain 2-Chloro-4-(ethyl(3-(4-methoxypyridin-3-yl)cyclohex-3-en-1-yl)amino)benzonitrile (5.6 mg), $^1$H NMR (400 MHz, CDCl$_3$): 1.23 (3 H, t), 1.86-2.03 (2 H, m), 2.38-2.52 (3 H, m), 2.52-2.63 (1 H, m), 3.31-3.48 (2 H, m), 3.90 (3 H, s), 3.99-4.10 (1 H, m), 5.78-5.84 (1 H, m), 6.64 (1 H, dd), 6.76-6.82 (2 H, m), 7.42 (1 H, d), 8.23-8.30 (1 H, m), 8.37-8.46 (1 H, m), [M+H]$^+$=368, and 2-Chloro-4-(ethyl(3-(4-methoxypyridin-3-yl)cyclohex-2-en-1-yl)amino)benzonitrile (7.6 mg): $^1$H NMR (400 MHz, CDCl$_3$): 1.18-1.27 (3 H, m), 2.00 (2 H, br. s.), 1.67-1.90 (2 H, m), 2.33-2.54 (2 H, m), 3.32-3.55 (2 H, m), 3.89 (3 H, br. s.), 4.48-4.58 (1 H, m), 5.67-5.74 (1 H, m), 6.65 (1 H, d), 6.81-6.86 (1 H, m), 6.76-6.81 (1 H, m), 7.41 (1 H, d), 8.27 (1H, br. s.), 8.42 (1H, br. s.). [M+H]$^+$=368. Enantiomers of 2-chloro-4-(ethyl-(3-(4-methoxypyridin-3-yl)cyclohex-2-en-1-yl)amino)benzonitrile were separated by chiral HPLC (Column: Daicel Chiralpak IA 20 mm×250 mm 5 pun, solvent A: n-hexane+0.1% DEA, solvent B: EtOH+0.1% DEA, isocratic B 10%, 20 ml/min) to obtain enantiomer 1 (yield 0.032 g, rt 28 min) and enantiomer 2 (yield 0.033 g, rt 31).

Example 79

2-Chloro-4-(ethyl(3-(4-methylpyridin-3-yl)cyclohex-3-en-1-yl)amino)benzonitrile a) 2-Chloro-4-(ethyl(3-hydroxy-3-(4-methylpyridin-3-yl)cyclohexyl)amino)-benzonitrile Title compound was prepared from 3-bromo-4-methylpyridine (1.342 g, 7.8 mmol), n-butyllithium (1.6 M in hexanes, 5.5 ml, 8.8 mmol) and 2-chloro-4-(ethyl(3-oxocyclohexyl)amino)benzonitrile (1.661 g, 6 mmol) as described in Example 75(a). Yield: 0.722 g. [M+H]$^+$=370.

b) 2-Chloro-4-(ethyl(3-(4-methylpyridin-3-yl)cyclohex-3-en-1-yl)amino)-benzonitrile Title compound was prepared from the compound of Example 79(a) (0.840 g, 2.27 mmol) and concentrated H$_2$SO$_4$ (9.0 ml) as described in Example 75(b). Yield 0.799 g. $^1$H NMR (400 MHz, CDCl$_3$): 1.23 (3 H, t), 1.84-2.06 (2 H, m), 2.32 (3 H, s), 2.34-2.52 (4 H, m), 3.31-3.47 (2 H, m), 4.02-4.12 (1 H, m), 5.65-5.71 (1 H, m), 6.62 (1 H, dd), 6.75 (1 H, d), 7.09 (1 H, d), 7.43 (1 H, d), 8.30 (1 H, s), 8.36 (1 H, d). [M+H]$^+$=352.

Example 80

4-((3-(1H-imidazol-4-yl)cyclohex-3-en-1-yl)amino)-2-(trifluoromethyl)benzonitrile a) 4-((3-Oxocyclohexyl)amino)-2-(trifluoromethyl)benzonitrile Title compound was prepared from 4-((3-hydroxycyclohexyl)amino)-2-(trifluoromethyl)benzonitrile (0.569 g, 2 mmol), sulfur trioxide-pyridine complex (0.637 mg, 4 mmol), triethylamine (2 ml, 1.452 g, 14.4 mmol) and DMSO (5 ml) as described in Example 77(b). Yield 0.560 g. [M+H]$^+$=283.

b) 4-((3-(1H-imidazol-4-yl)cyclohex-3-en-1-yl)amino)-2-(trifluoromethyl)-benzonitrile A solution of 4-iodo-1-trityl-1H-imidazole (0.916 g, 2.100 mmol) and THF (12 ml) was cooled to −78° C. n-Butyllithium (1.6 M in hexanes, 2.0 ml, 3.2 mmol) was added and the solution was stirred for 1 hour. The compound of Example 80(a) (0.282 g, 1.0 mmol) dissolved in THF (2 ml) was added and the mixture was stirred at −78° C. for 45 min and then warmed to RT. After 70 h the reaction was quenched with saturated NH$_4$Cl solution and diluted with water. Aqueous layer was extracted with EtOAc. Combined organic layers were dried and concentrated [M+H]$^+$=593. The impure alcohol intermediate from the reaction above was dissolved in concentrated H$_2$SO$_4$ (3.0 ml) at 0° C. Stirring at 0° C. was continued for 30 min and the mixture was allowed to warm to RT. The reaction was complete within 4 h after which it was quenched and worked as above. Crude material was purified by column chromatography to afford the title compound (0.126 g). $^1$H NMR (400 MHz, CDCl$_3$): 1.69-1.80 (1 H, m), 1.95-2.04 (1 H, m), 2.27-2.41 (3 H, m), 2.79-2.89 (1 H, m), 3.82-3.93 (1 H, m), 4.76 (1 H, d), 6.31-6.40 (1 H, m), 6.71 (1 H, dd), 6.87 (1 H, d), 6.95 (1 H, s), 7.53 (1 H, d), 7.60 (1 H, d), 10.03 (br. s., 1 H). [M+H]$^+$=333.

Example 81

4-((3-(1H-imidazol-4-yl)cyclohexyl)amino)-2-(trifluoromethyl)benzonitrile

The title compound was prepared from the compound of Example 80 (60 mg, 0.18 mmol) as described in Example 76. Crude product was purified by preparative HPLC. Yield 22.1 mg (5:2 mixture of diastereomers). Major diastereomer: $^1$H NMR (400 MHz, MeOH-d$_4$): 1.23-1.48 (2 H, m), 1.54-1.68 (1 H, m), 1.68-1.85 (1 H, m), 1.87-2.02 (1 H, m), 2.02-2.15 (2 H, m), 2.35 (1 H, m), 2.88 (1 H, tt), 3.54 (1 H, tt), 6.84 (1 H, m), 6.97 (1 H, d), 7.01-7.11 (2 H, m), 7.58 (1 H, d), 8.15 (1 H, s), 8.41 (1H, br. s.). [M+H]$^+$=335.

Example 82

2-Chloro-4-(ethyl(3-(5-methoxypyridin-3-yl)cyclohex-3-en-1-yl)amino)-benzonitrile and 2-Chloro-4-(ethyl(3-(3-methoxypyridin-4-yl)cyclohex-3-en-1-yl)-amino)benzonitrile a) 2-Chloro-4-(ethyl(3-hydroxy-3-(5-methoxypyridin-3-yl)cyclohexyl)amino)-benzonitrile The compound was prepared from 3-Bromo-5-methoxypyridine (0.530 g, 2.8 mmol), n-butyllithium (1.6 M in hexanes, 1.9 ml, 3.0 mmol) and 2-chloro-4-(ethyl(3-oxocyclohexyl)amino)benzonitrile (0.600 g, 2.17 mmol) as described in Example 75(a). Yield 0.501 g (a mixture of 5-methoxypyridin-3-yl and 3-methoxypyridin-4-yl isomers). [M+H]$^+$=386.

b) 2-Chloro-4-(ethyl(3-(5-methoxypyridin-3-yl)cyclohex-3-en-1-yl)amino)-benzonitrile and 2-Chloro-4-(ethyl(3-(3-methoxypyridin-4-yl)cyclohex-3-en-1-yl)-amino)benzonitrile Title compounds were prepared from the compound of Example 82(a) (0.500 g, 1.3 mmol) and concentrated sulphuric acid (4 ml) as described in Example 75(b). Isomers were separated by preparative HPLC to obtain 2-Chloro-4-(ethyl(3-(5-methoxypyridin-3-yl)cyclohex-3-en-1-yl)amino)benzonitrile (0.093 g), $^1$H NMR (400 MHz, CDCl$_3$): 1.27 (3 H, t), 1.89 (1 H, m), 1.95-2.03 (1 H, m), 2.43-2.52 (2 H, m), 2.53-2.60 (2 H, m), 3.35-3.48 (2 H, m), 3.87 (3 H, s), 4.07 (1 H, m), 6.16-6.21 (1 H, m), 6.64 (1 H, dd), 6.76 (1 H, d), 7.12 (1H, dd), 7.40-7.44 (1 H, m), 8.20 (1 H, d), 8.26 (1H, d), [M+H]$^+$=368, and 2-Chloro-4-(ethyl(3-(3-methoxypyridin-4-yl)-cyclohex-3-en-1-yl)amino)benzonitrile (0.026 g), $^1$H NMR (400 MHz, CDCl$_3$): 1.24 (3H, t), 1.85-2.02 (2H, m), 2.42-2.62 (4H, m), 3.31-3.49 (2H, m), 3.94 (3H, s), 3.98-4.09 (1H, m), 5.90-5.97 (1H, m), 6.64 (1H, dd), 6.78 (1H, d), 7.07 (1H, d), 7.42 (1H, d), 8.21-8.31 (2H, m), [M+H]$^+$=368.

Example 83

2-Chloro-4-(ethyl(3-(5-methoxypyridin-3-yl)cyclohexyl)amino)benzonitrile

The compound was prepared from 2-Chloro-4-(ethyl(3-(5-methoxypyridin-3-yl)cyclohex-3-en-1-yl)amino)benzonitrile of Example 82 (49 mg, 0.13 mmol) and EtOH (5 ml) as described in Example 76. Crude was purified by preparative HPLC to obtain cis-diastereomer (9.7 mg), $^1$H NMR (400 MHz, CDCl$_3$): 1.19 (3 H, t), 1.38-1.50 (1 H, m), 1.53-1.70 (3 H, m), 1.89-2.10 (4 H, m), 2.75 (1 H, tt), 3.37 (2 H, q), 3.74-3.83 (1 H, m), 3.87 (3 H, s), 6.59 (1 H, dd), 6.71 (1 H, d), 7.02-7.05 (1 H, m), 7.41 (1 H, d), 8.13 (1 H, d,) 8.17 (1 H, d), [M+H]$^+$=370, and trans-diastereomer (5.1 mg), $^1$H NMR (400 MHz, CDCl$_3$): 1.20 (3 H, t), 1.62-1.88 (5 H, m), 1.96-2.04 (1 H, m), 2.16-2.24 (1 H, m), 2.25-2.32 (1 H, m), 3.32-3.43 (3 H, m), 3.58-3.71 (1 H, m), 3.89 (3 H, s), 6.38 (1 H, dd), 6.47 (1 H, d), 7.17-7.19 (1 H, m), 7.33 (1 H, d), 8.23 (1 H, d), 8.28 (1 H, d), [M+H]$^+$=370.

Example 84

4-(Ethyl(3-(5-methoxypyridin-3-yl)cyclohex-3-en-1-yl)amino)-2-(trifluoromethyl)benzonitrile and 4-(Ethyl(3-(3-methoxypyridin-4-yl)cyclohex-3-en-1-yl)amino)-2-(trifluoromethyl)benzonitrile a) tert-Butyl ethyl(3-hydroxy-3-(5-methoxypyridin-3-yl)cyclohexyl)carbamate and tert-Butyl ethyl(3-hydroxy-3-(3-methoxypyridin-4-yl)cyclohexyl)carbamate Title compounds were prepared from 3-bromo-5-methoxypyridine (0.978 g, 5.2 mmol), n-butyllithium (1.6 M in hexanes, 3.5 ml, 5.6 mmol) and tert-butyl ethyl-(3-oxocyclohexyl)carbamate (0.965 g, 4 mmol) as described in Example 75(a). Yield 0.720 g. [M+H]$^+$=351.

b) N-Ethyl-3-(5-methoxypyridin-3-yl)cyclohex-3-enamine and N-Ethyl-3-(3-methoxypyridin-4-yl)cyclohex-3-enamine Title compounds were prepared from the product of Example 84(a) (0.600 g, 1.71 mmol) and concentrated H$_2$SO$_4$ (10 ml) as described in Example 75(b). Yield 0.373 g. [M+H]$^+$=333.

c) 4-(Ethyl(3-(5-methoxypyridin-3-yl)cyclohex-3-en-1-yl)amino)-2-(trifluoromethyl)benzonitrile and 4-(Ethyl(3-(3-methoxypyridin-4-yl)cyclohex-3-en-1-yl)-amino)-2-(trifluoromethyl)benzonitrile Title compounds were prepared from the product of Example 84(b) (0.209 g, 0.90 mmol), 4-fluoro-2-(trifluoromethyl)benzonitrile (0.142 g, 0.75 mmol) and cesium carbonate (0.489 g, 1.50 mmol) as described in Example 77(e). Isomers were separated by preparative HPLC to obtain 4-(Ethyl(3-(5-methoxypyridin-3-yl)cyclohex-3-en-1-yl)amino)-2-(trifluoromethyl)benzonitrile (31.7 mg), $^1$H NMR (400 MHz, CDCl$_3$): 1.29 (3 H, t), 1.85-2.04 (2 H, m), 2.40-2.61 (4 H, m), 3.41-3.53 (2 H, m), 3.88 (3 H, s), 4.14 (1 H, m), 6.19-6.23 (1 H, m), 6.86 (1 H, dd), 7.01 (1 H, d), 7.13-7.17 (1 H, m), 7.58 (1 H, d), 8.20 (1 H, d), 8.26 (1 H, d), [M+H]$^+$=402, and 4-(Ethyl(3-(3-methoxypyridin-4-yl)cyclohex-3-en-1-yl)amino)-2-(trifluoromethyl)-benzonitrile (10.8 mg), $^1$H NMR (400 MHz, CDCl$_3$): 1.26 (3 H, t), 1.88-2.04 (2 H, m), 2.44-2.64 (4 H, m), 3.37-3.54 (2 H, m), 3.92 (3 H, s), 4.05-4.15 (1 H, m), 5.91-5.97 (1 H, m), 6.85 (1 H, dd), 7.02 (1 H, d), 7.06 (1 H, d), 7.58 (1 H, d), 8.21 (1 H, d), 8.25 (1 H, s), [M+H]$^+$=402.

Example 85

4-(Ethyl(3-(pyridin-3-yl)cyclohexyl)amino)-2-(trifluoromethyl)benzonitrile

Title compounds were prepared from 4-(ethyl(3-(pyridin-3-yl)cyclohex-3-en-1-yl)amino)-2-(trifluoromethyl)benzonitrile (245 mg, 0.66 mmol), EtOH (6 ml) and acetic acid (0.15 ml) as in Example 76. Crude product was purified by preparative HPLC to obtain cis-diastereomer (11.3 mg), $^1$H NMR (400 MHz, CDCl$_3$): 1.21 (3 H, t), 1.40-1.53 (1 H, m), 1.56-1.65 (2 H, m), 1.67-1.71 (1 H, m), 1.90-2.12 (4 H, m), 2.77 (1 H, tt), 3.43 (2 H, q), 3.86 (1 H, tt), 6.81 (1 H, dd), 6.96 (1 H, d), 7.24 (1 H, dd), 7.53 (1 H, dt), 7.57 (1 H, d), 8.48 (1 H, dd), 8.52 (1 H, d), [M+H]$^+$=374, and trans-diastereomer (8.7 mg), $^1$H NMR (400 MHz, CDCl$_3$): 1.22 (3 H, t), 1.67-1.92 (5 H, m), 2.04 (1 H, m), 2.18-2.25 (1 H, m), 2.29-2.36 (1 H, m), 3.37-3.48 (3 H, m), 3.64-3.73 (1 H, m), 6.56 (1 H, dd), 6.74 (1 H, d), 7.32 (1 H, dd), 7.48 (1 H, d), 7.66-7.71 (1 H, m), 8.53 (1 H, d), 8.66 (1 H, s), [M+H]$^+$=374.

Example 86

4-((-3-(1H-imidazol-1-yl)cyclopentyl)(ethyl)amino)-2-(trifluoromethyl)benzonitrile a) 3-(1H-imidazol-1-yl)cyclopentanone oxime Title compound was prepared from 3-(1H-imidazol-1-yl)cyclopentanone (1.79 g, 9.8 mmol), hydroxylamine hydrochloride (0.7 g, 10.1 mmol) and pyridine (10 ml) as described in Example 72(a). Crude oxime was purified by filtrating through a pad of silica. Yield 1.40 g. [M+H]$^+$=166.

b) 3-(1H-imidazol-1-yl)cyclopentanamine

A flask was charged with the compound of Example 86(a) (1.40 g, 8.5 mmol) and THF (30 ml). The flask was placed on ice bath and LiAlH$_4$ (0.516 g, 13.6 mmol) was added in portions. Ice bath was removed and the mixture was heated to 60° C. for 4 h. The reaction mixture was quenched with water/2 M NaOH/water and filtered. Organic phase was dried and concentrated. The residue was partitioned between water and EtOAc. Organic layer was washed with water and brine. Combined aqueous layers were concentrated. The residue was treated with MeOH. The alcoholic layer was concentrated to give the title compound (0.33 g, a mixture of diastereomers), which was used as such in the following step. [M+H]$^+$=152.

c) 4-((3-(1H-imidazol-1-yl)cyclopentyl)amino)-2-(trifluoromethyl)benzonitrile

Title compound was prepared from the compound of Example 86(b) (0.33 g, 2.18 mmol), 4-fluoro-2-(trifluoromethyl)benzonitrile (0.66 g, 3.49 mmol), DIPEA (1.5 ml, 1.11 g, 8.6 mmol) and DMSO (5 m) as described in Example 72(c). The crude product was purified by column chromatography. Yield 0.171 g. [M+H]$^+$=321.

d) 4-((-3-(1H-imidazol-1-yl)cyclopentyl)(ethyl)amino)-2-(trifluoromethyl)-benzonitrile Title compounds were prepared from the compound of Example 86(c) (0.17 g, 0.53 mmol), NaH (0.03 g, 0.74 mmol) and iodoethane (0.055 ml, 0.108 g, 0.69 mmol) as described in Example 72(d). All four enantiomers were separated by chiral HPLC (Column: Daicel Chiralpak IA 20 mm×250 mm 5 μm, eluent A: n-hexane+0.1% DEA, eluent B: EtOH+0.1% DEA, isocratic B 10%, 20 ml/min) to obtain enantiomer 1 (yield 8.4 mg, rt 28 min) and enantiomer 2 (yield 4.9 mg, rt 51 min) of the cis-diastereomer, $^1$H NMR (400 MHz, CDCl$_3$): 1.25 (3 H, t), 1.89-2.05 (2 H, m), 2.07-2.16 (1 H, m), 2.16-2.27 (1 H, m), 2.34-2.45 (1 H, m), 2.64 (1 H, m), 3.42 (2 H, q), 4.26-4.38 (1 H, m), 4.51-4.62 (1 H, m), 6.85 (1 H, dd), 7.00 (2 H, d), 7.11 (1 H, s), 7.60 (2 H, d), [M+H]$^+$=349, and enantiomer 1 (yield 6.6 mg, rt 31 min) and enantiomer 2 (yield 8.0 mg, rt 33 min) of the trans-diastereomer, $^1$H NMR (400 MHz, CDCl$_3$): 1.27 (3 H, t), 1.80-1.93 (1 H, m), 1.98-2.10 (1 H, m), 2.19-2.36 (3 H, m), 2.44-2.54 (1 H, m), 3.43 (2 H, q), 4.48 (1 H, m), 4.71 (1 H, m), 6.82 (1 H, dd), 6.96-7.01 (2 H, m), 7.12 (1 H, s), 7.56-7.61 (2 H, m), [M+H]$^+$=349.

Example 87

4-(Ethyl(2-(pyridin-3-yl)tetrahydro-2H-pyran-4-yl)amino)-2-(trifluoromethyl)benzonitrile a) 2-(Pyridin-3-yl)dihydro-2H-pyran-4(3H)-one oxime Title compound was prepared from 2-(pyridin-3-yl)dihydro-2H-pyran-4(3H)-one (0.642 g, 3.6 mmol) prepared according to WO 2009/124882, hydroxylamine HCl (0.257 g, 3.6 mmol) and pyridine (4 ml) as described in Example 72(a). Crude oxime was used as such in the following step. [M+H]$^+$=193.

b) 2-(Pyridin-3-yl)tetrahydro-2H-pyran-4-amine

Title compound was prepared from the compound of Example 87(a), LiAlH$_4$ (0.113 g, 3.0 mmol) and THF (10 ml) as described in Example 86(b). Crude amine (0.161 g) was used as such in the following step. [M+2H]$^+$=180.

c) 4-((2-(pyridin-3-yl)tetrahydro-2H-pyran-4-yl)amino)-2-(trifluoromethyl)-benzonitrile The compound was prepared from the compound of Example 87(b) (0.157 g, 0.88 mmol), 4-fluoro-2-(trifluoromethyl)benzonitrile (0.151 g, 0.8 mmol), DIPEA (0.45 ml, 0.334 g, 2.58 mmol) and DMSO (4 ml) as in Example 72(c). The crude product was purified by column chromatography. Yield 0.058 g. [M+H]$^+$=348.

d) 4-(ethyl(2-(pyridin-3-yl)tetrahydro-2H-pyran-4-yl)amino)-2-(trifluoromethyl)benzonitrile Title compound was prepared from the compound of Example 87(c) (0.056 g, 0.16 mmol), NaH (0.009 g, 0.23 mmol) and iodoethane (0.020 ml, 0.039 g, 0.25 mmol) and DMF (3 ml) as described in Example 72(d). Diastereomers were separated by preparative HPLC to obtain cis-diastereomer (5.7 mg), $^1$H NMR (400 MHz, CDCl$_3$): 1.22 (3 H, t), 1.75-1.90 (2 H, m), 1.91-2.03 (1 H, m), 2.07 (1 H, m), 3.42 (2 H, q), 3.76 (1 H, td), 4.13 (1 H, tt), 4.32 (1 H, ddd), 4.55 (1 H, dd), 6.87 (1 H, dd), 7.01 (1 H, d,) 7.30 (1 H, dd), 7.61 (1 H, d), 7.70 (1 H, m), 8.56 (1 H, d), 8.59-8.65 (1 H, m), [M+H]$^+$=376, and trans-diastereomer (2.8 mg). $^1$H NMR (400 MHz, CDCl$_3$): 1.26 (3 H, t), 1.76 (1 H, m), 2.07 (1 H, m), 2.25-2.35 (1 H, m), 2.35-2.43 (1 H, m), 3.43-3.54 (2 H, m), 3.71 (1 H, td), 3.88-3.99 (2 H, m), 5.29 (1 H, d), 6.76 (1 H, dd), 6.93 (1 H, d), 7.39 (1 H, dd), 7.58 (1 H, d), 7.75 (1 H, m), 8.62 (1 H, d), 8.72-8.76 (1 H, m). [M+H]$^+$=376.

Example 88

4-((3-(1H-benzo[d]imidazol-1-yl)cyclopentyl)(ethyl)amino)-2-(trifluoromethyl)benzonitrile a) 3-(1H-benzo[d]imidazol-1-yl)cyclopentanone

The compound was prepared using the process of Srivastava, et al., J. Org. Chem., 2003, 68, 2109-2114 from cyclopentenone (0.834 ml, 0.821 g, 10 mmol), benzimidazole (3.54 g, 30 mmol), Bi(NO$_3$)$_3$.5H$_2$O (0.97 g, 2 mmol) and DCM (2 ml). Yield 1.87 g. [M+H]$^+$=201.

b) 3-(1H-benzo[d]imidazol-1-yl)cyclopentanone oxime

Title compound was prepared from the compound of Example 88(a) (1.87 g, 7.94 mmol), hydroxylamine hydrochloride (0.557 g, 8.02 mmol) and pyridine (6 ml) as described in Example 72(a). Crude oxime was used as such in the following step. [M+H]$^+$=216.

c) 3-(1H-benzo[d]imidazol-1-yl)cyclopentanamine

Title compound was prepared from the compound of Example 88(b) (0.30 g, 1.39 mmol), LiAlH$_4$ (0.154 g, 4.0 mmol) and THF (10 ml) as described in Example 86(b). Crude amine (0.257 g, a mixture of diastereomers) was used as such in the following step. [M+H]$^+$=202.

d) 4-((3-(1H-benzo[d]imidazol-1-yl)cyclopentyl)amino)-2-(trifluoromethyl)-benzonitrile Title compound was prepared from the compound of Example 88(c) (0.359 g, 1.78 mmol), 4-fluoro-2-(trifluoromethyl)benzonitrile (0.281 g, 1.48 mmol), DIPEA (0.77 ml, 0.57 g, 4.42 mmol) and DMSO (3 ml) as in Example 72(c). The crude product was purified by column chromatography. Yield 0.141 g. [M+H]$^+$=371.

e) 4-((3-(1H-benzo[d]imidazol-1-yl)cyclopentyl)(ethyl)amino)-2-(trifluoromethyl)benzonitrile Title compound was prepared from 4-((3-(1H-benzo[d]imidazol-1-yl)cyclopentyl)amino)-2-(trifluoromethyl)benzonitrile (0.14 g, 0.38 mmol), NaH (0.021 g, 0.53 mmol) and iodoethane (0.045 ml, 0.088 g, 0.57 mmol) and DMF (3 ml) as described in Example 72(d). Diastereomers were separated by preparative HPLC to obtain diastereomer 1 (17.4 mg), $^1$H NMR (400 MHz, CDCl$_3$): 1.30 (3 H, t), 1.91-2.04 (1 H, m), 2.24-2.52 (4 H, m), 2.52-2.63 (1 H, m), 3.48 (2 H, q), 4.56 (1 H, m), 4.93-5.03 (1 H, m), 6.84 (1 H, dd), 7.00 (1 H, d), 7.29-7.37 (2 H, m), 7.40-7.46 (1 H, m), 7.59 (1 H, d), 7.79-7.88 (1 H, m), 8.03 (1 H, s), [M+H]$^+$=399, and diastereomer 2 (15.3 mg). $^1$H NMR (400 MHz, CDCl$_3$): 1.25 (3 H, t), 2.00-2.12 (1 H, m), 2.14-2.25 (1 H, m), 2.25-2.40 (2 H, m), 2.45-2.57 (1 H, m), 2.72 (1 H, m), 3.45 (2 H, q), 4.36-4.47 (1 H, m), 4.81-4.91 (1 H, m), 6.88 (1 H, dd), 7.03 (1 H, d), 7.28-7.37 (2 H, m), 7.40-7.47 (1 H, m), 7.62 (1 H, d), 7.81-7.87 (1 H, m), 8.05 (1 H, s), [M+H]$^+$=399.

Example 89

4-((3-(1H-benzo[d]imidazol-1-yl)cyclohexyl)(ethyl)amino)-2-(trifluoromethyl)benzonitrile a) 3-(1H-benzo[d]imidazol-1-yl)cyclohexanone oxime

Title compound was prepared from 3-(1H-benzo[d]imidazol-1-yl)cyclohexanone (2.81 g, 11.1 mmol), hydroxylamine hydrochloride (0.782 g, 11.2 mmol) and pyridine (7 ml) as described in Example 72(a). Crude oxime was used as such in the following step. [M+H]$^+$=230.

b) 3-(1H-benzo[d]imidazol-1-yl)cyclohexanamine

Title compound was prepared from the compound of Example 89(a) (2.88 g, 10.7 mmol), LiAlH$_4$ (0.97 g, 25.6 mmol) and THF (40 ml) as described in Example 86(b). Crude amine was purified by filtrating it through a pad of silica. Yield 0.477 g (a mixture of diastereomers). [M+H]$^+$=216.

c) 4-((3-(1H-benzo[d]imidazol-1-yl)cyclohexyl)amino)-2-(trifluoromethyl)-benzonitrile Title compound was prepared from the compound of Example 89(b) (0.477 g, 2.22 mmol), 4-fluoro-2-(trifluoromethyl)benzonitrile (0.349 g, 1.85 mmol), DIPEA (0.97 ml, 0.72 g, 5.55 mmol) and DMSO (4 ml) as described in Example 72(c). Product crystallized during work up and it was filtered off and washed with water. Yield 0.307 g. [M+H]$^+$=385.

d) 4-((3-(1H-benzo[d]imidazol-1-yl)cyclohexyl)(ethyl)amino)-2-(trifluoromethyl)benzonitrile Title compound was prepared from the compound of Example 89(c) (0.375 g, 0.98 mmol), NaH (0.059 g, 1.46 mmol) and iodoethane (0.101 ml, 0.198 g, 1.26 mmol) and DMF (3 ml) as described in Example 72(d). Diastereomers were separated by reverse phase chromatography to obtain cis-diastereomer (0.102 g), $^1$H NMR (400 MHz, CDCl$_3$): 1.22 (3 H, t), 1.63-1.74 (2 H, m), 1.84-1.97 (1 H, m), 1.97-2.08 (2 H, m), 2.19 (1 H, m), 2.34 (1 H, m), 2.42 (1 H, m), 3.44 (2 H, q), 3.90-4.00 (1 H, m), 4.42 (1 H, tt), 6.84 (1 H, dd), 6.99 (1 H, d), 7.27-7.36 (2 H, m), 7.40-7.45 (1 H, m), 7.61 (1 H, d), 7.80-7.84 (1 H, m), 8.01 (1 H, s), [M+H]⁺=413, and trans-diastereomer (0.079 g), ¹H NMR (400 MHz, CDCl₃): 1.22 (3 H, t), 1.77-1.88 (1 H, m), 2.00-2.17 (5 H, m), 2.51 (2 H, m), 3.33-3.51 (2 H, m), 3.70-3.80 (1 H, m), 4.87-4.93 (1 H, m), 6.29 (1 H, dd), 6.70 (1 H, d), 7.25-7.36 (4 H, m), 7.84-7.91 (1 H, m), 8.21 (1 H, s), [M+H]⁺=413.

Example 90

4-((3-(1H-benzo[d]imidazol-1-yl)cyclohexyl)(methyl)amino)-2-(trifluoromethyl)benzonitrile Title compound was prepared from the compound of Example 89(c) (0.116 g, 0.30 mmol), NaH (0.018 g, 1.46 mmol) and iodomethane (0.024 ml, 0.056 g, 0.39 mmol) and DMF (2 ml) as described in Example 72(d). Yield 0.095 g (~1:1 mixture of diastereomers). cis-Diastereomer: ¹H NMR (400 MHz, CDCl₃): 1.66-1.74 (2 H, m), 1.92-2.19 (4 H, m), 2.39-2.50 (2 H, m), 2.94 (3 H, s), 3.98 (1 H, m), 4.45 (1 H, tt), 6.88 (1 H, dd), 7.01 (1 H, d), 7.22-7.37 (2 H, m), 7.43-7.48 (1 H, m), 7.56 (1 H, d),7.77-7.81 (1 H, m), 8.02 (1 H, s). [M+H]⁺=399.

Example 91

4-((3-(1H-imidazol-1-yl)cyclohexyl)(ethyl)amino)-2-chlorobenzonitrile a) 4-((3-(1H-imidazol-1-yl)cyclohexyl)amino)-2-chlorobenzonitrile Title compound was prepared from 3-(1H-imidazol-1-yl)cyclohexanamine (0.40 g, 2.42 mmol), 2-chloro-4-fluorobenzonitrile (0.377 g, 2.42 mmol), DIPEA (1.27 ml, 0.94 g, 7.26 mmol) and DMSO (5 ml) as in Example 72(c). The crude product was purified by column chromatography. Yield 0.424 g. [M+H]⁺=301.

b) 4-((3-(1H-imidazol-1-yl)cyclohexyl)(ethyl)amino)-2-chlorobenzonitrile

Title compound was prepared from the compound of Example 91(a) (0.420 g, 1.40 mmol), NaH (0.073 g, 1.82 mmol) and iodoethane (0.156 ml, 0.305 g, 1.96 mmol) and DMF (6 ml) as described in Example 72(d). Diastereomers were separated by reverse phase column chromatography to obtain cis-diastereomer (0.045 g), ¹H NMR (400 MHz, CDCl₃): 1.20 (3 H, t), 1.52-1.73 (3 H, m), 1.79-1.97 (2 H, m), 2.02-2.13 (1 H, m), 2.21 (2 H, m), 3.37 (2 H, q), 3.80 (1 H, tt), 4.13 (1 H, tt), 6.59 (1 H, dd), 6.71 (1 H, d), 6.98 (1 H, s), 7.07 (1 H, s), 7.42 (1 H, d), 7.57 (1 H, s), [M+H]⁺=329, and trans-diastereomer (0.033 g). ¹H NMR (400 MHz, CDCl₃): 1.21 (3 H, t), 1.62-1.73 (1 H, m), 1.78-1.87 (1 H, m), 1.87-1.98 (3 H, m), 1.98-2.08 (1 H, m), 2.32 (1 H, m), 2.41 (1 H, m), 3.35 (2 H, m), 3.66-3.75 (1 H, m), 4.52-4.58 (1 H, m), 6.41 (1 H, dd), 6.57 (1 H, d), 7.08 (1 H, s), 7.20 (1 H, s), 7.37 (1 H, d), 7.68 (1 H, s), [M+H]⁺=329.

Example 92

4-((3-(1H-imidazol-1-yl)-4,4-dimethylcyclohexyl)(ethyl)amino)-2-(trifluoromethyl)benzonitrile a) 3-(1H-imidazol-1-yl)-4,4-dimethylcyclohexanone The compound was prepared using the process of Srivastava, et al., J. Org. Chem., 2003, 68, 2109-2114 from 4,4-dimethylcyclohex-2-enone (0.789 ml, 0.745 g, 6 mmol), imidazole (1.23 g, 18 mmol), Bi(NO₃)₃.5H₂O (0.29 g, 0.6 mmol) and DCM (0.8 ml). Crude yield 1.058 g. [M+H]⁺=193.

b) 3-(1H-imidazol-1-yl)-4,4-dimethylcyclohexanone oxime

Title compound was prepared from crude compound of Example 92(a), hydroxylamine HCl (0.421 g, 6.05 mmol) and pyridine (6 ml) as described in Example 72(a). Crude oxime was used as such in the following step. [M+H]⁺=208.

c) 3-(1H-imidazol-1-yl)-4,4-dimethylcyclohexanamine

Title compound was prepared from the crude compound of Example 92(b), LiAlH₄ (0.47 g, 12.4 mmol) and THF (20 ml) as described in Example 86(b). Crude amine was used as such in the following step. [M+H]⁺=194.

d) 4-((3-(1H-imidazol-1-yl)-4,4-dimethylcyclohexyl)amino)-2-(trifluoromethyl)benzonitrile Title compound was prepared from crude compound of Example 92(c), 4-fluoro-2-(trifluoromethyl)benzonitrile (0.783 g, 4.14 mmol), DIPEA (2.2 ml, 1.63 g, 12.6 mmol) and DMSO (10 ml) as described in Example 72(c). Crude adduct was purified by column chromatography. Yield 0.235 g. [M+H]⁺=363.

e) 4-((3-(1H-imidazol-1-yl)-4,4-dimethylcyclohexyl)(ethyl)amino)-2-(trifluoromethyl)benzonitrile Title compound was prepared from the compound of Example 92(d), (0.225 g, 0.62 mmol), NaH (0.036 g, 0.90 mmol) and iodoethane (0.066 ml, 0.129 g, 0.83 mmol) and DMF (4 ml) as described in Example 72(d). All four enantiomers were separated by chiral HPLC (Column: Daicel Chiralpak IA 20 mm×250 mm 5 µm, eluent A: n-hexane+0.1% DEA, eluent B: EtOH+0.1% DEA, isocratic B 10%, 20 ml/min) to obtain enantiomer 1 (yield 0.017 g, rt 29 min) and enantiomer 2 (yield 0.019 g, rt 35 min) of the cis-diastereomer, ¹H NMR (400 MHz, CDCl₃): 0.94 (3 H, s), 1.00 (3 H, s), 1.26 (3 H, t), 1.48-1.59 (1 H, m), 1.72-1.90 (3 H, m), 1.96-2.04 (1 H, m), 2.24 (1 H, q), 3.47 (2 H, q), 3.84 (1 H, tt), 3.93 (1 H, dd), 6.81 (1 H, dd), 6.90 (1 H, s), 6.95 (1 H, d), 7.05 (1 H, s,) 7.48 (1 H, s), 7.57 (1 H, d), [M+H]⁺=391, and enantiomer 1 (yield 0.007 g, rt 43 min) and enantiomer 2 (yield 0.008 g, rt 52 min) of the trans-diastereomer, ¹H NMR (400 MHz, CDCl₃): 0.77 (3 H, s), 1.21-1.26 (6 H, m), 1.61-1.70 (1 H, m), 1.84-2.02 (4 H, m), 2.24 (1 H, ddd), 3.33-3.52 (2 H, m), 4.10-4.23 (2 H, m), 6.66 (1 H, dd), 6.87 (1 H, d), 7.17 (2 H, s), 7.53 (1 H, d), 7.57 (1 H, s), [M+H]⁺=391.

Example 93

4-(Ethyl(3-(5-propyl-1H-imidazol-1-yl)cyclohexyl)amino)-2-(trifluoromethyl)benzonitrile a) 4-((3-Aminocyclohexyl)(ethyl)amino)-2-(trifluoromethyl)benzonitrile A reaction flask was charged with 4-((3-aminocyclohexyl)amino)-2-(trifluoromethyl)benzonitrile (2.9 g, 10.2 mmol), benzaldehyde (1.04 ml, 1.09 g, 10.2 mmol) and toluene (50 ml). A Dean-Stark trap was attached and the mixture was heated to boiling. The reaction was complete in 3 h. Solvent was evaporated and the residue was dissolved in DMF (10 ml) at 0° C. NaH (0.6 g, 15 mmol) was added followed by iodoethane (0.98 ml, 1.92 g, 12.3 mmol). The mixture was allowed to react at RT. The reaction was quenched with 1 M NaHSO$_4$ and the aqueous layer was extracted with EtOAc. Combined organic layers were washed with 2 M NaOH, dried and concentrated. The intermediate imine was hydrolyzed by treating the residue with aqueous 6 M HCl in Et$_2$O and triturating the HCl salt with Et$_2$O. Title compound was released from its HCl salt with 2 M NaOH solution and EtOAc extraction. Crude yield 3.3 g. $^1$H NMR (400 MHz, MeOH-d$_4$): 1.22 (4 H, t), 1.43-1.58 (3 H, m), 1.76-1.87 (1 H, m), 1.88-1.99 (3 H, m), 1.99-2.07 (1 H, m), 2.93-3.00 (1 H, m), 3.48 (2 H, q), 3.88 (1 H, m), 7.01-7.07 (2 H, m), 7.67 (1 H, d).

b) 4-(Ethyl(3-(5-propyl-1H-imidazol-1-yl)cyclohexyl)amino)-2-(trifluoromethyl)benzonitrile The compound was prepared from the compound of Example 93(a) (0.311 g, 1 mmol), butyraldehyde (0.135 ml, 0.108 g, 1.5 mmol), tosylmethyl isocyanide (0.293 g, 1.5 mmol), K$_2$CO$_3$ (0.207, 1.5 mmol) and DMF (2 ml) as described in Example 73(b). The title compound was purified by preparative HPLC. Yield 0.040 g (cis-diastereomer). $^1$H NMR (400 MHz, CDCl$_3$): 1.03 (3 H, t), 1.22 (3 H, t), 1.54-1.74 (5 H, m), 1.84 (1 H, m), 1.98 (1 H, m), 2.06-2.24 (3 H, m), 2.51 (2 H, t), 3.43 (2 H, q), 3.78-3.88 (1 H, m), 3.95 (1 H, tt), 6.78 (1 H, s), 6.81 (1 H, dd), 6.96 (1 H, d), 7.53 (1 H, s), 7.59 (1 H, d). [M+H]$^+$=405.

Example 94

4-(Ethyl(3-(5-(2-(pyridin-3-yl)ethyl)-1H-imidazol-1-yl)cyclohexyl)amino)-2-(trifluoromethyl)benzonitrile Title compound was prepared from 4-((3-aminocyclohexyl)(ethyl)amino)-2-(trifluoromethyl)benzonitrile (0.409 g, 1.31 mmol), 3-pyridin-3-ylpropanal (0.266 g, 1.97 mmol), tosylmethyl isocyanide (0.385 g, 1.97 mmol), K$_2$CO$_3$ (0.272, 1.97 mmol) and DMF (4 ml) as described in Example 73(b). Title compound was purified by preparative HPLC. Yield 0.065 g (cis-diastereomer). $^1$H NMR (400 MHz, CDCl$_3$): 1.21 (3 H, t), 1.43-1.73 (3 H, m), 1.82 (1 H, m), 1.94 (1 H, m), 1.98-2.14 (3 H, m), 2.87 (2 H, m), 3.00 (2 H, m), 3.41 (2 H, q), 3.70-3.84 (2 H, m), 6.80 (1 H, dd), 6.85 (1 H, s), 6.89-6.96 (1 H, m), 7.21 (1 H, dd), 7.48 (1 H, d), 7.54 (1 H, s), 7.56 (1 H, d). [M+H]$^+$=468.

Example 95

4-((3-(5-(2-(Benzyloxy)ethyl)-1H-imidazol-1-yl)cyclohexyl)(ethyl)amino)-2-(trifluoromethyl)benzonitrile Title compound was prepared from 4-((3-aminocyclohexyl)(ethyl)amino)-2-(trifluoromethyl)benzonitrile (0.409 g, 2.06 mmol), 3-(benzyloxy)propanal (0.338 g, 2.06 mmol), tosylmethyl isocyanide (0.602 g, 3.08 mmol), K$_2$CO$_3$ (0.426, 3.08 mmol) and DMF (4 ml) as in Example 73(b). Title compound was purified by preparative HPLC. Yield: 0.013 g (cis-diastereomer). $^1$H NMR (400 MHz, CDCl$_3$): 1.19 (3 H, t), 1.37-1.47 (1 H, m), 1.47-1.55 (1 H, m), 1.63-1.69 (1 H, m), 1.78 (1 H, m), 1.89 (1 H, m), 1.95-2.10 (2 H, m), 2.16 (1 H, m), 2.87 (2 H, t), 3.38 (2 H, q), 3.64-3.75 (3 H, m), 4.09 (1 H, tt), 4.43-4.52 (2 H, m), 6.74 (1 H, dd), 6.83 (1 H, s), 6.91 (1 H, d), 7.18-7.35 (5 H, m), 7.53 (1 H, s), 7.56 (1 H, d). [M+H]$^+$=497.

Example 96

4-((3-(1H-imidazol-1-yl)-6,6-dimethylcyclohex-2-en-1-yl)(ethyl)amino)-2-(trifluoromethyl)benzonitrile a) 3-Chloro-6,6-dimethylcyclohex-2-enone The title compound was prepared from 4,4-dimethyl-1,3-cyclohexanedione (5 g, 35.7 mmol), oxalyl chloride (3.52 ml, 5.21 g, 41 mmol) and DCM (80 m) as described in Example 74(a). The compound was used as such in the following step. Yield 5.31 g. [M+H]$^+$=159.

b) 3-(1H-imidazol-1-yl)-6,6-dimethylcyclohex-2-enone

The title compound was prepared from the compound of Example 96(a) (5.3 g, 33.4 mmol), imidazole (4.55 g, 66.8 mmol), triethylamine (23 ml, 16.7 g, 165 mmol), KHCO$_3$ (0.669 g, 6.7 mmol) and toluene (100 m) as described in Example 74(b) except that the mixture was refluxed instead of using a microwave reactor. Crude yield 6.67 g. [M+H]$^+$=191.

c) 3-(1H-imidazol-1-yl)-6,6-dimethylcyclohex-2-enol

The title compound was prepared from crude compound of Example 96(b) (6.17 g), CeCl$_3$·7H$_2$O (13.29 g, 35.7 mmol), NaBH$_4$ (1.47 g, 38.9 mmol) and MeOH (60 ml) as described in Example 74(c). Crude yield 4.87 g. [M+H]$^+$=193.

d) 1-(3-Azido-4,4-dimethylcyclohex-1-en-1-yl)-1H-imidazole

The title compound was prepared from crude compound of Example 96(c) (3.5 g, 18.2 mmol), DPPA (5.9 ml, 7.53 g, 27.4 mmol), DBU (4.6 ml, 4.69 g, 30.8 mmol) and toluene (60 ml) as described in Example 74(d). Crude yield 1.98 g. $^1$H NMR (400 MHz, MeOH-d$_4$): 1.04 (3 H, s), 1.08 (3 H, s), 1.64 (1 H, m), 1.77 (1 H, m), 2.52-2.68 (2 H, m), 3.83-3.88 (1 H, m), 6.00-6.05 (1 H, m), 7.05 (1 H, s), 7.46 (1 H, m), 7.98 (1 H, s). [M+H]$^+$=218.

e) 3-(1H-imidazol-1-yl)-6,6-dimethylcyclohex-2-enamine

The title compound was prepared from crude compound of Example 96(d) (1.75 g, 8.05 mmol), PPh$_3$ (4.23 g, 16.1 mmol) and MeOH (50 ml) as described in Example 74(e). When all of the azide had reacted, the intermediate iminophosphorane was hydrolyzed with 1 M NaOH at RT. MeOH was evaporated and the aqueous layer was acidified with 1 M HCl and extracted with EtOAc. Aqueous layer was basified with 2 M NaOH and extracted with DCM. Combined DCM layers were washed with brine, dried and concentrated. Crude yield 1.078 g. [M+H]$^+$=192.

f) 4-((3-(1H-imidazol-1-yl)-6,6-dimethylcyclohex-2-en-1-yl)amino)-2-(trifluoromethyl)benzonitrile The title compound was prepared from crude compound of Example 96(e) (1.22 g, 6.4 mmol), 4-fluoro-2-(trifluoromethyl)benzonitrile (1.23 g, 6.5 mmol), DIPEA (2.8 ml, 2.09 g, 16.1 mmol) and DMSO (15 m) as described in Example 74(f). Title compound was purified by column chromatography. Yield 1.078 g. [M+H]$^+$=361.

g) 4-((3-(1H-imidazol-1-yl)-6,6-dimethylcyclohex-2-en-1-yl)(ethyl)amino)-2-(trifluoromethyl)benzonitrile Title compound was prepared from the compound of Example 96(f) (1.15 g, 3.2 mmol), NaH (0.191 g, 4.8 mmol) and iodoethane (0.306 ml, 0.597 g, 0.83 mmol) and DMF (15 ml) as described in Example 72(d). Yield 0.824 g. Enantiomers were separated by chiral HPLC (Column: Daicel Chiralpak IA 20 mm×250 mm 5 µm, solvent A: n-hexane+0.1% DEA, solvent B: EtOH+0.1% DEA, isocratic B 10%, 20 ml/min) to obtain of 0.068 g of enantiomer 1 (rt 22 min) and 0.070 g of enantiomer 2 (rt 27 min). $^1$H NMR (400 MHz, CDCl$_3$): 0.98 (3 H, s), 1.11 (3 H, s), 1.20 (3 H, t), 1.67-1.76 (1 H, m), 1.76-1.86 (1 H, m), 2.51-2.71 (2 H, m), 3.43-3.55 (2 H, m), 4.46-4.52 (1 H, m), 5.69-5.73 (1 H, m), 6.93 (1 H, dd), 7.09 (1 H, d), 7.12-7.14 (1 H, m), 7.15-7.18 (1 H, m), 7.60 (1 H, d), 7.76 (1 H, s). [M+H]$^+$=389.

Example 97

4-((2,2-dimethyl-3-(pyridin-3-yl)cyclohex-3-en-1-yl)(ethyl)amino)-2-(trifluoromethyl)benzonitrile a) 3,3,7,7-Tetramethyl-1,5-dioxaspiro[5.5]undecan-8-one oxime Title compound was prepared from 3,3,7,7-tetramethyl-1,5-dioxaspiro[5.5]-undecan-8-one (4.89 g, 21.6 mmol) prepared using a method of Törmakangas, O. et al, Tetrahedron 2002, 58, 2175-81, hydroxylamine HCl (1.5 g, 21.6 mmol) and pyridine (50 ml) as described in Example 72(a). Crude yield 3.489 g. [M+H]$^+$=242.

b) 3,3,7,7-Tetramethyl-1,5-dioxaspiro[5.5]undecan-8-amine

Title compound was prepared from the crude compound of Example 97(a) (3.498 g), LiAlH$_4$ (0.825 g, 21.7 mmol) and THF (50 ml) as described in Example 86(b). Crude amine (3.6 g) was used as such in the following step. $^1$H NMR (400 MHz, CDCl$_3$): 0.70 (3 H, s), 0.90 (3 H, s), 1.10 (3 H, s), 1.18 (3 H, s), 1.21-1.47 (6 H, m), 1.53 (1 H, m), 1.60-1.68 (1 H, m), 2.27-2.36 (1 H, m), 2.76-2.85 (1 H, m), 3.23-3.33 (2 H, m), 3.58 (1 H, d), 3.67 (1 H, d). [M+H]$^+$=228.

c) 4-((3,3,7,7-Tetramethyl-1,5-dioxaspiro[5.5]undecan-8-yl)amino)-2-(trifluoromethyl)benzonitrile Title compound was prepared from crude compound of Example 97(b) (3.3 g, 14.5 mmol), 4-fluoro-2-(trifluoromethyl)benzonitrile (2.75 g, 14.5 mmol), DIPEA (6.3 ml, 4.67 g, 36.2 mmol) and DMSO (20 m) as in Example 72(c). The crude product was purified by column chromatography. Yield 3.496 g. [M+H]$^+$=397.

d) 4-(Ethyl(3,3,7,7-tetramethyl-1,5-dioxaspiro[5.5]undecan-8-yl)amino)-2-(trifluoromethyl)benzonitrile Title compound was prepared from the compound of Example 97(c) (3.496 g, 8.8 mmol), NaH (0.529 g, 13.2 mmol) and iodoethane (0.92 ml, 1.79 g, 11.5 mmol) as described in Example 72(d). Crude product was purified by column chromatography. Yield 3.38 g. [M+H]$^+$=425.

e) 4-((2,2-Dimethyl-3-oxocyclohexyl)(ethyl)amino)-2-(trifluoromethyl)benzonitrile The compound of Example 97(d) (3.38 g, 8.0 mmol), THF (20 ml) and 4 M HCl (10 ml) were mixed together at RT. When all of the ketal had hydrolyzed to ketone, solution was diluted with water and EtOAc and phases were separated. The aqueous layer was extracted with EtOAc. Combined organic layers were washed with water, brine, dried and concentrated. Product was purified by triturating crude product with EtOAc. Yield 0.833 g. $^1$H NMR (400 MHz, CDCl$_3$): 1.07 (3 H, s), 1.21 (3 H, t), 1.24 (3 H, s), 1.62-1.77 (1 H, m), 1.93-2.03 (1 H, m), 2.07-2.18 (1 H, m), 2.22-2.35 (1 H, m), 2.42 (1 H, m), 2.54-2.65 (1 H, m), 3.55 (2 H, q), 3.95 (1 H, dd), 6.89 (1 H, dd), 7.03 (1 H, d), 7.58 (1 H, d). [M+H]$^+$=339.

f) 5-((4-Cyano-3-(trifluoromethyl)phenyl)(ethyl)amino)-6,6-dimethylcyclohex-1-en-1-yl trifluoromethanesulfonate Title compound was prepared from the compound of Example 97(e) (0.200 g, 0.59 mmol), N-phenyltrifluoromethanesulfonimide (0.253 g, 0.71 mmol) and THF (5 ml) as in Example 78(a). Crude product was purified by column chromatography. Yield 0.158 g. $^1$H NMR (400 MHz, CDCl$_3$): 1.12 (3 H, s), 1.16-1.23 (6 H, m), 1.86-1.94 (1 H, m), 2.04-2.16 (1 H, m), 2.37 (2 H, m), 3.48-3.56 (2 H, m), 4.06 (1 H, dd), 5.79 (1 H, t), 6.96 (1 H, dd), 7.10 (1 H, d), 7.60 (1 H, d). [M+H]$^+$=471.

g) 4-((2,2-Dimethyl-3-(pyridin-3-yl)cyclohex-3-en-1-yl)(ethyl)amino)-2-(trifluoromethyl)benzonitrile A solution of the compound of Example 97(e) (0.158 g, 0.34 mmol), THF (8 ml), pyridineboronic acid (0.103 g, 0.84 mmol), bis(triphenylphosphine)palladium(II) chloride (0.024 g, 0.03 mmol) and 2 M Na$_2$CO$_3$ (0.67 ml, 1.34 mmol) was degassed with N$_2$ and heated to 80° C. for 5 h. The mixture was partitioned between water and DCM. Aqueous layer was extracted with DCM. Combined organic layers were dried and concentrated. Crude product was purified by column chromatography. Yield 0.034 g. $^1$H NMR (400 MHz, CDCl$_3$): 0.87 (3 H, s), 1.15 (3 H, s), 1.22 (3 H, t), 1.88-1.98 (1 H, m), 2.18-2.31 (1 H, m), 2.37-2.45 (2 H, m), 3.47-3.66 (2 H, m), 4.16 (1 H, dd), 5.52 (1 H, t), 6.98 (1 H, dd), 7.12 (1 H, d), 7.23 (1 H, dd), 7.48 (1 H, dt), 7.57 (1 H, d), 8.41 (1 H, d), 8.52 (1 H, dd). [M+H]$^+$=400.

Example 98

4-((3-(1H-imidazol-1-yl)-2,2-dimethylcyclohex-3-en-1-yl)(ethyl)amino)-2-(trifluoromethyl)benzonitrile a) 4-((3-Chloro-4-formyl-2,2-dimethylcyclohex-3-en-1-yl)(ethyl)amino)-2-(trifluoromethyl)benzonitrile A flask was charged with phosphorous oxychloride (0.4 ml, 0.66 g, 4.3 mmol) and cooled to 0° C. DMF (0.4 ml) was added and the solution was stirred for 15 min at 0° C. before 4-((2,2-dimethyl-3-oxocyclohexyl)(ethyl)amino)-2-(trifluoromethyl)-benzonitrile (0.100 g, 0.3 mmol) in CHCl$_3$ (2 ml) was added. Cooling bath was removed and the mixture was heated to 60° C. for 3.5 h. The reaction was quenched with water and the aqueous layer was extracted with DCM. Combined organic layers were washed with water, brine, dried and concentrated. Crude product was purified by column chromatography. Yield 0.047 g (contains impurities). [M+H]$^+$=385.

b) 4-(Ethyl(4-formyl-3-(1H-imidazol-1-yl)-2,2-dimethylcyclohex-3-en-1-yl)amino)-2-(trifluoromethyl) benzonitrile A mixture of the compound of Example 98(a) (0.069 g, impure), DMF (2 ml), imidazole (0.0366 g, 0.54 mmol) and K$_2$CO$_3$ (0.099 g, 0.72 mmol) was heated to 80° C. for 6.5 h. Water was added while the flask was cooled on an ice bath. Aqueous layer was extracted with EtOAc. Combined organic layers were washed with water, brine, dried and concentrated. Crude product was purified by column chromatography. Yield 0.036 g. $^1$H NMR (400 MHz, CDCl$_3$): 1.03 (3 H, s), 1.18-1.31 (6 H, m), 2.05-2.13 (1 H, m), 2.19 (1 H, m), 2.32-2.47 (1 H, m), 2.72-2.85 (1 H, m), 3.49-3.62 (2 H, m), 4.18 (1 H, dd), 6.96-7.04 (1 H, m), 7.08 (1 H, s), 7.13 (1 H, m), 7.21 (1 H, s), 7.48 (1 H, s), 7.61 (1 H, d), 8.83 (1 H, s). [M+H]$^+$=417.

c) 4-((3-(1H-imidazol-1-yl)-2,2-dimethylcyclohex-3-en-1-yl)(ethyl)amino)-2-(trifluoromethyl)benzonitrile A microwave reactor vial was charged with the compound of Example 98(b) (0.036 g, 0.09 mmol), 10% Pd/C (0.037 g) and benzonitrile (1 ml). The flask was closed and heated to 200° C. for 3 h. The catalyst was filtered off and the filtrate was concentrated. Crude product was purified by column chromatography. Yield 0.0076 g. $^1$H NMR (400 MHz, CDCl$_3$): 0.89 (3 H, s), 1.19 (3 H, s), 1.22 (3 H, t), 1.92-2.00 (1 H, m), 2.16-2.28 (1 H, m), 2.42 (2 H, m), 3.55 (2 H, q), 4.16 (1 H, dd), 5.81 (1 H, t), 6.92 (1 H, br. s.), 6.98 (1 H, dd), 7.08 (1 H, br. s.), 7.12 (1 H, d), 7.43 (1 H, br. s.), 7.59 (1H, d). [M+H]$^+$=389.

Example 99

4-((3-(1H-imidazol-1-yl)-2,2-dimethylcyclohexyl) (ethyl)amino)-2-(trifluoromethyl)benzonitrile a) 2,2-Dimethylcyclohexane-1,3-dione To a solution of 2-methylcyclohexane-1,3-dione (30.0 g, 0.238 mol) in acetone (250 ml) were added MeI (37.1 ml, 84.6 g, 0.595 mol) and K$_2$CO$_3$ (65.7 g, 0.476 mol). The mixture was refluxed for 8 h, then concentrated, quenched with water and extracted with DCM. The organic layer was washed with water, dried, filtered and concentrated. The crude was purified by column chromatography. Yield 23.0 g. $^1$H-NMR (400 MHz; CDCl$_3$): 1.30 (6H, s), 1.87-1.98 (2H, m), 2.68 (4H, t).

b) 3-(Hydroxyimino)-2,2-dimethylcyclohexanone

To a mixture of the compound of Example 99(a) (23.0 g, 0.164 mol) and pyridine (26.5 ml, 0.329 mol) in MeOH (200 ml) was added NH$_2$OH.HCl (8.01 g, 0.114 mol) at 0° C. followed by stirring at RT for 3 h. The solvent was distilled off and the crude mass was purified by column chromatography. Yield 13.8 g. $^1$H-NMR (400 MHz; DMSO-d$_6$): 1.21 (6 H, s), 1.72-1.80 (2 H, m), 2.45 (2 H, t), 2.67 (2 H, t).

c) 3-Amino-2,2-dimethylcyclohexanol

To a suspension of LiAlH$_4$ (14.7 g, 0.387 mol) in THF (250 ml) was added a solution of the compound of Example 99(b) (6.0 g, 0.039 mol) in THF (100 ml) at 0° C. dropwise. The mixture was heated to reflux for 12 h, cooled to 0° C. and quenched by the addition of saturated aqueous Na$_2$SO$_4$ solution carefully. Once the white solid started forming, K$_2$CO$_3$ was added to the suspension with vigorous stirring. The white suspension was filtered and the filtrate was concentrated under reduced pressure. Yield 5.5 g (crude). [M+H]$^+$=144 d) 3-(1H-imidazol-1-yl)-2,2-dimethylcyclohexanol

To a solution of the compound of Example 99(c) (5.0 g, 0.035 mol) in MeOH (100 ml) were added glyoxal (40% aqueous solution, 15.1 ml, 0.104 mol), NH$_4$OAc (8.02 g, 0.104 mol) and HCHO (35% aqueous solution, 8.9 ml, 0.104 mol). The mixture was stirred at 60° C. for 8 h. The solvent was evaporated and the residue was basified with 2 M aqueous KOH solution (pH 10) and extracted with DCM. The organic layer was washed with brine, dried, filtered and concentrated. The crude was purified by column chromatography. Yield 4.1 g. [M+H]$^+$=195.

e) 3-(1H-imidazol-1-yl)-2,2-dimethylcyclohexanone

To a solution of the compound of Example 99(d) (1.5 g, 0.007 mol) in DCM (50 ml) was added Dess-Martin periodinane (9.8 g, 0.023 mol). The mixture was stirred at RT for 12 h. The reaction was quenched by the addition of aqueous Na$_2$S$_2$O$_3$.5H$_2$O solution followed by stirring for 30 min and extracting with DCM. The organic layer was washed with aqueous NaHCO$_3$ solution and brine, dried, filtered and concentrated. The crude was purified by column chromatography. Yield 1.5 g. [M+1]$^+$=193.

f) 3-(1H-imidazol-1-yl)-2,2-dimethylcyclohexanone oxime

To a mixture of the compound of Example 99(e) (1.5 g, 0.007 mol) and pyridine (1.6 ml, 0.02 mol) in MeOH (40 ml) was added NH$_2$OH.HCl (0.653 g, 0.009 mol) at 0° C. The mixture was stirred at RT for 2 h. The solvent was distilled off and the crude mass was diluted with MeCN and filtered. The filtrate was concentrated under reduced pressure. Yield 1.5 g (crude). [M+H]$^+$=208.

g) 3-(1H-imidazol-1-yl)-2,2-dimethylcyclohexanamine

The compound was prepared from the compound of Example 99(f) (2.0 g, 0.009 mmol), LiAlH$_4$ (1.83 g, 0.048 mol) and THF (150 ml) as described in Example 99(c). Yield 1.6 g. [M+H]$^+$=194.

h) tert-Butyl (3-(1H-imidazol-1-yl)-2,2-dimethylcyclohexyl)carbamate

To a solution the compound of Example 99(g) (1.6 g, 0.008 mol) in THF (20 ml) were added saturated aqueous solution of NaHCO$_3$ (10 ml) and Boc$_2$O (2.5 ml, 0.011 mol) followed by stirring at RT overnight. The reaction mixture was quenched with water and extracted with EtOAc, washed with water, dried, filtered and concentrated. The crude residue was triturated with MeCN and then filtered. The filter cake was washed with MeCN and dried under vacuum to give trans-isomer of the title compound. Yield 400 mg (trans-isomer). [M+H]$^+$=294. The filtrate was concentrated under reduced pressure and purified by column chromatography to give the cis-isomer of the title compound. Yield 510 mg (cis-isomer). [M+H]$^+$=294.

i) Cis-3-(1H-imidazol-1-yl)-2,2-dimethylcyclohexanamine

The title compound was prepared from the compound of Example 99(h) (cis-isomer, 450 mg, 1.5 mmol) in dioxane (1 ml) and 4 N HCl in dioxane (5 ml). The mixture was stirred at RT for 5 h and concentrated under reduced pressure. The solid formed was washed with DCM and dried under vacuum. Yield 0.340 g (crude); $^1$H-NMR (400 MHz; DMSO-$d_6$): δ 0.86 (3 H, s), 0.95 (3 H, s), 1.40-1.61 (2 H, m), 1.72-1.80 (1 H, m), 1.81-1.94 (2 H, m), 2.11-2.22 (1 H, m), 2.98-3.06 (1 H, m), 4.34 (1 H, dd), 7.74 (1 H, s), 7.79 (1 H, s), 8.36 (1 H, s), 9.26 (1 H, s); [M+H]$^+$=194.

j) 4-((3-(1H-imidazol-1-yl)-2,2-dimethylcyclohexyl)amino)-2-(trifluoromethyl)benzonitrile Title compound was prepared the compound of Example 99(i) (0.17 g, 0.64 mmol), 4-fluoro-2-(trifluoromethyl)benzonitrile (0.123 g, 0.65 mmol), DIPEA (0.40 ml, 0.297 g, 2.3 mmol) and DMSO (2 ml) as in Example 72(c). The crude product was purified by column chromatography. Yield: 0.09 g. $^1$H NMR (400 MHz, CDCl$_3$): 0.92 (3 H, s), 0.96 (3 H, s), 1.45-1.63 (2 H, m), 1.85-2.10 (4 H, m), 3.30-3.38 (1 H, m), 3.89 (1 H, dd), 4.38 (1 H, d), 6.73 (1 H, dd), 6:89 (1 H, d), 6.92 (1 H, s), 7.06 (1 H, s), 7.50 (1 H, s), 7.55 (1 H, d). [M+H]$^+$=363.

k) 4-((3-(1H-imidazol-1-yl)-2,2-dimethylcyclohexyl)(ethyl)amino)-2-(trifluoromethyl)benzonitrile Title compound was prepared from the compound of Example 99(j) (0.90 g, 0.25 mmol), NaH (0.020 g, 0.05 mmol) and iodoethane (0.026 ml, 0.05 g, 0.32 mmol) and DMF (1 ml) as in Example 72(d). Crude product was purified by column chromatography. Yield 0.02 g. $^1$H NMR (400 MHz, CDCl$_3$): 0.82 (3 H, s), 1.02 (3 H, s), 1.17 (3 H, t), 1.58-1.70 (1 H, m), 1.80 (1 H, m), 1.88-1.96 (1 H, m), 2.01-2.14 (3 H, m), 3.51 (2 H, q), 3.84 (1 H, dd), 3.93 (1 H, dd), 6.91 (1 H, s), 6.96 (1 H, dd), 7.04 (1 H, s), 7.09 (1 H, d), 7.49 (1 H, s), 7.59 (1 H, d). [M+H]$^+$=391.

Example 100

4-((3-(1H-imidazol-4-yl)-2,2-dimethylcyclohex-3-en-1-yl)(ethyl)amino)-2-(trifluoromethyl)benzonitrile a) 4-(Ethyl(3-hydroxy-2,2-dimethyl-3-(1-trityl-1H-imidazol-4-yl)cyclohexyl)-amino)-2-(trifluoromethyl)benzonitrile A flask was charged with 4-iodo-1-tritylimidazole (0.567 g, 1.3 mmol) and DCM (4 ml). Isopropylmagnesium bromide (1.0 M, 1.8 ml, 1.5 mmol) was added. The mixture was allowed to react at RT for 3 h. 4-((2,2-Dimethyl-3-oxocyclohexyl)(ethyl)amino)-2-(trifluoromethyl)benzonitrile (0.321 g, 0.95 mmol) in DCM (4 ml) was added. The mixture was stirred overnight and then quenched with saturated NH$_4$Cl. The solution diluted with water and DCM. Aqueous layer was extracted with DCM. Combined DCM layers were washed with brine, dried and concentrated. Crude product was purified by column chromatography. Yield 0.317 g (impure). [M+H]$^+$=649.

b) 4-((3-(1H-imidazol-4-yl)-2,2-dimethylcyclohex-3-en-1-yl)(ethyl)amino)-2-(trifluoromethyl)benzonitrile Flask was charged with the compound of Example 100(a) (0.317 g), DCM (1 ml) and concentrated H$_2$SO$_4$ (1 ml) at 0° C. The mixture was stirred for 3 h and then diluted with water and quenched with 48% NaOH-solution. Aqueous layer was extracted with EtOAc. Combined organic layers were dried and concentrated. Crude product was purified by preparative HPLC. Yield 0.0317 g. $^1$H NMR (400 MHz, CDCl$_3$): 1.03 (3 H, s), 1.21 (3 H, t), 1.31 (3 H, s), 1.84-1.92 (1 H, m), 2.15-2.26 (1 H, m), 2.36-2.42 (2 H, m), 3.49-3.62 (2 H, m), 4.10 (1 H, dd), 5.89 (1 H, t), 6.91-6.96 (2 H, m), 7.11 (1 H, d), 7.54 (1 H, d), 7.57-7.59 (1 H, m). [M+H]$^+$=389.

Example 101

N-((1-(3-((4-cyano-3-(trifluoromethyl)phenyl)(ethyl)amino)cyclohexyl)-1H-imidazol-5-yl)methyl)acetamide a) tert-Butyl ((1-(3-((4-cyano-3-(trifluoromethyl)phenyl)(ethyl)amino)cyclohexyl)-1H-imidazol-5-yl)methyl)carbamate The compound was prepared from 4-((3-aminocyclohexyl)(ethyl)amino)-2-(trifluoromethyl)benzonitrile (0.600 g, 1.73 mmol), tert-butyl N-(2-oxoethyl)carbamate (0.275 g, 1.73 mmol), tosylmethyl isocyanide (0.505 g, 2.59 mmol), K$_2$CO$_3$ (0.358, 2.59 mmol) and DMF (6 ml) as described in Example 73(b). Crude product was purified by column chromatography to yield the title compound (0.357 g, impure). [M+H]$^+$=492.

b) 4-((3-(5-(Aminomethyl)-1H-imidazol-1-yl)cyclohexyl)(ethyl)amino)-2-(trifluoromethyl)benzonitrile Flask was charged with impure compound of Example 101(a) (0.357 g), TFA (0.35 ml, 0.52 g, 4.57 mmol) and DCM (4 ml). The mixture was allowed to react overnight at RT. The mixture was partitioned between saturated NaHCO$_3$ and DCM. Aqueous layer was extracted with DCM. Combined organic layers were dried and concentrated. Crude product was purified by column chromatography to yield the title compound. Yield 0.067 g, impure. [M+H]$^+$=392.

c) N-((1-(3-((4-cyano-3-(trifluoromethyl)phenyl)(ethyl)amino)cyclohexyl)-1H-imidazol-5-yl)methyl)acetamide The compound of Example 101(b) (0.067 g, impure), DCM (2 ml), DIPEA (0.058 ml, 0.043 g, 0.33 mmol) and acetyl chloride (0.014 ml, 0.016 g, 0.2 mmol) were mixed together at 0° C. Reaction was complete in half an hour. The mixture was partitioned between saturated NaHCO$_3$ and DCM. Aqueous layer was extracted with DCM. Combined organic layers were dried and concentrated. Product was purified by preparative HPLC. Yield 0.007 g (cis-diastereomer). $^1$H NMR (400 MHz, CDCl$_3$); 1.21 (3 H, t), 1.52-1.72 (3 H, m), 1.77 (1 H, m), 1.88-1.93 (1 H, m), 1.94 (3 H, s), 2.03-2.14 (3 H, m), 3.33-3.48 (2 H, m), 3.88-3.98 (1 H, m), 4.30-4.40 (1 H, m), 4.40-4.56 (2 H, m), 5.78-5.86 (1 H, m), 6.92 (1 H, s), 6.96 (1 H, dd), 7.02 (1 H, d), 7.57 (1 H, s), 7.60 (1 H, d). [M+H]$^+$=434.

Example 102

4-(Ethyl(3-(1-(2-methoxyethyl)-1H-imidazol-5-yl)cyclopentyl)amino)-2-(trifluoromethyl)benzonitrile a) tert-butyl (3-(1-(2-methoxyethyl)-1H-imidazol-5-yl)cyclopentyl)carbamate To an ice cold stirred suspension of LiAlH$_4$ (4.0 g, 103 mmol) in THF (100 ml) was added dropwise tert-butyl (3-(methoxy(methyl)carbamoyl)cyclopentyl)-carbamate (28.0 g, 103 mmol, WO 2007/099385) in THF (200 ml). The mixture was stirred for 1 h at 0° C. and then quenched with saturated aqueous Na$_2$SO$_4$ solution. The precipitated solids were filtered on celite and washed with EtOAc. The filtrate was dried and concentrated to afford crude aldehyde product (20 g). A solution of aldehyde product (7.0 g, 32.8 mmol) and 2-methoxyethanamine (2.5 g, 32.8 mmol) in THF (100 ml) was stirred for 6 h. TosMIC (5.12 g, 26.25 mmol) and piperizine (2.54 g, 29.5 mmol) were added and the mixture was heated at 50° C. for 16 h. The mixture was cooled to RT, diluted with ice water and extracted with EtOAc. The organic layer was washed with brine, dried, filtered and concentrated to afford the title compound (1.7 g, crude). Diastereomers were separated by normal phase chiral preparative HPLC (Chiralpak ADH (4.6×250 mm) 5 μm, Solvent A: n-Hexane+0.1% DEA: Solvent B: 2-propanol, isocaratic 20% B, 1 ml/min) to obtain 700 mg of cis-isomer (as peak-1) and 550 mg of trans-isomer (as peak-2); [M+H]$^+$=194.

b) Cis-3-(1-(2-methoxyethyl)-1H-imidazol-5-yl)cyclopentanamine

To a stirred solution of the compound of Example 102(a) (cis-isomer, 700 mg, 2.26 mmol) was added 5 N HCl in methanol (7 ml) at 0° C. followed by stirring for 2 h. Solvent was evaporated to dryness and the crude compound was triturated with anhydrous Et$_2$O. Yield 0.50 g. [M+H]$^+$=210.

c) 4-((3-(1-(2-methoxyethyl)-1H-imidazol-5-yl)cyclopentyl)amino)-2-(trifluoromethyl)benzonitrile The compound was prepared from the compound of Example 102(b) (cis-diastereomer, 0.50 g, 0.64 mmol), 4-fluoro-2-(trifluoromethyl)benzonitrile (0.342 g, 1.81 mmol), DIPEA (1.0 ml, 0.742 g, 5.7 mmol) and DMSO (3 ml) as in Example 72(c). The crude product was purified by column chromatography. Yield 0.248 g. $^1$H NMR (400 MHz, CDCl$_3$): 1.63 (1 H, m), 1.71-1.92 (2 H, m), 2.10-2.23 (2 H, m), 2.59-2.68 (1 H, m), 3.16 (1 H, m), 3.33 (3 H, s), 3.62 (2 H, t), 3.93-4.01 (1 H, m), 4.03 (2 H, t), 5.09 (1 H, d), 6.68 (1 H, dd), 6.80 (1 H, s), 6.86 (1 H, d), 7.51 (1 H, s), 7.54 (1 H, d). [M+H]$^+$=379.

d) 4-(Ethyl(3-(1-(2-methoxyethyl)-1H-imidazol-5-yl)cyclopentyl)amino)-2-(trifluoromethyl)benzonitrile The compound was prepared from the compound of Example 102(c) (0.248 g, 0.66 mmol), NaH (0.042 g, 1.05 mmol) and iodoethane (0.068 ml, 0.133 g, 0.85 mmol) and DMF (2 ml) as in Example 72(d). Crude product was purified by column chromatography. Yield 0.202 g (cis-isomer). $^1$H NMR (400 MHz, CDCl$_3$): 1.24 (3 H, t), 1.71-1.93 (3 H, m), 2.09-2.25 (2 H, m), 2.41 (1 H, m), 3.09-3.19 (1 H, m), 3.34 (3 H, s), 3.42 (2 H, q), 3.63 (2 H, t), 4.04 (2 H, t), 4.24-4.36 (1 H, m), 6.83 (1 H, dd), 6.86 (1 H, s), 7.00 (1 H, d), 7.52 (1 H, s), 7.57 (1 H, d). [M+H]$^+$=407.

Example 103

4-(Ethyl(3-(1-propyl-1H-imidazol-5-yl)cyclopent-3-en-1-yl)amino)-2-(trifluoromethyl)benzonitrile a) (4-(4-((4-cyano-3-(trifluoromethyl)phenyl)(ethyl)amino)cyclopent-1-en-1-yl)-1H-imidazol-1-yl)methyl pivalate 4-((3-(1H-imidazol-4-yl)cyclopent-3-en-1-yl)(ethyl)amino)-2-(trifluoromethyl)benzonitrile (0.52 g, 1.5 mmol) was dissolved in DMF (6 ml). K$_2$CO$_3$ (0.249 g, 1.80 mmol) was added followed by chloromethyl pivalate (0.26 ml, 0.27 g, 1.80 mmol). The mixture was allowed react at RT for 2.5 h. Solvent was evaporated and the residue was partitioned between water and EtOAc. Aqueous layer was extracted with EtOAc. Combined organic layers were washed with water, brine, dried and concentrated. Crude product was purified by column chromatography. Yield 0.51 g. $^1$H NMR (400 MHz, CDCl$_3$): 1.17 (9 H, s), 1.22 (3 H, t), 2.60-2.76 (2 H, m), 2.88-3.06 (2 H, m), 3.46 (2 H, q), 4.65-4.74 (1 H, m), 5.82 (2 H, s), 6.28 (1 H, m), 6.79 (1 H, dd), 6.97 (1 H, s), 6.99 (1 H, d), 7.56 (1 H, d), 7.66 (1 H, d).

b) 4-(Ethyl(3-(1-propyl-1H-imidazol-5-yl)cyclopent-3-en-1-yl)amino)-2-(trifluoromethyl)benzonitrile A vial was charged with the compound of Example 103(a) (0.10 g, 0.22 mmol), MeCN (1 ml) and iodopropane (0.042 ml, 0.074 g, 0.43 mmol). The vial was closed and heated to 80° C. for 8 h and cooled to 60° C. overnight. Solvent was evaporated and the residue was treated with ammonia (7 M in MeOH, 0.31 ml, 2.2 mmol) for 2 h, and concentrated. Crude product was purified by preparative HPLC. Yield 0.012 g. $^1$H NMR (400 MHz, CDCl$_3$): 0.99 (3 H, t), 1.24 (3 H, t), 1.84 (2 H, sxt), 2.70 (1 H, m), 2.79-2.89 (1 H, m), 3.00 (1 H, m), 3.10 (1 H, m), 3.46 (2 H, q), 4.02 (2 H, t), 4.62-4.72 (1 H, m), 5.82-5.87 (1 H, m), 6.81 (1 H, dd), 6.98 (1 H, d), 7.01 (1 H, s), 7.48 (1 H, s), 7.58 (1 H, d). [M+H]$^+$=389.

Example 104

4-(Ethyl(3-(1-(3-hydroxypropyl)-1H-imidazol-5-yl)cyclopent-3-en-1-yl)-amino)-2-(trifluoromethyl)benzonitrile a) Ethyl 3-(5-(4-((4-cyano-3-(trifluoromethyl)phenyl)(ethyl)amino)cyclopent-1-en-1-yl)-1H-imidazol-1-yl)propanoate The compound was prepared from the compound of Example 103(a) (0.2 g, 0.43 mmol), ethyl 3-bromopropionate (0.111 ml, 0.157 g, 0.87 mmol) and MeCN (1 ml) as described in Example 103(b). Yield 0.05 g (impure). [M+H]$^+$=447.

b) 4-(Ethyl(3-(1-(3-hydroxypropyl)-1H-imidazol-5-yl)cyclopent-3-en-1-yl)-amino)-2-(trifluoromethyl)benzonitrile A mixture of the compound of Example 104(a) (0.05 g), EtOH (2 ml) and NaBH$_4$ (0.026 g, 0.69 mmol) were refluxed for 1 h. Solvent was evaporated and the residue was partitioned between water and EtOAc. Aqueous layer was extracted with EtOAc. Combined organic layers were dried and concentrated. Crude product was purified by column chromatography. Yield 0.008 g. $^1$H NMR (400 MHz, CDCl$_3$): 1.23 (3 H, t), 1.99-2.08 (2 H, m), 2.70 (1 H, m), 2.85 (1 H, m), 2.99 (1 H, m), 3.05-3.14 (1 H, m), 3.46 (2 H, q), 3.67 (2 H, t), 4.26 (2 H, t), 4.61-4.73 (1 H, m), 5.94-6.01 (1 H, m), 6.77-6.83 (1 H, m), 6.99 (2 H, d), 7.53 (1 H, br. s.), 7.57 (1 H, d). [M+H]$^+$=405.

Example 105

4-((6-(1H-imidazol-1-yl)spiro[2.5]oct-5-en-4-yl)(ethyl)amino)-2-(trifluoromethyl)benzonitrile a) 6-Chlorospiro[2.5]oct-5-en-4-one

The compound was prepared from spiro[2.5]octane-4,6-dione (2.2 g, 15.9 mmol), oxalyl chloride (1.5 ml, 2.2 g, 17.5 mmol) and DCM (30 ml) as described in Example 74(a). Title compound was used as such in the following step. Yield 2.25 g. [M+H]$^+$=157.

b) 6-(1H-imidazol-1-yl)spiro[2.5]oct-5-en-4-one

The compound was prepared from the compound of Example 105(a) (2.25 g, 14.4 mmol), imidazole (1.96 g, 28.7 mmol), triethylamine (6 ml, 4.36 g, 43 mmol) and toluene (40 ml) as described in Example 74(b) except that the mixture was refluxed instead of using a microwave reactor. Crude yield 2.11 g. [M+H]$^+$=189.

c) 6-(1H-imidazol-1-yl)spiro[2.5]oct-5-en-4-ol

The compound was prepared from crude compound of Example 105(b) (2.15 g, 11.5 mmol), CeCl$_3$.7H$_2$O (4.69 g, 12.6 mmol), NaBH$_4$ (0.52 g, 13.7 mmol) and MeOH (20 ml) as described in Example 74(c). Crude yield 1.64 g. [M+H]$^+$=191.

d) 1-(4-Azidospiro[2.5]oct-5-en-6-yl)-1H-imidazole

The compound was prepared from crude compound of Example 105(c) (1.64 g, 8.6 mmol), dppa (2.4 ml, 3.06 g, 11.1 mmol), DBU (1.9 ml, 1.94 g, 12.7 mmol) and toluene (25 ml) as described in Example 74(d). Crude product was purified by column chromatography. Yield 0.798 g. $^1$H NMR (400 MHz, CDCl$_3$): 0.44-0.52 (2 H, m), 0.60-0.68 (1 H, m), 0.80-0.87 (1 H, m), 1.13-1.23 (1 H, m), 2.26-2.36 (1 H, m), 2.53-2.69 (2 H, m), 3.35 (1 H, d), 5.93 (1 H, d), 7.12 (1 H, s), 7.18 (1 H, s), 7.77 (1 H, s). [M+H]$^+$=216.

e) 6-(1H-imidazol-1-yl)spiro[2.5]oct-5-en-4-amine

The compound was prepared from crude compound of Example 105(d) (0.798 g, 3.7 mmol), PPh$_3$ (1.95 g, 7.4 mmol) and MeOH (20 ml) as described in Example 74(e). When all of the azide had reacted, the intermediate iminophosphorane was hydrolyzed with 2 M NaOH at RT. MeOH was evaporated and the aqueous layer was acidified with 4 M HCl and extracted with EtOAc. Aqueous layer was basified with 2 M NaOH and extracted with DCM. Combined DCM layers were washed with brine, dried and concentrated. Crude yield 0.527 g. [M+H]$^+$=190.

f) 4-((6-(1H-imidazol-1-yl)spiro[2.5]oct-5-en-4-yl)amino)-2-(trifluoromethyl)benzonitrile The compound was prepared from crude compound of Example 105(e) (0.54 g, 2.9 mmol), DIPEA (1.22 ml, 0.9 g, 7 mmol) and DMSO (5 ml) as described in Example 74(f). Title compound was purified by column chromatography. Yield 0.737 g. $^1$H NMR (400 MHz, CDCl$_3$): 0.47-0.53 (1 H, m), 0.53-0.63 (2 H, m), 0.67-0.73 (1 H, m), 1.47 (1 H, dt), 2.05-2.12 (1 H, m), 2.55-2.70 (2 H, m), 3.78 (1 H, dd), 4.70 (1 H, d), 5.90 (1 H, d), 6.73 (1 H, dd), 6.86-6.90 (1 H, m), 7.11 (1 H, s), 7.14 (1 H, s), 7.55 (1 H, d), 7.72 (1 H, s). [M+H]$^+$=359.

g) 4-((6-(1H-imidazol-1-yl)spiro[2.5]oct-5-en-4-yl)(ethyl)amino)-2-(trifluoromethyl)benzonitrile The compound was prepared from the compound of Example 105(f) (0.54 g, 1.5 mmol), NaH (0.121 g, 3.0 mmol) and iodoethane (0.182 ml, 0.353 g, 2.26 mmol) and DMF (15 ml) as described in Example 72(d). Crude product was purified by column chromatography. Yield 0.416 g. $^1$H NMR (400 MHz, CDCl$_3$): 0.49-0.65 (4 H, m), 1.24 (3 H, t), 1.54 (1 H, dt), 2.00 (1 H, dt), 2.59-2.75 (2 H, m), 3.47-3.60 (2 H, m), 4.37 (1 H, br. s.), 5.71-5.75 (1 H, m), 6.78-6.84 (1 H, m), 6.96-7.00 (1 H, m), 7.14 (2 H, d), 7.57 (1 H, d), 7.75 (1 H, s). [M+H]$^+$=387.

Example 106

4-((6-(1H-imidazol-1-yl)spiro[2.5]oct-5-en-4-yl)(methyl)amino)-2-(trifluoromethyl)benzonitrile The compound was prepared from the compound of Example 105(f) (0.2 g, 0.56 mmol), NaH (0.067 g, 1.67 mmol) and iodomethane (0.069 ml, 0.158 g, 1.12 mmol) and DMF (4 ml) as described in Example 72(d). Crude product was purified by column chromatography. Yield 0.149 g. $^1$H NMR (400 MHz, CDCl$_3$): 0.46-0.59 (4 H, m), 1.64-1.73 (1 H, m), 1.84-1.95 (1 H, m), 2.55-2.66 (1 H, m), 2.66-2.77 (1 H, m), 2.99 (3 H, s), 4.53 (1 H, br. s.), 5.72-5.75 (1 H, m), 6.86 (1 H, dd), 7.00 (1 H, s), 7.13 (1 H, s), 7.17 (1 H, s), 7.59 (1 H, d), 7.76 (1 H, s). [M+H]$^+$=373.

Example 107

4-((4-(1H-imidazol-1-yl)spiro[2.5]oct-4-en-6-yl)(ethyl)amino)-2-(trifluoromethyl)benzonitrile a) 4-((4-Oxospiro[2.5]oct-5-en-6-yl)amino)-2-(trifluoromethyl)benzonitrile

The compound was prepared from spiro[2.5]octane-4,6-dione (1.38 g, 10 mmol), 4-amino-2-(trifluoromethyl)benzonitrile (1.86 g, 10 mmol), p-toluenesulfonic acid (0.038, 0.2 mmol) and toluene as described in Example 112(a). Yield 2.92 g. [M+H]$^+$=307.

b) 4-((4-Hydroxyspiro[2.5]octan-6-yl)amino)-2-(trifluoromethyl)benzonitrile The compound was prepared from the compound of Example 107(a) (2.91 g, 9.5 mmol), NaBH$_4$ (1.80 g+2×0.8 g, which were added after 24 h and 48 h) and MeOH (40 ml) as described in Example 112(b). Unreacted starting material was removed by column chromatography. Yield 1.72 g. [M+H]$^+$=311.

c) 4-((4-Oxospiro[2.5]octan-6-yl)amino)-2-(trifluoromethyl)benzonitrile

The compound was prepared from the compound of Example 107(b) (1.54 g, 5.0 mmol), Dess-Martin periodinane (3.8 g, 9.0 mmol), pyridine (1.2 ml, 1.18 g, 14.9 mmol) and DCM (30 ml) as in Example 112(f). Crude product was purified by column chromatography. Yield 1.04 g. $^1$H NMR (400 MHz, CDCl$_3$): 0.66-0.79 (2 H, m), 1.11-1.18 (1 H, m), 1.47 (1 H, dd), 1.64-1.74 (1 H, m), 1.79-1.90 (1 H, m), 1.93-2.03 (1 H, m), 2.27 (1 H, m), 2.37 (1 H, dd), 2.90 (1 H, dd), 3.92-4.06 (1 H, m), 4.52 (1 H, d), 6.71 (1 H, d), 6.87 (1 H, s), 7.58 (1 H, d). [M+H]$^+$=309.

d) 4-((4-(1H-imidazol-1-yl)spiro[2.5]oct-4-en-6-yl)amino)-2-(trifluoromethyl)benzonitrile Imidazole (0.464 g, 6.8 mmol) was dissolved in DCM (4 ml). The mixture was cooled on an ice bath and SOCl$_2$ (0.142 ml, 0.232 g, 1.95 mmol) was added. After 30 min of stirring compound of Example 107(c) (0.3 g, 0.97 mmol) in DCM (10 ml) was added. The mixture was stirred at RT for 20 h. The reaction was quenched with saturated NaHCO$_3$ and pH was adjusted to 12 with 2 M NaOH. Aqueous layer was extracted with DCM. Combined organic layers were washed with water, dried and concentrated. Crude product was purified by column chromatography. Yield 0.049 g (impure). [M+H]$^+$=359.

e) 4-((4-(1H-imidazol-1-yl)spiro[2.5]oct-4-en-6-yl)(ethyl)amino)-2-(trifluoromethyl)benzonitrile The compound was prepared from the compound of Example 107(d) (0.049 g), NaH (0.27 g, 0.68 mmol) and iodoethane (0.033 ml, 0.064 g, 0.41 mmol) and DMF (1 ml) as described in Example 72(d). Crude product was purified by preparative HPLC. Yield 0.012 g. $^1$H NMR (400 MHz, CDCl$_3$): 0.62-0.74 (4 H, m), 1.26 (3 H, t), 1.43-1.50 (1 H, m), 2.04-2.12 (2 H, m), 2.21-2.30 (1 H, m), 3.40-3.58 (2 H, m), 4.70 (1 H, m), 5.72-5.74 (1 H, m), 6.83 (1 H, s), 6.85 (1 H, dd), 7.05 (1 H, s), 7.08 (1 H, d), 7.34 (1 H, s), 7.60 (1 H, dd). [M+H]$^+$=387.

Example 108

4-((4-(1H-imidazol-1-yl)spiro[2.5]oct-4-en-6-yl)(methyl)amino)-2-(trifluoromethyl)benzonitrile The compound was prepared from the compound of Example 107(d) (0.120 g, 0.34 mmol), NaH (0.027 g, 0.68 mmol) and iodomethane (0.031 ml, 0.071 g, 0.50 mmol) and DMF (4 ml) as described in Example 72(d). Crude product was purified by column chromatography and enantiomers were separated by chiral HPLC (Column: Daicel Chiralpak IA 20 mm×250 mm 5 µm, eluent A: n-hexane+0.2% DEA, solvent B: EtOH+0.2% DEA, isocratic B 10%, 20 ml/min) to obtain enantiomer 1 (yield 0.017 g, rt 37 min) and enantiomer 2 (yield 0.021 g, rt 47 min). $^1$H NMR (400 MHz, CDCl$_3$): 0.60-0.67 (2 H, m), 0.67-0.74 (2 H, m), 1.45-1.52 (1 H, m), 1.93-2.04 (1 H, m), 2.04-2.12 (1 H, m), 2.18-2.27 (1 H, m), 3.01 (3 H, s), 4.81 (1 H, ddd), 5.72 (1 H, dd), 6.85 (1 H, t), 6.88 (1 H, dd), 7.04-7.07 (2 H, m), 7.36 (1 H, t), 7.59-7.63 (1 H, m). [M+H]$^+$=373.

Example 109

4-(Ethyl(3-(5-ethyl-1H-imidazol-1-yl)cyclopentyl)amino)-2-(trifluoromethyl)-benzonitrile a) 4-((3-(1,3-Dioxoisoindolin-2-yl)cyclopentyl)(ethyl)amino)-2-(trifluoromethyl)benzonitrile An oven-dried flask was charged with 4-(ethyl(3-hydroxycyclopentyl)amino)-2-(trifluoromethyl)benzonitrile (0.597 g, 2.0 mmol), THF (15 ml), phthalimide (0.383 g, 2.60 mmol) and triphenylphosphine (0.682 g, 2.60 mmol). The flask was placed on an ice bath and diisopropyl azodicarboxylate (0.512 ml, 0.526 g, 2.60 mmol) was added. The mixture was kept at 0° C. for 1.5 h before the cooling bath was removed. The mixture was stirred overnight at RT. The mixture was partitioned between water and EtOAc. The aqueous layer was extracted with EtOAc. Combined organic layers were dried and concentrated. Crude product was purified by column chromatography. Yield 1.26 g (a mixture of title compound and diisopropyl hydrazine-1,2-dicarboxylate). [M+H]$^+$=428.

b) 4-((3-Aminocyclopentyl)(ethyl)amino)-2-(trifluoromethyl)benzonitrile

The flask was charged with the compound of Example 109(a) (1.26 g), ethanol (20 ml) and hydrazine monohydrate (0.409 ml, 0.422 g, 8.4 mmol). The mixture was refluxed for 2 h and cooled to RT. Et$_2$O (30 ml) was added. The formed precipitate was filtered off and the mother liquor was concentrated to dryness. Et$_2$O (20 ml) was added. The formed precipitate was filtered off and the mother liquor was concentrated. 4 M HCl in 1,4-dioxane (0.5 ml) was added. The HCl salt was filtered and washed with Et$_2$O. The HCl salt was released with 2 M NaOH solution and the aqueous phase was extracted with EtOAc. Combined organic layers were dried and concentrated. Yield 0.415 g (3:2 mixture of diastereomers). [M+H]$^+$=298.

c) 4-(Ethyl(3-(5-ethyl-1H-imidazol-1-yl)cyclopentyl)amino)-2-(trifluoromethyl)benzonitrile The compound was prepared from the compound of Example 109(b) (0.415 g, 1.40 mmol), propionaldehyde (0.10 ml, 0.081 g, 1.40 mmol), tosylmethyl isocyanide (0.550 g, 2.82 mmol) and DBU (0.50 ml, 0.509 g, 2.4 mmol) in DCM (4 ml). Crude product was purified by column chromatography and all four enantiomers were separated by chiral HPLC (Column: Daicel Chiralpak IA 20 mm×250 mm 5 µm, solvent A: MTBE+0.2% DEA, solvent B: EtOH+0.2% DEA, isocratic B 3%, 20 ml/min) to obtain enantiomer 1 (yield 0.0255 g, rt 45 min) and enantiomer 2 (yield 0.0218 g, rt 67 min) of cis-diastereomer, $^1$H NMR (400 MHz, CDCl$_3$): 1.25 (3 H, t), 1.30 (3 H, t), 1.91-2.04 (2 H, m), 2.05-2.16 (1 H, m), 2.16-2.26 (1 H, m), 2.31-2.42 (1 H, m), 2.54-2.63 (3 H, m), 3.44 (2 H, q), 4.27-4.37 (1 H, m), 4.39-4.49 (1 H, m), 6.81 (1 H, m), 6.86 (1 H, dd), 7.00 (1 H, d), 7.59 (1 H, dd), 7.60-7.63 (1 H, m), [M+H]$^+$=378, and enantiomer 1 (yield 0.0367 g, rt 36 min) and enantiomer 2 (yield 0.0322 g, rt 52 min) of trans-diastereomer, $^1$H NMR (400 MHz, CDCl$_3$): 1.27 (3 H, t), 1.31 (3 H, t), 1.82-1.95 (1 H, m), 2.00-2.11 (1 H, m), 2.22 (2 H, dd), 2.33 (1 H, m), 2.47 (1 H, m), 2.58 (2 H, m), 3.44 (2 H, q), 4.45-4.54 (1 H, m), 4.57 (1 H, m), 6.81 (1 H, m), 6.84 (1 H, dd), 6.98 (1 H, d), 7.55-7.60 (2 H, m), [M+H]$^+$=378.

Example 110

4-((3-(1H-imidazol-1-yl)-4,4-dimethylcyclohex-2-en-1-yl)(ethyl)amino)-2-(trifluoromethyl)benzonitrile a) 4-((4,4-Dimethyl-3-oxocyclohex-1-en-1-yl)amino)-2-(trifluoromethyl)-benzonitrile The compound was prepared from 4,4-dimethyl-1,3-cyclohexanedione (4.21 g, 30 mmol), 4-amino-2-trifluoromethylbenzonitrile (5.64 g, 30.3 mmol) and p-toluenesulfonic acid monohydrate (0.031 g, 0.2 mmol) in toluene (45 ml) as in Example 112(a). Yield 9.25 g. $^1$H NMR (400 MHz, DMSO-d$_6$): 1.04 (6 H, s), 1.79 (2 H, t), 2.58 (2 H, t), 5.55 (1 H, s), 7.57-7.65 (2 H, m), 8.01-8.07 (1 H, m), 9.41 (1 H, s).

b) 4-((3-Hydroxy-4,4-dimethylcyclohexyl)amino)-2-(trifluoromethyl)benzonitrile

The compound was prepared from the compound of Example 110(a) (9.09 g, 29.5 mmol) and NaBH$_4$ (5.58 g, 148 mmol) in ethanol (60 ml) as described in Example 112(b). Yield 8.7 g. [M+H]$^+$=313.

c) 4-((4,4-Dimethyl-3-oxocyclohexyl)amino)-2-(trifluoromethyl)benzonitrile

The compound was prepared from the compound of Example 110(b) (8.7 g, 27.9 mmol), sulphur trioxide-pyridine complex (5.76 g, 36.2 mmol) and triethylamine (19.4 ml, 14.1 g, 139 mmol) in DMSO (40 ml) as described in Example 80(a). [M+H]$^+$=311.

d) 4-((3-(1H-imidazol-1-yl)-4,4-dimethylcyclohex-2-en-1-yl)amino)-2-(trifluoromethyl)benzonitrile The compound was prepared from the compound of Example 110(c) (1.24 g, 4.0 mmol), imidazole (1.63 g, 24.0 mmol), SOCl$_2$ (0.53 ml, 0.86 g, 7.2 mmol) in DCM (20 ml) as in Example 107(d). Yield 1.19 g (impure). [M+H]$^+$=361.

e) 4-((3-(1H-imidazol-1-yl)-4,4-dimethylcyclohex-2-en-1-yl)(ethyl)amino)-2-(trifluoromethyl)benzonitrile The compound was prepared from impure compound of Example 110(d) (0.5 g), NaH (0.111 g, 2.8 mmol), iodoethane (0.168 ml, 0.325 g, 2.08 mmol) and DMF (3 ml) as described in Example 72(d). Crude product was purified by preparative HPLC. Yield 0.018 g. $^1$H NMR (400 MHz, CDCl$_3$): 0.96 (3 H, s), 1.16 (3 H, t), 1.19 (3 H, s), 1.74-1.82 (2 H, m), 1.86-1.96 (2 H, m), 3.28-3.45 (2 H, m), 4.46-4.52 (1 H, m), 5.58 (1 H, d), 6.77 (1 H, dd), 6.85-6.89 (1 H, m), 6.98 (1 H, d), 6.99-7.04 (1 H, m), 7.33-7.38 (1 H, m), 7.47-7.54 (1 H, m). [M+H]$^+$=389.

Example 111

4-((3-(1H-imidazol-1-yl)-4,4-dimethylcyclohex-2-en-1-yl)(methyl)amino)-2-(trifluoromethyl)benzonitrile The compound was prepared from impure compound of Example 110(d) (0.55 g), NaH (0.20 g, 5 mmol), iodoethane (0.2 ml, 0.456 g, 3.21 mmol) and DMF (4 ml) as described in Example 72(d). Crude product was purified by preparative HPLC. Yield 0.104 g. $^1$H NMR (400 MHz, CDCl$_3$): 1.03 (3 H, s), 1.27 (3 H, s), 1.82-1.86 (2 H, m), 1.86-1.93 (1 H, m), 1.93-2.00 (1 H, m), 2.95 (3 H, s), 4.63-4.69 (1 H, m), 5.63 (1 H, dd), 6.86 (1 H, dd), 6.95 (1 H, t), 7.03 (1 H, d), 7.10 (1 H, t), 7.44 (1 H, t), 7.61 (1 H, d). [M+H]$^+$=375.

Example 112

4-{[3-(1H-imidazol-4-yl)cyclohex-3-enyl](ethyl)amino}-2-chlorobenzonitrile a) 2-Chloro-4-(3-oxocyclohex-1-enylamino)benzonitrile 4-Amino-2-chlorobenzonitrile (7.50 g, 49.2 mmol), cyclohexane-1,3-dione (5.79 g, 51.6 mmol) and p-toluenesulfonic acid monohydrate (1.74 g, 9.14 mmol) were boiled in toluene (300 ml) for 1 h using the Dean-Stark apparatus. The mixture was allowed to cool to RT. The precipitate was collected by filtration, washed with toluene and dried at vacuum. The crude product (13.16 g) was recrystallized from water (90 ml)/ethanol (70 ml) to afford the title product. Yield 10.45 g. $^1$H NMR (400 MHz, DMSO-d$_6$): 1.91 (2H, m), 2.23 (2H, t), 2.53 (2H, t), 5.59 (1H, s), 7.28 (1H, dd), 7.40 (1H, d), 7.88 (1H, d), 9.28 (1H, s).

b) 2-Chloro-4-(3-hydroxycyclohexylamino)benzonitrile

Sodium borohydride (9.60 g, 254 mmol) was added in portions to a solution of the compound of Example 112(a) (10.44 g, 42.3 mmol) in 200 ml of dry EtOH at RT under N$_2$. The mixture was stirred at RT for 6 h. Water (40 ml) was added and ethanol evaporated. Water (150 ml) was added and stirring was continued overnight. The precipitate was collected by filtration, washed with water and dried at vacuum. The product (10.23 g) was a mixture of diastereomers ($^1$H NMR x:y 67:33) and it was used as such in the next step.

c) 4-[3-(tert-Butyldimethylsilyloxy)cyclohexylamino]-2-chlorobenzonitrile

Imidazole (8.33 g, 122 mmol) was added to a solution of the compound of Example 112(b) (10.23 g, 40.8 mmol) in 210 ml of DCM at 0° C., followed by tert-butyldimethylchlorosilane (9.22 g, 61.2 mmol). The mixture was stirred at 0° C. for 10 min and then at RT for 5 h. Water (80 ml) was added and the layers were separated. After another extraction with DCM the combined organic layers were washed with brine, dried, filtered and evaporated under reduced pressure. The crude product (16.29 g) was the mixture of diastereomers ($^1$H NMR 68:32).

d) 4-{[3-(tert-Butyldimethylsilyloxy)cyclohexyl](ethyl)amino}-2-chlorobenzonitrile Sodium hydride (55% dispersion in mineral oil, 1.67 g, 38.4 mmol) was added in portions to a solution of the compound of Example 112(c) (7.00 g, 19.2 mmol) in 75 ml of dry DMF at 0° C. under a N$_2$. The mixture was stirred at 0° C. for 30 min. Then tetrabutyl ammonium iodide (0.71 g, 1.9 mmol) was added. Iodoethane (7.48 g, 47.9 mmol) was added slowly at 0° C. The mixture was stirred for 30 min at 0° C. and for 2 h at RT. The mixture was quenched with saturated NH₄Cl solution (75 ml) and water (50 ml). The product was extracted into toluene. The combined organic layers were washed with brine and water, dried, filtered and evaporated. The crude product (7.80 g) was a mixture of diastereomers (¹H NMR 70:30).

e) 2-Chloro-4-[ethyl(3-hydroxycyclohexyl)amino]benzonitrile

Thionyl chloride (9.79 g, 82 mmol) was added slowly to a solution of the compound of Example 112(d) (7.79 g, 19.8 mmol) in 100 ml of dry methanol at 0° C. under N₂. The solution was stirred at 0° C. for 15 min and at RT for 2 h. Solvents were evaporated. Ethyl acetate (80 ml) and 1 M NaOH solution (140 ml) were added. The water phase was extracted with ethyl acetate. Combined organic layers were washed with brine, dried, filtered and evaporated under reduced pressure. The crude product (5.69 g) was a mixture of diastereomers (¹H NMR 68:32). The diastereomers were purified and separated by flash chromatography on silica gel using heptane-EtOAc as a gradient eluent (7:3-6:4). The major diastereomer: ¹H NMR (400 MHz, CDCl₃): 1.18 (3H, t), 1.42-1.96 (9H, m), 3.31 (2H, m), 4.16 (1H, m), 4.34 (1H, m), 6.63 (1H, dd), 6.74 (1H, d), 7.38 (1H, d). The minor diastereomer: ¹H NMR (400 MHz, CDCl₃): 1.20 (3H, t), 1.21-1.28 (1H, m), 1.38 (2H, m), 1.48 (1H, m), 1.73-1.85 (2H, m), 1.86-1.94 (1H, m), 1.99-2.19 (1H, m), 2.10-2.18 (1H, m), 3.34 (2H, q), 3.58-3.66 (1H, m), 3.69-3.79 (1H, m), 6.56 (1H, dd), 6.67 (1H, d), 7.39 (1H, d).

f) 2-Chloro-4-[ethyl(3-oxocyclohexyl)amino]benzonitrile

Dess-Martin periodinane (12.17 g, 28.7 mmol) was added in small portions to a solution of the compound of Example 112(e) (4.00 g, 14.4 mmol) in 220 ml of dry DCM at 0° C. at N₂. The mixture was stirred at RT for 24 h. A saturated aqueous solution of NaHCO₃ (50 ml) and a saturated aqueous solution of Na₂S₂O₃ (50 ml) were added and stirring was continued for 15 min. The product was extracted into DCM. The combined organic layers were washed with brine, dried, filtered and evaporated. The crude product was triturated in isopropanol to give the title compound. ¹H NMR (400 MHz, CDCl₃): 1.24 (3H, t), 1.66 (1H, m), 1.88 (1H, m), 2.04-2.19 (2H, m), 2.27-2.35 (1H, m), 2.44-2.63 (3H, m), 3.39 (2H, m), 3.96 (1H, m), 6.59 (1H, dd), 6.71 (1H, d), 7.43 (1H, d).

g) 2-Chloro-4-{ethyl[3-hydroxy-3-(1-trityl-1H-imidazol-4-yl)cyclohexyl]-amino}benzonitrile EtMgBr (3 M solution in diethyl ether, 1.78 ml, 5.3 mmol) was added to a solution of 4-iodo-1-tritylimidazole (2.06 g, 4.7 mmol) in 45 ml of dry DCM at RT at N₂. The solution was stirred at RT for 2 h. Then the compound of Example 112(f) (870 mg, 3.1 mmol) in DCM (10 ml) was added slowly at RT. After stirring for 2 h at RT a saturated aqueous NH₄Cl solution was added. The product was extracted into DCM. The combined organic layers were washed with brine, dried, filtered and evaporated. The crude product was used as such in the next step.

h) 2-Chloro-4-{ethyl[3-hydroxy-3-(1H-imidazol-4-yl)cyclohexyl]amino}-benzonitrile Trifluoroacetic acid (7 ml, 94 mmol) was added slowly to a solution of the compound of Example 112(g) (1.84 g, 3.1 mmol) in 15 ml of dry DCM at 0° C. under N₂. After stirring at RT for 1.5 h the mixture was poured into ice water. The mixture was made alkaline with a saturated NaHCO₃ solution. The product was extracted into DCM. The combined organic layers were washed with brine, dried, filtered and evaporated. The crude product was purified by flash chromatography on silica gel by using the CH₂Cl₂-MeOH as a gradient eluent (98:2-90:10) to give the product as a mixture of diastereomers (¹H NMR 90:10). The major diastereomer: ¹H NMR (400 MHz, CDCl₃): 1.16 (3H, t), 1.55 (1H, m), 1.68-2.03 (6H, m), 2.10 (1H, d), 3.30 (2H, m), 4.26 (1H, m), 6.63 (1H, dd), 6.73 (1H, d), 6.88 (1H, s), 7.30 (1H, d), 7.51 (1H, s).

i) 4-{[3-(1H-Imidazol-4-yl)cyclohex-3-enyl](ethyl)amino}-2-chlorobenzonitrile

The compound of Example 112(h) (1.37 g, 4.0 mmol) was slowly added to concentrated sulfuric acid (30 ml) at 0° C. The temperature was then raised to RT, and the mixture was stirred for 30 min. The pH was then adjusted to 10-11 by addition of 5 M NaOH (cooling in an ice bath). The product was extracted into ethyl acetate. The combined organic layers were washed with water and brine, dried, filtered and concentrated in vacuum. The crude product was purified by flash chromatography on silica gel by using the CH₂Cl₂-MeOH as a gradient eluent (100:0-96:4) to give the title product. ¹H NMR (400 MHz, CDCl₃): 1.25 (3H, t), 1.82-1.94 (1H, m), 1.94-2.01 (1H, m), 2.40-2.52 (3H, m), 2.56-2.65 (1H, m), 3.40 (2H, m), 4.02-4.11 (1H, m), 6.35 (1H, broad s), 6.63 (1H, dd), 6.76 (1H, d), 6.93 (1H, s), 7.41 (1H, d), 7.61 (1H, d).

Example 113

4-{[3-(1H-Imidazol-4-yl)cyclohex-3-enyl](methyl)amino}-2-chlorobenzonitrile a) 4-{[3-(tert-Butyldimethylsilyloxy)cyclohexyl](methyl)amino}-2-chlorobenzonitrile The compound of Example 112(c) (6.00 g, 16.4 mmol) in 75 ml of dry DMF was added slowly to sodium hydride (55% dispersion in mineral oil, washed with pentane, 1.44 g, 32.9 mmol) in 25 ml of dry DMF at 0° C. under N₂. The mixture was stirred at 0° C. for 30 min. Iodomethane (5.83 g, 41.1 mmol) was added slowly at 0° C. and the mixture was stirred at 0° C. for 1 h and at RT for 3 h. The reaction mixture was quenched with a saturated NH₄Cl solution. The product was extracted into toluene. The combined organic layers were washed with brine and water, dried, filtered and evaporated under reduced pressure. The crude product (5.51 g) was a mixture of diastereomers (¹H NMR 73:27).

b) 2-Chloro-4-[(3-hydroxycyclohexyl)(methyl)amino]benzonitrile

Thionyl chloride (7.50 g, 63.0 mmol) was added slowly to a solution of the compound of Example 113(a) (5.51 g, 14.5 mmol) in 75 ml of dry methanol at 25° C. under N₂. The solution was stirred at RT for 18 h. Solvents were evaporated and ethyl acetate (100 ml) and water (50 ml) were added to the residue. The pH was adjusted to 8-9 by 1 M NaOH solution. The water phase was extracted with ethyl acetate. The combined organic layers were washed with water and brine, dried, filtered and evaporated. The crude product c) 2-Chloro-4-[methyl(3-oxocyclohexyl)amino]benzonitrile

Dess-Martin periodinane (15 w-% solution in DCM, 43.6 ml, 59.4 g, 21.0 mmol) was added dropwise to a solution of the compound of Example 113(b) (3.71 g, 14.0 mmol) in 150 ml of dry DCM at 4-5° C. under $N_2$. The solution was stirred at RT for 17 h. Then a saturated solution of $NaHCO_3$ (50 ml) and a saturated solution of $Na_2S_2O_3$ (50 ml) were added and stirring was continued for 20 min. The product was extracted into DCM. The combined organic layers were washed with brine, dried over $Na_2SO_4$, filtered and evaporated. The crude product was purified by flash chromatography on silica gel using $CH_2Cl_2$-acetone (96:4) as an eluent. Yield 2.58 g. $^1$H NMR (400 MHz, DMSO-$d_6$): 1.64-1.80 (2H, m), 1.87-1.97 (2H, m), 2.14-2.25 (2H, m), 2.35 (1H, td), 2.73 (1H, t), 2.87 (3H, s), 4.28 (1H, m), 6.85 (1H, dd), 7.03 (1 H, d), 7.60 (1H, d).

d) 2-Chloro-4-{[3-hydroxy-3-(1-trityl-1H-imidazol-4-yl)cyclohexyl](methyl)amino}benzonitrile The compound was prepared as in Example 112(g) using the compound of Example 113(c) as a starting material. The crude product was a mixture of diastereomers (LC-MS 76:24) and it was used as such in the next step.

e) 2-Chloro-4-{[3-hydroxy-3-(1H-imidazol-4-yl)cyclohexyl](methyl)amino}-benzonitrile The compound was prepared as in Example 112(h) using the compound of Example 113(d) as a starting material. The crude product was purified by flash chromatography on silica gel using the $CH_2Cl_2$-MeOH as a gradient eluent (100:0-90:10). The major diastereomer 1: $^1$H NMR (400 MHz, CDCl$_3$): 1.53-1.66 (1H, m), 1.75 (1H, td), 1.80-1.92 (3H, m), 1.93-2.07 (3H, m), 2.83 (3H, s), 4.29 (1H, m), 6.68 (1H, dd), 6.78 (1H, d), 6.91 (1H, d), 7.40 (1H, d), 7.59 (1H, s). The enantiomers of the major diastereomer 1 and the minor diastereomer 2 (780 mg, 80:20) were separated by preparative chiral HPLC (Column Chiralpak IC 20 mm×250 mm 5 µm, A MTBE+0.2% DEA, B EtOH+0.2% DEA, isocratic B 5%, flow 20 ml/min, λ 300 nm) to yield 50.5 mg of diastereomer 2 (rt 11.0 min), 198.8 mg of enantiomer 1 of diastereomer 1 (rt 13.3 min) (and 181.2 mg of enantiomer 2 of diastereomer 1 (rt 25.0 min). The minor diastereomer: $^1$H NMR (400 MHz, MeOH-$d_4$): 1.48-1.57 (1H, m), 1.60-1.70 (3H, m), 1.82-1.90 (2H, m), 2.46 (1H, m), 2.49-2.60 (1H, m), 2.91 (3H, s), 6.64 (1H, dd), 6.77 (1H, broad s), 7.14 (1H, s), 7.43 (1H, d), 7.71 (1H, d).

f) 4-{[3-(1H-Imidazol-4-yl)cyclohex-3-enyl](methyl)amino}-2-chlorobenzonitrile The compound was prepared as in Example 112(i) using the compound of Example 113(e), mixture of diastereomers, as a starting material. The crude product was purified by flash chromatography on silica gel using the $CH_2Cl_2$-MeOH as a gradient eluent (100:0-90:10). The product was triturated in ethyl acetate to obtain the title compound. $^1$H NMR (400 MHz, CDCl$_3$): 1.85-1.92 (2H, m), 2.41-2.60 (4H, m), 2.91 (3H, s), 4.08 (1H, m), 6.37 (1H, broad s), 6.66 (1H, dd), 6.78 (1H, d), 6.94 (1H, s), 7.42 (1H, d), 7.70 (1H, d).

Example 114

4-{[3-(1H-Imidazol-4-yl)cyclohex-3-enyl](benzyl)amino}-2-chlorobenzonitrile a) 4-{[3-(tert-Butyldimethylsilyloxy)cyclohexyl](benzyl)amino}-2-chlorobenzonitrile The compound was prepared as in Example 112(d) using 4-[3-(tert-butyldimethylsilyloxy)cyclohexylamino]-2-chlorobenzonitrile and benzyl bromide as starting materials. The crude product (mixture of diastereomers ($^1$H NMR 70:30)) was used as such in the next step.

b) 4-[Benzyl(3-hydroxycyclohexyl)amino]-2-chlorobenzonitrile

The compound was prepared as in Example 112(e) using the compound of Example 114(a) as a starting material. The product was extracted into ethyl acetate. The crude product was purified by flash chromatography on silica gel using $CH_2Cl_2$ as an eluent. The product was a mixture of diastereomers ($^1$H NMR 67:33).

c) 4-[Benzyl(3-oxocyclohexyl)amino]-2-chlorobenzonitrile

The compound was prepared as in Example 113(c) using the compound of Example 114(b) as a starting material. The crude product was purified by flash chromatography on silica gel using heptane-ethyl acetate (1:1) as an eluent. $^1$H NMR (400 MHz, CDCl$_3$): 1.60-1.74 (1H, m), 1.74-1.87 (1H, m), 2.22-2.31 (2H, m), 2.43-2-53 (2H, m), 2.63-2.68 (1H, m), 4.15 (1H, m), 4.59 (2H, m), 6.57 (1H, dd), 6.73 (1H, d), 7.17 (2H, m), 7.27-7.31 (1H, m), 7.32-7.37 (2H, m), 7.38 (1H, d).

d) 2-Chloro-4-{[3-hydroxy-3-(1-trityl-1H-imidazol-4-yl)cyclohexyl](benzyl)amino}benzonitrile The compound was prepared as in Example 112(g) using the compound of Example 114(c) as a starting material. The crude product was used as such in the next step.

e) 4-{Benzyl[3-hydroxy-3-(1H-imidazol-4-yl)cyclohexyl]amino}-2-chlorobenzonitrile The compound was prepared as in Example 112(h) using the compound of Example 114(d) as a starting material. The crude product was purified by flash chromatography on silica gel using the $CH_2Cl_2$-MeOH as a gradient eluent (100:0-90:10). The product was a mixture of diastereomers ($^1$H NMR 87:13).

f) 4-{[3-(1H-Imidazol-4-yl)cyclohex-3-enyl](benzyl)amino}-2-chlorobenzonitrile The compound was prepared as in Example 112(i) using the compound of Example 114(e) as a starting material. The crude product was purified by flash chromatography on silica gel using the $CH_2Cl_2$-MeOH (95:5) as an eluent. $^1$H NMR (400 MHz, CDCl$_3$): 1.73-1.84 (1H, m), 1.91-2.00 (1H, m), 2.34-2.50 (3H, m), 2.66-2.72 (1H, m), 4.21-4.29 (1H, m), 4.58 (2H, AB q), 6.31 (1H, broad s), 6.58 (1H, dd), 6.77 (1H, d), 6.87 (1H, d), 7.18-7.21 (2H, m), 7.23-7.28 (1H, m), 7.31-7.36 (3H, m), 7.57 (1H, d).

Example 115

4-{[3-(1H-Imidazol-4-yl)cyclohex-3-enyl](cyclopropylmethyl)amino}-2-chlorobenzonitrile a) 4-{[3-(tert-Butyldimethylsilyloxy)cyclohexyl](cyclopropylmethyl)amino}-2-chlorobenzonitrile The compound of Example 112(c) (180 mg, 0.49 mmol) in 3 ml of dry DMF was added dropwise to sodium hydride (55% dispersion in mineral oil washed with pentane, 43 mg, 0.99 mmol) in 1 ml of dry DMF at 0° C. under $N_2$. The mixture was stirred at 0° C. for 30 min. Then (bromomethyl)cyclopropane (166 mg, 1.23 mmol) was added at 0° C. The temperature was raised to RT, and the mixture was maintained at RT overnight and then at 50° C. for 4 h. The reaction mixture was quenched with ice water. The product was extracted into toluene. The combined organic layers were washed with brine and water, dried, filtered and evaporated under reduced pressure. The crude product was purified by CombiFlash using heptane-EtOAc as a gradient eluent (100:0-90:10). The product was a mixture of diastereomers ($^1$H NMR 74:26).

b) 2-Chloro-4-[(cyclopropylmethyl)(3-hydroxycyclohexyl)amino]benzonitrile

The compound was prepared as in Example 112(e) using the compound of Example 115(a) as a starting material. The crude product was a mixture of diastereomers ($^1$H NMR 74:26) and it was used as such in the next step.

c) 2-Chloro-4-[(cyclopropylmethyl)(3-oxocyclohexyl)amino]benzonitrile

The compound was prepared as in Example 113(c) using the compound of Example 115(b) as a starting material. The crude product was purified by flash chromatography on silica gel using DCM-acetone as a gradient eluent (100:0-98:2). $^1$H NMR (400 MHz, CDCl$_3$): 0.64-0.70 (2H, m), 0.95 (1H, m), 1.60-1.73 (1H, m), 1.85 (1H, m), 2.05-2.19 (2H, m), 2.25-2.34 (1H, m), 2.44-2.66 (3H, m), 3.20 (2H, m), 3.95 (1H, m), 6.70 (1H, dd), 6.84 (1H, d), 7.44 (1H, d).

d) 2-Chloro-4-{[3-hydroxy-3-(1-trityl-1H-imidazol-4-yl)cyclohexyl](cyclopropylmethyl)amino}benzonitrile The compound was prepared as in Example 112(g) using the compound of Example 115(c) as a starting material. The crude product was used as such in the next step.

e) 2-Chloro-4-{(cyclopropylmethyl)[3-hydroxy-3-(1H-imidazol-4-yl)cyclohexyl]amino}benzonitrile The title compound was prepared as in Example 112(h) using the compound of Example 115(d) as a starting material. The crude product was purified by flash chromatography on silica gel using the DCM-MeOH as a gradient eluent (100:0-98:2). The product was a mixture of diastereomers ($^1$H NMR 85:15).

f) 4-{[3-(1H-Imidazol-4-yl)cyclohex-3-enyl](cyclopropylmethyl)amino}-2-chlorobenzonitrile The title compound was prepared as in Example 112(i) using the compound of Example 115(e) as a starting material. The crude product was purified by flash chromatography on silica gel using the DCM-MeOH as a gradient eluent (100:0-95:5). $^1$H NMR (400 MHz, CDCl$_3$): 0.29 (2H, m), 0.61-0.67 (2H, m), 0.99 (1H, m), 1.76-1.88 (1H, m), 1.93-2.02 (1H, m), 2.38-2.52 (3H, m), 2.58-2.67 (1H, m), 3.21 (2H, m), 4.00-4.10 (1H, m), 6.32 (1H, br s), 6.74 (1H, dd), 6.88 (1H, d), 6.94 (1H, s), 7.41 (1H, d), 7.60 (1H, s).

Example 116

4-{[3-(1H-Imidazol-4-yl)cyclohex-3-enyl](propyl)amino}-2-chlorobenzonitrile a) 4-{[3-(tert-Butyldimethylsilyloxy)cyclohexyl](propyl)amino}-2-chlorobenzonitrile The compound was prepared as in Example 112(d) by using the compound of Example 112(c) and 1-iodopropane as starting materials. The mixture was stirred at RT for 48 h. The crude product was purified by flash chromatography on silica gel (eluent: 5-10% EtOAc/heptane) to obtain the product as a mixture of diastereomers ($^1$H NMR 71:29).

b) 2-Chloro-4-[(3-hydroxycyclohexyl)(propyl)amino]benzonitrile

The compound was prepared as in Example 112(e) using the compound of Example 116(a) as a starting material. The crude product was purified by flash chromatography on silica gel (eluent: 10-30% EtOAc/heptane) to obtain the product as a mixture of diastereomers. The major diastereomer: $^1$H NMR (400 MHz, CDCl$_3$): 0.94 (3H, t), 1.41-1.96 (11H, m), 3.02-3.19 (2H, m), 4.15 (1H, m), 4.34 (1H, m), 6.60 (1H, dd), 6.71 (1H, d), 7.38 (1H, d). The minor diastereomer: $^1$H NMR (400 MHz, CDCl$_3$): 0.95 (3H, t), 1.18-1.96 (9H, m), 2.04 (1H, m), 2.13 (1H, m), 3.10-3.18 (2H, m), 3.61 (1H, m), 3.74 (1H, m), 6.53 (1H, dd), 6.64 (1H, d), 7.39 (1H, d).

c) 2-Chloro-4-[(3-oxocyclohexyl)(propyl)amino]benzonitrile

The compound was prepared as in Example 113(c) using the compound of Example 116(b) as a starting material. The crude product was recrystallized in 2-propanol. $^1$H NMR (400 MHz, DMSO-d$_6$): 0.92 (3H, t), 1.50 (2H, m), 1.69 (1H, m), 1.77-1.98 (3H, m), 2.21 (2H, m), 2.38 (1H, m), 2.72 (1H, m), 3.18-3.35 (2H, m), 4.21-4.29 (1H, m), 6.80 (1H, dd), 6.98 (1H, d), 7.60 (1H, d).

d) 2-Chloro-4-{[3-hydroxy-3-(1-trityl-1H-imidazol-4-yl)cyclohexyl](propyl)amino}benzonitrile The compound was prepared as in Example 112(g) using the compound of Example 116(c) as a starting material. The product was extracted into EtOAc and it was used as such in the next step.

e) 2-Chloro-4-{[3-hydroxy-3-(1H-imidazol-4-yl)cyclohexyl](propyl)amino}-benzonitrile The compound was prepared as in Example 112(h) using the compound of Example 116(d) as a starting material. The crude product was purified by flash chromatography on silica gel (eluent: 0-5% MeOH/DCM to give the pure product as a mixture of diastereomers ($^1$H NMR 89:11). The major diastereomer: $^1$H NMR (400 MHz, CDCl$_3$): 0.93 (3H, t), 1.47-1.64 (3H, m), 1.70-2.10 (7H, m), 3.13 (2H, m), 4.26 (1H, m), 6.62 (1H, dd), 6.72 (1H, d), 6.91 (1H, s), 7.36 (1H, d), 7.58 (1H, s).

f) 4-{[3-(1H-Imidazol-4-yl)cyclohex-3-enyl](propyl)amino}-2-chlorobenzonitrile

The compound was prepared as in Example 112(i) using the compound of Example 116(e) as a starting material. The crude product was purified by flash chromatography on silica gel (eluent: 0-5% MeOH/DCM). $^1$H NMR (400 MHz, CDCl$_3$): 0.97 (3H, t), 1.65 (2H, m), 1.80-1.93 (1H, m), 1.93-2.00 (1H, m), 2.37-2.50 (3H, m), 2.54-2.63 (1H, m), 3.22 (2H, m), 4.00-4.10 (1H, m), 6.35 (1H, br s), 6.60 (1H, dd), 6.73 (1H, d), 6.93 (1H, s), 7.40 (1H, d), 7.61 (1H, s).

Example 117

4-{[3-(1H-Imidazol-4-yl)cyclohex-3-enyl](ethyl)amino}-2-(trifluoromethyl)benzonitrile a) 4-(3-Oxocyclohex-1-enylamino)-2-(trifluoromethyl)benzonitrile 4-Amino-2-(trifluoromethyl)benzonitrile (20.00 g, 107 mmol), cyclohexane-1,3-dione (13.25 g, 118 mmol) and p-toluenesulfonic acid pyridine salt (1.35 g, 5.37 mmol) were boiled in toluene (400 ml) for 2 h using the Dean-Stark apparatus. Then, the mixture was cooled to RT. The precipitate was collected by filtration, washed with toluene and dried. Yield 30 g. $^1$H NMR (400 MHz, DMSO-d$_6$): 1.93 (2H, m), 2.25 (2H, t), 2.55 (2H, t), 5.65 (1H, s), 7.59-7.62 (2H, m), 8.06 (1H, d), 9.44 (1H, s).

b) 4-(3-Hydroxycyclohexylamino)-2-(trifluoromethyl)benzonitrile PR-517A II

The compound was prepared as in Example 112(b) using the compound of Example 117(a) as a starting material. The product was a mixture of diastereomers ($^1$H NMR 61:39). Yield 98%.

c) 4-[3-(tert-Butyldimethylsilyloxy)cyclohexylamino]-2-(trifluoromethyl)benzonitrile The compound was prepared as in Example 112(c) using the compound of Example 117(b) as a starting material. The crude product (mixture of diastereomers $^1$H NMR 67:33) was triturated in heptane. The precipitate was the major isomer. The major diastereomer: $^1$H NMR (400 MHz, CDCl$_3$): 0.06 (3H, s), 0.07 (3H, s), 0.92 (9H, s), 1.19 (1H, m), 1.28 (1H, m), 1.40 (1H, m), 1.57-1.70 (2H, m), 1.86 (1H, m), 2.03 (2H, m), 3.81 (1H, m), 4.16 (1H, m), 4.22 (1H, m), 6.65 (1H, dd), 6.82 (1H, d), 7.52 (1H, d).

d) 4-{[3-(tert-Butyldimethylsilyloxy)cyclohexyl](ethyl)amino}-2-(trifluoromethyl)benzonitrile The compound was prepared as in Example 112(d) using the compound of Example 117(c) as a starting material. The crude product was a mixture of diastereomers ($^1$H NMR 68:32) and it was used as such in the next step.

e) 4-[Ethyl(3-hydroxycyclohexyl)amino]-2-(trifluoromethyl)benzonitrile

The compound was prepared as in Example 112(e) using the compound of Example 117(d) as a starting material. The crude product was a mixture of diastereomers ($^1$H NMR 66:34). The diastereomers were purified and separated by flash chromatography on silica gel (eluent: 30-40% EtOAc/heptane). The major diastereomer: $^1$H NMR (400 MHz, CDCl$_3$): 1.20 (3H, t), 1.43-1.59 (3H, m), 1.64 (1H, m), 1.69-1.76 (1H, m), 1.78 (1H, m), 1.90 (3H, m), 3.36 (2H, m), 4.23 (1H, m), 4.35 (1H, m), 6.85 (1H, dd), 6.99 (1H, d), 7.54 (1H, d).

f) 4-[Ethyl(3-oxocyclohexyl)amino]-2-(trifluoromethyl)benzonitrile

The compound was prepared as in Example 112(f) using the compound of Example 117(e) as a starting material. The crude product was triturated in isopropanol to give the title compound. $^1$H NMR (400 MHz, DMSO-d$_6$): 1.13 (3H, t), 1.65-1.79 (1H, m), 1.80-1.89 (1H, m), 1.90-2.00 (2H, m), 2.18-2.30 (2H, m), 2.39 (1H, m), 2.75 (1H, m), 3.50 (2H, m), 4.37 (1H, m), 7.07-7.13 (2H, m), 7.78 (1H, d).

g) 4-{Ethyl[3-hydroxy-3-(1H-imidazol-4-yl)cyclohexyl]amino}-2-(trifluoromethyl)benzonitrile To a stirred solution of 4-iodo-1-tritylimidazole (2.1 g, 4.81 mmol) in dry DCM (50 ml) was added EtMgBr (3 M solution in diethylether, 1.82 ml). The mixture was stirred at RT for 2 h. The compound of Example 117(f) (1.0 g, 3.22 mmol) in dry DCM (10 ml) was added dropwise and the mixture was stirred at RT overnight. The reaction was quenched by saturated aqueous NH$_4$Cl solution and extracted with EtOAc, washed with brine, dried, filtered and concentrated. The crude product was purified by column chromatography over silica gel using CH$_3$OH: DCM (2%) as the eluent to give white solid, yield: 1.1 g MS: m/z 621 [M+H]. The mixture was dissolved to THF (20 ml) and water (2 ml), and 20 ml of formic acid was added. The mixture was stirred at 65° C. for 4 h. The solvent was removed in vacuo. The crude was basified by saturated aqueous NaHCO$_3$ solution and extracted with EtOAc, washed with brine, dried, filtered and concentrated under reduced pressure. The crude product was purified by column chromatography over silica gel using CH$_3$OH: DCM (4%) as the eluent to give diastereomer 1 as white solid. Yield 150 mg. $^1$H-NMR (400 MHz, DMSO-d$_6$): 12.25 (bs, 1H), 7.79 (d, 1H), 7.64 (s, 1H), 7.04 (s, 1H), 7.03 (d, 1H), 6.91 (s, 1H), 5.02 (s, 1H), 4.23 (m$_c$, 1H), 3.41-3.48 (m, 2H), 1.53-1.94 (m, 8H), 1.17 (bt, 3H). m/z 379 [M+H].

h) 4-{[3-(1H-Imidazol-4-yl)cyclohex-3-enyl](ethyl)amino}-2-(trifluoromethyl)benzonitrile To the compound of Example 117(g) (900 mg, 2.38 mmol) was added concentrated H$_2$SO$_4$ (10 ml) at 0° C. and stirred for 15 min followed by stirring at RT for 30 min. The mixture was basified with 5 N NaOH solution and extracted with EtOAc, washed with brine, dried, filtered and concentrated. The crude product was purified by column chromatography over silica gel using CH$_3$OH: DCM (3%) as the eluent to give 560 mg of the title compound. $^1$H-NMR (400 MHz; DMSO-d$_6$): δ 11.93 (bs, 1H), 7.75 (d, 1H), 7.56 (s, 1H), 7.10 (d, 1H), 7.09 (s, 1H), 7.02 (bs, 1H), 6.23 (bs, 1H) 4.20 (m$_c$, 1H), 3.43-3.56 (m, 2H), 2.29-2.42 (m, 4H), 1.84-1.90 (m, 2H), 1.15 (t, 3H); MS: m/z 361 [M+H].

Example 118

4-{Ethyl[3-(5-methyl-1H-imidazol-4-yl)cyclohex-3-enyl]amino}-2-(trifluoromethyl)benzonitrile a) 4-{Ethyl[3-hydroxy-3-(5-methyl-1-trityl-1H-imidazol-4-yl)cyclohexyl]-amino}-2-(trifluoromethyl) benzonitrile and 4-{ethyl[3-hydroxy-3-(4-methyl-1-trityl-1H-imidazol-4-yl)cyclohexyl]amino}-2-(trifluoromethyl)benzonitrile The title compounds were prepared as in Example 112(g) using the mixture of 4-iodo-5-methyl-1-trityl-1H-imidazole and 5-iodo-4-methyl-1-trityl-1H-imidazole (prepared according to WO 2008/86131) and the compound of Example 117(f) as starting materials. The mixture was stirred for 22 h. The mixture of products was used as such in the next step.

b) 4-{Ethyl[3-hydroxy-3-(5-methyl-1H-imidazol-4-yl)cyclohexyl]amino}-2-(trifluoromethyl)benzonitrile The compound was prepared as in Example 112(h) using the mixture of Example 118(a) as a starting material. The mixture was stirred at RT overnight. The crude product was purified by flash chromatography on silica gel (eluent: 0-10% MeOH/DCM) to obtain the title compound as a mixture of diastereomers. The major diastereomer: $^1$H NMR (400 MHz, MeOH-$d_4$): 1.20 (3H, t), 1.68 (1H, m), 1.74-2.03 (6H, m), 2.09 (1H, m), 2.35 (3H, s), 3.48 (2H, m), 4.36 (1H, m), 7.05 (1H, dd), 7.12 (1H, d), 7.41 (1H, s), 7.63 (1H, d).

c) 4-{Ethyl[3-(5-methyl-1H-imidazol-4-yl)cyclohex-3-enyl]amino}-2-(trifluoromethyl)benzonitrile The compound was prepared as in Example 112(i) using the compound of Example 118(b) as a starting material. The crude product was purified by flash chromatography on silica (eluent: 0-2% MeOH/DCM) to obtain the title product. $^1$H NMR (400 MHz, CDCl$_3$): 1.23 (3H, t), 1.81-2.00 (2H, m), 2.32 (3H, s), 2.39-2.58 (3H, m), 2.75 (1H, m), 3.42 (2H, m), 4.08 (1H, m), 5.89 (1H, br s), 6.81 (1H, dd), 6.97 (1H, d), 7.43 (1H, s), 7.50 (1H, d).

Example 119

4-{Ethyl[3-(1-ethyl-5-methyl-1H-imidazol-4-yl)cyclohex-3-enyl]amino}-2-(trifluoromethyl)benzonitrile a) 1-Ethyl-4-iodo-5-methyl-1H-imidazole and 1-ethyl-5-iodo-4-methyl-1H-imidazole Iodoethane (4.72 g, 30.3 mmol) was added to the mixture of 4-iodo-5-methyl-1H-imidazole (4.50 g, 21.63 mmol), tetrabutylammonium bromide (237 mg, 0.74 mmol), 70 ml of toluene and 25 ml of 50% NaOH at 55° C. The mixture was stirred at 55-74° C. for 3 h. Water was then added and the products were extracted into toluene. The combined organic layers were washed with water, dried and evaporated. Yield 5.07 g. The crude product was the mixture of 1-ethyl-4-iodo-5-methyl-1H-imidazole and 1-ethyl-5-iodo-4-methyl-1H-imidazole (ratio 56:44). The isomers were separated by flash chromatography on silica gel (eluent: heptane-EtOAc 6:4). The major isomer 1-ethyl-4-iodo-5-methyl-1H-imidazole was confirmed by NMR techniques ($^1$H NMR, $^{13}$CPD, HSQC and HMBC). 1-Ethyl-4-iodo-5-methyl-1H-imidazole: $^1$H NMR (400 MHz, CDCl$_3$): 1.39 (3H, t), 2.21 (3H, s), 3.92 (2H, q), 7.42 (1H, s). 1-Ethyl-5-iodo-4-methyl-1H-imidazole: $^1$H NMR (400 MHz, CDCl$_3$): 1.40 (3H, t), 2.23 (3H, s), 3.91 (2H, q), 7.61 (1H, s).

b) 4-{Ethyl[3-(1-ethyl-5-methyl-1H-imidazol-4-yl)-3-hydroxycyclohexyl]-amino}-2-(trifluoromethyl) benzonitrile The compound was prepared as in Example 112(g) using 1-ethyl-4-iodo-5-methyl-1H-imidazole (Example 119(a)) and the compound of Example 117(f) as starting materials. The mixture was stirred overnight. The product was extracted into EtOAc and purified by flash chromatography on silica gel (eluent: 0-1% MeOH/DCM) to obtain the title compound as a mixture of diastereomers ($^1$H NMR x:y 84:16). The major diastereomer: $^1$H NMR (400 MHz, CDCl$_3$): 1.20 (3H, t), 1.39 (3H, t), 1.55-1.67 (2H, m), 1.78-2.04 (6H, m), 2.33 (3H, s), 2.92 (1H, s), 3.39 (2H, m), 3.86 (2H, q), 4.34 (1H, m), 6.89 (1H, dd), 7.03 (1H, d), 7.33 (1H, s), 7.54 (1H, d).

c) 4-{Ethyl[3-(1-ethyl-5-methyl-1H-imidazol-4-yl)cyclohex-3-enyl]amino}-2-(trifluoromethyl)benzonitrile The title compound was prepared as in Example 112(i) using the compound of Example 119(b) as a starting material. The crude product was purified by flash chromatography on silica gel using DCM as an eluent and then by the preparative HPLC to obtain the title product. $^1$H NMR (400 MHz, CDCl$_3$): 1.25 (3H, t), 1.40 (3H, t), 1.82-1.98 (2H, m), 2.29 (3H, s), 2.41-2.48 (2H, m), 2.52-2.63 (1H, m), 2.81 (1H, m), 3.44 (2H, m), 3.89 (2H, q), 4.10 (1H, m), 5.85 (1H, m), 6.85 (1H, dd), 6.99 (1H, d), 7.38 (1H, s), 7.55 (1H, d).

Example 120

4-{Ethyl[3-(1-ethyl-4-methyl-1H-imidazol-5-yl)cyclohex-3-enyl]amino}-2-(trifluoromethyl)benzonitrile a) 4-{Ethyl[3-(1-ethyl-4-methyl-1H-imidazol-5-yl)-3-hydroxycyclohexyl]-amino}-2-(trifluoromethyl) benzonitrile The compound was prepared as in Example 119(b) using 1-ethyl-5-iodo-4-methyl-1H-imidazole (Example 119(a)) and the compound of Example 117(f) as starting materials. The crude product (mixture of diastereomers) was purified by flash chromatography on silica gel using DCM as an eluent.

b) 4-{Ethyl[3-(1-ethyl-4-methyl-1H-imidazol-5-yl)cyclohex-3-enyl]amino}-2-(trifluoromethyl)benzonitrile The compound was prepared as in Example 112(i) using the compound of Example 120(a) as a starting material. The crude product was purified by flash chromatography on silica gel using DCM-MeOH (95:5) as an eluent. $^1$H NMR (400 MHz, CDCl$_3$): 1.25 (3H, t), 1.38 (3H, t), 1.85-1.97 (1H, m), 1.98-2.07 (1H, m), 2.17 (3H, s), 2.30-2.52 (4H, m), 3.43 (2H, m), 3.84 (2H, q), 4.04-4.13 (1H, m), 5.79 (1H, br s), 6.83 (1H, dd), 6.99 (1H, d), 7.36 (1H, s), 7.59 (1H, d).

Example 121

4-{Ethyl[3-(2-methyl-1H-imidazol-4-yl)cyclohex-3-enyl]amino}-2-(trifluoromethyl)benzonitrile a) 4-{Ethyl[3-hydroxy-3-(2-methyl-1-trityl-1H-imidazol-4-yl)cyclohexyl]-amino}-2-(trifluoromethyl)benzonitrile The compound was prepared as in Example 112(g) using 4-iodo-2-methyl-1-trityl-1H-imidazole (prepared as in Sebhat I. K. et al., ACS Medicinal Chemistry Letters 2(1), 43, 2011) and the compound of Example 117(f) as starting materials. The crude product was used as such in the next step.

b) 4-{Ethyl[3-hydroxy-3-(2-methyl-1H-imidazol-4-yl)cyclohexyl]amino}-2-(trifluoromethyl)benzonitrile The compound was prepared as in Example 112(h) using the compound of Example 121(a) as a starting material by stirring at RT for 27 h. The crude product was stirred in DCM/MeOH and filtered. The filtrate was evaporated to afford the crude product which was purified by CombiFlash (eluent: 5-20% MeOH/DCM) to obtain the title product as a mixture of diastereomers ($^1$H NMR 87:13). The major diastereomer: $^1$H NMR (400 MHz, CDCl$_3$): 1.19 (3H, t), 1.59 (1H, m), 1.67-2.04 (6H, m), 2.09 (1H, m), 2.41 (3H, s), 3.37 (2H, m), 4.32 (1H, m), 6.76 (1H, s), 6.89 (1H, dd), 6.99 (1H, d), 7.52 (1H, d).

c) 4-{Ethyl[3-(2-methyl-1H-imidazol-4-yl)cyclohex-3-enyl]amino}-2-(trifluoromethyl)benzonitrile The compound was prepared as in Example 112(i) using the compound of Example 121(b) as a starting material. The crude product was purified by CombiFlash (column silica, eluent: 1$^{st}$ 5-10% MeOH/DCM and 2$^{nd}$ 40% acetone/DCM) to obtain the title compound. $^1$H NMR (400 MHz, CDCl$_3$): 1.26 (3H, t), 1.82-2.01 (2H, m), 2.42 (3H, s), 2.38-2.50 (3H, m), 2.57 (1H, m), 3.44 (2H, m), 4.06-4.15 (1H, m), 6.32 (1H, br s), 6.77 (1H, s), 6.84 (1H, dd), 6.99 (1H, d), 7.56 (1H, d).

Example 122

4-(Ethyl{3-[1-(2-hydroxyethyl)-1H-imidazol-4-yl]cyclohex-3-enyl}amino)-2-(trifluoromethyl)benzonitrile a) 1-[2-(Benzyloxy)ethyl]-4-iodo-1H-imidazole and 1-[2-(benzyloxy)ethyl]-5-iodo-1H-imidazole Benzyl 2-bromoethyl ether (11.53 g, 53.6 mmol) was added to the mixture of 4-iodo-1H-imidazole (10.00 g, 51.6 mmol), TBABr (565 mg, 1.75 mmol), 150 ml of toluene and 50 ml of 50% NaOH at 90° C. The mixture was heated at 90° C. for 3 h and then cooled to RT. Water (500 ml) was added and the products were extracted into toluene. The combined organic layers were washed with water, dried and evaporated. The residue (yield 16.19 g) was a mixture of isomers ($^1$H NMR: ratio 71:29) which were purified and separated by reversed-phase chromatography to obtain 1-[2-(Benzyloxy)ethyl]-4-iodo-1H-imidazole (yield 9.00 g), $^1$H NMR (400 MHz, CDCl$_3$): 3.67 (2H, t), 4.09 (2H, t), 4.50 (2H, s), 7.05 (1H, d), 7.22-7.25 (2H, m), 7.28-7.38 (3H, m), 7.43 (1H, d), and 1-[2-(Benzyloxy)ethyl]-5-iodo-1H-imidazole (yield 3.20 g), $^1$H NMR (400 MHz, CDCl$_3$): 3.70 (2H, t), 4.12 (2H, t), 4.48 (2H, s), 7.13 (1H, d), 7.22-7.25 (2H, m), 7.27-7.36 (3H, m), 7.74 (1H, d).

b) 4-[(3-{1-[2-(Benzyloxy)ethyl]-1H-imidazol-4-yl}-3-hydroxycyclohexyl)(ethyl)amino]-2-(trifluoromethyl)benzonitrile The compound was prepared as in Example 112(g) using 1-[2-(benzyloxy)ethyl]-4-iodo-1H-imidazole (Example 122(a)) and the compound of Example 117(f) as starting materials. The crude product was purified by flash chromatography on silica gel (eluent: 0-1% MeOH/DCM).

c) 2-[4-(5-{[4-Cyano-3-(trifluoromethyl)phenyl](ethyl)amino}cyclohex-1-enyl)-1H-imidazol-1-yl]ethyl hydrogen sulfate The title compound was prepared as in Example 112(i) using the compound of Example 122(b) as a starting material. The crude product was first purified by flash chromatography on silica gel (eluent: 0-10% MeOH/DCM). Then, the product was dissolved in methanol, the solution was filtered and the filtrate was made alkaline by adding 1 M NaOH. The title compound (LC-MS FW 484) was extracted into ethyl acetate. $^1$H NMR (400 MHz, DMSO-d$_6$): 1.17 (3H, t), 1.79-1.91 (2H, m), 2.26-2.5 (4H, m), 3.50 (2H, m), 3.94 (2H, t), 4.09 (2H, t), 4.20 (1H, m), 6.26 (1H, m), 7.09-7.14 (3H, m), 7.51 (1H, s), 7.76 (1H, d).

d) 4-(Ethyl {3-[1-(2-hydroxyethyl)-1H-imidazol-4-yl]cyclohex-3-enyl}amino)-2-(trifluoromethyl)benzonitrile The compound of Example 122(c) (140 mg, 0.289 mmol) in the mixture of 1.5 ml of ethanol and 6 ml of 10% HCl was boiled for 1.5 h. Then, the cooled solution was made alkaline with 5 M NaOH. The product was extracted into ethyl acetate. The combined organic layers were washed with brine and water, dried and evaporated. The residue was purified first by flash chromatography on silica gel using CH$_2$Cl$_2$-MeOH (98:2) as an eluent and then by preparative HPLC. Yield 28.4 mg. $^1$H NMR (400 MHz, CDCl$_3$): 1.27 (3H, t), 1.83-2.02 (2H, m), 2.40-2.52 (3H, m), 2.60 (1H, m), 3.45 (2H, m), 3.90 (2H, t), 4.05 (2H, t), 4.07-4.16 (1H, m), 6.44 (1H, br s), 6.85 (1H, dd), 6.88 (1H, s), 7.00 (1H, d), 7.48 (1H, s), 7.57 (1H, d).

Example 123

4-(Ethyl{3-[1-(2-hydroxyethyl)-1H-imidazol-5-yl]cyclohex-3-enyl}amino)-2-(trifluoromethyl)benzonitrile a) 4-[(3-{1-[2-(Benzyloxy)ethyl]-1H-imidazol-5-yl}-3-hydroxycyclohexyl)-(ethyl)amino]-2-(trifluoromethyl)benzonitrile The compound was prepared as in Example 112(g) using 1-[2-(benzyloxy)ethyl]-5-iodo-1H-imidazole (Example 122(a)) and the compound of Example 117(f). The mixture was stirred overnight. The title compound was obtained as mixture of diastereomers (LC-MS 80:20). The crude product was purified first by flash chromatography on silica gel (eluent: 0-2% MeOH/DCM) and then by trituration in diethyl ether at RT.

b) 2-[5-(5-{[4-Cyano-3-(trifluoromethyl)phenyl] (ethyl)amino}cyclohex-1-enyl)-1H-imidazol-1-yl] ethyl hydrogen sulfate The compound was prepared as in Example 112(g) using the compound of Example 123(a) as a starting material and ethyl acetate as an extraction solvent. The crude product (LC-MS FW 484) was purified by flash chromatography on silica gel (eluent: 0-20% MeOH/DCM).

c) 4-(Ethyl {3-[1-(2-hydroxyethyl)-1H-imidazol-5-yl]cyclohex-3-enyl}amino)-2-(trifluoromethyl)benzonitrile The compound was prepared as in Example 122(d) using the compound of Example 123(b) as a starting material. The title compound was purified first by flash chromatography (eluent: 0-5% MeOH/DCM) and then by preparative HPLC. $^1$H NMR (400 MHz, CDCl$_3$): 1.24 (3H, t), 1.81-1.92 (1H, m), 1.94-2.04 (1H, m), 2.35-2.53 (4H, m), 3.12 (1H, br s), 3.42 (2H, m), 3.88 (2H, t), 4.01-4.12 (3H, m), 5.86 (1H, m), 6.79 (1H, s), 6.84 (1H, dd), 6.98 (1H, d), 7.41 (1H, s), 7.57 (1H, d).

Example 124

4-(Ethyl {3-[1-(2-hydroxyethyl)-1H-imidazol-5-yl] cyclopent-3-enyl}amino)-2-(trifluoromethyl)benzonitrile a) 4-[(3-{1-[2-(Benzyloxy)ethyl]-1H-imidazol-5-yl}-3-hydroxycyclopentyl)(ethyl)amino]-2-(trifluoromethyl)benzonitrile The compound was prepared as in Example 112(g) using 1-[2-(benzyloxy)ethyl]-5-iodo-1H-imidazole of Example 122(a) and the compound of Example 150(d) and stirring the mixture overnight. The crude product was purified by flash chromatography using DCM-MeOH (98:2) as an eluent. The title product was a mixture of diastereomers (2:1).

b) 4-(Ethyl {3-[1-(2-hydroxyethyl)-1H-imidazol-5-yl]cyclopent-3-enyl}-amino)-2-(trifluoromethyl) benzonitrile The title compound was prepared as in Example 112(i) using the compound of Example 124(a) as a starting material. The product was purified first by flash chromatography (eluent: 0-10% MeOH/DCM) and then by preparative HPLC. $^1$H NMR (400 MHz, CDCl$_3$): 1.23 (3H, t), 2.70 (1H, m), 2.83 (1H, m), 2.98 (1H, m), 3.07 (1H, m), 3.46 (2H, q), 3.96 (2H, t), 4.22 (2H, t), 4.64 (1H, m), 5.88 (1H, m), 6.79 (1H, dd), 6.92 (1H, s), 6.96 (1H, d), 7.49 (1H, s), 7.57 (1H, d).

Example 125

2-Chloro-4-(ethyl{3-[1-(2-hydroxy-2-methylpropyl)-1H-imidazol-4-yl]cyclohex-3-enyl}amino)benzonitrile A microwave oven reaction tube was charged with the compound of Example 112 (50 mg, 0.153 mmol), yttrium (III)nitrate hexahydrate (1.6 mg, 0.00428 mmol), THF (1.7 ml) and 2,2-dimethyloxirane (0.137 ml, 110 mg, 1.53 mmol). The mixture was stirred at 80° C. for 20 min in a microwave oven. The solvent was evaporated, and EtOAc was added to the residue. Then the solution was washed with water and dried over Na$_2$SO$_4$. After evaporation of the solvent the residue was purified first by flash chromatography on silica gel (eluent: 0-20% MeOH/DCM) and then by preparative HPLC to obtain the title product (yield 11 mg). $^1$H NMR (400 MHz, CDCl$_3$): 1.23 (6H, s), 1.25 (3H, t), 1.80-2.00 (2H, m), 2.36-2.52 (3H, m), 2.56 (1H, m), 2.87 (1h, br s), 3.39 (2H, m), 3.84 (2H, s), 4.05 (1H, m), 6.43 (1H, m), 6.63 (1H, dd), 6.75 (1H, d), 6.87 (1H, s), 7.41 (1H, d), 7.55 (1H, s).

Example 126

4-{Ethyl[3-(1-ethyl-2-methyl-1H-imidazol-4-yl) cyclohex-3-enyl]amino}-2-(trifluoromethyl)benzonitrile Iodoethane (0.125 ml, 243 mg, 1.56 mmol) was added to the mixture of the compound of Example 121 (417 mg, 1.11 mmol), TBABr (12.2 mg, 0.038 mmol), 6.5 ml of toluene and 2.5 ml of 50% NaOH in water at 60° C. The mixture was stirred at 60° C. for 3 h. Water was then added and the product was extracted into toluene. The combined organic layers were washed with water, dried and evaporated to afford the crude product which was purified first by flash chromatography on silica gel using EtOAc as an eluent and then by preparative HPLC. $^1$H NMR (400 MHz, CDCl$_3$): 1.26 (3H, t), 1.36 (3H, t), 1.82-2.01 (2H, m), 2.37 (3H, s), 2.38-2.50 (3H, m), 2.51-2.60 (1H, m), 3.44 (2H, m), 3.84 (2H, q), 4.10 (1H, m), 6.39 (1H, m), 6.70 (1H, s), 6.84 (1H, dd), 6.99 (1H, d), 7.56 (1H, d).

Example 127

4-{Ethyl[3-(1-ethyl-1H-imidazol-4-yl)cyclopent-3-enyl]amino}-2-(trifluoromethyl)benzonitrile and 4-{Ethyl[3-(1-ethyl-1H-imidazol-5-yl)cyclopent-3-enyl]-amino}-2-(trifluoromethyl)benzonitrile The compound of Example 150 (328 mg, 0.947 mmol) in 2 ml of dry DMF was added to sodium hydride (55% dispersion in mineral oil washed with pentane, 83 mg, 1.89 mmol) in 1 ml of dry DMF at 0° C. under N$_2$. The mixture was stirred at 0° C. for 30 min. Iodoethane (0.098 ml, 192 mg, 1.23 mmol) was then added. The mixture was stirred at 0° C. for 30 min and then at RT for 1.5 h. The mixture was poured into the icecold saturated aqueous NH$_4$Cl solution (4 ml). Water (3 ml) was added and the product was extracted into EtOAc. The combined organic layers were washed with brine and water, dried, filtered and evaporated to afford 1,4- and 1,5-isomers (70:30) which were purified and separated first by flash chromatography and then by preparative HPLC. 1,4-isomer: $^1$H NMR (400 MHz, CDCl$_3$): 1.22 (3H, t), 1.47 (3H, t), 2.59-2.77 (2H, m), 2.93 (1H, m), 3.03 (1H, m), 3.46 (2H, q), 3.98 (2H, q), 4.69 (1H, m), 6.22 (1H, m), 6.80 (1H, dd), 6.84 (1H, s), 6.99 (1H, d), 7.50 (1H, s), 7.56 (1H, d). 1,5-isomer: $^1$H NMR (400 MHz, CDCl$_3$): 1.24 (3H, t), 1.49 (3H, t), 2.66-2.77 (1H, m), 2.81-2.90 (1H, m), 3.00 (1H, m), 3.10 (1H, m), 3.46 (2H, q), 4.13 (2H, q), 4.67 (1H, m), 5.89 (1H, m), 6.81 (1H, dd), 6.98 (1H, d), 7.02 (1H, s), 7.56 (1H, s), 7.58 (1H, d).

Example 128

4-{[3-(1H-Imidazol-4-yl)cyclohex-3-enyl](2-hydroxyethyl)amino}-2-(trifluoromethyl)benzonitrile a) 2-(Trifluoromethyl)-4-[3-(1-trityl-1H-imidazol-4-yl)cyclohex-3-enylamino]benzonitrile To a solution of the compound of Example 80 (1.34 g, 4.03 mmol) in dry DMF (15 ml) was added triethylamine (0.843 ml, 612 mg, 6.05 mmol), followed by triphenylmethyl chloride (1.24 g, 4.44 mmol). The mixture was stirred at RT overnight. Then, the mixture was poured into 60 ml of water and stirred for 2 h. The precipitate was filtered and dried at vacuum. Crystallization in EtOAc-heptane afforded the title compound. Yield 2.29 g. $^1$H NMR (400 MHz, CDCl$_3$): 1.67-1.80 (1H, m), 1.89-2.01 (1H, m), 2.16-2.27 (1H, m), 2.27-2.40 (2H, m), 2.71 (1H, m), 3.83 (1H, m), 4.64 (1H, d), 6.48 (1H, m), 6.67 (1H, dd), 6.70 (1H, s), 6.83 (1H, d), 7.09-7.18 (6H, m), 7.26-7.37 (9H, m), 7.41 (1H, d), 7.52 (1H, d).

b) 4-{[2-(Tetrahydro-2H-pyran-2-yloxy)ethyl][3-(1-trityl-1H-imidazol-4-yl)-cyclohex-3-enyl]amino}-2-(trifluoromethyl)benzonitrile Sodium hydride (55% dispersion in mineral oil, 346 mg, 7.94 mmol) was added in portions to a solution of the compound of Example 128(a) (2.28 g, 3.97 mmol) in 20 ml of dry DMF at 0° C. under N$_2$. The mixture was stirred for 30 min. Tetrabutyl ammonium iodide (220 mg, 0.60 mmol) was added, followed by 2-(2-bromoethoxy)tetrahydro-2H-pyran (0.90 ml, 1.24 g, 5.95 mmol) at 0° C. The mixture was stirred at 0° C. for 7 h and at RT overnight. The mixture was quenched with saturated aqueous NH$_4$Cl solution. The product was extracted into EtOAc. The combined organic layers were washed with brine and water, dried, filtered and evaporated. The crude product was used as such in the next step.

c) 4-{(2-Hydroxyethyl) [3-(1-trityl-1H-imidazol-4-yl)cyclohex-3-enyl]amino}-2-(trifluoromethyl)benzonitrile 20% HCl in ethanol (12 ml) was added to a solution of the compound of Example 128(b) in ethanol (60 ml). The solution was stirred at RT for 1.5 h. Ethanol was evaporated and water was added to the residue. The solution was made alkaline (pH 9) with aqueous NaOH solution. The product was extracted into ethyl acetate. The combined organic layers were washed water, dried and concentrated. The product was purified first by flash chromatography on silica gel (eluent: 0-4% MeOH/DCM) and then by preparative HPLC. Yield 0.16 g. $^1$H NMR (400 MHz, CDCl$_3$): 1.78-1.96 (2H, m), 2.12 (1H, t), 2.37-2.55 (4H, m), 3.53 (2H, m), 3.79 (2H, m), 4.04-4.13 (1H, m), 6.39 (1H, m), 6.70 (1H, s), 6.92 (1H, dd), 7.08 (1H, d), 7.10-7.17 (6H, m), 7.29-7.37 (9H, m), 7.40 (1H, d), 7.56 (1H, d).

d) 4-{[3-(1H-Imidazol-4-yl)cyclohex-3-enyl](2-hydroxyethyl)amino}-2-(trifluoromethyl)benzonitrile The compound was prepared as in Example 112(h) using the compound of Example 128(c) as a starting material. The product was purified first by flash chromatography (eluent: 1-5% MeOH/DCM) and then by preparative HPLC. Yield 3.0 mg. $^1$H NMR (400 MHz, CDCl$_3$): 1.84-2.00 (2H, m), 2.42-2.69 (4H, m), 3.54 (2H, m), 3.82-3.88 (2H, m), 4.14 (1H, m), 6.46 (1H, br s), 6.93 (1H, s), 6.97 (1H, dd), 7.13 (1H, d), 7.58 (1H, s), 7.61 (1H, d).

Example 129

4-{[3-(1H-Imidazol-4-yl)cyclohex-3-enyl](allyl)amino}-2-(trifluoromethyl)-benzonitrile a) 4-{Allyl[3-(1-trityl-1H-imidazol-4-yl)cyclohex-3-enyl]amino}-2-(trifluoromethyl)benzonitrile The compound was prepared as in Example 128(b) using the compound of Example 128(a) and allylbromide as starting materials and stirring the reaction mixture at RT for 4.5 h. The product was extracted into EtOAc. The crude product was used as such in the next step.

b) 4-{[3-(1H-Imidazol-4-yl)cyclohex-3-enyl](allyl)amino}-2-(trifluoromethyl)benzonitrile The title compound was prepared as in Example 112(h) using the compound of Example 129(a) as a starting material. The product was purified first by flash chromatography (eluent: 1-5% MeOH/DCM) and then by preparative HPLC. Yield 2.7 mg. $^1$H NMR (400 MHz, CDCl$_3$): 1.85 (1H, m), 1.95-2.04 (1H, m), 2.41-2.53 (3H, m), 2.64 (1H, m), 3.92-4.10 (2H, m), 4.14-4.26 (1H, m), 5.19-5.28 (2H, m), 5.87 (1H, m), 6.50 (1H, br s), 6.87 (1H, dd), 6.91 (1H, s), 7.02 (1H, d), 7.57 (1H, d), 7.62 (1H, s), 9.10 (1H, br s).

Example 130

4-{[3-(1H-Imidazol-1-yl)-6,6-dimethylcyclohex-2-enyl](methyl)amino}-2-(trifluoromethyl)benzonitrile The compound was prepared from the compound of Example 96(f) (2.50 g, 6.94 mmol) in 15 ml of dry DMF, sodium hydride (60% dispersion in mineral oil, 555 mg, 13.87 mmol) in 11 ml of dry DMF and iodomethane (0.71 ml, 1.62 g, 10.41 mmol). The crude product (2.48 g) was recrystallized in EtOAc-heptane (4 ml: 1 ml) to afford the title product. Yield 1.60 g, 62%. $^1$H NMR (400 MHz, CDCl$_3$): 0.98 (3H, s), 1.11 (3H, s), 1.78 (2H, m), 2.51-2.60 (1H, m), 2.64-2.73 (1H, m), 2.98 (3H, s), 4.55 (1H, d), 5.63 (1H, m), 6.94 (1H, dd), 7.09 (1H, d), 7.14 (1H, s), 7.17 (1H, s), 7.62 (1H, d), 7.77 (1H, s). The enantiomers of the racemic mixture (1.50 g) were separated by preparative chiral HPLC (Column Chiralpak IA 20 mm×250 mm 5 um, A MTBE+0.1% DEA, B IPA+0.1% DEA, isocratic B 10%, flow 15 ml/min, 300 nm) to yield 523.7 mg of enantiomer 1 (rt 11.4 min) and 497.2 mg of enantiomer 2 (rt 15.9 min).

Example 131

N-[3-(1H-Imidazol-1-yl)-6,6-dimethylcyclohex-2-enyl]-N-methyl-4-nitro-3-(trifluoromethyl)aniline a) N-(3-(1H-imidazol-1-yl)-6,6-dimethylcyclohex-2-en-1-yl)-4-nitro-3-(trifluoromethyl)aniline A reaction flask was charged with 3-(1H-imidazol-1-yl)-6,6-dimethylcyclohex-2-enamine of Example 96(e) (650 mg, 3.40 mmol), 7 ml of dry DMSO, 4-fluoro-1-nitro-2-(trifluoromethyl)benzene (725 mg, 3.47 mmol) and DIPEA (1.50 ml, 1.11 g, 8.60 mmol). The mixture was heated at 80° C. for 1 h 45 min. The mixture was cooled to RT and water was added. The product was extracted into EtOAc. The combined organic layers were washed with water and brine, dried and evaporated. The residue (1.2 g) was triturated in boiling DCM (5 ml). The precipitate was filtered and dried under vacuum to afford the title product. Yield 514 mg, 40%. $^1$H NMR (400 MHz, CDCl$_3$): 1.13 (3H, s), 1.29 (3H, s), 1.73-1.85 (2H, m), 2.50-2.64 (2H, m), 4.03-4.08 (1H, m), 4.58 (1H, d), 5.63-5.65 (1H, m), 6.76 (1H, dd), 6.97 (1H, d), 7.10 (1H, m), 7.12 (1H, m), 7.70 (1H, m), 8.03 (1H, d).

b) N-[3-(1H-Imidazol-1-yl)-6,6-dimethylcyclohex-2-enyl]-N-methyl-4-nitro-3-(trifluoromethyl)aniline The compound was prepared as in Example 130 using the compound of Example 131(a) as a starting material. The product was purified by flash chromatography (eluent: 0-1% MeOH/DCM) to afford the title product. $^1$H NMR (400 MHz, CDCl$_3$): 0.99 (3H, s), 1.12 (3H, s), 1.73-1.86 (2H, m), 2.51-2.62 (1H, m), 2.63-2.74 (1H, m), 3.02 (3H, s), 4.59 (1H, m), 5.64 (1H, m), 6.91 (1H, dd), 7.10-7.22 (3H, m), 7.78 (1H, s), 8.07 (1H, d).

Example 132

2-Chloro-4-(ethyl(3-(pyridin-3-yl)cyclohex-3-en-1-yl)amino)-6-fluorobenzonitrile a) 2-Chloro-6-fluoro-4-((3-oxocyclohex-1-en-1-yl)amino)benzonitrile A mixture of 1,3-cyclopentanedione (3.53 g, 31.5 mmol), 4-amino-2-chloro-6-fluorobenzonitrile (5.12 g, 30 mmol) and TsOH (0.285 g, 1.5 mmol) in toluene (90 ml) was refluxed in a Dean-Stark apparatus until no more water separated. The mixture was cooled to RT and the solid product was collected. The solid was washed with 0.5 M NaOH, ice cold ethanol and ether, and dried in vacuo to afford 7.36 g of the title compound. $^1$H NMR (400 MHz, MeOH-d$_4$): 2.04 (2H, m), 2.39 (2H, t), 2.60 (2H, t), 5.78 (1H, s), 7.15 (1H, dd), 7.26 (1H, m).

b) 2-Chloro-6-fluoro-4-((3-hydroxycyclohexyl)amino)benzonitrile

Sodium borohydride (5.15 g, 136 mmol) was added stepwise to a cooled mixture of the compound of Example 132(a) (6.0 g, 22.67 mmol) and ethanol (125 ml). After 3.5 h of stirring at RT the reaction was quenched with water. The mixture was slowly stirred at RT overnight after which it was filtered. The solid product was washed with water and dried in vacuo to afford 6.0 g of the title compound as a mixture of diastereomers (ratio 65:35 by NMR). LC-MS: m/z=269.08 (M+1)$^+$.

c) 4-((3-((tert-Butyldimethylsilyl)oxy)cyclohexyl)amino)-2-chloro-6-fluorobenzonitrile tert-Butyldimethylchlorosilane (3.70 g, 24.56 mmol) was added stepwise to a mixture of the compound of Example 132(b) (6.0 g, 22.33 mmol) and imidazole (2.28 g, 33.5 mmol) in DMF (25 ml). After 5 h of stirring at RT the reaction was quenched with the addition of saturated NH$_4$Cl and water. The mixture was extracted with ethyl acetate. The combined organic extracts were washed with 2 M HCl, saturated NaHCO$_3$, and brine, dried, filtered and evaporated to afford 8.4 g of the title compound as a mixture of diastereomers. The product was used in the next step as such. LC-MS: m/z=383.21 (M+1)$^+$.

d) 4-((3-((tert-Butyldimethylsilyl)oxy)cyclohexyl)(ethyl)amino)-2-chloro-6-fluorobenzonitrile Sodium hydride (0.80 g, 20.0 mmol; 60% dispersion in mineral oil) was washed with pentane under N$_2$. Dry DMF (15 ml) was added and the suspension was cooled to 0-5° C. A solution of the compound of Example 132(c) (4.5 g, 11.75 mmol) in dry DMF (40 ml) was subsequently added and the mixture was stirred at 0-5° C. for 30 min. Then, iodoethane (2.0 ml, 25.01 mmol) was added and the mixture was allowed to warm to RT and stirred overnight. The mixture was diluted with water and saturated aqueous NaHCO$_3$ and extracted with TBME. The combined organic extracts were washed with water and brine, dried, filtered and evaporated to afford 4.9 g of the title compound as a mixture of diastereomers. The product was used as such in the next step. LC-MS: m/z=411.24 (M+1)$^+$.

e) 2-Chloro-4-(ethyl(3-hydroxycyclohexyl)amino)-6-fluorobenzonitrile

Thionyl chloride (5.15 g, 136 mmol) was added stepwise to a cooled mixture of the compound of Example 132(d) (4.4 g, 9.63 mmol) and methanol (50 ml). After 3.5 h stirring at RT the reaction was concentrated. Water and ethyl acetate were added and the pH was adjusted to 10 with 2 M NaOH. The organic phase was washed with water and brine, dried, filtered and evaporated to afford 2.77 g of the title compound as a mixture of diastereomers. The product was used as such in the next step. LC-MS: m/z=297.32 (M+1)$^+$.

f) 2-Chloro-4-(ethyl(3-oxocyclohexyl)amino)-6-fluorobenzonitrile

A solution of the compound of Example 132(e) (2.77 g, 9.34 mmol) in dry DCM (40 ml) was treated with Dess-Martin periodinane (25.0 ml, 12.04 mmol; 15 w-% solution in DCM). After stirring for 3 h at RT the mixture was treated with a 1:1 mixture of saturated NaHCO$_3$ and Na$_2$S$_2$O$_3$ (80 ml). After stirring the mixture for 15 min the phases were separated. The aqueous phase was extracted with DCM. The combined organic extracts were washed with 1 M HCl, saturated NaHCO$_3$, and brine, dried, filtered and evaporated. Purification by flash chromatography gave 2.12 g of the title compound. $^1$H NMR (400 MHz, CDCl$_3$): 1.24 (3H, t), 1.69 (1H, m), 1.88 (1H, m), 2.08 (1H, m), 2.16 (1H, m), 2.31 (1H, m), 2.54 (3H, m), 3.38 (2H, m), 3.90 (1H, m), 6.34 (1H, dd), 6.53 (1H, d).

g) 2-Chloro-4-(ethyl(3-hydroxy-3-(pyridin-3-yl)cyclohexyl)amino)-6-fluorobenzonitrile A solution of 3-bromopyridine (0.29 ml, 3.01 mmol) in dry THF (12 ml) was cooled to −78° C. n-Butyllithium (2.0 ml, 3.20 mmol; 1.6 M solution in hexane) was added and the mixture was stirred at −78° C. for 30 min. A solution of the compound of Example 132(f) (0.59 g, 2.00 mmol) in dry THF (8 ml) was added and the mixture was allowed to warm to RT overnight. The reaction was quenched with saturated NH$_4$Cl and then most of the solvents were evaporated. The residue was diluted with water and extracted with ethyl acetate. The combined organic extracts were washed with brine, dried, filtered and evaporated. Purification by flash chromatography gave 0.19 g of the title compound as a mixture of diastereomers. m/z=374.37 (M+1)$^+$.

h) 2-Chloro-4-(ethyl(3-(pyridin-3-yl)cyclohex-3-en-1-yl)amino)-6-fluorobenzonitrile The compound of Example 132(g) (0.19 g, 0.508) was treated stepwise with concentrated sulfuric acid (2.5 ml, 46.6 mmol). The mixture was stirred at 0-5° C. for 30 min and then at RT until reaction was complete. The mixture was poured into ice water, made alkaline with 25% NaOH and extracted with ethyl acetate. The combined organic extracts were washed with brine, dried, filtered and evaporated. Purification by flash chromatography gave 0.10 g of the title compound. $^1$H NMR (400 MHz, CDCl$_3$): 1.27 (3H, t), 1.89 (1H, m), 2.00 (1H, m), 2.49 (2H, m), 2.58 (2H, m), 3.41 (2H, m), 4.03 (1H, m), 6.19 (1H, m), 6.39 (1H, dd), 6.59 (1H, d), 7.25 (1H dd), 7.63 (1H, dt), 8.50 (1H, dd), 8.64 (1H, d).

Example 133

4-((3-(1H-Imidazol-4-yl)cyclopent-3-en-1-yl)(ethyl) amino)-2-chlorobenzonitrile a) 2-Chloro-4-((3-oxocyclopent-1-en-1-yl)amino) benzonitrile A mixture of 1,3-cyclopentanedione (2.452 g, 25 mmol), 4-amino-2-chlorobenzonitrile (3.81 g, 25 mmol) and TsOH (0.476 g, 2.5 mmol) in toluene (75 ml) was refluxed in a Dean-Stark apparatus until no more water separated. The mixture was cooled to RT and the solid product was collected by suction and recrystallized from aqueous ethanol. Yield 4.36 g. $^1$H NMR (400 MHz, MeOH-d$_4$): 2.46 (2H, m), 2.88 (2H, m), 5.73 (1H, s), 7.32 (1H, dd), 7.41 (1H, d), 7.78 (1H, d).

b) 2-Chloro-4-(ethyl(3-oxocyclopent-1-en-1-yl) amino)benzonitrile

The compound was prepared as in Example 132(d) from the compound of Example 133(a), sodium hydride (0.851 g, 21.28 mmol; 60% dispersion in mineral oil) and iodoethane (2.3 ml, 28.8 mmol). Extraction with EtOAc. Purification by flash chromatography afforded 3.70 g of the title compound. $^1$H NMR (400 MHz, MeOH-d$_4$): 1.21 (3H, t), 2.42 (2H, m), 2.68 (2H, m), 3.82 (2H, q), 5.13 (1H, s), 7.49 (1H, dd), 7.73 (1H, d), 7.93 (1H, d).

c) 2-Chloro-4-(ethyl(3-hydroxycyclopentyl)amino) benzonitrile

Sodium borohydride (0.60 g, 15.86 mmol) was added stepwise to a mixture of the compound of Example 133(b) (1.30 g, 4.99 mmol) and ethanol (25 ml). After stirring for 2 h a second batch of sodium borohydride (0.60 g, 15.86 mmol) was added and stirring continued for 48 h. The reaction was quenched with the addition of water and extracted with ethyl acetate. The combined organic extracts were washed with brine, dried, filtered and evaporated. Purification by flash chromatography gave 0.85 g of the title compound as a mixture of diastereomers. LC-MS: m/z=265.15 (M+1)$^+$.

d) 2-Chloro-4-(ethyl(3-oxocyclopentyl)amino)benzonitrile

The compound was prepared as in Example 132(f) from the compound of Example 133(c) (1.20 g, 4.53 mmol), pyridine (1.0 ml, 12.36 mmol) and Dess-Martin periodinane (13.0 ml, 6.26 mmol; 15 w-% solution in DCM). Purification by flash chromatography afforded 0.842 g of the title compound. $^1$H NMR (400 MHz, CDCl$_3$): 1.23 (3H, t), 2.05 (1H, m), 2.26-2.42 (3H, m), 2.51 (1H, m), 2.63 (1H, m), 3.39 (2H, m), 4.42 (1H, m), 6.65 (1H, dd), 6.78 (1H, d), 7.45 (1H, d).

e) 2-Chloro-4-(ethyl(3-hydroxy-3-(1-trityl-1H-imidazol-4-yl)cyclopentyl)-amino)benzonitrile A mixture of 4-iodo-1-tritylimidazole (0.863 g, 1.979 mmol) in dry DCM (8 ml) was treated with EtMgBr (0.8 ml, 2.40 mmol; 3 M in ether). After stirring the mixture for 2 h at RT the compound of Example 133(d) (0.40 g, 1.522 mmol) in dry DCM (4 ml) was added and stirring was continued at RT. The reaction was quenched with addition of a mixture of saturated NH$_4$Cl and water. The phases were separated and the aqueous phase was extracted with DCM. Combined organic extracts were washed with brine, dried, filtered and evaporated. Purification by flash chromatography gave 0.742 g of a mixture containing 75% of 2-chloro-4-(ethyl(3-hydroxy-3-(1-trityl-1H-imidazol-4-yl)cyclopentyl)amino)-benzonitrile and 25% of 1-trityl-1H-imidazole as analyzed by LC-MS. The mixture was used as such in the next step.

f) 4-((3-(1H-Imidazol-4-yl)cyclopent-3-en-1-yl) (ethyl)amino)-2-chlorobenzonitrile A solution of the compound of Example 133(e) (0.20 g, 0.329 mmol, purity 75% by LC-MS) in dry DCM (1 ml) was treated with trifluoroacetic acid (1.0 ml, 13.46 mmol). After stirring for 3 h at RT the mixture was cooled in an ice bath and treated with concentrated sulfuric acid (1 ml, 18.66 mmol). The mixture was stirred at RT for 2.5 h and then poured into ice water. The mixture was basified with 25% NaOH and extracted with ethyl acetate (2×). The combined organic extracts were washed with brine, dried, filtered and evaporated. Purification by flash chromatography gave 14 mg of the title compound. $^1$H NMR (400 MHz, CDCl$_3$): 1.21 (3H, t), 2.65 (1H, m), 2.75 (1H, m), 2.92 (1H, m), 3.01 (1H, m), 3.41 (2H, q), 4.66 (1H, m), 6.18 (1H, m), 6.59 (1H, dd), 6.74 (1H, d), 6.98 (1H s), 7.40 (1H, d), 7.66 (1H, s), 9.17 (1H, br s).

Example 134

2-Chloro-4-(ethyl(3-(pyridin-3-yl)cyclohexyl) amino)-6-fluorobenzonitrile

The compound of Example 132 (73 mg, 0.205 mmol) was dissolved in ethyl acetate (5 ml) and hydrogenated in a H-Cube continuous-flow hydrogenation apparatus (ThaleSNano Inc.) using 20% Pd(OH)$_2$/C catalyst cartridge. The reduction was conducted at 30° C. using 1 bar hydrogen pressure with a flow rate of 1 ml/min. After three reduction cycles the solvents were evaporated to afford 37 mg of the title compound as a mixture of diastereomers (ratio 69:31 by NMR). $^1$H NMR (400 MHz, CDCl$_3$) of the major isomer: 1.21 (3H, t), 1.55-2.05 (7H, m), 2.21 (1H, m), 2.34 (1H, m), 3.37 (2H, m), 3.52 (1H, m), 6.09 (1H, dd), 6.26 (1H, d), 7.35 (1H, dd), 7.69 (1H, d), 8.54 (1H, m), 8.67 (1H, d). LC-MS: m/z=358.20 (M+1)$^+$.

Example 135

4-((3-(1H-Imidazol-4-yl)cyclohex-3-en-1-yl)(ethyl) amino)-2-chloro-6-fluorobenzonitrile a) 4-(3-((3-Chloro-4-cyano-5-fluorophenyl)(ethyl) amino)-1-hydroxycyclohexyl)-N,N-dimethyl-1H-imidazole-1-sulfonamide A mixture of 4-iodo-N,N-dimethyl-1H-imidazole-1-sulfonamide (0.783 g, 2.60 mmol; prepared as in Heterocycles, 2000, 53, 729) in dry DCM-THF (7 ml:0.5 ml) was treated with EtMgBr (1.0 ml, 3.00 mmol; 3 M in ether). After stirring the mixture for 2 h at RT a solution of 2-chloro-4-(ethyl(3-oxocyclohexyl)amino)-6-fluorobenzonitrile (0.59 g, 2.00 mmol) in dry DCM (7 ml) was added and stirring was continued at RT until the reaction was complete (monitored by LC-MS and TLC). The reaction was quenched with addition of a mixture of saturated NH$_4$Cl and water. The aqueous phase was extracted with DCM. The combined organic extracts were washed brine, dried, filtered and evaporated. Purification by flash chromatography gave 0.482 g of the title compound as a mixture of diastereomers. LC-MS: m/z=470.43 (M+1)$^+$.

b) 4-((3-(1H-Imidazol-4-yl)cyclohex-3-en-1-yl)(ethyl)amino)-2-chloro-6-fluorobenzonitrile A solution of the compound of Example 135(a) (0.161 g, 0.343 mmol) in dioxane (0.5 ml) was treated with concentrated HCl (1.0 ml, 12.18 mmol). After stirring for 3.5 h at 90° C. the mixture was cooled to RT. The mixture was diluted with water, basified with 10% NaOH and extracted with ethyl acetate. The combined organic extracts were washed with brine, dried, filtered and evaporated. Purification by preparative HPLC gave 3 mg of the title compound. $^1$H NMR (400 MHz, CDCl$_3$): 1.26 (3H, t), 1.80-2.10 (3H, m), 2.46 (3H, m), 2.60 (1H, m), 3.39 (2H, m), 4.00 (1H, m), 6.38 (1H, dd), 6.58 (1H, d), 6.94 (1H, s), 7.62 (1H, d), 9.00 (1H, br s).

Example 136

4-((3-(1H-imidazol-4-yl)cyclopentyl)(ethyl)amino)-2-(trifluoromethyl)benzonitrile a) N,N-dimethyl-4-(3-oxocyclopent-1-en-1-yl)-1H-imidazole-1-sulfonamide The compound was prepared as in Example 135(a) from 3-ethoxycyclopenten-2-one (0.14 g, 1.11 mmol). Purification by flash chromatography gave 52 mg of the title compound. $^1$H NMR (400 MHz, CDCl$_3$): 2.56 (2H, m), 2.93 (6H, s), 2.97 (2H, m), 6.62 (1H, t), 7.56 (1H, d), 7.96 (1H, d).

b) N, N-dimethyl-4-(3-oxocyclopentyl)-1H-imidazole-1-sulfonamide

The compound of Example 136(a) (62 mg, 0.243 mmol) was dissolved in ethyl acetate-acetic acid (8 ml:2 ml) and hydrogenated in a H-Cube continuous-flow hydrogenation apparatus (ThalesNano Inc.) using 20% Pd(OH)$_2$/C catalyst cartridge. The reduction was conducted at 60° C. using 60 bar hydrogen pressure with a flow rate of 1 ml/min. After starting material was consumed solvents were evaporated. Yield 65 mg. $^1$H NMR (400 MHz, CDCl$_3$): 2.11 (1H, m), 2.29 (1H, m), 2.42 (3H, m), 2.62 (1H, m), 2.87 (1H, m), 2.88 (6H, s), 7.01 (1H, m), 7.85 (1H, d).

c) 4-(3-((4-Cyano-3-(trifluoromethyl)phenyl)amino)cyclopentyl)-N,N-dimethyl-1H-imidazole-1-sulfonamide A solution of the compound of Example 136(b) (0.114 g, 0.443 mmol), 4-amino-2-(trifluoromethyl)benzonitrile (0.091 g, 0.487 mmol), and acetic acid (0.051 ml, 0.886 mmol) in 1,2-dichloroethane was stirred at RT for 1 h. Sodium triacetoxyborohydride (0.188 g, 0.886 mmol) was added and stirring was continued for 72 h. The reaction was quenched with cold water and extracted with DCM. Combined organic extracts were washed with brine, dried, filtered and evaporated. Purification by flash chromatography gave 53 mg of the title compound as a mixture of diastereomers. LC-MS: m/z=428.48 (M+1)$^+$.

d) 4-(3-((4-Cyano-3-(trifluoromethyl)phenyl)(ethyl)amino)cyclopentyl)-N,N-dimethyl-1H-imidazole-1-sulfonamide Sodium hydride (8.0 mg, 0.20 mmol; 60% dispersion in mineral oil) was added to a cooled solution of the compound of Example 136(c) (53 mg, 0.124 mmol) in dry DMF (1 ml). The mixture was stirred at 0-5° C. for 30 min. Then, iodoethane (22 µl, 0.275 mmol) was added and the mixture was allowed to warm to RT and stirred until the reaction was complete. The reaction was quenched with a mixture of water and saturated aqueous NaHCO$_3$ and extracted with TBME. Combined organic extracts were washed with water and brine, dried, filtered and evaporated to afford 54 mg of the title compound as a mixture of diastereomers. LC-MS: m/z=456.55 (M+1)$^+$. Product was used as such in the next step.

e) 4-((3-(1H-imidazol-4-yl)cyclopentyl)(ethyl)amino)-2-(trifluoromethyl)-benzonitrile The compound was prepared as in Example 135(b) starting from the compound of Example 136(d) (52 mg, 0.114 mmol). Purification by preparative HPLC gave 14.5 mg of the title compound as a mixture of diastereomers (ratio 82:18 by NMR). $^1$H NMR (400 MHz, CDCl$_3$) of the main diastereomer: 1.22 (3H, t), 1.90 (3H, m), 2.15 (2H, m), 2.38 (1H, m), 3.20 (1H, m), 3.43 (2H, q), 4.28 (1H, m), 6.83 (2H, m), 6.99 (1H, d), 7.56 (1H, d), 7.64 (1H, br s).

Example 137

(R)-4-(Ethyl(1-(pyridin-3-yl)piperidin-3-yl)amino)-2-(trifluoromethylbenzonitrile a) (R)-tert-Butyl (1-(pyridin-3-yl)piperidin-3-yl)carbamate A mixture of (R)-tert-butyl piperidin-3-ylcarbamate (0.20 g, 1.00 mmol), 3-bromopyridine (0.12 ml, 1.246 mmol), Pd$_2$(dba)$_3$ (46 mg, 0.05 mmol), rac-BINAP (62 mg, 0.10 mmol), and sodium tert-butoxide (0.135 g, 1.40 mmol) in dry toluene (5 ml) was stirred at 80° C. After the reaction was completed the mixture was diluted with TBME and filtered. The filtrate was concentrated and the crude product was purified by flash chromatography. Yield 0.134 g. $^1$H NMR (400 MHz, CDCl$_3$): 1.46 (9H, s), 1.54 (1H, m), 1.72 (1H, m), 1.84 (2H, m), 2.95 (1H, m), 3.10 (1H, m), 3.20 (1H, m), 3.45 (1H, m), 3.85 (1H, br s), 4.90 (1H, br s), 7.14 (1H, dd), 7.21 (1H, m), 8.09 (1H, dd), 8.30 (1H, d).

b) (R)-1-(Pyridin-3-yl)piperidin-3-amine hydrochloride

Thionyl chloride (0.30 ml, 4.11 mmol) was added stepwise to a cooled mixture of the compound of Example 137(a) (0.134 g, 0.483 mmol) and methanol (2.5 ml). The mixture was stirred at RT until all the starting material had reacted. The mixture was concentrated to afford 0.128 g of the title compound. The product was used as such in the next step. $^1$H NMR (400 MHz, DMSO-d$_6$): 1.55-1.72 (2H, m), 1.83 (1H, m), 1.99 (1H, m), 3.19 (1H, m), 3.33 (2H, m), 3.64

(1H, m), 3.88 (1H, m), 7.80 (1H, dd), 8.01 (1H, dd), 8.18 (1H, d), 8.34 (3H, br s), 8.47 (1H, d).

c) (R)-4-((1-(Pyridin-3-yl)piperidin-3-yl)amino)-2-(trifluoromethyl)benzonitrile A mixture of the compound of Example 137(b) (0.128 g, 0.599 mmol), 4-fluoro-2-(trifluoromethyl)benzonitrile (0.10 g, 0.529 mmol) and DIPEA (0.40 ml, 2.296 mmol) in dry DMSO (5 ml) was stirred at 100° C. After the reaction was completed the reaction mixture was diluted with water and extracted with TBME. The combined organic extracts were washed with water and brine, dried, filtered and evaporated. Purification by flash chromatography gave 55 mg of the title compound. $^1$H NMR (400 MHz, CDCl$_3$): 1.77 (2H, m), 1.90 (2H, m), 3.15 (2H, m), 3.23 (1H, m), 3.42 (1H, dd), 3.80 (1H, m), 5.00 (1H, d), 6.74 (1H, dd), 6.90 (1H, d), 7.20 (2H, m), 7.56 (1H, d), 8.16 (1H, dd), 8.33 (1H, dd).

d) (R)-4-(Ethyl(1-(pyridin-3-yl)piperidin-3-yl)amino)-2-(trifluoromethyl)-benzonitrile Sodium hydride (10 mg, 0.250 mmol; 60% dispersion in mineral oil) was weighed in a dry flask under N$_2$. Dry DMF (1.5 ml) was added and the suspension was cooled to 0-5° C. The compound of Example 137(c) (50 mg, 0.144 mmol) in dry DMF (2.0 ml) was added and the mixture was stirred at 0-5° C. for 30 min. Then, iodoethane (25 µl, 0.318 mmol) was added and the mixture was allowed to warm to RT and stirred until the reaction was complete. Then the mixture was diluted with a mixture of water and saturated aqueous NaHCO$_3$ and extracted with TBME. The combined organic extracts were washed with water and brine, dried, filtered and evaporated. Crude product was purified by preparative HPLC. Yield 22 mg. $^1$H NMR (400 MHz, CDCl$_3$): 1.25 (3H, t), 1.76 (1H, m), 1.88 (1H, m), 2.00 (1H, m), 2.07 (1H, m), 2.74 (1H, dt), 2.79 (1H, t), 3.47 (2H, m), 3.68 (2H, m), 3.98 (1H, m), 6.87 (1H, dd), 7.02 (1H, d), 7.18 (2H, m), 7.60 (1H, d), 8.13 (1H, dd), 8.31 (1H, m).

Example 138

(S)-4-(Ethyl(1-(pyridin-3-yl)pyrrolidin-3-yl)amino)-2-(trifluoromethyl)benzonitrile a) (S)-tert-Butyl 3-((4-cyano-3-(trifluoromethyl)phenyl)amino)pyrrolidine-1-carboxylate The compound was prepared as in Example 137(c) starting from (S)-tert-butyl 3-aminopyrrolidine-1-carboxylate (0.745 g, 4.00 mmol), 4-fluoro-2-(trifluoromethyl)-benzonitrile (0.756 g, 4.00 mmol) and DIPEA (2.0 ml, 11.48 mmol) in dry DMSO (10 ml). Purification by flash chromatography gave 0.872 g of the title compound. $^1$H NMR (400 MHz, CDCl$_3$): 1.47 (9H, s), 1.94 (1H, m), 2.24 (1H, m), 3.30 (1H, m), 3.50 (1H, m), 3.71 (1H, m), 4.09 (1H, m), 4.68 (1H, d), 6.71 (1H, dd), 6.88 (1H, d), 7.58 (1H, d).

b) (S)-tert-Butyl 3-((4-cyano-3-(trifluoromethyl)phenyl)(ethyl)amino)pyrrolidine-1-carboxylate The compound was prepared as in Example 132(d) from the compound of Example 138(a) (0.872 g, 2.452 mmol). Extraction with EtOAc. Yield 0.89 g. $^1$H NMR (400 MHz, CDCl$_3$): 1.23 (3H, t), 1.48 (9H, s), 2.07 (1H, m), 2.20 (1H, m), 3.27 (1H, m), 3.41 (3H, m), 3.64 (2H, m), 4.39 (1H, br s), 6.86 (1H, dd), 7.01 (1H, d), 7.60 (1H, d).

c) (S)-4-(Ethyl(pyrrolidin-3-yl)amino)-2-(trifluoromethyl)benzonitrile

The compound was prepared as in Example 137(b) from the compound of Example 138(b) (0.89 g, 2.327 mmol) and thionyl chloride (4 equivalents) in methanol (10 ml). Yield 0.349 g. $^1$H NMR (400 MHz, CDCl$_3$): 1.25 (3H, t), 2.12 (1H, m), 2.33 (1H, m), 3.10 (1H, dd), 3.31 81H, m), 3.45-3.57 (4H, m), 4.59 (1H, m), 6.91 (1H, dd), 7.05 (1H, d), 7.63 (1H, d).

d) (S)-4-(Ethyl(1-(pyridin-3-yl)pyrrolidin-3-yl)amino)-2-(trifluoromethyl)-benzonitrile The compound was prepared as in Example 137(a) starting from the compound of Example 138(c) (0.156 g, 0.489 mmol). Purification by flash chromatography afforded 0.123 g of the title compound $^1$H NMR (400 MHz, CDCl$_3$): 1.26 (3H, t), 2.28 (1H, m), 2.41 (1H, m), 3.38 (1H, m), 3.48 (2H, m), 3.61 (2H, m), 4.62 (1H, m), 6.87 (1H, ddd), 6.91 (1H, dd), 7.06 (1H, d), 7.15 (1H, dd), 7.60 (1H, d), 8.03 (2H, m).

Example 139

(S)-4-(Ethyl(1-(pyridin-3-yl)piperidin-3-yl)amino)-2-(trifluoromethyl)benzonitrile a) (S)-tert-Butyl 3-((4-cyano-3-(trifluoromethyl)phenyl)amino)piperidine-1-carboxylate The compound was prepared as in Example 138(a) starting from (S)-tert-butyl 3-aminopiperidine-1-carboxylate (0.801 g, 4.00 mmol). Purification by flash chromatography gave 1.08 g of the title compound. $^1$H NMR (400 MHz, CDCl$_3$): 1.44 (9H, s), 1.62 (2H, m), 1.75 (1H, m), 1.98 (1H, m), 3.13 (1H, dd), 3.26 (1H, m), 3.50 (1H, m), 3.58 (1H, m), 3.84 (1H, dd), 4.52 (1H, br s), 6.73 (1H, dd), 6.86 (1H, d), 7.57 (1H, d).

b) (S)-tert-Butyl 3-((4-cyano-3-(trifluoromethyl)phenyl)(ethyl)amino)piperidine-1-carboxylate The compound was prepared as in Example 132(d) starting from the compound of Example 139(a) (1.08 g, 2.92 mmol). Yield 0.958 g. The compound was used as such in the next step. $^1$H NMR (400 MHz, CDCl$_3$): 1.20 (3H, t), 1.47 (9H, s), 1.64 (1H, m), 1.85 (1H, m), 1.92 (1H, m), 2.03 (1H, m), 2.78 (2H, m), 3.51 (2H, m), 3.76 (1H, m), 4.07 (2H, d), 7.08 (1H, dd), 7.13 (br s), 7.69 (1H, d).

c) (S)-4-(Ethyl(piperidin-3-yl)amino)-2-(trifluoromethyl)benzonitrile hydrochloride The compound was prepared as in Example 137(b) starting from the compound of Example 139(b) (0.958 g) and using 4 molar equivalent of thionyl chloride. Crude product was purified by trituration with ether. Yield 0.805 g. $^1$H NMR (400 MHz, DMSO-d$_6$): 1.10 (3H, t), 1.79-1.97 (4H, m), 2.83 (1H, m), 3.01 (1H, m), 3.12 (1H, m), 3.29 (1H, m), 3.47 (2H, m), 4.27 (1H, m), 7.16 (2H, m), 7.85 (1H, d), 8.95 (1H, br s), 9.10 (1H, br s).

d) (S)-4-(Ethyl (1-(pyridin-3-yl)piperidin-3-yl)amino)-2-(trifluoromethyl)-benzonitrile A mixture of the compound of Example 139(c) (83 mg, 0.25 mmol), 3-bromopyridine (26 µl, 0.275 mmol), DIPEA (45 μl, 0.258 mmol) and dry toluene (2.5 ml) was stirred at RT for 15 min. Then Pd$_2$(dba)$_3$ (11 mg, 0.013 mmol), rac-BINAP (16 mg, 0.025 mmol), and sodium tert-butoxide (34 mg, 0.35 mmol) were added and stirring was continued at 80° C. After the reaction was completed the mixture was diluted with TBME and filtered. The filtrate was concentrated and the crude product was purified by flash chromatography. Yield 59 mg. $^1$H NMR (400 MHz, CDCl$_3$): 1.25 (3H, t), 1.77 (1H, dq), 1.89 (1H, m), 2.01 (1H, m), 2.08 (1H, m), 2.75 (1H, dt), 2.79 (1H, t), 3.48 (2H, m), 3.68 (2H, m), 3.98 (1H, m), 6.87 (1H, dd), 7.02 (1H, d), 7.18 (2H, m), 7.60 (1H, d), 8.13 (1H, dd), 8.31 (1H, d).

Example 140

(S)-4-(ethyl(1-(5-methoxypyridin-3-yl)piperidin-3-yl)amino)-2-(trifluoromethyl)benzonitrile The compound was prepared as in Example 139(d) from the compound of Example 139(c) and 3-bromo-5-methoxypyridine. Yield 59 mg. $^1$H NMR (400 MHz, CDCl$_3$): 1.25 (3H, t), 1.72-1.93 (2H, m), 2.00 (1H, m), 2.07 (1H, m), 2.75 (1H, dt), 2.79 (1H, t), 3.47 (2H, m), 3.67 (2H, m), 3.84 (3H, s), 3.97 (1H, m), 6.69 (1H, m), 6.87 (1H, dd), 7.02 (1H, d), 7.60 (1H, d), 7.85 (1H, d), 7.95 (1H, d).

Example 141

(S)-4-(Ethyl(1-(6-methoxypyridin-3-yl)piperidin-3-yl)amino)-2-(trifluoromethyl)benzonitrile The compound was prepared as in Example 139(d) from the compound of Example 139(c) and 5-bromo-2-methoxypyridine. Yield 21 mg. $^1$H NMR (400 MHz, CDCl$_3$): 1.22 (3H, t), 1.70 (1H, dq), 1.88 (1H, m), 2.02 (2H, m), 2.64 (1H, dt), 2.68 (1H, t), 3.45 (4H, m), 3.89 (3H, s), 4.01 (1H, m), 6.68 (1H, d), 6.87 (1H, dd), 7.01 (1H, d), 7.27 (1H, dd), 7.59 (1H, d), 7.80 (1H, d).

Example 142

(S)-5-(3-((4-cyano-3-(trifluoromethyl)phenyl)(ethyl)amino)piperidin-1-yl)-nicotinonitrile The compound was prepared as in Example 139(d) from the compound of Example 139(c) and 5-bromopyridine-3-carbonitrile. Yield 19 mg. $^1$H NMR (400 MHz, CDCl$_3$): 1.26 (3H, t), 1.84 (2H, m), 2.10 (2H, m), 2.81 (1H, dt), 2.86 (1H, t), 3.48 (2H, m), 3.72 (2H, m), 3.97 (1H, m), 6.87 (1H, dd), 7.01 (1H, d), 7.33 (1H, m), 7.62 (1H, d), 8.33 (1H, d), 8.48 (1H, d).

Example 143

(R)-4-(Ethyl(1-(pyridin-3-yl)pyrrolidin-3-yl)amino)-2-(trifluoromethyl)benzonitrile a) (R)-tert-Butyl (1-(pyridin-3-yl)pyrrolidin-3-yl)carbamate The compound was prepared as in Example 137(a) from (R)-tert-butyl pyrrolidin-3-ylcarbamate (0.466 g, 2.50 mmol) and 3-bromopyridine (0.241 ml, 2.50 mmol). Purification by flash chromatography gave 0.263 g of the title compound. $^1$H NMR (400 MHz, CDCl$_3$): 1.46 (9H, s), 1.97 (1H, m), 2.30 (1H, m), 3.18 (1H, dd), 3.35 (1H, m), 3.45 (1H, m), 3.58 (1H, dd), 4.38 (1H, br s), 4.71 (1H, br s), 6.81 (1H, dd), 7.12 (1H, dd), 7.98 (2H, m).

b) (R)-1-(Pyridin-3-yl)pyrrolidin-3-amine hydrochloride

The compound was prepared as in Example 137(b) from the compound of Example 143(a) (0.263 g, 0.999 mmol). The crude product was purified by trituration with ether. Yield 0.217. $^1$H NMR (400 MHz, DMSO-d$_6$): 2.21 (1H, m), 2.34 (1H, m), 3.46 (2H, m), 3.60 (1H, m), 3.67 (1H, m), 3.99 (1H, br s), 7.65 (1H, dd), 7.78 (1H, dd), 8.10 (1H, d), 8.13 (1H, d), 8.51 (3H, br s).

c) (R)-4-((1-(pyridin-3-yl)pyrrolidin-3-yl)amino)-2-(trifluoromethyl)benzonitrile The compound was prepared as in Example 137(c) from the compound of Example 143(b) (0.217 g, 1.087 mmol). Purification by flash chromatography gave 0.166 g of the title compound. $^1$H NMR (400 MHz, CDCl$_3$): 2.13 (1H, m), 2.43 (1H, m), 3.31 (dd), 3.44 (1H, m), 3.54 (1H, m), 3.71 (1H, dd), 4.31 (1H, m), 4.80 (1H, d), 6.75 (1H, dd), 6.84 (1H, ddd), 6.91 (1H, d), 7.14 (1H, dd), 7.61 (1H, d), 8.01 (2H, d).

d) (R)-4-(Ethyl(1-(pyridin-3-yl)pyrrolidin-3-yl)amino)-2-(trifluoromethyl)-benzonitrile The compound was prepared as in Example 137(b) from the compound of Example 143(c) (0.166 g, 0.50 mmol). Purification by flash chromatography gave 0.123 g of the title compound. $^1$H NMR (400 MHz, CDCl$_3$): 1.26 (3H, t), 2.27 (1H, m), 2.41 (1H, m), 3.39 (2H, m), 3.48 (2H, m), 3.62 (2H, m), 4.61 (1H, m), 6.89 (2H, m), 7.05 (1H, d), 7.16 (1H, dd), 7.62 (1H, d), 8.04 (2H, m).

Example 144

(S)-4-(ethyl(1-(5-fluoropyridin-3-yl)piperidin-3-yl)amino)-2-(trifluoromethyl)benzonitrile The compound was prepared as in Example 139(d) from the compound of Example 139(c) and 3-bromo-5-fluoropyridine. Yield 17.8 mg. $^1$H NMR (400 MHz, CDCl$_3$): 1.26 (3H, t), 1.83 (2H, m), 2.02 (1H, m), 2.09 (1H, m), 2.78 (1H, dt), 2.83 (1H, t), 3.47 (2H, m), 3.70 (2H, m), 3.96 (1H, m), 6.87 (2H, m), 7.01 (1H, d), 7.62 (1H, d), 7.98 (1H, br s), 8.12 (1H, br s).

Example 145

(S)-4-(Ethyl(1-(5-(trifluoromethyl)pyridin-3-yl)piperidin-3-yl)amino)-2-(trifluoromethyl)-benzonitrile The compound was prepared as in Example 139(d) from the compound of Example 139(c) and 3-bromo-5-(trifluoromethyl)pyridine. Yield 48.6 mg. $^1$H NMR (400 MHz, CDCl$_3$): 1.27 (3H, t), 1.85 (2H, m), 2.03-2.13 (2H, m), 2.82 (1H, dt), 2.86 (1H, t), 3.49 (2H, m), 3.71 (1H, m), 3.77 (1H, m), 3.98 (1H, m), 6.88 (1H, dd), 7.02 (1H, d), 7.31 (1H, m), 7.61 (1H, d), 8.36 (1H, m), 8.46 (1H, d).

Example 146

(R)-4-(Ethyl(1-(5-(2,2,2-trifluoroethoxy)pyridin-3-yl)piperidin-3-yl)amino)-2-(trifluoromethyl)benzonitrile a) (R)-tert-butyl 3-((4-cyano-3-(trifluoromethyl)phenyl)amino)piperidine-1-carboxylate The compound was prepared as in Example 138(a) from (R)-tert-butyl 3-aminopiperidine-1-carboxylate (1.602 g, 8.00 mmol). Purification by flash chromatography gave 1.853 g of the title compound. $^1$H NMR (400 MHz, CDCl$_3$): 1.44 (9H, s), 1.62 (2H, m), 1.75 (1H, m), 1.98 (1H, m), 3.13 (1H, dd), 3.26 (1H, m), 3.50 (1H, m), 3.58 (1H, m), 3.84 (1H, d), 4.52 (1H, br s), 6.73 (1H, dd), 6.86 (1H, br s), 7.57 (1H, d).

b) (R)-tert-Butyl 3-((4-cyano-3-(trifluoromethyl)phenyl)(ethyl)amino)piperidine-1-carboxylate The compound was prepared as in Example 132(d) from the compound of Example 146(a) (1.853 g, 5.02 mmol). The crude product (1.97 g) was used as such in the next step. $^1$H NMR (400 MHz, CDCl$_3$): 1.22 (3H, t), 1.48 (9H, s), 1.64 (1H, m), 1.75 (1H, m), 1.85 (1H, m), 2.04 (1H, m), 2.68 (2H, m), 3.42 (2H, m), 3.65 (1H, m), 4.15 (2H, br s), 6.88 (1H, dd), 7.01 (1H, d), 7.60 (1H, d).

c) (R)-4-(Ethyl(piperidin-3-yl)amino)-2-(trifluoromethyl)benzonitrile hydrochloride The compound was prepared as in Example 137(b) starting from the compound of Example 146(b) (1.97 g) and using 4.3 molar equivalent of thionyl chloride. Crude product was purified by trituration with ether. Yield 1.23 g. $^1$H NMR (400 MHz, DMSO-d$_6$): 1.11 (3H, t), 1.90 (4H, m), 2.84 (1H, m), 3.01 (1H, m), 3.09 (1H, m), 3.27 (2H, m), 3.48 (2H, m), 4.34 (1H, m), 7.18 (2H, m), 7.84 (1H, d), 9.27 (2H, br s).

d) (R)-4-(Ethyl(1-(5-(2,2,2-trifluoroethoxy)pyridin-3-yl)piperidin-3-yl)amino)-2-(trifluoromethyl)-benzonitrile The compound was prepared as in Example 139(d) from the compound of Example 146(c) and 3-bromo-5-(2,2,2-trifluoroethoxy)pyridine (WO 2012/152983). Yield 24 mg. $^1$H NMR (400 MHz, CDCl$_3$): 1.25 (3H, t), 1.79 (1H, m), 1.87 (1H, m), 2.01 (1H, m), 2.09 (1H, m), 2.77 (1H, dt), 2.81 (1H, t), 3.47 (2H, m), 3.67 (1H, m), 3.72 (1H, m), 3.96 (1H, m), 4.39 (2H, q), 6.76 (1H, t), 6.87 (1H, dd), 7.01 (1H, d), 7.61 (1H, d), 7.84 (1H, d), 8.05 (1H, d).

Example 147

(R)-4-(Ethyl(1-(5-methylpyridin-3-yl)piperidin-3-yl)amino)-2-(trifluoromethyl)benzonitrile The compound was prepared as in Example 139(d) from the compound of Example 146(c) and 3-bromo-5-methylpyridine. Yield 48 mg. $^1$H NMR (400 MHz, CDCl$_3$): 1.25 (3H, t), 1.76 (1H, m), 1.87 (1H, m), 2.00 (1H, m), 2.07 (1H, m), 2.29 (3H, s), 2.72 (1H, dt), 2.76 (1H, t), 3.47 (2H, m), 3.66 (2H, m), 3.97 (1H, m), 6.87 (1H, dd), 7.01 (2H, m), 7.60 (1H, d), 7.98 (1H, d), 8.12 (1H, d).

Example 148

(R)-4-(Ethyl(1-(4-methylpyridin-3-yl)piperidin-3-yl)amino)-2-(trifluoromethyl)benzonitrile The compound was prepared as in Example 139(d) from the compound of Example 146(c) and 3-bromo-4-methylpyridine. Yield 57 mg. $^1$H NMR (400 MHz, CDCl$_3$): 1.23 (3H, t), 1.75 (1H, dt), 1.88 (1H, m), 2.00 (1H, m), 2.08 (1H, m), 2.35 (3H, s), 2.75 (1H, t), 2.79 (1H, dt), 3.17 (2H, m), 3.47 (2H, m), 4.03 (1H, m), 6.86 (1H, dd), 7.04 (1H, d), 7.09 (1H, d), 7.59 (1H, d), 8.21 (1H, d), 8.27 (1H, s).

Example 149

(R)-4-(Ethyl(1-(pyrazin-2-yl)piperidin-3-yl)amino)-2-(trifluoromethyl)benzonitrile A mixture of the compound of Example 146(c) (83 mg, 0.25 mmol), 2-chloropyrazine (25 µl, 0.275 mmol) and DIPEA (0.10 ml, 0.575 mmol) in dry DMSO (1.5 ml) was first heated for 1 h at 130° C. and then 2 h at 190° C. using a microwave reactor. The mixture was diluted with water and extracted with TBME. The combined organic extracts were washed with water and brine, dried, filtered and evaporated. Crude product was purified by flash chromatography. Yield 26 mg. $^1$H NMR (400 MHz, CDCl$_3$): 1.26 (3H, t), 1.74 (1H, m), 1.94 (2H, m), 2.11 (1H, m), 2.83 (1H, t), 3.00 (1H, dt), 3.49 (2H, m), 3.82 (1H, m), 4.20 (1H, m), 4.60 (1H, m), 6.93 (1H, dd), 7.21 (1H, d), 7.60 (1H, d), 7.88 (1H, d), 8.09 (1H, m), 8.19 (1H, s).

Example 150

4-((3-(1H-imidazol-4-yl)cyclopent-3-en-1-yl)(ethyl)amino)-2-(trifluoromethyl)benzonitrile a) 4-((3-Oxocyclopent-1-en-1-yl)amino)-2-(trifluoromethyl)benzonitrile The compound was prepared as in Example 133(a) from 1,3-cyclopentanedione (7.36 g, 75 mmol) and 4-amino-2-(trifluoromethyl)benzonitrile (13.96 g, 75 mmol). Yield 19.32 g. $^1$H NMR (400 MHz, MeOH-d$_4$): 2.47 (2H, m), 2.90 (2H, m), 5.76 (1H, t), 7.62 (1H, br s), 7.63 (1H, dd), 7.97 (1H, m).

b) 4-(Ethyl(3-oxocyclopent-1-en-1-yl)amino)-2-(trifluoromethyl)benzonitrile

The compound was prepared as in Example 133(b) from the compound of Example 150(a) (3.33 g, 12.5 mmol). Purification by flash chromatography gave 2.51 g of the title compound. $^1$H NMR (400 MHz, MeOH-d$_4$): 1.22 (3H, t), 2.43 (2H, m), 2.69 (2H, m), 3.86 (2H, q), 5.14 (1H, s), 7.81 (1H, dd), 7.96 (1H, d), 8.12 (1H, d).

c) 4-(Ethyl(3-hydroxycyclopentyl)amino)-2-(trifluoromethyl)benzonitrile

Sodium borohydride (0.777 g, 20.53 mmol) was added stepwise to a mixture of the compound of Example 150(b) (3.02 g, 10.26 mmol) and ethanol (55 ml). After stirring (2 h) at 40° C. a second batch of sodium borohydride (0.777 g, 20.53 mmol) was added and stirring continued (2 h). Then a third batch of sodium borohydride (0.777 g, 20.53 mmol) was added and stirring continued overnight at RT and at 40°

C. for 8 h. The reaction was quenched with the addition of water and extracted with ethyl acetate. The combined organic extracts were washed with brine, dried, filtered and evaporated. Purification by flash chromatography gave 1.61 g of the title compound as a mixture of diastereomers. LC-MS: m/z=299.23 (M+1)$^+$.

d) 4-(Ethyl(3-oxocyclopentyl)amino)-2-(trifluoromethyl)benzonitrile

The compound was prepared as in Example 133(d) from the compound of Example 150(c) (1.79 g, 6.00 ml). Purification by flash chromatography gave 0.826 g of the title compound. $^1$H NMR (400 MHz, CDCl$_3$): 1.25 (3H, t), 2.08 (1H, m), 2.28-2.44 (3H, m), 2.53 (1H, m), 2.65 (1H, dd), 3.44 (2H, m), 4.48 (1H, m), 6.88 (1H, dd), 7.02 (1H, d), 7.62 (1H, d).

e) 4-(Ethyl(3-hydroxy-3-(1-trityl-1H-imidazol-4-yl) cyclopentyl)amino)-2-(trifluoromethyl)benzonitrile The compound was prepared as in Example 133(e) from the compound of Example 150(d) (0.826 g, 2.79 mmol. Purification by flash chromatography gave 0.742 g of the title compound as a mixture of diastereomers. LC-MS: m/z=607.42 (M+1)$^+$.

f) 4-((3-(1H-imidazol-4-yl)cyclopent-3-en-1-yl) (ethyl)amino)-2-(trifluoromethyl)benzonitrile The compound was prepared as in Example 133(f) from the compound of Example 150(d) (0.742 g, 1.223 mmol). Purification by flash chromatography gave 87 mg of the title compound. $^1$H NMR (400 MHz, CDCl$_3$): 1.22 (3H, t), 2.65 (1H, m), 2.77 (1H, m), 2.94 (1H, m), 3.06 (1H, m), 3.47 (2H, q), 4.70 (1H, m), 6.15 (1H, br s), 6.80 (1H, dd), 7.55 (1H, d), 7.66 (1H, s). LC-MS: m/z=347.03 (M+1)$^+$.

Example 151

(R)-4-(Ethyl(1-(4-fluoropyridin-3-yl)piperidin-3-yl) amino)-2-(trifluoromethyl)benzonitrile The compound was prepared as in Example 139(d) from the compound of Example 146(c) and 3-bromo-4-fluoropyridine. Yield 33 mg. $^1$H NMR (400 MHz, CDCl$_3$): 1.23 (3H, t), 1.79 (1H, m), 1.93 (1H, m), 2.03 (1H, m), 2.11 (1H, m), 2.72 (1H, t), 2.83 (1H, dt), 3.39-3.55 (4H, m), 4.04 (1H, m), 6.90 (1H, dd), 7.00 (1H, dd), 7.06 (1H, d), 7.61 (1H, d), 8.24 (1H, dd), 8.27 (1H, d).

Example 152

(R)-4-(Ethyl(1-(pyrimidin-5-yl)piperidin-3-yl) amino)-2-(trifluoromethyl)-benzonitrile The compound was prepared as in Example 139(d) from the compound of Example 146(c) and 5-bromopyrimidine. Yield 42 mg. $^1$H NMR (400 MHz, CDCl$_3$): 1.26 (3H, t), 1.80 (1H, m), 1.89 (1H, m), 2.08 (2H, m), 2.79 (1H, dt), 2.83 (1H, t), 3.48 (2H, q), 3.71 (2H, m), 3.99 (1H, m), 6.87 (1H, dd), 7.02 (1H, dd), 7.62 (1H, d), 8.38 (2H, s), 8.73 (1H, s).

Example 153

(S)-4-(Ethyl(1-(5-methylpyridin-3-yl)pyrrolidin-3-yl)amino)-2-(trifluoromethyl)benzonitrile The compound was prepared as in Example 138(d) from the compound of Example 138(c) and 3-bromo-5-methylpyridine. Yield 47 mg. $^1$H NMR (400 MHz, CDCl$_3$): 1.26 (3H, t), 2.26 (1H, m), 2.30 (3H, s), 2.40 (1H, m), 3.37 (2H, m), 3.47 (2H, m), 3.60 (2H, m), 4.60 (1H, m), 6.68 (1H, m), 6.90 (1H, dd), 7.05 (1H, d), 7.61 (1H, d), 7.85 (1H, d), 7.88 (1H, s).

Example 154

(S)-4-(Ethyl(1-(4-methylpyridin-3-yl)pyrrolidin-3-yl)amino)-2-(trifluoromethyl)benzonitrile The compound was prepared as in Example 138(d) from the compound of Example 138(c) and 3-bromo-4-methylpyridine. Yield 39 mg. $^1$H NMR (400 MHz, CDCl$_3$): 1.28 (3H, t), 2.16 (1H, m), 2.33 (3H, s), 2.40 (1H, m), 3.29 (1H, m), 3.35-3.44 (2H, m), 3.49 (1H, dt), 3.59 (2H, m), 4.55 (1H, m), 6.93 (1H, dd), 7.05 (1H, dd), 7.08 (1H, d), 7.61 (1H, d), 8.15 (1H, d), 8.20 (1H, s).

Example 155

(R)-4-(Methyl(1-(5-methylpyridin-3-yl)piperidin-3-yl)amino)-2-(trifluoromethyl)benzonitrile a) (R)-tert-Butyl 3-((4-cyano-3-(trifluoromethyl) phenyl)(methyl)amino)-piperidine-1-carboxylate The compound was prepared as in Example 132(d) from the compound of Example 146(a) (0.223 g, 0.604 mmol) and iodomethane (80 µl, 1.285 mmol). The crude product (0.223 g) was used as such in the next step. $^1$H NMR (400 MHz, CDCl$_3$): 1.48 (9H, s), 1.63 (1H, m), 1.75 (1H, m), 1.83 (1H, m), 1.97 (1H, m), 2.66 (1H, m), 2.75 (1H, m), 2.85 (3H, s), 3.66 (1H, m), 4.13 (2H, br s), 6.90 (1H, dd), 7.03 (1H, d), 7.61 (1H, d).

b) (R)-4-(Methyl(piperidin-3-yl)amino)-2-(trifluoromethyl)benzonitrile hydrochloride The compound was prepared as in Example 137(b) from the compound of Example 155(a) (0.223 g) and using 3.93 molar equivalent of thionyl chloride. Crude product was purified by trituration with ether. Yield 0.109 g. $^1$H NMR (400 MHz, DMSO-d$_6$): 1.87 (4H, m), 2.81 (1H, m), 2.92 (3H, s), 3.05 (1H, t), 3.12 (1H, m), 3.28 (1H, m), 4.32 (1H, m), 7.19 (2H, m), 7.86 (1H, d), 9.19 (2H, br s).

c) (R)-4-(Methyl(1-(5-methylpyridin-3-yl)piperidin-3-yl)amino)-2-(trifluoromethyl)-benzonitrile The compound was prepared as in Example 139(d) from the compound of Example 155(b) (54 mg, 0.17 mmol) and 3-bromo-5-methylpyridine (22 µl, 0.187 mmol). Yield 43 mg. $^1$H NMR (400 MHz, CDCl$_3$): 1.78 (1H, m), 1.86 (1H, m), 1.99 (1H, m), 2.29 (3H, s), 2.73 (1H, dt), 2.84 (1H, t), 3.00 (3H, s), 3.66 (2H, m), 3.99 (1H, m), 6.90 (1H, dd), 7.00 (1H, br s), 7.03 (1H, d), 7.61 (1H, d), 7.97 (1H, s), 8.12 (1H, d).

Example 156

4-(Ethyl(3-(pyridin-3-yl)cyclopent-2-en-1-yl) amino)-2-(trifluoromethyl)-benzonitrile a) 3-(Pyridin-3-yl)cyclopent-2-enone Isopropylmagnesium bromide (13.3 ml, 13.3 mmol, 1 M in THF) was added to a solution of 3-iodopyridine (2.73 g, 13.3 mmol) in dry DCM (30 ml) under N$_2$. The mixture was stirred at RT for 4 h. A solution of 3-methoxycyclopent-2-enone (1.121 g, 10.0 mmol) in dry THF (4.5 ml) was added stepwise and the mixture was stirred 48 h at RT under N$_2$. The reaction was quenched with addition of water and saturated NH$_4$Cl. The mixture was extracted with ethyl acetate. Combined organic extracts were washed with brine, dried, filtered and evaporated. Purification by flash chromatography gave 0.369 g of the title compound. $^1$H NMR (400 MHz, CDCl$_3$): 2.63 (2H, m), 3.08 (2H, m), 6.65 (1H, t), 7.41 (1H, dd), 7.93 (1H, dt), 8.70 (1H, dd), 8.92 (1H, d).

b) 3-(Pyridin-3-yl)cyclopent-2-enol

Cerium chloride heptahydrate (1.143 g, 3.07 mmol) was added to a solution of the compound of Example 156(a) (0.444 g, 2.79 mmol) in methanol (12 ml). The mixture was cooled to 0-5° C. Sodium borohydride (0.127 g, 3.35 mmol) was added stepwise and the mixture was stirred. After the reaction was completed the reaction was quenched with the addition of water. Methanol was evaporated and the residue was diluted with water and saturated NH$_4$Cl and extracted with ethyl acetate. Combined organic extracts were washed with brine, dried, filtered and evaporated to afford 0.523 g of the title compound. $^1$H NMR (400 MHz, CDCl$_3$): 1.58 (1H, m), 1.91 (1H, m), 2.50 (1H, m), 2.68 (1H, m), 2.93 (1H, m), 5.05 (1H, m), 6.31 (1H, q), 7.27 (1H, m), 7.75 (1H, m), 8.51 (1H, dd), 8.74 (1H, m).

c) 3-(3-Azidocyclopent-1-en-1-yl)pyridine

A mixture of the compound of Example 156(b) (0.523 g, 2.79 mmol) in toluene-THF (1:1, 14 ml) was cooled to 0-5° C. and treated with diphenylphosphoryl azide (1.05 ml, 4.87 mmol) and DBU (0.80 ml, 5.31 mmol). The mixture was stirred overnight in a melting ice bath, diluted with water and toluene and filtered. The filtrate was acidified with 2 M HCl. The aqueous phase was made alkaline with 2M NaOH and extracted with ethyl acetate. The organic phase was washed with water and brine, dried, filtered and evaporated to afford 0.353 g of the title compound. $^1$H NMR (400 MHz, CDCl$_3$): 2.12 (1H, m), 2.49 (1H, m), 2.75 (1H, m), 2.95 (1H, m), 4.59 (1H, m), 6.26 (1H, d), 7.29 (1H, dd), 7.76 (1H, d), 8.54 (1H, d), 8.74 (1H, d).

d) 3-(Pyridin-3-yl)cyclopent-2-enamine

Polymer supported triphenylphosphine (0.358 g, 1.074 mmol; 3 mmol/g) was weighed in a flask. Methanol (5 ml) and the compound of Example 156(c) (0.10 g, 0.537 mol) dissolved in methanol (1 ml) were added. The mixture was stirred at 65° C. until the reaction completed. The cooled mixture was filtered and the solid material was washed with methanol. The filtrate was concentrated to afford 78 mg of the title compound. $^1$H NMR (400 MHz, CDCl$_3$): 1.65 (1H, m), 2.50 (1H, m), 2.66 (1H, m), 2.84 (1H, m), 4.17 (1H, m), 6.22 (1H, m), 7.26 (1H, dd), 7.72 (1H, dt), 8.47 (1H, dd), 8.69 (1H, d).

e) 4-((3-(Pyridin-3-yl)cyclopent-2-en-1-yl)amino)-2-(trifluoromethyl)-benzonitrile The compound was prepared as in Example 137(c) from the compound of Example 156(d) (0.25 g, 1.482 g) and 4-fluoro-2-(trifluoromethyl)benzonitrile (0.28 g, 1.482 mmol). Yield 0.288 g. $^1$H NMR (400 MHz, CDCl$_3$): 1.90 (1H, m), 2.63 (1H, m), 2.82 (1H, m), 2.94 (1H, m), 4.56 (1H, d), 4.80 (1H, m), 6.26 (1H, m), 6.75 (1H, dd), 6.90 (1H, d), 7.30 (1H, dd), 7.59 (1H, d), 7.75 (1H, dt), 8.55 (1H, dd), 8.74 (1H, d).

f) 4-(Ethyl(3-(pyridin-3-yl)cyclopent-2-en-1-yl) amino)-2-(trifluoromethyl)-benzonitrile The compound was prepared as in Example 137(d) from the compound of Example 156(d) (0.278 g, 0.844 g) and iodoethane (0.15 ml, 1.874 mmol). Purification by flash chromatography gave 0.183 g of the title compound. $^1$H NMR (400 MHz, CDCl$_3$): 1.22 (3H, t), 1.88 (1H, m), 2.65 (1H, m), 2.83 (1H, m), 2.97 (1H, m), 3.41 (2H, m), 5.15 (1H, m), 6.24 (1H, m), 6.87 (1H, dd), 7.04 (1H, d), 7.32 (1H, dd), 7.60 (1H, d), 7.77 (1H, dt), 8.56 (1H, dd), 8.77 (1H, d).

Example 157

Cis-4-(Ethyl(3-(pyridin-3-yl)cyclopentyl)amino)-2-(trifluoromethyl)benzonitrile

The compound was prepared as in Example 134 from the compound of Example 156 (61 mg, 0.171 mmol). The reduction was conducted at 50° C. using 1 bar hydrogen pressure with a flow rate of 1 ml/min and one reduction cycle. Purification by preparative HPLC gave 29 mg of the title compound (95% cis-diastereomer). $^1$H NMR (400 MHz, CDCl$_3$): 1.26 (3H, t), 1.77-1.94 (3H, m), 2.26 (2H, m), 2.43 (1H, m), 3.18 (1H, m), 3.45 (2H, m), 4.36 (1H, m), 6.85 (1H, dd), 7.01 (1H, d), 7.26 (1H, m), 7.58 (2H, m), 8.49 (1H, dd), 8.55 (1H, d).

Example 158

(S)-2-Chloro-4-(ethyl(1-(pyridin-3-yl)pyrrolidin-3-yl)amino)benzonitrile a) (S)-tert-Butyl (1-(pyridin-3-yl)pyrrolidin-3-yl) carbamate The compound was prepared as in Example 137(a) from (S)-tert-butyl pyrrolidin-3-ylcarbamate (0.373 g, 2.00 mmol) and 3-bromopyridine (0.212 ml, 2.20 mmol). Purification by flash chromatography gave 0.255 g of the title compound. $^1$H NMR (400 MHz, CDCl$_3$): 1.46 (9H, s), 1.97 (1H, m), 2.31 (1H, m), 3.18 (1H, dd), 3.35 (1H, m), 3.45 (1H, m), 3.58 (1H, dd), 4.38 (1H, br s), 4.71 (1H, br s), 6.81 (1H, dd), 7.12 (1H, dd), 7.98 (2H, m).

b) (S)-1-(Pyridin-3-yl)pyrrolidin-3-amine hydrochloride

The compound was prepared as in Example 137(b) from the compound of Example 158(a) (0.255 g, 0.968 mmol). Crude product was purified by trituration with ether. Yield 0.181 g. $^1$H NMR (400 MHz, DMSO-d$_6$): 2.18 (1H, m), 2.35 (1H, m), 3.38 (1H, m), 3.46 (1H, dd), 3.58 (1H, m), 3.66 (1H, dd), 4.00 (1H, br s), 7.64 (1H, dd), 7.77 (1H, dd), 8.10 (1H d), 8.14 (1H, d), 8.43 (3H, br s).

c) (S)-2-Chloro-4-((1-(pyridin-3-yl)pyrrolidin-3-yl) amino)benzonitrile

The compound was prepared as in Example 137(c) from the compound of Example 158(b) (0.181 g, 0.906 mmol) and 2-chloro-4-fluorobenzonitrile (0.155 g, 0.997 mmol). Purification by flash chromatography gave 54 mg of the title compound. ¹H NMR (400 MHz, CDCl₃): 2.13 (1H, m), 2.36 (1H, m), 3.27 (1H, dd), 3.39 (1H, dt), 3.47 (1H, m), 3.66 (1H, dd), 4.24 (1H, m), 5.35 (1H, d), 6.54 (1H, dd), 6.69 (1H, d), 6.76 (1H, dd), 7.08 (1H, dd), 7.40 (1H, d), 7.93 (1H, d).

d) (S)-2-Chloro-4-(ethyl(1-(pyridin-3-yl)pyrrolidin-3-yl)amino)benzonitrile

The compound was prepared as in Example 137(d) from the compound of Example 158(c) (54 mg, 0.181 mmol) and iodoethane (32 µl, 0.401 mmol). Purification by preparative HPLC gave 33 mg of the title compound. ¹H NMR (400 MHz, CDCl₃): 1.24 (3H, t), 2.25 (1H, m), 2.39 (1H, m), 3.33 (1H, dd), 3.41 (3H, m), 3.59 (2H, m), 4.56 (1H, m), 6.68 (1H, dd), 6.81 (1H, d), 6.86 (1H, dd), 7.15 (1H, dd), 7.45 (1H, d), 8.02 (2H, m).

Example 159

(R)-4-((1-(2-Chloropyrimidin-4-yl)piperidin-3-yl)(ethyl)amino)-2-(trifluoromethyl)benzonitrile and (R)-4-((1-(4-chloropyrimidin-2-yl)piperidin-3-yl)(ethyl)-amino)-2-(trifluoromethyl)benzonitrile A mixture of the compound of Example 146(c) ((0.167 g, 0.50 mmol), 2,4-dichloropyrimidine (0.10 g, 0.673 mmol) and DIPEA (0.30 ml, 1.725 mmol) in methanol (2.5 ml) was stirred at RT for 3.5 h. Methanol was evaporated and the residue was diluted with water and extracted with ethyl acetate. Organic phase was washed with water and brine, dried, filtered and evaporated. Crude product was purified by flash chromatography to afford 158 mg of (R)-4-((1-(2-chloropyrimidin-4-yl)piperidin-3-yl)(ethyl)amino)-2-(trifluoromethyl)-benzonitrile, ¹H NMR (400 MHz, CDCl₃): 1.26 (3H, t), 1.67 (1H, m), 1.89-2.03 (2H, m), 2.15 (1H, m), 2.85 (1H, m), 2.98, 1H, m), 3.48 (2H, m), 3.72 (1H, m), 4.23 (1H, br s), 4.65 (1H, br s), 6.44 (1H, dd), 7.01 (1H, d), 7.12 (1H, dd), 7.67 (1H, d), 8.09 (1H, d), and 70 mg of (R)-4-((1-(4-chloropyrimidin-2-yl)piperidin-3-yl)(ethyl)amino)-2-(trifluoromethyl)benzonitrile, ¹H NMR (400 MHz, CDCl₃): 1.27 (3H, t), 1.66 (1H, m), 1.93 (2H, m), 2.11 (1H, m), 2.85 (2H, m), 3.48 (2H, m), 3.68 (1H, m), 4.83 (2H, m), 6.56 (1H, d), 7.01 (1H, d), 7.11 (1H, br s), 7.62 (1H, d), 8.19 (1H, d).

Example 160

(R)-4-(Ethyl(1-(3-fluoropyridin-4-yl)piperidin-3-yl)amino)-2-(trifluoromethyl)benzonitrile The compound was prepared as in Example 139(d) from the compound of Example 146(c) and 4-bromo-3-fluoropyridine. Yield 51 mg. ¹H NMR (400 MHz, CDCl₃): 1.24 (3H, t), 1.86 (2H, m), 2.02 (1H, m), 2.12 (1H, m), 2.79 (2H, m), 3.46 (2H, m), 3.67 (1H, m), 3.77 (1H, m), 3.99 (1H, m), 6.75 (1H, dd), 6.89 (1H, dd), 7.05 (1H, d), 7.61 (1H, d), 8.18 (1H, d), 8.25 (1H, d).

Example 161

(S)-4-(Ethyl(1-(5-methoxypyridin-3-yl)pyrrolidin-3-yl)amino)-2-(trifluoromethyl)benzonitrile The compound was prepared as in Example 138(d) from the compound of Example 138(c) and 3-bromo-4-methylpyridine. Purification by preparative HPLC gave 35 mg of the title compound. ¹H NMR (400 MHz, CDCl₃): 1.26 (3H, t), 2.26 (1H, m), 2.40 (1H, m), 3.38 (2H, m), 3.47 (2H, m), 3.60 (2H, m), 4.61 (1H, m), 6.38 (1H, t), 6.90 (1H, dd), 7.05 (1H, d), 7.62 (1H, d), 7.69 (1H, d), 7.77 (1H, d).

Example 162

(R)-4-(ethyl(1-(pyrimidin-4-yl)piperidin-3-yl)amino)-2-(trifluoromethyl)-benzonitrile (R)-4-((1-(2-Chloropyrimidin-4-yl)piperidin-3-yl)(ethyl)amino)-2-(trifluoromethyl)-benzonitrile (Example 159) (77 mg, 0.188 mmol) was dissolved in MeOH-ethyl acetate (2:1, 4 ml) and hydrogenated in a H-Cube continuous-flow hydrogenation apparatus (ThalesNano Inc.) using 10% Pd/C catalyst cartridge. The reduction was conducted at 60° C. using 1 bar hydrogen pressure with a flow rate of 1 ml/min. The solvents were evaporated and the crude product was purified by preparative HPLC to afford 42 mg of the title compound. ¹H NMR (400 MHz, CDCl₃): 1.26 (3H, t), 1.69 (1H, m), 1.96 (2H, m), 2.13 (1H, m), 2.83 (1H, t), 2.96 (1H, m), 3.49 (2H, m), 3.72 (1H, m), 4.23 (1H, d), 4.75 (1H, d), 6.55 (1H, d), 6.94 (1H, dd), 7.16 (1H, d), 7.61 (1H, d), 8.24 (1H, dd), 8.63 (1H, s).

Example 163

(S)-4-(Ethyl(1-(3-fluoropyridin-4-yl)pyrrolidin-3-yl)amino)-2-(trifluoromethyl)benzonitrile The compound was prepared as in Example 138(d) from the compound of Example 138(c) and 4-bromo-3-fluoropyridine. Purification by preparative HPLC afforded 29 mg of the title compound. ¹H NMR (400 MHz, CDCl₃): 1.27 (3H, t), 2.23 (1H, m), 2.36 (1H, m), 3.48 (2H, m), 3.57 (2H, m), 3.82 (2H, m), 4.55 (1H, m), 6.48 (1H, dd), 6.90 (1H, dd), 7.05 (1H, d), 7.62 (1H, d), 8.09 (1H, d), 8.18 (1H, d).

Example 164

(S)-4-(Ethyl(1-(4-methoxypyridin-3-yl)pyrrolidin-3-yl)amino)-2-(trifluoromethyl)-benzonitrile The compound was prepared as in Example 138(d) from the compound of Example 138(c) and 4-bromo-3-fluoropyridine. Yield 35 mg. ¹H NMR (400 MHz, CDCl₃): 1.28 (3H, t), 2.08 (1H, m), 2.39 (1H, m), 3.33 (2H, dd), 3.55 (2H, m), 3.61 (1H, m), 3.70 (1H, dd), 3.89 (3H, s), 4.51 (1H, m), 6.77 (1H, d), 6.92 (1H, dd), 7.10 (1H, d), 7.60 (1H, d), 8.00 (1H, s), 8.15 (1H, d).

Example 165

(R)-4-(Ethyl(1-(4-methoxypyridin-3-yl)piperidin-3-yl)amino)-2-(trifluoromethyl)-benzonitrile The compound was prepared as in Example 139(d) from the compound of Example 146(c) and 3-bromo-4-methoxypyridine. Yield 32 mg. ¹H NMR (400 MHz, CDCl₃): 1.22 (3H, t), 1.76 (2H, dt), 1.93 (1H, m), 2.00 (1H, m), 2.08 (1H, m), 2.50 (1H, t), 2.80 (1H, dt), 3.45 (3H, m), 3.59 (1H, m), 3.91 (3H, s), 4.06 (1H, m), 6.78 (1H, d), 6.94 (1H, dd), 7.08 (1H, d), 7.60 (1H, d), 8.13 (1H, s), 8.23 (1H, d).

Example 166

(R)-4-(Ethyl(1-(5-methoxy-4-methylpyridin-3-yl)piperidin-3-yl)amino)-2-(trifluoromethyl)-benzonitrile The compound was prepared as in Example 139(d) from the compound of Example 146(c) and 3-bromo-5-methoxy-4-methylpyridine (prepared as in US 2006/135447). Yield 71 mg. $^1$H NMR (400 MHz, CDCl$_3$): 1.22 (3H, t), 1.74 (1H, m), 1.89 (1H, m), 1.99 (1H, m), 2.07 (1H, m), 2.20 (3H, s), 2.75 (2H, q), 3.16 (2H, m), 3.46 (2H, m), 3.91 (3H, s), 4.03 (1H, m), 6.86 (1H, dd), 7.04 (1H, d), 7.58 (1H, d), 8.01 (2H, d).

Example 167

(R)-4-((1-(4-Ethoxypyridin-3-yl)piperidin-3-yl)(ethyl)amino)-2-(trifluoromethyl)benzonitrile a) 3-Bromo-4-ethoxypyridine 1-oxide A mixture of 3-bromo-4-nitropyridine 1-oxide (0.50 g, 2.283 mmol) in EtOH (15 ml) was treated with sodium ethoxide (1.28 ml, 3.43 mmol, 21 w-% solution in EtOH). The mixture was stirred at RT until the reaction was complete. The mixture was concentrated and diluted with brine and extracted with DCM. Combined organic extracts were dried, filtered and evaporated to afford 0.408 g of the title compound. $^1$H NMR (400 MHz, CDCl$_3$): 1.51 (3H, t), 4.16 (2H, q), 6.74 (1H, d), 8.10 (1H, dd), 8.36 (1H, d). LC-MS: m/z=218.20 (M+1)$^+$.

b) 3-Bromo-4-ethoxypyridine

Phosphorus trichloride (0.30 ml, 3.44 mmol) was added dropwise to a mixture of the compound of Example 167(a) (0.408 g, 1.871 mmol) in dry chloroform (5 ml). The mixture was stirred at 60° C. After the reaction was complete ice was added and the mixture was neutralized with Na$_2$CO$_3$ solution. The mixture was extracted with DCM. Combined organic extracts were dried, filtered and evaporated to afford 0.317 g of the title compound. $^1$H NMR (400 MHz, CDCl$_3$): 1.51 (3H, t), 4.18 (2H, q), 6.79 (1H, d), 8.37 (1H, d), 8.58 (1H, s). LC-MS: m/z=201.55 (M+1)$^+$.

c) (R)-4-((1-(4-Ethoxypyridin-3-yl)piperidin-3-yl)(ethyl)amino)-2-(trifluoromethyl)-benzonitrile The compound was prepared as in Example 139(d) from the compound of Example 167(b) and (R)-4-(ethyl(piperidin-3-yl)amino)-2-(trifluoromethyl)benzonitrile hydrochloride. Purification by preparative HPLC afforded 42 mg of the title compound. $^1$H NMR (400 MHz, CDCl$_3$): 1.22 (3H, t), 1.45 (3H, t), 1.75 (1H, dq), 1.94 (2H, m), 2.05 (1H, m), 2.59 (1H, t), 2.77 (1H, dt), 3.44 (3H, m), 3.59 (1H, m), 4.11 (1H, m), 4.14 (2H, q), 6.75 (1H, dd), 6.93 (1H, dd), 7.05 (1H, d), 7.58 (1H, d), 8.13 (1H, s), 8.20 (1H, d).

Example 168

(R)-4-((1-(3-Chloropyridin-4-yl)piperidin-3-yl)(ethyl)amino)-2-(trifluoromethyl)benzonitrile The compound was prepared as in Example 139(d) from the compound of Example 146(c) and 4-bromo-3-chloropyridine. Yield 62 mg. $^1$H NMR (400 MHz, CDCl$_3$): 1.24 (3H, t), 1.79 (1H, dq), 1.93 (1H, m), 2.02 (1H, m), 2.11 (1H, m), 2.66 (1H, t), 2.77 (1H, dt), 3.46 (3H, m), 3.69 (1H, m), 4.08 (1H, m), 6.85 (1H, d), 6.91 (1H, dd), 7.11 (1H, d), 7.60 (1H, d), 8.33 (1H, d), 8.43 (1H, s).

Example 169

4-((3-(1H-imidazol-1-yl)cyclopent-2-en-1-yl)(ethyl)amino)-2-(trifluoromethyl)benzonitrile a) 3-(1H-imidazol-1-yl)cyclopent-2-enone A mixture of 3-chlorocyclopent-2-enone (4.98 g, 42.7 mmol), imidazole (5.82 g, 85.0 mmol), TEA (30 ml, 215 mmol) and potassium hydrogencarbonate (86 mg, 0.855 mmol) in benzene (25 ml) was stirred at RT for 48 h. The mixture was diluted with DCM and water. Phases were separated and the aqueous phase was extracted with DCM. The combined organic extracts were washed with brine, dried, filtered and evaporated to afford 3.2 g of the title compound. $^1$H NMR (400 MHz, CDCl$_3$): 2.66 (2H, m), 3.12 (2H, m), 6.13 (1H, m), 7.24 (1H, s), 7.28 (1H, m), 7.94 (1H, s).

b) 3-(1H-imidazol-1-yl)cyclopent-2-enol

The compound was prepared as in Example 156(b) from the compound of Example 169(a) (0.50 g, 3.37 mmol). Yield 0.324 g. $^1$H NMR (400 MHz, CDCl$_3$): 1.97 (1H, m), 2.50 (1H, m), 2.70 (1H, m), 2.95 (1H, m), 3.06 (1H, br s), 5.02 (1H, m), 5.77 (1H, m), 7.09 (1H, s), 7.16 (1H, s), 7.69 (1H, s).

c) 1-(3-Azidocyclopent-1-en-1-yl)-1H-imidazole

The compound was prepared as in Example 156(c) from the compound of Example 169(b) (0.324 g, 2.157 mmol). The reaction was performed in DCM. After the reaction was completed most of the solvent was evaporated and the residue was purified by flash chromatography. Yield 0.265 g. $^1$H NMR (400 MHz, CDCl$_3$): 2.14 (1H, m), 2.53 (1H, m), 2.80 (1H, m), 3.01 (1H, m), 4.59 (1H, m), 5.73 (1H, m), 7.13 (1H, s), 7.19 (1H, s), 7.73 (1H, s).

d) 3-(1H-imidazol-1-yl)cyclopent-2-enamine hydrochloride

The compound was prepared as in Example 156(c) from the compound of Example 169(c) (0.265 g, 1.513 mmol). Crude amine was dissolved in 2-propanol (3 ml) and treated with hydrogen chloride (0.47 ml, 1.88 mmol, 4 M in dioxane). The precipitated solid was filtered, washed with ice cold 2-propanol and dried in vacuo. Yield 0.162 g. $^1$H NMR (400 MHz, DMSO-d$_6$): 2.04 (1H, m), 2.46 (1H, m), 2.86 (1H, m), 3.10 (1H, m), 4.38 (1H, br s), 6.28 (1H, s), 7.75 (1H, s), 8.21 (1H, s), 8.43 (3H, br s), 9.35 (1H, s).

e) 4-((3-(1H-imidazol-1-yl)cyclopent-2-en-1-yl)amino)-2-(trifluoromethyl)-benzonitrile The compound was prepared as in Example 137(c) from the compound of Example 169(d) (0.16 g, 0.862 mmol). Yield 0.134 g. $^1$H NMR (400 MHz, CDCl$_3$): 1.95 (1H, m), 2.67 (1H, m), 2.88 (1H, m), 3.00 (1H, m), 4.69 (1H, d), 4.78 (1H, m), 5.73 (1H, m), 6.74 (1H, dd), 6.89 (1H, d), 7.14 (1H, s), 7.18 (1H, m), 7.59 (1H, d), 7.73 (1H, s).

f) 4-((3-(1H-imidazol-1-yl)cyclopent-2-en-1-yl)(ethyl)amino)-2-(trifluoromethyl)benzonitrile The compound was prepared as in Example 137(d) from the compound of Example 169(e) (0.13 g, 0.408 mmol). Purification by preparative HPLC afforded 26 mg of the title compound. $^1$H NMR (400 MHz, CDCl$_3$): 1.21 (3H, t), 1.91 (1H, m), 2.68 (1H, m), 2.89 (1H, m), 3.02 (1H, m), 3.42 (1H, m), 5.16 (1H, m), 5.68 (1H, m), 6.86 (1H, dd), 7.03 (1H, d), 7.16 (1H, s), 7.22 (1H, s), 7.60 (1H, d), 7.76 (1H, s).

Example 170

(S)-4-(Ethyl(1-(3-fluoropyridin-4-yl)piperidin-3-yl)amino)-2-(trifluoromethyl)benzonitrile The compound was prepared as in Example 139(d) from the compound of Example 139(c) and 4-bromo-3-fluoropyridine. Purification by preparative HPLC afforded 37 mg of the title compound. $^1$H NMR (400 MHz, CDCl$_3$): 1.24 (3H, t), 1.83 (1H, m), 1.90 (1H, m), 2.01 (1H, m), 2.12 (1H, m), 2.79 (2H, m), 3.46 (2H, m), 3.67 (1H, m), 3.77 (1H, m), 3.99 (1H, m), 6.75 (1H, dd), 6.89 (1H, dd), 7.05 (1H, d), 7.62 (1H, d), 8.18 (1H, d), 8.25 (1H, d).

Example 171

(R)-4-(Ethyl(1-(4-(methoxymethyl)pyridin-3-yl)piperidin-3-yl)amino)-2-(trifluoromethyl)-benzonitrile The compound was prepared as in Example 139(d) from the compound of Example 146(c) and 3-bromo-4-(methoxymethyl)pyridine (WO 2012/015723). Yield 39 mg. $^1$H NMR (400 MHz, CDCl$_3$): 1.23 (3H, t), 1.74 (1H, dq), 1.88 (1H, m), 1.99 (1H, m), 2.07 (1H, m), 2.81 (2H, m), 3.46 (2H, m), 3.46 (3H, s), 4.01 (1H, m), 4.54 (2H, s), 6.86 (1H, dd), 7.02 (1H, dd), 7.39 (1H, d), 7.59 (1H, d), 8.36 (1H, s), 8.37 (1H, d).

Example 172

(R)-3-Chloro-5-(ethyl(1-(pyridin-3-yl)piperidin-3-yl)amino)picolinonitrile a) (R)-3-Chloro-5-((1-(pyridin-3-yl)piperidin-3-yl)amino)picolinonitrile The compound was prepared as in Example 137(c) from (R)-1-(pyridin-3-yl)piperidin-3-amine (0.155 g, 0.831 mmol) and 5-bromo-3-chloropicolinonitrile (0.181 g, 0.831 mmol). Yield 28 mg. LC-MS: m/z=313.33 (M+1)$^+$.

b) (R)-3-Chloro-5-(ethyl(1-(pyridin-3-yl)piperidin-3-yl)amino)picolinonitrile

The compound was prepared as in Example 137(d) from the compound of Example 172(a) (28 mg, 0.089 mmol). Purification by preparative HPLC gave 2.3 mg of the title compound. $^1$H NMR (400 MHz, CDCl$_3$): 1.24 (3H, t), 1.76 (1H, dq), 1.88 (1H, m), 2.04 (2H, m), 2.74 (1H, dt), 2.80 (1H, t), 3.47 (2H, q), 3.67 (2H, m), 3.93 (1H, m), 6.99 (1H, d), 7.19 (2H, t), 8.11 (1H, d), 8.15 (1H, t), 8.31 (1H, br s).

Example 173

4-(Ethyl(3-(5-methyl-1H-1,2,3-triazol-1-yl)cyclopent-2-en-1-yl)amino)-2-(trifluoromethyl)-benzonitrile a) 3-Azidocyclopent-2-enone A solution of 3-chlorocyclopent-2-enone (1.0 g, 8.58 mmol) in DMF (5 ml) was treated with sodium azide (1.12 g, 17.23 mmol). The mixture was stirred overnight at RT. The mixture was diluted with water and extracted with TBME and DCM. Combined organic extracts were dried, filtered and evaporated. Crude product was filtered to afford 0.514 g of the unstable title compound. $^1$H NMR (400 MHz, CDCl$_3$): 2.55 (2H, m), 2.70 (2H, m), 5.78 (1H, m).

b) 3-(5-Methyl-1H-1,2,3-triazol-1-yl)cyclopent-2-enone

A mixture of the compound of Example 173(a) (0.23 g, 1.663 mmol) and 1-(triphenylphosphoranylidene)propan-2-one (0.529 g, 1.663 mmol) in DCM (5 ml) was stirred at RT for 48 h. Solvents were evaporated and the residue was purified by flash chromatography to afford 0.527 g of a mixture containing 46% of the title compound and 54% of triphenylphosphine oxide as analyzed by NMR. $^1$H NMR (400 MHz, CDCl$_3$) of the title compound: 2.53 (3H, d), 2.65 (2H, m), 3.48 (2H, m), 6.27 (1H, t), 7.59 (1H, br s).

c) 3-(5-Methyl-1H-1,2,3-triazol-1-yl)cyclopent-2-enol

The compound was prepared as in Example 156(b) from the compound of Example 173(b) (0.519 g, 1.463 mmol; purity 46% by NMR) to afford 0.509 g the title compound contaminated with triphenylphosphine oxide. $^1$H NMR (400 MHz, CDCl$_3$): 1.94 (1H, m), 2.10 (1H, d), 2.45 (3H, d), 2.52 (1H, m), 3.06 (1H, m), 3.25 (1H, m), 5.10 (1H, br s), 5.93 (1H, m), 7.48 (1H, s). LC-MS: m/z=166.34 (M+1)$^+$.

d) 1-(3-Azidocyclopent-1-en-1-yl)-5-methyl-1H-1,2,3-triazole

The compound was prepared as in Example 156(c) from the compound of Example 173(c) (0.493 g, 1.313 mmol; purity 44% by NMR) using DCM as the solvent. Purification by flash chromatography afforded 0.118 g of the title compound. $^1$H NMR (400 MHz, CDCl$_3$): 2.14 (1H, m), 2.48 (3H, d), 2.53 (1H, m), 3.21 (2H, m), 4.65 (1H, m), 5.87 (1H, m), 7.50 (1H, m).

e) 3-(5-Methyl-1H-1,2,3-triazol-1-yl)cyclopent-2-enamine

The compound was prepared as in Example 156(d) from the compound of Example 173(d) (0.118 g, 0.552 mmol; purity 89% by NMR). Yield 98 mg. $^1$H NMR (400 MHz, CDCl$_3$): 1.60 (2H, br s), 1.70 (1H, m), 2.43 (3H, s), 2.53 (1H, m), 3.02 (1H, m), 3.19 (1H, m), 4.24 (1H, m), 5.84 (1H, m), 7.47 (1H, s).

f) 4-((3-(5-Methyl-1H-1,2,3-triazol-1-yl)cyclopent-2-en-1-yl)amino)-2-(trifluoromethyl)-benzonitrile The compound was prepared as in Example 137(c) from the compound of Example 173(e) (98 mg, 0.531 mmol; 89% purity by NMR). Yield 98 mg. $^1$H NMR (400 MHz, CDCl$_3$): 1.95 (1H, m), 2.45 (3H, s), 2.66 (1H, m), 3.14 (1H, m), 3.27 (1H, m), 4.87 (1H, m), 4.97 (1H, m), 5.91 (1H, m), 6.77 (1H, dd), 6.93 (1H, d), 7.49 (1H, s), 7.58 (1H, d).

g) 4-(Ethyl(3-(5-methyl-1H-1,2,3-triazol-1-yl)cyclopent-2-en-1-yl)amino)-2-(trifluoromethyl)-benzonitrile The compound was prepared as in Example 137(d) from the compound of Example 173(f) (98 mg, 0.294 mg). Purification by flash chromatography afforded 80 mg of the title compound. $^1$H NMR (400 MHz, CDCl$_3$): 1.24 (3H, t), 1.93 (1H, m), 2.48 (3H, s), 2.67 (1H, m), 3.19 (1H, m), 3.32 (1H, m), 3.46 (2H, m), 5.25 (1H, m), 5.87 (1H, m), 6.89 (1H, dd), 7.05 (1H, d), 7.53 (1H, s), 7.62 (1H, d).

Example 174

4-(Ethyl(3-(3-fluoropyridin-4-yl)cyclohex-3-en-1-yl)amino)-2-(trifluoromethyl)benzonitrile a) 4-(Ethyl(3-(3-fluoropyridin-4-yl)-3-hydroxycyclohexyl)amino)-2-(trifluoromethyl)-benzonitrile The compound was prepared as in Example 156(a) from 3-fluoro-4-iodopyridine (0.78 g, 3.50 mmol), isopropylmagnesium bromide (4.0 ml, 4.00 mmol; 1 M in THF) and of 4-(ethyl(3-oxocyclohexyl)amino)-2-(trifluoromethyl)benzonitrile (0.808 g, 2.50 mmol). Reaction time was 24 h. Yield 0.357 g of the title compound as a mixture of diastereomers. LC-MS: m/z=407.75 (M+1)$^+$.

b) 4-(Ethyl(3-(3-fluoropyridin-4-yl)cyclohex-3-en-1-yl)amino)-2-(trifluoromethyl)-benzonitrile The compound was prepared as in Example 132(h) from the compound of Example 174(a) (0.286 g, 0.702 mmol. Yield 0.149 g. $^1$H NMR (400 MHz, CDCl$_3$): 1.28 (3H, t), 1.94 (1H, m), 2.01 (1H, m), 2.53 (3H, m), 2.65 (1H, m), 3.47 (2H, m), 4.12 (1H, m), 6.23 (1H, m), 6.86 (1H, dd), 7.00 (1H, d), 7.18 (1H, dd), 7.58 (1H, d), 8.36 (1H, d), 8.41 (1H, d).

Example 175 cis-4-(Ethyl(3-(1-(2-methoxyethyl)-1H-imidazol-5-yl)cyclohexyl)amino)-2-(trifluoromethyl)benzonitrile (enantiomer 1)

a) tert-Butyl (3-(1-(2-methoxyethyl)-1H-imidazol-5-yl)cyclohexyl)carbamate

To an ice cold stirred suspension of lithium aluminium hydride (0.69 g, 20.94 mmol) in THF (40 ml) was added dropwise tert-butyl (3-(methoxy(methyl)carbamoyl)cyclohexyl)carbamate (WO 2002/024679) (4.0 g, 13.96 mmol) in THF (20 ml) followed by stirring for 2 h at 0° C. The mixture was quenched with saturated Na$_2$SO$_4$ solution. The precipitated solids were filtered on celite and washed with EtOAc. The combined organic layer was dried, filtered and concentrated to give 3.0 g of the aldehyde product which was taken for the next step without further purification. A solution of the aldehyde product obtained above (5.0 g, 21.2 mmol) and 2-methoxyethanamine (1.6 g, 21.2 mmol) in THF (50 ml) was stirred for 6 h. Tosylmethyl isocyanide (3.3 g, 16.96 mmol) and piperazine (1.64 g, 19.08 mmol) were added and heated to 50° C. for 16 h. The mixture was cooled to RT, diluted with ice water and washed with EtOAc. The organic layer was washed with brine, dried, filtered and concentrated. Purification by flash chromatography afforded the title compound as a mixture of isomers (83% of the main cis-isomer by chiral LC). LC-MS: m/z=324.12 (M+1). Enantiomers of cis-isomer were separated using chiral preparative HPLC (Column: Daicel Chiralpak IA, 4.6×250 mm, 5 m particle size, eluent A: n-hexane+0.3% DEA, eluent B: EtOH, isocratic elution: 10% B, flow 1.0 ml/min, detection 300 nm) to afford 0.16 g of enantiomer 1 (rt 7.99 min) and 0.15 g of enantiomer 2 (rt 9.0 min).

b) cis-3-(1-(2-Methoxyethyl)-1H-imidazol-5-yl)cyclohexanamine dihydrochloride (enantiomer 1)

A solution of compound of Example 175(a), enantiomer 1, (0.20 g, 0.69 mmol) in 5 M HCl in methanol (5 ml) was stirred at 0° C. for 2 h. Solvents were evaporated. Yield 0.15 g. $^1$H NMR (300 MHz, DMSO-d$_6$): 1.37 (4H, m), 1.85 (2H, d), 2.0 (1H, d), 2.2 (1H, d), 2.95 (1H, m), 31.5 (1H, m), 3.28 (3H, s), 3.69 (2H, t), 4.36 (2H, t), 7.55 (1H, s), 8.33 (3H, br s), 9.04 (1H, s), 14.4 (1H, br s).

c) cis-4-((3-(1-(2-Methoxyethyl)-1H-imidazol-5-yl)cyclohexyl)amino)-2-(trifluoromethyl)benzonitrile (enantiomer 1)

The compound was prepared as in Example 137(c) from the compound of Example 175(b), enantiomer 1, (0.135 g, 0.605 mmol). Yield 40 mg. $^1$H NMR (400 MHz, CDCl$_3$): 1.26 (1H, m), 1.37 (1H, m), 1.55 (1H, m), 1.99 (2H, m), 2.18 (1H, m), 2.31 (1H, m), 2.70 (1H, m), 3.32 (3H, s), 3.46 (1H, m), 3.63 (2H, t), 4.03 (2H, t), 4.69 (1H, d), 6.68 (1H, dd), 6.78 (1H s), 6.84 (1H, d), 7.50 (1H, s), 7.53 (1H, d).

d) cis-4-(Ethyl(3-(1-(2-methoxyethyl)-1H-imidazol-5-yl)cyclohexyl)amino)-2-(trifluoromethyl)benzonitrile (enantiomer 1)

Title compound was prepared as described in Example 137(d) stating from the compound of Example 175(c) (40 mg, 0.102 mmol). Yield 25 mg. $^1$H NMR (400 MHz, CDCl$_3$): 1.21 (3H, t), 1.42 (1H, m), 1.59 (3H, m), 1.89-2.09 (4H, m), 2.73 (1H, m), 3.30 (3H, s), 3.41 (2H, q), 3.62 (2H, t), 3.78 (1H, m), 4.02 (2H, t), 6.80 (1H, dd), 6.81 (1H, s), 6.95 (1H, d), 7.48 (1H, s), 7.57 (1H, d).

Example 176 cis-4-(Ethyl((3-(1-(2-methoxyethyl)-1H-imidazol-5-yl)cyclohexyl)amino)-2-(trifluoromethyl)benzonitrile (enantiomer 2)

a) cis-3-(1-(2-Methoxyethyl)-1H-imidazol-5-yl)cyclohexanamine dihydrochloride (enantiomer 2)

The compound was prepared as in Example 175(b) from enantiomer 2 of cis-tert-butyl (3-(1-(2-methoxyethyl)-1H-imidazol-5-yl)cyclohexyl)carbamate (0.2 g, 0.69 mmol) to afford 0.15 g of the title compound. $^1$H NMR was identical with that of enantiomer 1.

b) cis-4-(Ethyl(3-(1-(2-methoxyethyl)-1H-imidazol-5-yl)cyclohexyl)amino)-2-(trifluoromethyl)benzonitrile (enantiomer 2)

The compound was prepared as in Example 175 from the compound of Example 176(a), enantiomer 2 (0.115 g, 0.515 mmol). Yield 26 mg. $^1$H NMR (400 MHz, CDCl$_3$): 1.21 (3H, t), 1.42 (1H, m), 1.59 (3H, m), 1.89-2.09 (4H, m), 2.73 (1H, m), 3.30 (3H, s), 3.41 (2H, q), 3.62 (2H, t), 3.78 (1H, m), 4.02 (2H, t), 6.80 (1H, dd), 6.81 (1H, s), 6.95 (1H, d), 7.48 (1H, s), 7.57 (1H, d).

Example 177 cis-4-((3-((1H-Imidazol-1-yl)methyl)cyclohexyl) (ethyl)amino)-2-(trifluoromethyl)-benzonitrile (enantiomer 1)

a) cis-tert-Butyl-(3-((1H-imidazol-1-yl)methyl)cy-clohexyl)carbamate

To an ice cold stirred solution of tert-butyl (3-(hydroxymethyl)cyclohexyl)carbamate (WO 2001/046199) (4.0 g, 17.45 mmol) in CH$_2$Cl$_2$ (40 ml) were added Et$_3$N (3.0 ml, 20.94 mmol), and MsCl (1.35 ml, 17.45 mmol). The mixture was stirred at RT for 4 h. The reaction was quenched with ice water and extracted with EtOAc. The organic layer was dried over anhydrous Na$_2$SO$_4$, filtered and concentrated. Purification by flash chromatography afforded 2.8 g of (3-((tert-butoxycarbonyl)amino)cyclohexyl)methyl methanesulfonate. Then, to an ice cold stirred suspension of NaH (0.328 g, 8.2 mmol, 60% in oil) in THF (10 ml) was added dropwise a solution of imidazole (0.744 g, 10.94 mmol) in THF (10 ml). After 15 min a solution of the methanesulfonate product (2.8 g, 9.12 mmol) obtained above in THF (20 ml) was added dropwise at 0° C. The mixture was heated at 50° C. for 16 h. The mixture was diluted with ice water and extracted with EtOAc. The organic layer was washed with brine, dried over Na$_2$SO$_4$, filtered and concentrated. Purification by flash chromatography afforded 0.715 g of the racemic title compound. LC-MS: m/z=280.1 (M+1). Enantiomers were separated using chiral preparative HPLC (Column: Daicel Chiralpak IA, 4.6×250 mm, 5 µm particle size, eluent A: n-hexane+0.1% DEA, eluent B: EtOH, isocratic elution: 15% B, flow 1.0 ml/min, detection 300 nm) to afford 0.16 g of enantiomer 1 (rt 6.36 min) and 0.15 g of enantiomer 2 (rt 7.55 min).

b) cis-3-((1H-imidazol-1-yl)methyl)cyclohexanamine dihydrochloride (enantiomer 1)

Title compound was prepared as in Example 175(b) from the compound of Example 177(a), enantiomer 1 (0.8 g, 28.69 mmol). Yield 0.40 g. $^1$H NMR (300 MHz, DMSO-d$_6$): 0.89 (1H, m), 1.04 (1H, m), 1.24 (2H, m), 1.48 (1H, d), 1.78 (2H, m), 1.94 (2H, m), 2.95 (1H, m), 4.12 (2H, d), 7.72 (1H, s), 7.76 (1H, s), 8.1 (3H, br s), 9.16 (1H, s), 14.6 (1H, br s).

c) cis-4-((3-((1H-imidazol-1-yl)methyl)cyclohexyl) (ethyl)amino)-2-(trifluoromethyl)-benzonitrile (enantiomer 1)

The compound was prepared as in Example 175 from the compound of Example 177(b), enantiomer 1 (0.180 g, 0.714 mmol). Yield 25 mg. $^1$H NMR (400 MHz, CDCl$_3$): 0.96 (1H, m), 1.18 (3H, t), 1.45 (2H, m), 1.73 (2H, m), 1.90 (4H, m), 3.35 (2H, q), 3.67 (1H, m), 3.86 (2H, d), 6.74 (1H, dd), 6.89 (2H, m), 7.07 (1H, s), 7.43 (1H, s), 7.55 (1H, d).

Example 178

Trans-4-(Ethyl(3-(1-(2-methoxyethyl)-1H-imidazol-5-yl)cyclopentyl)amino)-2-(trifluoromethyl)benzonitrile a) trans-3-(1-(2-Methoxyethyl)-1H-imidazol-5-yl) cyclopentanamine dihydrochloride Title compound was prepared as in Example 175(b) from the compound of Example 102(a) (trans diastereomer). Yield 0.4 g. $^1$H NMR (300 MHz, DMSO-d$_6$): 1.68 (2H, m), 1.97 (1H, m), 2.2 (3H, m), 3.28 (3H, s), 3.65 (2H, m), 3.7 (2H, t), 4.35 (3H, t), 7.59 (1H, s), 8.29 (3H, br s), 9.04 (1H, s), 14.3 (1H, br s).

b) trans-4-(ethyl(3-(1-(2-methoxyethyl)-1H-imidazol-5-yl)cyclopentyl)-amino)-2-(trifluoromethyl) benzonitrile The compound was prepared as in Example 175 from the compound of Example 178(a) (0.38 g, 1.347 mmol). Yield 78 mg. $^1$H NMR (400 MHz, CDCl$_3$): 1.25 (3H, t), 1.82 (2H, m), 2.07 (2H, m), 2.26 (2H, m), 3.31 (1H, m), 3.33 (3H, s), 3.43 (2H, q), 3.62 (2H, t), 4.03 (2H, t), 4.38 (1H, m), 6.81 (1H, dd), 6.85 (1H, s), 6.97 (1H, d), 7.52 (1H, s), 7.56 (1H, d).

Example 179

4-(Ethyl(3-(1-ethyl-1H-imidazol-5-yl)cyclopent-3-en-1-yl)amino)-2-(trifluoromethyl)benzonitrile a) 4-(Ethyl(3-(1-tosyl-1H-imidazol-4-yl)cyclopent-3-en-1-yl)amino)-2-(trifluoromethyl)benzonitrile A mixture of the compound of Example 150 (0.30 g, 0.866 mmol), p-toluenesulfonyl chloride (0.17 g, 0.892 mmol) and TEA (0.125 ml, 0.896 mmol) in dry DCM (5 ml) was stirred at RT for 1 h. The mixture was diluted with DCM and water. The organic phase was washed with brine, dried, filtered and evaporated to afford 0.34 g of the title compound which was used as such in the next step. LC-MS: m/z=501.77 (M+1)$^+$.

b) 4-(Ethyl(3-(1-ethyl-1H-imidazol-5-yl)cyclopent-3-en-1-yl)amino)-2-(trifluoromethyl)-benzonitrile A solution of the compound of Example 179(a) (0.34 g, 0.679 mmol) in dry DCM (7 ml) was treated with triethyloxonium tetrafluoroborate (0.136 g, 0.713 mmol). The mixture was stirred overnight at RT and then treated with methanol (3 ml). After stirring for 30 min the mixture was evaporated to dryness. The residue was purified by flash chromatography to afford the product as a fluoroborate salt. The salt was dissolved in DCM, washed with saturated NaHCO$_3$, water and brine, dried, filtered and evaporated to afford 0.157 g of the title compound. $^1$H NMR (400 MHz, CDCl$_3$): 1.24 (3H, t), 1.48 (3H, t), 2.70 (1H, m), 2.85 (1H, m), 3.00 (1H, m), 3.11 (1H, m), 3.46 (2H, q), 4.13 (2H, q), 4.67 (1H, m), 5.88 (1H, m), 6.81 (1H, dd), 6.98 (1H, d), 7.01 (1H, s), 7.51 (1H, s), 7.58 (1H, d). The enantiomers were separated using chiral preparative HPLC (Column: Daicel Chiralpak IA, 20 mm×250 mm, 5 µm particle size, eluent A: n-hexane+0.1% DEA, eluent B: EtOH+0.1% DEA, isocratic elution: 10% B, flow 20 ml/min, detection 300 nm) to afford 43.2 mg of enantiomer 1 (rt 35 min) and 43 mg of enantiomer 2 (rt 43 min).

Example 180

4-((3-(1H-imidazol-1-yl)-5,5-dimethylcyclopent-2-en-1-yl)(ethyl)amino)-2-(trifluoromethyl)benzonitrile a) 4,4-Dimethylcyclopentane-1,3-dione A solution of 3-isobutoxy-5,5-dimethylcyclopent-2-enone (2.13 g, 11.69 mmol) (prepared as in U.S. Pat. No. 4,546,194) in THF (12 ml) was treated with 10% aqueous HCl (36.5 ml, 105 mmol) and stirred at RT for 9 h. Methanol was evaporated and the residue was diluted with brine and extracted with DCM. Organic extracts were washed with brine, dried, filtered and evaporated to afford 0.958 g of the title compound as mixture of the keto and enol forms. Product was used in the next step without purification. $^1$H NMR (400 MHz, CDCl$_3$) enol form: 1.23 (6H, s), 2.47 (2H, s), 5.19 (1H, s), 9.92 (1H, br s).

b) 3-Chloro-5,5-dimethylcyclopent-2-enone

The compound of Example 180(a) (0.958 g, 7.59 mmol) in dry DCM (25 ml) at 0-5° C. was treated with a solution of oxalyl chloride (1.325 ml, 15.19 mmol) in dry DCM (6 ml). The mixture was stirred at RT. After the reaction was completed it was quenched with ice water and saturated NaHCO$_3$. The aqueous phase was extracted with DCM. Combined organic extracts were washed with brine, dried, filtered and evaporated to afford 1.16 g of the title compound which was used as such in the next step. $^1$H NMR (400 MHz, CDCl$_3$): 1.18 (6H, s), 2.72 (2H, d), 6.16 (1H, t).

c) 3-(1H-imidazol-1-yl)-5,5-dimethylcyclopent-2-enone

The compound was prepared as in Example 169(a) from the compound of Example 180(b) and imidazole (1.092 g, 16.04 mmol). The reaction was performed in toluene (13 ml) at 110° C. for 3.5 h. The cooled mixture was diluted with water and extracted with EtOAc. Combined organic extracts were washed with water and brine, dried, filtered and evaporated. Yield 1.06 g. $^1$H NMR (400 MHz, CDCl$_3$): 1.26 (6H, s), 2.96 (2H, d), 6.03 (1H, t), 7.23 (1H, m), 7.28 (1H, t), 7.91 (1H, s).

d) 3-(1H-imidazol-1-yl)-5,5-dimethylcyclopent-2-enol

The compound was prepared as in Example 156(b) starting from the compound of Example 180(c) (1.06 g, 6.02 mmol). Yield 1.03 g. $^1$H NMR (400 MHz, CDCl$_3$): 1.19 (6H, s), 2.51 (1H, d), 2.75 (1H, dt), 4.36 (1H, br s), 5.69 (1H, m), 7.11 (1H, s), 7.16 (1H, m), 7.68 (1H, s).

e) 1-(3-Azido-4,4-dimethylcyclopent-1-en-1-yl)-1H-imidazole

The compound was prepared as in Example 156(c) starting from the compound of Example 180(d) (0.376 g, 2.11 mmol). Purification by flash chromatography afforded 0.248 g of the title compound (purity 77% by NMR). $^1$H NMR (400 MHz, CDCl$_3$): 1.27 (3H, s), 1.28 (3H, s), 2.55 (1H, d), 2.78 (1H, dt), 4.02 (1H, m), 5.67 (1H, m), 7.13 (1H, m), 7.18 (1H, t), 7.69 (1H, s).

f) 3-(1H-imidazol-1-yl)-5,5-dimethylcyclopent-2-enamine

A mixture of the compound of Example 180(e) (0.58 g, 1.798 mmol; purity 63%) and triphenylphosphine (0.943 g, 3.60 mmol) in methanol (10 ml) was stirred at 65° C. until all the starting material had reacted (monitored by TLC and LC-MS). The cooled reaction mixture was treated with 1M NaOH (5 ml) and stirred at RT until complete. Methanol was evaporated, the residue was acidified with 2 M HCl and the aqueous phase was washed with EtOAc. Aqueous phase was basified with 2 M NaOH and extracted with EtOAc. Organic extracts were washed with brine, dried, filtered and evaporated to afford 0.231 g of the title compound. $^1$H NMR (400 MHz, CDCl$_3$): 1.11 (3H, s), 1.19 (3H, s), 2.55 (1H, dt), 2.65 (1H, dt), 3.61 (1H, m), 5.59 (1H, m), 7.08 (1H, s), 7.14 (1H, s), 7.65 (1H, s).

g) 4-((3-(1H-imidazol-1-yl)-5,5-dimethylcyclopent-2-en-1-yl)amino)-2-(trifluoromethyl)-benzonitrile The compound was prepared as in Example 137(c) from the compound of Example 180(f) (0.23 g, 1.298 mmol). Yield 0.284 g. $^1$H NMR (400 MHz, CDCl$_3$): 1.15 (3H, s), 1.37 (1H, s), 2.60 (1H, d), 2.73 (1H, dt), 4.36 (1H, m), 5.00 (1H, d), 5.56 (1H, m), 6.76 (1H, dd), 6.93 (1H, d), 7.11 (1H, s), 7.15 (1H, t), 7.55 (1H, d), 7.64 (1H, s).

h) 4-((3-(1H-imidazol-1-yl)-5,5-dimethylcyclopent-2-en-1-yl)(ethyl)amino)-2-(trifluoromethyl)benzonitrile The compound was prepared as in Example 136(d) from the compound of Example 180(g) (0.275 g, 0.794 mmol). Purification by preparative HPLC gave 0.145 g of the title compound. $^1$H NMR (400 MHz, CDCl$_3$): 0.98 (3H, s), 1.19 (3H, t), 1.39 (3H, s), 2.62 (1H, d), 2.86 (1H, dt), 3.17-3.42 (2H, m), 4.67 (1H, t), 5.64 (1H, m), 6.85 (1H, dd), 7.02 (1H, d), 7.16 (1H, s), m 7.21 (1H, m), 7.60 (1H, d), 7.74 (1H, s). The enantiomers were separated using chiral preparative HPLC (Column: Daicel Chiralpak IA, 20 mm×250 mm, 5 µm particle size, eluent A: n-hexane+0.1% DEA, eluent B: EtOH+0.1% DEA, isocratic elution: 10% B, flow 20 ml/min, detection 300 nm) to afford 54 mg of enantiomer 1 (rt 18 min) and 41 mg of enantiomer 2 (rt 22.1 min).

Example 181

(R)-4-((1-(1,3,4-thiadiazol-2-yl)piperidin-3-yl)(ethyl)amino)-2-(trifluoromethyl)benzonitrile The compound was prepared as in Example 137(c) from (R)-1-(pyridin-3-yl)piperidin-3-amine hydrochloride (0.167 g, 0.50 mmol) and 2-bromo-1,3,4-thiadiazole (83 mg, 0.50 mmol). Yield 88 mg. $^1$H NMR (400 MHz, CDCl$_3$): 1.26 (3H, t), 1.87 (2H, m), 2.00 (1H, m), 2.12 (1H, m), 3.14 (1H, m), 3.19 (1H, m), 3.46 (2H, m), 3.92 (2H, m), 4.20 (1H, m), 6.96 (1H, dd), 7.07 (1H, d), 8.51 (1H, s).

Example 182

4-((3-(2H-1,2,3-Triazol-2-yl)cyclopentyl)(ethyl)amino)-2-(trifluoromethyl)-benzonitrile a) 3-(2H-1,2,3-Triazol-2-yl)cyclopent-2-enone The compound was prepared as in Example 169(a) from 3-chlorocyclopent-2-one (1.0 g, 8.58 mmol) and 2H-1,2,3- triazole (1.0 ml, 17.26 mmol) at 80° C. Yield 1.10 g. $^1$H NMR (400 MHz, CDCl$_3$): 2.68 (2H, m), 3.31 (2H, m), 6.60 (1H, t), 7.92 (2H, s).

b) 3-(2H-1,2,3-Triazol-2-yl)cyclopent-2-enol

The compound was prepared as in Example 156(b) from the compound of Example 182(a) (1.08 g, 7.24 mmol). Yield 1.037 g. $^1$H NMR (400 MHz, CDCl$_3$): 1.98 (1H, m), 2.55 (1H, m), 2.96 (1H, m), 3.21 (1H, m), 5.08 (1H, m), 6.30 (1H, m), 7.74 (2H, s).

c) 3-(2H-1,2,3-Triazol-2-yl)cyclopentanol

The compound of Example 182(b) (0.151 g, 1.00 mmol) was dissolved in MeOH (20 ml) and hydrogenated in a H-Cube continuous-flow hydrogenation apparatus (ThalesNano Inc.) using 10% Pd/C catalyst cartridge. The reduction was conducted at 60° C. using 10 bar hydrogen pressure with a flow rate of 1 ml/min. The solvents were evaporated to afford 0.152 g of the title compound as a mixture of diastereomers (ratio 70:30 by NMR). The product was used as such in the next step.

d) 2-(3-Azidocyclopentyl)-2H-1,2,3-triazole

A cooled mixture of the compound of Example 182(c) (0.426 g, 2.78 ml) and TEA (0.58 ml, 4.16 mmol) in dry DCM (25 ml) was treated with a solution of methanesulfonyl chloride (0.32 ml, 4.13 mmol) in dry DCM (3 ml) and stirred overnight at RT. The mixture was washed with saturated NH$_4$Cl, water and brine, dried, filtered and evaporated to obtain 0.594 g of 3-(2H-1,2,3-triazol-2-yl)cyclopentyl methanesulfonate. This material was dissolved in DMSO (8 ml) and treated with sodium azide (0.334 g, 5.14 mmol) and stirred at 60° C. After the reaction was completed the cooled mixture was diluted with water and extracted with TBME. Combined organic extracts were washed with brine, dried, filtered and evaporated to afford 0.377 g of the title compound as a mixture of diastereomers. The product was used as such in the next step.

e) 3-(2H-1,2,3-Triazol-2-yl)cyclopentanamine hydrochloride

The compound was prepared as in Example 156(d) from the compound of Example 182(d) (0.377 g, 2.12 mmol). The crude product was dissolved in 2-propanol (3 ml) and treated with hydrogen chloride (0.822 ml, 3.29 mmol; 4 M in dioxane) to afford a gummy material which was triturated with ether to afford 0.173 g of the title compound as a mixture of diastereomers. $^1$H NMR (400 MHz, DMSO-d$_6$) of the main diastereomer: 1.75 (1H, m), 2.03 (1H, m), 2.20 (2H, m), 2.41 (2H, m), 3.80 (1H, m), 5.27 (1H, m), 7.79 (2H, s), 8.15 (3H, br s).

f) 4-((3-(2H-1,2,3-Triazol-2-yl)cyclopentyl)amino)-2-(trifluoromethyl)benzonitrile The compound was prepared as in Example 137(c) from the compound of Example 182(e) (0.173 g, 0.917 mmol) using 3.95 molar equivalent of DIPEA. Yield 0.168 g as a mixture of diastereomers. LC-MS: m/z=322.36 (M+1)$^+$.

g) 4-((3-(2H-1,2,3-Triazol-2-yl)cyclopentyl)(ethyl)amino)-2-(trifluoromethyl)-benzonitrile The compound was prepared as in Example 137(d) from the compound of Example 182(f) (0.182 g, 0.566 mmol).

Yield of the crude product was 0.191 g. The isomers were separated by chiral preparative HPLC (Column: Daicel Chiralpak IA, 20 mm×250 mm, 5 µm particle size, eluent A: n-hexane, eluent B: EtOH, isocratic elution: 10% B, flow 20 ml/min, detection 295 nm). Four stereoisomers were obtained. Enantiomer 1 of cis-diastereomer (rt 11.3 min, yield 12 mg) and enantiomer 2 of cis-diastereomer (rt 12.3 min, yield 10 mg), $^1$H NMR (400 MHz, CDCl$_3$): 1.25 (3H, t), 2.11 (2H, m), 2.20-2.40 (3H, m), 2.68 (1H, dt), 3.51 (2H, m), 4.32 (1H, m), 5.16 (1H, m), 6.85 (1H, dd), 7.01 (1H, d), 7.59 (1H, d), 7.63 (2H, s), and enantiomer 1 of trans-diastereomer, (rt 13.0 min, yield 39.5 mg) and enantiomer 2 of trans-diastereomer (rt 14.5 min, yield 47.8 mg), $^1$H NMR (400 MHz, CDCl$_3$): 1.25 (3H, t), 1.84 (1H, m), 2.08 (1H, m), 2.24 (2H, m), 2.53 (2H, m), 3.43 (2H, m), 4.74 (1H, m), 5.23 (1H, m), 6.89 (1H, dd), 7.10 (1H, d), 7.59 (1H, d), 7.63 (2H, s).

Example 183

4-((3-(1-(2-(dimethylamino)ethyl)-1H-imidazol-5-yl)cyclopent-3-en-1-yl)(ethyl)amino)-2-(trifluoromethyl)benzonitrile a) tert-Butyl (3-formylcyclopent-3-en-1-yl)carbamate

A mixture of cis-tert-butyl (4-(hydroxymethyl)cyclopent-2-en-1-yl)carbamate (WO 2005/075426) (5.33 g, 25.0 mmol), TEA (12.50 ml, 90.0 mmol), DMSO (25 ml) and DCM (45 ml) was cooled to 0-5° C. and treated portionwise with a solution of sulfur trioxide-pyridine complex (7.96 g, 50.0 mmol) in DMSO (25 ml). The mixture was stirred at RT. After the reaction was completed the mixture was diluted with water and brine and extracted with DCM. Combined organic extracts were washed with saturated NH$_4$Cl, water and brine, dried, filtered and evaporated. Crude product was purified by flash chromatography to afford 2.65 g of the title compound. $^1$H NMR (400 MHz, CDCl$_3$): 1.44 (9H, s), 2.40 (1H, m), 2.51 (1H, m), 2.92 (1H, m), 3.02 (1H, m), 4.39 (1H, br s), 4.68 (1H, br s), 6.80 (1H, m), 9.75 (1H, s).

b) tert-Butyl (3-(1-(2-(dimethylamino)ethyl)-1H-imidazol-5-yl)cyclopent-3-en-1-yl)carbamate A mixture of the compound of Example 183(a) (0.423 g, 2.00 mmol) and N,N-dimethylethane-1,2-diamine (0.274 ml, 2.50 mmol) in DCM (10 ml) was stirred at RT until all the aldehyde had reacted. Then tosylmethyl isocyanide (0.469 g, 2.40 mmol) and DBU (0.603 ml, 2.00 mmol) were added and the stirring was continued at RT. After the reaction was completed the mixture was diluted with DCM and washed with water and brine. Organic phase was dried, filtered and evaporated. Purification by flash chromatography gave 0.416 g of the title compound. $^1$H NMR (400 MHz, CDCl$_3$): 1.45 (9H, s), 2.28 (6H, s), 2.41 (1H, m), 2.55 (1H, m), 2.61 (2H, t), 2.95 (1H, dd), 3.08 (1H, dd), 4.10 (2H, t), 4.37 (1H, br s), 4.77 (1H, br s), 5.75 (1H, s), 6.97 (1H, s), 7.50 (1H, s).

c) 3-(1-(2-(Dimethylamino)ethyl)-1H-imidazol-5-yl)cyclopent-3-enamine dihydrochloride A mixture of the compound of Example 183(b) (0.416 g, 1.298 mmol) and methanol (6 ml) was treated with hydrogen chloride (1.30 ml, 5.20 mmol; 4 M solution in dioxane) and stirred at RT. After the reaction was completed the mixture was concentrated. The residue was triturated with ether to afford 0.408 g of the title compound. ¹H NMR (400 MHz, DMSO-d₆): 2.70 (2H, m), 2.85 (6H, s), 2.94 (1H, m), 2.99 (1H, m), 3.09 (1H, m), 3.13 (1H, m), 3.96 (1H, br s), 4.82 (2H, m), 6.35 (1H, s), 7.80 (1H, s), 8.39 (3H, br s), 9.29 (1H, s), 11.26 (1H, br s).

d) 4-((3-(1-(2-(Dimethylamino)ethyl)-1H-imidazol-5-yl)cyclopent-3-en-1-yl)amino)-2-(trifluoromethyl)benzonitrile The compound was prepared as in Example 137(c) starting from the compound of Example 183(c) (0.408 g, 1.294 mmol) and using 4.44 equivalent of DIPEA. Yield 0.139 g. ¹H NMR (400 MHz, CDCl₃): 2.29 (6H, s), 2.53 (1H, m), 2.63 (3H, m), 3.10 (1H, m), 3.21 (1H, m), 4.13 (2H, t), 4.28 (1H, m), 5.05 (1H, d), 5.83 (1H, m), 6.72 (1H, dd), 6.88 (1H, d), 6.97 (1H, s), 7.53 (1H, s), 7.57 (1H, d).

e) 4-((3-(1-(2-(Dimethylamino)ethyl)-1H-imidazol-5-yl)cyclopent-3-en-1-yl)(ethyl)amino)-2-(trifluoromethyl)benzonitrile The compound was prepared as in Example 137(d) starting from the compound of Example 183(d) (0.139 g, 0.357 mmol). Extraction with DCM. Purification by preparative HPLC afforded 57 mg of the title compound. ¹H NMR (400 MHz, CDCl₃): 1.24 (3H, t), 2.31 (6H, s), 2.67 (2H, t), 2.70 (1H, m), 2.84 (1H, m), 3.00 (1H, m), 3.11 (1H, m), 3.47 (2H, q), 4.17 (2H, t), 4.67 (1H, m), 5.90 (1H, m), 6.81 (1H, dd), 6.98 (1H, d), 7.00 (1H, s), 7.56 (1H, s), 7.58 (1H, d).

Example 184

4-((5,5-Dimethyl-3-(1H-1,2,4-triazol-1-yl)cyclopent-2-en-1-yl)(ethyl)amino)-2-(trifluoromethyl)benzonitrile a) 5,5-Dimethyl-3-(1H-1,2,4-triazol-1-yl)cyclopent-2-enone A mixture of the compound of Example 180(b) (1.71 g, 11.83 mmol) and sodium 1,2,4-triazol-1-ide (1.507 g, 16.56 mmol) in DMF (20 ml) was stirred at 80° C. After the reaction was completed the cooled mixture was diluted with water and extracted with DCM. Combined organic extracts were washed water and brine, dried, filtered and evaporated to afford 2.14 g of the title compound which was in the next step without purification. ¹H NMR (400 MHz, CDCl₃): 1.27 (6H, s), 3.04 (2H, d), 6.37 (1H, m), 8.14 (1H, s), 8.52 (1H, s).

b) 5,5-Dimethyl-3-(1H-1,2,4-triazol-1-yl)cyclopent-2-enol

The compound was prepared as in Example 156(b) from the compound of Example 184(a) (2.10 g, 11.85 mmol). Yield 1.85 g. ¹H NMR (400 MHz, CDCl₃): 1.20 (3H, s), 1.21 (3H, s), 1.70 (1H, m), 2.61 (dd), 2.82 (1H, dt), 4.41 (br s), 6.97 (1H, m), 8.01 (1H, s), 8.23 (1H, s).

c) 1-(3-Azido-4,4-dimethylcyclopent-1-en-1-yl)-1H-1,2,4-triazole

The compound was prepared as in Example 156(c) from the compound of Example 184(b). After the reaction was completed the mixture was diluted with water and extracted with EtOAc. Organic phase was washed with 2 M HCl, water and brine, dried, filtered and evaporated. Purification by flash chromatography afforded 0.797 g of the title compound. ¹H NMR (400 MHz, CDCl₃): 1.26 (3H, s), 1.28 (3H, s), 2.65 (1H, d), 2.85 (1H, dt), 4.07 (1H, s), 6.06 (1H, m), 8.02 (1H, s), 8.25 (1H, s).

d) 5,5-Dimethyl-3-(1H-1,2,4-triazol-1-yl)cyclopent-2-enamine hydrochloride

The compound was prepared as in Example 180(f) starting from the compound of Example 184(c) (0.797 g, 3.90 mmol). Crude product was dissolved in 2-propanol (2.5 ml) and treated with HCl (1.20 ml, 4.80 mmol; 4 M in dioxane) and ether. The precipitated solid was filtered, washed with ether and dried in vacuo. Yield 0.604 g. ¹H NMR (400 MHz, DMSO-d₆): 1.22 (2×3H, 2×s), 2.73 (1H, d), 2.95 (1H, dt), 3.85 (1H, m), 5.99 (1H, m), 8.21 (1H, s), 8.38 (3H, br s), 8.96 (1H, s).

e) 4-((5,5-Dimethyl-3-(1H-1,2,4-triazol-1-yl)cyclopent-2-en-1-yl)amino)-2-(trifluoromethyl)benzonitrile The compound was prepared as in Example 137(c) starting from the compound of Example 184(d) (0.604 g, 2.81 mmol). Yield 0.36 g. ¹H NMR (400 MHz, CDCl₃): 1.17 (3H, s), 1.40 (1H, s), 2.73 (1H, m), 2.85 (1H, dt), 4.42 (1H, m), 4.52 (1H, d), 5.98 (1H, m), 6.75 (1H, dd), 6.91 (1H, d), 7.59 (1H, d), 8.02 (1H, s), 8.23 (1H, s).

f) 4-((5,5-Dimethyl-3-(1H-1,2,4-triazol-1-yl)cyclopent-2-en-1-yl)(ethyl)-amino)-2-(trifluoromethyl)benzonitrile The compound was prepared as in Example 137(d) from the compound of Example 184(e) (0.36 g, 1.036 mmol). Extracted with DCM. Purification by flash chromatography afforded 0.30 g of the title compound. ¹H NMR (400 MHz, CDCl₃): 1.00 (3H, s), 1.20 (3H, t), 1.41 (3H, s), 2.71 (1H, d), 2.91 (1H, dt), 3.23 (1H, m), 3.39 (1H, m), 4.72 (1H, t), 6.08 (1H, m), 6.86 (1H, dd), 7.03 (1H, d), 7.61 (1H, d), 8.06 (1H, s), 8.27 (1H, s). The enantiomers of were separated using chiral preparative HPLC (Column: Daicel Chiralpak IA, 20 mm×250 mm, 5 µm particle size, eluent A: n-hexane+0.2% DEA, eluent B: IPA+0.2% DEA, isocratic elution: 5% B, flow 20 ml/min, detection 300 nm) to afford 71 mg of enantiomer 1 (rt 25.5 min) and 67 mg of enantiomer 2 (rt 28 min).

Example 185

4-(Ethyl(3-(1-(2-morpholinoethyl)-1H-imidazol-5-yl)cyclopent-3-en-1-yl)-amino)-2-(trifluoromethyl)benzonitrile a) tert-Butyl (3-(1-(2-morpholinoethyl)-1H-imidazol-5-yl)cyclopent-3-en-1-yl)carbamate The compound was prepared as in Example 183(b) starting from tert-butyl (3-formylcyclopent-3-en-1-yl)carbamate (0.423 g, 2.00 mmol) and 2-morpholinoethan-amine (0.394 ml, 3.00 mmol). Yield 0.370 g. ¹H NMR (400 MHz, CDCl₃): 1.45 (9H, s), 2.41 (1H, m), 2.46 (4H, m), 2.55 (1H, m), 2.68

(2H, t), 2.96 (1H, dd), 3.08 (1H, dd), 3.70 (4H, m), 4.13 (1H, t), 4.37 (1H, br s), 4.75 (1H, br s), 5.74/1H, s), 6.98 (1H, s), 7.53 (1H, s).

b) 3-(1-(2-Morpholinoethyl)-1H-imidazol-5-yl)cyclopent-3-enamine dihydrochloride The compound was prepared as in Example 183(c) starting from the compound of Example 185(a) (0.37 g, 1.021 mmol). Yield 0.394 g. $^1$H NMR (400 MHz, DMSO-$d_6$): 2.70 (2H, m), 2.96 (1H, m), 3.11 (1H, m), 3.2-3.7 (6H, m), 3.92 (6H, m), 4.83 (1H, s), 6.36 (1H, s), 7.78 (1H, s), 8.36 (3H, br s), 9.24 (1H, s), 11.86 (1H, br s).

c) 4-((3-(1-(2-Morpholinoethyl)-1H-imidazol-5-yl)cyclopent-3-en-1-yl)-amino)-2-(trifluoromethyl)benzonitrile The compound was prepared as in Example 137(c) starting from the compound of Example 185(b) (0.394 g, 1.022 mmol). Yield 0.158 g. $^1$H NMR (400 MHz, CDCl$_3$): 2.48 (4H, m), 2.53 (1H, m), 2.65 (1H, m), 2.70 (2H, t), 3.11 (1H, m), 3.23 (1H, m), 3.70 (4H, m), 4.16 (2H, t), 4.29 (1H, m), 4.74 (1H, d), 5.81 (1H, m), 6.71 (1H, dd), 6.87 (1H, d), 7.00 (1H, s), 7.57 (1H, s), 7.59 (1H, d).

d) 4-(Ethyl(3-(1-(2-morpholinoethyl)-1H-imidazol-5-yl)cyclopent-3-en-1-yl)-amino)-2-(trifluoromethyl)benzonitrile The compound was prepared as in Example 137(d) starting from the compound of Example 185(c) (0.158 g, 0.366 mmol). Extraction with DCM. Yield 99 mg. $^1$H NMR (400 MHz, CDCl$_3$): 1.24 (3H, t), 2.49 (4H, m), 2.71 (1H, m), 2.72 (2H, t), 2.85 (1H, m), 3.00 (1H, m), 3.10 (1H, m), 3.47 (2H, q), 3.71 (4H, m), 4.18 (2H, t), 4.67 (1H, m), 5.89 (1H, m), 6.81 (1H, dd), 6.98 (1H, d), 7.00 (1H, br s), 7.57 (1H, d), 7.59 (1H s).

Example 186

4-((3-(1H-imidazol-1-yl)-2,2-dimethylcyclopentyl)(ethyl)amino)-2-(trifluoromethyl)benzonitrile a) 3-(1H-imidazol-1-yl)-2,2-dimethylcyclopentanol

To a solution of 3-amino-2,2-dimethylcyclopentanol (WO 2012/125886) (10.0 g, 0.078 mol) in MeOH (120 ml) were added glyoxal (40% aqueous solution, 15.1 ml, 0.104 mol), NH$_4$OAc (17.91 g, 0.233 mol) and HCHO (35% aqueous solution, 17.46 ml, 0.233 mol). The mixture was stirred at 60° C. for 8 h. The solvent was evaporated and the residue was basified by 2 M KOH solution and extracted with DCM. The organic layer was washed with brine, dried, filtered and concentrated. Purification by column chromatography afforded 3.8 g of the title compound. $^1$HNMR (400 MHz; DMSO-$d_6$): 7.65 (s, 1H), 7.18 (s, 1H), 6.88 (s, 1H), 4.78 (bs, 1H), 4.28-4.40 (m, 1H), 3.64-3.72 (m, 1H), 2.02-2.20 (m, 3H), 1.54 (bs, 1H), 0.89 (s, 3H), 0.56 (s, 3H). LC-MS: m/z=181.08 (M+1)$^+$.

b) 3-(1H-imidazol-1-yl)-2,2-dimethylcyclopentanone

To a solution of the compound of Example 186(a) (1.7 g, 0.011 mol) in DCM (65 ml) was added Dess-Martin periodinane (12.7 g, 0.023 mol). The mixture was stirred at RT for 12 h and quenched with aqueous Na$_2$S$_2$O$_3$.5H$_2$O solution. The mixture was stirred for 30 min and extracted with DCM. The organic layer was washed with aqueous NaHCO$_3$ solution and brine, dried, filtered and concentrated. Purification by column chromatography afforded 1.4 g of the title compound. $^1$HNMR (400 MHz; DMSO-$d_6$): 7.73 (s, 1H), 7.25 (s, 1H), 6.94 (s, 1H), 4.57 (t, 1H), 2.30-2.58 (m, 4H), 1.03 (s, 3H), 0.58 (s, 3H). LC-MS: m/z=179.30 (M+1)$^+$.

c) tert-butyl (3-(1H-imidazol-1-yl)-2,2-dimethylcyclopentyl)carbamate

To a solution of the compound of Example 186(b) (3.0 g, 0.017 mol) in EtOH (50 ml) were added molecular sieves (4° A, 12.9 g) and NH$_4$OAc (12.9 g, 0.167 mol). The mixture was heated at 45° C. for 2 h, cooled to RT. NaCNBH$_3$ (3.14 g, 0.050 mol) was added and the mixture was refluxed for 20 h. The reaction mass was filtered through a Celite bed and washed with EtOH. The filtrate was concentrated under reduced pressure to afford 3.0 g of a viscous oil. LC-MS: m/z=180.15 (M+1)$^+$. Oil was dissolved in DCM (15 ml). TEA (5.6 ml, 0.040 mol) and Boc$_2$O (6.0 ml, 0.020 mol) were added and the mixture was stirred at RT for overnight. The reaction was quenched with water and extracted with DCM. The organic phase was washed with water, dried, filtered and concentrated. Purification by column chromatography gave 300 mg of the title compound as a mixture of diastereomers. $^1$H-NMR (400 MHz; DMSO-$d_6$) of the major diastereomer: 7.65 (s, 1H), 7.20 (s, 1H), 7.16 (s, 1H), 6.85 (s, 1H), 4.17-4.25 (m, 1H), 3.72-3.76 (m, 1H), 2.10-2.19 (m, 1H), 1.92-12.07 (m, 2H), 1.70-1.79 (m, 1H), 1.39 (s, 9H), 0.83 (s, 3H), 0.49 (s, 3H).

d) 3-(1H-imidazol-1-yl)-2,2-dimethylcyclopentanamine dihydrochloride

To a solution of the compound of Example 186(c) (0.250 g, 0.892 mmol) in dioxane (2 ml) was added 4 M HCl in dioxane (5 ml). The mixture was stirred at RT for 5 h. The mixture was concentrated under reduced pressure and the solid formed was washed with DCM and dried under vacuum to give 150 mg of the title compound as a mixture of diastereomers. LC-MS: m/z=180.15 (M+1)$^+$ e) 4-((3-(1H-imidazol-1-yl)-2,2-dimethylcyclopentyl)amino)-2-(trifluoromethyl)benzonitrile The compound was prepared as in Example 183(d) from the compound of Example 186(d) (97 mg, 0.385 mmol). Yield 70 mg as a mixture of diastereomers. $^1$H NMR (400 MHz, CDCl$_3$) of the major diastereomer: 0.77 (3H, s), 1.10 (3H, s), 1.67 (1H, m), 2.24-2.4 (3H, m), 3.75 (1H, q), 4.22 (1H, m), 4.53 (1H, d), 6.76 (1H, dd), 6.93 (1H, d), 6.97 (1H, s), 7.10 (1H, s), 7.55 (1H, s), 7.56 (1H, d).

f) 4-((3-(1H-imidazol-1-yl)-2,2-dimethylcyclopentyl)(ethyl)amino)-2-(trifluoromethyl)-benzonitrile The compound was prepared as in Example 137(d) from the compound of Example 186(e) (70 mg, 0.201 mmol). Extracted with DCM. Preparative HPLC afforded 32 mg of the title compound as a mixture of diastereomers. $^1$H NMR (400 MHz, CDCl$_3$) of the major diastereomer: 0.74 (3H, s), 1.06 (3H, s), 1.18 (3H, t), 2.12 (1H, m), 2.30 (3H, m), 3.54

(2H, q), 4.27 (2H, m), 6.96 (2H, m), 7.10 (1H, s), 7.14 (1H, s), 7.58 (1H, d), 7.59 (1H, s).

Example 187

4-(Ethyl(3-(1-(2-(4-methoxyphenoxy)ethyl)-1H-imidazol-5-yl)cyclopent-3-en-1-yl)amino)-2-(trifluoromethyl)benzonitrile a) tert-Butyl (3-(1-(2-(4-methoxyphenoxy)ethyl)-1H-imidazol-5-yl)cyclopent-3-en-1-yl)carbamate The compound was prepared as in Example 183(b) starting from tert-butyl (3-formylcyclopent-3-en-1-yl)carbamate (0.423 g, 2.00 mmol) and 2-(4-methoxyphenoxy)ethanamine (0.401 g, 2.40 mmol). Yield 0.434 g. $^1$H NMR (400 MHz, CDCl$_3$): 1.45 (9H, s), 2.40 (1H, m), 2.55 (1H, m), 2.94 (1H, dd), 3.08 (1H, dd), 3.75 (3H, s), 4.17 (2H, t), 4.36 (1H, m), 4.39 (2H, t), 4.79 (1H, br s), 5.74 (1H, m), 6.76-6.83 (4H, m), 6.99 (1H, s), 7.56 (1H, s).

b) 3-(1-(2-(4-Methoxyphenoxy)ethyl)-1H-imidazol-5-yl)cyclopent-3-enamine

The compound was prepared as in Example 183(c) from the compound of Example 187(a) (0.434 g, 1.086 mmol). Crude product was dissolved in water, basified with 2 M NaOH and extracted with DCM. Combined organic extracts were washed brine, dried, filtered and evaporated. Yield 0.31 g. $^1$H NMR (400 MHz, CDCl$_3$): 2.31 (1H, m), 2.45 (1H, m), 2.86 (1H, m), 2.99 (1H, m), 3.75 (1H, m), 3.76 (3H, s), 4.18 (2H, t), 4.41 (2H, t), 5.73 (1H, m), 6.80 (4H, m), 6.99 (1H, s), 7.58 (1H, s).

c) 4-((3-(1-(2-(4-Methoxyphenoxy)ethyl)-1H-imidazol-5-yl)cyclopent-3-en-1-yl)amino)-2-(trifluoromethyl)benzonitrile The compound was prepared as in Example 137(c) from the compound of Example 187(b) (0.456 g, 1.523 mmol). Yield 0.369 g. $^1$H NMR (400 MHz, CDCl$_3$): 2.51 (1H, m), 2.64 (1H, m), 3.09 (1H, m), 3.23 (1H, m), 3.76 (3H, s), 4.19 (2H, t), 4.28 (1H, m), 4.43 (2H, t), 4.69 (1H, d), 5.81 (1H, m), 6.69 (1H, dd), 6.80 (4H, m), 6.85 (1H, d), 7.02 (1H, s), 7.58 (1H, d), 7.63 (1H, s).

d) 4-(Ethyl(3-(1-(2-(4-methoxyphenoxy)ethyl)-1H-imidazol-5-yl)cyclopent-3-en-1-yl)amino)-2-(trifluoromethyl)benzonitrile The compound was prepared as in Example 137(d) from the compound of Example 187(c) (0.369 g, 0.788 mmol). Extracted with DCM. Yield 0.285 g. $^1$H NMR (400 MHz, CDCl$_3$): 1.23 (3H, t), 2.69 (1H, m), 2.85 (1H, m), 2.99 (1H, m), 3.10 (1H, m), 3.45 (2H, q), 3.77 (3H, s), 4.22 (2H, t), 4.45 (2H, t), 4.66 (1H, m), 5.88 (1H, m), 6.81 (5H, m), 6.98 (1H, d), 7.02 (1H, s), 7.57 (1H, d), 7.64 (1H, s).

Example 188

4-(Ethyl(3-(1-isobutyl-1H-imidazol-5-yl)cyclopent-3-en-1-yl)amino)-2-(trifluoromethyl)benzonitrile a) tert-Butyl (3-(1-isobutyl-1H-imidazol-5-yl)cyclopent-3-en-1-yl)carbamate The compound was prepared as in Example 183(b) from tert-butyl (3-formylcyclopent-3-en-1-yl)carbamate (0.423 g, 2.00 mmol) and isobutylamine (0.28 ml, 2.82 mmol). Yield 0.447 g. $^1$H NMR (400 MHz, CDCl$_3$): 0.92 (6H, d), 1.45 (9H, s), 2.04 (1H, m), 2.40 (1H, m), 2.54 (1H, m), 2.95 (1H, dd), 3.07 (1H, dd), 3.80 (2H, d), 4.36 (1H, br s), 4.75 (1H, br s), 5.69 (1H, br s), 6.99 (1H, s), 7.39 (1H, s).

b) 3-(1-Isobutyl-1H-imidazol-5-yl)cyclopent-3-enamine

The compound was prepared as in Example 187(b) from the compound of Example 188(a) (0.433 g, 1.418 mmol). Yield 0.166 g. $^1$H NMR (400 MHz, CDCl$_3$): 0.92 (6H, d), 2.06 (1H, m), 2.32 (1H, m), 2.44 (1H, m), 2.86 (1H, dd), 2.98 (1H, dd), 3.73 (1H, m), 3.80 (2H, m), 5.69 (1H, s), 6.98 (1H, s), 7.38 (1H, s).

c) 4-((3-(1-Isobutyl-1H-imidazol-5-yl)cyclopent-3-en-1-yl)amino)-2-(trifluoromethyl)benzonitrile The compound was prepared as in Example 137(c) from the compound of Example 188(b) (0.166 g, 0.809 mmol). Yield 0.120 g. $^1$H NMR (400 MHz, CDCl$_3$): 0.94 (6H, d), 2.05 (1H, m), 2.51 (1H, d), 2.64 (1H, d), 3.10 (1H, dd), 3.22 (1H, dd), 3.82 (2H, d), 4.28 (1H, m), 4.67 (1H, d), 5.75 (1H, br s), 6.71 (1H, dd), 6.87 (1H, d), 7.01 (1H, s), 7.42 (1H, s), 7.58 (1H, d).

d) 4-(Ethyl(3-(1-isobutyl-1H-imidazol-5-yl)cyclopent-3-en-1-yl)amino)-2-(trifluoromethyl)-benzonitrile The compound was prepared as in Example 137(d) from the compound of Example 188(c). Extracted with DCM. Yield 86 mg. $^1$H NMR (400 MHz, CDCl$_3$): 0.95 (6H, m), 1.23 (3H, t), 2.08 (1H, m), 2.69 (1H, m), 2.84 (1H, m), 2.99 (1H, dd), 3.09 (1H, dd), 3.46 (2H, q), 3.85 (2H, m), 4.66 (1H, m), 5.82 (1H, m), 6.81 (1H, dd), 6.98 (1H, d), 7.01 (1H, s), 7.44 (1H, s), 7.58 (1H, d).

Example 189

4-(Ethyl(3-(1-(2-methoxyethyl)-1H-imidazol-5-yl)cyclopent-3-en-1-yl)-amino)-2-(trifluoromethyl)benzonitrile a) tert-Butyl (3-(1-(2-methoxyethyl)-1H-imidazol-5-yl)cyclopent-3-en-1-yl)carbamate The compound was prepared as in Example 183(b) from tert-butyl (3-formylcyclopent-3-en-1-yl)carbamate (0.423 g, 2.00 mmol) and 2-methoxyethylamine (0.25 ml, 2.88 mmol). Yield 0.361 g. $^1$H NMR (400 MHz, CDCl$_3$): 1.45 (9H, s), 2.40 (1H, m), 2.54 (1H, m), 2.95 (1H, dd), 3.07 (1H, dd), 3.34 (3H, s), 3.64 (2H, t), 4.19 (2H, t), 4.36 (1H, br s), 4.77 (1H, br s), 5.71 (1H, s), 6.98 (1H, s), 7.52 (1H, s).

b) 3-(1-(2-Methoxyethyl)-1H-imidazol-5-yl)cyclopent-3-enamine dihydrochloride

The compound was prepared as in Example 183(c) from the compound of Example 189(a) (0.361 g, 1.174 mmol). Yield 0.244 g. $^1$H NMR (400 MHz, DMSO-d$_6$): 2.63 (1H, m), 2.71 (1H, m), 2.94 (1H, m), 3.08 (1H, m), 3.27 (3H, s), 3.73 (2H, m), 3.94 (1H, m), 4.48 (2H, t), 6.25 (1H, s), 7.80 (1H, s), 8.33 (3H, br s), 9.14 (1H, d).

c) 4-((3-(1-(2-Methoxyethyl)-1H-imidazol-5-yl)
cyclopent-3-en-1-yl)amino)-2-(trifluoromethyl)benzonitrile The compound was prepared as in Example 183(d) from the compound of Example 189(b) (0.344 g, 1.166 mmol). Yield 0.219 g. ¹H NMR (400 MHz, CDCl₃): 2.51 (1H, m), 2.64 (1H, m), 3.09 (1H, m), 3.22 (1H, m), 3.34 (3H, s), 3.67 (2H, t), 4.21 (2H, t), 4.28 (1H, m), 4.71 (1H, d), 5.78 (1H, br s), 6.71 (1H, dd), 6.87 (1H, d), 7.00 (1H, s), 7.55 (1H, s), 7.58 (1H, d).

d) 4-(Ethyl(3-(1-(2-methoxyethyl)-1H-imidazol-5-yl)cyclopent-3-en-1-yl)-amino)-2-(trifluoromethyl)benzonitrile The compound was prepared as in Example 137(d) from the compound of Example 189(c) (0.109 g, 0.29 mmol). Extraction with DCM. Yield 79 mg. ¹H NMR (400 MHz, CDCl₃): 1.24 (3H, t), 2.69 (1H, m), 2.84 (1H, m), 2.99 (1H, dd), 3.10 (1H, dd), 3.36 (3H, s), 3.47 (2H, q), 3.69 (2H, t), 4.24 (2H, t), 4.67 (1H, m), 5.85 (1H, s), 6.81 (1H, dd), 6.98 (1H, d), 7.01 (1H, s), 7.57 (1H, s), 7.58 (1H, d).

Example 190

4-((3-(1-(2-Methoxyethyl)-1H-imidazol-5-yl)cyclopent-3-en-1-yl)(methyl)-amino)-2-(trifluoromethyl)benzonitrile The compound was prepared as in Example 137(d) from the compound of Example 189(c) (0.11 g, 0.292 mmol) and iodomethane (45 µl, 0.731 mmol). Yield 59 mg. ¹H NMR (400 MHz, CDCl₃): 2.64 (1H, m), 2.79 (1H, m), 2.79 (1H, dd), 2.93 (3H, s), 3.02 (1H, dd), 3.13 (1H, dd), 3.36 (3H, s), 3.68 (2H, t), 4.24 (2H, t), 4.80 (1H, m), 5.84 (1H, br s), 6.87 (1H, dd), 7.03 (2H, m), 7.56 (1H, s), 7.60 (1H, d).

Example 191

4-(Ethyl(3-(1-(2-methoxy-2-methylpropyl)-1H-imidazol-5-yl)cyclopent-3-en-1-yl)amino)-2-(trifluoromethyl)benzonitrile (enantiomer 1)

a) tert-Butyl (3-(1-(2-methoxy-2-methylpropyl)-1H-imidazol-5-yl)cyclopent-3-en-1-yl)carbamate A solution of tert-butyl (3-formylcyclopent-3-en-1-yl)carbamate (5.0 g, 23.66 mmol) and 2-methoxy-2-methylpropan-1-amine (2.44 g, 23.66 mmol) in THF (50 ml) was stirred for 6 h. TosMIC (3.7 g, 18.96 mmol) and K₂CO₃ (2.94 g, 21.29 mmol) were added and stirred for 16 h (monitored by TLC). The mixture was diluted with cold water and extracted with EtOAc. The combined organic layers were washed with brine, dried, filtered and concentrated. Purification by flash chromatography afforded 1.0 g of the title compound. LC-MS: m/z=336.2 (M+1). Enantiomers were separated using chiral preparative HPLC (Column: Daicel Chiralpak IA, 4.6×250 mm, 5 µm particle size, eluent A: n-hexane+0.1% DEA, eluent B: EtOH, isocratic elution: 30% B, flow 1.0 ml/min, detection 300 nm) to afford 0.35 g of enantiomer 1 (rt 4.04 min) and 0.35 g of enantiomer 2 (rt 4.83 min).

b) 3-(1-(2-Methoxy-2-methylpropyl)-1H-imidazol-5-yl)cyclopent-3-enamine dihydrochloride (enantiomer 1)

The compound was prepared as in Example 175(b) from the compound of Example 191(a), enantiomer 1 (0.35 g). Yield 0.2 g. ¹H NMR (300 MHz, d₆-DMSO): 1.11 (6H, s), 2.62 (1H, m), 2.71 (1H, m), 2.93 (1H, dd), 3.05 (1H, dd), 3.14 83H, s), 3.93 (1H, m), 4.28 (2H, s), 6.27 (1H, s), 7.75 (1H, s), 8.3 (3H, br s), 8.9 (1H, s), 14.8 (1H, br s).

c) (4-((3-(1-(2-Methoxy-2-methylpropyl)-1H-imidazol-5-yl)cyclopent-3-en-1-yl)amino)-2-(trifluoromethyl)benzonitrile (enantiomer 1)

The compound was prepared as in Example 183(d) from the compound of Example 191(b), enantiomer 1 (0.188 g, 0.61 mmol). Yield 0.124 g. ¹H NMR (400 MHz, CDCl₃): 1.12 (3H, s), 1.13 (3H, s), 2.50 (1H, m), 2.62 (1H, m), 3.07 (1H, m), 3.19 (3H, s), 3.20 (1H, m), 4.01 (2H, s), 4.27 (1H, m), 4.90 (1H, d), 5.84 (1H, br s), 6.70 (1H, dd), 6.86 (1H, d), 7.00 (1H, s), 7.57 (1H, d), 7.61 (1H, s).

d) 4-(Ethyl(3-(1-(2-methoxy-2-methylpropyl)-1H-imidazol-5-yl)cyclopent-3-en-1-yl)amino)-2-(trifluoromethyl)benzonitrile (enantiomer 1)

The compound was prepared as in Example 137(d) starting from the compound of Example 191(c), enantiomer 1 (0.124 mg, 0.307 mmol). Extracted with DCM. Yield 76 mg. ¹H NMR (400 MHz, CDCl₃): 1.14 (3H, s), 1.15 (3H, s), 1.23 (3H, t), 2.68 (1H, m), 2.83 (1H, m), 2.97 (1H, m), 3.08 (1H, m), 3.21 (3H, s), 3.46 (2H, q), 4.05 (2H, s), 4.65 (1H, m), 5.91 (1H, m), 6.81 (1H, dd), 6.98 (1H, d), 6.99 (1H, s), 7.57 (1H, dd), 7.64 (1H, s).

Example 192

4-(Ethyl(3-(1-(2-methoxy-2-methylpropyl)-1H-imidazol-5-yl)cyclopent-3-en-1-yl)amino)-2-(trifluoromethyl)benzonitrile (enantiomer 2)

The compound was prepared as in Example 191 from the compound of Example 191(b), enantiomer 2 (0.162 g, 0.526 mmol). Yield 49 mg. ¹H NMR (400 MHz, CDCl₃): 1.14 (3H, s), 1.15 (3H, s), 1.23 (3H, t), 2.68 (1H, m), 2.83 (1H, m), 2.97 (1H, m), 3.08 (1H, m), 3.21 (3H, s), 3.46 (2H, q), 4.05 (2H, s), 4.65 (1H, m), 5.91 (1H, m), 6.81 (1H, dd), 6.98 (1H, d), 6.99 (1H, s), 7.57 (1H, dd), 7.64 (1H, s).

Example 193

4-((3-(1H-imidazol-1-yl)-5,5-dimethylcyclopent-2-en-1-yl)(methyl)amino)-2-(trifluoromethyl)benzonitrile The compound was prepared as in Example 137(d) starting from the compound of Example 180(g) (0.435 g, 1.256 mmol) and iodomethane (0.172 ml, 2.76 mmol). Yield 0.322 g. ¹H NMR (400 MHz, CDCl₃): 1.01 (1H, s), 1.40 (3H, s), 2.64 (1H, dd), 2.85 (1H, dt), 2.90 (3H, s), 4.69 (1H, t), 5.55 (1H, m), 6.88 (1H, dd), 7.04 (1H, d), 7.16 (1H, m), 7.21 (1H, m), 7.62 (1H, dd), 7.74 (1H, s). The enantiomers were separated using chiral preparative HPLC (Column: Daicel Chiralpak IA, 20 mm×250 mm, 5 µm particle size, eluent A: MTBE+0.2% DEA, eluent B: THF+0.2% DEA, isocratic elution: 2% B, flow 20 ml/min, detection 300 nm) to afford 83 mg of enantiomer 1 (rt 17 min) and 81 mg of enantiomer 2 (rt 22.5 min).

Example 194

4-((3-Chloro-4-(1-ethyl-1H-imidazol-5-yl)-2,2-dimethylcyclopent-3-en-1-yl)-(ethyl)amino)-2-(trifluoromethyl)benzonitrile a) 6,6-Dimethyl-1,4-dioxaspiro[4.4]nonan-7-one

To a solution of 2,2-dimethylcyclopentane-1,3-dione (20.0 g, 0.159 mol) in toluene (250 ml) were added ethylene glycol (9 ml, 0.159 mol) and p-TSOH (cat). The mixture was refluxed under Dean-Stark trap for 4 h. The solvent was removed and the residue was purified by column chromatography to give 12.1 g of the title compound. $^1$H NMR (400 MHz; DMSO-$d_6$): 3.85-3.97 (m, 4H), 2.32 (t, 2H), 2.05 (t, 2H), 0.92 (s, 6H).

b) 6,6-Dimethyl-1,4-dioxaspiro[4.4]nonan-7-one oxime

To a solution of the compound of Example 194(a) (8.0 g, 0.047 mol) in MeOH (150 ml) were added pyridine (5.7 ml, 0.071 mol) and NH$_2$OH.HCl (4.91 g, 0.071 mol) at 0° C. The mixture was stirred at RT for 4 h. Solvent was distilled off and the mixture was treated with water and extracted with DCM. The organic layer was washed with water, dried, filtered and concentrated. Yield 8.1 g. $^1$H NMR (400 MHz; CDCl$_3$): 3.97 (s, 4H), 2.58 (t, 2H), 1.93 (t, 2H), 1.12 (s, 6H).

c) 6,6-Dimethyl-1,4-dioxaspiro[4.4]nonan-7-amine

To a solution of the compound of Example 194(b) (2.0 g, 0.014 mol) in EtOH (35 ml) was added Raney nickel (3.0 g). The mixture was stirred under hydrogen (1 atm) at RT for 16 h. The mixture was filtered through a Celite bed, washed with EtOH and the filtrate was concentrated under reduced pressure. The residue was purified by column chromatography over basic alumina. Yield 0.9 g. $^1$H NMR (400 MHz; DMSO-$d_6$): 3.80 (bs, 4H), 2.86 (t, 1H), 1.71-1.90 (m, 2H), 1.57-1.65 (m, 1H), 1.21-1.32 (m, 1H), 0.81 (s, 3H), 0.76 (s, 3H); MS: m/z=172.10 [M+1]$^+$.

d) 4-((6,6-Dimethyl-1,4-dioxaspiro[4.4]nonan-7-yl)amino)-2-(trifluoromethyl)benzonitrile The compound was prepared as in Example 137(c) from the compound of Example 194(c) (1.62 g, 9.46 mmol) and using 2.2 equivalent of DIPEA. Purification by flash chromatography afforded 2.33 g of the title compound. $^1$H NMR (400 MHz, CDCl$_3$): 0.96 (3H, s), 1.06 (3H, s), 1.51 (1H, m), 1.92 (2H, m), 2.27 (1H, m), 3.69 (1H, m), 3.96 (4H, m), 4.95 (1H, d), 6.68 (1H, dd), 6.84 (1H, d), 7.52 (1H, d).

e) 4-((6,6-Dimethyl-1,4-dioxaspiro[4.4]nonan-7-yl)(ethyl)amino)-2-(trifluoromethyl)-benzonitrile The compound was prepared as in Example 132(d) from the compound of Example 194(d) (1.16 g, 3.41 mmol). Extraction with DCM. Yield 1.06 g. $^1$H NMR (400 MHz, CDCl$_3$): 0.82 (3H, s), 1.09 (3H, s), 1.17 (3H, t), 1.89 (2H, m), 2.00 (2H, m), 3.39 (1H, m), 3.65 (1H, m), 2.95 (4H, m), 4.28 (1H, t), 6.89 (1H, dd), 7.08 (1H, d), 7.54 (1H, d).

f) 4-((2,2-Dimethyl-3-oxocyclopentyl)(ethyl)amino)-2-(trifluoromethyl)-benzonitrile A solution of the compound of Example 194(e) (1.06 g, 2.68 mmol) and TsOH (0.127 g, 0.669 mmol) in acetone-water (12.5 ml-5 ml) was stirred at RT until the reaction was completed. The mixture was neutralized by saturated NaHCO$_3$. Acetone was evaporated and the residue was diluted with water and extracted with DCM. The combined organic extracts were washed water and brine, dried, filtered and evaporated. Yield 0.886 g. $^1$H NMR (400 MHz, CDCl$_3$): 0.96 (3H, s), 1.18 (3H, s), 1.22 (3H, t), 2.26 (1H, m), 2.26 (1H, m), 2.45-2.62 (2H, m), 3.32 (1H, m), 3.47 (1H, m), 4.37 (1H, t), 6.91 (1H, dd), 7.08 (1H, d), 7.59 (1H, d).

g) 4-((3-Chloro-4-formyl-2,2-dimethylcyclopent-3-en-1-yl)(ethyl)amino)-2-(trifluoromethyl)benzonitrile A solution of the compound of Example 194(f) (0.488 g, 1.505 mmol) and 1-tert-butoxy-N,N,N',N'-tetramethylmethanediamine (1.5 ml, 7.26 mmol) in dry toluene (7.5 ml) was stirred at 70° C. temperature until the reaction was completed. Water and saturated NH$_4$Cl were added to the cooled mixture which was extracted with ethyl acetate. The organic phase was washed water and brine, dried, filtered and evaporated to afford 0.649 g 4-((4-((dimethylamino)methylene)-2,2-dimethyl-3-oxocyclopentyl)(ethyl)amino)-2-(trifluoromethyl)benzonitrile. This material was dissolved in dry DMF (7.5 ml) and treated with oxalyl chloride (0.40 ml, 4.59 mmol). The mixture was stirred at 70° C. until the reaction reached completion. The cooled mixture was diluted with water and saturated NH$_4$Cl and extracted with TBME. The combined organic extracts were washed with water and brine, dried, filtered and evaporated to afford 0.440 g of the title compound. $^1$H NMR (400 MHz, CDCl$_3$): 1.05 (3H, s), 1.23 (3H, t), 1.36 (3H, s), 2.86 (1H, dd), 3.02 (1H, dd), 3.25-3.45 (2H, m), 4.52 (1H, dd), 6.87 (1H, dd), 7.04 (1H, d), 7.61 (1H, dd), 10.04 (1H, s).

h) 4-((3-Chloro-4-(1-ethyl-1H-imidazol-5-yl)-2,2-dimethylcyclopent-3-en-1-yl)(ethyl)amino)-2-(trifluoromethyl)benzonitrile The compound was prepared as in Example 183(b) from the compound of Example 194(g) (0.225 g, 0.607 mml) and ethylamine (0.50 ml, 1.00 mmol; 2 M in THF). Yield 0.162 g. $^1$H NMR (400 MHz, CDCl$_3$): 1.04 (3H, s), 1.27 (3H, t), 1.35 (3H, s), 1.44 (3H, t), 2.87 (1H, dd), 3.15 (1H, dd), 3.49 (2H, m), 3.99 (2H, q), 4.56 (1H, dd), 6.90 (1H, dd), 7.08 (1H, d), 7.14 (1H, s), 7.56 (1H, s), 7.61 (1H, dd).

Example 195

4-(Ethyl(3-(1-methyl-1H-imidazol-5-yl)cyclopent-3-en-1-yl)amino)-2-(trifluoromethyl)-benzonitrile a) tert-Butyl (3-(1-methyl-1H-imidazol-5-yl)cyclopent-3-en-1-yl)carbamate

A mixture of tert-butyl (3-formylcyclopent-3-en-1-yl)carbamate (0.423 g, 2.00 mmol) and methylamine (2.5 ml, 5.0 mmol; 2 M in MeOH) in DCM (7.5 ml) was stirred at RT until all the aldehyde had reacted. Solvents were evaporated. The residue was dissolved in 1,2 dichloroethane (10 ml) and treated with tosylmethyl isocyanide (0.488 g, 2.50 mmol) and DBU (0.603 ml, 2.00 mmol). The mixture was stirred at 60° C. After the reaction was completed the mixture was cooled, diluted with DCM and washed with water and brine. Organic phase was dried, filtered and evaporated. Purification by flash chromatography afforded 0.249 g of the title compound. $^1$H NMR (400 MHz, CDCl$_3$): 1.45 (9H, s), 2.41

(1H, m), 2.54 (1H, m), 2.95 (1H, m), 3.07 (1H, m), 3.72 (3H, s), 4.37 (1H, br s), 4.81 (1H, br s), 5.81 (1H, m), 6.97 (1H, s), 7.39 (1H, s).

b) 3-(1-Methyl-1H-imidazol-5-yl)cyclopent-3-enamine dihydrochloride

The compound was prepared as in Example 183(c) starting from the compound of Example 195(a) (0.249 g, 0.946 mmol). Yield 0.206 g. $^1$H NMR (400 MHz, DMSO-$d_6$): 2.63 (1H, m), 2.69 (1H, m), 2.95 (1H, m), 3.07 (1H, m), 3.92 (3H, s), 3.94 (1H, m), 6.27 (1H, m), 7.72 (1H, d), 8.28 (3H, br s), 9.02 (1H, s).

c) 4-((3-(1-Methyl-1H-imidazol-5-yl)cyclopent-3-en-1-yl)amino)-2-(trifluoromethyl)-benzonitrile The compound was prepared as in Example 183(d) starting from the compound of Example 195(b) (0.206 g, 0.872 mmol). Yield 0.132 g. $^1$H NMR (400 MHz, CDCl$_3$): 2.53 (1H, m), 2.63 (1H, m), 3.10 (1H, m), 3.21 (1H, m), 3.75 (3H, s), 4.28 (1H, m), 4.98 (1H, d), 5.88 (1H, m), 6.71 (1H, dd), 6.88 (1H, d), 6.98 (1H, s), 7.42 (1H, s), 7.57 (1H, d).

d) 4-(Ethyl(3-(1-methyl-1H-imidazol-5-yl)cyclopent-3-en-1-yl)amino)-2-(trifluoromethyl)-benzonitrile The compound was prepared as in Example 183(e) starting from the compound of Example 195(c) (0.127 g, 0.382 mmol). Yield 0.116 g. $^1$H NMR (400 MHz, CDCl$_3$): 1.24 (3H, t), 2.70 (1H, m), 2.84 (1H, m), 3.00 (1H, m), 3.10 (1H, m), 3.46 (2H, q), 3.78 (3H, d), 4.67 (1H, m), 5.94 (1H, m), 6.80 (1H, dd), 6.99 (1H, d), 7.00 (1H, s), 7.44 (1H, s), 7.58 (1H, dd). The enantiomers of were separated using chiral preparative HPLC (Column: Daicel Chiralpak IA, 20 mm×250 mm, 5 µm particle size, eluent A: n-hexane+0.2% DEA, eluent B: EtOH+0.2% DEA, isocratic elution: 15% B, flow 20 ml/min, detection 300 nm) to afford 29 mg of enantiomer 1 (rt 21.3 min) and 28 mg of enantiomer 2 (rt 25 min).

Example 196

4-((3-(1-(2-(Benzyloxy)ethyl)-1H-imidazol-5-yl) cyclopent-3-en-1-yl)(ethyl)-amino)-2-(trifluoromethyl)benzonitrile a) tert-Butyl (3-(1-(2-(benzyloxy)ethyl)-1H-imidazol-5-yl)cyclopent-3-en-1-yl)carbamate The compound was prepared as in Example 183(b) starting from tert-butyl (3-formylcyclopent-3-en-1-yl)carbamate (0.528 g, 2.5 mmol), 2-(benzyloxy)ethanamine hydrochloride (0.563 g, 3.00 mmol), DIPEA (0.55 ml, 3.16 mmol), tosylmethyl isocyanide (0.635 g, 3.25 mmol) and DBU (0.75 ml, 5.02 mmol). Yield 0.669 g. LC-MS: m/z=384.38 (M+1)$^+$.

b) 3-(1-(2-(Benzyloxy)ethyl)-1H-imidazol-5-yl)cyclopent-3-enamine

The compound was prepared as in Example 187(b) starting from the compound of Example 196(a) (0.669 g, 1.745 mmol). Yield 0.325 g. $^1$H NMR (400 MHz, CDCl$_3$): 2.26 (1H, m), 2.41 (1H, m), 2.82 (1H, m), 2.95 (1H, m), 3.71 (1H, m), 3.72 (2H, t), 4.23 (2H, t), 4.48 (2H, s), 5.64 (1H, m), 6.98 (1H, s), 7.23-7.35 (5H, m), 7.53 (1H, d).

c) 4-((3-(1-(2-(Benzyloxy)ethyl)-1H-imidazol-5-yl) cyclopent-3-en-1-yl)amino)-2-(trifluoromethyl)benzonitrile The compound was prepared as in Example 187(c) starting from the compound of Example 196(b) (0.325 g, 1.147 mmol). Yield 0.233 g. $^1$H NMR (400 MHz, CDCl$_3$): 2.46 (1H, m), 2.58 (1H, m), 3.01 (1H, m), 3.15 (1H, m), 3.72 (2H, t), 4.21 (1H, m), 4.23 (2H, t), 4.48 (2H, s), 5.07 (1H, d), 5.72 (1H, m), 6.68 (1H, dd), 6.84 (1H, d), 6.97 (1H, s), 7.2-7.34 (5H, m), 7.54 (2H, m).

d) 4-((3-(1-(2-(Benzyloxy)ethyl)-1H-imidazol-5-yl) cyclopent-3-en-1-yl)-(ethyl)amino)-2-(trifluoromethyl)benzonitrile The compound was prepared as in Example 183(e) starting from the compound of Example 196(c) (0.233 g, 0.515 mmol). Yield 0.146 g. $^1$H NMR (400 MHz, CDCl$_3$): 1.21 (3H, t), 2.63 (1H, m), 2.93 (1H, m), 2.80 (1H, m), 3.05 (1H, m), 3.41 (2H, m), 3.75 (2H, t), 4.27 (2H, t), 4.51 (2H, s), 4.61 (1H, m), 5.79 (1H, m), 6.78 (1H, dd), 6.96 (1H, d), 7.01 (1H, s), 7.23 (2H, m), 7.28-7.36 (3H, m), 7.56 (1H, dd), 7.58 (1H, s).

Example 197

4-((3-(1-(1,3-Dihydroxypropan-2-yl)-1H-imidazol-5-yl)cyclopent-3-en-1-yl)-(ethyl)amino)-2-(trifluoromethyl)benzonitrile a) 4-(3-Oxo-2-azabicyclo[2.2.1]hept-5-en-2-yl)-2-(trifluoromethyl)benzonitrile A mixture of 4-iodo-2-(trifluoromethyl)benzonitrile (2.97 g, 10.0 mmol), 2-azabicyclo[2.2.1]hept-5-en-3-one (1.20 g, 11.0 mmol), N,N'-dimethylethylenediamine (0.16 ml, 1.50 mmol), copper iodide (0.143 g, 0.750 mmol) and potassium phosphate (4.25 g, 20.0 mmol) in dry toluene (12.5 ml) was stirred at 110° C. After the reaction was completed the cooled mixture was filtered. The filter cake was washed with toluene and the filtrate was evaporated. Purification by flash chromatography afforded 1.872 g of the title compound. $^1$H NMR (400 MHz, CDCl$_3$): 2.39 (1H, dt), 2.50 (1H, dt), 3.58 (1H, m), 4.93 (1H, m), 6.76 (1H, m), 7.04 (1H, ddd), 7.77 (2H, m), 7.88 (1H, m).

b) 4-((4-(Hydroxymethyl)cyclopent-2-en-1-yl) amino)-2-(trifluoromethyl)-benzonitrile Sodium borohydride (0.509 g, 13.45 mmol) was stepwise added to a cooled solution of the compound of Example 197(a) (1.871 g, 6.72 mmol) in MeOH (30 ml). The mixture was stirred at RT until all starting material was consumed. Most of the methanol was evaporated, water and DCM was added. Aqueous phase was extracted with DCM. Combined organic extracts were washed with water and brine, dried, filtered and evaporated. Purification by flash chromatography afforded 1.517 g of the title compound. $^1$H NMR (400 MHz, CDCl$_3$): 1.54 (1H, dt), 1.56 (1H, br s), 2.58 (1H, m), 2.96 (1H, m), 3.62 (1H, dd), 3.71 (1H, dd), 4.57 (1H, m), 4.91 (1H, br s), 5.92 (2H, m), 6.70 (1H, dd), 6.86 (1H, d), 7.53 (1H, dd).

c) 4-((3-Formylcyclopent-3-en-1-yl)amino)-2-(trifluoromethyl)benzonitrile

The compound was prepared as in Example 183(a) starting from the compound of Example 197(b) (1.503 g, 5.32 mmol). Yield 0.658 g. $^1$H NMR (400 MHz, CDCl$_3$): 2.53 (1H, m), 2.59 (1H, m), 3.08 (1H, m), 3.17 (1H, m), 4.33 (1H, m), 4.61 (1H, m), 6.69 (1H, dd), 6.86 (2H, m), 7.58 (1H, d), 9.80 (1H, s). LC-MS: m/z=281.14 (M+1)$^+$.

d) 4-((3-(1-(2-Phenyl-1,3-dioxan-5-yl)-1H-imidazol-5-yl)cyclopent-3-en-1-yl)amino)-2-(trifluoromethyl)benzonitrile The compound was prepared as in Example 183(b) starting from the compound of Example 197(c) (0.366 g, 1.306 mmol) and 2-phenyl-1,3-dioxan-5-amine (*Bioorg. Med. Chem.* 2006, 14, 2850) (0.293 g, 1.632 mmol). Yield 0.228 g. $^1$H NMR (400 MHz, CDCl$_3$): 2.52 (1H, m), 2.67 (1H, m), 3.10 (1H, m), 3.25 (1H, m), 4.29 (1H, m), 4.34 (1H, m), 4.43 (4H, m), 4.68 (1H, d), 5.53 (1H, m), 5.68 (1H, s), 6.71 (1H, dd), 6.87 (1H, d), 7.07 (1H, s), 7.40 (3H, m), 7.51 (2H, m), 7.59 (1H, d), 8.43 (1H, d).

e) 4-(Ethyl(3-(1-(2-phenyl-1,3-dioxan-5-yl)-1H-imidazol-5-yl)cyclopent-3-en-1-yl)amino)-2-(trifluoromethyl)benzonitrile The compound was prepared as in Example 137(d) starting from the compound of Example 197(d) (0.228 g, 0.475 mmol). Extracted with DCM. Purification by flash chromatography afforded 0.163 g of the title compound. $^1$H NMR (400 MHz, CDCl$_3$): 1.24 (3H, t), 2.69 (1H, m), 2.88 (1H, m), 2.99 (1H, m), 3.11 (1H, m), 3.47 (2H, q), 4.36 (1H, m), 4.40-4.50 (4H, m), 4.67 (1H, m), 5.60 (1H, m), 5.70 (1H, s), 6.81 (1H, dd), 6.97 (1H, d), 7.07 (1H, s), 7.40 (3H, m), 7.52 (2H, m), 7.59 (1H, dd), 8.45 (1H, d).

f) 4-((3-(1-(1,3-Dihydroxypropan-2-yl)-1H-imidazol-5-yl)cyclopent-3-en-1-yl)(ethyl)amino)-2-(trifluoromethyl)benzonitrile A solution of the compound of Example 197(e) (0.163 g, 0.321 mmol) in methanol (2 ml) was treated with 37% aqueous HCl (0.133 ml, 1.603 mmol) and stirred overnight at RT. The mixture was concentrated, diluted with water and neutralized with saturated NaHCO$_3$. The aqueous phase was extracted with DCM. Combined organic extracts were washed with brine, dried, filtered and evaporated. Purification by flash chromatography afforded 70 mg of the title compound. $^1$H NMR (400 MHz, CDCl$_3$): 1.23 (3H, t), 2.70 (1H, m), 2.81 (1H, m), 2.93-3.10 (2H, m), 3.47 (2H, q), 4.07 (4H, m), 4.55 (1H, m), 4.65 (1H, m), 5.92 (1H, m), 6.79 (1H, dd), 6.91 (1H, s), 6.96 (1H, d), 7.58 (1H, d), 7.74 (1H, s). LC-MS: m/z=421.73 (M+1)$^+$.

Example 198

4-(Ethyl(3-(1-(2-(2-hydroxyethoxy)ethyl)-1H-imidazol-5-yl)cyclopent-3-en-1-yl)amino)-2-(trifluoromethyl)benzonitrile a) 2-(2-((4-Methoxybenzyl)oxy)ethoxy)ethanamine

A solution of 2-(2-aminoethoxy)ethanol (2.5 ml, 24.92 mkol) in dry THF (27 ml) was treated with NaH (1.0 g, 25.0 mmol; 60 wt-% in mineral oil). The mixture was refluxed for 30 min and then 4-methoxybenzyl chloride (3.0 ml, 22.13 mmol) was added. Rexluxing was continued for 5 h. The cooled mixture was treated with water and THF was evaporated. The residue was treated with 1M HCl and washed with DCM. The aqueous phase was made alkaline with 2M NaOH and extracted with DCM. Combined organic phases were dried, filtered and evaporated to afford 2.51 g of the title compound. $^1$H NMR (400 MHz, CDCl$_3$): 1.69 (2H, br s), 2.85 (2H, t), 3.50 (2H, t), 3.62 (4H, m), 3.80 (3H, s), 4.50 (2H, s), 6.88 (2H, m), 7.27 (2H, m).

b) 4-((3-(1-(2-(2-((4-Methoxybenzyl)oxy)ethoxy)ethyl)-1H-imidazol-5-yl)-cyclopent-3-en-1-yl)amino)-2-(trifluoromethyl)benzonitrile The compound was prepared as in Example 183(b) from 4-((3-formylcyclopent-3-en-1-yl)amino)-2-(trifluoromethyl)benzonitrile (0.358 g, 1.277 mmol) and the compound of Example 198(a) (0.36 g, 1.597 mmol). Yield 0.546 g. $^1$H NMR (400 MHz, CDCl$_3$): 2.46 (1H, m), 2.61 (1H, m), 3.05 (1H, m), 3.19 (1H, m), 3.54-3.60 (5H, m), 3.76-3.81 (2H, m), 3.80 (3H, s), 4.22 (2H, dt), 4.45 (2H, s), 4.77 (1H, d), 5.77 (1H, m), 6.68 (1H, dd), 6.85 (1H, d), 6.86 (2H, m), 6.99 (1H, m), 7.23 (1H, m), 7.56 (1H, m).

c) 4-(Ethyl(3-(1-(2-(2-((4-methoxybenzyl)oxy)ethoxy)ethyl)-1H-imidazol-5-yl)cyclopent-3-en-1-yl)amino)-2-(trifluoromethyl)benzonitrile The compound was prepared as in Example 137(d) from the compound of Example 198(b) (0.546 g, 1.037 mmol). Extracted with DCM. Yield 0.37 g after flash chromatography. $^1$H NMR (400 MHz, CDCl$_3$): 1.22 (3H, t), 2.67 (1H, m), 2.83 (1H, m), 2.95 (1H, m), 3.08 (1H, m), 3.44 (2H, q), 3.558 (2H, m), 3.61 (2H, m), 3.78-3.81 (2H, m), 3.80 (3H, s), 4.25 (2H, t), 4.47 (2H, s), 4.63 (1H, m), 5.84 (1H, m), 6.79 (1H, m), 6.87 (2H, m), 6.97 (1H, d), 7.00 (1H, s), 7.25 (2H, m), 7.57 (2H, m).

d) 4-(Ethyl(3-(1-(2-(2-hydroxyethoxy)ethyl)-1H-imidazol-5-yl)cyclopent-3-en-1-yl)amino)-2-(trifluoromethyl)benzonitrile A solution of the compound of Example 198(c) (0.139 g, 0.25 mmol) in acetonitrile (1.5 ml) was treated with triphenylphosphine hydrobromide (0.094 g, 0.275 mmol) and reacted for 1 h at 100° C. in a microwave synthesizer (Biotage Initiator). Solvent was evaporated. The residue was diluted with DCM, washed with saturated NaHCO$_3$, water and brine. Organic phase was dried, filtered and evaporated. Purification by flash chromatography afforded 21 mg of the title compound. $^1$H NMR (400 MHz, CDCl$_3$): 1.24 (3H, t), 2.69 (1H, m), 2.85 (1H, m), 2.99 (1H, m), 3.10 (1H, m), 3.46 (2H, q), 3.49 (1H, s), 3.56 (2H, m), 3.72 (2H, m), 3.81 (2H, t), 4.28 (2H, t), 4.67 (1H, m), 5.86 (1H, m), 6.81 (1H, dd), 6.98 (1H, d), 7.01 (1H, s), 7.58 (1H, d), 7.59 (1H, dd).

Example 199

4-(Ethyl(3-(1-(2-hydroxy-2-methylpropyl)-1H-imidazol-5-yl)cyclopent-3-en-1-yl)amino)-2-(trifluoromethyl)benzonitrile a) tert-Butyl (3-(1-(2-hydroxy-2-methylpropyl)-1H-imidazol-5-yl)cyclopent-3-en-1-yl)carbamate The compound was prepared as in Example 183(b) from tert-butyl (3-formylcyclopent-3-en-1-yl)carbamate (0.634 g, 3.0 mmol) and 1-amino-2-methylpropan-2-ol (0.40 g, 4.49 mmol). Yield 0.446 g. $^1$H NMR (400 MHz, CDCl$_3$): 1.22 (3H, s), 1.23 (3H, s), 1.45 (9H, s), 2.39 (1H, m), 2.54 (1H, m), 2.92 (1H, m), 3.05 (1H, m), 4.03 (2H, s), 4.35 (1H, br s), 4.81 (1H, br s), 5.84 (1H, m), 6.97 (1H, d), 7.57 (1H, d).

b) 1-(5-(4-Aminocyclopent-1-en-1-yl)-1H-imidazol-1-yl)-2-methylpropan-2-ol dihydrochloride The compound was prepared as in Example 183(c) from the compound of Example 199(a) (0.446 g, 1.388 mmol). Yield 0.447 g. $^1$H NMR (400 MHz, DMSO-d$_6$): 1.10 (3H, s), 1.13 (3H, s), 2.63 (1H, m), 2.73 (1H, m), 2.92 (1H, m), 3.05 (1H, m), 3.93 (1H, m), 4.21 (1H, m), 6.29 (1H, m), 7.76 (1H, d), 8.35 (3H, br s), 9.04 (1H, d), 14.8 (1H, br s).

c) 4-((3-(1-(2-Hydroxy-2-methylpropyl)-1H-imidazol-5-yl)cyclopent-3-en-1-yl)amino)-2-(trifluoromethyl)benzonitrile The compound was prepared as in Example 183(d) from the compound of Example 199(b) (0.447 g, 1.383 mmol). Yield 0.243 g. $^1$H NMR (400 MHz, CDCl$_3$): 1.22 (3H, s), 1.23 (3H, s), 2.50 (1H, m), 2.61 (1H, m), 3.02 (1H, m), 3.13 (1H, m), 4.02 (2H, m), 4.24 (1H, m), 5.48 (1H, d), 5.89 (1H, m), 6.69 (1H, dd), 6.86 (1H, d), 6.88 (1H, d), 7.52 (1H, d), 7.53 (1H, d).

d) 4-(Ethyl(3-(1-(2-hydroxy-2-methylpropyl)-1H-imidazol-5-yl)cyclopent-3-en-1-yl)amino)-2-(trifluoromethyl)benzonitrile The compound was prepared as in Example 137(d) from the compound of Example 199(c) (0.193 g, 0.494 mmol). Extracted with DCM. Yield 40.8 mg after preparative HPLC. $^1$H NMR (400 MHz, CDCl$_3$): 1.23 (3H, t), 1.26 (3H, s), 1.28 (3H, s), 1.74 (1H, br s), 2.68 (1H, m), 2.84 (1H, m), 2.97 (1H, m), 3.09 (1H, m), 3.46 (2H, q), 4.07 (2H, s), 4.65 (1H, m), 5.99 (1H, m), 6.80 (1H, dd), 6.98 (1H, d), 7.01 (1H, br s), 7.57 (1H, dd), 7.61 (1H, d).

Example 200

4-((3-(1-Ethyl-1H-imidazol-5-yl)cyclopent-3-en-1-yl)(2-hydroxyethyl)amino)-2-(trifluoromethyl)benzonitrile a) tert-Butyl (3-(1-ethyl-1H-imidazol-5-yl)cyclopent-3-en-1-yl)carbamate

The compound was prepared as in Example 183(b) from tert-butyl (3-formylcyclopent-3-en-1-yl)carbamate (0.634 g, 3.0 mmol) and ethylamine (3.0 ml, 6.0 mmol; 2M in THF). Yield 0.674 g. $^1$H NMR (400 MHz, CDCl$_3$): 1.44 (3H, t), 1.46 (9H, s), 2.41 (1H, m), 2.55 (1H, m), 2.96 (1H, m), 3.08 (1H, m), 4.08 (2H, q), 4.37 (1H, br s), 4.76 (1H, br s), 5.75 (1H, m), 6.98 (1H, br s), 7.46 (1H, d)

b) 3-(1-Ethyl-1H-imidazol-5-yl)cyclopent-3-enamine dihydrochloride

The compound was prepared as in Example 183(c) from the compound of Example 200(a) (0.674 g, 2.43 mmol). Yield 0.59 g. $^1$H NMR (400 MHz, DMSO-d$_6$): 1.44 (3H, t), 2.65 (1H, m), 2.72 (1H, m), 2.96 (1H, m), 3.08 (1H, m), 3.95 (1H, m), 4.32 (2H, q), 6.24 (1H, m), 7.79 (1H, d), 8.33 (3H, br s), 9.18 (1H, d), 14.8 (1H, br s).

c) 4-((3-(1-Ethyl-1H-imidazol-5-yl)cyclopent-3-en-1-yl)amino)-2-(trifluoromethyl)benzonitrile The compound was prepared as in Example 183(d) from the compound of Example 200(b) (0.59 g, 2.358 mmol). Yield 0.354 g. $^1$H NMR (400 MHz, CDCl$_3$): 1.46 (3H, t), 2.52 (1H, m), 2.65 (1H, m), 3.11 (1H, m), 3.23 (1H, m), 4.11 (2H, q), 4.29 (1H, m), 4.67 (1H, d), 5.81 (1H, m), 6.71 (1H, dd), 6.87 (1H, d), 7.01 (1H, br s), 7.50 (1H, d), 7.58 (1H, d).

d) 4-((3-(1-Ethyl-1H-imidazol-5-yl)cyclopent-3-en-1-yl)(2-((tetrahydro-2H-pyran-2-yl)oxy)ethyl)amino)-2-(trifluoromethyl)benzonitrile The compound was prepared as in Example 137(d) from the compound of Example 200(c) (0.15 g, 0.433 mmol) and 2-(2-bromoethoxy)tetrahydro-2H-pyran (94 µl, 0.622 mmol). Extracted with DCM. Yield 39 mg after flash chromatography. $^1$H NMR (400 MHz, CDCl$_3$): 1.43 (3H, t), 1.53 (4H, m), 1.72 (2H, m), 2.75 (1H, m), 2.92 (1H, m), 3.01 (1H, m), 3.11 (1H, m), 3.49 (1H, m), 3.59 (1H, m), 3.65 (2H, m), 3.77 (1H, m), 3.91 (1H, m), 4.14 (2H, q), 4.57 (1H, m), 4.69 (1H, m), 5.89 (1H, m), 6.88 (1H, dd), 7.01 (1H, d), 7.12 (1H, d), 7.57 (1H, d), 7.59 (1H, s).

e) 4-((3-(1-Ethyl-1H-imidazol-5-yl)cyclopent-3-en-1-yl)(2-hydroxyethyl)amino)-2-(trifluoromethyl)benzonitrile A solution of the compound of Example 200(d) (39 mg, 0.082 mmol) in MeOH (2 ml) was treated with TsOH (19 mg, 0.099 mmol) and stirred at 50° C. until the reaction was completed. MeOH was evaporated and the residue was diluted with DCM. Saturated NaHCO$_3$ was added. Aqueous phase was extracted with DCM. Combined organic extracts were dried, filtered and evaporated. Purification by preparative HPLC afforded 16 mg of the title compound. $^1$H NMR (400 MHz, CDCl$_3$): 1.47 (3H, t), 1.62 (1H, br s), 2.76 (1H, m), 2.90 (1H, m), 3.01 (1H, m), 3.10 (1H, m), 3.60 (2H, m), 3.84 (2H, t), 4.11 (2H, q), 4.69 (1H, m), 5.87 (1H, m), 6.88 (1H, dd), 6.92 (1H, br s), 7.06 (1H, d), 7.44 (1H, d), 7.56 81H dd).

Example 201

4-(Ethyl(3-(1-(2-(2-hydroxyethoxy)ethyl)-1H-imidazol-5-yl)cyclopent-3-en-1-yl)amino)-2-(trifluoromethyl)benzonitrile a) 4-((3-(1-(2-(2-((tert-Butyldimethylsilyl)oxy)ethoxy)ethyl)-1H-imidazol-5-yl)cyclopent-3-en-1-yl)amino)-2-(trifluoromethyl)benzonitrile The compound was prepared as in Example 183(b) from the compound of Example 197(c) (0.28 g, 1.00 mmol) and 2-(2-(tert-butyldimethylsilyloxy)ethoxy)-ethanamine (0.263 g, 1.2 mmol) (*J. Am. Chem. Soc.*, 2000, 122, 5905). Yield 0.348 g. $^1$H NMR (400 MHz, CDCl$_3$): 0.05 (6H, s), 0.89 (9H, s), 2.50 (1H, m), 2.63 (1H, m), 3.09 (1H, m), 3.22 (1H, m), 3.51 (1H, m), 3.73 (2H, t), 3.79 (2H, t), 4.21 (2H, t), 4.27 (1H, m), 4.74 (1H, d), 5.77 (1H, m), 6.71 (1H, dd), 6.87 (1H, d), 6.99 (1H, s), 7.57 (1H, s), 7.58 (1H, d).

b) 4-((3-(1-(2-2-((tert-Butyldimethylsilyl)oxy) ethoxy)ethyl)-1H-imidazol-5-yl)cyclopent-3-en-1-yl) (ethyl)amino)-2-(trifluoromethyl)benzonitrile The compound was prepared as in Example 137(d) starting from the compound of Example 201(a) (0.174 g, 0.334 mmol). Extracted with DCM. Yield 0.135 g after flash chromatography. $^1$H NMR (400 MHz, CDCl$_3$): 0.06 (6H, s), 0.90 (9H, s), 1.24 (3H, t), 2.68 (1H, m), 2.84 (1H, m), 2.98 (1H, m), 3.09 (1H, m), 3.46 (2H, q), 3.52 (2H, t), 3.74 (2H, t), 3.81 (2H, t), 4.24 (2H, t), 4.66 (1H, m), 5.84 (1H, m), 6.81 (1H, dd), 6.98 (1H, d), 7.00 (1H, s), 7.58 (1H, dd), 7.59 (1H, s).

c) 4-(Ethyl(3-(1-(2-(2-hydroxyethoxy)ethyl)-1H-imidazol-5-yl)cyclopent-3-en-1-yl)amino)-2-(trifluoromethyl)benzonitrile A solution of the compound of Example 201(b) (0.135 g, 0.23 mmol) in MeOH (2 ml) was treated with ammonium fluoride (0.085 g, 2.295 mmol) and stirred at 50° C. until the reaction was completed. MeOH was evaporated and the residue was diluted with DCM. Water was added and aqueous phase was extracted with DCM. Combined organic extracts were washed with water and brine, dried, filtered and evaporated to afford 74 mg of the title compound. $^1$H NMR was identical with the compound of Example 198. The enantiomers of were separated using chiral preparative HPLC (Column: Daicel Chiralpak IA, 20 mm×250 mm, 5 µm particle size, eluent A: n-hexane+0.2% DEA, eluent B: EtOH+0.2% DEA, isocratic elution: 20% B, flow 20 ml/min, detection 300 nm) to afford 21.8 mg of enantiomer 1 (rt 19 min) and 21.2 mg of enantiomer 2 (rt 25.5 min).

Example 202

4-(Ethyl(3-(1-(2-(2-methoxyethoxy)ethyl)-1H-imidazol-5-yl)cyclopent-3-en-1-yl)amino)-2-(trifluoromethyl)benzonitrile a) tert-Butyl (3-(1-(2-(2-methoxyethoxy)ethyl)-1H-imidazol-5-yl)cyclopent-3-en-1-yl)carbamate The compound was prepared as in Example 183(b) from tert-butyl (3-formylcyclopent-3-en-1-yl)carbamate (0.528 g, 2.5 mmol) and 2-(2-methoxyethoxy)ethanamine (0.357 g, 3.0 mmol). Yield 0.257 g. $^1$H NMR (400 MHz, CDCl$_3$): 1.45 (9H, s), 2.40 (1H, m), 2.54 (1H, m), 2.94 (1H, m), 3.07 (1H, m), 3.36 (3H, s), 3.51 (2H, m), 3.57 (2H, m), 3.75 (2H, t), 4.21 (2H, t), 4.36 (1H, br s), 4.77 (1H, br s), 5.71 (1H, m), 6.97 (1H, d), 7.54 (1H, d).

b) 3-(1-(2-(2-Methoxyethoxy)ethyl)-1H-imidazol-5-yl)cyclopent-3-enamine dihydrochloride The compound was prepared as in Example 183(c) from the compound of Example 202(a) (0.257 g, 0.731 mmol). Yield 0.259 g. $^1$H NMR (400 MHz, DMSO-d$_6$): 2.64 (1H, m), 2.72 (1H, m), 2.94 (1H, m), 3.08 (1H, m), 3.21 (3H, s), 3.40 (2H, m), 3.55 (2H, m), 3.75-3.85 (2H, m), 3.94 (1H, m), 4.47 (2H, t), 6.25 (1H, m), 7.80 (1H, d), 8.37 (3H, br s), 9.11 (1H, d), 14.8 (1H, br s).

c) 4-((3-(1-(2-(2-Methoxyethoxy)ethyl)-1H-imidazol-5-yl)cyclopent-3-en-1-yl)amino)-2-(trifluoromethyl)benzonitrile The compound was prepared as in Example 183(d) from the compound of Example 202(b) (0.259 g, 0.731 mmol). Yield 94 mg. $^1$H NMR (400 MHz, CDCl$_3$): 2.52 (1H, m), 2.64 (1H, m), 3.07 (1H, m), 3.20 (1H, m), 3.36 (3H, s), 3.50 (2H, m), 3.57 (2H, m), 3.77 (2H, t), 4.23 (2H, t), 4.27 (1H, m), 5.24 (1H, d), 5.78 (1H, m), 6.71 (1H, dd), 6.88 (1H, d), 6.97 (1H br s), 7.55 (1H, d), 7.56 (1H, d).

d) 4-(Ethyl(3-(1-(2-(2-methoxyethoxy)ethyl)-1H-imidazol-5-yl)cyclopent-3-en-1-yl)amino)-2-(trifluoromethyl)benzonitrile The compound was prepared as in Example 137(d) from the compound of Example 202(c) (94 mg, 0.224 mmol). Extracted with DCM. Yield 21 mg after preparative HPLC. $^1$H NMR (400 MHz, CDCl$_3$): 1.24 (3H, t), 2.69 (1H, m), 2.84 (1H, m), 2.98 (1H, m), 3.10 (1H, m), 3.37 (3H, s), 3.46 (2H, q), 352 (2H, m), 3.59 (2H, m), 3.80 (2H, t), 4.26 (2H, t), 4.66 (1H, m), 5.85 (1H, m), 6.81 (1H, dd), 6.98 (1H, d), 7.00 (1H br s), 7.58 (1H, dd), 7.59 (1H, br s).

Example 203

N-[3-(1H-Imidazol-1-yl)-6,6-dimethylcyclohex-2-enyl]-N,6-dimethyl-5-nitropyridin-2-amine a) N-[3-(1H-imidazol-1-yl)-6,6-dimethylcyclohex-2-enyl]-6-methyl-5-nitropyridin-2-amine The compound was prepared as in Example 131(a) starting from 6-fluoro-2-methyl-3-nitropyridine and the compound of Example 96(e). Yield 36%. $^1$H NMR (400 MHz, CDCl$_3$): 1.02 (3H, s), 1.10 (3H, s), 1.77 (2H, t), 2.55 (2H, m), 2.78 (3H, s), about 4.7 (1H, broad s), 5.08 (1H, m), 5.67-5.68 (1H, m), 6.32 (1H, d), 7.09 (1H, s), 7.12 (1H, s), 7.70 (1H, s), 8.21 (1H, d).

b) N-[3-(1H-Imidazol-1-yl)-6,6-dimethylcyclohex-2-enyl]-N,6-dimethyl-5-nitropyridin-2-amine The compound was prepared as in Example 130 starting from the compound of Example 203(a). After the addition of iodomethane the mixture was maintained at 0° C. for 1 h 15 min. The product was purified by flash chromatography (eluent: 0-1% MeOH/DCM) and then trituration in DCM afforded the title product. Yield 45%. $^1$H NMR (400 MHz, CDCl$_3$): 0.93 (3H, s), 1.08 (3H, s), 1.70-1.81 (1H, m), 2.51-2.59 (1H, m), 2.62-2.70 (1H, m), 2.80 (3H, s), 3.01 (3H, s), 5.63-5.64 (1H, m), 5.88-5.95 (1H, m), 6.40 (1H, d), 7.12 (1H, s), 7.17 (1H, s), 7.76 (1H, s), 8.28 (1H, d). The enantiomers (45 mg) were separated by preparative chiral HPLC (Column Chiralpak IC 20 mm×250 mm 5 µm, A MTBE+0.2% DEA, B EtOH+0.2% DEA, isocratic B 10%, flow 20 ml/min, λ 300 nm) to yield 5.3 mg of enantiomer 1 (rt 23.4 min) and 5.6 mg of enantiomer 2 (rt 27.1 min). The $^1$H NMR spectra of enantiomers were identical with the spectrum of the racemate.

Example 204

5-{[3-(1H-Imidazol-1-yl)-6,6-dimethylcyclohex-2-enyl](methyl)amino}-3-chloropicolinonitrile a) 5-[3-(1H-Imidazol-1-yl)-6,6-dimethylcyclohex-2-enylamino]-3-chloropicolinonitrile The compound was prepared as in Example 131(a) starting from 3-chloro-5-fluoropicolinonitrile and the compound of Example 96(e). The reaction mixture was heated at 100°

C. for 1 h 30 min. The crude product was crystallized in DCM to afford the title product. Yield 58%. $^1$H NMR (400 MHz, CDCl$_3$): 1.04 (3H, s), 1.13 (3H, s), 1.72-1.84 (2H, m), 2.49-2.61 (2H, m), 3.95 (1H, m), 4.55 (1H, d), 5.61-5.63 (1H, m), 6.95 (1H, d), 7.10 (1H, s), 7.12 (1H, s), 7.69 (1H, s), 8.00 (1H, d).

b) 5-{[3-(1H-Imidazol-1-yl)-6,6-dimethylcyclohex-2-enyl](methyl)amino}-3-chloropicolinonitrile The compound was prepared as in Example 203(b) starting from the compound of Example 204(a). The product was purified by flash chromatography (eluent: 0-1% MeOH/DCM) to afford the title compound. Yield 46%. $^1$H NMR (400 MHz, CDCl$_3$): 0.99 (3H, s), 1.12 (3H, s), 1.73-1.84 (2H, m), 2.52-2.61 (1H, m), 2.64-2.72 (1H, m), 2.97 (3H, s), 4.51-4.52 (1H, m), 5.61-5.63 (1H, m), 7.05 (1H, d), 7.14 (1H, s), 7.17 (1H, s), 7.76 (1H, s), 8.23 (1H, d).

Example 205

5-{[3-(1H-Imidazol-1-yl)-6,6-dimethylcyclohex-2-enyl](methyl)amino}-3-fluoropicolinonitrile a) 5-[3-(1H-Imidazol-1-yl)-6,6-dimethylcyclohex-2-enylamino]-3-fluoropicolinonitrile The compound was prepared as in Example 131(a) starting from 3,5-difluoropicolinonitrile and the compound of Example 96(e). The mixture was heated at 100° C. for 1 h. The crude product was purified by flash chromatography (eluent: 0-3% MeOH/DCM) to afford the title product. $^1$H NMR (400 MHz, CDCl$_3$): 1.04 (3H, s), 1.12 (3H, s), 1.69-1.84 (2H, m), 2.49-2.60 (2H, m), 3.92 (1H, m), 4.81 (1H, d), 5.62-5.63 (1H, m), 6.67 (1H, dd), 7.09 (1H, s), 7.12 (1H, s), 7.68 (1H, s), 8.00 (1H, dd).

b) 5-{[3-(1H-Imidazol-1-yl)-6,6-dimethylcyclohex-2-enyl](methyl)amino}-3-fluoropicolinonitrile The compound was prepared as in Example 203(b) starting from the compound of Example 205(a). The product was purified by flash chromatography (eluent: 0-3% MeOH/DCM) to afford the title product. $^1$H NMR (400 MHz, CDCl$_3$): 0.99 (3H, s), 1.12 (3H, s), 1.72-1.85 (2H, m), 2.52-2.61 (1H, m), 2.65-2.73 (1H, m), 2.98 (3H, s), 4.51 (1H, m), 5.64 (1H, m), 6.77 (1H, dd), 7.14 (1H, s), 7.18 (1H, s), 7.78 (1H, s), 8.16 (1H, dd).

Example 206

4-((3-(1H-imidazol-5-yl)cyclohexyl)(ethyl)amino)-2-(trifluoromethyl)benzonitrile To a solution of 4-((3-(1H-imidazol-5-yl)cyclohex-3-en-1-yl)(ethyl)amino)-2-(trifluoromethyl)benzonitrile (250 mg, 0.694 mmol) in EtOH (10 ml) was added Pd—C (25 mg). The mixture was kept under H$_2$ pressure (1 bar) at RT for 4 h, filtered through celite and concentrated to give the title compound as a mixture of diastereomers. Yield 107 mg. The racemic mixture of the title compound (30 mg) was purified by chiral HPLC chromatography (Chiralpak IA 20 mm×250 mm column, n-hexane/ethanol/0.1% DEA, 1 ml/min) to yield 5.7 mg of enantiomer 1 (rt 5.9 min) and 2.4 mg of enantiomer 2 of trans-diastereomer (rt 6.5 min), $^1$H NMR (400 MHz, CDCl$_3$): 1.21 (t, 3 H), 1.58-1.87 (m, 6 H), 2.09-2.15 (m, 1 H), 2.34 (d, 1 H), 3.25-3.50 (m, 3 H), 3.99-4.08 (m, 1 H), 6.78 (dd, 1 H), 6.87 (s, 1 H), 7.11 (br. s., 1 H), 7.51 (d, 1 H), 7.66 (d, 1 H), and 4.4 mg of enantiomer 1 (rt 9.5 min) and 5.6 mg of enantiomer 2 of cis-diastereomer (rt 10.8 min), $^1$H NMR (400 MHz, CDCl$_3$): 1.20 (t, 3 H), 1.40-1.62 (m, 3 H), 1.69 (q, 1 H), 1.90 (d, 1 H), 1.98-2.11 (m, 2 H), 2.17 (d, 1 H), 2.77-2.86 (m, 1 H), 3.34-3.46 (m, 2 H), 3.78-3.86 (m, 1 H), 6.76-6.82 (m, 2 H), 6.95 (d, 1 H), 7.53-7.60 (m, 2 H). All compounds had LC-MS MS: m/z 362[M+H].

Example 207

4-(Ethyl(3-(1-methyl-1H-imidazol-4-yl)cyclohex-3-en-1-yl)amino)-2-(trifluoromethyl)benzonitrile and 4-(ethyl(3-(1-methyl-1H-imidazol-5-yl)cyclohex-3-en-1-yl)amino)-2-(trifluoromethyl)benzonitrile To a stirred solution of 4-((3-(1H-imidazol-5-yl)cyclohex-3-en-1-yl)(ethyl)-amino)-2-(trifluoromethyl)benzonitrile (200 mg, 0.555 mmol) in toluene (5 ml) was added TBABr (0.055 mmol) and 50% NaOH solution (1.17 ml). The mixture was heated to 40° C. and iodomethane (95 mg, 0.666 mmol) was added. After stirring 3 h at 40° C. the mixture was cooled to RT and stirred overnight. The organic layer was washed twice with water and brine, dried and evaporated. The crude product was purified by flash chromatography (DCM:MeOH 98:2) to give 12.5 mg of 1,4-isomer, $^1$H NMR (400 MHz, CDCl$_3$): 1.26 (t, 3 H), 1.82-2.04 (m, 2 H), 2.36-2.52 (m, 3 H), 2.54-2.65 (m, 1 H), 3.35-3.55 (m, 2 H), 3.65 (s, 3 H), 4.06-4.17 (m, 1 H), 6.42 (br. s., 1 H), 6.77 (s, 1 H), 6.84 (dd, 1 H), 7.00 (d, 1 H), 7.37 (s, 1 H), 7.56 (d, 1 H), and 18 mg of 1,5-isomer, $^1$H NMR (400 MHz, CDCl$_3$): 1.26 (t, 3 H), 1.82-1.94 (m, 1 H), 1.95-2.03 (m, 1 H), 2.43-2.56 (m, 4 H), 3.38-3.51 (m, 2 H), 3.67 (s, 3 H), 4.05-4.16 (m, 1 H), 5.90 (br. s., 1 H), 6.85 (dd, 1 H), 6.93 (s, 1 H), 7.00 (d, 1 H), 7.39 (s, 1 H), 7.59 (d, 1 H).

Example 208

4-(Ethyl(3-(1-ethyl-1H-imidazol-4-yl)cyclohex-3-en-1-yl)amino)-2-(trifluoromethyl)benzonitrile and 4-(ethyl(3-(1-ethyl-1H-imidazol-5-yl)cyclohex-3-en-1-yl)-amino)-2-(trifluoromethyl)benzonitrile To a stirred solution of the compound of Example 117 (200 mg, 0.555 mmol) in toluene (5 ml) was added TBABr (0.055 mmol) and 50% NaOH solution (1.17 ml). The mixture was heated to 40° C. and iodoethane (91 mg, 0.583 mmol) was added. After stirring for 3 h at 40° C. the mixture was cooled to RT. The organic layer was washed with water and brine, dried and evaporated. The crude product was purified by flash chromatography (DCM:MeOH 98:2) to give 85.5 mg of 1,4 isomer, $^1$H NMR (400 MHz, CDCl$_3$): 1.27 (t, 3 H), 1.44 (t, 3 H), 1.83-2.02 (m, 2 H), 2.40-2.51 (m, 3 H), 2.55-2.65 (m, 1 H), 3.36-3.53 (m, 2 H), 3.95 (q, 2 H), 4.06-4.16 (m, 1 H), 6.43 (m, 1 H), 6.79-6.82 (m, 1 H), 6.85 (dd, 1 H), 7.00 (d, 1 H), 7.42 (d, 1 H), 7.56 (d, 1 H), and 12.7 mg the 1,5-isomer, $^1$H NMR (400 MHz, CDCl$_3$): 1.26 (t, 3 H), 1.44 (t, 3 H), 1.82-2.03 (m, 2 H), 2.45-2.51 (m, 3 H), 3.36-3.52 (m, 2 H), 4.00 (q, 2 H), 4.05-4.15 (m, 1 H), 5.85 (m, 1 H), 6.85 (dd, 1 H), 6.91 (s, 1 H), 6.99 (d, 1 H), 7.46 (s, 1 H), 7.59 (d, 1 H).

Example 209

4-((3-(1H-1,2,4-triazol-1-yl)cyclohexyl)(ethyl) amino)-2-(trifluoromethyl)-benzonitrile a) (Z)-3-(1H-1,2,4-triazol-1-yl)cyclohexanone oxime 3-(1H-1,2,4-triazol-1-yl)cyclohexanone (5.6 g, 33.9 mmol) was dissolved into dry pyridine (20 ml). Solid hydroxylamine HCl (2.47 g, 35.6 mmol) was added and the mixture was stirred at RT for 4 h. Pyridine was evaporated and the residue was dissolved to ethyl acetate (30 ml). The organic layer was washed with water, dried and evaporated to give 2.3 g white solid. More oxime was precipitated from water phase 2.2 g to yield 4.5 g of combined solids which was used as such in the next step. LC-MS MS: m/z 181[M+H].

b) 3-(1H-1,2,4-triazol-1-yl)cyclohexanamine

The compound of Example 209(a) (4.5 g, 25 mmol) was reduced with LiAlH$_4$ (1.42 g, 37.5 mmol) in dry THF (100 ml) as in Example 86(b) to yield 2.45 g of the title compound as a 2:1 mixture of cis:trans diastereomers and it was used as such in the next step.

c) 4-((3-(1H-1,2,4-triazol-1-yl)cyclohexyl)amino)-2-(trifluoromethyl)benzonitrile A mixture of 4-fluoro-(2-trifluoromethyl)benzonitrile (0.57 g, 3.01 mmol), the compound of Example 209(b) (0.50 g, 3.01 mmol), DIPEA (1.57 ml, 9.02 mmol) and DMSO (10 ml) was heated to 80° C. for 2 h. The aqueous work up afforded 0.67 g of tile compound as a 3:2 mixture of cis:trans diastereomers. The mixture was used as such in the next step.

d) 4-((3-(1H-1,2,4-triazol-1-yl)cyclohexyl)(ethyl) amino)-2-(trifluoromethyl)-benzonitrile The compound of Example 209(c) (658 mg, 1.96 mmol) was ethylated as in Example 130. The crude product was purified by flash chromatography using DCM acetone (5-10%) gradient to give 108 mg of cis-diastereomer, $^1$H NMR (400 MHz, CDCl$_3$): 1.22 (t, 3 H), 1.60-1.66 (m, 2 H), 1.87 (qd, 1 H), 1.92-2.00 (m, 1 H), 2.06-2.15 (m, 2 H), 2.22 (m, 1 H), 2.32 (m, 1 H), 3.43 (q, 2 H), 3.82-3.92 (m, 1 H), 4.39 (m, 1 H), 6.82 (dd, 1 H), 6.96 (d, 1 H), 7.59 (d, 1 H), 7.95 (s, 1 H), 8.12 (s, 1 H), and 53.9 mg of trans-diastereomer, $^1$H NMR (400 MHz, CDCl$_3$): 1.24 (t, 3 H), 1.63-1.82 (m, 2 H), 1.82-1.95 (m, 3 H), 1.95-2.08 (m, 1 H), 2.09-2.26 (m, 1 H), 2.49 (d, 1 H), 3.28-3.55 (m, 2 H), 4.43-4.58 (m, 1 H), 4.78 (br. s., 1 H), 6.86 (d, 1 H), 7.31 (br. s., 1 H), 7.56 (d, 1 H), 8.04 (s, 1 H), 8.17 (s, 1 H). The enantiomers of cis-diastereomer (80 mg) were purified by chiral HPLC chromatography (Chiralpak IA 20 mm×250 mm column, n-hexane/ethanol/0.1% DEA, 20 ml/min) to yield enantiomer 1 (rt 1 min) and enantiomer 2 (rt 2 min).

Example 210

4-((3-(1H-1,2,4-triazol-1-yl)cyclohex-2-en-1-yl) (ethyl)amino)-2-(trifluoromethyl)benzonitrile a) 3-(1H-1,2,4-triazol-1-yl)cyclohex-2-enone

3-Chlorocyclohex-2-enone (1.5 g, 11.5 mmol) and 1,2,4-triazole sodium salt (1.26 g, 13.8 mmol) were dissolved into dry DMF (15 ml). The mixture was stirred at 80° C. for 5 h. Water was added, and the mixture was extracted with ethyl acetate and with DCM. The combined organic phases were washed with water and brine, dried and evaporated to yield 1.6 g of the title compound. LC-MS MS: m/z 164[M+H]. This material was used as such in the next step.

b) 3-(1H-1,2,4-triazol-1-yl)cyclohex-2-enol

The compound was prepared using the compound of Example 210(a) (1.6 g, 10 mmol), CeCl$_3$ heptahydrate (4.1 g, 11 mmol) and NaHB4 (0.45 g, 12 mml) in MeOH (20 ml). Yield 1.05 g. LC-MS MS: m/z 166[M+H]. This material was used as such in the next step.

c) 1-(3-azidocyclohex-1-en-1-yl)-1H-1,2,4-triazole

The compound was prepared using the compound of Example 210(b) (0.82 g, 4.9 mmol), DPPA (2.0 g, 7.4 mmol) and DBU (1.3 ml) by stirring in toluene (12 ml) overnight at RT as described in Example 74(d). Yield 0.58 g. LC-MS MS: m/z 191 [M+H]. This material was used as such in the next step.

d) 3-(1H-1,2,4-triazol-1-yl)cyclohex-2-enamine hydrochloride

The compound was prepared as in Example 74(e) using the compound of Example 210(c) (0.35 g, 1.8 mmol), polymer supported PPh$_3$ (2 equivalent) in MeOH (20 ml). After 3 h at 65° C. the polymer was filtered off and the reaction repeated. The polymer was filtered and washed with MeOH. The solvent was evaporated to dryness. The residue was dissolved to EtOAc and 3-(1H-1,2,4-triazol-1-yl)cyclohex-2-enamine was converted to HCl salt by addition of HCl ether solution. After filtration 0.19 g of the title compound was obtained. LC-MS MS: m/z 165[M+H]. This material was used as such in the next step.

e) 4-((3-(1H-1,2,4-triazol-1-yl)cyclohex-2-en-1-yl) amino)-2-(trifluoromethyl)-benzonitrile The compound was prepared from the compound of Example 210(d) (0.19 g, 0.96 mmol), 4-fluoro-2-(trifluoromethyl)benzonitrile (0.18 g, 0.96 mmol) and DIPEA (0.5 ml, 2.9 mmol) in DMSO (5 ml), 3 h, 80° C. Yield 0.11 g. LC-MS MS: m/z=334, (M+1)$^+$.

f) 4-((3-(1H-1,2,4-triazol-1-yl)cyclohex-2-en-1-yl) (ethyl)amino)-2-(trifluoromethyl)benzonitrile The compound of Example 210(e) (54 mg, 0.16 mmol) was N-alkylated using 60% NaH dispersion (51 mg, 0.32 mmol) and iodoethane (16 mg, 0.41 mmol) in DMF (3 ml), 3 h, yielding 54 mg of the title compound. $^1$H NMR (400 MHz, CDCl$_3$): 1.25 (t, 3 H), 1.69-1.83 (m, 1 H), 1.87-2.02 (m, 1 H), 2.03-2.22 (m, 2 H), 2.66-2.74 (m, 2 H), 3.35-3.53 (m, 2 H), 4.66-4.74 (m, 1 H), 6.26 (br. s., 1 H), 6.86 (dd, 1 H), 7.00-7.04 (m, 1H), 7.60 (d, 1 H), 8.01 (s, 1 H), 8.29 (s, 1 H).

Example 211

4-((3-(1H-1,2,4-triazol-1-yl)cyclopentyl)(ethyl) amino)-2-(trifluoromethyl)-benzonitrile a) (E,Z)-3-(1H-1,2,4-triazol-1-yl)cyclopentanone oxime 3-(1H-1,2,4-triazol-1-yl)cyclopentanone (3.9 g, 25.8 mmol) was dissolved to dry pyridine (15). Hydroxylamine HCl (1.9 g, 27.1 mmol) was added and the mixture was stirred at RT for 4 h. The precipitate was filtered off and the white solid was washed with ether to yield 3.8 g of the title compound. The structure was confirmed with LC-MS. This material used as such in the next step. m/z=167 (M+1)$^+$ b) 3-(1H-1,2,4-triazol-1-yl)cyclopentanamine A mixture of the compound of Example 211(a) (3.8 g, 22.8 mmol) and THF (80 ml) was cooled to 0° C. Solid LiAlH$_4$ (1.3 g, 34.1 mmol) was added in small portions and the mixture that was warmed to RT and then refluxed for 4 h. Small portion of water (1.5 ml) was added the mixture was stirred for 15 min. Another 4.5 ml of water and 3 ml of 2 M NaOH was added and the mixture was stirred at RT overnight, filtered through celite pad and washed with THF. The filtrate was evaporated to give 1.5 g of the title compound as an oil. This material was used as such in next step.

c) 4-((3-(1H-1,2,4-triazol-1-yl)cyclopentyl)amino)-2-(trifluoromethyl)benzonitrile The compound was prepared from the compound of Example 211(b) (1.48 g, 7.84 mmol), 4-fluoro-2-(trifluoromethyl)benzonitrile (1.48 g, 7.84 mmol) and DIPEA (4.1 ml, 23.5 mmol) in DMSO (10 ml). The mixture was stirred for 2 h in 80° C. yielding 0.49 g of cis-diastereomer and 0.69 g of trans-diastereomer after column chromatography. Both diastereomers had LC-MS m/z=322, (M+1)$^+$.

d) 4-((3-(1H-1,2,4-triazol-1-yl)cyclopentyl)(ethyl) amino)-2-(trifluoromethyl)-benzonitrile Trans-diastereomer of Example 211(c) (0.69 g, 2.15 mmol) was alkylated using 60% NaH dispersion (0.22 mg, 5.37 mmol) and iodoethane (0.67 mg, 4.30 mmol) in DMF (12 ml), 2 h, to yield 0.73 g of the trans-diastereomer of the title compound, $^1$H NMR (400 MHz, CDCl$_3$): 1.25 (t, 3 H), 1.86 (m, 1 H), 2.04-2.18 (m, 2 H), 2.25-2.35 (m, 1 H), 2.39 (m, 1 H), 2.48 (m, 1 H), 3.42 (m, 2 H), 4.79 (m, 1 H), 4.93 (m, 1 H), 6.89 (dd, 1 H), 7.08 (d, 1 H), 7.59 (d, 1 H), 7.99 (s, 1 H), 8.11 (s, 1 H). Cis-diastereomer of Example 212(c) (0.49 g, 1.53 mmol) was alkylated using 60% NaH dispersion (0.15 mg, 3.81 mmol) and iodoethane (0.47 mg, 3.05 mmol) in DMF (10 ml), 2 h, to yield 0.25 g of the cis-diastereomer of the title compound, $^1$H NMR (400 MHz, CDCl$_3$): 1.23-1.29 (m, 3 H), 2.16-2.30 (m, 5 H), 2.57-2.76 (m, 1 H), 3.46-3.61 (m, 2 H), 4.26-4.36 (m, 1 H), 4.79-4.88 (m, 1 H), 6.85 (dd, 1 H), 7.01 (d, 1 H), 7.59 (d, 1 H), 7.98 (s, 1 H), 8.11 (s, 1 H). The two enantiomers of cis-diastereomer (150 mg) were purified by chiral HPLC chromatography (Chiralpak IA 20 mm×250 mm column, n-hexane/ethanol/0.1% DEA, 1 ml/min) to yield enantiomer 1 (rt 4.28 min) and enantiomer 2 (rt 4.66 min). The two enantiomers of trans-diastereomer (150 mg) were purified similarly to yield enantiomer 1 (rt 4.13 min) and enantiomer 2 (rt 4.38 min).

Example 212

4-((3-(4H-1,2,4-triazol-4-yl)cyclohexyl)(ethyl) amino)-2-(trifluoromethyl)-benzonitrile a) 4-((3-(4H-1,2,4-triazol-4-yl)cyclohexyl)amino)-2-(trifluoromethyl)benzonitrile 4-((3-Aminocyclohexyl)amino)-2-(trifluoromethyl)benzonitrile (200 mg, 0.706 mmol) was dissolved into toluene (10 ml). N,N'-Bis(dimethylaminomethylene)hydrazine (120 mg, 0.847 mmol) and PPTS (18 mg, 0.072 mmol) was added and the mixture was heated to reflux for 8 h. During the reflux brown oil was formed. The crude product was purified by flash chromatography using DCM methanol gradient 2.5-10% as an eluent to give (172 mg) of the title compound as a mixture of diastereomers (1:5 ratio).

b) 4-((3-(4H-1,2,4-triazol-4-yl)cyclohexyl)(ethyl) amino)-2-(trifluoromethyl) benzonitrile The compound of Example 212(a) (172 mg, 0.513 mmol) was ethylated as in Example 130. The crude product was purified by flash chromatography using DCM methanol gradient 2.5-10% as an eluent to give 92 mg of cis-diastereomer, $^1$H NMR (400 MHz, CDCl$_3$): 1.23 (t, 3 H), 1.56-1.77 (m, 4 H), 1.95-2.03 (m, 1 H), 2.11-2.19 (m, 1 H), 2.24-2.38 (m, 2 H), 3.43 (q, 2 H), 3.90 (ddd, 1 H), 4.25-4.36 (m, 1 H), 6.83 (dd, 1 H), 6.96 (d, 1 H), 7.59 (d, 1 H), 8.25 (s, 2 H), and 16.8 mg trans-diastereomer, $^1$H NMR (400 MHz, CDCl$_3$): 1.24 (t, 3 H), 1.66-1.80 (m, 2 H), 1.91-2.05 (m, 3 H), 2.09-2.23 (m, 1 H), 2.27-2.47 (m, 2 H), 3.42 (q, 2 H), 3.66-3.81 (m, 1 H), 4.68 (br. s., 1 H), 6.61 (dd, 1 H), 6.86 (d, 1 H), 7.49-7.60 (m, 1 H), 8.37 (br. s., 2 H). LC-MS m/z=364 (M+1)$^+$ Example 213

4-((3-(1H-1,2,4-triazol-1-yl)cyclohexyl)(ethyl) amino)-2-chlorobenzonitrile a) 4-((3-(1H-1,2,4-triazol-1-yl)cyclohexyl)amino)-2-chlorobenzonitrile A mixture of 4-fluoro-(2-chloro)benzonitrile (0.47 g, 3.01 mmol), 3-(1H-1,2,4-triazol-1-yl)cyclohexanamine (0.50 g, 3.01 mmol), DIPEA (1.57 ml, 9.02 mmol) and DMSO (10 ml) was heated to 80° C. for 2 h. The aqueous work up afforded 0.67 g of the title compound as 3:2 mixture of cis:trans diastereomers. The mixture was used as such in the next step.

b) 4-((3-(1H-1,2,4-triazol-1-yl)cyclohexyl)(ethyl) amino)-2-chlorobenzonitrile

The compound of Example 213(a) (193 mg, 0.62 mmol) was ethylated as in Example 130. The crude product was purified by flash chromatography using DCM methanol gradient 2.5-10% as an eluent to give 92 mg of cis-diastereomer, $^1$H NMR (400 MHz, CDCl$_3$): 1.20 (t, 3 H), 1.57-1.64 (m, 2 H), 1.78-1.98 (m, 2 H), 2.00-2.15 (m, 2 H), 2.21 (m, 1 H), 2.27-2.35 (m, 1 H), 3.38 (q, 2 H), 3.76-3.86 (m, 1 H), 4.37 (m, 1 H), 6.59 (dd, 1 H), 6.72 (d, 1 H), 7.43 (d, 1 H), 7.95 (s, 1 H), 8.11 (s, 1 H), and 16.8 mg trans-diastereomer, $^1$H NMR (400 MHz, CDCl$_3$): 1.21 (t, 3 H), 1.62-1.82 (m, 2 H), 1.82-2.02 (m, 4 H), 2.21 (m, 1 H), 2.48 (m, 1 H), 3.25-3.45 (m, 2 H), 4.35 (tt, 1 H), 4.73-4.81 (m, 1 H), 6.65 (dd, 1 H), 6.93 (d, 1 H), 7.39 (d, 1 H), 8.07 (s, 1 H), 8.17 (s, 1 H). LC-MS m/z=330, (M+1)$^+$

Example 214

4-((3-(1H-1,2,4-triazol-1-yl)cyclopent-2-en-1-yl)(ethyl)amino)-2-(trifluoromethyl)benzonitrile a) 3-(1H-1,2,4-triazol-1-yl)cyclopent-2-enamine

The title compound was prepared from 3-chlorocyclopent-2-enone using the methods described in Examples 210 (a-d). [M+H]$^+$=151.

b) 4-((3-(1H-1,2,4-triazol-1-yl)cyclopent-2-en-1-yl)amino)-2-(trifluoromethyl)benzonitrile A mixture of 4-fluoro-(2-trifluoromethyl)benzonitrile (0.19 g, 1.0 mmol), the compound of Example 214(a) (0.15 g, 1.0 mmol), DIPEA (0.52 ml, 3.0 mmol) and DMSO (5 ml) was heated to 80° C. for 2 h. The aqueous work up afforded 0.32 g of the title compound as an oil. The mixture was used as such in the next step. LC-MS m/z=320, (M+1)$^+$ c) 4-((3-(1H-1,2,4-triazol-1-yl)cyclopent-2-en-1-yl)(ethyl)amino)-2-(trifluoromethyl)benzonitrile The compound of Example 214(b) (231 mg, 0.72 mmol) was ethylated as in Example 130. The crude product was purified by flash chromatography using DCM methanol gradient 2.5-10% as an eluent. Yield 91 mg. $^1$H NMR (400 MHz, CDCl$_3$): 1.23 (t, 3 H), 1.88-2.02 (m, 1 H), 2.65-2.80 (m, 1 H), 2.90-3.02 (m, 1 H), 3.04-3.17 (m, 1 H), 3.43 (m, 2 H), 5.19 (m, 1 H), 6.12 (d, 1 H), 6.87 (dd, 1 H), 7.03 (d, 1 H), 7.61 (d, 1 H), 8.05 (s, 1 H), 8.29 (s, 1 H). LC-MS m/z=348, (M+1)$^+$

Example 215

4-((3-(1H-1,2,4-triazol-1-yl)cyclopent-2-en-1-yl)(ethyl)amino)-2-(trifluoromethyl)benzonitrile a) 4-((3-(1H-imidazol-1-yl)cyclohex-3-en-1-yl)amino)-2-(trifluoromethyl)-benzonitrile A mixture of 4-fluoro-(2-trifluoromethyl)benzonitrile (0.12 g, 0.65 mmol), 3-(1H-imidazol-1-yl)cyclohex-3-enamine (0.11 g, 0.64 mmol), DIPEA (0.34 ml, 3.0 mmol) and DMSO (5 ml) was heated to 80° C. for 2 h. The aqueous work up afforded 0.16 g of the title compound as an oil. The mixture was used as such in the next step. LC-MS m/z=333, (M+1)$^+$ b) 4-((3-(1H-1,2,4-triazol-1-yl)cyclopent-2-en-1-yl)(ethyl)amino)-2-(trifluoromethyl)benzonitrile The compound of Example 215(a) (141 mg, 0.42 mmol) was ethylated as in Example 130. The crude product was purified by flash chromatography using DCM methanol gradient 2-10% as an eluent. Yield 80 mg. $^1$H NMR (400 MHz, CDCl$_3$): 1.28 (t, 3 H), 1.85-1.99 (m, 1 H), 1.99-2.07 (m, 1 H), 2.41-2.50 (m, 2 H), 2.61-2.68 (m, 2 H), 3.38-3.54 (m, 2 H), 4.13-4.24 (m, 1 H), 5.86-5.94 (m, 1 H), 6.87 (dd, 1 H), 7.01 (d, 1 H), 7.07-7.13 (m, 2 H), 7.60 (d, 1 H), 7.66 (s, 1 H). LC-MS m/z=361, (M+1)$^+$

Example 216

4-(Ethyl(3-hydroxy-3-(pyridin-3-yl)cyclohexyl)amino)-2-(trifluoromethyl)-benzonitrile To a stirred solution of 3-bromopyridine (509 mg, 3.20 mmol) in dry diethylether (30 ml) at −78° C. was added n-BuLi (1.6 M solution, 2.2 ml). After stirring at −78° C. for 30 min 4-(Ethyl(3-oxocyclohexyl)amino)-2-(trifluoromethyl)-benzonitrile (500 mg, 1.61 mmol) in THF (5 ml) was added. The mixture was stirred at −78° C. for 4 h. The mixture was quenched by saturated aqueous NH$_4$Cl solution and extracted with EtOAc, washed with brine, dried, filtered and concentrated under reduced pressure. The crude diasteromeric mixtures were purified by column chromatography over silica gel using hexane:EtOAc (50-70%) as the eluent to give 110 mg (18%) of diastereomer 1, $^1$H-NMR (400 MHz; DMSO-d$_6$): 8.77 (d, 1H), 8.43 (d, 1H), 7.91 (d, 1H), 7.79 (d, 1H), 7.35 (dd, 1H), 7.05 (m, 2H), 5.34 (s, 1H), 4.30 (m, 1H), 3.56 (q, 2H), 1.60-2.10 (m, 8H), 1.10 (t, 3H), and 50 mg (8%) of diastereomer 2, $^1$H-NMR (400 MHz; DMSO-d$_6$): 8.74 (d, 1H), 8.53 (d, 1H), 7.92 (d, 2H), 7.71 (d, 1H), 7.42 (dd, 1H), 6.79 (d, 1H), 6.69 (s, 1H), 5.34 (s, 1H), 3.37-3.49 (m, 3H), 2.38-2.52 (m, 2H), 1.41-1.98 (m, 6H), 1.15 (t, 3H); MS: m/z 390 [M+H]. The enantiomers of diastereomer 1 (69 mg) were separated by preparative chiral HPLC (Column Chiralpak IC 20 mm×250 mm 5 µm, A MTBE+0.2% DEA, B EtOH+0.2% DEA, isocratic B 5%, flow 20 ml/min, λ 300 nm) to yield 10.9 mg of enantiomer 1 (rt 5.9 min) and 11.7 mg of enantiomer 2 (rt 7.0 min). The $^1$H NMR spectra of enantiomers were identical: $^1$H NMR (400 MHz, CDCl$_3$): 1.21 (3H, t), 1.63 (1H, m), 1.77-2.08 (7H, m), 2.65 (1H, broad s), 3.40 (2H, m), 4.41 (1H, m), 6.88 (1H, dd), 7.01 (1H, d), 7.28 (1H, m), 7.53 (1H, d), 7.85 (1H, m), 8.46 (1H, dd), 8.70 (1H, d).

Example 217

4-(Ethyl(3-methoxy-3-(pyridin-3-yl)cyclohexyl)amino)-2-(trifluoromethyl)-benzonitrile (diastereomer 1)

To a stirred solution of NaH (9.2 mg, 0.231 mmol) in dry DMF (3 ml) under N$_2$ at 0° C. was added diastereomer 1 of Example 216 (30 mg, 0.077 mmol). The mixture was stirred at RT for 30 min. Iodomethane (16.4 mg, 0.116 mmol) was added. After stirring overnight at RT saturated NaHCO$_3$ solution (10 ml) was added. The product was extracted twice into ethyl acetate. The organic phase was washed with water, dried and evaporated. The crude product was purified by flash chromatography using DCM:methanol 95:5 as an eluent to give 13.75 mg of the title compound. $^1$H NMR (400 MHz, CDCl$_3$): 1.19 (t, 3 H), 1.53-1.68 (m, 2 H), 1.71-1.99 (m, 4 H), 2.11 (dd, 1 H), 2.24 (d, 1 H), 3.03 (s, 3 H), 3.36 (quin, 2 H), 4.30-4.42 (m, 1 H), 6.89 (dd, 1 H), 7.05 (d, 1 H), 7.28-7.33 (m, 1 H), 7.59 (d, 1 H), 7.70-7.76 (m, 1 H), 8.54 (dd, 1 H), 8.64 (d, 1 H).

Example 218

4-(Ethyl(3-(pyridin-3-yl)cyclohex-3-en-1-yl)amino)-2-(trifluoromethyl)benzonitrile To diastereomer 1 of Example 216 (90 mg, 0.23 mmol) was added concentrated H$_2$SO$_4$ (2 ml) at 0° C. The mixture was stirred 15 min at 0° C. and 30 min at RT. The mixture was basified with 5 N NaOH and extracted with EtOAc followed by washing with brine, drying, filtering and concentrating. The crude product was purified by column chromatography over silica gel using CH$_3$OH: DCM (3%) as the eluent to give the title compound. Yield: 25 mg (30%). $^1$H-NMR (400 MHz; DMSO-d$_6$): 8.67 (s, 1H), 8.43 (bs, 1H), 7.81 (d, 1H), 7.77 (d, 1H), 7.35 (dd, 1H), 7.13 (m$_c$, 1H), 7.12 (s, 1H), 6.30 (bs, 1H), 4.27 (m$_c$, 1H), 3.54 (q, 2H), 2.50-2.64 (m, 4H), 1.86 (m, 2H). The enantiomers were purified by chiral HPLC chromatography (Chiralpak IA 20 mm×250 mm column, MTBE:EtOH 98:2, 8.9 ml/min) to yield enantiomer 1 (rt 13.4 min) and enantiomer 2 (rt 26.6 min). LC-MS MS: m/z 372[M+H].

Example 219

4-((3-(1H-imidazol-5-yl)cyclopentyl)(ethyl)amino)-2-(trifluoromethyl)-benzonitrile A mixture of the compound of Example 150 (1.05 g, 3.0 mmol), 10% Pd/C (0.76 g), AcOH (1 ml) and MeOH (25 ml) was hydrogenated in Parr-hydrogenation apparatus (50 psi) for 2 h. Catalyst was filtered off and the filtrate was concentrated. The residue was partitioned between saturated $NaHCO_3$ solution and DCM. Aqueous layer was extracted with DCM. Combined organic layers were washed with brine, dried and concentrated. After column chromatography the title compound was collected as a mixture of enantiomers. Yield 0.7 g. $^1$H NMR (400 MHz, $CDCl_3$): 1.22 (3 H, t) 1.77-2.02 (3 H, m) 2.08-2.22 (2 H, m) 2.33-2.42 (1 H, m) 3.15-3.25 (1 H, m) 3.43 (2 H, q) 4.23-4.33 (1 H, m) 6.80-6.85 (2 H, m) 6.99 (1 H, d) 7.56 (1 H, d) 7.61 (1 H, m). [M+H]I=349.

Example 220

4-((3-(1-(2-(benzyloxy)ethyl)-1H-imidazol-5-yl)-6,6-dimethylcyclohex-2-en-1-yl)(methyl)amino)-2-(trifluoromethyl)benzonitrile a) 5-(3-Azido-4,4-dimethylcyclohex-1-en-1-yl)-1-(2-(benzyloxy)ethyl)-1H-imidazole The title compound was prepared from crude 3-(1-(2-(benzyloxy)ethyl)-1H-imidazol-5-yl)-6,6-dimethylcyclohex-2-enol (2.39 g, 7.3 mmol), DPPA (2.23 ml, 2.84 g, 10.3 mmol), DBU (1.64 ml, 1.67 g, 11.0 mmol) and toluene (12 ml) as described in Example 74(d). Crude yield 3.34 g. [M+H]$^+$=352.

b) 3-(1-(2-(Benzyloxy)ethyl)-1H-imidazol-5-yl)-6,6-dimethylcyclohex-2-enamine

The compound was prepared from the crude compound of Example 220(a) (3.34 g), $PPh_3$ (3.07 g, 11.7 mmol) and MeOH (20 ml) as described in Example 74(e). When all of the azide had reacted, the intermediate iminophosphorane was hydrolyzed with 2 M NaOH and water under reflux. Formed triphenylphosphine oxide was filtered off and the remaining MeOH was evaporated. Aqueous layer was acidified with 2 M HCl and extracted with EtOAc. Finally aqueous layer was basified with 2 M NaOH and extracted with DCM. Combined DCM layers were washed with water, brine, dried and concentrated. Crude yield 1.17 g. [M+H]$^+$= 326.

c) 4-((3-(1-(2-(Benzyloxy)ethyl)-1H-imidazol-5-yl)-6,6-dimethylcyclohex-2-en-1-yl)amino)-2-(trifluoromethyl)benzonitrile The compound was prepared from crude compound of Example 220(b) (1.17 g, 3.6 mmol), 4-fluoro-2-(trifluoromethyl)benzonitrile (0.726 g, 3.8 mmol), DIPEA (1.6 ml, 1.19 g, 9.2 mmol) and DMSO (6 ml) as described in Example 74(f). Title compound was purified by column chromatography. Yield 1.01 g. [M+H]$^+$=495.

d) 4-((3-(1-(2-(Benzyloxy)ethyl)-1H-imidazol-5-yl)-6,6-dimethylcyclohex-2-en-1-yl)(methyl)amino)-2-(trifluoromethyl)benzonitrile The compound was prepared from the compound of Example 220(c) (0.5 g, 1.0 mmol), NaH (0.081 g, 2.0 mmol) and iodomethane (0.10 ml, 0.23 g, 1.6 mmol) and DMF (4 ml) as described in Example 74(g). Crude product was purified by column chromatography. Yield 0.22 g. $^1$H NMR (400 MHz, $CDCl_3$): 0.91 (3 H, s) 1.03 (3 H, s) 1.62 (2 H, m) 2.25-2.36 (1 H, m) 2.36-2.47 (1 H, m) 2.87 (3 H, s) 3.68 (2 H, t) 4.17 (2 H, t) 4.38-4.42 (1 H, m) 4.45 (2 H, s) 5.49-5.54 (1 H, m) 6.89 (1 H, dd) 7.01 (1 H, s) 7.04 (1 H, d) 7.13-7.19 (2 H, m) 7.23-7.28 (3 H, m) 7.56-7.60 (2 H, m). [M+H]$^+$= 509.

Example 221

4-((3-(1-(2-Hydroxyethyl)-1H-imidazol-5-yl)-6,6-dimethylcyclohex-2-en-1-yl)(methyl)amino)-2-(trifluoromethyl)benzonitrile A flask flushed with $N_2$ was charged with the compound of Example 220 (0.107 g, 0.21 mmol) and DCM (3 ml). The flask was cooled to −78° C. and 1 M $BCl_3$ in THF (0.53 ml, 0.53 mmol) was added. When the reaction was completed, it was quenched with MeOH (3 ml) and saturated $NaHCO_3$ solution was added. The aqueous layer was extracted with DCM. Combined organic layers were washed with brine, dried and concentrated. Title compound was purified by column chromatography. Yield 0.013 g. $^1$H NMR (400 MHz, $CDCl_3$): 0.96 (3 H, s), 1.08 (3 H, s), 1.69 (2 H, m), 2.31-2.41 (1 H, m), 2.43-2.53 (1 H, m), 2.90-3.05 (1 H, br. s.), 2.97 (3 H, s), 3.91 (2 H, t), 4.16 (2 H, t), 4.48 (1 H, m), 5.61-5.65 (1 H, m), 6.92 (1 H, dd), 7.02 (1 H, s), 7.08 (1 H, d), 7.60 (1 H, d), 7.72 (1 H, s). [M+H]$^+$=419.

Example 222

4-(Ethyl(3-(oxazol-5-yl)cyclopent-3-enyl)amino)-2-(trifluoromethyl)benzonitrile a) 4-(3-(Oxazol-5-yl)cyclopent-3-enylamino)-2-(trifluoromethyl)benzonitrile To a solution of the compound of Example 197(c) (0.60 g) in DCM (10 ml) and MeOH (10 ml) tosylmethyl isocyanide (0.50 g) and DBU (0.645 ml) were added at RT. The mixture was stirred overnight. More DCM was added and the mixture was washed with water and brine, dried and evaporated to dryness. Crude product was purified by chromatography (silica column, eluent 0-2% MeOH/DCM) to obtain the product as a mixture of enantiomers. Yield 0.205 g. $^1$H NMR (400 MHz, $CDCl_3$): 2.45-2.62 (m, 2H), 3.05-3.20 (m, 2H), 4.31-4.39 (m, 1H), 4.85 (d, 1H), 6.17-6.20 (m, 1H), 6.71 (dd, 1H), 6.87 (d, 1H), 6.94 (s, 1H), 7.56 (d, 1H), 7.82 (s, 1H).

b) 4-(Ethyl(3-(oxazol-5-yl)cyclopent-3-enyl)amino)-2-(trifluoromethyl)benzonitrile The compound was prepared from the compound of Example 222(a) (0.050 g), iodoethane (0.019 ml) and sodium hydride (60% dispersion in mineral oil, 0.013 g) as described in Example 74(g). Crude product was purified by chromatography (silica column, eluent 1:1 heptane/EtOAc) to obtain the product as a mixture of enantiomers. Yield 0.015 g. $^1$H NMR (400 MHz, CDCl$_3$): 1.24 (t, 3H), 2.63-2.80 (m, 2H), 2.92-3.09 (m, 2H), 3.45 (q, 2H), 4.71-4.79 (m, 1H), 6.22-6.26 (m, 1H), 6.80 (dd, 1H), 6.95 (s, 1H), 6.98 (d, 1H), 7.58 (dd, 1H), 7.85 (s, 1H).

Example 223

4-((3-(1H-1,2,3-triazol-1-yl)cyclohexyl)(ethyl) amino)-2-(trifluoromethyl)-benzonitrile (cis-diastereomer)

a) 4-((3-(1H-1,2,3-triazol-1-yl)cyclohexyl)amino)-2-(trifluoromethyl)benzonitrile (cis-diastereomer)

A mixture of 4-fluoro-(2-trifluoromethyl)benzonitrile (1.87 g, 9.87 mmol), the cis-diastereomer of 3-(1H-1,2,3-triazol-1-yl)cyclohexanamine hydrochloride (2.0 g, 9.87 mmol) DIPEA (5.2 ml) and DMSO (10 ml) was heated to 120° C. for 3 h as described in Example 73(a). The aqueous work up afforded 2.5 g of the crude product. Column chromatography over silica gel using DCM as the eluent gave 1.42 g of the title compound. $^1$H NMR (400 MHz, CDCl$_3$): 0.87-1.56 (m, 1 H), 1.28-1.44 (m, 2 H), 1.80-1.93 (m, 2 H), 2.09 (m, 1 H), 2.19-2.32 (m, 2 H), 2.60-2.66 (m, 1 H), 3.55-3.64 (m, 1 H), 4.58-4.66 (m, 1 H), 4.85 (d, 1 H), 6.72 (dd, 1 H), 6.87 (d, 1 H), 7.27 (s, 1 H), 7.54-7.60 (m, 2 H), 7.72 (d, 1 H).

b) 4-((3-(1H-1,2,3-triazol-1-yl)cyclohexyl)(ethyl) amino)-2-(trifluoromethyl)-benzonitrile (cis-diastereomer)

The compound of Example 223(a) (300 mg, 0.90 mmol) was ethylated as in Example 73(c). The crude (308 mg) was purified by trituration with n-heptane. The white precipitate (258 mg) was filtered off and dried in vacuo. $^1$H NMR (400 MHz, CDCl$_3$): 1.23 (t, 3 H), 1.59-1.69 (m, 3 H), 1.83-2.04 (m, 2 H), 2.10-2.18 (m, 2 H), 2.25-2.33 (m, 1 H), 2.36-2.44 (m, 1 H), 3.44 (q, 2 H), 3.90 (m, 1 H), 4.62 (m, 1 H), 6.82 (dd, 1 H), 6.97 (d, 1 H), 7.57-7.61 (m, 2 H), 7.71 (d, 1 H).

Example 224

4-((3-(1H-imidazol-5-yl)cyclohexyl)(ethyl)amino)-2-(trifluoromethyl)benzonitrile The cis and trans diastereomers of the racemic compound of Example 206 were separated by preparative HPLC. Cis-diastereomer: $^1$H NMR (400 MHz, CDCl$_3$): 1.20 (t, 3 H), 1.40-1.50 (m, 1 H), 1.53-1.74 (m, 3 H), 1.90 (m, 1 H), 2.07 (d, 1 H), 2.17 (d, 1 H), 2.76-2.86 (m, 1 H), 3.41 (m, 2 H), 3.77-3.86 (m, 1 H), 6.76-6.83 (m, 2 H), 6.95 (d, 1 H), 7.53-7.60 (m, 2 H). Trans-diastereomer: $^1$H NMR (400 MHz, CDCl$_3$): 1.21 (t, 3 H), 1.58-1.87 (m, 6 H), 2.09-2.15 (m, 1 H), 2.34 (d, 1 H), 3.25-3.50 (m, 3 H), 3.99-4.08 (m, 1 H), 6.78 (dd, 1 H), 6.87 (s, 1 H), 7.11 (br. s., 1 H), 7.51 (d, 1 H), 7.66 (d, 1 H).

Example 225

4-((5-(1H-imidazol-1-yl)-3,6-dihydro-2H-thiopyran-3-yl)(methyl)amino)-2-(trifluoromethyl)benzonitrile a) 5-Chloro-2H-thiopyran-3(6H)-one The title compound was prepared from 2H-thiopyran-3,5(4H,6H)-dione (6.3 g, 48.4 mmol), oxalyl chloride (4.9 ml, 7.3 g, 58.1 mmol) and DCM (60 ml) as described in Example 74(a). The compound was used as such in the following step. Yield 4.0 g. [M+H]$^+$=149.

b) 5-(1H-imidazol-1-yl)-2H-thiopyran-3(6H)-one

The title compound was prepared from the compound of Example 225(a) (25.0 g, 168.2 mmol), imidazole (4.6 g, 336.5 mmol), DIPEA (55.5 ml, 336.5 mmol), and EtOH (250 ml) as described in Example 74(b). The mixture was heated to 60° C. for 4 h instead of using a microwave reactor. Crude yield 20 g. [M+H]$^+$=181. The compound was used as such without purification.

c) 5-(1H-imidazol-1-yl)-3,6-dihydro-2H-thiopyran-3-amine

To a compound of Example 225(b) (1.0 g, 5.54 mmol) in MeOH (20 ml) was added NH$_4$OAc (3.4 g, 44.4 mmol) and NaCNBH$_4$ (0.7 g, 11.1 mmol) at RT. The mixture was stirred at RT overnight. The mixture was concentrated and extracted with 10% MeOH in DCM. Yield 0.15 mg [M+H]$^+$= 182.

d) 4-((5-(1H-imidazol-1-yl)-3,6-dihydro-2H-thiopyran-3-yl)amino)-2-(trifluoromethyl)benzonitrile A mixture of 4-fluoro-(2-trifluoromethyl)benzonitrile (150 mg, 0.79 mmol), the compound of Example 225(c) (144 mg, 0.79 mmol) DIPEA (0.22 ml) and DMSO (5 ml) was heated to 80° C. for 8 h as described in Example 73(a). The aqueous work up afforded 129 mg of the title compound that was used as such in the next step. LC-MS m/z=351 (M+1)$^+$ e) 4-((5-(1H-imidazol-1-yl)-3,6-dihydro-2H-thiopyran-3-yl)(methyl)amino)-2-(trifluoromethyl)benzonitrile The compound of Example 225(d) (111 mg, 0.32 mmol) was methylated as in Example 73(c). The enantiomers were purified by chiral HPLC chromatography (Chiralpak IA 20 mm×250 mm column, n-hexane/ethanol/0.1% DEA, 1 ml/min) to yield enantiomer 1 (rt 25.3 min) and enantiomer 2 (rt 27.1 min). $^1$H NMR (400 MHz, CDCl$_3$): 2.69-2.93 (m, 3 H), 3.00 (s, 3 H), 3.18 (dd, 1 H), 4.58 (m, 1 H), 6.27-6.33 (m, 1 H), 6.95 (dd, 1 H), 7.03-7.15 (m, 3 H), 7.60-7.71 (m, 2 H).

Example 226

4-((Cyclopropylmethyl)(3-(1-ethyl-1H-imidazol-5-yl)cyclopent-3-en-1-yl)-amino)-2-(trifluoromethyl) benzonitrile The compound was prepared as in Example 137(d) starting from the compound of Example 200(c) (0.20 g, 0.577 mmol) and (bromomethyl)cyclopropane (84 µl, 0.866 mmol). 117 mg of the title compound was obtained after preparative HPLC. $^1$H NMR (400 MHz, CDCl$_3$): 0.27 (2H, m), 0.63 (2H, m), 1.00 (1H, m), 1.48 (3H, t), 2.76 (1H, m), 2.92 (1H, m), 3.02 (1H, m), 3.13 (1H, m), 3.31 (2H, m), 4.13 (2H, q), 4.66 (1H, m), 5.87 (1H, m), 6.88 (1H, dd), 7.00 (1H, s), 7.07 (1H, d), 7.51 (1H, d), 7.58 (1H, dd). The enantiomers were separated using chiral preparative HPLC (column: Daicel Chiralpak IA, 20 mm×250 mm, 5 µm particle size, eluent A: n-hexane+0.2% DEA, eluent B: EtOH+0.2%

DEA, isocratic elution: 20% B, flow 20 ml/min, detection 300 nm) to afford 31.7 mg of enantiomer 1 (rt 12.1 min) and 32.4 mg of enantiomer 2 (rt 15.0 min).

Example 227

2-Chloro-4-(ethyl(3-(1-ethyl-1H-imidazol-5-yl)cyclopent-3-en-1-yl)amino)-benzonitrile a) 2-Chloro-4-(3-oxo-2-azabicyclo[2.2.1]hept-5-en-2-yl)benzonitrile The compound was prepared as in Example 197(a) starting from 2-chloro-4-iodobenzonitrile (2.63 g, 10 mmol). 2.206 g of the title compound was obtained. $^1$H NMR (400 MHz, CDCl$_3$): 2.35 (1H, dt), 2.48 (1H, dt), 3.56 (1H, m), 4.87 (1H, m), 6.74 (1H, m), 7.02 (1H, dd), 7.46 (1H, dd), 7.60 (1H, d), 7.66 (1H, d).

b) 2-Chloro-4-((4-(hydroxymethyl)cyclopent-2-en-1-yl)amino)benzonitrile

The compound was prepared as in Example 197(b) starting from the compound of Example 227(a) (0.91 g, 3.72 mmol) and sodium borohydride (0.421 g, 11.13 mmol). Reaction was performed at 40° C. 0.593 g of the title compound was obtained after column chromatography. $^1$H NMR (400 MHz, CDCl$_3$): 1.43 (1H, m), 1.51 (1H, dt), 2.56 (1H, m), 2.95 (1H, m), 3.62 (1H, m), 3.70 (1H, dt), 4.51 (1H, m), 4.70 (1H, d), 5.91 (2H, m), 6.46 (1H, dd), 6.63 (1H, d), 7.36 (1H, d)

c) 2-Chloro-4-((3-formylcyclopent-3-en-1-yl)amino)benzonitrile

The compound was prepared as in Example 183(a) starting from the compound of Example 227(b) (0.753 g, 3.03 mmol). 0.177 g of the title compound was obtained after flash chromatography. $^1$H NMR (400 MHz, CDCl$_3$): 2.52 (1H, m), 2.59 (1H, m), 3.04 (1H, m), 3.14 (1H, m), 4.27 (1H, m), 4.59 (1H, d), 6.47 (1H, dd), 6.61 (1H, d), 6.87 (1H, m), 7.38 (1H, d), 9.78 (1H, s).

d) 2-Chloro-4-((3-(1-ethyl-1H-imidazol-5-yl)cyclopent-3-en-1-yl)amino)-benzonitrile The compound was prepared as in Example 183(b) starting from the compound of Example 227(c) (0.177 g, 0.717 mmol) and ethylamine (0.717 ml, 1.435 mmol; 2 M in THF). 0.226 g of crude title product was obtained which was used as such in the next step. $^1$H NMR (400 MHz, CDCl$_3$): 1.46 (3H, t), 2.51 (1H, m), 2.63 (1H, m), 3.08 (1H, m), 3.21 (1H, m), 4.10 (2H, q), 4.23 (1H, m), 4.51 (1H, d), 5.80 (1H, m), 6.47 (1H, dd), 6.63 (1H, d), 7.01 (1H, s), 7.20 (1H, d), 7.49 (1H, d).

e) 2-Chloro-4-(ethyl(3-(1-ethyl-1H-imidazol-5-yl)cyclopent-3-en-1-yl)-amino)benzonitrile The compound was prepared as in Example 137(d) starting from the compound of Example 227(d) (0.226 g, 0.723 mmol). 102 mg of the title compound was obtained after flash chromatography. $^1$H NMR (400 MHz, CDCl$_3$): 1.22 (3H, t), 1.48 (3H, t), 2.68 (1H, m), 2.82 (1H, m), 2.97 (1H, m), 3.08 (1H, m), 3.41 (2H, q), 4.13 (2H, q), 4.62 (1H, m), 5.87 (1H, m), 6.60 (1H, dd), 6.74 (1H, d), 7.00 (1H, s), 7.41 (1H, d), 7.50 (1H, d). The enantiomers were separated using chiral preparative HPLC (column: Daicel Chiralpak IA, 20 mm×250 mm, 5 μm particle size, eluent A: n-hexane+0.2% DEA, eluent B: EtOH+0.2% DEA, isocratic elution: 20% B, flow 20 ml/min, detection 300 nm) to afford 33.3 mg of enantiomer 1 (rt 16.1 min) and 35.7 mg of enantiomer 2 (rt 19.0 min).

Example 228

4-(Methyl(3-(4-methylpyridin-3-yl)cyclohex-2-en-1-yl)amino)-2-(trifluoromethyl)benzonitrile 3-((4-cyano-3-(trifluoromethyl)phenyl)(methyl)amino) cyclohex-1-enyl trifluoromethanesulfonate (0.192 g, 0.45 mmol), (4-methyl-3-pyridinyl)boronic acid (0.123 g, 0.90 mmol), tricyclohexylphosphine (6.28 mg, 0.022 mmol), Pd$_2$(dba)$_3$ (21 mg, 0.022 mmol) and potassium phosphate (0.162 mg, 0.76 mmol) were dissolved in mixture of 1,4-dioxane (7 ml) and water (3 ml) under N$_2$-atmosphere. The mixture was heated in microwave (100° C., 1 h), diluted with ethyl acetate (5 ml) and filtrated through a short plug of silica. The crude product was purified with flash chromatography (acetone/DCM) giving 76 mg of the title product. The enantiomers were separated with chiral preparative chromatography (column: Chiralpak IA No: P33, eluent: 0.1% DEA in hexanes/EtOH+0.2% DEA (20% of B), Q=20 ml/min) to afford 30 mg of enantiomer 1 (rt=11.96 min) and 30 mg of enantiomer 2 (rt=15.72 min). $^1$H NMR (400 MHz, CDCl$_3$): 1.64-1.79 (m, 1 H), 1.90 (d, 1 H), 1.97-2.10 (m, 2 H), 2.19-2.30 (m, 1 H), 2.32 (s, 3 H), 2.35-2.46 (m, 1 H), 2.98 (s, 3 H), 4.69 (m, 1 H), 5.49-5.57 (m, 1 H), 6.87 (dd, 1 H), 7.03 (d, 1 H), 7.11 (d, 1 H), 7.53-7.65 (m, 1 H), 8.31 (s, 1 H), 8.39 (d, 1 H).

Example 229

4-(Ethyl(3-(4-methoxypyridin-3-yl)cyclohex-2-en-1-yl)amino)-2-(trifluoromethyl)benzonitrile 3-((4-Cyano-3-(trifluoromethyl)phenyl)(ethyl)amino)cyclohex-1-en-1-yl trifluoromethanesulfonate (0.105 g, 0.24 mmol), (6-methoxypyridin-3-yl)boronic acid (0.044 g, 0.29 mmol), tricyclohexylphosphine (3.33 mg, 0.012 mmol), Pd$_2$(dba)$_3$ (10.87 mg, 0.012 mmol) and potassium phosphate (0.086 mg, 0.40 mmol) were dissolved in mixture of 1,4-dioxane (1.6 ml) and water (0.8 ml) under N$_2$. The mixture was heated in microwave (100° C., 1 h), diluted with DCM (2 ml) and filtrated through a phase separation cartridge. The crude product was purified with strong cation exchange (SCX) tube (DCM/DCM-TEA) and preparative chromatography to give 34 mg of the title product. $^1$H NMR (400 MHz, CDCl$_3$): 1.18-1.32 (m, 3 H), 1.76-1.89 (m, 2 H), 1.95-2.08 (m, 2 H), 2.34-2.54 (m, 2 H), 3.38-3.59 (m, 2 H), 3.87 (s, 3 H), 4.58 (dd, 1 H), 5.71 (dt, 1 H), 6.81 (d, 1 H), 6.86 (dd, 1 H), 7.05 (d, 1 H), 7.56 (dd, 1 H), 8.25 (s, 1 H), 8.41 (d, 1 H).

Example 230

4-((6,6-Dimethyl-3-(oxazol-5-yl)cyclohex-2-en-1-yl)(methyl)amino)-2-(trifluoromethyl)benzonitrile a) 3-((tert-Butyldimethylsilyl)oxy)-4,4-dimethylcyclohex-1-enecarbaldehyde A solution of tert-butyl((3-iodo-6,6-dimethylcyclohex-2-en-1-yl)oxy)dimethylsilane (45.0 g) in THF (500 ml) was cooled to −78° C. before adding 160 g of t-BuLi (1.5 M in pentane) dropwise over a period of 1 h. After 2 h DMF (13.5 ml) was added at −78° C. and the temperature maintained another 1 h. The reaction mixture was quenched with saturated NH₄Cl solution (30 ml) at −78° C., warmed to RT and extracted with EtOAc (3×500 ml). The organic layer was washed with water, dried and evaporated to obtain the crude compound. The compound was purified by flash column using 10% ethyl acetate in petroleum ether as eluent. Yield 17 g. LCMS: no ionization.

b) 5-(3-((tert-Butyldimethylsilyl)oxy)-4,4-dimethyl-cyclohex-1-en-1-yl)-oxazole

A suspension of TosMIC (5.79 g) and K₂CO₃ (5.14 g) in dry MeOH (100 ml) was stirred at RT for 30 min before adding the compound of Example 230(a) (10.0 g) at RT followed by stirring for 20 h. The reaction mixture was quenched with cold water and most of the solvent was evaporated. The aqueous layer was extracted with EtOAc (3×200 ml) and the organic layer was washed with water, dried and evaporated to obtain crude product. The compound was purified by flash column using 3% MeOH in CH₂Cl₂ as eluent. Yield: 1.4 g. LCMS: m/z=308.3 (m+1)⁺.

c) 6,6-Dimethyl-3-(oxazol-5-yl)cyclohex-2-enol

To a solution of the compound of Example 230(b) (2.0 g) in THF (10 ml) was added TBAF (1.0 M in THF) at RT followed by stirring for 4 h. The reaction mixture was quenched with cold water and extracted with EtOAc (3×200 ml). The organic layer was washed with water, dried and evaporated to obtain the crude compound. The compound was purified by flash column using 5% methanol in CH₂Cl₂ as eluent. Yield: 1.0 g. LCMS: no ionization.

d) 5-(3-Azido-4,4-dimethylcyclohex-1-en-1-yl)oxazole

Title compound was prepared from the compound of Example 230(c) (4.0 g), DBU (6.3 g) and DPPA (8.54 g) in toluene (40 ml) as described in Example 6(d). The crude compound was used in the next step as such. Yield: 1.6 g.

e) 6,6-Dimethyl-3-(oxazol-5-yl)cyclohex-2-enamine

To a solution of the compound of Example 230(d) (2.0 g) in THF (10 ml) and H₂O (5 ml) was added PPh₃ (1.20 g) at 60° C. followed by stirring for 16 h. The reaction mixture was quenched with cold water and extracted with EtOAc (2×100 ml). The organic layer was washed with water, dried and evaporated to obtain the crude compound. The crude compound was purified by flash column using 5% methanol in CH₂Cl₂ as eluent. Yield: 0.5 g. ¹HNMR (400 MHz, DMSO-d₆): 0.78 (s, 3H), 0.88 (s, 3H), 1.35-1.43 (m, 1H), 1.53-1.60 (m, 1H), 1.65-1.99 (br, 2H) 2.18-2.25 (m, 2H), 3.00-3.05 (m, 1H), 6.05-6.10 (m, 1H), 7.10 (s, 1H), 8.25 (s, 1H).

f) 4-((6,6-Dimethyl-3-(oxazol-5-yl)cyclohex-2-en-1-yl)amino)-2-(trifluoromethyl)benzonitrile The compound of Example 230(e) (360 mg, 1.56 mmol), 4-fluoro-2-(trifluoromethyl)benzonitrile (300 mg, 1.59 mmol), DIPEA (0.54 ml, 3.12 mmol) and DMSO (3 ml) were mixed and heated at 100° C. When the reaction was complete, the mixture was poured in water and extracted in EtOAc. The mixture was washed with water and brine, dried and evaporated. The product (0.25 g) was purified with flash chromatography. [M+1]⁺=362.

g) 4-((6,6-Dimethyl-3-(oxazol-5-yl)cyclohex-2-en-1-yl)(methyl)amino)-2-(trifluoromethyl)benzonitrile 60% Sodium hydride (0.083 g, 2.07 mmol) was washed with heptane. Dry DMF (5 ml) was added and the mixture was cooled to 0° C. Compound of Example 230(f) (250 mg, 0.69 mmol) in dry DMF (5 ml) was added and the mixture was stirred at 0° C. for 25 min. Iodomethane (0.086 ml, 1.384 mmol) was added followed by stirring at 0° C. for 30 min. The mixture was left to reach RT during 2.5 h. Iodomethane (0.2 eq.) was added followed by stirring for additional 2 h. Water was added and the product was extracted in EtOAc, dried and evaporated. The final product was purified with column chromatography (DCM-MeOH) to afford 220 mg of the title compound. ¹H NMR (400 MHz, CDCl₃): 0.96 (s, 3 H), 1.08 (s, 3 H), 1.65-1.77 (m, 2 H), 2.30-2.59 (m, 2 H), 2.98 (s, 3 H), 4.52 (d, 1 H), 6.06-6.12 (m, 1H), 6.96 (dd, 1 H), 7.05 (s, 1 H), 7.10 (d, 1 H), 7.55-7.64 (m, 1 H), 7.83 (s, 1 H). The enantiomers were separated using chiral HPLC (column: Chiralpak IA No: P33, eluent: 0.2% DEA in MTBE/EtOH+0.2% DEA (3% of B), Q=20 ml/min) to afford 69 mg of enantiomer 1 (rt=5.97 min) and 72 mg of enantiomer 2 (rt=7.33 min).

Example 231

2-Chloro-4-((6,6-dimethyl-3-(oxazol-5-yl)cyclohex-2-en-1-yl)(methyl)-amino)benzonitrile a) 2-Chloro-4-((6,6-dimethyl-3-(oxazol-5-yl)cyclohex-2-en-1-yl)amino)-benzonitrile The compound of Example 230(e) (370 mg, 1.93 mmol), 2-chloro-4-fluorobenzonitrile (305 mg, 1.96 mmol), DIPEA (0.67 ml, 3.85 mmol) and DMSO (4 ml) were mixed and heated at 100° C. When the reaction was complete the mixture was poured in water and extracted in EtOAc. The mixture was washed with water and brine, dried and evaporated. The product was purified with flash chromatography to afford 0.103 g of the title compound. [M+1]=328.

b) 2-Chloro-4-((6,6-dimethyl-3-(oxazol-5-yl)cyclohex-2-en-1-yl)(methyl)-amino)benzonitrile 60% Sodium hydride (0.015 g, 0.61 mmol) was washed with pentane. Dry DMF (2 ml) was added and the mixture was cooled to 0° C. Compound of Example 231(a) (100 mg, 0.305 mmol) in dry DMF (3 ml) was added and the mixture was stirred at 0° C. for 30 min. Iodomethane (0.019 ml, 0.305 mmol) was added and the mixture was stirred at 0° C. for 30 min and left to reach RT overnight. Iodoethane (1.5 eq.) and NaH (2 eq.) were added and the mixture was stirred for 24 h. Water was added and the product was extracted in EtOAc, dried and evaporated. The final product was purified with preparative HPLC. Yield 18 mg. ¹H NMR (400 MHz, CDCl₃): 0.94 (s, 3 H), 1.06 (s, 3 H), 1.61-1.75 (m, 2 H), 2.32-2.54 (m, 2 H), 2.91 (s, 3 H), 4.38-4.47 (m, 1 H), 6.06 (dt, 1 H), 6.72 (dd, 1 H), 6.83 (d, 1 H), 7.03 (s, 1 H), 7.44 (d, 1 H), 7.82 (s, 1 H).

Example 232

4-(Methyl(3-(thiazol-5-yl)cyclohex-2-en-1-yl)amino)-2-(trifluoromethyl)-benzonitrile a) 3-(Thiazol-5-yl)cyclohex-2-enone Potassium carbonate (2.073 g, 15.0 mmol), palladium(II) acetate (0.067 g, 0.300 mmol) and toluene (20 ml) were charged into microvial. 2-Ethylene hexanoic acid (0.160 ml, 1.00 mmol), thiazole (1.419 ml, 20.0 mmol) and 3-chlorocyclohex-2-enone (1.109 ml, 10 mmol) were added and air was removed with $N_2$. Tricyclohexylphosphine (0.252 g, 0.90 mmol) was added, tube sealed followed by heating at 110° C. overnight. Water (50 ml) was added and mixture was extracted with EtOAc. Combined organic phases were washed with brine, dried and evaporated. The mixture was filtrated through a pad of celite and purified with flash chromatography (EtOAc/heptane) giving 611 mg of the title compound. [M+1]=180.

b) 3-(Thiazol-5-yl)cyclohex-2-enamine

2 M Ammonia in IPA (5.8 ml) was added dropwise to an ice-cold compound of Example 232(a) (0.60 g, 3.35 mmol) under $N_2$ atmosphere. The mixture was stirred for 10 min at 0° C. Titanium(IV)isopropoxide (1.98 ml, 6.69 mmol) was added and the mixture was left to reach RT overnight. The mixture was cooled to 0° C. and sodium borohydride (127 mg, 3.35 mmol) was added. The mixture was stirred at RT for 24 h. 1 M $NH_3$ (aq.) was added and the product was extracted in EtOAc, dried and evaporated, giving 420 mg of the title compound. [M+1]=181.

c) 4-((3-(Thiazol-5-yl)cyclohex-2-en-1-yl)amino)-2-(trifluoromethyl)benzonitrile Compound of Example 232(b) (500 mg, 2.77 mmol), 4-fluoro-2-(trifluoromethyl)benzonitrile (535 mg, 2.83 mmol), DIPEA (0.97 ml, 5.55 mmol) and DMSO (7 ml) were mixed and heated at 100° C. When the reaction was complete the mixture was poured in water and extracted in EtOAc. The mixture was washed with water and brine, dried and evaporated. The product was purified with flash chromatography affording 0.38 g of the title compound. [M+1]=350.

d) 4-(Methyl(3-(thiazol-5-yl)cyclohex-2-en-1-yl) amino)-2-(trifluoromethyl)-benzonitrile 60% Sodium hydride (0.065 g, 1.63 mmol) was washed with heptane. Dry DMF (4 ml) was added and the mixture was cooled to 0° C. Compound of Example 232(c) (380 mg, 1.09 mmol) in dry DMF (4 ml) was added and the mixture was stirred at 0° C. for 30 min. Iodomethane (0.135 ml, 2.18 mmol) was added and the mixture was stirred at 0° C. for 10 min and after that for 4.5 h at RT. Water was added and the product was extracted in EtOAc, washed with water and brine, dried and evaporated. The final product was purified with flash chromatography (EtOAc-Heptane) giving 242 mg of the title compound. $^1$H NMR (400 MHz, $CDCl_3$): 1.62-1.75 (m, 1 H), 1.86 (d, 1 H), 1.96-2.11 (m, 3 H), 2.51-2.59 (m, 2 H), 2.94 (s, 3 H), 4.67 (dt, 1 H), 5.99 (d, 1 H), 6.87 (dd, 1 H), 7.02 (d, 1 H), 7.56-7.64 (m, 1 H), 7.83 (s, 1 H), 8.64-8.70 (m, 1 H). The enantiomers were separated using chiral HPLC (column: Chiralpak IA No: P39, eluent: 0.2% DEA in MTBE/IPA+0.2% DEA (5% of B), Q=20 ml/min) to give 60 mg of enantiomer 1 (rt=8.132 min) and 70 mg of enantiomer 2 (rt=12.403 min).

Example 233

4-(Ethyl(3-(oxazol-5-yl)cyclopent-3-enyl)amino)-2-(trifluoromethyl)benzonitrile (enantiomer 1 and 2)

The enantiomers of the racemic compound of Example 222 were separated from the racemic mixture by chiral HPLC chromatography (Chiralpak 1A 20 mm×250 mm column, eluent A: n-hexane+0.2% DEA, eluent B: EtOH+0.2% DEA, isocratic B 15%, 20 ml/min) to give enantiomer 1 (rt 14.5 min) and enantiomer 2 (rt 16.0 min).

Example 234

4-((5-(1H-imidazol-1-yl)-2,2-dimethylcyclohexyl) (methyl)amino)-2-chlorobenzonitrile a) 3-(3-Chloro-4-cyanophenylamino)-4,4-dimethylcyclohexyl methanesulfonate

The compound was prepared from the compound of Example 2(b) (6.16 g, 22.1 mmol), methanesulfonyl chloride (3.29 g, 28.7 mmol) and TEA (6.16 ml, 44.2 mmol) in DCM (90 ml) as in Example 44(a) yielding 6.27 g of the title compound as a mixture of diastereomers ($^1$H NMR trans:cis 84:16). LCMS: m/z=357.3 $(M+1)^+$.

b) 3-((3-Chloro-4-cyanophenyl)(methyl)amino)-4,4-dimethylcyclohexyl methanesulfonate The compound was prepared from the compound of Example 234(a) (3.15 g), sodium hydride (60% dispersion in mineral oil, 1.06 g) and iodomethane (1.65 ml) in DMF (25 ml) yielding 3.64 g (raw material) of the title product as a mixture of diastereomers ($^1$H NMR trans:cis 89:11). Crude product was used as such in the next step. LCMS: m/z=371.3 $(M+1)^+$ c) 4-((5-(1H-imidazol-1-yl)-2,2-dimethylcyclohexyl) (methyl)amino)-2-chlorobenzonitrile The compound was prepared from the compound of Example 234(b) (1.50 g) and sodium imidazole-1-ide (0.728 g) in DMF as in Example 44(c). Crude product was purified and isomers were separated by chromatography (1$^{st}$ silica column, eluent DCM+0.5% MeOH, 2$^{nd}$ Chiralpak IA 20×250 mm, 5 um, eluent A: MTBE+0.2% DEA, eluent B: EtOH+0.2% DEA, isocratic B 5%, 20 ml/min) to obtain enantiomer 1 (yield 0.080 g, rt 19.6 min) and enantiomer 2 (yield 0.077 g, rt 24 min) of the trans-diastereomer, $^1$H NMR (400 MHz, $CDCl_3$): 0.87 (s, 3 H), 1.15 (s, 3 H), 1.42-1.57 (m, 1 H), 1.65 (td, 1 H), 2.02-2.18 (m, 2 H), 2.21-2.28 (m, 1H), 2.42-2.52 (m, 1 H) 2.91 (s, 3 H) 3.79 (dd, 1 H), 4.52-4.56 (m, 1 H), 6.53 (dd, 1 H), 6.67 (d, 1 H), 7.03 (t, 1 H), 7.15 (t, 1 H), 7.34 (d, 1 H), 7.65 (s, 1 H), and enantiomer 1 (rt 48 min, yield 0.0045 g) and enantiomer 2 (rt 63 min, yield 0.0059 g) of the cis-diastereomer, $^1$H NMR (400 MHz, $CDCl_3$): 0.99 (s, 3 H), 1.16 (s, 3 H), 1.52-1.73 (m, 2 H), 1.86-1.97 (m, 1H), 1.98-2.10 (m, 2 H), 2.26 (q, 1 H), 2.88 (s, 3 H), 3.78 (dd, 1 H), 4.10-4.20 (m, 1 H), 6.71 (dd, 1 H), 6.83 (d, 1 H), 6.99 (t, 1 H), 7.08 (t, 1 H), 7.44 (d, 1 H), 7.58 (t, 1 H). LCMS: m/z=343.4 $(M+1)^+$.

Example 235

4-((5-(1H-imidazol-1-yl)-2,2-dimethylcyclohexyl) (ethyl)amino)-2-chlorobenzonitrile a) 3-((3-Chloro-4-cyanophenyl)(ethyl)amino)-4,4-dimethylcyclohexyl methanesulfonate The compound was prepared from the compound of Example 234(a) (3.12 g), sodium hydride (60% dispersion in mineral oil, 1.05 g) and iodoethane (1.76 ml) in DMF (25 ml) yielding 3.40 g (raw material) of the title product as a mixture of diastereomers. ($^1$H NMR trans:cis 89:11). Crude product was used as such in the next step. LCMS: m/z=385.4 (M+1)$^+$.

b) 4-((5-(1H-imidazol-1-yl)-2,2-dimethylcyclohexyl)(ethyl)amino)-2-chlorobenzonitrile The compound was prepared from the compound of Example 235(a) 1.50 g and sodium imidazole-1-ide (0.702 g) in DMF (15 ml) as in Example 44(c). Crude product was purified and isomers were separated by chromatography (1$^{st}$ silica column, eluent DCM+2% MeOH, 2$^{nd}$ Chiralpak IA 20×250 mm, eluent A: MTBE+0.4% DEA, eluent B: EtOH+ 0.4% DEA, isocratic B 5%, 20 ml/min) to obtain enantiomer 1 (rt 16.4 min, yield 0.080 g) and enantiomer 2 (rt 23.5 min, yield 0.077 g) of the trans-diastereomer, $^1$H NMR (400 MHz, CDCl$_3$): 0.86 (s, 3 H), 1.13 (s, 3 H), 1.18 (t, 3 H), 1.44-1.52 (m, 1 H), 1.59-1.68 (m, 1 H), 2.01-2.13 (m, 1 H), 2.16-2.28 (m, 2 H), 2.40-2.49 (m, 1 H), 3.41 (q, 2 H), 3.83 (dd, 1 H), 4.52-4.55 (m, 1H), 6.53 (dd, 1H), 6.67 (d, 1H), 7.03 (t, 1H), 7.15 (t, 1H), 7.35 (d, 1H), 7.65 (t, 1H), and enantiomer 1 (rt 33.5 min, yield 0.0045 g) and enantiomer 2 (rt 38.5 min, yield 0.0059 g) of the cis-diastereomer, $^1$H NMR (400 MHz, CDCl$_3$): 0.96 (s, 3 H), 1.09-1.16 (m, 6 H), 1.51-1.61 (m, 1 H), 1.64-1.72 (m, 1 H), 1.86-1.98 (m, 1 H), 1.99-2.14 (m, 2 H), 2.23 (q, 1 H), 3.33-3.43 (m, 2 H), 3.81 (dd, 1 H), 4.08-4.18 (m, 1 H), 6.70 (dd, 1 H), 6.83 (d, 1 H), 7.00 (t, 1 H), 7.09 (t, 1 H), 7.42 (d, 1 H), 7.59 (t, 1 H). LCMS: m/z=357.3 (M+1)$^+$.

Example 236

Cis-4-((4-hydroxy-3-(1H-imidazol-1-yl)-6,6-dimethylcyclohex-2-enyl)-(methyl)amino)-2-(trifluoromethyl)benzonitrile a) Cis-(4-((4-cyano-3-(trifluoromethyl)phenyl)(methyl)amino)-2-(1H-imidazol-1-yl)-5,5-dimethylcyclohex-2-enyl 4-nitrobenzoate A suspension of the compound of Example 262 (0.105 g), triphenylphosphine (0.560 g) and 4-nitrobenzoic acid (0.321 g) in toluene (12 ml) was stirred at RT for 30 min under N$_2$. Diethyl azodicarboxylate (0.336 ml solution in toluene 5 ml) was added dropwise and stirring was continued overnight. EtOAc was added and the mixture was washed with 1M Na$_2$CO$_3$, water and brine. Organic phase was dried and evaporated. Impurities and excess of the reagents were partly removed by chromatography (silica column, eluent 0-3% MeOH/DCM). Yield 0.464 g (crude). LCMS: m/z=540.3 (M+1)$^+$.

(b) Cis-4-((4-hydroxy-3-(1H-imidazol-1-yl)-6,6-dimethylcyclohex-2-enyl)-(methyl)amino)-2-(trifluoromethyl)benzonitrile The compound from Example 236(a) (0.464 g, crude) was suspended to a mixture of MeOH (4 ml) and water (1 ml). At ice-bath K$_2$CO$_3$ (0.186 g) was added and stirring continued for 1 h. EtOAc was added, the mixture washed with 1 M Na$_2$CO$_3$ and brine. Organic phase was dried and evaporated. Compound was purified by chromatography (silica column, eluent 0-2.5% MeOH/DCM). Yield 0.062 g. LCMS: m/z=391.3 (M+1)$^+$. $^1$H NMR (400 MHz, CDCl$_3$): 1.06 (s, 3 H), 1.15 (s, 3 H), 1.5 (br, s., 1H), 1.93-2.09 (m, 2 H), 3.05 (s, 3 H), 4.48-4.52 (m, 1 H), 4.61-4.66 (m, 1 H), 5.70 (d, 1 H), 6.94 (dd, 1 H), 7.01 (t, 1 H), 7.08 (d, 1 H), 7.19 (t, 1 H), 7.59 (d, 1 H), 7.68 (t, 1 H).

Example 237

4-((6,6-Dimethyl-3-(thiazol-5-yl)cyclohex-2-enyl)(methyl)amino)-2-(trifluoromethyl)benzonitrile a) 6,6-Dimethyl-3-(thiazol-5-yl)cyclohex-2-enone The compound was prepared from 3-chloro-6,6-dimethylcyclohex-2-enone (1.60 g), thiazole (1.12 g), 2-ethylhexanoic acid (0.145 g), Pd(Ac)$_2$ (0.113 g), K$_2$CO$_3$ (2.09 g) and tricyclohexylphosphine (0.424 g) as in Example 232(a) except that mixture of toluene (24 ml) and DMF (4 ml) was used as a solvent. Reaction time at microwave reactor was 10 h at 110° C. Crude product was purified by chromatography (silica column, eluent 0-30% EtOAc/heptane) to obtain the title compound. Yield 0.70 g. LCMS: m/z=208.1 (M+1)$^+$.

b) 6,6-Dimethyl-3-(thiazol-5-yl)cyclohex-2-enamine

The compound was prepared from the compound of Example 237(a) (0.65 g), titanium(IV)isopropoxide (1.79 g), ammonia 2 M in IPA (5.5 ml) and NaBH$_4$ (0.119 g) as in Example 232(b) Yield 0.56 g. $^1$H NMR (400 MHz, CDCl$_3$): 0.88 (s, 3 H), 1.01 (s, 3 H), 1.30 (br, s, 2H), 1.51-1.59 (m, 1 H), 1.62-1.69 (m, 1 H), 2.33-2.49 (m, 2 H), 3.13-3.16 (m, 1 H), 5.97-6.02 (m, 1 H), 7.75 (s, 1 H), 8.61 (s, 1 H).

c) 4-(6,6-Dimethyl-3-(thiazol-5-yl)cyclohex-2-enylamino)-2-(trifluoromethyl)benzonitrile The compound was prepared from the compound of Example 237(b) (0.56 g), 4-fluoro-2-(trifluoromethyl)benzonitrile (0.51 g) and DIPEA (0.70 g) in DMSO (10 ml). Reaction time was 5 h at 100° C. Crude product was purified by chromatography (silica column, eluent 0-60% EtOAc/heptane) to obtain the title compound as a mixture of enantiomers. Yield 0.44 g. LCMS: m/z=378.7 (M+1)$^+$.

d) 4-((6,6-Dimethyl-3-(thiazol-5-yl)cyclohex-2-enyl)(methyl)amino)-2-(trifluoromethyl)benzonitrile The compound was prepared from the compound of Example 237(c) (0.44 g), sodium hydride (60% dispersion in mineral oil, 0.070 g) and iodomethane (0.145 ml) in DMF (8 ml). Reaction time was 1 h at ice bath. Crude product was purified and isomers were separated by chromatography (1$^{st}$ silica column, eluent 10-50% EtOAc/heptane, 2$^{nd}$ Chiralpak IA 20×250 mm, eluent A: MTBE+0.2% DEA, eluent B: IPA+0.2% DEA, isocratic B 5%, 20 ml/min) to obtain enantiomer 1 (rt 5.8 min, yield 0.130 g) and enantiomer 2 (rt 8.7 min, yield 0.138 g). LCMS: m/z=392.8 (M+1)$^+$. $^1$H NMR (400 MHz, CDCl$_3$): 0.96 (s, 3 H), 1.08 (s, 3 H), 1.67-1.80 (m, 2 H), 2.46-2.71 (m, 2 H), 2.98 (s, 3 H), 4.43-4.47-4.53 (m, 1 H), 5.86-5.95 (m, 1 H), 6.94 (dd, 1 H), 7.09 (d, 1 H), 7.60 (d, 1 H), 7.85 (s, 1 H), 8.68 (s, 1 H).

Example 238

4-(Ethyl(3-hydroxy-3-(isoxazol-4-yl)cyclohexyl)amino)-2-(trifluoromethyl)-benzonitrile The compound was prepared from the compound of Example 117(f) (0.80 g), 3 M EtMgBr solution in Et$_2$O (1.37 ml) and 4-iodoisoxazole (0.503 g) in DCM (25 ml). Reaction time was 2 h at RT. The crude product was purified and isomers were separated by chromatography (1st silica column, eluent 0-10% MeOH/DCM, 2nd silica column, eluent 50-80% EtOAc/heptane) to obtain cis- and trans-diastereomers of the title compound. Yields: 0.108 g (trans-diastereomer), 0.025 g (cis-diastereomer). LCMS: m/z=380 (M+1)+. Trans-diastereomer: $^1$H NMR (400 MHz, CDCl$_3$): 1.21 (t, 3 H), 1.55-1.65 (m, 1 H), 1.65-1.76 (m, 2 H), 1.84-1.92 (m, 1 H), 1.93-2.05 (m, 2 H), 2.07-2.14 (m, 2 H), 2.28 (br. s., 1 H), 3.32-3.45 (m, 2 H), 4.33 (m, 1 H), 6.88 (dd, 1 H), 7.01 (d, 1 H), 7.53 (d, 1 H), 8.30 (s, 1 H), 8.36 (s, 1 H). Cis-diastereomer: $^1$H NMR (400 MHz, CDCl$_3$): 1.24 (t, 3 H), 1.40-1.50 (m, 1 H), 1.55-1.63 (m, 1 H), 1.73-1.80 (m, 1 H), 1.83-1.88 (m, 1H), 1.95-2.04 (m, 2 H), 2.09 (br. s., 1 H), 2.28-2.36 (m, 2 H), 3.42 (q, 2 H), 3.52-3.59 (m, 1 H), 6.61 (dd, 1 H), 6.79 (d, 1 H), 7.54 (d, 1 H), 8.40 (s, 1 H), 8.51 (s, 1 H).

Example 239

4-(Ethyl(3-(isoxazol-4-yl)cyclohex-3-enyl)amino)-2-(trifluoromethyl)benzonitrile To an ice cold concentrated H$_2$SO$_4$ (0.70 ml) the compound of Example 238 (0.050 g) was added. After stirring for 10 min ice cold water was added, the mixture neutralized with 6 M NaOH and the product extracted into EtOAc. EtOAc was washed with brine, dried and evaporated. The residue was dissolved into Et$_2$O, drops of heptane were added and the precipitated title compound filtered. Yield: 0.023 g. LCMS: m/z=362 (M+1)+. $^1$H NMR (400 MHz, CDCl$_3$): 1.28 (t, 3 H), 1.83-2.04 (m, 2 H), 2.42-2.49 (m, 4H), 3.37-3.52 (m, 2 H), 4.08-4.16 (m, 1 H), 6.08-6.13 (m, 1 H), 6.86 (dd, 1 H), 7.00 (d, 1 H), 7.59 (d, 1 H), 8.29 (s, 1 H), 8.38 (s, 1 H).

Example 240

Trans-2-(difluoromethyl)-4-((4-hydroxy-3-(1H-imidazol-1-yl)-6,6-dimethylcyclohex-2-enyl)(methyl)amino)benzonitrile a) 2-(Difluoromethyl)-4-(4-hydroxy-3-(1H-imidazol-1-yl)-6,6-dimethylcyclohex-2-enyl)(methyl)amino)benzonitrile (pure enantiomer)

The compound was prepared from 2-(difluoromethyl)-4-fluorobenzonitrile (5.18 g), compound of Example 21(a) (pure enantiomer) (5.79 g) and DIPEA (13.2 ml) in DMSO (30 ml). Reaction time was 12 h at 100° C. Crude product was purified by chromatography (silica column, eluent 0-10% MeOH/DCM) yielding 3.76 g of the title compound. LCMS: m/z=343.6 (M+1)+.

b) 4-((3-(1H-imidazol-1-yl)-6,6-dimethylcyclohex-2-enyl)(methyl)amino)-2-(difluoromethyl)benzonitrile (pure enantiomer)

The compound was prepared from the compound of Example 240(a) (1.46 g), sodium hydride (60% dispersion in mineral oil, 0.26 g) and iodomethane (0.48 ml) in DMF (23 ml) at −10° C. Crude product was purified by chromatography (silica column, eluent 0-10% MeOH/DCM) yielding 0.71 g of the title compound. LCMS: m/z=358.1 (M+1)+.

c) Trans-2-(difluoromethyl)-4-((4-hydroxy-3-(1H-imidazol-1-yl)-6,6-dimethylcyclohex-2-enyl)(methyl)amino)benzonitrile The compound was prepared from the compound of Example 240(b) (1.20 g), SeO2 (0.374 g) and pyridine 1-oxide (1.50 g) in 1,3-dioxane (12 ml) as in Example 253(a). Reaction time at microwave reactor was 2 h at 140° C. Crude product was purified by chromatography (silica column, eluent 0-10% MeOH/DCM) yielding 0.225 g of the title compound. LCMS: m/z=373.6 (M+1)+. $^1$H NMR (400 MHz, CDCl$_3$): 1.05 (s, 3 H), 1.16 (s, 3 H), 1.7 (br, s., 1H), 1.88 (dd, 1 H), 2.13-2.21 (m, 1 H), 2.94 (s, 3 H), 4.71-4.78 (m, 2 H), 5.70-5.72 (m, 1 H), 6.87 (t, 1H), 6.90 (dd, 1 H), 7.08 (d, 1 H), 7.10-7.13 (m, 1 H), 7.17 (t, 1 H), 7.52-7.59 (m, 1 H), 7.66-7.76 (m, 1 H).

Example 241

Cis-2-(difluoromethyl)-4-((4-hydroxy-3-(1H-imidazol-1-yl)-6,6-dimethylcyclohex-2-enyl)(methyl)amino)benzonitrile a) Cis-4-((4-cyano-3-(difluoromethyl)phenyl)(methyl)amino)-2-(1H-imidazol-1-yl)-5,5-dimethylcyclohex-2-enyl 4-nitrobenzoate The compound was prepared from Example 240(c) (0.28 g), triphenylphosphine (1.56 g), 4-nitrobenzoic acid (0.89 g) and diethyl azodicarboxylate (0.933 ml) in toluene (46 ml) as in Example 236(a). Impurities and excess of the reagents were partly removed by chromatography (silica column, eluent 0-10% MeOH/DCM). Yield: 2.30 g (crude). LCMS: m/z=522.4 (M+1)+.

b) Cis-2-(difluoromethyl)-4-((4-hydroxy-3-(1H-imidazol-1-yl)-6,6-dimethylcyclohex-2-enyl)(methyl)amino)benzonitrile The compound was prepared from the compound of Example 241(a) (2.3 g, crude) and K$_2$CO$_3$ (0.515 g) in the mixture of MeOH (12 ml) and water (3 ml) as described in Example 236(b). Yield: 0.21 g. LCMS: m/z=373.6 (M+1). $^1$H NMR (400 MHz, CDCl$_3$): 1.07 (s, 3 H), 1.15 (s, 3 H), 1.5 (br, s., 1H), 1.91-1.99 (m, 1 H), 2.02-2.10 (m, 1 H), 3.05 (s, 3 H), 4.52-4.56 (m, 1 H), 4.63-4.68 (m, 1 H), 5.70-5.74 (m, 1 H), 6.87 (t, 1H), 6.89 (dd, 1 H), 7.08 (d, 1 H), 7.09-7.11 (m, 1 H), 7.19 (t, 1 H), 7.53-7.58 (m, 1 H), 7.72 (t, 1 H).

Example 242

4-((6-Hydroxy-3-(1H-imidazol-1-yl)cyclohex-2-enyl)(methyl)amino)-2-(trifluoromethyl)benzonitrile a) 4-(1H-Imidazol-1-yl)-2-oxocyclohex-3-en-1-yl acetate To 4-bromo-2-oxocyclohex-3-en-1-yl acetate (8.0 g) in toluene (80 ml) were added Et$_3$N (7.2 ml), KHCO$_3$ (4.12 g) and imidazole (6.9 g) and the resulting mixture was heated to 100° C. for 6 h. The mixture was concentrated, poured into water (100 ml) and extracted with EtOAc (2×100 ml). The organic layer was dried and concentrated to obtain the crude compound. The compound was purified by flash column using 100-200 mesh silica gel and eluted with 4% MeOH in CH$_2$Cl$_2$ to afford 4.5 g of the title compound. LCMS: m/z=221 (M+1)+.

b) 2-Amino-4-(1H-imidazol-1-yl)cyclohex-3-enol

To a cold stirred solution of the compound of Example 242(a) (4.0 g) in IPA (40 ml) 5 M NH$_3$ in IPA (40 ml) was added followed by dropwise addition of 10.3 ml of Ti(iOPr)$_4$. The mixture was allowed to warm up to RT and stirred for 4 h. The mixture was again cooled to 0° C., sodium borohydride (2.06 g) was added, and the mixture was stirred at RT for 16 h. The mixture was poured into ice cold water (100 ml) and extracted with 15% MeOH in CH$_2$Cl$_2$ (2×100 ml). The organic layer was dried, filtered and concentrated to afford crude compound which was directly used to next step. Yield 2.5 g (crude). LCMS: m/z=180 (M+1)$^+$.

c) tert-Butyl (6-hydroxy-3-(1H-imidazol-1-yl)cyclohex-2-en-1-yl)carbamate

To a cold stirred solution of the compound of Example 242(b) (2.5 g crude) in CH$_2$Cl$_2$ (25 ml) was added Et$_3$N (2.8 ml) followed by Boc$_2$O (3.6 ml). The mixture was stirred at RT for 16 h, poured into water (75 ml) and extracted with CH$_2$Cl$_2$ (2×75 ml). The organic layer was dried, filtered and concentrated to afford crude compound. The compound was purified by flash column using 100-200 mesh silica gel and eluted with 3% MeOH in CH$_2$Cl$_2$ to afford 1.5 g of the title compound. LCMS: m/z=280 (M+1)$^+$.

d) tert-Butyl (6-(benzyloxy)-3-(1H-imidazol-1-yl)cyclohex-2-en-1-yl)carbamate To an ice cold stirred suspension of NaH 60% (0.372 g) in THF was added the compound of Example 242(c) (2.0 g) in THF (10 ml) at 0° C. After 15 min benzyl bromide (1.0 ml) was added and the mixture was allowed to stir at RT for 16 h. The mixture was poured into ice cold water (40 ml) and extracted with EtOAc (2×100 ml). The organic layer was washed with brine, dried, filtered and concentrated to afford crude compound. The compound was purified by flash column using 100-200 mesh silica gel and eluted with 3% MeOH in CH$_2$Cl$_2$ to afford 0.7 g of the title compound. Isomers were separated by chiral chromatography (Chiralcel OJ-H 250×30 mm, CO$_2$ 85%, Co solvent 15% (0.5% DEA in MeOH), flow 70 g/min). Yields: (1) 0.02 g, (2) 0.1 g, (3) 0.02 g and (4) 0.15 g. Using chiral column Chiracel OJ-H (4.6×250 mm), 5 um and eluent CO$_2$ 80%, Co solvent 20% (0.5% DEA in MeOH), flow 3 g/min, retention times of the isomers are: (1) 2.26 min, (2) 2.53 min, (3) 2.87 min and (4) 6.22 min. Based on 1HNMR (1) and (3) are enantiomers, and (2) and (4) are a second pair of enantiomers. LCMS: m/z=370 (M+1)$^+$.

e) 6-(Benzyloxy)-3-(1H-imidazol-1-yl)cyclohex-2-enanmine hydrochloride (isomer 2)

The compound of Example 242(d) (isomer 2) (0.30 g), was added to a solution of 5 M HCl in dioxane (20 ml) at 0° C. The resulting mixture was stirred at RT for 6 h and concentrated under reduced pressure to afford crude compound. The compound was triturated with anhydrous Et$_2$O to afford 0.23 g of the title compound. LCMS: m/z=270 (M+1)$^+$.

f) 4-(6-(Benzyloxy)-3-(1H-imidazol-1-yl)cyclohex-2-enylamino)-2-(trifluoromethyl)benzonitrile (isomer 2)

The compound was prepared from the compound of Example 242(e) (isomer 2) (0.213 g), 4-fluoro-2-(trifluoromethyl)benzonitrile (0.132 g) and DIPEA (0.606 ml) in DMSO (5 ml). Reaction time was 3 h at 100° C. The crude product was purified by chromatography (silica column, eluent 0-10% MeOH/DCM) to obtain the title compound. Yield 0.105 g. LCMS: m/z 439.6 (M+1)$^+$.

g) 4-((6-(Benzyloxy)-3-(1H-imidazol-1-yl)cyclohex-2-enyl)(methyl)amino)-2-(trifluoromethyl)benzonitrile (isomer 2)

The compound was prepared from the compound of Example 242(f) (0.105 g), sodium hydride (60% dispersion in mineral oil, 0.019 g) and iodomethane (0.030 ml) in DMF (2 ml) at ice-bath. Reaction time was 1 h. Yield 0.059 g. The crude compound was used to next step without purification. LCMS: m/z=453.7 (M+1)$^+$.

h) 4-((6-Hydroxy-3-(1H-imidazol-1-yl)cyclohex-2-enyl)(methyl)amino)-2-(trifluoromethyl)benzonitrile (isomer 2)

The compound of Example 242(g) (0.058 g), BCl$_3$ (1M solution in heptane, 0.39 ml) and DCM (1 ml) were stirred at ice-bath for 1 h. The mixture was neutralized with NH$_3$ (25% in H$_2$O) and evaporated to dryness. The crude product was purified by chromatography (silica column, eluent 0-10% MeOH/DCM) to give 0.021 g of the title compound. LCMS: m/z=363.6 (M+1)$^+$. $^1$H NMR (400 MHz, CDCl$_3$): 2.05-2.15 (m, 1 H), 2.22-2.32 (m, 1 H), 2.63-2.81 (m, 2 H), 2.8 (br, 1H), 2.97 (s, 3 H), 4.06 (m, 1 H), 4.64-4.70 (m, 1 H), 5.58 (m, 1 H), 7.01 (dd, 1 H), 7.05-7.07 (m, 1 H), 7.12 (t, 1 H), 7.14 (d, 1 H), 7.56 (d, 1 H), 7.60-7.68 (m, 1 H). Similarly, starting from isomer 4 of the compound of Ex 241(d) an other enantiomer of the compound of Ex 241(h) was prepared.

Example 243

2-Chloro-4-{[5-hydroxy-5-(1H-imidazol-4-yl)-2,2-dimethylcyclohexyl](methyl)amino}benzonitrile The title compound was prepared as in Example 112(h) using 2-chloro-4-{[5-hydroxy-2,2-dimethyl-5-(1-trityl-1H-imidazol-4-yl)cyclohexyl](methyl)amino}-benzonitrile (Example 2(g), mixture of diastereomers 77:23) as a starting material. After adjustment of pH to 8-9 with aqueous NaHCO$_3$ the precipitation (diastereomer 1) was filtered, washed with water and dried in vacuum (40° C.) overnight. This crude product was triturated in boiling DCM, the mixture was cooled, the solid material was filtered and dried in vacuum (40° C.) to give the major diastereomer 1. The basic water phase was extracted with DCM. The combined organic layers were washed with water, dried, filtered and evaporated. This crude product was purified by flash chromatography on silica gel by using DCM-MeOH as a gradient eluent (100:0-90:10) to give the product as a mixture of diastereomers ($^1$H NMR 10:90). Diastereomer 2 was purified by preparative chiral HPLC (Column Chiralpak IC 20 mm×250 mm 5 μm, A n-hexane+0.2% DEA, B EtOH+0.2% DEA, isocratic B 10%, flow 20 ml/min, λ 300 nm) to yield pure diastereomer 2. The major diastereomer 1: $^1$H NMR (400 MHz, MeOH-d$_4$): 0.93 (3H, s), 1.16 (3H, s), 1.36 (1H, m), 1.70 (2H, m), 2.02 (2H, m), 2.51 (1H, t), 2.90 (3H, s), 4.37 (1H, dd), 6.91 (1H, dd), 6.97 (1H, d), 6.99 (1H, d), 7.48 (1H, d), 7.60 (1H, d). The minor diastereomer 2: $^1$H NMR (400 MHz, CDCl$_3$): 0.79 (3H, s), 1.13 (3H, s), 1.37-1.44

(2H, m), 1.90 (1H, m), 2.28 (3H, m), 2.87 (3H, s), 3.71 (1H, dd), 6.53 (1H, dd), 6.67 (1H, d), 7.00 (1H, d), 7.32 (1H, d), 7.55 (1H, d).

Example 244

4-{[3-(1H-Imidazol-4-yl)-6,6-dimethylcyclohex-3-enyl](methyl)amino}-2-(trifluoromethyl)benzonitrile a) 4-{[5-(tert-Butyldimethylsilyloxy)-2,2-dimethyl-cyclohexyl](methyl)-amino}-2-(trifluoromethyl)benzonitrile Sodium hydride (60% dispersion in mineral oil, 3.42 g, 85 mmol) was added in portions to a solution of the compound of Example 1(c) (mixture of diastereomers, 18.22 g, 42.7 mmol) in 140 ml of dry DMF at 0° C. under $N_2$. The mixture was allowed to stir at 0° C. for 40 min. Iodomethane (12.12 g, 85 mmol) was added slowly at 0° C. and the mixture was stirred for 20 min at 0° C. and for 3 h at RT. The mixture was quenched with saturated aqueous $NH_4Cl$ solution (250 ml) and water (150 ml) (the ice bath cooling). The product was extracted into toluene (3×200 ml). The combined organic layers were washed with brine (375 ml) and water (2×200 ml), dried, filtered and evaporated. Crystallization of the crude product (20.15 g, mixture of diastereomers) in heptane (70 ml) gave 11.78 g of pure major diastereomer 1. More (1.49 g) of the product (mixture of diastereomers 36:64) was crystallized from the mother liquor. The major diastereomer 1: $^1$H NMR (400 MHz, $CDCl_3$): 0.06 (3H, s), 0.07 (3H, s), 0.89 (12H, s), 1.07 (3H, s), 1.32-1.55 (3H, m), 1.70-1.77 (2H, m), 1.95 (1H, m), 2.91 (3H, s), 3.64 (1H, dd), 3.71 (1H, m), 6.90 (1H, dd), 7.05 (1H, d), 7.57 (1H, d).

b) 4-[(5-Hydroxy-2,2-dimethylcyclohexyl)(methyl)amino]-2-(trifluoromethyl)benzonitrile Thionyl chloride (14.33 g, 120 mmol) was added slowly to a solution of the compound of Example 244(a) (mixture of diastereomers, 13.27 g, 30.1 mmol) in 250 ml of dry methanol at 0° C. under $N_2$. Thereafter the solution was allowed to stir at RT for 2 h. The solvent was evaporated and ethyl acetate (350 ml) and water (175 ml) were added. The mixture was made basic (pH 8) with 1 M aqueous NaOH solution and the layers were separated. The water phase was extracted with ethyl acetate (150 ml). The combined organic layers were washed with water (250 ml) and brine (200 ml), dried, filtered and evaporated. The crude product was the mixture of diastereomers ($^1$H NMR 93:7).

c) 4-[(2,2-Dimethyl-5-oxocyclohexyl)(methyl)amino]-2-(trifluoromethyl)-benzonitrile The title compound was prepared as in Example 112(f) from the compound of Example 244(b) (mixture of diastereomers, 9.83 g, 30.1 mmol). Yield 6.31 g. $^1$H NMR (400 MHz, DMSO-$d_6$): 0.89 (3H, s), 1.16 (3H, s), 1.54 (1H, m), 1.81 (1H, td), 2.16 (2H, m), 2.44 (1H, td), 2.90 (3H, s), 3.07 (1H, t), 4.42 (1H, dd), 7.22-7.26 (2H, m), 7.76 (1H, d).

d) 4-{[5-Hydroxy-2,2-dimethyl-5-(1-trityl-1H-imidazol-4-yl)cyclohexyl]-(methyl)amino}-2-(trifluoromethyl)benzonitrile The title compound was prepared as in Example 112(g) from the compound of Example 244(c). The crude product was used as such in the next step.

e) 4-{[5-Hydroxy-5-(1H-imidazol-4-yl)-2,2-dimethylcyclohexyl](methyl)-amino}-2-(trifluoromethyl)benzonitrile Deprotection of the compound of Example 244(d) was done as in Example 112(h). The precipitated crude major diastereomer 1 was filtered from the basic DCM-water mixture. Methanol was added to this filtered product and the insoluble product was filtered and recrystallized from DCM to obtain the pure major diastereomer 1. The minor diastereomer 2 was extracted into DCM from the basic water layer. The combined organic layers were washed with water, dried, filtered and evaporated. The crude product was purified by flash chromatography on silica gel by using the DCM-MeOH as a gradient eluent (97:3-90:10) to give the minor diastereomer 2. The final purification of the minor diastereomer 2 was performed by preparative chiral HPLC (Column Chiralpak IC 20 mm×250 mm 5 µm, A n-hexane+ 0.2% DEA, B EtOH+0.2% DEA, isocratic B 15%, flow 20 ml/min, λ 300 nm) to yield pure diastereomer 2 (rt 10.5 min). The major diastereomer 1: $^1$H NMR (400 MHz, MeOH-$d_4$): 0.94 (3H, s), 1.18 (3H, s), 1.35-1.40 (1H, m), 1.67-1.75 (2H, m), 2.03 (2H, m), 2.54 (1H, t), 2.96 (3H, s), 4.45 (1H, dd), 6.98 (1H, d), 7.14 (1H, dd), 7.22 (1H, d), 7.61 (1H, d), 7.66 (1H, d). The minor diastereomer 2: $^1$H NMR (400 MHz, $CDCl_3$): 0.79 (3H, s), 1.15 (3H, s), 1.39-1.46 (2H, m), 1.93 (1H, m), 2.23-2.36 (3H, m), 2.93 (1H, s), 3.85 (1H, m), 6.75 (1H, dd), 6.97 (1H, d), 7.02 (1H, d), 7.50 (1H, d), 7.58 (1H, d).

f) 4-{[3-(1H-Imidazol-4-yl)-6,6-dimethylcyclohex-3-enyl](methyl)amino}-2-(trifluoromethyl)benzonitrile The title compound was prepared as in Example 112(i) from the compound of Example 244(e) (diastereomer 1, 1.78 g). Yield 0.64 g. $^1$H NMR (400 MHz, $CDCl_3$): 1.01 (3H, s), 1.06 (3H, s), 2.12-2.19 (1H, m), 2.25-2.32 (1H, m), 2.63-2.74 (2H, m), 3.01 (3H, s), 4.16 (1H, t), 6.33 (1H, broad s), 6.93 (1H, dd), 6.97 (1H, s), 7.07 (1H, d), 7.57 (1H, d), 7.63 (1H, d).

Example 245

4-{[2-Hydroxy-3-(1H-imidazol-4-yl)-6,6-dimethyl-cyclohex-3-enyl](methyl)-amino}-2-(trifluoromethyl)benzonitrile The compound of Example 244 (210 mg, 0.561 mmol), pyridine 1-oxide (251 mg, 2.64 mmol) and selenium dioxide (62.2 mg, 0.561 mmol) were heated in dry 1,4-dioxane (2.1 ml) in a microwave oven at 80° C. for 25 min. The cooled mixture was diluted with ethyl acetate and pH was adjusted to 9 with aqueous $NaHCO_3$. The layers were separated. The organic phase was washed with water, dried, evaporated and dried at vacuum. The crude product was purified by flash chromatography on neutral silica gel by using DCM-MeOH as a gradient eluent to give 4.6 mg of the title compound. The stereochemistry of the compound is unknown. $^1$H NMR (400 MHz, $CDCl_3$): 0.97 (3H, s), 1.13 (3H, s), 2.06 (1H, m), 2.44 (1H, m), 3.10 (3H, s), 4.13 (1H, d), 5.00 (1H, m), 6.12 (1H, m), 7.03 (1H, dd), 7.15 (1H, s), 7.16 (1H, d), 7.55 (1H, d), 7.57 (1H, s).

Example 246

4-({6,6-Dimethyl-3-[4-(pyridin-3-yl)-1H-imidazol-1-yl]cyclohex-2-enyl}-(methyl)amino)-2-(trifluoromethyl)benzonitrile a) 3-(4-Bromo-1H-imidazol-1-yl)-6,6-dimethylcyclohex-2-enone A mixture of the compound of Example 96(a), 1.50 g, 9.46 mmol), 4-bromo-1H-imidazole (1.95 g, 13.24 mmol), triethylamine (3.3 ml, 2.39 g, 23.64 mmol) and toluene (30 ml) was heated under reflux for 9 h. The mixture was allowed to cool to RT. Water (15 ml) was added and stirring was continued for 30 min. The aqueous phase was extracted with DCM (3×5 ml). The combined organic phases were washed with water (10 ml) and brine (10 ml), dried, filtered and concentrated to give the crude product which was dried under vacuum overnight. The crude product was purified by flash chromatography on silica gel by using DCM-MeOH as a gradient eluent to give 760 mg of the title compound. $^1$H NMR (400 MHz, CDCl$_3$): 1.18 (6H, s), 2.03 (2H, t), 2.83 (2H, td), 6.04 (1H, t), 7.25 (1H, d), 7.79 (1H, d).

b) 3-(4-Bromo-1H-imidazol-1-yl)-6,6-dimethylcyclohex-2-enamine

Ammonia (2 M solution in IPA, 4.94 ml, 9.88 mmol) was slowly added to the compound of Example 246(a) (760 mg, 2.82 mmol) in IPA at 0° C. under N$_2$. After 10 min titanium(IV)isopropoxide (1.67 ml, 1.61 g, 5.65 mmol) was added at 0° C. Stirring was continued at RT overnight. Then sodium borohydride (107 mg, 2.82 mmol) was added at 0° C. and stirring was continued for 10 min at 0° C. and at RT overnight. Ammonia (1 M aqueous solution, 10 ml) was added. The product was extracted into DCM. The combined organic extracts were washed with water, dried and concentrated. The residue was purified by silica gel flash chromatography (the gradient eluent DCM-MeOH 100:0-90:10) to obtain 350 mg of the title compound. $^1$H NMR (400 MHz, CDCl$_3$): δ0.90 (3H, s), 1.02 (3H, s), 1.54-1.61 (1H, m), 1.68-1.74 (1H, m), 2.32 (2H, m), 3.18 (1H, m), 5.70 (1H, m), 7.10 (1H, d), 7.56 (1H, d).

c) 4-[3-(4-Bromo-1H-imidazol-1-yl)-6,6-dimethylcyclohex-2-enylamino]-2-(trifluoromethyl)benzonitrile The compound was prepared as in Example 131(a) starting from 4-fluoro-2-(trifluoromethyl)benzonitrile and the compound of Example 246(b). The mixture was heated at 100° C. for 10 h. The crude product was crystallized in IPA. Yield 44%. $^1$H NMR (400 MHz, CDCl$_3$): δ 1.02 (3H, s), 1.12 (3H, s), 1.79 (2H, m), 2.51 (2H, m), 4.02 (1H, m), 4.42 (1H, d), 5.63 (1H, m), 6.77 (1H, dd), 6.93 (1H, d), 7.10 (1H, d), 7.57 (1H, d), 7.58 (1H, d).

d) 4-{[3-(4-Bromo-1H-imidazol-1-yl)-6,6-dimethylcyclohex-2-enyl](methyl)-amino}-2-(trifluoromethyl)benzonitrile The compound of Example 246(c) (252 mg, 0.574 mmol) in 1.5 ml of dry DMF was added to sodium hydride (60% dispersion in mineral oil washed with pentane, 45.9 mg, 1.15 mmol) in 1 ml of dry DMF at 0° C. under N$_2$. The mixture was allowed to stir at 0° C. for 30 min. Then iodomethane (0.061 ml, 138 mg, 0.975 mmol) was added at 0° C. The mixture was maintained at 0° C. for 30 min and quenched with 3 ml of saturated aqueous NH$_4$Cl solution and 9 ml of water. The product was extracted into EtOAc (3×5 ml). The combined organic layers were washed with water (3×5 ml) and brine (1×5 ml), dried, filtered and evaporated to afford the title product. Yield 181 mg, 70%. $^1$H NMR (400 MHz, CDCl$_3$): δ0.97 (3H, s), 1.10 (3H, s), 1.78 (2H, m), 2.47-2.55 (1H, m), 2.60-2.68 (1H, m), 2.96 (3H, s), 4.54 (1H, m), 5.64 (1H, m), 6.93 (1H, dd), 7.08 (1H, d), 7.15 (1H, d), 7.62 (1H, d), 7.62 (1H, d).

e) 4-({6,6-Dimethyl-3-[4-(pyridin-3-yl)-1H-imidazol-1-yl]cyclohex-2-enyl}(methyl)amino)-2-(trifluoromethyl)benzonitrile Tetrabutyl ammonium iodide (6.1 mg, 0.017 mmol), the compound of Example 246(d) (150 mg, 0.331 mmol), 0.7 ml of DMF and palladium(II) acetate (2.2 mg, 9.7 μmol) were added to a reaction flask at RT. Then a solution of K$_3$PO$_4$ in water (2 M, 0.33 ml, 0.662 mmol) was added. The mixture was degassed and then filled with argon (three times). Tricyclohexylphosphine (5.6 mg, 0.020 mmol) and diethyl (3-pyridyl)borane (51.1 mg, 0.347 mmol) were added into a reaction flask at RT. The mixture was again degassed and filled with argon. The mixture was stirred and heated at 100° C. for 3 h and cooled to RT. Water (3 ml) and methylene chloride (20 ml) were added. The layers were separated, and the aqueous layer was extracted with methylene chloride (20 ml). The combined organic layers were filtered through Celite, washed with water, dried, filtered and evaporated. The crude product was purified by silica gel flash chromatography (the gradient eluent DCM-MeOH) to give 39 mg of the title product. $^1$H NMR (400 MHz, CDCl$_3$): 1.00 (3H, s), 1.13 (3H, s), 1.76-1.88 (2H, m), 2.56-2.66 (1H, m), 2.69-2.78 (1H, m), 3.01 (3H, s), 4.58 (1H, m), 5.73 (1H, m), 6.96 (1H, dd), 7.11 (1H, d), 7.33 (1H, m), 7.52 (1H, d), 7.63 (1H, d), 7.83 (1H, d), 8.11 (1H, m), 8.51 (1H, dd), 8.98 (1H, m).

Example 247

6-{[3-(1H-Imidazol-1-yl)-6,6-dimethylcyclohex-2-enyl](methyl)amino}-2-methylnicotinonitrile a) 6-[3-(1H-Imidazol-1-yl)-6,6-dimethylcyclohex-2-enylamino]-2-methylnicotinonitrile The compound was prepared as in Example 131(a) starting from 6-fluoro-2-methylnicotinonitrile and the compound of Example 96(e). The mixture was heated at 100° C. for 3.5 h. Yield 61%. $^1$H NMR (400 MHz, CDCl$_3$): 1.01 (3H, s), 1.09 (3H, s), 1.76 (2H, t), 2.53 (2H, m), 2.56 (3H, s), 4.58 (1H, broad s), 4.84 (1H, m), 5.66 (1H, m), 6.28 (1H, d), 7.12 (2H, broad s), 7.53 (1H, d), 7.73 (1H, broad s).

b) 6-{[3-(1H-Imidazol-1-yl)-6,6-dimethylcyclohex-2-enyl](methyl)amino}-2-methylnicotinonitrile The compound was prepared as in Example 246(d) starting from the compound of Example 247(a). The crude product was purified by flash chromatography on silica gel using DCM-MeOH as a gradient eluent (100:0-99:1). Yield 230 mg, 36%. $^1$H NMR (400 MHz, CDCl$_3$): 0.91 (3H, s), 1.06 (3H, s), 1.74 (2H, m), 2.48-2.58 (1H, m), 2.57 (3H, s), 2.60-2.68 (1H, m), 2.95 (3H, s), 5.62 (1H, m), 5.80 (1H, broad s), 6.36 (1H, d), 7.12 (1H, s), 7.17 (1H, s), 7.59 (1H, d), 7.76 (1H, s).

Example 248

6-{[3-(1H-Imidazol-1-yl)cyclohex-2-enyl](methyl)amino}-2-methylnicotinonitrile a) 6-[3-(1H-Imidazol-1-yl)cyclohex-2-enylamino]-2-methylnicotinonitrile The compound was prepared as in Example 131(a) starting from 6-fluoro-2-methylnicotinonitrile and the compound of Example 6(e). The mixture was heated at 90° C. for 2.5 h. Yield 36%. $^1$H NMR (400 MHz, CDCl$_3$): 1.63-1.72 (1H, m), 1.89-2.09 (3H, m), 2.52 (2H, m), 2.57 (3H, s), 4.74 (1H, broad s), 4.98 (1H, d), 5.85 (1H, m), 6.25 (1H, d), 7.10 (1H, s), 7.13 (1H, s), 7.53 (1H, d), 7.71 (1H, s).

b) 6-{[3-(1H-Imidazol-1-yl)cyclohex-2-enyl](methyl)amino}-2-methylnicotinonitrile The compound was prepared as in Example 246(d) starting from the compound of Example 248(a). Yield 25%. $^1$H NMR (400 MHz, CDCl$_3$): 1.61 (1H, m), 1.88-2.01 (2H, m), 2.06 (1H, m), 2.41-2.52 (1H, m), 2.57 (3H, s), 2.56-2.65 (1H, m), 2.91 (3H, s), 5.67 (1H, m), 5.78 (1H, broad s), 6.35 (1H, d), 7.12 (1H, s), 7.15 (1H, s), 7.58 (1H, d), 7.73 (1H, s).

Example 249

6-{[3-(1H-Imidazol-1-yl)-6,6-dimethylcyclohex-2-enyl](methyl)amino}-2-chloronicotinonitrile a) 6-[3-(1H-Imidazol-1-yl)-6,6-dimethylcyclohex-2-enylamino]-2-chloronicotinonitrile The compound was prepared as in Example 131(a) starting from 2,6-dichloronicotinonitrile and the compound of Example 96(e). The mixture was heated at 100° C. for 1.5 h. The crude product was crystallized in DCM. Yield 38%. $^1$H NMR (400 MHz, CDCl$_3$): 1.01 (3H, s), 1.09 (3H, s), 1.76 (2H, t), 2.47-2.61 (2H, m), 4.60-4.65 (1H, broad s), 5.17 (1H, d), 5.64 (1H, m), 6.38 (1H, d), 7.09 (1H, s), 7.12 (1H, s), 7.57 (1H, d), 7.69 (1H, s).

b) 6-{[3-(1H-Imidazol-1-yl)-6,6-dimethylcyclohex-2-enyl](methyl)amino}-2-chloronicotinonitrile The compound was prepared as in Example 246(d) starting from the compound of Example 249(a). The crude product was purified by flash chromatography on silica gel using DCM-MeOH as a gradient eluent (100:0-99:1). Yield 21%. $^1$H NMR (400 MHz, CDCl$_3$): 0.93 (3H, s), 1.08 (3H, s), 1.75 (2H, t), 2.50-2.58 (1H, m), 2.62-2.69 (1H, m), 2.98 (3H, s), 5.60 (1H, m), 5.66 (1H, broad s), 6.44 (1H, d), 7.14 (1H, s), 7.18 (1H, s), 7.64 (1H, d), 7.77 (1H, s).

Example 250

6-{[3-(1H-Imidazol-1-yl)-6,6-dimethylcyclohex-2-enyl](methyl)amino}-2-(trifluoromethyl)nicotinonitrile a) 6-Fluoro-2-(trifluoromethyl)nicotinonitrile 215 mg (1.15 mmol) of 6-amino-2-(trifluoromethyl)nicotinonitrile (prepared according to WO 2010/072352) in 70% HF in pyridine (2.7 ml) was chilled in an ice bath and NaNO$_2$ (198 mg, 2.87 mmol) was added in small portions. The mixture was stirred in an ice bath for 3 h and at RT for 3 h. The mixture was poured into ice water and pH was adjusted to 10 with 2 M aqueous NaOH. The product was extracted into EtOAc. The combined organic layers were washed with water and brine, dried, filtered and evaporated. Yield 110 mg, 50%. $^1$H NMR (400 MHz, CDCl$_3$): 7.32 (1H, dd), 8.30 (1H, dd).

b) 6-[3-(1H-Imidazol-1-yl)-6,6-dimethylcyclohex-2-enylamino]-2-(trifluoromethyl)nicotinonitrile The compound was prepared as in Example 131(a) starting from the compound of Example 250(a) and the compound of Example 96(e). The mixture was heated at 90° C. for 2 h. The crude product was crystallized in DCM. Yield 17%. $^1$H NMR (400 MHz, CDCl$_3$): 1.01 (3H, s), 1.09 (3H, s), 1.76 (2H, t), 2.48-2.59 (2H, m), 4.6-4.9 (1H, broad s), 5.28 (1H, broad s), 5.66 (1H, m), 6.62 (1H, d), 7.10 (1H, s), 7.12 (1H, s), 7.69 (1H, s), 7.71 (1H, d).

c) 6-{[3-(1H-Imidazol-1-yl)-6,6-dimethylcyclohex-2-enyl](methyl)amino}-2-(trifluoromethyl)nicotinonitrile The compound was prepared as in Example 246(d) starting from the compound of Example 250(b). The crude product was purified by flash chromatography on silica gel using DCM-MeOH as a gradient eluent (100:0-99:1). Yield 14%. $^1$H NMR (400 MHz, CDCl$_3$): 0.92 (3H, s), 1.07 (3H, s), 1.76 (2H, t), 2.52-2.59 (1H, m), 2.62-2.70 (1H, m), 3.02 (3H, s), 5.62 (1H, m), 5.7-5.9 (1H, broad s), 6.68 (1H, d), 7.13 (1H, s), 7.17 (1H, s), 7.76 (1H, s), 7.80 (1H, d).

Example 251

4-{[3-(1H-Imidazol-1-yl)cyclohex-2-enyl](methyl)amino}-2-chlorobenzonitrile a) 3-(1H-Imidazol-1-yl)cyclohex-2-enamine Ammonia (2 M solution in IPA, 432 ml, 863 mmol) was added slowly to the compound of Example 6(b) (40.00 g, 247 mmol) in IPA at 0° C. under N$_2$. After 20 min titanium (IV) isopropoxide (146 ml, 140 g, 493 mmol) was added at 0° C. and stirring was continued at RT overnight. Then the mixture was cooled to 0° C. Sodium borohydride (9.33 g, 247 mmol) was added in small portions and the resulting mixture was stirred at 0° C. for 30 min and then at RT overnight. The reaction was quenched by adding 1 M aqueous ammonia (480 ml) in an ice bath. The mixture was extracted with DCM (4×400 ml). The combined organic extracts were washed with water (3×), dried and concentrated in vacuum to afford the title compound. Yield: 32.19 g (80%). $^1$H NMR (400 MHz, CDCl$_3$): δ 1.39-1.46 (1H, m), 1.72-1.83 (1H, m), 1.93 (2H, m), 2.36-2.51 (2H, m)), 3.58 (1H, m), 5.79 (1H, m), 7.07 (1H, s), 7.12 (1H, s) 7.69 (1H, s).

b) 4-{[3-(1H-Imidazol-1-yl)cyclohex-2-enylamino]-2-chlorobenzonitrile

The compound was prepared as in Example 131(a) starting from 2-chloro-4-fluorobenzonitrile and the compound of Example 251(a). The mixture was heated at 100° C. for 6.5 h. The product was partly extracted into EtOAc, partly it crystallized during the work-up and the precipitate was collected by filtration. The crude product was triturated in IPA. Yield 58%. $^1$H NMR (400 MHz, CDCl$_3$): 1.70-1.76 (1H, m), 1.84-2.04 (3H, m), 2.54 (2H, m), 4.26 (1H, m), 4.44 (1H, d), 5.82 (1H, m), 6.50 (1H, dd), 6.66 (1H, d), 7.11 (1H, s), 7.14 (1H, sd), 7.41 (1H, d), 7.71 (1H, s).

c) 4-{[3-(1H-Imidazol-1-yl)cyclohex-2-enyl](methyl)amino}-2-chlorobenzonitrile

The compound was prepared as in Example 246(d) starting from the compound of Example 251(b). During the work-up a minor part of the product was filtered and a major part of the product was extracted into EtOAc. The filtered product was washed with heptane and the extracted product was triturated in heptane. Yield 76%. $^1$H NMR (400 MHz, CDCl$_3$): 1.63-1.72 (1H, m), 1.84-1.96 (1H, m), 1.98-2.04 (1H, m), 2.06-2.14 (1H, m), 2.49-2.56 (1H, m), 2.57-2.67 (1H, m), 2.90 (3H, s), 4.67 (1H, m), 5.72 (1H, m), 6.66 (1H, dd), 6.78 (1H, d), 7.12 (1H, s), 7.16 (1H, s), 7.44 (1H, d), 7.74 (1H, s).

Example 252

4-{[3-(1H-Imidazol-1-yl)-6,6-dimethylcyclohex-2-enyl](methyl)amino}-2-methoxybenzonitrile a) 4-[3-(1H-Imidazol-1-yl)-6,6-dimethylcyclohex-2-enylamino]-2-methoxybenzonitrile The compound was prepared as in Example 131(a) starting from 4-fluoro-2-methoxybenzonitrile and 3-(1H-imidazol-1-yl)-6,6-dimethylcyclohex-2-enamine (prepared as in Example 251(a)). The mixture was heated at 100-115° C. for 16 h. The crude product was stirred in IPA overnight. The precipitation was filtered off and the mother liquor was evaporated. The residue was purified by flash chromatography on silica gel using DCM-MeOH as a gradient eluent (100:0-99:1). Yield 16%. $^1$H NMR (400 MHz, CDCl$_3$): 1.03 (3H, s), 1.12 (3H, s), 1.72-1.83 (2H, m), 2.45-2.62 (2H, m), 3.88 (3H, s), 3.97 (1H, m), 4.13 (1H, d), 5.65 (1H, m), 6.12 (1H, d), 6.23 (1H, dd), 7.09 (1H, s), 7.12 (1H, s), 7.33 (1H, d), 7.70 (1H, s).

b) 4-{[3-(1H-Imidazol-1-yl)-6,6-dimethylcyclohex-2-enyl](methyl)amino}-2-methoxybenzonitrile The compound was prepared as in Example 246(d) starting from the compound of Example 252(a). The crude product was purified by flash chromatography on silica gel using DCM-MeOH as a gradient eluent (100:0-99:1). The additional purification was performed by preparative HPLC (X-Bridge Shield RP18 19 mm×250 mm 5 μm OBD, A H$_2$O+0.2% NH$_4$OH, B ACN+0.2% NH$_4$OH, B % 40-53-95 1-13-14 min, flow 30 ml/min, λ 300 nm and 213 nm) to yield the title compound (rt 8-10 min). Yield 4%. $^1$H NMR (400 MHz, CDCl$_3$): 0.98 (3H, s), 1.10 (3H, s), 1.69-1.84 (2H, m), 2.49-2.58 (1H, m), 2.62-2.70 (1H, m), 2.94 (3H, s), 3.91 (3H, s), 4.50 (1H, m), 5.65 (1H, m), 6.24 (1H, d), 6.43 (1H, dd), 7.13 (1H, s), 7.17 (1H, s), 7.35 (1H, d), 7.76 (1H, s).

Example 253 cis-2-Chloro-4-{[4-hydroxy-3-(1H-imidazol-1-yl)-6,6-dimethylcyclohex-2-enyl](methyl)amino}benzonitrile (enantiomer 1)

a) trans-2-Chloro-4-{[4-hydroxy-3-(1H-imidazol-1-yl)-6,6-dimethylcyclohex-2-enyl](methyl)amino}benzonitrile (enantiomer 1)

The compound of Example 22, enantiomer 1, (2.00 g, 5.87 mmol), pyridine 1-oxide (2.62 g, 27.6 mmol) and selenium dioxide (0.65 g, 5.87 mmol) in dry 1,4-dioxane (22 ml) (divided into four batches, 4×500 mg) were heated in a microwave oven at 140° C. for 2 h. The reaction batches were combined, diluted with EtOAc and filtered through Celite. The solution was washed with water, dried, filtered and evaporated. The crude product was purified by flash chromatography on neutral silica gel using DCM-MeOH as a gradient eluent. Yield 516 mg. $^1$H NMR (400 MHz, CDCl$_3$): δ 1.04 (3H, s), 1.16 (3H, s), 1.86 (1H, dd), 2.15 (1H, dd), 2.89 (3H, s), 4.64 (1H, m), 4.73 (1H, m), 5.69 (1H, d), 6.73 (1H, dd), 6.84 (1H, d), 7.11 (1H, s), 7.17 (1H, s), 7.46 (1H, d), 7.72 (1H, s).

b) cis-2-Chloro-4-{[4-hydroxy-3-(1H-imidazol-1-yl)-6,6-dimethylcyclohex-2-enyl](methyl)amino}benzonitrile (enantiomer 1)

The compound of Example 253(a), enantiomer 1 of diastereomer 1, 430 mg, 1.21 mmol), 4-nitrobenzoic acid (1.44 g, 8.60 mmol) and triphenylphosphine (2.51 g, 9.57 mmol) in 55 ml of dry toluene were stirred at RT for 30 min under N$_2$. Diethyl azodicarboxylate in 15 ml of dry toluene was added at RT. The mixture was stirred at RT overnight. Then EtOAc (100 ml) was added. The organic solution was washed with aqueous 1 M Na$_2$CO$_3$ solution (3×100 ml), water (1×100 ml), brine (1×100 ml), dried and evaporated. The crude product was purified by flash chromatography on neutral silica gel using DCM-MeOH as a gradient eluent (100:0-97:3). The impure residue was dissolved in the mixture of methanol (20 ml) and water (5 ml) and the solution was cooled to 0° C. Potassium carbonate (833 mg) was added and the mixture was stirred at 0° C. for 1 h. Then EtOAc (100 ml) was added. The organic solution was washed twice with aqueous 1 M Na$_2$CO$_3$ solution and brine, dried, filtered and evaporated. The crude product was purified by flash chromatography on silica gel using DCM-MeOH as a gradient eluent (99:1-90:10). The purified product was triturated in diethyl ether. Yield: 21.3 mg. $^1$H NMR (400 MHz, CDCl$_3$): 1.05 (3H, s), 1.14 (3H, s), 1.91 (1H, m), 2.04 (1H, m), 3.00 (3H, s), 4.43 (1H, m), 4.62 (1H, m), 5.68 (1H, d), 6.71 (1H, dd), 6.82 (1H, s), 7.03 (1H, d), 7.18 (1H, s), 7.44 (1H, d), 7.66 (1H, s).

Example 254

4-{[4-Hydroxy-3-(1H-imidazol-1-yl)cyclohex-2-enyl](methyl)amino}-2-(trifluoromethyl)benzonitrile a) 4-{[4-Hydroxy-3-(1H-imidazol-1-yl)cyclohex-2-enyl](methyl)amino}-2-(trifluoromethyl)benzonitrile (diastereomer 1)

The compound of Example 6 (17.00 g, 49.1 mmol) was oxidized as in Example 253(a) at 140° C. for 1.5 h. The crude product (diastereomer 1) was triturated in DCM-MeOH (10:1). Yield: 2.22 g, 12%. $^1$H NMR (400 MHz, DMSO-d$_6$): 1.64-1.73 (1H, m), 1.77-1.87 (1H, m), 1.93-1.98 (1H, m), 2.07-2.15 (1H, m), 2.89 (3H, s), 4.65 (1H, m), 4.93 (1H, m), 5.36 (1H, d), 5.89 (1H, d), 6.96 (1H, s), 7.16-7.19 (2H, m), 7.47 (1H, s), 7.82 (1H, d), 7.93 (1H, s). The enantiomers of diastereomer 1 were separated by preparative chiral HPLC (Column Chiralpak IA 20 mm×250 mm 5 μm, A n-hexane+0.2% DEA, B EtOH+0.2% DEA, isocratic B 20%, flow 20 ml/min, λ 300 nm) to yield enantiomer 1 (rt 12.0 min) and enantiomer 2 (rt 14.5 min). The enantiomer 1: $^1$H NMR (400 MHz, MeOH-d$_4$): 1.70-1.86 (2H, m), 1.96-2.03 (1H, m), 2.16-2.24 (1H, m), 2.87 (3H, s), 4.62 (1H, m), under the water signal (1H), 5.88 (1H, d), 6.93 (1H, s), 7.02 (1H, dd), 7.06 (1H, d), 7.32 (1H, s), 7.60 (1H, d), 7.86 (1H, s). The $^1$H NMR spectrum of enantiomer 2 was identical with the former one.

b) 4-{[4-Hydroxy-3-(1H-imidazol-1-yl)cyclohex-2-enyl](methyl)amino}-2-(trifluoromethyl)benzonitrile (diastereomer 2)

Inversion of the OH bond of the compound of Example 254(a), diastereomer 1, (2.02 g, 5.59 mmol), and the following hydrolysis were performed as in Example 253(b). The crude product (diastereomer 2) was triturated in DCM. Yield: 640 mg. $^1$H NMR (400 MHz, DMSO-d$_6$): 1.66-1.73 (1H, m), 1.84-2.02 (3H, m), 2.92 (3H, s), 4.50 (1H, m), 4.88-4.93 (1H, m), 5.51 (1H, d), 5.95 (1H, d), 6.97 (1H, s), 7.16-7.21 (2H, m), 7.56 (1H, s), 7.81 (1H, d), 8.01 (1H, s).

Example 255

2-Chloro-4-{[4-hydroxy-3-(1H-imidazol-1-yl)cyclohex-2-enyl](methyl)-amino}benzonitrile a) 2-Chloro-4-{[4-hydroxy-3-(1H-imidazol-1-yl)cyclohex-2-enyl](methyl)-amino}benzonitrile (diastereomer 1)

The compound of Example 251 (2.00 g, 6.39 mmol) was oxidized as in Example 254(a) at 140° C. for 1.5 h. The crude product (diastereomer 1) was triturated in DCM-MeOH (10:1). Yield: 340 mg, 16%. $^1$H NMR (400 MHz, DMSO-d$_6$): 1.62-1.70 (1H, m), 1.75-1.86 (1H, m), 1.90-1.97 (1H, m), 2.06-2.14 (1H, m), 2.83 (3H, s), 4.64 (1H, m), 4.84 (1H, m), 5.35 (1H, d), 5.88 (1H, d), 6.91 (1H, dd), 6.95 (1H, s), 7.05 (1H, d), 7.47 (1H, s), 7.64 (1H, d), 7.92 (1H, s). The enantiomers of the diastereomer 1 were separated by preparative chiral HPLC (Column Chiralpak IA 20 mm×250 mm 5 µm, A n-hexane+0.2% DEA, B EtOH+0.2% DEA, isocratic B 20%, flow 20 ml/min, λ 300 nm) to yield enantiomer 1 (rt 16.3 min) and enantiomer 2 (rt 19.7 min). The $^1$H NMR spectra of the enantiomers were identical with the spectrum of the diastereomer 1.

b) 2-Chloro-4-{[4-hydroxy-3-(1H-imidazol-1-yl)cyclohex-2-enyl](methyl)-amino}benzonitrile (diastereomer 2)

Inversion of the OH bond of the compound of Example 255(a), diastereomer 1, (1.51 g, 4.59 mmol) and the following hydrolysis were performed as in Example 253(b). The crude product (diastereomer 2) was triturated in DCM. Yield 323 mg. $^1$H NMR (400 MHz, DMSO-d$_6$): 1.64-1.71 (1H, m), 1.82-2.00 (3H, m), 2.86 (3H, s), 4.50 (1H, m), 4.81 (1H, m), 5.50 (1H, d), 5.93 (1H, d), 6.91 (1H, dd), 6.97 (1H, s), 7.07 (1H, d), 7.56 (1H, s), 7.63 (1H, d), 8.01 (1H, s).

Example 256

4-{[3-(1H-Imidazol-1-yl)-6-methylcyclohex-2-enyl](methyl)amino}-2-(trifluoromethyl)benzonitrile (enantiomer 2 and enantiomer 4, enantiomer 1 and enantiomer 3)

a) 3-Isobutoxycyclohex-2-enone

A mixture of cyclohexane-1,3-dione (25 g, 223 mmol), isobutanol (125 ml) and p-toluenesulfonic acid monohydrate (2.12 g, 11.15 mmol) in benzene (500 ml) was heated at 100° C. for 16 h. The mixture was concentrated under reduced pressure, poured into water (250 ml) and extracted with EtOAc (2×250 ml). The organic layer was dried, filtered and concentrated to obtain the crude compound which was purified by flash column chromatography using 230-400 mesh silica gel and eluted with 20% EtOAc in petroleum ether to afford the title compound. Yield: 20 g. LC-MS: m/z=169.2 (M+1)$^+$ b) 3-Isobutoxy-6-methylcyclohex-2-enone To a solution of the compound of Example 256(a) (12 g, 71.33 mmol) and hexamethylphosphoramide (12.41 ml, 71.33 mmol) in dry THF (250 ml) was added 2 M lithium diisopropylamide in THF (39.23 ml, 78.46 mmol) at −78° C. dropwise followed by stirring at this temperature for 1 h. Then MeI (4.89 ml, 78.46 mmol) was added at −78° C. dropwise, the mixture was allowed to warm to RT and stirred for 16 h. The mixture was poured into ice cold water (100 ml) and extracted with EtOAc (2×150 ml). The organic layer was dried, filtered and concentrated to obtain the crude compound which was purified by flash column chromatography using 230-400 mesh silica gel and eluted with 15% EtOAc in petroleum ether to afford the title compound. Yield: 7.1 g. LC-MS: No ionization.

c) 3-Hydroxy-6-methylcyclohex-2-enone

Aqueous HCl (1 N, 70 ml) was added to a cold stirred solution of the compound of Example 256(b) (7.1 g, 38.95 mmol) in acetone (70 ml). The solution was allowed to warm to RT and stirred for 16 h. The mixture was concentrated under reduced pressure and poured into water (70 ml) and extracted with EtOAc (2×200 ml). The organic layer was dried, filtered and concentrated to afford the crude compound which was purified by flash column chromatography using 230-400 mesh silica gel and eluted with 80% EtOAc in petroleum ether to afford the title compound. Yield 3.5 g.

d) 3-Iodo-6-methylcyclohex-2-enone

Triphenyl phosphine (8.00 g, 30.52 mmol) was added to a stirred solution of iodine (7.75 g, 30.52 mmol) in ACN (35 mL) at RT and stirring was continued for 30 min. Then Et$_3$N (4.23 ml, 30.52) was added followed by the compound of Example 256(c) (3.5 g, 27.74 mmol) in ACN (35 ml). Stirring was continued at RT for 1 h and heated to reflux for 16 h. The mixture was concentrated, poured into water (100 ml) and extracted with Et$_2$O (2×100 ml) The organic layer was dried, filtered and concentrated to obtain the crude compound which was purified by flash column chromatography using 230-400 mesh silica gel and eluted with 8% EtOAc in petroleum ether to afford the title compound. Yield: 2.2 g. LC-MS: No ionization.

e) 3-(1H-Imidazol-1-yl)-6-methylcyclohex-2-enone

Et$_3$N (0.70 ml, 5.08 mmol), KHCO$_3$ (0.34 g, 3.39 mmol) and imidazole (0.69 g, 10.17 mmol) were added to a stirred solution of the compound of Example 256(d) (0.8 g, 3.39 mmol) in toluene (20 ml) and the resulting mixture was heated at reflux temperature for 16 h. Then the mixture was concentrated, poured into water (50 ml) and extracted with 5% MeOH in DCM (2×75 ml). The organic layer was dried and concentrated to obtain the crude compound which was purified by flash column chromatography using 230-400 mesh silica gel and eluted with 4% MeOH in DCM to afford the title compound. Yield: 0.3 g. LC-MS: m/z=177.1 (M+1)⁺.

f) 3-(1H-Imidazol-1-yl)-6-methylcyclohex-2-enamine

Ammonia (5 M solution in IPA, 80 ml) was added to a cold stirred solution of the compound of Example 256(e) (4 g, 22.70 mmol) in IPA (80 ml), followed by dropwise addition of Ti(iOPr)$_4$ (13.51 ml, 45.40 mmol). The mixture was allowed to warm to RT and stirred for 4 h. The mixture was again cooled to 0° C., sodium borohydride (2.58 g, 68.10 mmol) was added and the mixture was allowed to warm to RT and stirred for 16 h. The mixture was poured into ice cold water (50 ml) and extracted with 5% MeOH in DCM (2×75 ml). The organic layer was dried, filtered and concentrated to afford the title compound which was directly used to the next step without any further purification. Yield: 4 g (crude).

g) tert-Butyl [3-(1H-imidazol-1-yl)-6-methylcyclohex-2-en-1-yl]carbamate

Et$_3$N (7.82 ml, 56.41 mmol) was added to a cold stirred solution of the compound of Example 256(f) (4.00 g (crude), 22.57 mmol) in DCM (80 ml) followed by addition of Boc$_2$O (7.78 ml, 33.85 mmol). The mixture was allowed to warm to RT and stirred for 16 h. The mixture was poured into water (100 ml) and extracted with DCM (2×100 ml). The organic layer was dried, filtered and concentrated to afford the crude compound which was purified by flash column chromatography using 230-400 mesh silica gel and eluted with 2% MeOH in DCM to afford the title compound. Yield: 1.9 g. Four enantiomers were isolated by using preparative chiral chromatography. Preparative SFC conditions: Column Chiralcel OZ—H 30 mm×250 mm 5 μm, CO$_2$ 85%, Co solvent 0.5% DEA in MeOH 15%, total flow 70.0 g/min, back pressure 100 bar, T 24° C., λ 229 nm, stack time 12 min). Analytical SFC conditions: Column Chiralcel OZ—H 4.6 mm×250 mm 5 μm, CO$_2$ 80%, Co solvent 0.5% DEA in MeOH 20%, total flow 3.0 g/min, back pressure 100 bar, T 25.6° C., λ 229 nm): Enantiomer 1 (rt 3.19 min), enantiomer 2 (rt 3.74 min), enantiomer 3 (rt 4.33 min) and enantiomer 4 (rt 6.92 min). All enantiomers have identical LC-MS: m/z=278.2 (M+1)⁺.

h) [3-(1H-Imidazol-1-yl)-6-methylcyclohex-2-enamine, dihydrochloride salt

5 M HCl in dioxane (20 ml) was added to a cold stirred solution of enantiomer 1 of the compound of Example 256(g) (0.60 g, 2.16 mmol) in 1,4-dioxane (10 ml). The solution was allowed to warm to RT and stirred for 6 h. The mixture was concentrated to afford crude compound which was triturated with anhydrous Et$_2$O to afford enantiomer 1 of the title compound as a dihydrochloride salt. Yield 0.46 g. Similarly the dihydrochloride salts of enantiomer 2, 3 and 4 were synthesized.

i) 4-[3-(1H-Imidazol-1-yl)-6-methylcyclohex-2-enylamino]-2-(trifluoromethyl)benzonitrile A reaction flask was charged with the compound of Example 256(h), enantiomer 2, (180.4 mg, 0.721 mmol), 2.85 ml of dry DMSO, 4-fluoro-2-(trifluoromethyl)benzonitrile (160 mg, 0.844 mmol) and DIPEA (0.735 ml, 546 mg, 4.22 mmol). The mixture was heated at 100° C. for 5.5 h. Then the cooled mixture was poured into EtOAc (10 ml) and water (12 ml) was added. The phases were separated and the water phase was extracted with EtOAc (2×15 ml). The combined organic layers were washed with water (2×10 ml) and brine (1×10 ml), dried, filtered and evaporated. The residue (206 mg) was purified by Combiflash on silica gel using DCM-MeOH as a gradient eluent (100:0-90:10) to afford the title product, enantiomer 2. Yield 98.4 mg. $^1$H NMR (400 MHz, CDCl$_3$): 1.02 (3H, d), 1.71-1.82 (1H, m), 1.83-1.91 (1H, m), 2.16-2.25 (1H, m), 2.50-2.57 (2H, m), 4.32 (1H, m), 5.07 (1H, d), 5.79 (1H, m), 6.81 (1H, dd), 6.98 (1H, d), 7.08 (1H, s), 7.13 (1H, s), 7.54 (1H, d), 7.67 (1H, s). Similarly the enantiomer 4 of the title compound was synthesized starting from enantiomer 4 the compound of Example 256(h). Yield 41%. The $^1$H NMR spectrum was identical with one of the enantiomer 2. Similarly the enantiomer 1 of the title compound was synthesized starting from enantiomer 1 the compound of Example 256(h). Yield 65%. $^1$H NMR (400 MHz, CDCl$_3$): 1.14 (3H, d), 1.66-1.76 (1H, m), 1.83 (1H, m), 2.04 (1H, m), 2.53-2.57 (2H, m), 3.89 (1H, m), 4.69 (1H, d), 5.71 (1H, m), 6.74 (1H, dd), 6.91 (1H, d), 7.07 (1H, s), 7.12 (1H, s), 7.55 (1H, d), 7.67 (1H, s). Similarly the enantiomer 3 of the title compound was synthesized starting from enantiomer 3 the compound of Example 256(h). Yield 52%. The $^1$H NMR spectrum was identical with the enantiomer 1.

j) 4-{[3-(1H-Imidazol-1-yl)-6-methylcyclohex-2-enyl](methyl)amino}-2-(trifluoromethyl)benzonitrile The compound of Example 256(i), enantiomer 2, (68 mg, 0.196 mmol) in 1 of dry DMF was added to sodium hydride (60% dispersion in mineral oil, 15.7 mg, 0.393 mmol) in 1 ml of dry DMF at 0° C. under N$_2$. The mixture was allowed to stir at 0° C. for 30 min. Then iodomethane (0.018 ml, 41.8 mg, 0.295 mmol) was added at 0° C. The mixture was maintained at 0° C. for 1 h and quenched with saturated aqueous NH$_4$Cl solution and water. The product was extracted into EtOAc (4×). The combined organic layers were washed with water (3×) and brine (1×), dried, filtered and evaporated to afford the crude product. The residue was purified by Combiflash on silica gel using DCM-MeOH as a gradient eluent (100:0-90:10) to afford the enantiomer 2 of the title compound. Yield: 29.4 mg. $^1$H NMR (400 MHz, CDCl$_3$): 0.95 (3H, d), 1.80-1.89 (1H, m), 1.94-2.02 (1H, m), 2.31-2.40 (1H, m), 2.48-2.58 (1H, m), 2.67-2.77 (1H, m), 3.00 (3H, s), 4.83 (1H, m), 5.72 (1H, m), 6.91 (1H, dd), 7.05 (1H, d), 7.14 (1H, s), 7.18 (1H, s), 7.62 (1H, d), 7.77 (1H, s). Similarly the enantiomer 4 of the title compound was synthesized starting from the enantiomer 4 of the compound of Example 256(i). Yield 26%. The $^1$H NMR spectrum was identical with one of the enantiomer 2. Similarly the enantiomer 1 of the title compound was synthesized starting from the enantiomer 1 of the compound of Example 256(i). Yield 41%. $^1$H NMR (400 MHz, CDCl$_3$): 0.98 (3H, d), 1.69-1.80 (1H, m), 1.93-2.03 (1H, m), 2.03-2.1 (1H, m), 2.53-2.61 (1H, m), 2.63-2.75 (1H, m), 2.92 (3H, s), 4.37 (1H, m), 5.61 (1H, m), 6.90 (1H, dd), 7.05 (1H, d), 7.11 (1H, s), 7.14 (1H, s), 7.60 (1H, d), 7.72 (1H, s). Similarly the enantiomer 3 of the title compound was synthesized starting from the enantiomer 3 of the compound of Example 256(i). Yield 24%. The $^1$H NMR spectrum was identical with the enantiomer 1.

Example 257

4-((Cyclopropylmethyl)(3-(1-ethyl-1H-imidazol-5-yl)cyclopent-3-en-1-yl)-amino)-2-(trifluoromethyl)benzonitrile a) 4-((Cyclopropylmethyl)(3-(1-ethyl-1H-imidazol-5-yl)cyclopent-3-en-1-yl)amino)-2-(trifluoromethyl)benzonitrile The compound was prepared as in Example 136(d) from 4-((3-(1-ethyl-1H-imidazol-5-yl)cyclopent-3-en-1-yl)amino)-2-(trifluoromethyl)benzonitrile (0.20 g, 0.577 mmol) and (bromomethyl)cyclopropane (84 µl, 0.866 mmol). Extracted with DCM. Yield 117 mg after preparative HPLC. $^1$H NMR (400 MHz, CDCl$_3$): 0.27 (2H, m), 0.63 (2H, m), 1.00 (1H, m), 1.48 (3H, t), 2.76 (1H, m), 2.92 (1H, m), 3.02 (1H, m), 3.13 (1H, m), 3.31 (2H, m), 4.13 (2H, q), 4.66 (1H, m), 5.87 (1H, m), 6.88 (1H, dd), 7.00 (1H, s), 7.07 (1H, d), 7.51 (1H, d), 7.58 (1H, dd). Enantiomers were separated using chiral preparative HPLC (column: Daicel Chiralpak IA, 20 mm×250 mm, 5 µm particle size, eluent A: n-hexane+0.2% DEA, eluent B: EtOH+0.2% DEA, isocratic elution: 20% B, flow 20 ml/min, detection 300 nm) to afford 31.7 mg of enantiomer 1 (rt 12.1 min) and 32.4 mg enantiomer 2 (rt 15.0 min).

Example 258

2-Chloro-4-(ethyl(3-(1-ethyl-1H-imidazol-5-yl)cyclopent-3-en-1-yl)amino)-benzonitrile a) 2-Chloro-4-(3-oxo-2-azabicyclo[2.2.1]hept-5-en-2-yl)benzonitrile

The compound was prepared as in Example 197(a) from 2-chloro-4-iodobenzonitrile (2.63 g, 10 mmol). Yield 2.206 g. $^1$H NMR (400 MHz, CDCl$_3$): 2.35 (1H, dt), 2.48 (1H, dt), 3.56 (1H, m), 4.87 (1H, m), 6.74 (1H, m), 7.02 (1H, dd), 7.46 (1H, dd), 7.60 (1H, d), 7.66 (1H, d).

b) 2-Chloro-4-((4-(hydroxymethyl)cyclopent-2-en-1-yl)amino)benzonitrile

The compound was prepared as in Example 197(b) from the compound of Example 258(a) (0.91 g, 3.72 mmol) and sodium borohydride (0.421 g, 11.13 mmol). Reaction was performed at 40° C. Yield 0.593 g after column chromatography. $^1$H NMR (400 MHz, CDCl$_3$): 1.43 (1H, m), 1.51 (1H, dt), 2.56 (1H, m), 2.95 (1H, m), 3.62 (1H, m), 3.70 (1H, dt), 4.51 (1H, m), 4.70 (1H, d), 5.91 (2H, m), 6.46 (1H, dd), 6.63 (1H, d), 7.36 (1H, d)

c) 2-Chloro-4-((3-formylcyclopent-3-en-1-yl)amino)benzonitrile

The compound was prepared as in Example 183(a) from the compound of Example 258(b) (0.753 g, 3.03 mmol). Yield 0.177 g. $^1$H NMR (400 MHz, CDCl$_3$): 2.52 (1H, m), 2.59 (1H, m), 3.04 (1H, m), 3.14 (1H, m), 4.27 (1H, m), 4.59 (1H, d), 6.47 (1H, dd), 6.61 (1H, d), 6.87 (1H, m), 7.38 (1H, d), 9.78 (1H, s).

d) 2-Chloro-4-((3-(1-ethyl-1H-imidazol-5-yl)cyclopent-3-en-1-yl)amino)-benzonitrile The compound was prepared as in Example 183(b) from the compound of Example 258(c) (0.177 g, 0.717 mmol) and ethylamine (0.717 ml, 1.435 mmol; 2 M in THF). Yield 0.226 g. $^1$H NMR (400 MHz, CDCl$_3$): 1.46 (3H, t), 2.51 (1H, m), 2.63 (1H, m), 3.08 (1H, m), 3.21 (1H, m), 4.10 (2H, q), 4.23 (1H, m), 4.51 (1H, d), 5.80 (1H, m), 6.47 (1H, dd), 6.63 (1H, d), 7.01 (1H, s), 7.20 (1H, d), 7.49 (1H, d).

e) 2-Chloro-4-(ethyl(3-(1-ethyl-1H-imidazol-5-yl)cyclopent-3-en-1-yl)-amino)benzonitrile The compound was prepared as in Example 136(d) from the compound of Example 258(d) (0.226 g, 0.723 mmol). Extracted with DCM. Yield 102 mg after flash chromatography. $^1$H NMR (400 MHz, CDCl$_3$): 1.22 (3H, t), 1.48 (3H, t), 2.68 (1H, m), 2.82 (1H, m), 2.97 (1H, m), 3.08 (1H, m), 3.41 (2H, q), 4.13 (2H, q), 4.62 (1H, m), 5.87 (1H, m), 6.60 (1H, dd), 6.74 (1H, d), 7.00 (1H, s), 7.41 (1H, d), 7.50 (1H, d). The enantiomers were separated using chiral preparative HPLC (column: Daicel Chiralpak IA, 20 mm×250 mm, 5 µm particle size, eluent A: n-hexane+0.2% DEA, eluent B: EtOH+0.2% DEA, isocratic elution: 20% B, flow 20 ml/min, detection 300 nm) to afford 33.3 mg of enantiomer 1 (rt 16.1 min) and 35.7 mg of enantiomer 2 (rt 19.0 min).

Example 259

4-((3-(1H-1,2,3-triazol-1-yl)cyclopent-2-en-1-yl)(ethyl)amino)-2-(trifluoromethyl)-benzonitrile a) 3-(1H-1,2,3-triazol-1-yl)cyclopent-2-enone

A mixture of 3-chlorocyclopent-2-enone (0.583 g, 5.0 mmol) and 2H-1,2,3-triazole (1.4 ml, 24.16 mmol) was stirred at RT for 2 days. Water, DCM and brine were added. Phases were separated. The aqueous phase was extracted with DCM. The combined organic phases were dried, filtered and evaporated. Purification by flash chromatography afforded 0.57 g of the title compound. $^1$H NMR (400 MHz, CDCl$_3$): 2.72 (2H, m), 3.38 (2H, m), 6.41 (1H, t), 7.88 (1H, d), 7.97 (1H, d).

b) 3-(1H-1,2,3-triazol-1-yl)cyclopent-2-enol

The compound was prepared as in Example 156(b) from the compound of Example 259(a) (0.69 g, 4.63 mmol). Yield 0.632 g. $^1$H NMR (400 MHz, CDCl$_3$): 1.75 (1H, d), 2.01 (1H, m), 2.58 (1H, m), 2.97 (1H, m), 3.20 (1H, m), 5.09 (1H, m), 6.14 (1H, m), 7.75 (1H, d), 7.81 (1H, d).

c) 1-(3-azidocyclopent-1-en-1-yl)-1H-1,2,3-triazole

The compound was prepared as in Example 156(c) from the compound of Example 259(b) (0.632 g, 4.18 mmol). Reaction was performed in toluene-THF (2.1). Purification by flash chromatography afforded 0.475 g of the title compound. $^1$H NMR (400 MHz, CDCl$_3$): 2.18 (1H, m), 2.58 (1H, m), 3.05 (1H, m), 3.22 (1H, m), 4.65 (1H, m), 6.11 (1H, m), 7.77 (1H, d), 7.83 (1H, d).

d) 3-(1H-1,2,3-triazol-1-yl)cyclopent-2-enamine

The compound was prepared as in Example 156(d) from the compound of Example 259(c). Yield 0.391 g. $^1$H NMR (400 MHz, CDCl$_3$): 1.62 (2H, br s), 1.76 (1H, m), 2.58 (1H, m), 2.90-2.99 (1H, m), 3.08-3.17 (1H, m), 4.23 (1H, m), 6.05 (1H, q), 7.74 (1H, d), 7.77 (1H, d).

e) 4-((3-(1H-1,2,3-triazol-1-yl)cyclopent-2-en-1-yl)amino)-2-(trifluoromethyl)benzonitrile The compound was prepared as in Example 137(c) from the compound of Example 259(d) (0.391 g, 2.60 mmol). Yield 0.562 g. $^1$H NMR (400 MHz, CDCl$_3$): 2.00 (1H, m), 2.73 (1H, m), 3.05-3.13 (1H, m), 3.18-3.26 (1H, m), 4.65 (1H, br d), 4.86 (1H, m), 6.15 (1H, q), 6.75 (1H, dd), 6.91 (1H, d), 7.60 (1H, d), 7.78 (1H, d), 7.80 (1H, d).

f) 4-((3-(1H-1,2,3-triazol-1-yl)cyclopent-2-en-1-yl)(ethyl)amino)-2-(trifluoromethyl)-benzonitrile The compound was prepared as in Example 136(d) from the compound of Example 259(e). (0.562 g, 1.76 mmol). Extracted with DCM. Yield 0.595 g. $^1$H NMR (400 MHz, CDCl$_3$): 1.23 (3H, t), 1.97 (1H, m), 2.73 (1H, m), 3.09 (1H, m), 3.23 (1H, m), 3.44 (2H, m), 5.22 (1H, m), 6.14 (1H, q), 6.88 (1H, dd), 7.04 (1H, d), 7.61 (1H, dd), 7.80 (1H, d), 7.82 (1H, d). The enantiomers were separated using chiral preparative HPLC (column: Daicel Chiralpak IA, 20 mm×250 mm, 5 μm particle size, eluent A: MTBE+0.2% DEA, eluent B: IPA+0.2% DEA, isocratic elution: 3% B, flow 20 ml/min, detection 300 nm) to afford 49.2 mg of enantiomer 1 (rt 18.4 min) and 47.5 mg of enantiomer 2 (rt 25 min).

Example 260

4-(ethyl(3-(1-(1-hydroxy-2-methylpropan-2-yl)-1H-imidazol-5-yl)cyclopent-3-en-1-yl)amino)-2-(trifluoromethyl)benzonitrile a) 4-((3-(1-(1-hydroxy-2-methylpropan-2-yl)-1H-imidazol-5-yl)cyclopent-3-en-1-yl)amino)-2-(trifluoromethyl)benzonitrile The compound was prepared as in Example 183(b) from 4-((3-formylcyclopent-3-en-1-yl)amino)-2-(trifluoromethyl)benzonitrile (0.28 g, 1.00 mmol) and 2-amino-2-methyl-1-propanol (0.178 g, 2.00 mmol). Yield 0.129 g. $^1$H NMR (400 MHz, CDCl$_3$): 1.59 (6H, s), 2.45 (1H, m), 2.57 (1H, m), 3.05 (1H, m), 3.14 (1H, m), 3.77 (2H, m), 4.29 (1H, m), 4.90 (1H, br d), 5.87 (1H, m), 6.70 (1H, dd), 6.83 (1H, d), 6.87 (1H, d), 7.57 (1H, d), 7.59 (1H, d).

b) 4-(3-(1-(1-((tert-butyldimethylsilyloxy)-2-methylpropan-2-yl)-1H-imidazol-5-yl)cyclopent-3-enylamino)-2-(trifluoromethyl)benzonitrile tert-Butyldimethylchlorosilane (52 mg, 0.347 mmol) was added to a solution of the compound of Example 260(a) (0.129 g, 0.33 mol) and imidazole (45 mg, 0.661 mmol) in DCM (1 ml). The mixture was stirred at RT overnight. The mixture was diluted with DCM, water was added, and the phases separated. The aqueous phase was extracted with DCM. The combined organic phases were washed with water and brine, dried, filtered and evaporated. Yield 0.149 g.

c) 4-((3-(1-(1-((tert-butyldimethylsilyl)oxy)-2-methylpropan-2-yl)-1H-imidazol-5-yl)cyclopent-3-en-1-yl)(ethyl)amino)-2-(trifluoromethyl)benzonitrile The compound was prepared as in Example 136(d) from the compound of Example 260(b) (0.149 mg, 0.295 mmol). Extraction with DCM. Yield 62 mg after flash chromatography. $^1$H NMR (400 MHz, CDCl$_3$): 0.0 (6H, s), 0.85 (9H, s), 1.25 (3H, t), 1.57 (3H, s), 1.58 (3H, s), 2.65 (1H, m), 2.76 (1H, m), 2.90 (1H, m), 3.01 (1H, m), 3.49 (2H, q), 3.73 (2H, m), 4.67 (1H, m), 5.91 (1H, m), 6.81 (1H, dd), 6.90 (1H, d), 6.98 (1H, d), 7.58 (1H, dd), 7.66 (1H, d).

d) 4-(Ethyl(3-(1-(1-hydroxy-2-methylpropan-2-yl)-1H-imidazol-5-yl)cyclopent-3-en-1-yl)amino)-2-(trifluoromethyl)benzonitrile A mixture of the compound of Example 260(c) (68 mg, 0.128 mmol) and ammonium fluoride (47 mg, 1.276 mmol) in methanol (1.5 ml) was stirred at 50° C. for 7 h. Then more ammonium fluoride (47 mg, 1.276 mmol) was added and stirring continued for 5 h at 50° C. and 8 h at 60° C. The mixture was concentrated in vacuo. Water and DCM were added and the phases separated. The aqueous phase was extracted with DCM. The combined organic phases were washed with water and brine, dried, filtered and evaporated. Purification by preparative HPLC afforded 28 mg of the title compound. $^1$H NMR (400 MHz, CDCl$_3$): 1.25 (3H, t), 1.605 (3H, s), 1.61 (3H, s), 2.66 (1H, m), 2.75 (1H, m), 2.90 (1H, m), 3.02 (1H, m), 3.49 (2H, q), 3.78 (2H, m), 4.67 (1H, m), 5.94 (1H, m), 6.80 (1H, br s), 6.81 (1H, dd), 7.55 (1H, br s), 7.58 (1H, d). LC-MS: m/z=419.2 (M+1)$^+$.

Example 261

4-(Ethyl(3-(1-(2-(phenylamino)ethyl)-1H-imidazol-5-yl)cyclopent-3-en-1-yl)-amino)-2-(trifluoromethyl)benzonitrile a) tert-Butyl (2-(5-(4-((4-cyano-3-(trifluoromethyl)phenyl)amino)cyclopent-1-en-1-yl)-1H-imidazol-1-yl)ethyl)(phenyl)carbamate The compound was prepared as in Example 183(b) from 4-((3-formylcyclopent-3-en-1-yl)amino)-2-(trifluoromethyl)benzonitrile (0.168 g, 0.60 mmol) and tert-butyl 2-aminoethyl(phenyl)carbamate (prepared as in EP 301751) (0.173 g, 0.732 mmol). Yield 0.109 g. $^1$H NMR (400 MHz, CDCl$_3$): 1.37 (9H, s), 2.47 (1H, d), 2.56 (1H, d), 2.95 (1H, m), 3.13 (1H, m), 3.78 (1H, m), 4.22 (4H, m), 5.55 (1H, br s), 5.75 (1H, br s), 6.68 (1H, dd), 6.86 (1H, d), 6.96 (1H, br s), 6.98 (1H, d), 7.23 (1H, m), 7.32 (3H, m), 7.55 (1H, d).

b) tert-butyl (2-(5-(4-((4-cyano-3-(trifluoromethyl)phenyl)(ethyl)amino)cyclopent-1-en-1-yl)-1H-imidazol-1-yl)ethyl)(phenyl)carbamate The compound was prepared as in Example 136(d) from the compound of Example 261(a). Extracted with DCM. Yield 82 mg after flash chromatography. $^1$H NMR (400 MHz, CDCl$_3$): 1.18 (3H, t), 1.40 (9H, s), 2.55 (1H, m), 2.72 (1H, m), 2.85 (1H, m), 2.94 (1H, m), 3.37 (2H, q), 3.95 (2H, t), 4.32 (2H, m), 4.57 (1H, m), 5.69 (1H, br s), 6.76 (1H, dd), 6.94 (1H, d), 6.96 (3H, br s), 7.21 (1H, m), 7.30 (2H, m), 7.44 (1H, d), 7.54 (1H, dd).

c) 4-(Ethyl(3-(1-(2-(phenylamino)ethyl)-1H-imidazol-5-yl)cyclopent-3-en-1-yl)amino)-2-(trifluoromethyl)benzonitrile Trimethylsilyl trifluoromethanesulfonate (91 μl, 0.502 mmol) was added to the compound of Example 261(b) (71 mg, 0.126 mmol) and 2,6-dimethylpyridine (73 μl, 0.628 mmol) in DCM (1.5 ml) at 0-5° C. The mixture was stirred at 0-5° C. for 15 min at RT until completion. The mixture was diluted with DCM and the reaction quenched with cold saturated NH$_4$Cl. Phases were separated and the aqueous phase was extracted with DCM. The combined organic phases were washed with saturated NaHCO$_3$ and brine, dried, filtered and evaporated. Purification by preparative HPLC afforded 22 mg of the title compound. $^1$H NMR (400 MHz, CDCl$_3$): 1.23 (3H, t), 2.65 (1H, m), 2.82 (1H, m), 2.92 (1H, m), 3.06 (1H, m), 3.43 (2H, q), 3.56 (2H, q), 3.73 (1H, t), 4.29 (2H, m), 4.61 (1H, m), 5.85 (1H, m), 6.60 (2H, m), 6.78 (2H, m), 6.97 (1H, d), 7.03 (1H, br s), 7.21 (2H, m), 7.44 (1H, d), 7.57 (1H, dd).

Example 262

4-(((1R,4S)-4-hydroxy-3-(1H-imidazol-1-yl)-6,6-dimethylcyclohex-2-en-1-yl)(methyl)-amino)-2-(trifluoromethyl)benzonitrile A mixture of (R)-4-((3-(1H-imidazol-1-yl)-6,6-dimethylcyclohex-2-en-1-yl)-(methyl)amino)-2-(trifluoromethyl) benzonitrile (0.40 g, 1.068 mmol), selenium dioxide (83 mg, 0.748 mmol) and pyridine N-oxide (0.508 g, 5.34 mmol) in 1,4-dioxane (4.5 ml) was heated for 2 h at 160° C. in a microwave synthesizer (Biotage Initiator). The cooled mixture was diluted with EtOAc and filtered through Celite. The filter cake was washed with EtOAc and the filtrate evaporated. The residue was re-dissolved in EtOAc and washed with water and brine, dried, filtered and evaporated. Purification by flash chromatography afforded 57 mg of the title compound. $^1$H NMR (400 MHz, CDCl$_3$): 1.05 (3H, s), 1.16 (3H, s), 1.90 (1H, dd), 2.16 (1H, dd), 2.94 (3H, s), 4.71 (1H, m), 4.74 (1H, m), 5.69 (1H, m), 6.95 (1H, dd), 7.07 (1H, m), 7.09 (1H, d), 7.16 (1H, t), 7.62 (1H, d), 7.66 (1H, m).

Example 263

4-((3-(1H-imidazol-1-yl)-6,6-dimethylcyclohex-2-en-1-yl)(methyl)amino)-2-bromobenzonitrile and its enantiomers a) 4-((3-(1H-imidazol-1-yl)-6,6-dimethylcyclohex-2-en-1-yl)amino)-2-bromobenzonitrile The compound was prepared as in Example 137(c) from 3-(1H-imidazol-1-yl)-6,6-dimethylcyclohex-2-enamine (1.58 g), 8.26 mmol), 2-bromo-4-fluorobenzonitrile (1.735 g, 8.67 mmol) and DIPEA (3.6 ml, 20.65 mmol) in DMSO (20 ml) at 100° C. Extraction was performed with EtOAc. Yield 1.34 g. $^1$H NMR (400 MHz, CDCl$_3$): 1.01 (3H, s), 1.11 (3H, s), 1.76 (2H, m), 2.54 (2H, m), 3.95 (1H, m), 4.33 (1H, br d), 5.62 (1H, m), 6.58 (1H, dd), 6.88 (1H, d), 7.09 (1H, m), 7.12 (1H, t), 7.39 (1H, d), 7.69 (1H, t).

b) 4-((3-(1H-imidazol-1-yl)-6,6-dimethylcyclohex-2-en-1-yl)(methyl)amino)-2-bromobenzonitrile The compound was prepared as in Example 136(d) from the compound of Example 263(a) (93 mg, 0.25 mmol) and iodomethane (28 µl, 0.45 mmol). Extracted with DCM. Purification by preparative HPLC afforded 53 mg of the title compound. $^1$H NMR (400 MHz, CDCl$_3$): 0.96 (3H, s), 1.10 (3H, s), 1.76 (2H, m), 2.50-2.59 (1H, m), 2.62-2.70 (1H, m), 2.92 (3H, s), 4.47 (1H, m), 5.63 (1H, m), 6.77 (1H, dd), 7.01 (1H, d), 7.12 (1H, m), 7.17 (1H, t), 7.43 (1H, d), 7.75 (1H, t). The enantiomers of the title compound (172 mg) were separated using chiral preparative HPLC (Column: Daicel Chiralpak IA, 20 mm×250 mm, 5 µm particle size, eluent A: MTBE+0.2% DEA, eluent B: EtOH+0.2% DEA, isocratic elution: 10% B, flow 20 m/min, detection 300 nm) to afford 63 mg of enantiomer 1 (rt 12.5 min) and 60 mg of enantiomer 2 (rt 37 min).

Example 264

4-((3-(1-ethyl-1H-imidazol-5-yl)cyclopent-3-en-1-yl)(2-methoxyethyl)-amino)-2-(trifluoromethyl)benzonitrile The compound was prepared as in Example 136(d) from 4-(3-(1-ethyl-1H-imidazol-5-yl)cyclopent-3-enylamino)-2-(trifluoromethyl)benzonitrile (57 mg, 0.165 mmol) and 2-bromoethyl methyl ether (34 µl, 0.362 mmol) with catalytic amount of tetra-butylammmonium iodide (15 mg, 0.041 mmol). Extraction with DCM. Purification by preparative HPLC afforded 15 mg of the title compound. $^1$H NMR (400 MHz, CDCl$_3$): 1.48 (3H, t), 2.73 (1H, m), 2.89 (1H, m), 3.00 (1H, m), 3.11 (1H, m), 3.35 (3H, s), 3.57 (4H, m), 4.12 (2H, q), 4.68 (1H, m), 5.87 (1H, m), 6.85 (1H, dd), 7.00 (1H, br s), 7.06 (1H, d), 7.51 (1H, br s), 7.58 (1H, dd).

Example 265

4-((6,6-Dimethyl-3-(1H-1,2,3-triazol-4-yl)cyclohex-2-en-1-yl)amino)-2-(trifluoromethyl)benzonitrile a) 6,6-Dimethyl-3-((trimethylsilyl)ethynyl)cyclohex-2-enone To a stirred solution of 3-iodo-6,6-dimethylcyclohex-2-enone (3.0 g, 12.0 mmol) in DMF (40 ml) was added trimethylsilylacetylene (3.5 g, 36.0 mmol) followed by diisopropylamine (3.63 g, 36.0 mmol), Pd(pph$_3$)$_2$Cl$_2$ (0.42 g, 0.6 mmol) and CuI (0.228 g, 1.2 mmol) at 0° C. The resulting suspension was stirred at RT for 16 h. The reaction mixture was quenched with ice water and extracted with EtOAc. Organic layer was washed with water, brine, dried and evaporated. Purification by flash chromatography afforded 1.0 g of the title compound. $^1$H NMR (300 MHz, CDCl$_3$): 0.22 (9H, s), 1.11 (6H, s), 1.84 (2H, t), 2.48 (2H, m), 6.14 (1H, s).

b) 3-(1-Benzyl-1H-1,2,3-triazol-4-yl)-6,6-dimethylcyclohex-2-enone

To an ice cold stirred solution of the compound of Example 265(a) (3.0 g, 13.63 mmol) in EtOH (20 ml) was added potassium carbonate (3.77 g, 27.27 mmol). The mixture was stirred for 4 h at 0° C. Water (20 ml) was added to the mixture together with CuSO$_4$.H$_2$O (1.51 g, 6.08 mmol), benzylazide (2.7 g, 20.27 mmol) and sodium ascorbate (1.60 g, 8.10 mmol). The mixture was allowed to warm to RT and stirred for 16 h. The reaction mixture was quenched with saturated Na$_2$CO$_3$ solution and extracted with EtOAc. Organic layer was washed with water, dried and evaporated. Purification by flash chromatography afforded 1.2 g of the title compound. $^1$H NMR (300 MHz, CDCl$_3$): 1.14 (6H, s), 1.94 (2H, t), 2.87 (2H, m), 5.54 (2H, s), 6.40 (1H, s), 7.3 (2H, m), 7.4 (3H, m), 7.63 (1H, s).

c) 3-(1-Benzyl-1H-1,2,3-triazol-4-yl)-6,6-dimethylcyclohex-2-enol

The compound was prepared as in Example 156(b) from the compound of Example 265(b) (4.0 g, 16.0 mmol) using CeCl₃.7H₂O (7.45 g, 20.0 mmol) and NaBH₄ (0.76 g, 20.0 mmol). Purification by flash chromatography afforded 2.0 g of the title compound. $^1$H NMR (300 MHz, DMSO-d₆): 0.81 (3H, s), 0.92 (3H, s), 1.41 (1H, m), 1.56 (1H, m), 2.27 (2H, m), 3.76 (1H, m), 4.65 (1H, d), 6.22 (1H, m), 7.27-7.39 (5H, m), 8.20 (1H, s).

d) 4-(3-Azido-4,4-dimethylcyclohex-1-en-1-yl)-1-benzyl-1H-1,2,3-triazole

The compound was prepared as in Example 184(c) from the compound of Example 265(c) (2.0 g, 7.93 mmol), DPPA (3.27 g, 11.9 mmol) and DBU (2.4 g, 15.87 mmol) in toluene. Yield: 0.8 g. $^1$H NMR (300 MHz, DMSO-d₆): 0.93 (3H, s), 0.97 (3H, s), 1.53 (2H, m), 2.38 (2H, m), 3.89 (1H, m), 5.58 (2H, d), 6.38 (1H, m), 7.26-7.49 (5H, m), 8.32 (1H, s).

e) 3-(1-Benzyl-1H-1,2,3-triazol-4-yl)-6,6-dimethyl-cyclohex-2-enamine

To a stirred solution of the compound of Example 265(d) (2.0 g, 6.48 mmol) in THF—H₂O (15 ml, 2:1) was added PPh₃ (0.85 g, 3.24 mmol) at RT and the resulting mixture was refluxed for 4 h. The reaction mixture was quenched with ice cold water and extracted with EtOAc. Organic layer was washed with water, dried and evaporated. Purification by flash chromatography afforded 0.5 g of the title compound. $^1$H NMR (300 MHz, DMSO-d₆): 0.82 (3H, s), 0.97 (3H, s), 1.24 (2H, s), 1.45 (1H, m), 1.57 (1H, m), 2.29 (2H, m), 3.21 (1H, m), 5.56 (2H, s), 6.21 (1H, m), 7.29-7.38 (5H, m), 8.20 (1H, s).

f) 4-((3-(1-Benzyl-1H-1,2,3-triazol-4-yl)-6,6-dimethylcyclohex-2-en-1-yl)-amino)-2-(trifluoromethyl)benzonitrile The compound was prepared as in Example 137(c) from the compound of Example 265(e) (0.26 g, 0.921 mmol) at 100° C. Yield 0.20 g. $^1$H NMR (400 MHz, CDCl₃): 0.97 (3H, s), 1.07 (3H, s), 1.68 (2H, t), 2.45 (2H, m), 3.95 (1H, m), 4.37 (1H, br d), 5.51 (2H, s), 6.21 (1H, m), 6.74 (1H, dd), 6.90 (1H, d), 7.24-7.40 (6H, m), 7.54 81H, d)

g) 4-((3-(1-Benzyl-1H-1,2,3-triazol-4-yl)-6,6-dimethylcyclohex-2-en-1-yl)-(methyl)amino)-2-(trifluoromethyl)benzonitrile The compound was prepared as in Example 136(d) from the compound of Example 265(f) (0.20 g, 0.443 mmol). Extraction with DCM. Purification by preparative HPLC afforded 83 mg of the title compound. $^1$H NMR (400 MHz, CDCl₃): 0.92 (3H, s), 1.05 (3H, s), 1.67 (2H, m), 2.42 (1H, m), 2.58 (1H, m), 2.94 (3H, s), 4.47 (1H, m), 5.53 (2H, m), 6.24 (1H, m), 6.91 (1H, dd), 7.06 (1H, d), 7.29 (2H, m), 7.34-7.42 (4H, m), 7.58 (1H, dd).

h) 4-((6,6-Dimethyl-3-(1H-1,2,3-triazol-4-yl)cyclohex-2-en-1-yl)amino)-2-(trifluoromethyl)benzonitrile Potassium tert-butoxide (0.127 g, 1.128 mmol) was added the compound of Example 265(g) (75 mg, 0.161 mmol) in DMSO-THF (0.2 ml-2 ml). Oxygen was bubbled through the mixture for 1 h and then the mixture was stirred overnight in an open flask. Reaction was quenched with saturated NH₄Cl and water, extracted with EtOAc. Organic phases were washed with water and brine, dried, filtered and evaporated. Purification by preparative HPLC afforded 8 mg of the title compound. $^1$H NMR (400 MHz, CDCl₃): 0.96 (3H, s), 1.08 (3H, s), 1.72 (2H, m), 2.53 (1H, m), 2.67 (1H, m), 2.97 (3H, s), 4.51 (1H, m), 6.18 (1H, m), 6.94 (1H, dd), 7.09 (1H, d), 7.60 (1H, d), 7.7 (1H, s). LC-MS: m/z=376.3 (M+1).

Example 266

2-Chloro-4-(ethyl(3-(1-methyl-1H-imidazol-5-yl)cyclohex-2-en-1-yl)amino)-benzonitrile a) tert-Butyl((3-iodocyclohex-2-en-1-yl)oxy)dimethylsilane The compound was prepared as in Example 260(b) from 3-iodocyclohex-2-enol (*Synth. Commun.* 2003, 33, 2487) (3.51 g, 15.67 mmol). Purification by flash chromatography afforded 3.64 g of the title compound. $^1$H NMR (400 MHz, CDCl₃): 0.06 (3H, s), 0.07 (3H, s), 0.89 (9H, s), 1.60 (2H, m), 1.83 (2H, m), 2.47 (2H, m), 4.18 (1H, m), 6.30 (1H, m).

b) 3-((tert-Butyldimethylsilyl)oxy)cyclohex-1-enecarbaldehyde

The compound of Example 266(a) (3.63 g, 10.73 mmol) was dissolved in dry THF (50 ml) and cooled to −78° C. tert-Butyllithium (13 ml, 22.1 mmol; 1.7 M in pentanes) was added and the mixture was stirred 30 min at −78° C. N,N-dimethylformamide (5.0 ml, 64.6 mmol) was added and the mixture was stirred for 1 h at −78° C. and then allowed to reach RT. The reaction was quenched with cold saturated NH₄Cl and water and extracted with TBME. The organic phases were washed with water and brine, dried, filtered and evaporated. Purification by flash chromatography afforded 1.251 g of the title compound. $^1$H NMR (400 MHz, CDCl₃): 0.12 (3H, s), 0.13 (3H, s), 0.92 (9H, s), 1.51-1.64 (2H, m), 1.81-1.97 (2H, m), 2.08-2.24 (2H, m), 4.46 (1H, m), 6.56 (1H, m), 9.47 (1H, s).

c) 3-Hydroxycyclohex-1-enecarbaldehyde

A mixture of the compound of Example 266(b) (1.442 g, 6.0 mmol), acetic acid (3 ml), THF (1 ml) and water (1 ml) was stirred at RT until reaction reached completion. Solvents were evaporated. Toluene was added and evaporation was repeated. The residue was purified by flash chromatography to afford 0.674 g of the title compound. $^1$H NMR (400 MHz, CDCl₃): 1.58 (1H, br S), 1.63 (2H, m), 1.85 (1H, m), 2.04 (1H, m), 2.20 (2H, m), 4.50 (1H, m), 6.69 (1H, m), 9.50) 1H, s).

d) 3-(1-Methyl-1H-imidazol-5-yl)cyclohex-2-enol

The compound was prepared as in Example 183(b) from the compound of Example 266(c) (0.445 g, 3.53 mmol) and methylamine (3.53 ml, 7.05 mmol; 2 M in MeOH) in DCM (10 ml). Solvents were evaporated and the residue was dissolved in DCM (13 ml). TosMIC (0.882 g, 4.52 mmol) and DBU (1.055 ml, 7.05 mmol) were added. The procedure was completed as in Example 183(b). Yield 0.130 g. $^1$H NMR (400 MHz, CDCl₃): 1.69 (2H, m), 1.93 (2H, m), 2.29 (2H, m), 2.63 (1H, br s), 3.67 (3H, d), 4.39 (1H, m), 5.91 (1H, m), 6.96 (1H, d), 7.37 (1H, m).

e) 5-(3-Azidocyclohex-1-enyl)-1-methyl-1H-imidazole

The compound was prepared as in Example 156(c) from the compound of Example 266(d) (0.26 g, 1.459 mmol).

Purification by flash chromatography afforded 0.192 of the title compound. $^1$H NMR (400 MHz, CDCl$_3$): 1.78 (2H, m), 1.87-2.02 (2H, m), 2.36 (2H, m), 3.69 (3H, d), 4.08 (1H, m), 5.83 (1H, m), 7.03 (1H, d), 7.41 (1H, br s).

f) 3-(1-Methyl-1H-imidazol-5-yl)cyclohex-2-enamine

The compound was prepared as in Example 156(d) from the compound of Example 266(e) (0.192 g, 0.945 mmol). Yield 0.161 g. $^1$H NMR (400 MHz, CDCl$_3$): 1.40 (1H, m), 1.70 (1H, m), 1.88 (1H, m), 1.99 (1H, m), 2.27 (2H, m), 3.52 (1H, m), 3.66 (3H, d), 5.80 (1H, m), 6.95 (1H, d), 7.37 (1H, d). LC-MS: m/z=178.2 (M+1).

g) 2-Chloro-4-((3-(1-methyl-1H-imidazol-5-yl)cyclohex-2-en-1-yl)amino)-benzonitrile The compound was prepared as in Example 137(c) from the compound of Example 266(f) (0.161 g, 0.908 mmol) and 2-chloro-4-fluorobenzonitrile (0.141 g, 0.908 mmol). Yield 0.10 g. $^1$H NMR (400 MHz, CDCl$_3$): 1.70 (1H, m), 1.77-1.92 (2H, m), 1.99 (1H, m), 2.37 (2H, m), 3.66 (3H, d), 4.21 (1H, m), 4.43 (1H, br d), 5.81 (1H, m), 6.49 (1H, dd), 6.66 (1H, d), 7.01 (1H, d), 7.40 (2H, m).

h) 2-Chloro-4-(ethyl(3-(1-methyl-1H-imidazol-5-yl)cyclohex-2-en-1-yl)-amino)benzonitrile The compound was prepared as in Example 136(d) from the compound of Example 266(g) (0.10 g, 0.32 mmol). Purification by preparative LC afforded 78 mg of the title compound. $^1$H NMR (400 MHz, CDCl$_3$): 1.22 (3H, t), 1.68-1.89 (2H, m), 2.02 (2H, m), 2.41 (2H, m), 3.40 (2H, m), 3.66 (3H, s), 4.54 (1H, m), 5.71 (1H, m), 6.64 (1H, dd), 6.78 (1H, d), 7.01 (1H, d), 7.40 (1H br s), 7.41 (1H, d).

Example 267

4-(Ethyl(3-(1-(2-hydroxypropyl)-1H-imidazol-5-yl)cyclopent-3-en-1-yl)-amino)-2-(trifluoromethyl)benzonitrile a) tert-Butyl (3-(1-(2-hydroxypropyl)-1H-imidazol-5-yl)cyclopent-3-en-1-yl)-carbamate The compound was prepared as in Example 183(b) from tert-butyl (3-formylcyclopent-3-en-1-yl)carbamate (0.423 g, 2.0 mmol) and 1-amino-2-propanol (0.232 ml, 3.0 mmol). Yield 0.293 g. $^1$H NMR (400 MHz, CDCl$_3$): 1.28 (3H, d), 1.45 (9H, s), 2.40 (1H, m), 2.54 (1H, m), 2.94 (1H, m), 3.05 (1H, m), 3.92 (1H, m), 4.07 (2H, m), 4.35 (1H, m), 4.81 (1H, br d), 5.71 (1H, m), 6.92 (1H, d), 7.47 (1H, br s).

b) 1-(5-(4-Aminocyclopent-1-en-1-yl)-1H-imidazol-1-yl)propan-2-ol dihydrochloride The compound was prepared as in Example 183(c) from the compound of Example 267(a) (0.289 g, 0.94 mmol). Purification by trituration with ether afforded 0.3 g of the title compound. $^1$H NMR (400 MHz, d$_6$-DMSO): 1.17 (3H, d), 2.65 (1H, m), 2.72 (1H, m), 2.94 (1H, m), 3.07 (1H, m), 3.96 (2H, m), 4.08 (1H, dd), 4.33 (1H, m), 6.23 (1H, m), 7.78 (1H, m), 8.37 (3H, br s), 9.11 (1H, d), 14.9 (1H, br s).

c) 4-((3-(1-(2-Hydroxypropyl)-1H-imidazol-5-yl)cyclopent-3-en-1-yl)amino)-2-(trifluoromethyl)benzonitrile The compound was prepared as in Example 137(c) from the compound of Example 267(b) (0.30 g, 0.94 mmol) using 4.5 molar equivalent of DIPEA. Yield 96 mg. $^1$H NMR (400 MHz, CDCl$_3$): 1.27 (3H, dd), 2.52 (1H, m), 2.61 (1H, m), 3.06 (1H, m), 3.16 (1H, m), 3.91 (1H, m), 4.02-4.10 (2H, m), 4.25 (1H, m), 5.22 (1H, dd), 5.79 (1H, m), 6.70 (1H, dt), 6.87 (2H, m), 7.42 (1H, br s), 7.55 (1H, d).

d) 4-((3-(1-(2-((tert-Butyldimethylsilyl)oxy)propyl)-1H-imidazol-5-yl)cyclopent-3-en-1-yl)amino)-2-(trifluoromethyl)benzonitrile tert-Butyldimethylsilyl trifluoromethanesulfonate (67 mg, 0.255 mmol) was added to a solution of the compound of Example 267(c) (96 mg, 0.255 mol) and DIPEA (89 µl, 0.51 mmol) in DCM (2.5 ml). The mixture was stirred overnight at RT. Another portion of tert-butyldimethylsilyl trifluoromethanesulfonate (0.101 g, 0.383 mmol) was added and stirring was continued. The reaction was quenched by addition of water and diluted with DCM. The phases were separated and the aqueous phase was extracted with DCM. The combined organic extracts were washed with water and brine, dried, filtered and evaporated. Purification by flash chromatography afforded 58 mg of the title compound. $^1$H NMR (400 MHz, CDCl$_3$): −0.26 (3H, d), −0.09 (3H, d), 0.82 (9H, s), 1.21 (3H, d), 2.52 (1H, m), 2.64 (1H, m), 3.09 (1H, m), 3.21 (1H, m), 3.87-4.06 (3H, m), 4.27 (1H, m), 4.90 (1H, dd), 5.75 (1H, m), 6.71 (1H, dd), 6.88 (1H, d), 6.98 (1H, br s), 7.46 (1H, m), 7.57 (1H, d).

e) 4-((3-(1-(2-((tert-Butyldimethylsilyl)oxy)propyl)-1H-imidazol-5-yl)cyclopent-3-en-1-yl)(ethyl)amino)-2-(trifluoromethyl)benzonitrile The compound was prepared as in Example 136(d) from the compound of Example 267(d) (58 mg, 0.118 mmol). Extraction with DCM. Purification by flash chromatography afforded 35 mg of the title compound. $^1$H NMR (400 MHz, CDCl$_3$): −0.25 (3H, d), −0.08 (3H, d), 0.83 (9H, s), 1.23 (3H, dd), 1.24 (3H, t), 2.69 (1H, m), 2.84 (1H, m), 2.99 (1H, m), 3.09 (1H, m), 3.45 (2H, m), 3.94 (1H, m), 4.03 (1H, m), 4.06 (1H, mm), 4.66 (1H, m), 5.82 (1H, m), 6.81 (1H dd), 6.99 (1H, d), 7.00 (1H, br s), 7.48 (1H br s), 7.58 (1H, d).

f) 4-(Ethyl(3-(1-(2-hydroxypropyl)-1H-imidazol-5-yl)cyclopent-3-en-1-yl)-amino)-2-(trifluoromethyl)benzonitrile tetra-Butylammonium fluoride (0.10 ml, 0.10 mmol; 1 M in THF) was added to a solution of the compound of Example 267(e) (35 mg, 0.067 mmol) in THF (1.0 ml). The mixture was stirred at RT until reaction reached completion. Solvent was evaporated and DCM and water were added. Phases were separated and the aqueous phase was extracted with DCM. The combined organic extracts were dried, filtered and evaporated. Purification by preparative HPLC afforded 11 mg of the title compound. $^1$H NMR (400 MHz, d$_4$-MeOH): 1.21 (3H, dd), 1.22 (3H, t), 2.71 (1H, m), 2.84 (1H, m), 3.03 (1H, m), 3.15 (1H, m), 3.32 (1H, m, obscured by MeOH), 3.53 (2H, q), 4.04 (2H, m), 4.17 (1H, m), 6.03

(1H, m), 6.99 (1H, s), 7.03 (1H, d), 7.07 (1H, t), 7.66 (1H, d), 7.67 (1H, br s). LC-MS: m/z=405.8 (M+1).

Example 268

4-((4-Fluoro-3-(1H-imidazol-1-yl)-6,6-dimethylcyclohex-2-en-1-yl)(methyl)-amino)-2-(trifluoromethyl)benzonitrile (cis and trans isomers)

A solution of diethylaminosulfur trifluoride (38 µl, 0.289 mmol) in DCM (0.5 ml) was added to a cooled solution (−78° C.) of the compound of Example 262 (94 mg, 0.241 mmol) in DCM (2 ml). The mixture was stirred and allowed to reach RT overnight. The mixture was cooled to −10° C. and more diethylaminosulfur trifluoride (50 µl, 0.38 mmol) was added and stirring was continued at RT. The reaction was quenched with saturated $NaHCO_3$. DCM was added and phases were separated. The organic phase was washed with brine, dried, filtered and evaporated. Purification by preparative HPLC afforded 22 mg of the cis-isomer and 17.6 mg of the trans-isomer. $^1$H NMR (400 MHz, $CDCl_3$) of the cis-isomer: 1.09 (3H, d), 1.18 (3H, s), 2.22 (1H, m), 2.51 (1H, s), 3.10 (3H, s), 4.33 1H, dd), 5.49 (1H, m), 6.12 (1H, m), 7.03 (1H, dd), 7.13 (2H, m), 7.17 (1H, m), 7.64 (1H, d), 7.72 (1H, m). $^1$H NMR (400 MHz, $CDCl_3$) of the trans-isomer: 1.11 (3H, s), 1.17 (3H, d), 2.04-2.27 (2H, m), 3.05 (3H, s), 4.66 (1H, dd), 5.31 (1H, m), 5.91 (1H, t), 6.95 (1H, dd), 7.11 (1H, d), 7.15 (1H, m), 7.22 (1H, m), 7.63 (1H, m), 7.81 (1H, m).

Example 269

4-((4-Hydroxy-3-(1H-imidazol-1-yl)-6,6-dimethylcyclohex-2-en-1-yl)-(methyl)amino)-2-(trifluoromethyl)benzonitrile a) 4-((3-(1H-imidazol-1-yl)-6,6-dimethyl-4-oxocyclohex-2-en-1-yl)(methyl)-amino)-2-(trifluoromethyl)benzonitrile The compound was prepared as in Example 132(f) from the compound of Example 262 (0.168 g, 0.43 mmol). Yield 0.154 g. $^1$H NMR (400 MHz, $CDCl_3$-$d_4$-MeOH): 1.13 (3H, s), 1.22 (3H, s), 2.70 (2H, m), 3.09 (3H, s), 5.03 (1H, d), 6.66 (1H, d), 7.02 (1H, dd), 7.15 (2H, m), 7.16 (1H, d), 7.68 (1H, dd), 7.84 (1H, t).

b) 4-((4-Hydroxy-3-(1H-imidazol-1-yl)-6,6-dimethylcyclohex-2-en-1-yl)-(methyl)amino)-2-(trifluoromethyl)benzonitrile The compound was prepared as in Example 156(b) from the compound of Example 269(a) (0.209 g, 0.42 mmol). Purification by flash chromatography afforded 90 mg of the title compound as a mixture of isomers. Stereoisomers of the title compound (175 mg) were separated using chiral preparative HPLC (Column: Daicel Chiralpak IA, 20 mm×250 mm, 5 µm particle size, eluent A: MTBE+0.2% DEA, eluent B: EtOH+0.2% DEA, isocratic elution: 1% B, flow 20 ml/min, detection 300 nm). The separation afforded 28 mg of enantiomer 1 of the cis-isomer (rt 43.1 min), 25 mg of enantiomer 2 of the cis-isomer (rt 64.6 min), $^1$H NMR (400 MHz, $CDCl_3$): 1.06 (3H, s), 1.15 (3H, s), 2.01 (2H, m), 3.06 (3H, s), 4.50 (1Hm m), 4.64 (1H, m), 5.69 (1H, d), 6.94 (1H, dd), 7.05 (1H, m), 7.09 (1H, d), 7.19 (1H, t), 7.61 (1H, dd), 7.72 (1H, t). LC-MS: m/z=391.33 (M+1), 25 mg of enantiomer 1 of the trans-isomer (rt 54.1 min) and 24.5 mg of enantiomer 2 of the trans-isomer (rt 73.9 min), $^1$H NMR (400 MHz, $CDCl_3$): 1.05 (3H, s), 1.13 (3H, s), 1.87 (1H, m), 2.11 (1H, m), 2.96 (3H, s), 4.70 (1H, m), 4.75 (1H, m), 5.71 (1H, m), 6.98 (1H, dd), 7.06 (1H, m), 7.11 (1H, m), 7.20 (1H, m), 7.63 (1H, d), 7.83 (1H, m). LC-MS: m/z=391.29 (M+1).

Example 270

4-(Ethyl(4-(hydroxymethyl)-3-(1H-imidazol-1-yl)-2,2-dimethylcyclopent-3-en-1-yl)amino)-2-(trifluoromethyl)benzonitrile a) 4-(Ethyl(4-formyl-3-(1H-imidazol-1-yl)-2,2-dimethylcyclopent-3-en-1-yl)amino)-2-(trifluoromethyl)benzonitrile A mixture of the compound of Example 194(g) (0.691 g, 1.864 mmol), imidazole (0.381 g, 5.59 mmol) and potassium carbonate (0.966 g, 6.69 mmol) in DMF (8 ml) was stirred at 60° C. until reaction was completed. Water and DCM were added. The phases were separated and the aqueous phase was extracted with DCM. The combined organic phases were washed with water and brine, dried, filtered and evaporated. Purification by flash chromatography afforded 0.515 g of the title compound. $^1$H NMR (400 MHz, $CDCl_3$): 1.08 (3H, s), 1.27 (3H, t), 1.37 (3H, s), 2.98 (1H, dd), 3.14 (1H, dd), 3.37-3.56 (2H, m), 4.62 (1H, dd), 6.93 (1H, dd), 7.09 (1H, d), 7.10 (1H, t), 7.28 (1H, m), 7.61 (1H, t), 7.63 (1H, dd), 9.63 (1H, s).

b) 4-(Ethyl(4-(hydroxymethyl)-3-(1H-imidazol-1-yl)-2,2-dimethylcyclopent-3-en-1-yl)amino)-2-(trifluoromethyl)benzonitrile Sodium borohydride (24 mg, 0.626 mmol) was added to a cooled (0-5° C.) solution of the compound of Example 270(a) (0.126 g, 0.313 mmol) in methanol (3 ml). The mixture was stirred until reaction was completed. Methanol was evaporated. Saturated $NH_4Cl$, water and EtOAc were added. The phases were separated and the aqueous phase was extracted with EtOAc. The combined organic phases were washed brine, dried, filtered and evaporated to afford the title compound. Yield 0.121 g. $^1$H NMR (400 MHz, $CDCl_3$): 0.91 (3H, s), 1.24 (3H, s), 1.30 (3H, t), 2.95 (1H, dd), 3.06 (1H, dd), 3.46-3.64 (2H, m), 4.06 (2H, m), 4.57 (1H, dd), 6.89 (1H, br s), 6.92 (1H, dd), 7.10 (2H, m), 7.34 (1H, br s), 7.60 (1H, d). LC-MS: m/z=405.71 (M+1). The enantiomers of the title compound (105 mg) were separated using chiral preparative HPLC (Column: Daicel Chiralpak IA, 20 mm×250 mm, 5 m particle size, eluent A: n-hexane+ 0.2% DEA, eluent B: EtOH+0.5% DEA, isocratic elution: 8% B, flow 20 ml/min, detection 300 nm) to afford 38 mg of enantiomer 1 (rt 26.3 min) and 41 mg of enantiomer 2 (rt 31 min).

Example 271

4-((3-(1H-imidazol-1-yl)-6,6-dimethylcyclohex-2-en-1-yl)(methyl)amino)-2-(difluoromethyl)benzonitrile a) 2-(Difluoromethyl)-4-fluorobenzonitrile Diethylaminosulfur trifluoride (6.0 ml, 45.8 mmol) was added to a cooled (0-5° C.) solution of 4-fluoro-2-formylbenzonitrile (3.1 g, 20.79 mmol) in DCM (60 ml). The mixture was stirred until the reaction was completed. The reaction was quenched by carefully adding saturated NaHCO₃. The phases were separated and the aqueous phase was extracted with DCM. The combined organic phases were washed water and brine, dried, filtered and evaporated. The product (3.31 g) was used in the next step without purification. $^1$H NMR (400 MHz, CDCl₃): 6.92 (1H, dt), 7.32 (1H, m), 7.48 (1H, dd), 7.79 (1H, m).

b) 4-((3-(1H-imidazol-1-yl)-6,6-dimethylcyclohex-2-en-1-yl)amino)-2-(difluoromethyl)-benzonitrile The compound was prepared as in Example 263(a) from the compound of Example 271(a) (0.539 g, 3.15 mmol) and 3-(1H-imidazol-1-yl)-6,6-dimethylcyclohex-2-enamine (0.574 g, 3.0 mmol) at 120° C. Purification by flash chromatography afforded 0.334 g of the title compound. $^1$H NMR (400 MHz, CDCl₃): 7.70 (1H, t), 7.51 (1H, dt), 7.12 (1H, t), 7.09 (1H, dd), 6.91 (1H, d), 6.84 (1H, t), 6.73 (1H, dd), 5.64 (1H, m), 4.36 (1H, d), 4.03 (1H, m), 2.55 (2H, m), 1.78 (2H, m), 1.12 (3H, s), 1.03 (3H, s).

c) 4-((3-(1H-imidazol-1-yl)-6,6-dimethylcyclohex-2-en-1-yl)(methyl)amino)-2-(difluoromethyl)benzonitrile Sodium hydride (54 mg, 1.341 mmol; 60% dispersion in mineral oil) was weighed in a flask under N₂. Dry DMF (3 ml) was added and the suspension was cooled to −10° C. Compound of Example 271(b) (0.306 g, 0.894 mmol) in dry DMF (2 ml) was added and the mixture was stirred at −10° C. for 30 min. Then, iodomethane (0.10 ml, 1.609 mmol) was added and stirring continued in less than 0° C. until reaction was completed. The mixture was diluted with a mixture of water and saturated NaHCO₃ and extracted with DCM. The organic phase was washed with water and brine, dried, filtered and evaporated. Purification by flash chromatography afforded 0.208 g of the title compound. $^1$H NMR (400 MHz, CDCl₃): 0.97 (3H, s), 1.11 (3H, s), 1.78 (2H, m), 2.51-2.59 (1H, m), 2.63-2.72 (1H, m), 2.97 (3H, s), 4.56 81H, m), 5.64 (1H, m), 6.87 (1H, t), 6.90 (dd), 7.08 (1H, d), 7.13 (1H, dd), 7.17 (1H, t), 7.55 (1H, dt), 7.76 (1H, t). The enantiomers of the title compound (208 mg) were separated using chiral preparative HPLC (Column: Daicel Chiralpak IC, 20 mm×250 mm, 5 μm particle size, eluent A: MTBE+0.2% DEA, eluent B: EtOH+0.2% DEA, isocratic elution: 5% B, flow 20 ml/min, detection 300 nm) to afford 74 mg of enantiomer 1 (rt 33 min) and 75 mg of enantiomer 2 (rt 38.5 min).

Example 272

(R)-2-chloro-4-(methyl(1-(pyridin-3-yl)piperidin-3-yl)amino)benzonitrile a) (R)-2-chloro-4-((1-(pyridin-3-yl)piperidin-3-yl)amino)benzonitrile The compound was prepared as in Example 137(c) from (R)-1-(pyridin-3-yl)piperidin-3-amine dihydrochloride (0.15 g, 0.6 mmol) and 2-chloro-4-fluorobenzonitrile (0.103 g, 0.66 mmol) at 120° C. Yield 0.132 g. $^1$H NMR (400 MHz, CDCl₃): 1.76 (2H, m), 1.89 (2H, m), 3.09-3.26 (3H, m), 3.41 (1H, dd), 3.74 (1H, m), 4.69 (1H, br d), 6.50 (1H, dd), 6.66 (1H, d), 7.20 (2H, m), 7.41 (1H, d), 8.16 (1H, dd), 8.33 (1H, dd).

b) (R)-2-chloro-4-(methyl(1-(pyridin-3-yl)piperidin-3-yl)amino)benzonitrile

The compound was prepared as in Example 136(d) from the compound of Example 272(a) (66 mg, 0.211 mmol) and iodomethane (26 μl, 0.422 mmol). Purification by flash chromatography afforded 24 mg of the title compound. $^1$H NMR (400 MHz, CDCl₃): 1.7-1.9 (2H, m), 1.98 (2H, m), 2.73 (1H, dt), 2.84 (1H, dt), 2.94 (3H, s), 3.64 (1H, m), 3.69 (1H, m), 3.94 (1H, m), 6.67 (1H, dd), 6.79 (1H, d), 7.18 (2H, m), 7.45 (1H, d), 8.13 (1H, br s), 8.32 (1H, br s).

Example 273

(R)-2-chloro-4-(ethyl(1-(pyridin-3-yl)piperidin-3-yl)amino)benzonitrile

The compound was prepared as in Example 136(d) from (R)-2-chloro-4-((1-(pyridin-3-yl)piperidin-3-yl)amino)benzonitrile (66 mg, 0.211 mmol) and iodoethane (34 μl, 0.422 mmol). Purification by flash chromatography afforded 19 mg of the title compound. $^1$H NMR (400 MHz, CDCl₃): 1.23 (3H, t), 1.75 (1H, dt), 1.87 (1H, m), 1.97-2.08 (2H, m), 2.74 (2H, m), 3.42 (2H, m), 3.64-3.73 (2H, m), 3.92 (1H, m), 6.65 (1H, dd), 6.77 (1H, d), 7.18 (2H, m), 7.44 (1H, d), 8.14 (1H, br s), 8.31 (1H, br s).

Example 274

Cis-4-((3-(1H-imidazol-1-yl)-4-methoxy-6,6-dimethylcyclohex-2-en-1-yl)-(methyl)amino)-2-(trifluoromethyl)benzonitrile The compound was prepared as in Example 136(d) from 4-((4-hydroxy-3-(1H-imidazol-1-yl)-6,6-dimethylcyclohex-2-en-1-yl)(methyl)amino)-2-(trifluoroethyl)benzonitrile (cis-enantiomer 1) (28 mg, 0.072 mmol) and iodomethane (10 μl, 0.161 mmol). Purification by preparative HPLC afforded 4.3 mg of the title compound. $^1$H NMR (400 MHz, CDCl₃): 1.09 (3H, s), 1.12 (3H, s), 1.91 (1H, dd), 2.03 (1H, dd), 3.02 (3H, s), 3.42 (3H, s), 4.08 (1H, m), 4.56 (1H, m), 5.73 (1H, d), 6.93 (1H, dd), 7.09 (1H, d), 7.11 (1H, m), 7.17 (1H, t), 7.62 (1H, d), 7.76 (1H, m).

Example 275

4-((3-(1H-imidazol-1-yl)-2,2-dimethylcyclopent-3-en-1-yl)(ethyl)amino)-2-(trifluoromethyl)benzonitrile A microvial was charged with palladium (0.160 g, 0.15 mmol, 10% on activated carbon) and washed with dry methanol. The compound of Example 270(a) (60 mg, 0.15 mmol) dissolved in benzonitrile (1 ml) was added and the mixture was stirred at 160° C. The mixture was filtered, washed with methanol and evaporated. Purification by preparative HPLC afforded 17.9 mg of the title compound. $^1$H NMR (400 MHz, CDCl₃): 1.03 (3H, s), 1.27 (3H, t), 1.33 (3H, s), 2.72 (1H, ddd), 2.94 (1H, ddd), 3.52 (2H, m), 4.59 (1H, dd), 5.81 (1H, t), 6.91 (1H, dd), 7.01 (1H, m), 7.09 (1H, 1H, d), 7.13 (1H, br s), 7.56 (1H, br s), 7.60 (1H, dd).

Example 276

4-(Methyl(2-(pyridin-3-yl)-2-azabicyclo[2.2.1]heptan-6-yl)amino)-2-(trifluoromethyl)benzonitrile a) tert-Butyl 6-((4-cyano-3-(trifluoromethyl)phenyl)amino)-2-azabicyclo-[2.2.1]heptane-2-carboxylate The compound was prepared as in Example 137(c) from tert-butyl 6-amino-2-azabicyclo[2.2.1]heptane-2-carboxylate (0.425 g, 2.0 mmol) using 2.5 equivalent of DIPEA. Yield 0.436 g. LC-MS: m/z=382.2 (M+1).

b) tert-Butyl 6-((4-cyano-3-(trifluoromethyl)phenyl)(methyl)amino)-2-azabicyclo[2.2.1]heptane-2-carboxylate The compound was prepared as in Example 137(d) from the compound of Example 276(a) (0.436 g, 1.143 mmol). Yield 0.469 g. LC-MS: m/z=396.6 (M+1).

c) 4-(2-Azabicyclo[2.2.1]heptan-6-yl(methyl)amino)-2-(trifluoromethyl)-benzonitrile The compound was prepared as in Example 187(b) from Example 276(b) (0.469 g, 1.204 mmol). Yield 0.361 g. $^1$H NMR (400 MHz, CDCl$_3$): 1.38 (1H, m), 1.83 (1H, m), 1.92 (1H, m), 2.13 (1H, m), 2.62 (1H, m), 2.92 (1H, m), 3.09 (3H, s), 3.16 (1H, dt), 3.85 (1H, m), 4.00 (1H, br s), 7.10 (1H, dd), 7.18 (1H, d), 7.64 (1H, d).

d) 4-(Methyl(2-(pyridin-3-yl)-2-azabicyclo[2.2.1]heptan-6-yl)amino)-2-(trifluoromethyl)benzonitrile The compound was prepared as in Example 137(a) from Example 276(c) (0.13 g, 0.44 mmol). Yield 77 mg. $^1$H NMR (400 MHz, CDCl$_3$): 1.75-1.82 (2H, m), 1.84 (1H, m), 2.19 (1H, m), 2.64 (3H, s), 2.86 (1H, m), 3.10 (1H, d), 3.53 (1H, dt), 4.40 (1H, m), 4.42 (1H, m), 6.53 (1H, ddd), 6.82 (1H, dd), 6.95 (2H, m), 7.62 (1H, dd), 7.78 (1H, d), 7.84 (1H, dd).

Example 277

2-Chloro-4-((4,4-dimethyl-1-(pyridin-3-yl)piperidin-3-yl)(ethyl)amino)benzonitrile a) 4-((1-Benzyl-4,4-dimethylpiperidin-3-yl)amino)-2-chlorobenzonitrile The compound was prepared as in Example 137(c) from 1-benzyl-4,4-dimethylpiperidin-3-amine (1.528 g, 7.0 mmol) using 2.5 equivalents of DIPEA. Yield 1.667 g. LC-MS: m/z=354.58 (M+1).

b) 4-((1-Benzyl-4,4-dimethylpiperidin-3-yl)(ethyl)amino)-2-chlorobenzonitrile

The compound was prepared as in Example 137(d) from the compound of Example 277(a) (0.774 g, 2.187 mmol). Yield 0.478 g after flash chromatography. LC-MS: m/z=382.6 (M+1).

c) 2-Chloro-4-((4,4-dimethylpiperidin-3-yl)(ethyl)amino)benzonitrile hydrochloride 1-Chloroethyl chloroformate (35 μl, 0.327 mmol) was added the compound of Example 277(b) (0.10 g, 0.262 mmol) in 1,2-dichloroethane (2 ml). The mixture was stirred at RT for 30 min and then refluxed for 2 h. Solvent was evaporated. Methanol (2 ml) was added to the residue and the mixture was refluxed for 3 h. Solvent was evaporated and the residue was triturated with ether to afford 74 mg of the title compound. $^1$H NMR (400 MHz, DMSO-d$_6$): 0.83 (3H, s), 1.10 (3H, t), 1.12 (3H, s), 1.54 (1H, m), 1.80 (1H, dt), 2.91 (1H, m), 3.17 (1H, m), 3.5 (2H, m), 4.31 (1H, dd), 6.94 (1H, dd), 7.06 (1H, d), 7.67 (1H, d), 8.84 (1H, br s), 9.09 (1H, br s). Some signals obscured by solvent. LC-MS: m/z=292.29 (M+1-HCl).

d) 4-((1-Benzyl-4,4-dimethylpiperidin-3-yl)(ethyl)amino)-2-chlorobenzonitrile

The compound was prepared s in Example 8(d) from the compound of Example 277(c) (74 mg, 0.225 mmol). Yield 57 mg. $^1$H NMR (400 MHz, CDCl$_3$): 1.01 (3H, s), 1.14 (3H, s), 1.18 (3H, t), 1.64 (1H, dt), 1.82 (1H, m), 3.03 (1H, dt), 3.28 (1H, dd), 3.5 (4H, m), 4.01 (1H, dd), 6.73 (1H, dd), 6.85 (1H, d), 7.16-7.22 (2H, m), 7.42 (1H, d), 8.13 (1H, dd), 8.32 (1H, dd).

Example 278

4-(Ethyl(3-(1-(2-hydroxyethyl)-1H-imidazol-5-yl)-6,6-dimethylcyclohex-2-en-1-yl)amino)-2-(trifluoromethyl)benzonitrile a) 4-((3-(1-(2-(Benzyloxy)ethyl)-1H-imidazol-5-yl)-6,6-dimethylcyclohex-2-en-1-yl)(ethyl)amino)-2-(trifluoromethyl)benzonitrile The title compound was prepared from the compound of Example 220(c) (0.5 g, 1.0 mmol), NaH (0.081 g, 2.0 mmol) and iodoethane (0.122 ml, 0.237 g, 1.5 mmol) and DMF (4 ml) as described in Example 74(g). Crude product was purified by column chromatography. Yield: 0.22 g. $^1$H NMR (400 MHz, CDCl$_3$): 0.92 (3 H, s), 1.00 (3 H, s), 1.12 (3 H, t), 1.53-1.70 (2 H, m), 2.24-2.46 (2 H, m), 3.36-3.47 (2 H, m), 3.65-3.71 (2 H, m), 4.14-4.20 (2 H, m), 4.32-4.38 (1 H, m), 4.46 (2 H, s), 5.58-5.62 (1 H, m), 6.88 (1 H, dd), 6.97-7.03 (1 H, m), 7.06 (1 H, d), 7.15-7.22 (2 H, m), 7.27 (3 H, m), 7.54-7.60 (2 H, m). [M+H]$^+$=523.

b) 4-(Ethyl(3-(1-(2-hydroxyethyl)-1H-imidazol-5-yl)-6,6-dimethylcyclohex-2-en-1-yl)amino)-2-(trifluoromethyl)benzonitrile The compound was prepared from the compound of Example 278(a) (0.17 g, 0.33 mmol), BCl$_3$ (1 M solution in heptane, 0.81 ml, 0.81 mmol) and DCM (3 ml) as in Example 221. Crude product was purified by column chromatography. Yield 0.007 g. $^1$H NMR (400 MHz, CDCl$_3$): 0.96 (3 H, s), 1.06 (3 H, s), 1.19 (3 H, t), 1.59-1.74 (2 H, m), 2.22 (1 H, br. s.), 2.32-2.50 (2 H, m), 3.40-3.56 (2 H, m), 3.87-3.92 (2 H, m), 4.10-4.16 (2 H, m), 4.41-4.45 (1 H, m), 5.66-5.72 (1 H, m), 6.91 (1 H, dd), 6.97 (1 H, s), 7.09 (1 H, d), 7.54 (1 H, s), 7.58 (1 H, d). [M+H]$^+$=433.

Example 279

2-Chloro-4-((6,6-dimethyl-3-(1H-1,2,4-triazol-1-yl)cyclohex-2-en-1-yl)-(methyl)amino)benzonitrile a) 2-Chloro-4-((6,6-dimethyl-3-(1H-1,2,4-triazol-1-yl)cyclohex-2-en-1-yl)-amino)benzonitrile The compound was prepared from the compound of Example 15(d) (1.0 g, 5.2 mmol), 2-chloro-4-fluorobenzonitrile (0.809 g, 5.2 mmol), DIPEA (2 ml, 1.48 g, 11.5 mmol) and DMSO (10 ml) as described in Example 74(f). Crude product was purified by column chromatography. Yield: 0.7 g. [M+H]$^+$=328.

b) 2-Chloro-4-((6,6-dimethyl-3-(1H-1,2,4-triazol-1-yl)cyclohex-2-en-1-yl)-(methyl)amino)benzonitrile The compound was prepared from the compound of Example 279(a) (0.35 g, 1.07 mmol), NaH (0.085 g, 2.1 mmol), iodomethane (0.13 ml, 0.3 g, 2.1 mmol) and DMF (3 ml) as described in Example 74(g). Crude product was purified by column chromatography. Yield: 0.26 g. Enantiomers were separated by chiral HPLC (Column: Daicel Chiralpak IA 20 mm×250 mm 5 μm, eluent A: MTBE+0.2% DEA, solvent B: EtOH+0.2% DEA, isocratic B 8%, 20 ml/min) to obtain enantiomer 1 (yield 0.107 g, rt 13 min) and enantiomer 2 (yield 0.12 g, rt 19 min). $^1$H NMR (400 MHz, CDCl$_3$): 0.98 (3 H, s), 1.13 (3 H, s), 1.71-1.88 (2 H, m), 2.57-2.68 (1 H, m), 2.74-2.84 (1 H, m), 2.93 (3 H, s), 4.46-4.56 (1 H, m), 6.10-6.16 (1 H, m), 6.73 (1 H, dd), 6.83 (1 H, d), 7.40-7.49 (1 H, m), 7.97-8.05 (1 H, m), 8.27-8.36 (1 H, m). [M+H]$^+$=342.

Example 280

2-Chloro-4-((6,6-dimethyl-3-(1H-1,2,4-triazol-1-yl)cyclohex-2-en-1-yl)-(ethyl)amino)benzonitrile The compound was prepared from the compound of Example 2(a) (0.35 g, 1.07 mmol), NaH (0.125 g, 3.1 mmol), iodoethane (0.13 ml, 0.24 g, 1.6 mmol) and DMF (3 ml) as described in Example 74(g). Crude product was purified by column chromatography. Yield: 0.20 g. Enantiomers were separated by chiral HPLC (Column: Daicel Chiralpak IA 20 mm×250 mm 5 μm, eluent A: MTBE+0.2% DEA, solvent B: EtOH+0.2% DEA, isocratic B 10%, 20 ml/min) to obtain enantiomer 1 (yield 0.145 g, rt 7 min) and enantiomer 2 (yield 0.084 g, rt 14 min). $^1$H NMR (400 MHz, CDCl$_3$): 0.99 (3 H, s), 1.10 (3 H, s), 1.19 (3 H, t), 1.72-1.77 (1 H, m), 1.78-1.88 (1 H, m), 2.54-2.69 (1 H, m), 2.71-2.82 (1 H, m), 3.43 (2 H, m), 4.41-4.51 (1 H, m), 6.17-6.27 (1 H, m), 6.71 (1 H, dd), 6.83 (1 H, d), 7.39-7.47 (1 H, m), 7.95-8.05 (1 H, m), 8.31 (1 H, s). [M+H]$^+$=356.

Example 281 trans-4-((6-(Hydroxymethyl)-3-(1H-imidazol-1-yl)-6-methylcyclohex-2-en-1-yl)(methyl)amino)-2-(trifluoromethyl)benzonitrile a) 6-((Benzyloxy)methyl)-3-isobutoxy-6-methylcyclohex-2-enone

To a stirred solution of 3-isobutoxy-6-methylcyclohex-2-enone (13.10 g, 71.87 mmol) in dry THF (250 ml) was added lithium diisopropylamide (2 M solution in THF, 39.5 ml, 79 mmol) at −78° C. followed by stirring at this temperature for 1 h. Benzyl chloromethyl ether (15 ml, 107.8 mmol) was added at −78° C. dropwise. The mixture was allowed to warm to RT followed by stirring for 16 h. The mixture was poured into ice cold water and extracted with EtOAc. The organic layer was dried and concentrated to obtain the crude compound. Column chromatography provided 6.5 g of the title compound. [M+H]$^+$=303.

b) 6-((Benzyloxy)methyl)-3-hydroxy-6-methylcyclohex-2-enone

To an ice cold stirred solution of the compound of Example 281(a) (6 g, 20 mmol) in acetone (60 ml) was added 1 N aqueous HCl (60 ml, 60 mmol). The solution was allowed to warm to RT and was stirred for 16 h. The mixture was concentrated and poured into water and extracted with EtOAc. The organic layer was dried, filtered and concentrated. Crude product was purified by column chromatography. Yield 3 g. [M−H]$^+$=245.

c) 6-((Benzyloxy)methyl)-3-chloro-6-methylcyclohex-2-enone

To an ice cold stirred solution of the compound of Example 281(b) (3.0 g, 12.2 mmol) in CHCl$_3$ (60 ml) was added oxalyl chloride (1.57 ml, 2.32 g, 18.3 mmol) followed by one drop of dry DMF. Ice bath was removed and the solution was allowed to warm to RT and stirred for 6 h. The mixture was poured into saturated NaHCO$_3$ and extracted with DCM. The organic layer was dried and concentrated to obtain the crude compound. Crude product was used as such in the following step. Yield: 3.0 g (crude). [M+H]$^+$=245.

d) 6-((Benzyloxy)methyl)-3-(1H-imidazol-1-yl)-6-methylcyclohex-2-enone

To a stirred solution of the compound of Example 281(c) (3 g, 11.3 mmol) in toluene (60 ml) were added Et$_3$N (2.36 ml, 1.71 g, 17 mmol), KHCO$_3$ (1.13 g, 11.3 mmol) and imidazole (2.31 g, 34 mmol). The mixture was heated at reflux temperature for 16 h. The mixture was concentrated, poured into water and extracted with 5% MeOH in DCM. The organic layer was dried and concentrated to obtain the crude compound. Column chromatographic purification provided 1.8 g of the title compound. [M+H]$^+$=297.

e) tert-Butyl (6-((benzyloxy)methyl)-3-(1H-imidazol-1-yl)-6-methylcyclohex-2-en-1-yl)carbamate To an ice cold stirred solution of the compound of Example 281(d) (1.8 g, 6.1 mmol) in IPA (36 ml) was added 5 M NH$_3$ in IPA (36 ml) followed by Ti(iOPr)$_4$ (3.6 ml, 3.46 g, 12.1 mmol). Ice bath was removed and the solution was allowed to warm to RT followed by stirring for 4 h. The mixture was again cooled to 0° C. and sodium borohydride (0.69 g, 18.22 mmol) was added. The mixture was allowed to react at RT for 16 h. The mixture was poured into ice cold water and extracted with 5% MeOH in DCM. The organic layer was dried, filtered and to afford crude compound. This crude amine was dissolved in DCM (35 ml) and cooled on ice bath. Et$_3$N (2.1 ml, 1.52 g, 15.1 mmol) was added followed by Boc$_2$O (2.09 ml, 1.99 g, 9.1 mmol). The mixture was allowed to react at RT for 16 h. Then it was poured into water and extracted with DCM (2×75 ml). The organic layer was dried, filtered and concentrated to afford crude compound. Column chromatography provided 0.8 g of the title compound. [M+H]$^+$=398.

f) 6-((Benzyloxy)methyl)-3-(1H-imidazol-1-yl)-6-methylcyclohex-2-enamine

To a cold stirred solution of the compound of Example 281(e) (0.8 g, 2.01 mmol) in 1,4-dioxane (30 ml) was added 5 M HCl in dioxane (30 ml, 150 mmol). The solution was allowed to warm to RT followed by stirring for 6 h. The mixture was concentrated to afford crude compound, which was triturated with ether. Yield: 0.55 g (crude, hydrochloride salt). [M+H]$^+$=298.

g) 4-((6-((Benzyloxy)methyl)-3-(1H-imidazol-1-yl)-6-methylcyclohex-2-en-1-yl)amino)-2-(trifluoromethyl)benzonitrile The compound was prepared from the compound of Example 281(f) (0.5 g, 1.35 mmol), 4-fluoro-2-(trifluoromethyl)benzonitrile (0.281 g, 1.49 mmol), DIPEA (0.94 ml, 0.7 g, 5.4 mmol) and DMSO (3 ml) as described in Example 74(f). Crude product was purified by column chromatography. Yield: 0.33 g. [M+H]$^+$=467.

h) 4-((6-((Benzyloxy)methyl)-3-(1H-imidazol-1-yl)-6-methylcyclohex-2-en-1-yl)(methyl)amino)-2-(trifluoromethyl)benzonitrile The compound was prepared from the compound of Example 281(g) (0.33 g, 0.7 mmol), NaH (0.057 g, 1.4 mmol), iodomethane (0.066 ml, 0.150 g, 1.06 mmol) and DMF (2 ml) as described in Example 74(g). Crude product was purified by column chromatography. Yield 0.3 g (diastereomeric ratio ~2.6:1). [M+H]$^+$=481.

i) 4-((6-(Hydroxymethyl)-3-(1H-imidazol-1-yl)-6-methylcyclohex-2-en-1-yl)(methyl)amino)-2-(trifluoromethyl)benzonitrile Compound of Example 281(h) (0.15 g, 0.31 mmol)) was dissolved in DCM (4 ml) and the solution was cooled to 0° C. Boron trichloride (1 M solution, 0.94 ml, 0.94 mmol) was added and the solution was allowed to react at 0° C. When the reaction was complete it was quenched with EtOH and NaHCO$_3$. Solid material was filtered off and the solution was concentrated. The crude material was purified by reverse phase chromatography. Yield: 0.039 g (trans-isomer, formate salt). $^1$H NMR (400 MHz, MeOH-d$_4$): 0.93 (s, 3 H), 1.78 (m, 1 H), 1.92-2.05 (m, 1 H), 2.53-2.65 (m, 1 H), 2.67-2.80 (m, 1 H), 3.02 (s, 3 H), 3.32-3.38 (m, 1 H), 3.41-3.48 (m, 1 H), 4.97-5.03 (m, 1 H), 5.90 (m, 1 H), 7.10 (br. s., 1 H), 7.22 (dd, 1 H), 7.43-7.48 (m, 1 H), 7.49-7.55 (m, 1 H), 7.68 (d, 1 H), 8.07-8.14 (m, 1 H). [M+H]$^+$=391. Cis-isomer was isolated from a 30 mg sample by basic preparative reverse phase HPLC to obtain cis-isomer as a free base. $^1$H NMR (400 MHz, MeOH-d$_4$): 1.14 (3 H, s), 1.75 (1 H, m), 1.92-2.02 (1 H, m), 2.56-2.69 (1 H, m), 2.73-2.82 (1 H, m), 2.98 (3 H, s), 3.33-3.38 (1 H, d), 3.40-3.46 (1 H, d), 4.70-4.75 (1 H, m), 5.81-5.86 (1 H, m), 7.04-7.06 (1 H, m), 7.19 (1 H, dd), 7.26 (1 H, d), 7.47 (1 H, m), 7.68 (1 H, d), 8.01 (1 H, m). [M+H]$^+$=391.

Example 282

4-((6-(Hydroxymethyl)-3-(1H-imidazol-1-yl)cyclohex-2-en-1-yl)(methyl)-amino)-2-(trifluoromethyl)benzonitrile a) 6-((Benzyloxy)methyl)-3-isobutoxycyclohex-2-enone

To 3-isobutoxycyclohex-2-enone (5.0 g, 29.72 mmol) in dry THF (100 ml) was added HMPA (5.3 ml, 5.46 g, 29.7 mmol) and lithium diisopropylamide (2 M in solution THF, 16.3 ml, 32.6 mmol) at −78° C. The mixture was stirred at this temperature for 1 h and benzyl chloromethyl ether (7.0 ml, 44.6 mmol) was added. The mixture was allowed to warm to RT followed by stirring for 16 h. The mixture was poured into ice cold water and extracted with EtOAc. The organic layer was dried, filtered and concentrated to obtain the crude compound. The crude compound was used for next step without further purification. Yield 3.0 g. [M+H]$^+$=289.

b) 6-((Benzyloxy)methyl)-3-hydroxycyclohex-2-enone

The title compound was prepared from the compound of Example 282(a) (5 g, 17.4 mmol), 1 N HCl (30 ml, 30 mmol) and acetone (30 ml) as in Example 281(b). Crude product was purified by column chromatography. Yield 2.3 g. [M+H]$^+$=233.

c) 6-((Benzyloxy)methyl)-3-chlorocyclohex-2-enone

The compound was prepared from the compound of Example 282(b) (1.0 g, 4.3 mmol), oxalyl chloride (0.55 ml, 0.81 g, 6.4 mmol), DMF (0.05 ml) and DCM (15 ml) as in Example 281(c). Crude product was purified by column chromatography. Yield 0.25 g. [M+H]$^+$=251. Further elution of the column provided 4-((benzyloxy)methyl)-3-chlorocyclohex-2-enone as a byproduct. Yield: 0.1 g. [M+H]$^+$=251.

d) 6-((Benzyloxy)methyl)-3-(1H-imidazol-1-yl)cyclohex-2-enone

The compound was prepared from the compound of Example 282(c) (3.0 g, 12.0 mmol), Et$_3$N (2.5 ml, 1.81 g, 18 mmol), KHCO$_3$ (1.2 g, 12 mmol), imidazole (2.44 g, 35.9 mmol) and toluene (30 ml) as described in Example 281(d). Crude product was purified by column chromatography. Yield 1.5 g. [M+H]$^+$=283.

e) tert-Butyl (6-((benzyloxy)methyl)-3-(1H-imidazol-1-yl)cyclohex-2-en-1-yl)carbamate The title compound was prepared from the compound of Example 282(d) (1.5 g, 5.3 mmol), 5 M NH$_3$ in IPA (30 ml, 150 mmol), Ti(iOPr)$_4$ (3.15 ml, 3.02 g, 10.6 mmol), sodium borohydride (0.6 g, 15.9 mmol) and IPA (30 ml) as described in Example 281(e). Crude amine was Boc protected as in Example 281(e) using Et$_3$N (1.6 ml, 1.16 g, 11.4 mmol), Boc$_2$O (1.5 ml, 1.42 g, 9.08 mmol) and DCM (25 ml). Crude material was purified by column chromatography. Yield 1.1 g. [M+H]$^+$=384.

f) 6-((Benzyloxy)methyl)-3-(1H-imidazol-1-yl)cyclohex-2-enamine

The compound was prepared from the compound of Example 282(e) (1.0 g, 2.6 mmol), 5 M HCl in 1,4-dioxane (30 ml, 150 mmol) and 1,4-dioxane (30 ml) as described in Example 281(f). Crude product was used as such in the following step. Yield 0.75 g (crude, hydrochloride salt). [M+H]$^+$=284.

g) 4-((6-((Benzyloxy)methyl)-3-(1H-imidazol-1-yl)cyclohex-2-en-1-yl)-amino)-2-(trifluoromethyl)benzonitrile The compound was prepared from the compound of Example 282(f) (0.575 g, 1.61 mmol), 4-fluoro-2-(trifluoromethyl)benzonitrile (0.458 g, 2.42 mmol), DIPEA (1.1 ml, 0.83 g, 6.4 mmol) and DMSO (10 ml) as described in Example 74(f). Crude product was purified by filtration through a pad of silica. Yield 0.397 g (70:30 mixture of diastereomers). [M+H]$^+$=453.

h) 4-((6-((Benzyloxy)methyl)-3-(1H-imidazol-1-yl)cyclohex-2-en-1-yl)-(methyl)amino)-2-(trifluoromethyl)benzonitrile The compound was prepared from the compound of Example 282(g) (0.4 g, 0.88 mmol), NaH (0.053 g, 1.32 mmol), iodomethane (0.11 ml, 0.25 g, 1.77 mmol) and DMF (10 ml) as described in Example 74(g). Crude product was purified by column chromatography. Yield 0.21 g. [M+H]$^+$=467.

i) 4-((6-(Hydroxymethyl)-3-(1H-imidazol-1-yl)cyclohex-2-en-1-yl)(methyl)-amino)-2-(trifluoromethyl)benzonitrile The compound was prepared from the compound of Example 282(h) (0.16 g, 0.34 mmol), BCl$_3$ (1 M solution, 1.03 ml, 1.03 mmol) and DCM (4 ml) as described in Example 281(i). Crude product was first purified by column chromatography and all four enantiomers separated by chiral HPLC. (Column: Daicel Chiralpak IA 20 mm×250 mm 5 µm, eluent A: n-hexane+0.2% DEA, solvent B: EtOH+0.2% DEA, isocratic B 16%, 20 ml/min) to obtain enantiomer 1 (yield 0.011 g, rt 20 min) and enantiomer 2 (yield 0.013 g, rt 24 min) of diastereomer 1, $^1$H NMR (400 MHz, CDCl$_3$): 1.93-2.16 (3 H, m), 2.36 (br. s, 1 H), 2.55-2.65 (1 H, m), 2.65-2.77 (1 H, m), 2.90 (3 H, s), 3.57 (1 H, dd), 3.68 (1 H, dd), 4.84-4.91 (1 H, m), 5.65 (1 H, m), 7.00 (1 H, dd), 7.08 (1 H, s), 7.14 (1 H, m), 7.19 (1 H, d), 7.58 (1 H, d), 7.70 (1 H, s). [M+H]$^+$=377, and enantiomer 1 (yield 0.003 g, rt 28 min) and enantiomer 2 (yield 0.002 g, rt 35 min) of diastereomer 2, $^1$H NMR (400 MHz, CDCl$_3$): 1.73 (br. s., 1 H), 1.90-2.04 (2 H, m), 2.26-2.38 (1 H, m), 2.55-2.67 (1 H, m), 2.73-2.84 (1 H, m), 2.97 (3 H, s), 3.54-3.66 (2 H, m), 4.98 (1 H, m), 5.73-5.80 (1 H, m), 7.01 (1 H, dd), 7.10-7.15 (1 H, m), 7.15-7.20 (2 H, m), 7.63 (1 H, d), 7.77 (1 H, s). [M+H]$^+$=377.

Example 283 trans-4-((3-(Cyclopenta-2,4-dien-1-yl)-6-methoxycyclohex-2-en-1-yl)-(methyl)amino)-2-(trifluoromethyl)benzonitrile a) trans-4-((6-Hydroxy-3-(1H-imidazol-1-yl)cyclohex-2-en-1-yl)amino)-2-(trifluoromethyl)benzonitrile Compound from the Example 242(b) (1.5 g, 8.4 mmol), 4-fluoro-2-(trifluoromethyl)benzonitrile (1.77 g, 9.4 mmol), DIPEA (5.0 ml, 3.7 g, 29 mmol) and DMSO (10 ml) were mixed together in a 25 ml microwave reactor. The mixture was kept at 100° C. in a microwave reactor for 12 h. EtOAc and water were added. Title compound (trans-isomer) crystallized out from this mixture and it was filtered off. Yield 0.606 g. $^1$H NMR (400 MHz, DMSO-d$_6$): 1.77-1.97 (2 H, m), 2.60 (2 H, m), 3.64-3.72 (1 H, m), 4.07 (1 H, m), 5.15-5.22 (1 H, m), 5.84 (1 H, m), 6.94-7.01 (2 H, m), 7.12 (1 H, d), 7.36 (1 H, d), 7.56 (1 H, m), 7.74 (1 H, d), 8.01 (1 H, m). [M+H]$^+$=349. Filtrate was concentrated in vacuo and the crude product was purified by column chromatography. Yield 0.92 g (a mixture of cis and trans isomers). [M+H]$^+$=349.

b) trans-4-((3-(Cyclopenta-2,4-dien-1-yl)-6-methoxycyclohex-2-en-1-yl)-(methyl)amino)-2-(trifluoromethyl)benzonitrile The title compound was prepared from the compound of Example 283(a) (0.1 g, 0.29 mmol), NaH (0.046 g, 1.15 mmol), iodomethane (0.054 ml, 0.12 g, 0.86 mmol) and DMF (1 ml) as described in Example 74(g). Crude product was purified by filtration through a pad of silica. Yield: 0.073 g. $^1$H NMR (400 MHz, CDCl$_3$): 1.98 (1 H, m), 2.22-2.31 (1 H, m), 2.65-2.75 (2 H, m), 2.97 (3 H, s), 3.35 (3 H, s), 3.53 (1 H, m), 4.62-4.69 (1 H, m), 5.56-5.62 (1 H, m), 6.94-7.00 (1 H, m), 7.09-7.17 (3 H, m), 7.58-7.64 (1 H, m), 7.70-7.77 (1 H, m). [M+H]$^+$=376.

Example 284

4-((4-(hydroxymethyl)-3-(1H-imidazol-1-yl)cyclohex-2-en-1-yl)(methyl)-amino)-2-(trifluoromethyl)benzonitrile a) 4-((Benzyloxy)methyl)-3-(1H-imidazol-1-yl)cyclohex-2-enone

The compound was prepared from the compound of Example 282(c) byproduct (1.2 g, 4.8 mmol), Et$_3$N (1.0 ml, 0.73 g, 7.2 mmol), KHCO$_3$ (0.48 g, 4.8 mmol), imidazole (0.97 g, 14.4 mmol) and toluene (20 ml) as in Example 281(d). Crude product was purified by column chromatography. Yield 0.6 g. [M+H]$^+$=283.

b) tert-Butyl (4-((benzyloxy)methyl)-3-(1H-imidazol-1-yl)cyclohex-2-en-1-yl)carbamate The compound was prepared from the compound of Example 284 (a) (0.7 g, 2.5 mmol), 5M NH$_3$ in IPA (15 ml, 75 mmol), Ti(iOPr)$_4$ (1.45 ml, 5.0 mmol), sodium borohydride (0.28 g, 7.4 mmol) and IPA (15 ml) as described in Example 281(e). Crude amine was Boc protected as in Example 281(e) using Et$_3$N (0.73 ml, 0.53 g, 5.3 mmol), Boc$_2$O (0.7 ml, 0.67 g, 3.2 mmol) and DCM (15 ml). Crude material was purified by column chromatography. Yield 0.5 g. [M+H]$^+$=384.

c) 4-((Benzyloxy)methyl)-3-(1H-imidazol-1-yl)cyclohex-2-enamine

The title compound was prepared from the compound of Example 284(b) (0.7 g, 1.8 mmol), 5 M HCl in 1,4-dioxane (20 ml, 100 mmol) and 1,4-dioxane (20 ml) as described in Example 281(f). Crude product was used as such in the following step. Yield 0.4 g (crude, hydrochloride salt). [M+H]$^+$=284.

d) 4-((4-((Benzyloxy)methyl)-3-(1H-imidazol-1-yl)cyclohex-2-en-1-yl)-amino)-2-(trifluoromethyl)benzonitrile (EV-015-09)

The compound was prepared from the compound of Example 284(c) (0.37 g, 1.04 mmol), 4-fluoro-2-(trifluoromethyl)benzonitrile (0.196 g, 1.04 mmol), DIPEA (0.72 ml, 0.54 g, 4.2 mmol) and DMSO (5 ml) as described in Example 74(f). Crude product was purified by filtration through a pad of silica. Yield 0.31 g (80:20 mixture of diastereomers). [M+H]$^+$=453.

e) 4-((4-((Benzyloxy)methyl)-3-(1H-imidazol-1-yl)cyclohex-2-en-1-yl)-(methyl)amino)-2-(trifluoromethyl)benzonitrile The compound was prepared from the compound of Example 284(d) (0.31 g, 0.69 mmol), NaH (0.041 g, 1.03 mmol), iodomethane (0.085 ml, 0.194 g, 1.37 mmol) and DMF (8 ml) as described in Example 74(g). Crude product was purified by column chromatography. Yield 0.213 g. [M+H]⁺=467.

f) 4-((4-(hydroxymethyl)-3-(1H-imidazol-1-yl)cyclohex-2-en-1-yl)(methyl)-amino)-2-(trifluoromethyl)benzonitrile The compound was prepared from the compound of Example 284(e) (0.16 g, 0.34 mmol), BCl₃ (1 M solution, 1.03 ml, 1.03 mmol) and DCM (5 ml) as described in Example 281(i). Crude product was first purified by column chromatography and all four enantiomers separated by chiral HPLC. (Column: Daicel Chiralpak IC 20 mm×250 mm 5 µm, eluent A: MTBE+0.2% DEA, solvent B: EtOH+0.2% DEA, B isocratic 3% (0-54 min); 6% (55-70 min); 3% 71-80 min, 20 ml/min) to obtain enantiomer 1 (yield 0.017 g, rt 45 min) and enantiomer 2 (yield 0.015 g, rt 64 min) of diastereomer 1, ¹H NMR (400 MHz, CDCl₃): 1.87-2.03 (3 H, m), 2.07 (1 H, br. s.), 2.21-2.29 (1 H, m), 2.74-2.83 (1 H, m), 2.95 (3 H, s), 3.55-3.64 (2 H, m), 4.62-4.71 (1 H, m), 5.77 (1 H, m), 6.87 (1 H, dd), 7.02 (1 H, d), 7.04-7.07 (1 H, m), 7.07-7.11 (1 H, m), 7.58 (1 H, d), 7.66 (1 H, s). [M+H]⁺=377, and enantiomer 1 (yield 0.002 g, rt 52 min) and enantiomer 2 (yield 0.004 g, rt 60 min) of diastereomer 2, ¹H NMR (400 MHz, CDCl₃): 1.70 (1 H, br. s.), 1.77-1.84 (1 H, m), 2.02-2.12 (3 H, m), 2.80-2.88 (1 H, m), 2.91 (3 H, s), 3.42-3.54 (2 H, m), 4.70 (1 H, m), 5.81-5.86 (1 H, m), 6.86 (1 H, dd), 7.02 (1 H, d), 7.06 (1 H, br. s.), 7.09 (1 H, br. s.), 7.60 (1 H, d), 7.65 (1 H, br. s.). [M+H]⁺=377.

Example 285

4-((6-Hydroxy-3-(1H-imidazol-1-yl)-6-methylcyclohex-2-enyl)(methyl)-amino)-2-(trifluoromethyl)benzonitrile a) 6-Hydroxy-3-isobutoxy-6-methylcyclohex-2-enone

To a solution of the compound of Example 256(b) (20 g) in THF (200 ml) was added 2 M lithium diidopropylamide in THF (82 ml) at −78° C. dropwise and the mixture was stirred at the same temperature for 1 h. Then oxodiperoxymolybdenum(pyridine)(hexamethylphosphorictriamide) (MoOPH) (71.1 g) was added at −78° C. The mixture was allowed to warm to RT and stirred for 16 h. The mixture was poured into saturated aqueous sodium sulphite (200 ml) and extracted with EtOAc (2×200 ml). The organic layer was dried and concentrated to obtain the crude compound. The compound was purified by flash column using 230-400 mesh silica gel and eluted with EtOAc in petroleum ether to afford 10.5 g of the title compound. 1H NMR (400 MHz, DMSO-d₆): 0.82 (d, 6H), 1.15 (s, 3H), 1.75-2.02 (m, 3H), 2.35-2.55 (m, 2H), 3.65 (d, 2H), 4.90 (s, 1H), 5.22 (s, 1H).

b) 3,6-Dihydroxy-6-methylcyclohex-2-enone

To a cold stirred solution of the compound of Example 285(a) (10.0 g) in acetone (100 ml) was added 1 N aqueous HCl (100 ml) and the mixture was allowed to warm to RT and stirred for 16 h. The mixture was concentrated, poured into water (60 ml) and extracted with EtOAc (2×150 ml). The organic layer was dried, filtered and concentrated to afford crude compound. The compound was purified by flash column using 230-400 mesh silica gel and eluted with 65% EtOAc in petroleum ether to afford 5 g of the title compound.

c) 3-Chloro-6-hydroxy-6-methylcyclohex-2-enone

To a cold stirred solution of the compound of Example 285(b) (20.0 g) in CH₂Cl₂ (200 ml) was added oxalyl chloride (18.2 ml) followed by 1 ml of dry DMF. The mixture was stirred for 1 h at −5° C. and then poured into saturated aqueous NaHCO₃ (100 ml). The mixture was extracted with CH₂Cl₂ (2×100 ml). The organic layer was dried and concentrated to obtain the crude title compound. The compound was directly used to next step without further purification. Yield 26 g (crude).

d) 6-Hydroxy-3-(1H-imidazol-1-yl)-6-methylcyclohex-2-enone

To a stirred solution of the compound of Example 285(c) (25.0 g, crude) in toluene (200 ml) were added Et₃N (29.1 ml), KHCO₃ (15.61 g) and imidazole (31.8 g). The mixture was heated at reflux temperature for 12 h. The mixture was concentrated, poured into water (100 ml) and extracted with 5% MeOH in CH₂Cl₂ (2×100 ml). The organic layer was dried and concentrated to obtain the crude compound. The compound was purified by flash column using 230-400 mesh silica gel and eluted with 4% MeOH in CH₂Cl₂ to afford 3.0 g of the title compound. LCMS: m/z=193.1 (M+1)⁺.

e) 2-Amino-4-(1H-imidazol-1-yl)-1-methylcyclohex-3-enol

The compound was prepared from the compound of Example 285(d) (4.50 g) in IPA (10 ml), 5 M NH₃ in IPA (50 ml), Ti(iOPr)₄ (13.5 ml) and NaBH₄ (2.60 g) as in Example 242(b). The mixture was poured into ice cold water (40 ml) and filtered. The filtrate was concentrated under reduced pressure to afford crude title compound. The compound was directly used to next step without further purification. Yield 5.0 g (crude). LCMS: m/z=194.2 (M+1)⁺.

f) tert-Butyl (6-hydroxy-3-(1H-imidazol-1-yl)-6-methylcyclohex-2-en-1-yl)-carbamate The compound was prepared from the compound of Example 285(e) (5.0 g, crude), Et₃N (8.5 ml) and (Boc)₂O (8.5 ml) in CH₂Cl₂ (50 ml) as in Example 242(c). The compound was purified by flash column using 230-400 mesh silica gel and eluted with 4% MeOH in CH₂Cl₂ to afford 2.8 g of the title compound. LCMS: m/z=294.2 (M+1)⁺.

g) 2-Amino-4-(1H-imidazol-1-yl)-1-methylcyclohex-3-enol hydrochloride

The compound was prepared from the compound of Example 285(f) (2.80 g) and 5 M HCl in 1,4-dioxane (30 ml) as described in Example 242(e). Yield: 1.8 g. LCMS: m/z=194.2 (M+1)⁺.

h) 4-(6-Hydroxy-3-(1H-imidazol-1-yl)-6-methylcyclohex-2-enylamino)-2-(trifluoromethyl)benzonitrile The compound was prepared from the compound of Example 285(g) (0.90 g), 4-fluoro-2-(trifluoromethyl)benzonitrile (0.741 g) and DIPEA (3.41 ml) in DMSO (25 ml). Reaction time was 3.5 h at 90° C. Yield: 1.58 g (crude). Part of the crude product (1.1 g) was purified and diastereomers separated by flash chromatography (column Silica RediSepRf gold 12 g, eluent 0-5% MeOH/DCM). Yields: 0.102 g (first eluted, diastereomer 1), 0.079 g (diastereomer 2). LCMS: m/z=363.3 (M+1)$^+$.

i) 4-((6-Hydroxy-3-(1H-imidazol-1-yl)-6-methylcyclohex-2-enyl)(methyl)-amino)-2-(trifluoromethyl)benzonitrile The compound of Example 285(h) (diastereomer 1) (0.113 g) was dissolved to mixture of dry DMF (0.60 ml and THF (0.25 ml) N$_2$. Sodium tert-butoxide (0.027 g) was added and at 0° C. iodomethane (0.019 ml). After stirring for 3 h at 0° C. an other batch of sodium tert-butoxide (0.010 g) and iodomethane (0.010 ml) were added and stirring continued for 0.5 h. MTBE (6 ml) was added and the mixture was allowed to warm to RT. Water was added and the mixture was stirred for 15 min. Organic layer was separated and water phase was extracted twice with MTBE. Combined organic phases were dried and evaporated. The crude product was purified by chromatography (silica column, eluent 0-10% MeOH/DCM) to obtain the title compound. LCMS: m/z=377.6 (M+1). $^1$H NMR (400 MHz, MeOH-d$_4$): 1.28 (s, 3H), 1.96-2.04 (m, 1H), 2.07-2.17 (m, 1H), 2.54-2.64 (m, 1H), 2.87-2.98 (m, 1 H), 3.11 (s, 3H), 4.89 (br. s., 1H), 6.13 (t, 1H), 7.18 (dd, 1H), 7.25 (d, 1H), 7.59 (br, s, 1H), 7.69 (d, 1H), 7.91 (br, s, 1H), 9.09 (s, 1H).

Example 286

4-((6-Hydroxy-3-(1H-imidazol-1-yl)-6-methylcyclohex-2-enyl)(methyl)-amino)-2-(trifluoromethyl)benzonitrile and 4-((3-(1H-imidazol-1-yl)-6-methoxy-6-methylcyclohex-2-enyl)(methyl)amino)-2-(trifluoromethyl)benzonitrile The title compounds were prepared starting from the compound of Example 285(h) (diastereomer 2) (0.079 g) as described in Example 285(i) except one batch of sodium tert-butoxide (0.019 g) and iodomethane (0.014 ml) were used. Crude product was purified by chromatography (silica column, eluent 0-10% MeOH/DCM) to obtain hydroxy (1) and methoxy (2) title compounds. Yields: (1) 0.0083 g, (2) 0.0072 g. LCMS: m/z=(1) 377.7, (2) 391.7 (M+1)$^+$. (1): H NMR (400 MHz, MeOH-d$_4$): 1.22 (s, 3 H), 1.89-2.00 (m, 1 H), 2.00-2.11 (m, 1 H), 2.71-2.76 (m, 2 H), 3.00 (s, 3 H), 4.80-4.87 (m, 1 H), 5.83-5.86 (m, 1 H), 7.05 (s, 1 H), 7.24 (dd, 1 H), 7.39 (d, 1 H), 7.47 (s, 1 H), 7.67-7.73 (m, 1 H), 8.01 (s, 1 H). (2): $^1$H NMR (400 MHz, MeOH-d$_4$): 1.19 (s, 3 H), 1.97-2.16 (m, 2 H), 2.62-2.71 (m, 2 H), 3.01 (s, 3 H), 3.28 (s, 3 H), 4.81-4.95 (m, 1 H), 5.80-5.84 (m, 1 H), 7.06 (br. s., 1 H), 7.21 (dd, 1 H), 7.35 (d, 1 H), 7.48 (s, 1 H), 7.70 (d, 1 H), 8.03 (s, 1 H).

ABBREVIATIONS

ACN—Acetonitrile
DCM—Dichloromethane
DEA—Diethanolamine
DIPEA—N,N-diisopropylethylamine
DMF—N,N-Dimethylformamide
DMSO—Dimethylsulfoxide
DPPA—Diphenylphosphoryl azide
DBU—1,8-Diazabicyclo[5.4.0]undec-7-ene
EtOAc—Ethyl acetate
EtOH—Ethanol
IPA—Isopropyl Alcohol
MeOH—Methanol
MTBE—Methyl Tertiary Butyl Ether
PPh$_3$—Triphenylphosphine
Pd$_2$(dba)$_3$—Tris(dibenzylideneacetone)dipalladium(0)
Pd(PPh$_3$)$_4$—Tetrakis(triphenylphosphine)palladium(0)
PPTS—Pyridinium p-toluenesulfonate
rac-BINAP—rac-2,2'-bis(diphenylphosphino)-1,1'-binaphthyl
RT—Room temperature
rt—Retention time
TBABr—Tetrabutylammonium bromide
TBAF—Tetrabutylammonium fluoride
TBME—Methyl tert-butyl ether
TBSCl—tert-Butyldimethylsilyl chloride
TEA—Triethylamine
TFA—Trifluoroacetic acid
THF—Tetrahydrofuran
TMEDA—Tetramethylethylenediamine
TsOH—p-Toluenesulfonic acid monohydrate

The invention claimed is:
1. A compound of formula (I)

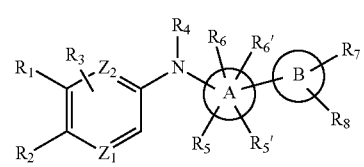

wherein
ring atoms $Z_1$ and $Z_2$ are C;
ring A is a non-aromatic 3-7 membered carbocyclic ring;
ring B is a 5-6 membered heterocyclic ring;
$R_1$ is halogen, CHF$_2$, CF$_3$, C$_{1-7}$ alkyl, or C$_{1-7}$ alkoxy;
$R_2$ is cyano or nitro;
$R_3$ is H, halogen, or C$_{1-7}$ alkyl;
$R_4$ is C$_{1-7}$ alkyl, C$_{2-7}$ alkenyl, C$_{3-7}$ cycloalkyl, C$_{3-7}$ cycloalkyl C$_{1-7}$ alkyl, hydroxy C$_{1-7}$ alkyl, halo C$_{1-7}$ alkyl, C$_{1-7}$ alkoxy C$_{1-7}$ alkyl, C$_{1-7}$ alkylcarbonyl, or phenyl C$_{1-7}$ alkyl,
or when ring A is a non-aromatic 3-7 membered carbocyclic ring and ring B is an aromatic 5-6 membered heterocyclic ring, $R_4$ is C$_{1-7}$ alkyl, C$_{2-7}$ alkenyl, C$_{3-7}$ cycloalkyl, C$_{3-7}$ cycloalkyl C$_{1-7}$ alkyl, hydroxy C$_{1-7}$ alkyl, halo C$_{1-7}$ alkyl, C$_{1-7}$ alkoxy C$_{1-7}$ alkyl, C$_{1-7}$ alkylcarbonyl, phenyl C$_{1-7}$ alkyl, or hydrogen;
$R_5$ is H, OH, C$_{1-7}$ alkyl, C$_{1-7}$ alkoxy, or hydroxy C$_{1-7}$ alkyl;
$R_5'$, $R_6'$ and $R_6$ are, independently, H, OH, C$_{1-7}$ alkyl, or halogen;
or, when $R_6'$ and $R_6$ are attached to the same carbon atom of ring A, $R_6'$ and $R_6$ may, together with the carbon atom to which they are attached, form a C$_{3-7}$ cycloalkyl ring;
$R_7$ is H, OH, cyano, halogen, C$_{1-7}$ alkyl, C$_{3-7}$ cycloalkyl, C$_{1-7}$ alkoxy, hydroxy C$_{1-7}$ alkyl, halo C$_{1-7}$ alkyl, cyano C$_{1-7}$ alkyl, halo C$_{1-7}$ alkoxy, C$_{1-7}$ alkoxy C$_{1-7}$ alkyl, hydroxy C$_{1-7}$ alkoxy C$_{1-7}$ alkyl, C$_{1-7}$ alkyl carbonyl C$_{1-7}$ alkyl or —C$_{1-7}$ alkyl-X—(CH$_2$)$_n$—R$_9$, or R$_9$;
$R_8$ is H or C$_{1-7}$ alkyl;
$R_9$ is an optionally substituted 3-7 membered carbocyclic ring, an optionally substituted 4-6 membered heterocyclic ring, or —NR$_{10}$R$_{11}$;

X is a bond, oxygen, or —NH—;

n is 0, 1, 2, or 3;

$R_{10}$ and $R_{11}$ are, independently, H, $C_{1-7}$ alkyl, or $C_{1-7}$ alkyl carbonyl;

or a pharmaceutically acceptable salt thereof.

2. The compound according to claim 1, wherein ring A is a cyclobutyl, cyclopentyl, cyclohexyl, cyclopentenyl, or cyclohexenyl.

3. The compound according to claim 1, wherein ring A is selected from the following groups wherein an asterisk denotes the point of attachment to the non-cyclic nitrogen atom of formula (I)

(1)

(2)

(3)

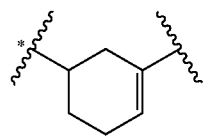
(4)

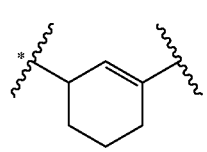
(5)

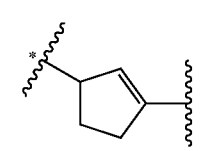
(6)

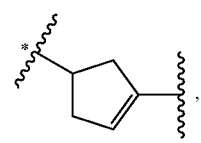
(7)

and wherein the ring is substituted by $R_5$, $R_5'$, $R_6$, and $R_6'$.

4. The compound according to claim 1 wherein ring A is a cyclopentyl, cyclohexyl, cyclopentenyl, or cyclohexenyl ring.

5. The compound according to claim 1, wherein ring B is a imidazolyl, 1,2,4-triazolyl, 1,2 3-triazolyl, pyridinyl, tetrazolyl, pyrimidinyl, 1,3,4-oxadiazolyl, pyrazolyl, pyrazinyl, 1,3,4-thiadiazolyl, oxazolyl, thiazolyl, or isoxazolyl ring.

6. The compound according to claim 1, wherein ring B is selected from the following groups or tautomers thereof wherein an asterisk denotes the point of attachment to ring A

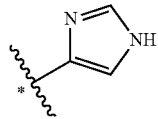
(1')

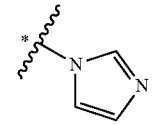
(2')

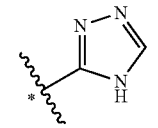
(3')

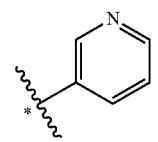
(4')

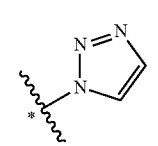
(5')

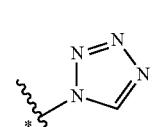
(6')

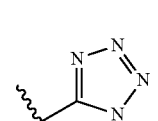
(7')

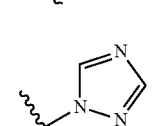
(8')

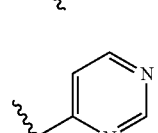
(9')

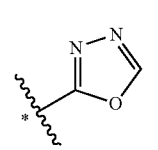
(10')

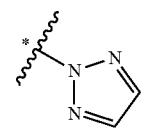
(11')

-continued (12') 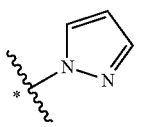

(13') 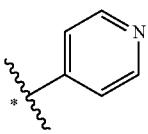

(14') 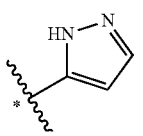

(16') 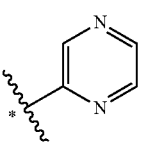

(17') 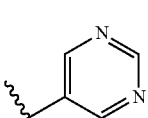

(18') 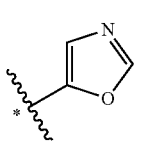

(19') 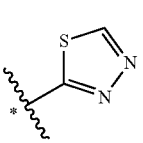

(20') 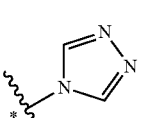

(21') 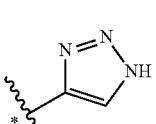

(22') 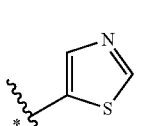

(23') 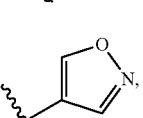

and wherein the ring is substituted by $R_7$ and $R_8$.

7. The compound according to claim 1, wherein ring B is a imidazolyl, pyridinyl, 1,2,4-triazolyl, 1,2,3-triazolyl, thiazolyl, or oxazolyl ring.

8. The compound according to claim 1, wherein $R_1$ is $CF_3$ or chloro; $R_2$ is cyano; and $R_3$ is H, methyl, or fluoro.

9. The compound according to claim 1, wherein $R_4$ is $C_{1-7}$ alkyl, $C_{2-7}$ alkenyl, $C_{3-7}$ cycloalkyl, or $C_{3-7}$ cycloalkyl $C_{1-7}$ alkyl.

10. The compound according to claim 9, wherein $R_4$ is $C_{1-7}$ alkyl.

11. The compound according to claim 10, wherein $R_4$ is methyl or ethyl.

12. The compound according to claim 1, wherein $R_5$ and $R_5'$ are, independently, H or $C_{1-7}$ alkyl, and $R_6$ and $R_6'$ are, independently, H or OH.

13. The compound according to claim 12, wherein $R_5$ and $R_5'$ are, independently, H or methyl, and $R_6$ and $R_6'$ are, independently, H or OH.

14. The compound according to claim 13, wherein $R_5$ and $R_5'$ are methyl, and $R_6$ and $R_6'$ are, independently, H or OH.

15. The compound according to claim 14, wherein $R_5$ and $R_5'$ are attached to a same carbon atom of ring A.

16. The compound according to claim 1, wherein $R_7$ is H, halogen, $C_{1-7}$ alkyl, $C_{1-7}$ alkoxy, hydroxy $C_{1-7}$ alkyl, or $C_{1-7}$ alkoxy $C_{1-7}$ alkyl.

17. The compound according to claim 1, wherein $R_9$ is a imidazolyl, pyrazolyl, oxetanyl, thiazolyl, pyridinyl, phenyl, or morpholnyl ring, which may be substituted with one $C_{1-7}$ alkyl or one $C_{1-7}$ alkoxy group.

18. The compound according to claim 1, wherein the compound is
4-(Ethyl(3-(2-methyl-2H-tetrazol-5-yl)cyclohexyl)amino)-2-(trifluoromethyl)-benzonitrile;
4-((3-(1H-imidazol-1-yl)-6,6-dimethylcyclohex-2-en-1-yl)(ethyl)amino)-2-(tri-fluoromethyl)benzonitrile;
4-((3-(1H-imidazol-1-yl)cyclohexyl)(ethyl)amino)-2-chloro-3-methylbenzonitrile;
4-((3-(1,3,4-Oxadiazol-2-yl)cyclohexyl)(ethyl)amino)-2-(trifluoromethyl)benzo-nitrile;
4-((3-(1H-imidazol-1-yl)-6,6-dimethylcyclohex-2-enyl)(ethyl)amino)-2-chloro-benzonitrile;
4-((3-(1H-imidazol-1-yl)-6,6-dimethylcyclohex-2-enyl)(ethyl)amino)-2-(di-fluoromethyl)benzonitrile;
4-((5-(1H-Imidazol-1-yl)-2,2-dimethylcyclohexyl)(ethyl)amino)-2-(trifluoro-methyl)benzonitrile;
4-((3-(1H-Pyrazol-1-yl)cyclohexyl)(ethyl)amino)-2-(trifluoromethyl)benzonitrile;
4-(Ethyl(3-(1-isopropyl-1H-imidazol-5-yl)cyclopent-3-enyl)amino)-2-(trifluoro-methyl)benzonitrile;
4((3-(1-Cyclopropyl-1H-imidazol-5-yl)cyclopent-3-enyl)(ethyl)amino)-2-(tri-fluoromethyl)benzonitrile;
4-(Ethyl(3-(pyridin-4-yl)cyclohexyl)amino)-2-(trifluoromethyl)benzonitrile;
4-((3-(1H-imidazol-1-yl)cyclohex-2-en-1-yl)(ethyl)amino)-2-(trifluoromethyl)-benzonitrile;
4-((3-(1H-imidazol-1-yl)cyclohexyl)(ethyl)amino)-2-(tri-fluoromethyl)benzonitrile;
2-Chloro-4-(ethyl(3-(pyridin-3-yl)cyclohexyl)amino)benzonitrile;
4-(Ethyl(3-(pyridin-4-yl)cyclohex-3-en-1-yl)amino)-2-(trifluoromethyl)benzonitrile;
2-Chloro-4-(ethyl(3-(5-methoxypyridin-3-yl)cyclohexyl)amino)benzonitrile;
4-(Ethyl(3-(3-methoxypyridin-4-yl)cyclohex-3-en-1-yl)amino)-2-(trifluoromethyl)-benzonitrile;
4-((-3-(1H-imidazol-1-yl)cyclopentyl)(ethyl)amino)-2-(trifluoromethyl)benzonitrile;

4-((3-(1H-imidazol-1-yl)cyclohexyl)(ethyl)amino)-2-chlorobenzonitrile;

4-(Ethyl(3-(1-propyl-1H-imidazol-5-yl)cyclopent-3-en-1-yl)amino)-2-(trifluoro-methyl)benzonitrile;

4-((4-(1H-imidazol-1-yl)spiro[2.5]oct-4-en-6-yl)(ethyl)amino)-2-(trifluoromethyl)-benzonitrile;

4-{[3-(1H-Imidazol-1-yl)-6,6-dimethylcyclohex-2-enyl](methyl)amino}-2-(tri-fluoromethyl)benzonitrile;

2-Chloro-4-(ethyl(3-(pyridin-3-yl)cyclohex-3-en-1-yl)amino)-6-fluorobenzonitrile;

4-(ethyl(3-(1-ethyl-1H-imidazol-5-yl)cyclohex-3-en-1-yl)amino)-2-(trifluoro-methyl)benzonitrile;

4-((3-(1H-1,2,4-triazol-1-yl)cyclohexyl)(ethyl)amino)-2-(trifluoromethyl)benzo-nitrile;

4-((3-(1H-1,2,4-triazol-1-yl)cyclohex-2-en-1-yl)(ethyl)amino)-2-(trifluoro-methyl)benzonitrile;

4-(Ethyl(3-hydroxy-3-(pyridin-3-yl)cyclohexyl)amino)-2-(trifluoromethyl)-benzonitrile;

4-((3-(1H-1,2,3-triazol-1-yl)cyclohexyl)(ethyl)amino)-2-(trifluoromethyl)benzo-nitrile;

4-((Cyclopropylmethyl)(3-(1-ethyl-1H-imidazol-5-yl)cyclopent-3-en-1-yl)amino)-2-(trifluoromethyl)benzonitrile;

2-Chloro-4-(ethyl(3-(1-ethyl-1H-imidazol-5-yl)cyclopent-3-en-1-yl)amino)-benzonitrile;

4-((3-(1H-imidazol-4-yl)-6,6-dimethylcyclohex-3-enyl)(methyl)amino)-2-chloro-benzonitrile;

4-((3-(1H-imidazol-1-yl)cyclohex-2-enyl)(methyl)amino)-2-(trifluoromethyl)-benzonitrile;

4-(-3-(1H-imidazol-1-yl)cyclohexyl)(ethyl)amino)-2,6-difluorobenzonitrile;

4-((5-(1H-Imidazol-1-yl)-2,2-dimethylcyclohexyl)(methyl)amino)-2-(trifluoro-methyl)benzonitrile;

4-((2,2-dimethyl-3-(pyridin-3-yl)cyclohex-3-en-1-yl)(ethyl)amino)-2-(trifluoro-methyl)benzonitrile;

4-((3-(1H-imidazol-4-yl)-2,2-dimethylcyclohex-3-en-1-yl)(ethyl)amino)-2-(tri-fluoromethyl)benzonitrile;

4-((3-(1H-Imidazol-4-yl)cyclopent-3-en-1-yl)(ethyl)amino)-2-chlorobenzonitrile;

4-((3-(1H-imidazol-4-yl)cyclopent-3-en-1-yl)(ethyl)amino)-2-(trifluoromethyl)-benzonitrile;

4-((3-(1H-imidazol-5-yl)cyclopentyl)(ethyl)amino)-2-(trifluoromethyl)benzonitrile;

4-((3-(1-(2-(benzyloxy)ethyl)-1H-imidazol-5-yl)-6,6-dimethylcyclohex-2-en-1-yl)(methyl)amino)-2-(trifluoromethyl)benzonitrile;

4-((3-(1H-imidazol-5-yl)cyclohexyl)(ethyl)amino)-2-(trifluoromethyl)benzonitrile;

4-((6,6-Dimethyl-3-(oxazol-5-yl)cyclohex-2-en-1yl)(methyl)amino)-2-(trifluoromethyl)benzonitrile;

2-Chloro-4-((6,6-dimethyl-3-(oxazol-5-yl)cyclohex-2-en-1-yl)amino)benzonitrile;

2-Chloro-4-{[4-hydroxy-3-(1H-imidazol-1-yl)-6,6-dimethylcyclohex-2-enyl]-(methyl)amino}benzonitrile;

4-((3-(1H-imidazol-1-yl)-6,6-dimethylcyclohex-2-en-1-yl)(methyl)amino)-2-bromobenzonitrile;

4-((3-(1-ethyl-1H-imidazol-5-yl)cyclopent-3-en-1-yl)(2-methoxyethyl)amino -2-(trifluoromethyl)benzonitrile;

Cis-4-((4-hydroxy-3-(1H-imidazol-1-yl)-6,6-dimethylcyclohex-2-enyl)(methyl)-amino)-2-(trifluoromethyl)benzonitrile;

4-{[3-(1H-Imidazol-1-yl)-6,6-dimethylcyclohex-2-enyl](methyl)amino}-2-methoxybenzonitrile;

4-(((1R,4S)-4-hydroxy-3-(1H-imidazol-1-yl)-6,6-dimethylcyclohex-2-en-1-yl)(methyl)-amino)-2-(trifluoromethyl)benzonitrile;

4-((3-(1H-imidazol-1-yl)-2,2-dimethylcyclopent-3-en-1-yl)(ethyl)amino)-2-(trifluoromethyl)benzonitrile; or 4-{[2-Hydroxy-3-(1H-imidazol-4-yl)-6,6-dimethylcyclohex-3-enyl](methyl)amino}-2(trifluoromethyl)benzonitrile;

or a tautomer thereof or a pharmaceutically acceptable salt thereof.

19. A pharmaceutical composition comprising a compound according to claim 1 and a pharmaceutically acceptable carrier.

20. A method for the treatment or prevention of androgen receptor dependent conditions, comprising administering to a subject in need thereof a therapeutically effective amount of a compound according to claim 1, where the condition is selected from prostate cancer, benign prostate hyperplasia, androgenic allopecia, and acne.

21. The method according to claim 20, wherein the androgen receptor dependent condition is prostate cancer.

22. The method according to claim 21, wherein the androgen receptor dependent condition is castration-resistant prostate cancer.

* * * * *

UNITED STATES PATENT AND TRADEMARK OFFICE
CERTIFICATE OF CORRECTION

| | |
|---|---|
| PATENT NO. | : 9,890,139 B2 |
| APPLICATION NO. | : 14/897326 |
| DATED | : February 13, 2018 |
| INVENTOR(S) | : Gerd Wohlfahrt et al. |

Page 1 of 1

It is certified that error appears in the above-identified patent and that said Letters Patent is hereby corrected as shown below:

In the Claims

Claim 18, Column 230, Lines 6-7, "4-((6,6-Dimethyl-3-(oxazol-5-yl)cyclohex-2-en-1yl)(methyl)amino)-2-(trifluoromethyl)benzonitrile;" should read as --4-((6,6-Dimethyl-3-(oxazol-5-yl)cyclohex-2-en-1-yl)(methyl)amino)-2-(trifluoromethyl)benzonitrile;--.

Claim 18, Column 230, Line 18-19, "4-{[3-(1H-Imidazol-1-yl)-6,6-dimethylcyclohex-2-enyl](methyl)amino}-2-methoxybenzonitrile;" should read as --4-{[3-(1H-imidazol-1-yl)-6,6-dimethylcyclohex-2-enyl](methyl)amino}-2-methoxybenzonitrile;--.

Signed and Sealed this
First Day of May, 2018

Andrei Iancu
*Director of the United States Patent and Trademark Office*